US007264963B1

(12) United States Patent
Knappik et al.

(10) Patent No.: US 7,264,963 B1
(45) Date of Patent: Sep. 4, 2007

(54) PROTEIN(POLY)PEPTIDE LIBRARIES

(75) Inventors: Achim Knappik, Gräfelfing (DE);
Peter Pack, München (DE); Liming Ge, München (DE); Simon Moroney, München (DE); Andreas Plückthun, Zürich (CH)

(73) Assignee: Morphosys AG, Munich (DE)

( * ) Notice: Subject to any disclaimer, the term of this patent is extended or adjusted under 35 U.S.C. 154(b) by 0 days.

(21) Appl. No.: 09/490,064

(22) Filed: Jan. 24, 2000

Related U.S. Application Data

(60) Division of application No. 09/025,769, filed on Feb. 18, 1998, now Pat. No. 6,300,064, which is a continuation of application No. PCT/EP96/03647, filed on Aug. 19, 1995.

(30) Foreign Application Priority Data

Aug. 18, 1995 (EP) .................................. 95113021

(51) Int. Cl.
*C12N 15/00* (2006.01)
*C12Q 1/68* (2006.01)
*C07H 21/00* (2006.01)

(52) U.S. Cl. .................... 435/320.1; 435/6; 536/23.1; 536/25.3

(58) Field of Classification Search ................ 435/6, 435/320.1, 69.1, 69.3; 536/23.1
See application file for complete search history.

(56) References Cited

U.S. PATENT DOCUMENTS

| 5,476,786 | A |   | 12/1995 | Huston |          |
|-----------|---|---|---------|--------|----------|
| 5,580,717 | A |   | 12/1996 | Dower et al. | .................. 435/5 |
| 5,693,493 | A | * | 12/1997 | Robinson et al. |    |
| 5,693,761 | A | * | 12/1997 | Queen et al. |       |
| 5,780,225 | A |   | 7/1998  | Wigler et al. | .................. 435/6 |
| 5,840,479 | A |   | 11/1998 | Little et al. |     |
| 5,885,793 | A |   | 3/1999  | Griffiths et al. | ............ 435/69.1 |
| 5,969,108 | A |   | 10/1999 | McCafferty et al. | ...... 530/387.3 |
| 6,248,516 | B1|   | 6/2001  | Winter et al. | .................. 435/6 |
| 6,291,158 | B1|   | 9/2001  | Winter et al. | .................. 435/6 |
| 6,291,159 | B1|   | 9/2001  | Winter et al. | .................. 436/6 |
| 6,291,160 | B1|   | 9/2001  | Lerner et al. | .................. 435/6 |
| 6,291,161 | B1|   | 9/2001  | Lerner et al. | .................. 435/6 |
| 6,303,313 | B1|   | 10/2001 | Wigler et al. | .................. 435/6 |

OTHER PUBLICATIONS

Maneewannakul et al. Plasmid (1994) vol. 31, pp. 300-307.*
Sigma Catalogue (1993) Product No. D1915, D2040, D2165, D2290.*
Marks, et al. "By-Passing Immunization: Building High Affinity Human Antibodies by Chai Shuffling." 1992 Bio/Technology, vol. 10: p. 779-783.

(Continued)

*Primary Examiner*—Mary K. Zeman
*Assistant Examiner*—Lori A. Clow
(74) *Attorney, Agent, or Firm*—Heller Ehrman White and McAuliffe LLP

(57) ABSTRACT

The present invention relates to synthetic DNA sequences which encode one or more collections of homologous proteins/(poly)peptides, and methods for generating and applying libraries of these DNA sequences. In particular, the invention relates to the preparation of a library of human-derived antibody genes by the use of synthetic consensus sequences which cover the structural repertoire of antibodies encoded in the human genome. Furthermore, the invention relates to the use of a single consensus antibody gene as a universal framework for highly diverse antibody libraries.

13 Claims, 220 Drawing Sheets

OTHER PUBLICATIONS

Figure 1:
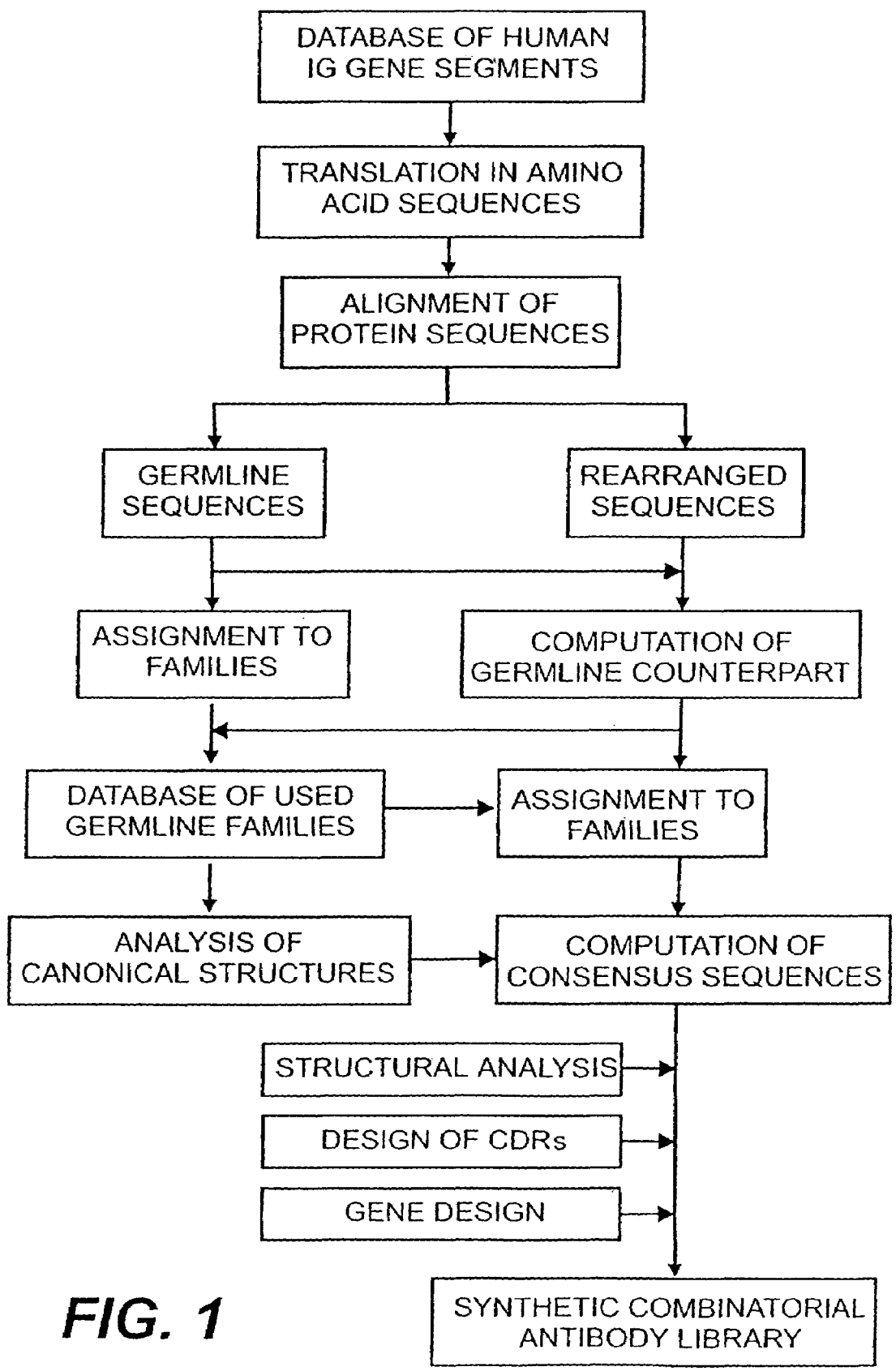
Figure 7E:
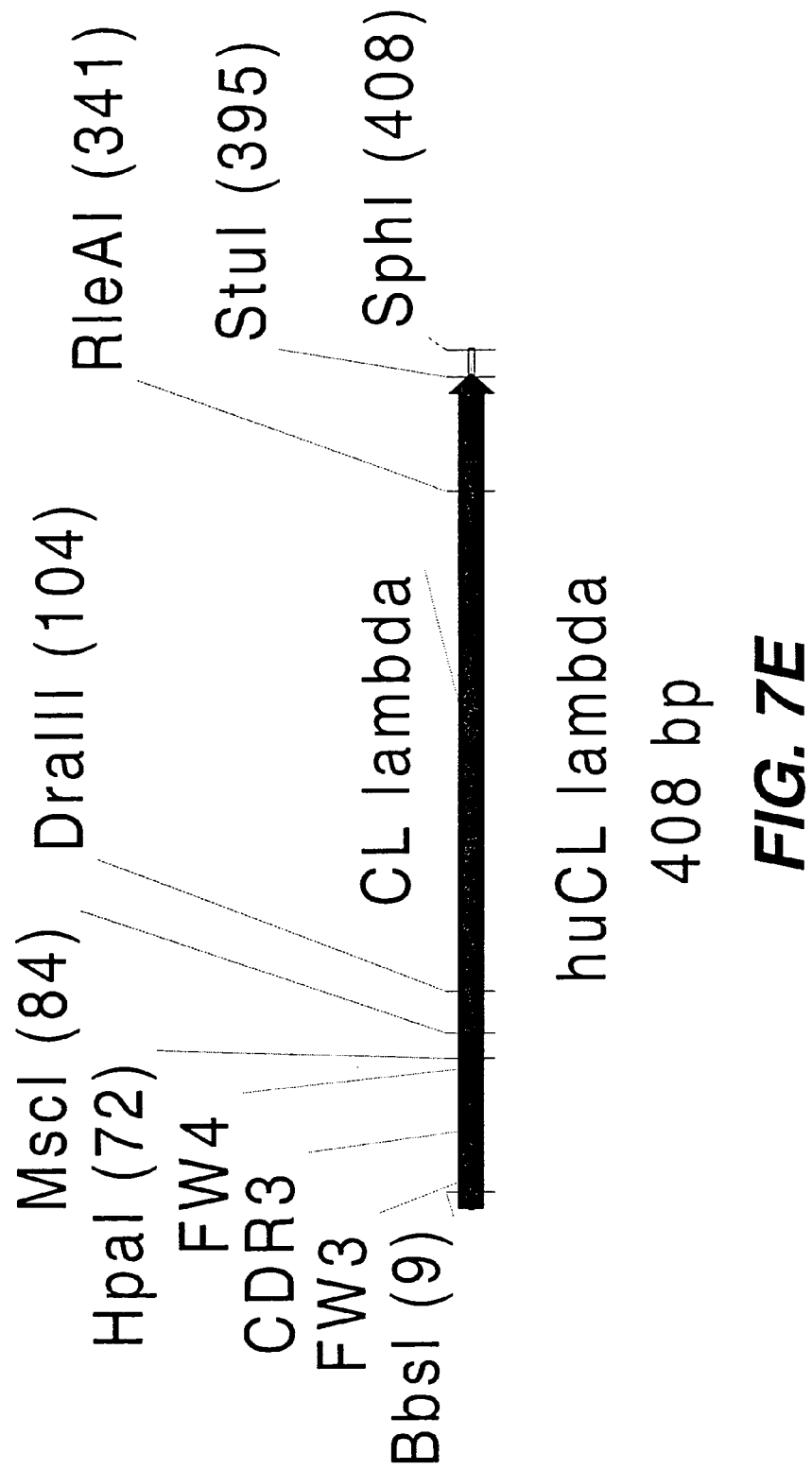

Hoogenboom, et al. "Building Antibodies From Their Genes." 1993 Rev. Fr. Transfus. Hemobiol vol. 36: p. 19-47.

Griffiths, et al. "Isolation of High Affinity Human Antibodies Directly from Large Syntheti Repertoires." 1994 EMBO J., vol. 13: p. 3245-3260

Winter and Milstein "Man-Made Antibodies." 1991 Nature, vol. 349: p. 293-299.

John De Kruif et al., "Selection and Application of Human Single Chain Fv Antibody Fragments from a Semi-synthetic Phage Antibody Display Library with Designed CDR3 Regions", J. Mol. Biol. (1995) 248, pp. 97-105.

Robert Schier et al., "Identification of functional and structural amino-acid residues by parsimonious mutagenesis", Gene, 169 (1996) pp. 147-155.

Lisa J. Garrard et al., "Selection of anti-IGF-1 Fab from a Fab phage library created by mutagenesis of multiple CDR loops", Gene, 128 (1993) pp. 103-109.

Carlos F. Barbas, III, "Semisynthetic combinatorial antibody libraries: A chemical solution to the diversity problem", Proc. Natl. Acad. Sci. USA, vol. 89, May 1992, pp. 4457-4461.

* cited by examiner

FIG. 2A

| | framework 1 | | | | | | | | | | | | | | | | | | | | | CDRI | | | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C |
| Vκ1 | D | I | Q | M | T | Q | S | P | S | S | L | S | A | S | V | G | D | R | V | T | I | T | C | R | A | S | Q | - | - | - |
| Vκ2 | D | I | V | M | T | Q | S | P | L | S | L | P | V | T | P | G | E | P | A | S | I | S | C | R | S | S | Q | S | - | - |
| Vκ3 | D | I | V | L | T | Q | S | P | A | T | L | S | L | S | P | G | E | R | A | T | L | S | C | R | A | S | Q | - | - | - |
| Vκ4 | D | I | V | M | T | Q | S | P | D | S | L | A | V | S | L | G | E | R | A | T | I | N | C | R | S | S | Q | S | V | L |

| | CDRI | | | | | | | | framework 2 | | | | | | | | | | | | | | | CDR II | | | | | |
|---|---|---|---|---|---|---|---|---|---|---|---|---|---|---|---|---|---|---|---|---|---|---|---|---|---|---|---|---|---|
| | D | E | F | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
| Vκ5 | - | - | - | G | I | S | S | Y | L | A | W | Y | Q | Q | K | P | G | K | A | P | K | L | L | I | Y | A | A | S | S | L |
| Vκ6 | H | S | - | N | G | Y | N | Y | L | D | W | Y | L | Q | K | P | G | Q | S | P | Q | L | L | I | Y | L | G | S | N | R |
| Vκ7 | - | - | - | V | S | S | S | Y | L | A | W | Y | Q | Q | K | P | G | Q | A | P | R | L | L | I | Y | G | A | S | S | R |
| Vκ8 | Y | S | S | N | N | K | N | Y | L | A | W | Y | Q | Q | K | P | G | Q | P | P | K | L | L | I | Y | W | A | S | T | R |

FIG. 2B

| | CDRII | | | | | | | | | | | | | | framework 3 | | | | | | | | | | | | | | |
|---|---|---|---|---|---|---|---|---|---|---|---|---|---|---|---|---|---|---|---|---|---|---|---|---|---|---|---|---|---|
| | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
| Vk1 | Q | S | G | V | P | S | R | F | S | G | S | G | S | G | T | D | F | T | L | T | I | S | S | L | Q | P | E | D | F | A |
| Vk2 | A | S | G | V | P | D | R | F | S | G | S | G | S | G | T | D | F | T | L | K | I | S | R | V | E | A | E | D | V | G |
| Vk3 | A | T | G | V | P | A | R | F | S | G | S | G | S | G | T | D | F | T | L | T | I | S | S | L | E | P | E | D | F | A |
| Vk4 | E | S | G | V | P | D | R | F | S | G | S | G | S | G | T | D | F | T | L | T | I | S | S | L | Q | A | E | D | V | A |

| | framework 3 | | | CDRIII | | | | | | | | | framework 4 | | | | | | | | | | | | |
|---|---|---|---|---|---|---|---|---|---|---|---|---|---|---|---|---|---|---|---|---|---|---|---|---|---|
| | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 |
| Vk1 | T | Y | Y | C | Q | Q | H | Y | T | T | P | P | T | F | G | Q | G | T | K | V | E | I | K | R | T |
| Vk2 | V | Y | Y | C | Q | Q | H | Y | T | T | P | P | T | F | G | Q | G | T | K | V | E | I | K | R | T |
| Vk3 | V | Y | Y | C | Q | Q | H | Y | T | T | P | P | T | F | G | Q | G | T | K | V | E | I | K | R | T |
| Vk4 | V | Y | Y | C | Q | Q | H | Y | T | T | P | P | T | F | G | Q | G | T | K | V | E | I | K | R | T |

FIG. 2C

| | framework 1 | | CDR I | |
|---|---|---|---|---|
| | 1 2 3 4 5 6 7 8 9 10 11 12 13 14 15 16 17 18 19 20 21 22 23 | 24 25 26 27 D E 28 | | |
| vλ1 | Q S V L T Q P P S - V S G A P G Q R V T I S C | S G S S N I - - | | |
| vλ2 | Q S A L T Q P A S - V S G S P G Q S I T I S C | T G T S S D V - | | |
| vλ3 | S Y E L T Q P P S - V S V A P G Q T A R I S C | S G D A - - - L | | |

| | CDR I | framework 2 | CDR II |
|---|---|---|---|
| | 29 30 31 32 A 33 34 35 36 37 38 39 | 40 41 42 43 44 45 46 47 48 49 | 50 51 52 53 54 55 56 57 |
| vλ1 | G S N - Y V S W Y Q Q | L P G T A P K L L I | Y D N N Q R P S G |
| vλ2 | G G Y N Y V S W Y Q Q | H P G K A P K L M I | Y D V S N R P S G |
| vλ3 | G D K - Y A S W Y Q Q | K P G Q A P V L V I | Y D D S D R P S G |

FIG. 2D framework 3

| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
|---|---|---|---|---|---|---|---|---|---|---|---|---|---|---|---|---|---|---|---|---|---|---|---|---|---|---|---|---|---|---|
| vλ1 | V | P | D | R | F | S | G | S | K | S | G | T | S | A | S | L | A | I | T | G | L | Q | S | E | D | E | A | D | Y | Y |
| vλ2 | V | S | N | R | F | S | G | S | K | S | G | N | T | A | S | L | T | I | S | G | L | Q | A | E | D | E | A | D | Y | Y |
| vλ3 | I | P | E | R | F | S | G | S | N | S | G | N | T | A | T | L | T | I | S | G | T | Q | A | E | D | E | A | D | Y | Y |

CDRIII | framework 4

| | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|
| vλ1 | C | Q | Q | H | Y | T | T | P | P | V | F | G | G | G | T | K | L | T | V | L G |
| vλ2 | C | Q | Q | H | Y | T | T | P | P | V | F | G | G | G | T | K | L | T | V | L G |
| vλ3 | C | Q | Q | H | Y | T | T | P | P | V | F | G | G | G | T | K | L | T | V | L G |

FIG. 2E framework 1 (positions 1–30)

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| VH1A | Q | V | Q | L | V | Q | S | G | A | E | V | K | K | P | G | S | S | V | K | V | S | C | K | A | S | G | G | T | F | S |
| VH1B | Q | V | Q | L | V | Q | S | G | A | E | V | K | K | P | G | A | S | V | K | V | S | C | K | A | S | G | G | T | F | T |
| VH2  | Q | V | Q | L | K | E | S | G | P | A | L | V | K | P | T | Q | T | L | T | L | T | C | T | F | S | G | F | S | L | S |
| VH3  | E | V | Q | L | V | E | S | G | G | G | L | V | Q | P | G | G | S | L | R | L | S | C | A | A | S | G | F | T | F | S |
| VH4  | Q | V | Q | L | Q | E | S | G | P | G | L | V | K | P | S | E | T | L | S | L | T | C | T | V | S | G | G | S | I | S |
| VH5  | E | V | Q | L | V | Q | S | G | A | E | V | K | K | P | G | E | S | L | K | I | S | C | K | G | S | G | Y | S | F | T |
| VH6  | Q | V | Q | L | Q | Q | S | G | P | G | L | V | K | P | S | Q | T | L | S | L | T | C | A | I | S | G | D | S | V | S |

CDR I (positions 31–35 with insertions) / framework 2 (36–49) / CDR II (50–57 with insertions)

| | 31 | 32 | A | B | 33 | 34 | 35 | 36 | 37 | 38 | 39 | 40 | 41 | 42 | 43 | 44 | 45 | 46 | 47 | 48 | 49 | 50 | 51 | 52 | A | B | C | 53 | 54 | 55 | 56 | 57 |
|---|---|---|---|---|---|---|---|---|---|---|---|---|---|---|---|---|---|---|---|---|---|---|---|---|---|---|---|---|---|---|---|---|
| VH1A | S | – | – | Y | A | I | S | W | V | R | Q | A | P | G | Q | G | L | E | W | M | G | G | I | I | P | – | – | I | F | G | T | A |
| VH1B | S | – | – | Y | Y | M | H | W | V | R | Q | A | P | G | Q | G | L | E | W | M | G | G | I | I | N | – | – | P | N | S | G | G T |
| VH2  | T | S | G | V | G | V | G | W | I | R | Q | P | P | G | K | A | L | E | W | L | A | L | I | D | – | – | – | W | D | D | D | K |
| VH3  | S | – | – | Y | A | M | S | W | V | R | Q | A | P | G | K | G | L | E | W | V | S | A | I | S | G | – | – | S | G | G | S | T |
| VH4  | S | – | – | Y | Y | W | S | W | I | R | Q | P | P | G | K | G | L | E | W | I | G | Y | I | Y | – | – | – | Y | S | G | S | T |
| VH5  | S | – | – | Y | W | I | G | W | V | R | Q | M | P | G | K | G | L | E | W | M | G | I | I | Y | P | – | – | G | D | S | D | T |

FIG. 2F

| | | framework 3 | | | | | | | | | CDRII | | | | | | | framework 3 | | | | | | | | | | | | | | |
|---|---|---|---|---|---|---|---|---|---|---|---|---|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 |
| VH6 | S | N | S | A | A | W | N | W | I | R | Q | S | P | G | R | G | L | E | W | L | G | R | T | Y | Y | R | – | S | K | W | Y | N |
| VH1A | N | Y | A | Q | K | F | Q | G | R | V | T | I | T | A | D | E | S | T | S | T | A | Y | M | E | L | S | S | L | R | S | E |
| VH1B | N | Y | A | Q | K | F | Q | G | R | V | T | M | T | R | D | T | S | I | S | T | A | Y | M | E | L | S | S | L | R | S | E |
| VH2 | Y | Y | S | T | S | L | K | T | R | L | T | I | S | K | D | T | S | K | N | Q | V | V | L | T | M | T | N | M | D | P | V |
| VH3 | Y | Y | A | D | S | V | K | G | R | F | T | I | S | R | D | N | S | K | N | T | L | Y | L | Q | M | N | S | L | R | A | E |
| VH4 | N | Y | N | P | S | L | K | S | R | V | T | I | S | V | D | T | S | K | N | Q | F | S | L | K | L | S | S | V | T | A | A |
| VH5 | R | Y | S | P | S | F | Q | G | Q | V | T | I | S | A | D | K | S | I | S | T | A | Y | L | Q | W | S | S | L | K | A | S |
| VH6 | D | Y | A | V | S | V | K | S | R | I | T | I | N | P | D | T | S | K | N | Q | F | S | L | Q | L | N | S | V | T | P | E |

| | framework 3 | | | | | | | | | | CDRIII | | | | | | | framework 4 | | | | | | | | | | | | | |
|---|---|---|---|---|---|---|---|---|---|---|---|---|---|---|---|---|---|---|---|---|---|---|---|---|---|---|---|---|---|---|---|
| | 86 | 87 | 88 | 89 | 90 | 91 | 92 | 93 | 94 | 95 | 96 | 97 | 98 | 99 | 100 | 100A | 100B | 100C | 101 | 102 | 103 | 104 | 105 | 106 | 107 | 108 | 109 | 110 | 111 | 112 | 113 |
| VH1A | D | T | A | V | Y | Y | C | A | R | W | G | G | D | G | F | Y | A | M | D | Y | W | G | Q | G | T | L | V | T | V | S | S |
| VH1B | D | T | A | V | Y | Y | C | A | R | W | G | G | D | G | F | Y | A | M | D | Y | W | G | Q | G | T | L | V | T | V | S | S |
| VH2 | D | T | A | T | Y | Y | C | A | R | W | G | G | D | G | F | Y | A | M | D | Y | W | G | Q | G | T | L | V | T | V | S | S |
| VH3 | D | T | A | V | Y | Y | C | A | R | W | G | G | D | G | F | Y | A | M | D | Y | W | G | Q | G | T | L | V | T | V | S | S |
| VH4 | D | T | A | V | Y | Y | C | A | R | W | G | G | D | G | F | Y | A | M | D | Y | W | G | Q | G | T | L | V | T | V | S | S |

VH5  DTAMYYCARWGGDGFYAMDYWGQGTLVTVSS
VH6  DTAVYYCARWGGDGFYAMDYWGQGTLVTVSS

FIG. 2G

```
 D   I   Q   M   T   Q   S   P   S   S   L   S   A   S   V   G   D
EcoRV           BanII
~~~~~~                  ~~~~~~
GATATCCAGA TGACCCAGAG CCCGTCTAGC CTGAGCGCGA GCGTGGGTGA
CTATAGGTCT ACTGGGTCTC GGGCAGATCG GACTCGCGCT CGCACCCACT

R   V   T   I   T   C   R   A   S   Q   G   I   S   S   Y   L
                    PstI
                    ~~~~~~
TCGTGTGACC ATTACCTGCA GAGCGAGCCA GGGCATTAGC AGCTATCTGG
AGCACACTGG TAATGGACGT CTCGCTCGGT CCCGTAATCG TCGATAGACC

A   W   Y   Q   Q   K   P   G   K   A   P   K   L   L   I   Y   A
KpnI            SexAI                           AseI
~~~~~~          ~~~~~~                          ~~~~~~
CGTGGTACCA GCAGAAACCA GGTAAAGCAC CGAAAACTATT AATTTATGCA
GCACCATGGT CGTCTTTGGT CCATTTCGTG GCTTTGATAA TTAAATACGT

A   S   S   L   Q   S   G   V   P   S   R   F   S   G   S   G   S
             SanDI                                      BamHI
             ~~~~~~                                     ~~~~~~
GCCAGCAGCT TGCAAAGCGG GGTCCCGTCC CGTTTTAGCG GCTCTGGATC
CGGTCGTCGA ACGTTTCGCC CCAGGGCAGG GCAAAATCGC CGAGACCTAG
```

FIG. 3A

```
                                                             Eco57I          BbsI
         G  T  D  F  T  L  T  I  S  S  L  Q  P  E  D  F         ~~~~~       ~~~~
         CGGCACTGAT TTTACCCTGA CCATTAGCAG CCTGCAACCT GAAGACTTTG
BamHI    GCCGTGACTA AAATGGGACT GGTAATCGTC GGACGTTGGA CTTCTGAAAC
~

MscI
         A  T  Y  Y  C  Q  Q  H  Y  T  T  P  P  T  F  G  Q         ~~~~~
         TTGCCAGCAG CATTATACCA CCCCGCCGAC CTTTGGCCAG
         AACGGTCGTC GTAATATGGT GGGGCGGCTG GAAACCGGTC

BsiWI
         G  T  K  V  E  I  K  R  T        ~~~~
         GGTACGAAAG TTGAAATTAA ACGTACG
         CCATGCTTTC AACTTTAATT TGCATGC
```

*FIG. 3B*

```
D   I   V   M   T   Q   S   P   L   S   L   P   V   T   P   G   E
EcoRV                       BanII
~~~~~~                      ~~~~~~
GATATCGTGA TGACCCAGAG CCCACTGAGC CTGCCAGTGA CTCCGGGCGA
CTATAGCACT ACTGGGTCTC GGGTGACTCG GACGGTCACT GAGGCCCGCT

P   A   S   I   S   C   R   S   S   Q   S   L   L   H   S   N
                        PstI
                        ~~~~~~
GCCTGCGAGC ATTAGCTGCA GAAGCAGCCA AAGCCTGCTG CATAGCAACG
CGGACGCTCG TAATCGACGT CTTCGTCGGT TTCGGACGAC GTATCGTTGC

G   Y   N   Y   L   D   W   Y   L   Q   K   P   G   Q   S   P   Q
                            KpnI                  SexAI
                            ~~~~~~                ~~~~~~
GCTATAACTA TCTGGATTGG TACCTTCAAA AACCAGGTCA AAGCCCGCAG
CGATATTGAT AGACCTAACC ATGGAAGTTT TTGGTCCAGT TTCGGGCGTC
```

*FIG. 3C*

```
 L   L   I   Y   L   G   S   N   R   A   S   G   V   P   D   R   F
     AseI                                       SanDI
     ~~~~~                                      ~~~~~~~~~~~~

CTATTAATTT ATCTGGGCAG CAACCGTGCC AGTGGGGTCC CGGATCGTTT
GATAATTAAA TAGACCCGTC GTTGGCACGG TCACCCCAGG GCCTAGCAAA

S   G   S   G   G   T   D   F   T   L   K   I   S   R   V
             BamHI
             ~~~~~~

TAGCGGCTCT GGATCCGGCA CCGATTTTAC CCTGAAAATT AGCCCTGTGG
ATCGCCGAGA CCTAGGCCGT GGCTAAAATG GGACTTTTAA TCGGGACACC

E   A   E   D   V   G   V   Y   Y   C   Q   Q   H   Y   T   T   P
     Eco57I
     ~~~~~~
         BbsI
         ~~~~

AAGCTGAAGA CGTGGGGCGTG TATTATTGCC AGCAGCATTA TACCACCCCG
TTCGACTTCT GCACCCCGCAC ATAATAACGG TCGTCGTAAT ATGGTGGGGC
```

*FIG. 3D*

```
P  T  F  G  Q   G  T  K  V  E   I  K  R  T
         MscI                      BsiWI
         ~~~~~~                    ~~~~~~
CCGACCTTTG GCCAGGGTAC GAAAGTTGAA ATTAAACGTA CG
GGCTGGAAAC CGGTCCCATG CTTTCAACTT TAATTTGCAT GC
```

FIG. 3E

```
D  I  V  L  T  Q  S  P  A  T  L  S  L  S  P  G  E
EcoRV                BanII
GATATCGTGC TGACCCAGAG CCCGGGCGACC CTGAGCCTGT CTCCGGGCGA
CTATAGCACG ACTGGGTCTC GGGCCCGCTGG GACTCGGACA GAGGCCCGCT

R  A  T  L  S  C  R  A  S  Q  S  V  S  S  S  Y
              PstI
ACGTGCGACC CTGAGCTGCA GAGCGAGCCA GAGCGTGAGC AGCAGCTATC
TGCACGCTGG GACTCGACGT CTCGCTCGGT CTCGCACTCG TCGTCGATAG

L  A  W  Y  Q  Q  K  P  G  Q  A  P  R  L  L  I  Y
KpnI                    SexAI                  AseI
```

FIG. 3F

```
TGGCGTGGTA CCAGCAGAAA CCAGGTCAAG CACCGCGTCT ATTAATTTAT
ACCGCACCAT GGTCGTCTTT GGTCCAGTTC GTGGCGCAGA TAATTAAATA
 G   A   S   S   R   A   T   G   V   P   A   R   F   S   G   S   G
                                         SanDI              BamHI

GGCGCGAGCA GCCGTGCAAC TGGGGTCCCG GCGCGTTTTA GCGGCTCTGG
CCGCGCTCGT CGGCACGTTG ACCCCAGGGC CGCGCAAAAT CGCCGAGACC
 S   G   T   D   F   T   L   T   I   S   S   L   E   P   E   D
                                                  Eco57I      BbsI

ATCCGGCACG GATTTTACCC TGACCATTAG CAGCCTGGAA CCTGAAGACT
TAGGCCGTGC CTAAAATGGG ACTGGTAATC GTCGGACCTT GGACTTCTGA
BamHI
```

FIG. 3G

```
F   A   V   Y   Y   C   Q   Q   H   Y   T   P   P   T   F   G
                                                            MscI
                                                            ~~
TTGCGGTGTA TTATTGCCAG CAGCATTATA CCACCCCGCC GACCTTTGGC
AACGCCACAT AATAACGGTC GTCGTAATAT GGTGGGGCGG CTGGAAACCG

Q   G   T   K   V   E   I   K   R   T
MscI                        BsiWI
~                           ~~~~~~
CAGGGTACGA AAGTTGAAAT TAAAACGTACG
GTCCCATGCT TTCAACTTTA ATTTGCATGC
```

*FIG. 3H*

```
D   I   V   M   T   Q   S   P   D   S   L   A   V   S   L   G   E
        EcoRV                   BanII
~~~~~~~                     ~~~~~~~
GATATCGTGA TGACCCAGAG CCCGGATAGC CTGGCGGTGA GCCTGGGCGA
CTATAGCACT ACTGGGTCTC GGGCCTATCG GACCGCCACT CGGACCCGCT

R   A   T   I   N   C   R   S   S   Q   S   V   L   Y   S   S
                    PstI
                ~~~~~~~
ACGTGCGACC ATTAACTGCA GAAGCAGCCA GAGCGTGCTG TATAGCAGCA
TGCACGCTGG TAATTGACGT CTTCGTCGGT CTCGCACGAC ATATCGTCGT

N   N   K   N   Y   L   A   W   Y   Q   Q   K   P   G   Q   P   P
                            KpnI                    SexAI
                        ~~~~~~~                 ~~~~~~~
ACAACAAAAA CTATCTGGCG TGGTACCAGC AGAAACCAGG TCAGCCGCCG
TGTTGTTTTT GATAGACCGC ACCATGGTCG TCTTTGGTCC AGTCGGCGGC
```

*FIG. 31*

```
K   L   L   I   Y   W   A   S   T   R   E   S   G   V   P   D   R
AACTATTAA TTTATTGGGC ATCCACCCGT GAAAGCGGGG TCCCGGATCG
TTTGATAATT AAATAACCCG TAGGTGGGCA CTTTCGCCCC AGGGCCTAGC
         AseI                                  SanDI

F   S   G   S   G   S   G   T   D   F   T   L   T   I   S   S
TTTTAGCGGC TCTGGATCCG GCACTGATTT TACCCTGACC ATTTCGTCCC
AAAATCGCCG AGACCTAGGC CGTGACTAAA ATGGGACTGG TAAAGCAGGG
                 BamHI

L   Q   A   E   D   V   A   V   Y   Y   C   Q   Q   H   Y   T   T
    Eco57I
         BbsI
```

FIG. 3J

```
TGCAAGCTGA AGACGTGGCG GTGTATTATT GCCAGCAGCA TTATACCACC
ACGTTCGACT TCTGCACCGC CACATAATAA CGGTCGTCGT AATATGGTGG

P  P  T  F  G  Q  G     T  K  V     E  I  K  R    T
              MscI                           BsiWI
              ~~~~~~                         ~~~~~

CCGCCGACCT TTGGCCAGGG TACGAAAGTT GAAATTAAAC GTACG
GGCGGCTGGA AACCGGTCCC ATGCTTTCAA CTTTAATTTG CATGC
```

*FIG. 3K*

```
Q  S  V  L  T  Q  P  P  S  V  S  G  A  P  G  Q  R
CAGAGCGTGC TGACCCAGCC GCCTTCAGTG AGTGGGCAC CAGGTCAGCG
GTCTCGCACG ACTGGGTCGG CGGAAGTCAC TCACCGCGTG GTCCAGTCGC
                                 Eco57I           SexAI
                                 ~~~~~~           ~~~~~

V  T  I  S  C  S  G  S  S  S  N  I  G  S  N  Y
       BssSI

TGTGACCATC TCGTGTAGCG GCAGCAGCAG CAACATTGGC AGCAACTATG
ACACTGGTAG AGCACATCGC CGTCGTCGTC GTTGTAACCG TCGTTGATAC

V  S  W  Y  Q  Q  L  P  G  T  A  P  K  L  L  I  Y
       KpnI           XmaI       BbeI
       ~~~~           ~~~~       ~~~~

TGAGCTGGTA CCAGCAGTTG CCCGGGACGG CGCCGAAACT GCTGATTTAT
ACTCGACCAT GGTCGTCAAC GGGCCCTGCC GCGGCTTTGA CGACTAAATA
```

FIG. 4A

```
D  N  N  Q  R  P  S  G  V  P  D  R  F  S  G  S  K
                  Bsu36I                    BamHI
                  ~~~~~                     ~~~~~
GATAACAACC AGCGTCCCTC AGGCGTGCCG GATCGTTTTA GCGGATCCAA
CTATTGTTGG TCGCAGGGAG TCCGCACGGC CTAGCAAAAT CGCCTAGGTT

S  G  T  S  A  S  L  A  I  T  G  L  Q  S  E  D
                                              BbsI
                                              ~~~~~
AAGCGGCACC AGCGCCGAGCC TTGCGATTAC GGGCCTGCAA AGCGAAGACG
TTCGCCGTGG TCGCGCTCGG AACGCTAATG CCCGGACGTT TCGCTTCTGC

E  A  D  Y  C  Q  Q  H  Y  T  P  P  V  F  G
AAGCGGATTA TTATTGCCAG CAGCATTATA CCACCCCGCC TGTGTTTGGC
TTCGCCTAAT AATAACGGTC GTCGTAATAT GGTGGGGCGG ACACAAACCG
```

FIG. 4B

```
G  G  T  K  L  T  V  L  G
         HpaI       MscI
         ~~~~       ~~~
GGCGGCACGA AGTTAACCGT TCTTGGC
CCGCCGTGCT TCAATTGGCA AGAACCG
```

FIG. 4C

```
Q  S  A  L  T  Q  P  A  S  V  S  G  S  P  G  Q  S
CAGAGGCCAC TGACCCAGCC AGCTTCAGTG AGCGGGCTCAC CAGGTCAGAG
GTCTCGCGTG ACTGGGTCGG TCGAAGTCAC TCGCCCGAGTG GTCCAGTCTC
                                 Eco57I
                                 ~~~~~
                                         SexAI
                                         ~~~~~

I  T  I  S  C  T  G  T  S  S  D  V  G  G  Y  N
CATTACCATC TCGTGTACGG GTACTAGCAG CGATGTGGGC GGCTATAACT
GTAATGGTAG AGCACATGCC CATGATCGTC GCTACACCCG CCGATATTGA
       BssSI
       ~~~~~
                      KpnI
                      ~~~~~

Y  V  S  W  Y  Q  Q  H  P  G  K  A  P  K  L  M  I
ATGTGAGCTG GTACCAGCAG CATCCCGGGA AGGCGCCGAA ACTGATGATT
TACACTCGAC CATGGTCGTC GTAGGGCCCT TCCGCGGCTT TGACTACTAA
                            XmaI       BbeI
                            ~~~~~      ~~~~~
```

FIG. 4D

```
Y  D  V  S    N  R  P  S    G  V  S    N  R  F    S  G  S
                 Bsu36I                                BamHI
                 ~~~~~~~~                              ~~~~~
TATGATGTGA  GCAACCGTCC  CTCAGGGCGTG  AGCAACCGTT  TTAGCGGATC
ATACTACACT  CGTTGGCAGG  GAGTCCCGCAC  TCGTTGGCAA  AATCGCCTAG

K  S  G    N  T  A  S    L  T  I    S  G  L    Q  A  E
BamHI                                                 BbsI
~                                                     ~~~~
CAAAAGCGGC  AACACCGCGA  GCCTGACCAT  TAGCGGCCTG  CAAGCGGAAG
GTTTTCGCCG  TTGTGGCGCT  CGGACTGGTA  ATCGCCGGAC  GTTCGCCTTC

D  E  A  D    Y  Y  C    Q  Q  H    Y  T  T  P    P  V  F
BbsI
~
ACGAAGCGGA  TTATTATTGC  CAGCAGCATT  ATACCACCCC  GCCTGTGTTT
TGCTTCGCCT  AATAATAACG  GTCGTCGTAA  TATGGTGGGG  CGGACACAAA
```

FIG. 4E

```
G  G  G  T  K  L  T  V  L  G
               HpaI        MscI
            ~~~~~~~~~    ~~~~~~
GGCGGCGGCA CGAAGTTAAC CGTTCTTGGC
CCGCCGCCGT GCTTCAATTG GCAAGAACCG
```

FIG. 4F

```
S  Y  E  L  T  Q  P  P  S  V  S  V  A  P  G  Q  T
AGCTATGAAC TGACCCAGCC GCCTTCAGTG AGCGGTTGCAC CAGGTCAGAC
TCGATACTTG ACTGGGTCGG CGGAAGTCAC TCGCAACGTG GTCCAGTCTG
                                 Eco57I         SexAI

A  R  I  S  C  S  G  D  A  L  G  D  K  Y  A  S
         BssSI

CGGCGCGTATC TCGTGTAGCG GCGATGCGCT GGGCGATAAA TACGCGAGCT
GCCGCGCATAG AGCACATCGC CGCTACGCGA CCCGCTATTT ATGCGCTCGA

W  Y  Q  Q  K  P  G  Q  A  P  V  L  V  I  Y  D  D
   KpnI              XmaI    BbeI
```

FIG. 4G

```
GGTACCAGCA GAAACCCGGG CAGGGCCCAG TTCTGGTGAT TTATGATGAT
CCATGGTCGT CTTTGGGCCC GTCCGCGGTC AAGACCACTA AATACTACTA

S  D  R  P  S  G  I  P  E  R  F  S  G  S  N  S  G
              Bsu36I
              ~~~~~~

TCTGACCCGTC CCTCAGGCAT CCCGGAACGC TTTAGCGGAT CCAACAGCGG
AGACTGGGCAG GGAGTCCGTA GGGCCTTGCG AAATCGCCTA GGTTGTCGCC
                                        BamHI
                                        ~~~~~

N  T  A  T  L  T  I  S  G  T  Q  A  E  D  E  A
                                      BbsI
                                      ~~~~
```

FIG. 4H

```
CAACACCGCG ACCCTGACCA TTAGCGGCAC TCAGGCGGAA GACGAAGCGG
GTTGTGGCGC TGGGACTGGT AATCGCCGTG AGTCCGCCTT CTGCTTCGCC
   D  Y  C     Q  Q  H    Y   T  P     P  V  F    G   G   G
ATTATTATTG CCAGCAGCAT TATACCACCC CGCCTGTGTT TGGCGGCGGC
TAATAATAAC GGTCGTCGTA ATATGGTGGG GCGGACACAA ACCGCCGCCG

T  K  L  T    V  L  G
         HpaI      MscI
         ~~~~      ~~~~
ACGAAGTTAA CCGTTCTTGG C
TGCTTCAATT GGCAAGAACC G
```

FIG. 41

```
Q  V  Q  L    V  Q  S    G  A  E    V  K  K    P  G  S  S
       MfeI
CAGGTGCAAT TGGTTCAGTC TGGCGCGGAA GTGAAAAAAC CGGGCAGCAG
GTCCACGTTA ACCAAGTCAG ACCGCGCCTT CACTTTTTTG GCCCGTCGTC
       ~~~~

V  K  V    S  C  K  A    S  G  G    T  F  S    S  Y  A
CGTGAAAGTG AGCTGCAAAG CCTCCGGAGG CACTTTTAGC AGCTATGCGA
GCACTTTCAC TCGACGTTTC GGAGGCCTCC GTGAAAATCG TCGATACGCT
                       BspEI
                       ~~~~~

I  S  W  V    R  Q  A    P  G  Q  G    L  E  W    M  G  G
                                             XhoI
TTAGCTGGGT GCGGCCAAGCC CCTGGGCAGG GTCTCGAGTG GATGGGCGGC
AATCGACCCA CGCCGGTTCGG GGACCCGTCC CAGAGCTCAC CTACCCGCCG
            BstXI                      ~~~~~~
            ~~~~~~~~~~~~
```

FIG. 5A

```
I  I  P  I  F  G  T     A  N  Y        A  Q  K  F     Q  G  R
ATTATTCCGA TTTTTGGCAC GGGCGAACTAC GGCGCAGAAGT TTCAGGGCCG
TAATAAGGCT AAAAACCGTG CCCGCTTGATG CGCGTCTTCA AAGTCCCGGC

V  T  I     T  A  D  E  S  T  S        T  A  Y  M  E  L
GGTGACCATT ACCGCGGATG AAAGCACCAG CACCGCGTAT ATGGAACTGA
CCACTGGTAA TGGCGCCTAC TTTCGTGGTC GTGGCGCATA TACCTTGACT
BstEII                                 
~~~~~~~~~~

S  S  L  R  S  E  D     T  A  V  Y  Y  C  A  R  W  G
GCAGCCTGCG TAGCGAAGAT ACGGCCGTGT ATTATTGCGC GCGTTGGGGC
CGTCGGACGC ATCGCTTCTA TGCCGGCACA TAATAACGCG CGCAACCCCG
                         EagI           BssHII
                       ~~~~~~~      ~~~~~~~
```

FIG. 5B

```
G  D  G  F  Y  A  M  D  Y  W  G  Q  G  T  L  V  T
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG
                                 StyI
                                 ~~~~

V  S  S
BlpI
~~~~~
GGTTAGCTCA G
CCAATCGAGT C
```

FIG. 5C

```
Q  V  Q  L  V  Q  S  G  A  E  V  K  K  P  G  A  S
   MfeI
CAGGTGCAAT TGGTTCAGAG CGGGCGGGAA GTGAAAAAAC CGGGGCGGAG
GTCCACGTTA ACCAAGTCTC GCCCGCCCTT CACTTTTTTG GCCCCGCCTC

V  K  V  S  C  K  A  S  G  Y  T  F  T  S  Y  Y
                       BspEI
CGTGAAAGTG AGCTGCAAAG CCTCCGGATA TACCTTTACC AGCTATTATA
GCACTTTCAC TCGACGTTTC GGAGGCCTAT ATGGAAATGG TCGATAATAT

M  H  W  V  R  Q  A  P  G  Q  G  L  E  W  M  G  W
                  BstXI                XhoI
TGCACTGGGT CCGCCAAGCC CCTGGGCAGG GTCTCGAGTG GATGGGCTGG
ACGTGACCCA GGCGGTTCGG GGACCCGTCC CAGAGCTCAC CTACCCGACC
```

*FIG. 5D*

```
        I  N  P  N  S  G  G     T  N  Y     A  Q  K  F  Q  G  R
        ATTAACCCGA ATAGCGGCGG CACGAACTAC GCGCAGAAGT TTCAGGGCCG
        TAATTGGGCT TATCGCCGCC GTGCTTGATG CGCGTCTTCA AAGTCCCGGC

V  T  M  T  R  D  T  S  I  S     T  A  Y  M  E  L
        BstEII
        ~~~~~~
        GGTGACCATG ACCCGTGATA CCAGCATTAG CACCGCGTAT ATGGAACTGA
        CCACTGGTAC TGGGCACTAT GGTCGTAATC GTGGCGCATA TACCTTGACT

S  S  L  R  S  E  D     T  A  V  Y  Y  C  A  R  W  G
                          EagI              BssHII
                          ~~~~              ~~~~~~
        GCAGCCTGCG TAGCGAAGAT ACGGCCCGTGT ATTATTGCGC GCGTTGGGGC
        CGTCGGACGC ATCGCTTCTA TGCCGGGCACA TAATAACGCG CGCAACCCCG
```

*FIG. 5E*

```
G  D  G  F  Y  A  M  D  Y  W  G  Q  G  T  L  V  T
                                      StyI
                                      ~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

V  S  S
   BlpI
   ~~~~
GGTTAGCTCA G
CCAATCGAGT C
```

FIG. 5F

```
  Q   V   Q   L   K   E   S   G   P   A   L   V   K   P   T   Q   T
CAGGTGCAAT TGAAAGAAAG CGGCCCGGCC CTGGTGAAAC CGACCCAAAC
GTCCACGTTA ACTTTCTTTC GCCGGGCCGG GACCACTTTG GCTGGGTTTG
        MfeI
       ~~~~~~

L   T   L   T   C   T   F   S   G   F   S   L   S   T   S   G
CCTGACCCTG ACCTGTACCT TTTCCGGATT TAGCCTGTGTCC ACGTCTGGCG
GGACTGGGAC TGGACATGGA AAAGGCCTAA ATCGGACAGG TGCAGACCGC
                            BspEI
                         ~~~~~~~~

V   G   V   G   W   I   R   Q   P   P   G   K   A   L   E   W   L
TTGGCGTGGG CTGGATTCGC CAGCCGCCTG GGAAAGCCCT CGAGTGGCTG
AACCGCACCC GACCTAAGCG GTCGGCGGAC CCTTTCGGGA GCTCACCGAC
                             BstXI                XhoI
                           ~~~~~~~~~           ~~~~~~~~

FIG. 5G
```

FIG. 5H

```
 A   L   I   D   W   D   D   D   K   Y   Y   S   T   S   L   K   T
GCTCTGATTG ATTGGGATGA TGATAAGTAT TATAGCACCA GCCTGAAAAC
CGAGACTAAC TAACCCTACT ACTATTCATA ATATCGTGGT CGGACTTTTG
                                                  MluI
                                                  ~~~~

R   L   T   I   S   K   D   T   S   K   N   Q   V   V   L   T
MluI
~~~~
GCGTCTGACC ATTAGCAAAG ATACTTCGAA AAATCAGGTG GTGCTGACTA
CGCAGACTGG TAATCGTTTC TATGAAGCTT TTTAGTCCAC CACGACTGAT
                          NspV
                          ~~~~

M   T   N   M   D   P   V   D   T   A   T   Y   Y   C   A   R   W
                                                    BsshII
                                                    ~~~~~~
TGACCAACAT GGACCCGGTG GATACGGCCA CCTATTATTG CGCGCGTTGG
ACTGGTTGTA CCTGGGCCAC CTATGCCGGT GGATAATAAC GCGCGCAACC
```

```
G  G  D  G  F  Y  A  M  D  Y  W  G  Q  G  T  L  V
                                     StyI
                                     ~~~~~~~
GGCGGCGATG GCTTTTATGC GATGGATTAT TGGGGCCAAG GCACCCCTGGT
CCGCCGCTAC CGAAAATACG CTACCTAATA ACCCCGGTTC CGTGGGACCA

T  V  S  S
     BlpI
     ~~~~
GACGGTTAGC TCAG
CTGCCAATCG AGTC
```

FIG. 5I

```
                E  V  Q  L  V  E  S  G  G  G  L  V  Q  P  G  G  S
                    MfeI
          GAAGTGCAAT TGGTGGAAAG CGGGGGCGGC CTGGTGCAAC CGGGGCGGCAG
          CTTCACGTTA ACCACCTTTC GCCCCCGCCG GACCACGTTG GCCCCGCCGTC

L  R  L  S  C  A  A  S  G  F  T  F  S  S  Y  A
                                    BspEI
                                   ~~~~~~
          CCTGCGTCTG AGCTGCGCGG CCTCCGGATT TACCTTTAGC AGCTATGCGA
          GGACGCAGAC TCGACGCGCC GGAGGCCTAA ATGGAAATCG TCGATACGCT

M  S  W  V  R  Q  A  P  G  K  G  L  E  W  V  S  A
                              BstXI                    XhoI
                            ~~~~~~~                   ~~~~~~
          TGAGCTGGGT GCGCCAAGCC CCTGGGAAGG GTCTCGAGTG GGTGAGCGCG
          ACTCGACCCA CGCGGTTCGG GGACCCTTCC CAGAGCTCAC CCACTCGCGC
```

*FIG. 5J*

```
  I   S   G   S   G   G   S       T   Y   Y       A   D   S   V   K   G   R
ATTAGCGGGTA GCGGCGGCAG CACCTATTAT GCGGATAGCG TGAAAGGCCG
TAATCGCCCAT CGCCGCCGTC GTGGATAATA CGCCTATCGC ACTTTCCGGC

F   T   I       S   R   D   N       S   K   N       T   L   Y   L   Q   M
                      PmlI                  NspV
                      ~~~~~~                ~~~~~~
TTTTACCATT TCACGTGATA ATTCGAAAAA CACCCTGTAT CTGCAAATGA
AAAATGGTAA AGTGCACTAT TAAGCTTTTT GTGGGACATA GACGTTTACT

N   S   L   R       A   E   D       T   A   V   Y       Y   C   A   R   W   G
              EagI                                      BssHII
              ~~~~~~                                    ~~~~~~
ACAGCCTGCG TGCCGAAGAT ACGGCCGTGT ATTATTGCGC GCGTTGGGGC
TGTCGGACGC ACGGCCTTCTA TGCCGGCACA TAATAACGCG CGCAACCCCG
```

*FIG. 5K*

```
        G  D  G  F  Y  A  M  D  Y  W  G  Q  G  T  L  V  T
                                         StyI
                                         ~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

V  S  S
 BlpI
 ~~~~
GGTTAGCTCA G
CCAATCGAGT C
```

FIG. 5L

```
Q  V  Q  L   Q  E  S   G  P  G   L  V  K  P   S  E  T
CAGGTGCAAT TGCAAGAAAG TGGTCCGGGC CTGGTGAAAC CGAGCGAAAC
GTCCACGTTA ACGTTCTTTC ACCAGGCCCG GACCACTTTG GCTCGCTTTG
    MfeI

L  S  L   T  C  T  V   S  G  G        S  I  S   S  Y   Y
CTGAGCCTG ACCTGCACCG TTTCCGGAGG CAGCATTAGC AGCTATTATT
GACTCGGAC TGGACGTGGC AAAGGCCTCC GTCGTAATAA TCGATAATAA
                          BspEI

W  S  W  I   R  Q  P   P  G  K  G   L  E  W   I  G   Y
                              BstXI              XhoI
```

*FIG. 5M*

```
GGAGCTGGAT TCGCCAGCCG CCTGGGAAGG GTCTCGAGTG GATTGGCTAT
CCTCGACCTA AGCGGTCGGC GGACCCTTCC CAGAGCTCAC CTAACCGATA
  I   Y   Y   S   G   S   T   N   Y   N   P   S   L   K   S   R   V
                                                          BstEII
                                                          ~~~~~~

ATTATTATA GCGGCAGCAC CAACTATAAT CCGAGCCTGA AAAGCCGGGT
TAAATAATAT CGCCGTCGTG GTTGATATTA GGCTCGGACT TTTCGGCCCA
  I    I    S   V   D   T   S   K   N   Q   F   S   L   K   L   S
  BstEII          NspV
  ~~~~~           ~~~~~

GACCATTAGC GTTGATACTT CGAAAAACCA GTTTAGCCTG AAACTGAGCA
CTGGTAATCG CAACTATGAA GCTTTTTGGT CAAATCGGAC TTTGACTCGT
  S   V   T   A   A   D   T   A   V   Y   Y   C   A   R   W   G   G
              EagI                          BssHII
              ~~~~~                         ~~~~~~
```

FIG. 5N

```
GCCGTGACGGC  GGCGGATACG  GCCGTGTATT  ATTGCGCGCG  TTGGGGCGGC
CGCACTGCCG   CCGCCTATGC  CGGCACATAA  TAACGCGCGC  AACCCCGCCG
 D  G  F  Y   A  M  D    Y  W  G     Q  G  T  L   V  T  V
                                     StyI
                                     ~~~~~
GATGGCTTTT   ATGCGATGGA  TTATTGGGGC  CAAGGCACCC  TGGTGACGGT
CTACCGAAAA   TACGCTACCT  AATAACCCCG  GTTCCGTGGG  ACCACTGCCA
 S  S
 BlpI
 ~~~~
TAGCTCAG
ATCGAGTC
```

FIG. 50

```
E   V   Q   L   V   Q   S   G   A   E   V   K   K   P   G   E   S
GAAGTGCAAT TGGTTCAGAG CGGCGCGGAA CGGGCGGAAAG GTGAAAAAAC CGGGGCGAAAG
CTTCACGTTA ACCAAGTCTC GCCGCGCCTT GCCCGCCTT   CACTTTTTTG GCCCGCTTTC

L   K   I   S   C   K   G   S   G   Y   S   F   T   S   Y   W
CCTGAAAATT AGCTGCAAAG GTTCCGGATA TTCCTTTACG AGCTATTGGA
GGACTTTTAA TCGACGTTTC CAAGGCCTAT AAGGAAATGC TCGATAACCT
                      BspEI

I   G   W   V   R   Q   M   P   G   K   G   L   E   W   M   G   I
TTGGCTGGGT GCGCCAGATG CCTGGGAAGG GTCTCGAGTG GATGGGCATT
AACCGACCCA CGCGGTCTAC GGACCCTTCC CAGAGCTCAC CTACCCGTAA
                BstXI                  XhoI
```

FIG. 5P

```
  I   Y   P   G   D   S   D   T   R   Y   S   P   S   F   Q   G   Q
ATTTATCCGG GCGATAGCGA TACCCGTTAT TCTCCGAGCT TTCAGGGCCA
TAAATAGGCC CGCTATCGCT ATGGGCAATA AGAGGCTCGA AAGTCCCGGT

V   T   I   S   A   D   K   S   I   S   T   A   Y   L   Q   W
BstEII
~~~~~~
GGTGACCATT AGCGCGGATA AAAGCATTAG CACCGCGTAT CTTCAATGGA
CCACTGGTAA TCGCGCCTAT TTTCGTAATC GTGGCGCATA GAAGTTACCT

S   S   L   K   A   S   D   T   A   M   Y   Y   C   A   R   W   G
                                                    BsshII
                                                    ~~~~~~
GCAGCCTGAA AGCGAGCGAT ACGGCCATGT ATTATTGCGC GCGTTGGGGC
CGTCGGACTT TCGCTCGCTA TGCCGGTACA TAATAACGCG CGCAACCCCG
```

*FIG. 5Q*

```
  G  D  G  F  Y  A  M  D  Y  W  G  Q  G  T  L  V  T
                                    StyI
                                    ~~~~
GGGGATGGCT TTTATGCGAT GGATTATTGG GGCCAAGGCA CCCTGGTGAC
CCGCTACCGA AAATACGCTA CCTAATAACC CCGGTTCCGT GGGACCACTG

V  S  S
     BlpI
     ~~~~
GGTTAGCTCA G
CCAATCGAGT C
```

*FIG. 5R*

```
Q  V  Q  L  Q  Q  S  G  P  G  L  V  K  P  S  Q  T
        MfeI
CAGGTGCAAT TGCAACAGTC TGGTCCGGGC CTGGTGAAAC CGAGCCAAAC
GTCCACGTTA ACGTTGTCAG ACCAGGCCCG GACCACTTTG GCTCGGTTTG

L  S  L  T  C  A  I  S  G  D  S  V  S  S  N  S
                        BspEI
CCTGAGCCTG ACCTGTGCGA TTTCCGGAGA TAGCGTGAGC AGCAACAGCG
GGACTCGGAC TGGACACGCT AAAGGCCTCT ATCGCACTCG TCGTTGTCGC

A  A  W  N  W  I  R  Q  S  P  G  R  G  L  E  W  L
                          BstXI                XhoI
CGGCGGTGGAA CTGGATTCGC CAGTCTCCTG GGCGTGGCCT CGAGTGGCTG
GCCGCCACCTT GACCTAAGCG GTCAGAGGAC CCGCACCGGA GCTCACCGAC
```

FIG. 5S

```
 G   R   T   Y   Y   R   S       K   W   Y       N   D   Y   A       V   S   V
GGCCGTACCT ATTATCGTAG CAAATGGTAT AACGATTATG CGGTGAGCGT
CCGGCATGGA TAATAGCATC GTTTACCATA TTGCTAATAC GCCACTCGCA

K   S   R       I   T   I   N   P   D   T       S   K   N   Q   F   S
GAAAAGCCCG ATTACCATCA ACCCGGATAC TTCGAAAAAC CAGTTTAGCC
CTTTTCGGGC TAATGGTAGT TGGGCCTATG AAGCTTTTTG GTCAAATCGG
           ~~~~~~~~~~~                        ~~~~~~~~~~
             BsaBI                               NspV

L   Q   L   N       S   V   T       P   E   D   T       A   V   Y   Y   C   A
TGCAACTGAA CAGCGTGACC CCGGAAGATA CGGCCGTGTA TTATTGCGCG
ACGTTGACTT GTCGCACTGG GGCCTTCTAT GCCGGCACAT AATAACGCGC
                                  ~~~~~~~~~              ~~~~~~
                                     EagI                 BssHII
```

FIG. 5T

```
R   W   G   G   D   G   F       Y   A   M   D   Y   W   G       Q   G   T
BssHII                                                           StyI
  ~                                                               ~~~~~
CGTTGGGGCG GCGATGGCTT TTATGCGATG GATTATTGGG GCCAAGGCAC
GCAACCCCGC CGCTACCGAA AATACGCTAC CTAATAACCC CGGTTCCGTG

L   V   T   V   S   S
            BlpI
            ~~~~~
CCTGGTGACG GTTAGCTCAG
GGACCACTGC CAATCGAGTC
```

FIG. 5U

O1K1 5'- GAATGCATACGCTGATATCCAGATGACCCAGAG-
CCCGTCTAGCCTGAGC -3'
O1K2 5'- CGCTCTGCAGGTAATGGTCACACGATCACCCAC-
GCTCGCGCTCAGGCTAGACGGGC -3'
O1K3 5'- GACCATTACCTGCAGAGCGAGCCAGGGCATTAG-
CAGCTATCTGGCGTGGTACCAGCAG -3'
O1K4 5'- CTTTGCAAGCTGCTGGCTGCATAAATTAATAGT-
TTCGGTGCTTTACCTGGTTTCTGCTGGTACCACGCCAG -3'
O1K5 5'- CAGCCAGCAGCTTGCAAAGCGGGGTCCCGTCCC-
GTTTTAGCGGCTCTGGATCCGGCACTGATTTTAC -3'
O1K6 5'- GATAATAGGTCGCAAAGTCTTCAGGTTGCAGGC-
TGCTAATGGTCAGGGTAAAATCAGTGCCGGATCC -3'
O2K1 5'- CGATATCGTGATGACCCAGAGCCCACTGAGCCT-
GCCAGTGACTCCGGGCGAGCC -3'
O2K2 5'- GCCGTTGCTATGCAGCAGGCTTTGGCTGCTTCT-
GCAGCTAATGCTCGCAGGCTCGCCCGGAGTCAC -3'
O2K3 5'- CTGCTGCATAGCAACGGCTATAACTATCTGGAT-
TGGTACCTTCAAAAACCAGGTCAAAGCCC -3'
O2K4 5'- CGATCCGGGACCCCACTGGCACGGTTGCTGCCC-
AGATAAATTAATAGCTGCGGGCTTTGACCTGGTTTTTG -3'
O2K5 5'- AGTGGGGTCCCGGATCGTTTTAGCGGCTCTGGA-
TCCGGCACCGATTTTACCCTGAAAATTAGCCGTGTG -3'
O2K6 5'- CCATGCAATAATACACGCCCACGTCTTCAGCTT-
CCACACGGCTAATTTTCAGGG -3'
O3K1 5'- GAATGCATACGCTGATATCGTGCTGACCCAGAG
CCCGG -3'
O3K2 5'- CGCTCTGCAGCTCAGGGTCGCACGTTCGCCCGG-
AGACAGGCTCAGGGTCGCCGGGCTCTGGGTCAGC -3'
O3K3 5'- CCCTGAGCTGCAGAGCGAGCCAGAGCGTGAGCA-
GCAGCTATCTGGCGTGGTACCAG -3'

*FIG. 6A*

O3K4 5'- GCACGGCTGCTCGCGCCATAAATTAATAGACGC-GGTGCTTGACCTGGTTTCTGCTGGTACCACGCCAGATAG -3'

O3K5 5'- GCGCGAGCAGCCGTGCAACTGGGGTCCCGGCGC-GTTTTAGCGGCTCTGGATCCGGCACGGATTTTAC -3'

O3K6 5'- GATAATACACCGCAAAGTCTTCAGGTTCCAGGC-TGCTAATGGTCAGGGTAAAATCCGTGCCGGATC -3'

O4K1 5'- GAATGCATACGCTGATATCGTGATGACCCAGAG-CCCGGATAGCCTGGCG -3'

O4K2 5'- GCTTCTGCAGTTAATGGTCGCACGTTCGCCCAG-GCTCACCGCCAGGCTATCCGGGC -3'

O4K3 5'- CGACCATTAACTGCAGAAGCAGCCAGAGCGTGC-TGTATAGCAGCAACAACAAAACTATCTGGCGTGGTACCAG 3'

O4K4 5'- GATGCCCAATAAATTAATAGTTTCGGCGGCTGA-CCTGGTTTCTGCTGGTACCACGCCAGATAG -3'

O4K5 5'- AAACTATTAATTTATTGGGCATCCACCCGTGAA-AGCGGGGTCCCGGATCGTTTTAGCGGCTCTGGATCCGGCAC- 3'

O4K6 5'- GATAATACACCGCCACGTCTTCAGCTTGCAGGG-ACGAAATGGTCAGGGTAAAATCAGTGCCGGATCCAGAGCC- 3'

O1L1 5'- GAATGCATACGCTCAGAGCGTGCTGACCCAGCC-GCCTTCAGTGAGTGG -3'

O1L2 5'- CAATGTTGCTGCTGCTGCCGCTACACGAGATGG-TCACGCTGACCTGGTGCGCCACTCACTGAAGGCGGC -3'

O1L3 5'- GGCAGCAGCAGCAACATTGGCAGCAACTATGTG-AGCTGGTACCAGCAGTTGCCCGGGAC -3'

O1L4 5'- CCGGCACGCCTGAGGGACGCTGGTTGTTATCAT-AAATCAGCAGTTTCGGCGCCGTCCCGGGCAACTGC -3

O1L5 5'- CCCTCAGGCGTGCCGGATCGTTTTAGCGGATCC-AAAAGCGGCACCAGCGCGAGCCTTGCG -3'

*FIG. 6B*

O1L6 5'- CCGCTTCGTCTTCGCTTTGCAGGCCCGTAATCG-CAAGGCTCGCGCTGG -3'
O2L1 5'- GAATGCATACGCTCAGAGCGCACTGACCCAGCC-AGCTTCAGTGAGCGGC -3'
O2L2 5'- CGCTGCTAGTACCCGTACACGAGATGGTAATGC-TCTGACCTGGTGAGCCGCTCACTGAAGCTGG -3'
O2L3 5'- GTACGGGTACTAGCAGCGATGTGGGCGGCTATA-ACTATGTGAGCTGGTACCAGCAGCATCCCGG -3'
O2L4 5'- CGCCTGAGGGACGGTTGCTCACATCATAAATCA-TCAGTTTCGGCGCCTTCCCGGGATGCTGCTGGTAC -3'
O2L5 5'- CAACCGTCCCTCAGGCGTGAGCAACCGTTTTAG-CGGATCCAAAAGCGGCAACACCGCGAGCC -3'
O2L6 5'- CCGCTTCGTCTTCCGCTTGCAGGCCGCTAATGG-TCAGGCTCGCGGTGTTGCCG -3'
O3L1 5'- GAATGCATACGCTAGCTATGAACTGACCCAGCC-GCCTTCAGTGAGCG -3'
O3L2 5'- CGCCCAGCGCATCGCCGCTACACGAGATACGCG-CGGTCTGACCTGGTGCAACGCTCACTGAAGGCGGC -3'
O3L3 5'- GGCGATGCGCTGGGCGATAAATACGCGAGCTGG-TACCAGCAGAAACCCGGGCAGGCGC -3'
O3L4 5'- GCGTTCCGGGATGCCTGAGGGACGGTCAGAATC-ATCATAAATCACCAGAACTGGCGCCTGCCCGGGTTTC -3'
O3L5 5'- CAGGCATCCCGGAACGCTTTAGCGGATCCAACA-GCGGCAACACCGCGACCCTGACCATTAGCGG -3'
O3L6 5'- CCGCTTCGTCTTCCGCCTGAGTGCCGCTAATGG-TCAGGGTC -3'
O1246H1 5'- GCTCTTCACCCCTGTTACCAAAGCCCAG-GTGCAATTG -3'
O1AH2 5'- GGCTTTGCAGCTCACTTTCACGCTGCTGCCCGGT-TTTTTCACTTCCGCGCCAGACTGAACCAATTGCACCTGGGC-TTTG -3'

*FIG. 6C*

O1AH3 5'- GAAAGTGAGCTGCAAAGCCTCCGGAGGCACTTT-
TAGCAGCTATGCGATTAGCTGGGTGCGCCAAGCCCCTGGGCAG
GGTC -3'

O1AH4 5'- GCCCTGAAACTTCTGCGCGTAGTTCGCCGTGCCA-
AAAATCGGAATAATGCCGCCCATCCACTCGAGACCCTGCCC-
AGGGGC -3'

O1AH5 5'- GCGCAGAAGTTTCAGGGCCGGGTGACCATTACC-
GCGGATGAAAGCACCAGCACCGCGTATATGGAACTGAGCAGCC
TGCG -3'

O1ABH6 5'- GCGCGCAATAATACACGGCCGTATCTTCGCT-
ACGCAGGCTGCTCAGTTCC -3'

O1BH2 5'- GGCTTTGCAGCTCACTTTCACGCTCGCGCCCGGT-
TTTTTCACTTCCGCGCCGCTCTGAACCAATTGCACCTGGGC-
TTTG -3'

O1BH3 5'- GAAAGTGAGCTGCAAAGCCTCCGGATATACCTTT-
ACCAGCTATTATATGCACTGGGTCCGCCAAGCCCCTGGGCAG
GGTC -3'

O1BH4 5'- GCCCTGAAACTTCTGCGCGTAGTTCGTGCCGCC-
GCTATTCGGGTTAATCCAGCCCATCCACTCGAGACCCTGCCCA
GGGGC -3'

O1BH5 5'- GCGCAGAAGTTTCAGGGCCGGGTGACCATGACC-
CGTGATACCAGCATTAGCACCGCGTATATGGAACTGAGCAGCC
TGCG -3'

O2H2 5'- GGTACAGGTCAGGGTCAGGGTTTGGGTCGGTTT-
CACCAGGGCCGGGCCGCTTTCTTTCAATTGCACCTGGGCTTTG
-3'

O2H3 5'- CTGACCCTGACCTGTACCTTTTCCGGATTTAGC-
CTGTCCACGTCTGGCGTTGGCGTGGGCTGGATTCGCCAGCCGC
CTGGGAAAG -3

O2H4 5'- GCGTTTTCAGGCTGGTGCTATAATACTTATCAT-
CATCCCAATCAATCAGAGCCAGCCACTCGAGGGCTTTCCCAGG
CGGCTGG -3'

*FIG. 6D*

O2H5 5'- GCACCAGCCTGAAAACGCGTCTGACCATTAGCA-
AAGATACTTCGAAAAATCAGGTGGTGCTGACTATGACCAACAT
GG -3'

O2H6 5'- GCGCGCAATAATAGGTGGCCGTATCCACCGGGT-
CCATGTTGGTCATAGTCAGC -3'

O3H1 5'- CGAAGTGCAATTGGTGGAAAGCGGCGGCGGCCT-
GGTGCAACCGGGCGGCAG -3'

O3H2 5'- CATAGCTGCTAAAGGTAAATCCGGAGGCCGCGC-
AGCTCAGACGCAGGCTGCCGCCCGGTTGCAC -3'

O3H3 5'- GATTTACCTTTAGCAGCTATGCGATGAGCTGGG-
TGCGCCAAGCCCCTGGGAAGGGTCTCGAGTGGGTGAG -3'

O3H4 5'- GGCCTTTCACGCTATCCGCATAATAGGTGCTGC-
CGCCGCTACCGCTAATCGCGCTCACCCACTCGAGACCC -3'

O3H5 5'- CGGATAGCGTGAAAGGCCGTTTTACCATTTCAC-
GTGATAATTCGAAAAACACCCTGTATCTGCAAATGAACAG-3'

O3H6 5'- CACGCGCAATAATACACGGCCGTATCTTCCG-
CACGCAGGCTGTTCATTTGCAGATACAGG -3'

O4H2 5'- GGTCAGGCTCAGGGTTTCGCTCGGTTTCACCAG-
GCCCGGACCACTTTCTTGCAATTGCACCTGGGCTTTG -3'

O4H3 5'- GAAACCCTGAGCCTGACCTGCACCGTTTCCGGAGG-
CAGCATTAGCAGCTATTATTGGAGCTGGATTCGCCAGCCGC
-3'

O4H4 5'- GATTATAGTTGGTGCTGCCGCTATAATAAATAT-
AGCCAATCCACTCGAGACCCTTCCCAGGCGGCTGGCGAATCCA
G -3'

O4H5 5'- CGGCAGCACCAACTATAATCCGAGCCTGAAAAG-
CCGGGTGACCATTAGCGTTGATACTTCGAAAACCAGTTTAGC
CTG -3'

O4H6 5'- GCGCGCAATAATACACGGCCGTATCCGCCGCCG-
TCACGCTGCTCAGTTTCAGGCTAAACTGGTTTTTCG -3'

*FIG. 6E*

O5H1 5'- GCTCTTCACCCCTGTTACCAAAGCCGAAGTGCAATTG -3'
O5H2 5'- CCTTTGCAGCTAATTTTCAGGCTTTCGCCCGGTTTTTTCACTTCCGCGCCGCTCTGAACCAATTGCACTTCGGCTTTGG -3'
O5H3 5'- CCTGAAAATTAGCTGCAAAGGTTCCGGATATTCCTTTACGAGCTATTGGATTGGCTGGGTGCGCCAGATGCCTGG -3'
O5H4 5'- CGGAGAATAACGGGTATCGCTATCGCCCGGATAAATAATGCCCATCCACTCGAGACCCTTCCCAGGCATCTGGCGCAC -3'
O5H5 5'- CGATACCCGTTATTCTCCGAGCTTTCAGGGCCAGGTGACCATTAGCGCGGATAAAAGCATTAGCACCGCGTATCTTC -3'
O5H6 5'- GCGCGCAATAATACATGGCCGTATCGCTCGCTTTCAGGCTGCTCCATTGAAGATACGCGGTGCTAATG -3'
O6H2 5'- GAAATCGCACAGGTCAGGCTCAGGGTTTGGCTCGGTTTCACCAGGCCCGGACCAGACTGTTGCAATTGCACCTGGGCTTTG -3'
O6H3 5'- GCCTGACCTGTGCGATTTCCGGAGATAGCGTGAGCAGCAACAGCGCGGCGTGGAACTGGATTCGCCAGTCTCCTGGGCG -3'
O6H4 5'- CACCGCATAATCGTTATACCATTTGCTACGATAATAGGTACGGCCCAGCCACTCGAGGCCACGCCCAGGAGACTGGCG -3'
O6H5 5'- GGTATAACGATTATGCGGTGAGCGTGAAAAGCCGGATTACCATCAACCCGGATACTTCGAAAAACCAGTTTAGCCTGC -3'
O6H6 5'- GCGCGCAATAATACACGGCCGTATCTTCCGGGGTCACGCTGTTCAGTTGCAGGCTAAACTGGTTTTTC -3'
OCLK1 5'- GGCTGAAGACGTGGGCGTGTATTATTGCCAGCAGCATTATACCACCCCGCCGACCTTTGGCCAGGGTAC -3'

*FIG. 6F*

OCLK2 5'- GCGAAAAATAAACACGCTCGGAGCAGCCACCG-TACGTTTAATTTCAACTTTCGTACCCTGGCCAAAGGTC -3'
OCLK3 5'- GAGCGTGTTTATTTTTCCGCCGAGCGATGAACA-ACTGAAAAGCGGCACGGCGAGCGTGGTGTGCCTGCTG -3'
OCLK4 5'- CAGCGCGTTGTCTACTTTCCACTGAACTTTCGC-TTCACGCGGATAAAAGTTGTTCAGCAGGCACACCACGC -3'
OCLK5 5'- GAAAGTAGACAACGCGCTGCAAAGCGGCAACAG-CCAGGAAAGCGTGACCGAACAGGATAGCAAAGATAG -3'
OCLK6 5'- GTTTTTCATAATCCGCTTTGCTCAGGGTCAGGG-TGCTGCTCAGAGAATAGGTGCTATCTTTGCTATCCTGTTCG -3'
OCLK7 5'- GCAAAGCGGATTATGAAAAACATAAAGTGTATG-CGTGCGAAGTGACCCATCAAGGTCTGAGCAGCCCGGTG -3'
OCLK8 5'- GGCATGCTTATCAGGCCTCGCCACGATTAAAAG-ATTTAGTCACCGGGCTGCTCAGAC -3'
OCH1 5'- GGCGTCTAGAGGCCAAGGCACCCTGGTGACGGT-TAGCTCAGCGTCGAC -3'
OCH2 5'- GTGCTTTTGCTGCTCGGAGCCAGCGGAAACACG-CTTGGACCTTTGGTCGACGCTGAGCTAACC -3'
OCH3 5'- CTCCGAGCAGCAAAAGCACCAGCGGCGGCACGG-CTGCCCTGGGCTGCCTGGTTAAAGATTATTTCC -3'
OCH4 5'- CTGGTCAGCGCCCCGCTGTTCCAGCTCACGGTG-ACTGGTTCCGGGAAATAATCTTTAACCAGGCA -3'
OCH5 5'- AGCGGGGCGCTGACCAGCGGCGTGCATACCTTT-CCGGCGGTGCTGCAAAGCAGCGGCCTG -3'
OCH6 5'- GTGCCTAAGCTGCTGCTCGGCACGGTCACAACG-CTGCTCAGGCTATACAGGCCGCTGCTTTGCAG -3'
OCH7 5'- GAGCAGCAGCTTAGGCACTCAGACCTATATTTG-CAACGTGAACCATAAACCGAGCAACACC -3'
OCH8 5'- GCGCGAATTCGCTTTTCGGTTCCACTTTTTTAT-CCACTTTGGTGTTGCTCGGTTTATGG -3'

FIG. 6G

```
              V   A   A   P   S       V   F   I       F   P   P   S       D   E   Q
BsiWI
~~~~~~
CGTACGGTGG  CTGCTCCGAG  CGTGTTTATT  TTTCCGCCGA  GCGATGAACA
GCATGCCACC  GACGAGGCTC  GCACAAATAA  AAAGGCGGCT  CGCTACTTGT

L   K   S       G   T   A   S       V   V   C       L   L   N       N   F   Y
ACTGAAAAGC  GGCACGGGCGA GCGTGGTGTG  CCTGCTGAAC  AACTTTATC
TGACTTTTCG  CCGTGCCGCT  CGCACCACAC  GGACGACTTG  TTGAAATAG

P   R   E   A       K   V   Q       W   K   V   D       N   A   L       Q   S   G
CGGCGTGAAGC  GAAAGTTCAG  TGGAAAGTAG  ACAACGCGCT  GCAAAGCGGC
GCCGCACTTCG  CTTTCAAGTC  ACCTTTCATC  TGTTGCGCGA  CGTTTCGCCG

N   S   Q   E       S   V   T       E   Q   D       S   K   D   S       T   Y   S
AACAGCCAGG  AAAGCGTGAC  CGAACAGGAT  AGCAAAGATA  GCACCTATTC
TTGTCGGTCC  TTTCGCACTG  GCTTGTCCTA  TCGTTTCTAT  CGTGGATAAG
```

FIG. 7A

```
L   S   S   T   L   T   L   S   K   A   D   Y   E   K   H   H   K
TCTGAGCAGC ACCCTGACCC TGAGCAAAGC GGATTATGAA AAACATAAAG
AGACTCGTCG TGGGACTGGG ACTCGTTTCG CCTAATACTT TTTGTATTTC

V   Y   A   C   E   V   T   H   Q   G   L   S   S   P   V   T   K
TGTATGCGGTG CGAAGTGACC CATCAAGGTC TGAGCAGCCC GGTGACTAAA
ACATACGCAC GCTTCACTGG GTAGTTCCAG ACTCGTCGGG CCACTGATTT

S   F   N   R   G   E   A   *
                        StuI           SphI
                        ~~~~~~~        ~~~~~~~
TCTTTTAATC GTGGCCGAGGC CTGATAAGCA TGC
AGAAAATTAG CACCGGCTCCG GACTATTCGT ACG
```

*FIG. 7B*

```
              A   S      T   K   G      P   S   V   F      P   L   A      P   S   S
    BlpI    SalI
    ~~~~~   ~~~~
    GCTCAGCGTC GACCAAAGGT CCAAGCGTGT TTCCGCTGGC TCCGAGCAGC
    CGAGTCGCAG CTGGTTTCCA GGTTCGCACA AAGGCGACCG AGGCTCGTCG

K   S   T      S   G   G   T      A   A   L      G   C   L   V      K   D   Y
    AAAGCACCA  GCGGCGGCAC GGCTGCCCTG GGCTGCCTGG TTAAAGATTA
    TTTCGTGGT  CGCCGCCGTG CCGACGGGAC CCGACGGACC AATTTCTAAT

F   P   E      P   V   T   V      S   W   N      S   G   A      L   T   S
    TTTCCCCGAA CCAGTCACCG TGAGCTGGAA CAGCGGGGCG CTGACCAGCG
    AAAGGGGCTT GGTCAGTGGC ACTCGACCTT GTCGCCCCGC GACTGGTCGC

G   V   H      T   F   P   A      V   L   Q   S      S   G   L      Y   S   L
    GCGTGCATAC CTTTCCGGCG GTGCTGCAAA GCAGCGGGCT GTATAGCCTG
    CGCACGTATG GAAAGGCCGC CACGACGTTT CGTCGCCCGA CATATCGGAC
```

*FIG. 7C*

```
S  S  V  V  T  V  P     S  S  S     L  G  T  Q     T  Y  I
AGCAGCGTTG TGACCGTGCC GAGCAGCAGC TTAGGCACTC AGACCTATAT
TCGTCGCAAC ACTGGCACGG CTCGTCGTCG AATCCGTGAG TCTGGATATA

C  N  V     N  H  K  P  S  N  T     K  V  D     K  K  V
TTGCAACGTG AACCATAAAC CGAGCAACAC CAAAGTGGAT AAAAAAGTGG
AACGTTGCAC TTGGTATTTG GCTCGTTGTG GTTTCACCTA TTTTTTCACC

E  P  K  S     E  F  *
                EcoRI     HindIII
                ~~~~~     ~~~~~
AACCGAAAAAG CGAATTCTGA TAAGCTT
TTGGCTTTTC GCTTAAGACT ATTCGAA
```

*FIG. 7D*

```
     BbsI
     ~~~~~
1    GAAGACGAAG CGGATTATTA TTGCCAGCAG CATTATACCA CCCCGCGCCTGT
     CTTCTGCTTC GCCTAATAAT AACGGTCGTC GTAATATGGT GGGGCGGACA

HpaI                MscI              DraIII
                    ~~~~~~              ~~~~~             ~~~~~
51   GTTTGGCGGC GGCACGAAGT TAACCGTTCT TGGCCAGCCG AAAGCCCGCAC
     CAAACCGCCG CCGTGCTTCA ATTGGCAAGA ACCGGTCGGC TTTCGGCGTG

DraIII
     ~~~~~
101  CGAGTGTGAC GCTGTTTCCG CCGAGCAGCG AAGAATTGCA GGCGAACAAA
     GCTCACACTG CGACAAAGGC GGCTCGTCGC TTCTTAACGT CCGCTTGTTT

151  GCGACCCCTGG TGTGCCCTGAT TAGCGACTTT TATCCGGGAG CCGTGACAGT
     CGCTGGGACC ACACGGACTA ATCGCTGAAA ATAGGCCCTC GGCACTGTCA
```

FIG. 7F

```
201  GGCCTGGAAG GCAGATAGCA GCCCCGTCAA GGCGGGAGTG GAGACCACCA
     CCGGACCTTC CGTCTATCGT CGGGGCAGTT CCGCCCTCAC CTCTGGTGGT

251  CACCCTCCAA ACAAAGCAAC AACAAGTACG CGGCCAGCAG CTATCTGAGC
     GTGGGAGGTT TGTTTCGTTG TTGTTCATGC GCCGGTCGTC GATAGACTCG
                                     RleAI
                                     ~~~~~~~

301  CTGACGCCTG AGCAGTGGAA GTCCCACAGA AGCTACAGCT GCCAGGTCAC
     GACTGCGGAC TCGTCACCTT CAGGGTGTCT TCGATGTCGA CGGTCCAGTG
                                                StuI
                                                ~~~~~~~
```

FIG. 7G

```
351  GCATGAGGGG AGCACCGTGG AAAAAACCGT TGCGCCGACT GAGGCCTGAT
     CGTACTCCCC TCGTGGCACC TTTTTTGGCA ACGCGGCTGA CTCCGGACTA
     SphI
     ~~~~~
401  AAGCATGC
     TTCGTACG
```

FIG. 7H

M24: assembly PCR

M24-A:
GAAGACAAGCGGATTATTATTGCCAGCAGCATTATACCACCCCGCCTGTGTTTGGCGGCG-
GCACGAAGTTAACCGTTC

M24-B:
CAATTCTTCGCTGCTCGGCGGGAAACAGCGTCACACTCGGTGCGGCTTTCGGCTGGCCAA-
GAACGGTTAACTTCGTGCCGC

M24-C:
CGCCGAGCAGCGAAGAATTGCAGGCGAACAAAGCGACCCTGGTGTGCCTGATTAGCGACT-
TTTATCCGGGAGCCGTGACA

FIG. 71

M24-D:
TGTTTGGAGGGTGTGGTGGTCTCCACTCCCGCCCTTGACGGGGGCTGCTATCTGCCTTCCAG-
GCCACTGTCACGGCTCCCGG

M24-E:
CCACACCCTCCAAACAAAGCAACAACAAGTACGGGCCAGCAGCTATCTGAGCCTGACGC-
CTGAGCAGTGGAAGTCCCACAGAAGCTACAGCTG

M24-F:
GCATGCTTATCAGGCCTCAGTCGGCCGCAACGGTTTTTTCCACGGTGCTCCCCTCATGCGT-
GACCTGGCAGCTGTAGCTTC

FIG. 7J

```
M  K  Q  S  T  I  A     L  A  L     L  P  L  L     F  T  P
ATGAAACAAA GCACTATTGC ACTGGCACTC TTACCGTTGC TCTTCACCCC
TACTTTGTTT CGTGATAACG TGACCGTGAG AATGGCAACG AGAAGTGGGG
                                           SapI
                                           ~~~~~~~~~~

V  T  K     A  D  Y  K     D  E  V     Q  L  V  E  S  G
                                       MfeI
                                       ~~~~~
TGTTACCAAA GCCGACTACA AAGATGAAGT GCAATTGGTG GAAAGCGGCG
ACAATGGTTT CGGCTGATGT TTCTACTTCA CGTTAACCAC CTTTCGCCGC

G  G  L  V     Q  P  G     G  S  L  R  L  S  C     A  A  S
                                                   BspEI
                                                   ~~~
GCGGCCTGGT GCAACCGGGC GGCAGCCTGC GTCTGAGCTG CGCGGCCTCC
CGCCGGACCA CGTTGGCCCG CCGTCGGACG CAGACTCGAC GCGCCGGAGG

G  F  T  F  S  S  Y     A  M  S     W  V  R  Q     A  P  G
BspEI                                               BstXI
~~~                                                 ~~~~~
GGATTTACCT TTAGCAGCTA TGCGATGAGC TGGGTGCGCC AAGCCCCTGG
CCTAAATGGA AATCGTCGAT ACGCTACTCG ACCCACGCGG TTCGGGGACC
```

FIG. 8A

```
K  G  L  E  W  V  S      A  I  S      G  S  G      G  S  T
         XhoI
         ~~~~~~~
GAAGGGTCTC GAGTGGGTGA GCGCGATTAG CGGTAGCGGC GGCAGCACCT
CTTCCCAGAG CTCACCCACT CGCGCTAATC GCCATCGCCG CCGTCGTGGA

Y  Y  A  D  S  V  K      G  R  F  T      I  S  R      D  N  S
                                                  PmlI        NspV
                                                  ~~~~~       ~~~~
ATTATGCGGA TAGCGTGAAA GGCCGTTTTA CCATTTCACG TGATAATTCG
TAATACGCCT ATCGCACTTT CCGGCAAAAT GGTAAAGTGC ACTATTAAGC

K  N  T  L  Y  L  Q      M  N  S      L  R  A  E      D  T  A
NspV                                                       EagI
~~                                                         ~~~~
AAAAACACCC TGTATCTGCA AATGAACAGC CTGCGTGCGG AAGATACGGC
TTTTTGTGGG ACATAGACGT TTACTTGTCG GACGCACGCC TTCTATGCCG

V  Y  Y  C  A  R  W      G  G  D      G  F  Y      A  M  D
EagI    BssHII
~~      ~~~~~~
CGTGTATTAT TGCGCGCGTT GGGGCGGCGA TGGCTTTTAT GCGATGGATT
```

*FIG. 8B*

```
GCACATAATAACGGCGCAA CCCCGCCGCT ACCGAAAATA CGTACCTAA
 Y  W  G  Q   G  T  L  V  T  V  S  S  A  G  G  G  S
              StyI                     BlpI
              ~~~~~                    ~~~~~~

ATTGGGGCCA AGGCACCCTG GTGACGGTTA GCTCAGCGGG TGGCGGTTCT
TAACCCCGGT TCCGTGGGAC CACTGCCAAT CGAGTCGCCC ACCGCCAAGA
 G  G  G  S  G  G  G  S  G  G  G  G  S  D  I
                                          EcoRV
                                          ~~~~

GGCGGCGGTG GGAGCGGTGG CGGTGGTTCT GGCGGTGGTG GTTCCGATAT
CCGCCGCCAC CCTCGCCACC GCCACCAAGA CCGCCACCAC CAAGGCTATA
 G  G  G  G  S  G  G  G  G  S  G  G  G  G  S  D  I

V  M  T  Q  S  P  L  S  L  P  V  T  P  G  E  P
EcoRV      BanII
 ~          ~~~~~

CGTGATGACC CAGAGCCCAC TGAGCCTGCC AGTGACTCCG GGCGAGCCTG
GCACTACTGG GTCTCGGGTG ACTCGGACGG TCACTGAGGC CCGCTCGGAC
 A  S  I  S  C  R  S  S  Q  S  L  L  H  S  N  G  Y
       PstI
       ~~~~~~

CGAGCATTAG CTGCAGAAGC AGCCAAAGCC TGCTGCATAG CAACGGCTAT
GCTCGTAATC GACGTCTTCG TCGGTTTCGG ACGACGTATC GTTGCCGATA
```

*FIG. 8C*

```
 N   Y   L   D   W   Y   L    Q   K   P   G   Q   S   P   Q   L   L
                KpnI                SexAI                        AseI
              ~~~~~~                ~~~~~~~~~                   ~~~~~~
AACTATCTGG ATTGGTACCT TCAAAAACCA GGTCAAAGCC CGCAGCTATT
TTGATAGACC TAACCATGGA AGTTTTTGGT CCAGTTTCGG GCGTCGATAA

I   Y   L   G   S   N   R   A   S   G   V   P   D   R   F   S
AseI                                   EcoO109I
~~~~                                 ~~~~~~~~
AATTTATCTG GGCAGCAACC GTGCCAGTGG GGTCCCGGAT CGTTTTAGCG
TTAAATAGAC CCGTCGTTGG CACGGTCACC CCAGGGCCTA GCAAAATCGC

G   S   G   G   T   D   F   T   L   K   I   S   R   V   E   A
     BamHI
    ~~~~~~
GCTCTGGATC CGGCACCGAT TTTACCCTGA AAATTAGCCG TGTGGAAGCT
CGAGACCTAG GCCGTGGCTA AAATGGGACT TTTAATCGGC ACACCTTCGA

E   D   V   G   V   V   Y   Y   C   Q   Q   H   Y   T   P   P   T
     BbsI
    ~~~~~
GAAGACGTGG GCGTGGTGTATTA TTGCCAGCAG CATTATACCA CCCCGCCGAC
CTTCTGCACC CGCACCATAAT AACGGTCGTC GTAATATGGT GGGGCGGCTG
```

*FIG. 8D*

```
F  G  Q    G  T  K  V    E  I  K    R    T  E    F
   MscI                              BsiWI EcoRI
   ~~~~~                             ~~~~~ ~~~~~
CTTTGGCCAG GGTACGAAAG TTGAAATTAA ACGTACGGAA TTC
GAAACCGGTC CCATGCTTTC AACTTTAATT TGCATGCCTT AAG
```

FIG. 8E

FIG. 10A

| | 92 | 93 | 94 | 95 | 96 | 97 | 98 | 99 | 100 | 100A | 100B | 100C | 100D | 100E | 101 | 102 | 103 |
|---|---|---|---|---|---|---|---|---|---|---|---|---|---|---|---|---|---|
| A | C | A | R | W | G | G | D | G | F | Y | A | - | - | M | D | Y | W |
| B | C | A | R | F | G | K | M | N | Y | - | - | - | - | - | D | Y | W |
| B | C | A | R | H | R | T | E | W | H | - | - | - | - | - | D | Y | W |
| B | C | A | R | V | R | E | L | Y | H | - | - | - | - | - | D | Y | W |
| B | C | A | R | K | F | L | K | A | R | - | - | - | - | - | D | Y | W |
| B | C | A | R | W | N | T | T | G | Y | - | - | - | - | - | D | Y | W |
| B | C | A | R | I | N | E | A | Q | P | - | - | - | - | - | D | Y | W |
| B | C | A | R | T | A | I | T | R | - | - | - | - | - | - | D | Y | W |
| B | C | A | R | W | Y | N | R | N | S | - | - | - | - | - | D | Y | W |
| B | C | A | R | S | V | G | D | S | K | - | - | - | - | - | D | Y | W |
| B | C | A | R | V | K | T | F | A | A | - | - | - | - | - | D | Y | W |
| B | C | A | R | M | A | P | Q | Y | D | - | - | - | - | - | D | Y | W |
| B | C | A | R | | Q | S | E | W | M | - | - | - | - | - | D | Y | W |

FIG. 10B

| 92 | 93 | 94 | 95 | 96 | 97 | 98 | 99 | 100 | 100A | 100B | 100C | 100D | 100E | 101 | 102 | 103 | Frequency |
|---|---|---|---|---|---|---|---|---|---|---|---|---|---|---|---|---|---|
| C | A | R | K | R | M | M | Q | N | P | R | F | R | F | D | V | W | 1 |
| C | A | R | R | S | K | Q | K | R | K | M | R | R | F | D | V | W | 3 |
| C | A | R | R | N | G | K | R | H | L | R | H | R | F | D | V | W | 1 |
| C | A | R | R | K | M | R | K | R | I | K | R | R | F | D | V | W | 2 |
| C | A | R | Y | R | K | I | M | K | W | K | N | S | M | D | V | W | 1 |
| C | A | R | L | I | E | V | H | P | S | F | D | F | F | D | V | W | 1 |
| C | A | R | R | K | P | M | F | L | K | K | A | Q | F | D | Y | W | 2 |
| C | A | R | R | K | F | H | R | R | Y | K | V | V | F | D | Y | W | 1 |
| C | A | R | R | K | T | M | R | S | R | M | K | K | F | D | V | W | 1 |
| C | A | R | R | K | R | S | W | R | R | D | D | Y | F | D | V | W | 1 |
| C | A | R | R | N | P | R | R | R | G | M | N | R | R | D | V | W | 1 |
| C | A | R | R | G | K | K | K | G | K | N | R | R | F | D | V | W | 1 |
| C | A | R | R | M | V | H | K | F | A | R | P | P | I | D | V | W | 1 |
| C | A | R | R | K | H | I | T | R | R | R | K | R | F | Q | V | W | 1 |
| C | A | R | W | K | K | R | Y | R | S | S | A | Q | R | D | V | W | 1 |
| C | A | R | K | L | L | P | Q | R | F | R | R | R | F | D | Y | W | 1 |

FIG. 15

| | 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|---|
| | C | A | R | Y | I | K | Q | A | K | R | K | L | A | F | D | Y | W | 4 |
| | C | A | R | Y | N | R | H | A | W | Q | K | M | Q | F | D | Y | W | 3 |
| | C | A | R | Y | V | K | Y | A | R | N | K | M | Q | F | D | Y | W | 2 |
| | C | A | R | Y | K | R | G | A | W | M | K | T | M | F | D | V | W | 1 |
| | C | A | R | R | K | P | L | R | R | H | M | K | W | F | D | Y | W | 1 |
| | C | A | R | Y | R | K | R | A | S | R | Q | M | Q | F | D | Y | W | 1 |

FIG. 21

FIG. 22

| FREQUENCY | 16 | 1 | 1 | 1 | 1 | 1 | 1 | 1 |
|---|---|---|---|---|---|---|---|---|
| 103 | W | W | W | W | W | W | W | W |
| 102 | V | Y | Y | Y | Y | V | Y | Y |
| 101 | D | D | D | D | D | D | D | D |
| 100E | F | M | F | M | M | F | M | F |
| 100D | H | P | Q | W | V | S | W | W |
| 100C | G | D | V | H | H | Q | E | Y |
| 100B | K | Y | W | H | D | T | N | W |
| 100A | H | S | Y | P | R | F | E | F |
| 100 | K | N | N | K | A | Q | T | L |
| 99 | S | F | D | L | Q | S | Q | L |
| 98 | R | D | L | Y | E | N | F | P |
| 97 | Y | R | D | A | H | H | H | P |
| 96 | R | W | A | Q | L | W | D | W |
| 95 | Q | – | M | L | R | S | V | D |
| 94 | R | R | R | R | R | R | R | R |
| 93 | A | A | A | A | A | A | A | A |
| 92 | C | C | C | C | C | C | C | C |

FIG. 23

| | 92 | 93 | 94 | 95 | 96 | 97 | 98 | 99 | 100 | 100A | 100B | 100C | 100Ca | 100D | 100E | 101 | 102 | 103 | FREQUENCY |
|---|---|---|---|---|---|---|---|---|---|---|---|---|---|---|---|---|---|---|---|
| | C | A | R | G | F | G | F | T | E | – | – | – | – | – | – | D | Y | W | 4 |
| | C | A | R | Q | F | D | E | D | S | F | V | R | – | R | F | D | V | W | 4 |
| | C | A | R | H | L | K | E | S | S | K | S | R | – | Q | M | D | V | W | 2 |
| | C | A | R | E | Q | D | E | Y | Y | A | H | R | – | H | Q | D | Y | W | 1 |
| | C | A | R | N | H | F | Y | A | D | W | I | P | R | Q | M | D | Y | W | 1 |
| | C | A | R | E | N | E | W | V | R | M | V | R | – | D | M | D | Y | W | 2 |
| | C | A | R | Q | Y | S | E | T | K | W | R | L | – | K | F | D | Y | W | 1 |
| | C | A | R | Q | F | K | Q | S | V | T | D | R | – | K | F | D | V | W | 13 |
| | C | A | R | K | K | T | E | Y | H | H | K | R | – | R | M | D | V | W | 3 |
| | C | A | R | R | W | R | M | T | S | S | D | R | – | F | F | D | V | W | 1 |
| | C | A | R | D | Y | I | M | E | F | – | – | – | – | – | – | D | Y | W | 1 |
| | C | A | R | Q | F | E | E | T | K | Q | R | R | – | L | M | D | Y | W | 1 |

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | D | Q | G | F | Y | A | I | D | Y | V | M | D | Y | W | 5 |
| C | A | R | V | F | T | Y | M | Y | N | Y | F | R | F | D | V | W | 1 |
| C | A | R | V | F | F | E | Q | M | E | Y | V | R | M | D | V | W | 1 |
| C | A | R | E | K | E | Y | R | L | S | W | S | Q | M | D | Y | W | 1 |
| C | A | R | Y | P | S | R | W | A | P | N | W | Y | M | D | Y | W | 1 |
| C | A | R | D | G | G | F | K | P | L | T | H | F | F | D | V | W | 1 |

FIG. 24

| unique restriction site | Isoschizomers |
|---|---|
| AatII | / |
| AflII | BfrI, BspTI, Bst98I |
| AscI | / |
| AseI | VspI, AsnI, PshBI |
| BamHI | BstI |
| BbeI | EheI, KasI, NarI |
| BbsI | BpuAI, BpiI |
| BglII | / |
| BlpI | Bpu1102I, CelII, BlpI |
| BsaBI | MamI, Bsh1365I, BsrBRI |
| BsiWI | Pfl23II, SplI, SunI |
| BspEI | AccIII, BseAI, BsiMI, Kpn2I, MroI |
| BsrGI | Bsp1407I, SspBI |
| BssHII | PauI |
| BstEII | BstPI, Eco91I, EcoO65I |
| BstXI | / |
| Bsu36I | AocI, CvnI, Eco81I |
| DraIII | / |
| DsmAI |  |
| EagI | BstZI, EclXI, Eco52I, XmaIII |
| Eco57I | / |
| EcoO109I | DraII |
| EcoRI | / |
| EcoRV | Eco32I |
| FseI | / |
| HindIII | / |
| HpaI | / |
| KpnI | Acc65I, Asp718I |
| MluI | / |
| MscI | BalI, MluNI |

FIG. 25B

| unique restriction site | Isoschizomers |
|---|---|
| MunI | MfeI |
| NheI | / |
| NsiI | Ppu10I, EcoT22I, Mph1103I |
| NspV | Bsp119I, BstBI, Csp45I, LspI, SfuI |
| PacI | / |
| PmeI | / |
| PmlI | BbrPI, Eco72I, PmaCI |
| Psp5II | PpuMI |
| PstI | / |
| RsrII | (RsriI), CpoI, CspI |
| SanDI | / |
| SapI | / |
| SexAI | / |
| SpeI | / |
| SfiI | / |
| SphI | BbuI, PaeI, NspI |
| StuI | AatI, Eco147I |
| StyI | Eco130I, EcoT14I |
| XbaI | BspLU11II |
| XhoI | PaeR7I |
| XmaI | AvaI, SmaI, Cfr9I, PspAI |

FIG. 25C

| No | module/flanking restriction sites | functional element | sites to be removed | sites to be inserted | template | reference |
|---|---|---|---|---|---|---|
| M1 | AatII-lacp/o-XbaI | lac promotor/operator | 2x VspI (AseI) | AatII | vector pASK30 | Skerra et al. (1991) Bio/Technology 9, 273-278 |
| M2 | BglII-lox-AatII | Cre/lox recombination site | 2x VspI (AseI) | lox, BglII | (synthetic) | Hoess et al. (1986) Nucleic Acids Res. 2287-2300 |
| M3 | XbaI-lox'-SphI | Cre/lox' recombination site | none | lox', SphI | (synthetic) | see M2 |
| M7-1 | EcoRI-gIIIlong-HindIII | gIIIp of filamentous phage with N-terminal myctail/amber codon | SphI, BamHI | none | vector pIG10 | Ge et al., (1994) Expressing antibodies in E. coli. In: Antibody engineering: A practical approach. IRL Press, New York, pp 229-266 |

FIG. 26A

| | | | | |
|---|---|---|---|---|
| M7-II | EcoRI-gIIIss-HindIII | truncated gIIIp of filamentous phage with N-terminal Gly-Ser linker | SphI | | vector pIG10 | see M7-I |
| M7-III | EcoRI-gIIIss-HindIII | truncated gIIIp of filamentous phage with N-terminal myctail/amber codon | SphI, BbsI | | vector pIG10 | see M7-I |
| M8 | SphI-lox-HindIII | Cre/lox recombination site | none | lox | (synthetic) | see M3 |
| M9-II | HindIII-Ipp-PacI | lpp-terminator | none | PacI, FseI | (synthetic) | see M1 |
| M10-II | PacI/FseI-bla-BsrGI | beta-lactamase/bla (ampR) | VspI, Eco57I, BssSI | PacI, FseI, BsrGI | pASK30 | see M1 |
| M11-II | BsrGI-f1 ori-NheI | origin of single-stranded replication | DraIII (BanII not removed) | BsrGI, NheI | pASK30 | see M1 |
| M11-III | BsrGI-f1 ori-NheI | origin of single-stranded replication | DraIII, BanII | BsrGI, NheI | pASK30 | see M1 |

FIG. 26B

| | | | | | |
|---|---|---|---|---|---|
| M12 | NheI-p15A-BglII | origin of double-stranded replication | BssSI, VspI, NspV | NheI, BglII | pACYC184 | Rose, R.E. (1988) Nucleic Acids Res. 16, 355 |
| M13 | BglII-lox-BglII | Cre/lox recombination site | none | BglII, lox, XmnI | (synthetic) | see M3 |
| M14-Ext2 | BglII-ColEI-NheI | origin of double-stranded replication | Eco57I (BssSI not removed) | BglII, NheI | pUC19 | Yanisch-Peron, C. (1985) Gene 33, 103-119 |
| M17 | AatII-cat-BglII | chloramphenicol-acetyltransferase/cat (camR) | BspEI, MscI, StyI/NcoI | | pACYC184 | Cardoso, M. & Schwarz, S. (1992) J. Appl. Bacteriol. 72, 289-293 |
| M19 | XbaI-phoA-EcoRI | signal sequence of phosphatase A | (synthetic) | | (synthetic) | see M1 |
| M20 | XbaI-phoA-FLAG-EcoRI | signal sequence of phosphatase A + FLAG detection tag | (synthetic) | | (synthetic) | Knappik, A & Plückthun, A. (1994) BioTechniques 17, 754-761 |

FIG. 26C

| | | | | |
|---|---|---|---|---|
| M21 | XbaI-stII-SapI | heat-stable enterotoxin II signal sequence | (synthetic) | (synthetic) | Lee et al. (1983) Infect. Immunol. 264-268 |
| M41 | AflII-lacI-NheI | lac-repressor | BstXI, MluI,BbsI, BanII, BstEII, HpaI, BbeI, VspI | pASK30 | see M1 |
| M42 | EcoRI-Histail-HindIII | poly-histidine tail | | (synthetic) | Lindner et al., (1992) Methods: a companion to methods in enzymology 4, 41-56 |

FIG. 26D

```
              HindIII           PacI               BsrGI
              ~~~~~~~            ~~~~~~             ~~~~~~
  1   ACATGTAAGC TTCCCCCCCC CCTTAATTAA CCCCCCCCC TGTACACCCC
      TGTACATTCG AAGGGGGGGG GGAATTAATT GGGGGGGGG ACATGTGGGG NheI              BglII            AatII  XbaI
              ~~~~              ~~~~~~           ~~~~~  ~~~~~
 51   CCCCCCGCTA GCCCCCCCCC CCAGATCTCC CCCCCCCGA CGTCCCCCT
      GGGGGGCGAT CGGGGGGGGG GGTCTAGAGG GGGGGGGCT GCAGGGGGA SphI                        EcoRI AatII
              ~~~~                        ~~~~~ ~~~~~
101   CTAGACCCCC CCCCCGCATG CCCCCCCCC CGAATTCGAC GTC
      GATCTGGGGG GGGGGCGTAC GGGGGGGGG GCTTAAGCTG CAG
```

*FIG. 27B*

```
  1 CAGGTGGCAC TTTTCGGGGA AATGTGCGCG GAACCCCTAT TTGTTTATTT
    GTCCACCGTG AAAAGCCCCT TTACACGCGC CTTGGGGATA AACAAATAAA

51 TTCTAAATAC ATTCAAATAT GTATCCGCTC ATGAGACAAT AACCCTGATA
    AAGATTTATG TAAGTTTATA CATAGGCGAG TACTCTGTTA TTGGGACTAT

101 AATGCTTCAA TAATATTGAA AAAGGAAGAG TATGAGTATT CAACATTTCC
    TTACGAAGTT ATTATAACTT TTTCCTTCTC ATACTCATAA GTTGTAAAGG

151 GTGTCGCCCT TATTCCCTTT TTTGCGGCAT TTTGCCTTCC TGTTTTTGCT
    CACAGCGGGA ATAAGGGAAA AAACGCCGTA AAACGGAAGG ACAAAAACGA

Eco57I
                                           ~~~~~~~
201 CACCCAGAAA CGCTGGTGAA AGTAAAAGAT GCTGAAGATC AGTTGGGTGC
    GTGGGTCTTT GCGACCACTT TCATTTTCTA CGACTTCTAG TCAACCCACG
                                                  BssSI
                                                  ~~~~~~~
251 ACGAGTGGGT TACATCGAAC TGGATCTCAA CAGCGGTAAG ATCCCTTGAGA
    TGCTCACCCA ATGTAGCTTG ACCTAGAGTT GTCGCCATTC TAGGAACTCT
    BssSI
    ~~~~~
```

FIG. 28B

```
            XmnI
            ~~~~~~~~~~
     GTTTTCGCCC  CGAAGAACGT  TTTCCAATGA  TGAGCACTTT  TAAAGTTCTG
301
     CAAAAGCGGG  GCTTCTTGCA  AAAGGTTACT  ACTCGTGAAA  ATTTCAAGAC

CTATGTGGCG  CGGTATTATC  CCGTATTGAC  GCCGGGCAAG  AGCAACTCGG
351
     GATACACCGC  GCCATAATAG  GGCATAACTG  CGGCCCGTTC  TCGTTGAGCC

TCGCCGCATA  CACTATTCTC  AGAATGACTT  GGTTGAGTAC  TCACCAGTCA
401
     AGCGGCGTAT  GTGATAAGAG  TCTTACTGAA  CCAACTCATG  AGTGGTCAGT

CAGAAAAGCA  TCTTACGGAT  GGCATGACAG  TAAGAGAATT  ATGCAGTGCT
451
     GTCTTTTCGT  AGAATGCCTA  CCGTACTGTC  ATTCTCTTAA  TACGTCACGA

GCCATAACCA  TGAGTGATAA  CACTGCGGCC  AACTTACTTC  TGACAACGAT
501
     CGGTATTGGT  ACTCACTATT  GTGACGCCGG  TTGAATGAAG  ACTGTTGCTA

CGGAGGACCG  AAGGAGCTAA  CCGCTTTTTT  GCACAACATG  GGGGATCATG
551
     GCCTCCTGGC  TTCCTCGATT  GGCGAAAAAA  CGTGTTGTAC  CCCCTAGTAC

TAACTCGCCT  TGATCGTTGG  GAACCGGAGC  TGAATGAAGC  CATACCAAAC
601
     ATTGAGCGGA  ACTAGCAACC  CTTGGCCTCG  ACTTACTTCG  GTATGGTTTG

651  GACGAGCGTG  ACACCACGAT  GCCTGTAGCA  ATGGCAACAA  CGTTGCGCAA
```

*FIG. 28C*

```
                                                                        AseI
                                                                        ------
     CTGCTCGCAC TGTGGTGCTA CGGACATCGT TACCGTTGTT GCAACGCGTT
701  ACTATTAACT GGCGAACTAC TTACTCTAGC TTCCCGGCAA CAATTAATAG
     TGATAATTGA CCGCTTGATG AATGAGATCG AAGGGCCGTT GTTAATTATC
751  ACTGGATGGA GGCGGATAAA GTTGCAGGAC CACTTCTGCG CTCGGCCCTT
     TGACCTACCT CCGCCTATTT CAACGTCCTG GTGAAGACGC GAGCCGGGAA
801  CCGGCTGGCT GTTTATTGC  TGATAAATCT GGAGCCGGTG AGCGTGGGTC
     GGCCGACCGA CCAAATAACG ACTATTTAGA CCTCGGCCAC TCGCACCCAG
851  TCGCGGTATC ATTGCAGCCA TGGGGCCAGA TGGTAAGCCC TCCCGTATCG
     AGCGCCATAG TAACGTCGTG ACCCCGGTCT ACCATTCGGG AGGGCATAGC
901  TAGTTATCTA CACGACGGGG AGTCAGGCAA CTATGGATGA ACGAAATAGA
     ATCAATAGAT GTGCTGCCCC TCAGTCCGTT GATACCTACT TGCTTTATCT
951  CAGATCGCTG AGATAGGTGC CTCACTGATT AAGCATTGGT AACTGTCAGA
     GTCTAGCGAC TCTATCCACG GAGTGACTAA TTCGTAACCA TTGACAGTCT
1001 CCAAGTTTAC TCATATATAC TTTAGATTGA TTTAAAACTT CATTTTTAAT
     GGTTCAAATG AGTATATATG AAATCTAACT AAATTTTGAA GTAAAAATTA
```

*FIG. 28D*

```
1051  TTAAAAGGAT CTAGGTGAAG ATCCTTTTTG ATAATCTCAT GACCAAAATC
      AATTTTCCTA GATCCACTTC TAGGAAAAAC TATTAGAGTA CTGGTTTTAG

1101  CCTTAACGTG AGTTTTCGTT CCACTGAGCG TCAGACCCCG TAGAAAAGAT
      GGAATTGCAC TCAAAAGCAA GGTGACTCGC AGTCTGGGGC ATCTTTTCTA

1151  CAAAGGATCT TCTTGAGATC CTTTTTTTCT GCGCGTAATC TGCTGCTTGC
      GTTTCCTAGA AGAACTCTAG GAAAAAAAGA CGCGCATTAG ACGACGAACG

1201  AAACAAAAAA ACCACCGCTA CCAGCGGTGG TTTGTTTGCC GGATCAAGAG
      TTTGTTTTTT TGGTGGCGAT GGTCGCCACC AAACAAACGG CCTAGTTCTC

1251  CTACCAACTC TTTTTCCGAA GGTAACTGGC TTCAGCAGAG CGCAGATACC
      GATGGTTGAG AAAAAGGCTT CCATTGACCG AAGTCGTCTC GCGTCTATGG
                                      Eco57I
                                      ~~~~~~~

1301  AAATACTGTC CTTCTAGTGT AGCCGTAGTT AGGCCACCAC TTCAAGAACT
      TTTATGACAG GAAGATCACA TCGGCATCAA TCCGGTGGTG AAGTTCTTGA

1351  CTGTAGCACC GCCTACATAC CTCGCTCTGC TAATCCTGTT ACCAGTGGCT
      GACATCGTGG CGGATGTATG GAGCGAGACG ATTAGGACAA TGGTCACCGA
```

*FIG. 28E*

```
1401  GCTGCCAGTG GCGATAAGTC GTGTCTTACC GGTTGGACT  CAAGACGATA
      CGACGGTCAC CGCTATTCAG CACAGAATGG CCCAACCTGA GTTCTGCTAT

1451  GTTACCGGAT AAGGCGCAGC GGTCGGGCTG AACGGGGGGT TCGTGCACAC
      CAATGGCCTA TTCCGCGTCG CCAGCCCGAC TTGCCCCCCA AGCACGTGTG

1501  AGCCCAGCTT GGAGCGAACG ACCTACACCG AACTGAGATA CCTACAGCGT
      TCGGGTCGAA CCTCGCTTGC TGGATGTGGC TTGACTCTAT GGATGTCGCA

1551  GAGCTATGAG AAAGCGCCAC GCTTCCCGAA GGGAGAAAGG CGGACAGGTA
      CTCGATACTC TTTCGCGGTG CGAAGGGCTT CCCTCTTTCC GCCTGTCCAT

1601  TCCGGTAAGC GGCAGGGTCG GAACAGGAGA GCGCACGAGG GAGCTTCCAG
      AGGCCATTCG CCGTCCCAGC CTTGTCCTCT CGCGTGCTCC CTCGAAGGTC
                                        BssSI
                                        ~~~~~~~

1651  GGGAAACGC  CTGGTATCTT TATAGTCCTG TCGGGTTTCG CCACCTCTGA
      CCCCTTTGCG GACCATAGAA ATATCAGGAC AGCCCAAAGC GGTGGAGACT

1701  CTTGAGCGTC ATGCTCGTCA GATTTTTGTG GGGGGGCGGA GCCTATGGAA
      GAACTCGCAG TACGAGCAGT CTAAAAACAC CCCCCCGCCT CGGATACCTT

1751  AAACGCCAGC AACGCGGCCT TTTTACGGTT CCTGGCCTTT TGCTGGCCTT
```

*FIG. 28F*

```
                 TTTGCGGTCG TTGCGCCGGA AAAATGCCAA GGACCGGAAA ACGACCGGAA
                                 HindIII              PacI              BsrGI
                                 ------                ------            --
     TTGCTCACAT GTAAGCTTCC CCCCCCCCTT AATTAACCCC CCCCCCTGTA
1801 AACGAGTGTA CATTCGAAGG GGGGGGGGAA TTAATTGGGG GGGGGGACAT
     BsrGI                       BglII                       AatII
     --                          ------                       -----
     CACCCCCCCC CCGCTAGCCC CCCCCCCCAG ATCTCCCCCC CCCCGACGTC
1851 GTGGGGGGGG GGCGATCGGG GGGGGGGGTC TAGAGGGGGG GGGGCTGCAG
          XbaI                     SphI             EcoRI
          ------                   ------           ------
     CCCCCTCTAG ACCCCCCCCC CGCATGCCCC CCCCCCCGAA TTCACGT
1901 GGGGGAGATC TGGGGGGGGG GCGTACGGGG GGGGGGGCTT AAGTGCA
```

FIG. 28G

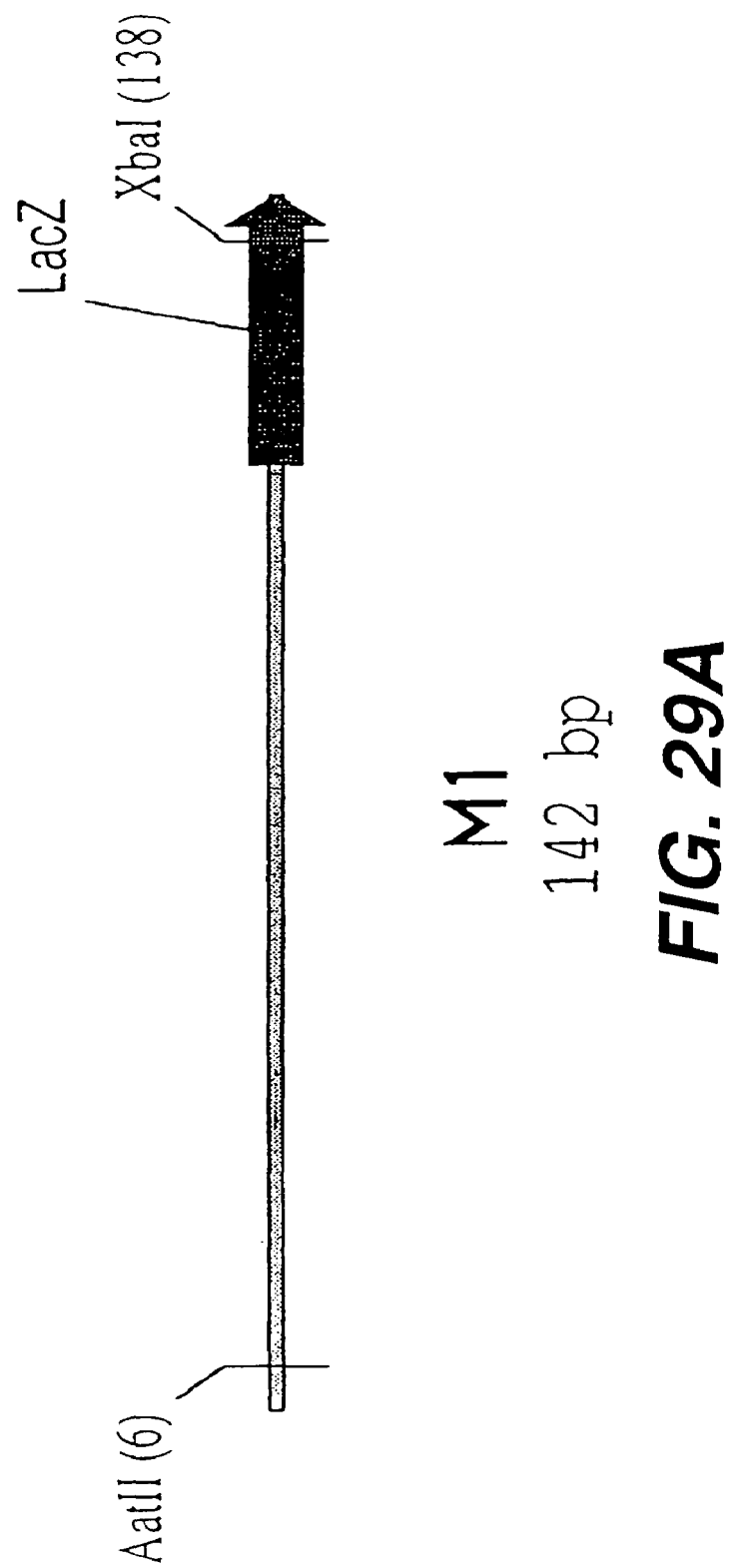

```
       AatII
       ------
  1    GACGTCTTAA  TGTGAGTTAG  CTCACTCATT  AGGCACCCCA  GGCTTTACAC
       CTGCAGAATT  ACACTCAATC  GAGTGAGTAA  TCCGTGGGGT  CCGAAATGTG

51    TTTATGCTTC  CGGCTCGTAT  GTTGTGTGGA  ATTGTGAGCG  GATAACAATT
       AAATACGAAG  GCCGAGCATA  CAACACACCT  TAACACTCGC  CTATTGTTAA

XbaI
                                                        ------
101    TCACACAGGA  AACAGCTATG  ACCATGATTA  CGAATTTCTA  GA
       AGTGTGTCCT  TTGTCGATAC  TGGTACTAAT  GCTTAAAGAT  CT
```

*FIG. 29B*

```
      EcoRI
      ~~~~~~~
  1   GAATTCGAGC AGAAGCTGAT CTCTGAGGAG GATCTGTAGG GTGGTGGCTC
      CTTAAGCTCG TCTTCGACTA GAGACTCCTC CTAGACATCC CACCACCGAG

51   TGGTTCCGGT GATTTTGATT ATGAAAAGAT GGCAAACGCT AATAAGGGGG
      ACCAAGGCCA CTAAAACTAA TACTTTTCTA CCGTTTGCGA TTATTCCCCC

101   CTATGACCGA AAATGCCGAT GAAAACGCGC TACAGTCTGA CGCTAAAGGC
      GATACTGGCT TTTACGGCTA CTTTTGCGCG ATGTCAGACT GCGATTTCCG

151   AAACTTGATT CTGTCGCTAC TGATTACGGT GCTGCTATCG ATGGTTTCAT
      TTTGAACTAA GACAGCGATG ACTAATGCCA CGACGATAGC TACCAAAGTA

201   TGGTGACGTT TCCGGCCTTG CTAATGGTAA TGGTGCTACT GGTGATTTTG
      ACCACTGCAA AGGCCGGAAC GATTACCATT ACCACGATGA CCACTAAAAC

251   CTGGCTCTAA TTCCCAAATG GCTCAAGTCG GTGACGGTGA TAATTCACCT
      GACCGAGATT AAGGGTTTAC CGAGTTCAGC CACTGCCACT ATTAAGTGGA

XmnI
            ----------
301   TTAATGAATA ATTTCCGTCA ATATTTACCT TCCCTCCCTC AATCGGTTGA
      AATTACTTAT TAAAGGCAGT TATAAATGGA AGGGAGGGAG TTAGCCAACT
```

*FIG. 30B*

```
351  ATGTCGCCCT TTTGTCTTTG GCGCTGGTAA ACCATATGAA TTTTCTATTG
     TACAGCGGGA AAACAGAAAC CGCGACCATT TGGTATACTT AAAAGATAAC

401  ATTGTGACAA AATAAACTTA TTCCGTGGTG TCTTTGCGTT TCTTTTATAT
     TAACACTGTT TTATTTGAAT AAGGCACCAC AGAAACGCAA AGAAAATATA

451  GTTGCCACCT TTATGTATGT ATTTTCTACG TTTGCTAACA TACTGCGTAA
     CAACGGTGGA AATACATACA TAAAAGATGC AAACGATTGT ATGACGCATT

HindIII
                            ------
501  TAAGGAGTCT TGATAAGCTT
     ATTCCCTCAGA ACTATTCGAA
```

*FIG. 30C*

```
            HindIII
            ~~~~~~
  1  GGGGGGGGGG AAGCTTGACC TGTGAAGTGA AAAATGGCGC AGATTGTGCG
     CCCCCCCCCC TTCGAACTGG ACACTTCACT TTTTACCGCG TCTAACACGC PacI                   FseI
                           ~~~~~~~~                ~~~~~~~~
 51  ACATTTTTTT TGTCTGCCGT TTAATTAAAG GGGGGGGGGG GCCGGCCTGG
     TGTAAAAAAA ACAGACGGCA AATTAATTTC CCCCCCCCCC CGGCCGGACC BsrGI
     ~~~~~~
101  GGGGGGGTGT ACAGGGGGGG GGG
     CCCCCCCACA TGTCCCCCCC CCC
```

FIG. 31B

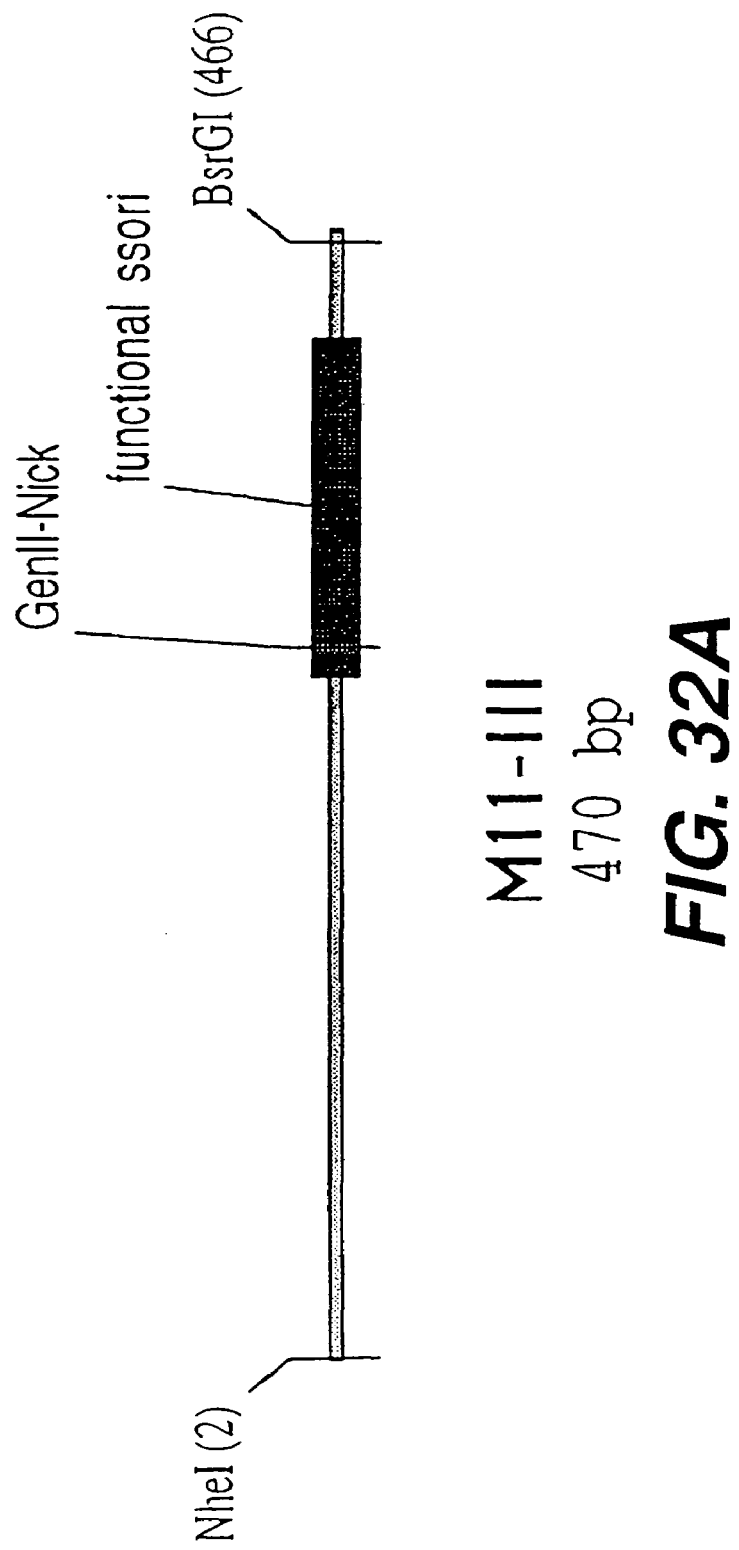

```
     NheI
     ------
  1  GCTAGCACGC GCCCTGTAGC GGCGCATTAA GCGCGGCGGG TGTGGTGGTT
     CGATCGTGCG CGGGACATCG CCGCGTAATT CGCGCCGCCC ACACCACCAA

51  ACGCGCAGCG TGACCGCTAC ACTTGCCAGC GCCCTAGCGC CCGCTCCTTT
     TGCGCGTCGC ACTGGCGATG TGAACGGTCG CGGGATCGCG GGCGAGGAAA

101  CGCTTTCTTC CCTTCCTTTC TCGCCACGTT CGCCCGGCTTT CCCCGTCAAG
     GCGAAAGAAG GGAAGGAAAG AGCGGTGCAA GCGGCCGAAA GGGGCAGTTC

151  CTCTAAATCG GGGCATCCCT TTAGGGTTCC GATTAGTGC TTTACGGCAC
     GAGATTTAGC CCCGTAGGGA AATCCCAAGG CTAAATCACG AAATGCCGTG

201  CTCGACCCCA AAAAACTTGA TTAGGGTGAT GGTTCTCGTA GTGGCCATC
     GAGCTGGGGT TTTTTGAACT AATCCCACTA CCAAGAGCAT CACCCGGTAG

251  GCCCTGATAG ACGGTTTTTC GCCCTTTGAC GTTGGAGTCC ACGTTCTTTA
     CGGGACTATC TGCCAAAAAG CGGGAAACTG CAACCTCAGG TGCAAGAAAT

301  ATAGTGGACT CTTGTTCCAA ACTGGAACAA CACTCAACCC TATCTCGGTC
     TATCACCTGA GAACAAGGTT TGACCTTGTT GTGAGTTGGG ATAGAGCCAG

351  TATTCTTTTG ATTTATAAGG GATTTTGCCG ATTTCGGCCT ATTGGTTAAA
```

*FIG. 32B*

```
        ATAAGAAAAC TAAATATTCC CTAAAACGGC TAAAGCCCGA TAACCAATTT
401     AAATGAGCTG ATTTAACAAA AATTTAACGC GAATTTTAAC AAAATATTAA
        TTTACTCGAC TAAATTGTTT TTAAATTGCG CTTAAAATTG TTTTATAATT

BsrGI
                                              ~~~~~~
451     CGTTTACAAT TTCATGTACA
        GCAAATGTTA AAGTACATGT
```

*FIG. 32C*

M14-EXT2
733 bp

```
       BglII
       ~~~~~~~
  1    AGATCTGACC AAAATCCCTT AACGTGAGTT TTCGTTCCAC TGAGCGTCAG
       TCTAGACTGG TTTTAGGGAA TTGCACTCAA AAGCAAGGTG ACTCGCAGTC

51    ACCCCGTAGA AAAGATCAAA GGATCTTCTT GAGATCCTTT TTTTCTGCGC
       TGGGGCATCT TTTCTAGTTT CCTAGAAGAA CTCTAGGAAA AAAAGACGCG

101    GTAATCTGCT GCTTGCAAAC AAAAAAACCA CCGCTACCAG CGGTGGTTTG
       CATTAGACGA CGAACGTTTG TTTTTTTGGT GGCGATGGTC GCCACCAAAC

151    TTTGCCGGAT CAAGAGCTAC CAACTCTTTT TCCGAAGGTA ACTGGCTACA
       AAACGGCCTA GTTCTCGATG GTTGAGAAAA AGGCTTCCAT TGACCGATGT

201    GCAGAGCGCA GATACCAAAT ACTGTTCTTC TAGTGTAGCC GTAGTTAGGC
       CGTCTCGCGT CTATGGTTTA TGACAAGAAG ATCACATCGG CATCAATCCG

251    CACCACTTCA AGAACTCTGT AGCACCGCCT ACATACCTCG CTCTGCTAAT
       GTGGTGAAGT TCTTGAGACA TCGTGGCGGA TGTATGGAGC GAGACGATTA

301    CCTGTTACCA GTGGCTGCTG CCAGTGGCGA TAAGTCGTGT CTTACCGGGT
       GGACAATGGT CACCGACGAC GGTCACCGCT ATTCAGCACA GAATGGCCCA

351    TGGACTCAAG ACGATAGTTA CCGGATAAGG CGCAGCGGTC GGGCTGAACG
```

FIG. 33B

```
     ACCTGAGTTC TGCTATCAAT GGCCTATTCC GCGTCGCCAG CCCGACTTGC
401  GGGGGTTCGT GCACACAGCC CAGCTTGGAG CGAACGACCT ACACCGAACT
     CCCCAAGCA  CGTGTGTCGG GTCGAACCTC GCTTGCTGGA TGTGGCTTGA
451  GAGATACCTA CAGCGTGAGC TATGAGAAAG CGCCACGCTT CCCGAAGGGA
     CTCTATGGAT GTCGCAGTCG ATACTCTTTC GCGGTGCGAA GGGCTTCCCT
501  GAAAGGCGGA CAGGTATCCG GTAAGCGGCA GGGTCGGAAC AGGAGAGCGC
     CTTTCCGCCT GTCCATAGGC CATTCGCCGT CCCAGCCTTG TCCTCTCGCG
                BssSI                                BssSI
551  ACGAGGGAGC TTCCAGGGGG AAACGCCTGG TATCTTTATA GTCCTGTGTCGG
     TGCTCCCTCG AAGGTCCCCC TTTGCGGACC ATAGAAATAT CAGGACAGCC
     BssSI
601  GTTTCGCCAC CTCTGACTTG AGCGTCGATT TTTGTGATGC TCGTCAGGGG
     CAAAGCGGTG GAGACTGAAC TCGCAGCTAA AAACACTACG AGCAGTCCCC
651  GGCGGAGCCT ATGGAAAAAC GCCAGCAACG CGGCCTTTTT ACGGTTCCTG
     CCGCCTCGGA TACCTTTTTG CGGTCGTTGC GCCGGAAAAA TGCCAAGGAC
```

FIG. 33C

701 GCCTTTTGCT GGCCTTTGC TCACATGGCT AGC
    CGGAAAACGA CCGGAAAACG AGTGTACCGA TCG
                                    NheI

FIG. 33D

```
      AatII
      ~~~~~~
  1   GGGACGTCGG  GTGAGGTTCC  AACTTTCACC  ATAATGAAAT  AAGATCACTA
      CCCTGCAGCC  CACTCCAAGG  TTGAAAGTGG  TATTACTTTA  TTCTAGTGAT

51   CCGGGCGTAT  TTTTTGAGTT  ATCGAGATTT  TCAGGAGCTA  AGGAAGCTAA
      GGCCCGCATA  AAAAACTCAA  TAGCTCTAAA  AGTCCTCGAT  TCCTTCGATT

101   AATGGAGAAA  AAAATCACTG  GATATACCAC  CGTTGATATA  TCCCAATGGC
      TTACCTCTTT  TTTTAGTGAC  CTATATGGTG  GCAACTATAT  AGGGTTACCG

151   ATCGTAAAGA  ACATTTTGAG  GCATTTCAGT  CAGTTGCTCA  ATGTACCTAT
      TAGCATTTCT  TGTAAAACTC  CGTAAAGTCA  GTCAACGAGT  TACATGGATA

201   AACCAGACCG  TTCAGCTGGA  TATTACGGCC  TTTTTAAAGA  CCGTAAAGAA
      TTGGTCTGGC  AAGTCGACCT  ATAATGCCGG  AAAAATTTCT  GGCATTTCTT

251   AAATAAGCAC  AAGTTTTATC  CGGCCTTTAT  TCACATTCTT  GCCCGCCTGA
      TTTATTCGTG  TTCAAAATAG  GCCGGAAATA  AGTGTAAGAA  CGGGCGGACT

301   TGAATGCTCA  CCCGGAGTTC  CGTATGGCAA  TGAAAGACGG  TGAGCTGGTG
      ACTTACGAGT  GGGCCTCAAG  GCATACCGTT  ACTTTCTGCC  ACTCGACCAC

351   ATATGGGATA  GTGTTCACCC  TTGTTACACC  GTTTTCCATG  AGCAAACTGA
```

FIG. 34B

```
        TATACCCTAT  CACAAGTGGG  AACAATGTGG  CAAAAGGTAC  TCGTTTGACT
   401  AACGTTTTCA  TCGCTCTGGA  GTGAATACCA  CGACGATTTC  CGGCAGTTTC
        TTGCAAAAGT  AGCGAGACCT  CACTTATGGT  GCTGCTAAAG  GCCGTCAAAG
   451  TACACATATA  TTCGCAAGAT  GTGGCGTGTT  ACGGTGAAAA  CCTGGCCTAT
        ATGTGTATAT  AAGCGTTCTA  CACCGCACAA  TGCCACTTTT  GGACCGGATA
   501  TTCCCTAAAG  GGTTTATTGA  GAATATGTTT  TTCGTCTCAG  CCAATCCCTG
        AAGGGATTTC  CCAAATAACT  CTTATACAAA  AAGCAGAGTC  GGTTAGGGAC
   551  GGTGAGTTTC  ACCAGTTTGT  ATTTAAACGT  AGCCAATATG  GACAACTTCT
        CCACTCAAAG  TGGTCAAACA  TAAATTTGCA  TCGGTTATAC  CTGTTGAAGA
   601  TCGCCCCCGT  TTTCACTATG  GGCAAATATT  ATACGCAAGG  CGACAAGGTG
        AGCGGGGGCA  AAAGTGATAC  CCGTTTATAA  TATGCGTTCC  GCTGTTCCAC
   651  CTGATGCCGC  TGGCGATTCA  GGTTCATCAT  GCCGTTTGTG  ATGGCTTCCA
        GACTACGGCG  ACCGCTAAGT  CCAAGTAGTA  CGGCAAACAC  TACCGAAGGT
   701  TGTCGGCAGA  ATGCTTAATG  AATTACAACA  GTACTGCGAT  GAGTGGCAGG
        ACAGCCGTCT  TACGAATTAC  TTAATGTTGT  CATGACGCTA  CTCACCGTCC
   751  GCGGGGCGTA  ATTTTTTTAA  GGCAGTTATT  GGGTGCCCTT  AAACGCCTGG
```

*FIG. 34C*

CGCCCCGCAT TAAAAAAATT CCGTCAATAA CCCACGGGAA TTTGCGGACC

```
      BglII
      ~~~~~~
801   TGCTAGATCT TCC
      ACGATCTAGA AGG
```

FIG. 34D

```
      EcoRI
      -----
  1   AATTCGAGCA GAAGCTGATC TCTGAGGAGG ATCTGTAGGG TGGTGGCTCT
      TTAAGCTCGT CTTCGACTAG AGACTCCTCC TAGACATCCC ACCACGAGA

51   GGTTCCGGTG ATTTTGATTA TGAAAAGATG GCAAACGCTA ATAAGGGGC
      CCAAGGCCAC TAAAACTAAT ACTTTTCTAC CGTTTGCGAT TATTCCCCG

101   TATGACCGAA AATGCCGATG AAAACGCGCT ACAGTCTGAC GCTAAAGGCA
      ATACTGGCTT TTACGGCTAC TTTTGCGCGA TGTCAGACTG CGATTTCCGT

151   AACTTGATTC TGTCGCTACT GATTACGGTG CTGCTATCGA TGGTTTCATT
      TTGAACTAAG ACAGCGATGA CTAATGCCAC GACGATAGCT ACCAAAGTAA

201   GGTGACGTTT CCGGCCTTGC TAATGGTAAT GGTGCTACTG GTGATTTTGC
      CCACTGCAAA GGCCGGAACG ATTACCATTA CCACGATGAC CACTAAAACG

251   TGGCTCTAAT TCCCAAATGG CTCAAGTCGG CTGACGGTGAT AATTCACCTT
      ACCGAGATTA AGGGTTTACC GAGTTCAGCC ACTGCCACTA TTAAGTGGAA

XmnI
              ----
301   TAATGAATAA TTTCCGTCAA TATTTACCTT CCCTCCCTCA ATCGGTTGAA
      ATTACTTATT AAAGGCAGTT ATAAATGGAA GGGAGGGAGT TAGCCAACTT
```

FIG. 35A-1

```
351  TGTCGCCCTT TTGTCTTTGG CGCTGGTAAA CCATATGAAT TTTCTATTGA
     ACAGCGGGAA AACAGAAACC GCGACCATTT GGTATACTTA AAAGATAACT

401  TTGTGACAAA ATAAACTTAT TCCGTGGTGT CTTTGCGTTT CTTTTATATG
     AACACTGTTT TATTTGAATA AGGCACCACA GAAACGCAAA GAAAATATAC

451  TTGCCACCTT TATGTATGTA TTTTCTACGT TTGCTAACAT ACTGCGTAAT
     AACGGTGGAA ATACATACAT AAAAGATGCA AACGATTGTA TGACGCATTA
                           HindIII
                           ~~~~~~

501  AAGGAGTCTT GATAAGCTTG ACCTGTGAAG TGAAAAATGG CGCAGATTGT
     TTCCTCAGAA CTATTCGAAC TGGACACTTC ACTTTTTACC GCGTCTAACA
                                             PacI              FseI
                                             ~~~~              ~~~

551  GCCACATTTT TTTTGTCTGC CGTTTAATTA AAGGGGGGGG GGGGCCGGCC
     CGCTGTAAAA AAAACAGACG GCAAATTAAT TTCCCCCCCC CCCCGGCCGG
            BsrGI
            ~~~~~

601  TGGGGGGGGG TGTACATGAA ATTGTAAACG TTAATATTTT GTTAAAATTC
     ACCCCCCCCC ACATGTACTT TAACATTGC AATTATAAAA CAATTTTAAG
```

FIG. 35A-2

```
651  GCGTTAAATT TTTGTTAAAT CAGCTCATTT TTTAACCAAT AGGCCGAAAT
     CGCAATTTAA AAACAATTTA GTCGAGTAAA AAATTGGTTA TCCGGCTTTA

701  CGGCAAAATC CCTTATAAAT CAAAAGAATA GACCGAGATA GGGTTGAGTG
     GCCGTTTTAG GGAATATTTA GTTTTCTTAT CTGGCTCTAT CCCAACTCAC

751  TTGTTCCAGT TTGGAACAAG AGTCCACTAT TAAAGAACGT GGACTCCAAC
     AACAAGGTCA AACCTTGTTC TCAGGTGATA ATTTCTTGCA CCTGAGGTTG

801  GTCAAAGGGC GAAAAACCGT CTATCAGGGC GATGGCCCAC TACGAGAACC
     CAGTTTCCCG CTTTTTGGCA GATAGTCCCG CTACCGGGTG ATGCTCTTGG

851  ATCACCCTAA TCAAGTTTTT TGGGGTCGAG GTGCCGTAAA GCACTAAATC
     TAGTGGGATT AGTTCAAAAA ACCCCAGCTC CACGGCATTT CGTGATTTAG
                BanII
                ------

901  GGAACCCTAA AGGGAGCCCC CGATTTAGAG CTTGACGGGG AAAGCCGGCG
     CCTTGGGATT TCCCTCGGGG GCTAAATCTC GAACTGCCCC TTTCGGCCGC

951  AACGTGGCGA GAAAGGAAGG GAAGAAAGCG AAAGGAGCGG GCGCTAGGGC
     TTGCACCGCT CTTTCCTTCC CTTCTTTCGC TTTCCTCGCC CGCGATCCCG
```

FIG. 35A-3

```
1001  GCTGGCAAGT GTAGCGGTCA CGCTGCGCGT AACCACCACA CCCGCCGCGC
      CGACCGTTCA CATCGCCAGT GCGACGCGCA TTGGTGGTGT GGGCGGCGCG

1051  TTAATGCGCC GCTACAGGGC GCGTGCTAGC CATGTGAGCA AAAGGCCAGC
      AATTACGCGG CGATGTCCCG CGCACGATCG GTACACTCGT TTTCCGGTCG
                                NheI
                                ------

1101  AAAAGGCCAG GAACCGTAAA AAGGCCGCGT TGCTGGCGTT TTTCCATAGG
      TTTTCCGGTC CTTGGCATTT TTCCGGCGCA ACGACCGCAA AAAGGTATCC

1151  CTCCGCCCCC CTGACGAGCA TCACAAAAAT CGACGCTCAA GTCAGAGGTG
      GAGGCGGGGG GACTGCTCGT AGTGTTTTTA GCTGCGAGTT CAGTCTCCAC

1201  GCGAAACCCG ACAGGACTAT AAAGATACCA GGCGTTTCCC CCTGGAAGCT
      CGCTTTGGGC TGTCCTGATA TTTCTATGGT CCGCAAAGGG GGACCTTCGA
      BssSI
      ------

1251  CCCTCGTGCG CTCTCCTGTT CCGACCCTGC CGCTTACCGG ATACCTGTCC
      GGGAGCACGC GAGAGGACAA GGCTGGGACG GCGAATGGCC TATGGACAGG

1301  GCCTTTCTCC CTTCGGGAAG CGTGGCGCTT TCTCATAGCT CACGCTGTAG
      CGGAAAGAGG GAAGCCCTTC GCACCGCGAA AGAGTATCGA GTGCGACATC
```

FIG. 35A-4

```
1351  GTATCTCAGT TCGGTGTAGG TCGTTCGCTC CAAGCTGGGC TGTGTGCACG
      CATAGAGTCA AGCCACATCC AGCAAGCGAG GTTCGACCCG ACACACGTGC

1401  AACCCCCCGT TCAGCCCGAC CGCTGCGCCT TATCCGGTAA CTATCGTCTT
      TTGGGGGCA AGTCGGGCTG GCGACGCGGA ATAGGCCATT GATAGCAGAA

1451  GAGTCCAACC CGGTAAGACA CGACTTATCG CCACTGGCAG CAGCCACTGG
      CTCAGGTTGG GCCATTCTGT GCTGAATAGC GGTGACCGTC GTCGGTGACC

1501  TAACAGGATT AGCAGAGCGA GGTATGTAGG CGGTGCTACA GAGTTCTTGA
      ATTGTCCTAA TCGTCTCGCT CCATACATCC GCCACGATGT CTCAAGAACT

1551  AGTGGTGGCC TAACTACGGC TACACTAGAA GAACAGTATT TGGTATCTGC
      TCACCACCGG ATTGATGCCG ATGTGATCTT CTTGTCATAA ACCATAGACG

1601  GCTCTGCTGT AGCCAGTTAC CTTCGGAAAA AGAGTTGGTA GCTCTTGATC
      CGAGACGACA TCGGTCAATG GAAGCCTTTT TCTCAACCAT CGAGAACTAG

1651  CGGCAAACAA ACCACCGCTG GTAGCGGTGG TTTTTTTGTT TGCAAGCAGC
      GCCGTTTGTT TGGTGGCGAC CATCGCCACC AAAAAAACAA ACGTTCGTCG

1701  AGATTACGCG CAGAAAAAAA GGATCTCAAG AAGATCCTTT GATCTTTTCT
      TCTAATGCGC GTCTTTTTTT CCTAGAGTTC TTCTAGGAAA CTAGAAAAGA
```

FIG. 35A-5

```
1751  ACGGGGTCTG  ACGCTCAGTG  GAACGAAAAC  TCACGTTAAG  GGATTTTGT
      TGCCCCAGAC  TGCGAGTCAC  CTTGCTTTTG  AGTGCAATTC  CCTAAAACCA
         BglII
         ~~~~~~
1801  CAGATCTAGC  ACCAGGCGTT  TAAGGGCACC  AATAACTGCC  TTAAAAAAAT
      GTCTAGATCG  TGGTCCGCAA  ATTCCCGTGG  TTATTGACGG  AATTTTTTA

1851  TACGCCCCGC  CCTGCCACTC  ATCGCAGTAC  TGTTGTAATT  CATTAAGCAT
      ATGCGGGGCG  GGACGGTGAG  TAGCGTCATG  ACAACATTAA  GTAATTCGTA

1901  TCTGCCGACA  TGGAAGCCAT  CACAAACGGC  ATGATGAACC  TGAATCGCCA
      AGACGGCTGT  ACCTTCGGTA  GTGTTTGCCG  TACTACTTGG  ACTTAGCGGT

1951  GCGGCATCAG  CACCTTGTCG  CCTTGCGTAT  AATATTTGCC  CATAGTGAAA
      CGCCGTAGTC  GTGGAACAGC  GGAACGCATA  TTATAAACGG  GTATCACTTT

2001  ACGGGGGCGA  AGAAGTTGTC  CATATTGGCT  ACGTTTAAAT  CAAAACTGGT
      TGCCCCCGCT  TCTTCAACAG  GTATAACCGA  TGCAAATTTA  GTTTTGACCA

2051  GAAACTCACC  CAGGGATTGG  CTGAGACGAA  AAACATATTC  TCAATAAACC
      CTTTGAGTGG  GTCCCTAACC  GACTCTGCTT  TTTGTATAAG  AGTTATTTGG
```

FIG. 35A-6

```
2101  CTTTAGGGAA ATAGGCCAGG TTTTCACCGT AACACGCCAC ATCTTGCGAA
      GAAATCCCTT TATCCGGTCC AAAAGTGGCA TTGTGCGGTG TAGAACGCTT

2151  TATATGTGTA GAAACTGCCG GAAATCGTCG TGGTATTCAC TCCAGAGCGA
      ATATACACAT CTTTGACGGC CTTTAGCAGC ACCATAAGTG AGGTCTCGCT

2201  TGAAAACGTT TCAGTTTGCT CATGGAAAAC GGTGTAACAA GGGTGAACAC
      ACTTTTGCAA AGTCAAACGA GTACCTTTTG CCACATTGTT CCCACTTGTG

2251  TATCCCATAT CACCAGCTCA CCGTCTTTCA TTGCCATACG GAACTCCGGG
      ATAGGGTATA GTGGTCGAGT GGCAGAAAGT AACGGTATGC CTTGAGGCCC

2301  TGAGCATTCA TCAGGCGGGC AAGAATGTGA ATAAAGGCCG GATAAAACTT
      ACTCGTAAGT AGTCCGCCCG TTCTTACACT TATTTCCGGC CTATTTTGAA

2351  GTGCTTATTT TTCTTTACGG TCTTTAAAAA GGCCGTAATA TCCAGCTGAA
      CACGAATAAA AAGAAATGCC AGAAATTTTT CCGGCATTAT AGGTCGACTT

2401  CGGTCTGGTT ATAGGTACAT TGAGCAACTG ACTGAAATGC CTCAAAATGT
      GCCAGACCAA TATCCATGTA ACTCGTTGAC TGACTTTACG GAGTTTTACA

2451  TCTTTACGAT GCCATTGGGA TATATCAACG GTGGTATATC CAGTGATTTT
      AGAAATGCTA CGGTAACCCT ATATAGTTGC CACCATATAG GTCACTAAAA
```

FIG. 35A-7

```
2501  TTTCTCCATT TTAGCTTCCT TAGCTCCTGA AAATCTCGAT AACTCAAAAA
      AAAGAGGTAA AATCGAAGGA ATCGAGGACT TTTAGAGCTA TTGAGTTTTT

2551  ATACGCCCGG TAGTGATCTT ATTTCATTAT GGTGAAAGTT GGAACCCTCAC
      TATGCGGGCC ATCACTAGAA TAAAGTAATA CCACTTTCAA CCTTGGAGTG
                 AatII
                 ------

2601  CCGACGTCTA ATGTGAGTTA GCTCACTCAT TAGGCACCCC AGGCTTTACA
      GGCTGCAGAT TACACTCAAT CGAGTGAGTA ATCCGTGGGG TCCGAAATGT

2651  CTTTATGCTT CCGGCTCGTA TGTTGTGTGG AATTGTGAGC GGATAACAAT
      GAAATACGAA GGCCGAGCAT ACAACACACC TTAACACTCG CCTATTGTTA
                                                 XbaI   SphI
                                                 ----   ----

2701  TTCACACAGG AAACAGCTAT GACCATGATT ACGAATTTCT AGAGCATGCG
      AAGTGTGTCC TTTGTCGATA CTGGTACTAA TGCTTAAAGA TCTCGTACGC
      EcoRI

2751  GGGGG
      CCCCC
```

FIG. 35A-8

M 2:

```
       AatII
       ------
  1  GACGTCTTAA TGTGAGTTAG CTCACTCATT AGGCACCCCA GGCTTTACAC
     CTGCAGAATT ACACTCAATC GAGTGAGTAA TCCGTGGGGT CCGAAATGTG

51  TTTATGCTTC CGGCTCGTAT GTTGTGTGGA ATTGTGAGCG GATAACAATT
     AAATACGAAG GCCGAGCATA CAACACACCT TAACACTCGC CTATTGTTAA
                                             XmnI
                                             ------

101  TCACACAGGA AACAGCTATG ACCATGTCTA GAATAACTTC GTATAATGTA
     AGTGTGTCCT TTGTCGATAC TGGTACAGAT CTTATTGAAG CATATTACAT
                   SphI                XbaI
                   ------              ------

151  CGCTATACGA AGTTATCGCA TGC
     GCGATATGCT TCAATAGCGT ACG
```

FIG. 35A-10

M3
47 bp

M 3:

```
    BglII                                              AatII
    ------                                             ------
  1 AGATCTCATA ACTTCGTATA ATGTATGCTA TACGAAGTTA TGACGTC
    TCTAGAGTAT TGAAGCATAT TACATACGAT ATGCTTCAAT ACTGCAG
```

FIG. 35A-12

M 7-I (long):

EcoRI
------
```
  1  GAATTCGGTG GTGGTGGATC TGCGTGCGCT GAAACGGGTG AAAGTTGTTT
     CTTAAGCCAC CACCACCTAG ACGCACGCGA CTTTGCCCAC TTTCAACAAA

51  AGCAAAATCC CATACAGAAA ATTCATTTAC TAACGTCTGG AAAGACGACA
     TCGTTTTAGG GTATGTCTTT TAAGTAAATG ATTGCAGACC TTTCTGCTGT

101  AAACTTTAGA TCGTTACGCT AACTATGAGG GCTGTCTGTG GAATGCTACA
     TTTGAAATCT AGCAATGCGA TTGATACTCC CGACAGACAC CTTACGATGT

151  GGCGTTGTAG TTTGTACTGG TGACGAAACT CAGTGTTACG GTACATGGGT
     CCGCAACATC AAACATGACC ACTGCTTTGA GTCACAATGC CATGTACCCA

201  TCCTATTGGG CTTGCTATCC CTGAAAATGA GGGTGGTGGC TCTGAGGGTG
     AGGATAACCC GAACGATAGG GACTTTTACT CCCACCACCG AGACTCCCAC

251  GCGGTTCTGA GGGTGGCGGT TCTGAGGGTG GCGGTACTAA ACCTCCTGAG
     CGCCAAGACT CCCACCGCCA AGACTCCCAC CGCCATGATT TGGAGGACTC

301  TACGGTGATA CACCTATTCC GGGCTATACT TATATCAACC CTCTCGACGG
     ATGCCACTAT GTGGATAAGG CCCGATATGA ATATAGTTGG GAGAGCTGCC
```

FIG. 35A-14

```
351  CACTTATCCG CCTGGTACTG AGCAAAACCC CGCTAATCCT AATCCTTCTC
     GTGAATAGGC GGACCATGAC TCGTTTTGGG GCGATTAGGA TTAGGAAGAG

401  TTGAGGAGTC TCAGCCTCTT AATACTTTCA TGTTTCAGAA TAATAGGTTC
     AACTCCTCAG AGTCGGAGAA TTATGAAAGT ACAAAGTCTT ATTATCCAAG

451  CGAAATAGGC AGGGGGCATT AACTGTTTAT ACGGGCACTG TTACTCAAGG
     GCTTTATCCG TCCCCCGTAA TTGACAAATA TGCCCGTGAC AATGAGTTCC

501  CACTGACCCC GTTAAAAACTT ATTACCAGTA CACTCCCTGTA TCATCAAAAG
     GTGACTGGGG CAATTTTTGAA TAATGGTCAT GTGAGGACAT AGTAGTTTTC

551  CCATGTATGA CGCTTACTGG AACGGTAAAT TCAGAGACTG CGCTTTCCAT
     GGTACATACT GCGAATGACC TTGCCATTTA AGTCTCTGAC GCGAAAGGTA

601  TCTGGCTTTA ATGAGGATTT ATTTGTTTGT GAATATCAAG GCCAATCGTC
     AGACCGAAAT TACTCCTAAA TAAACAAACA CTTATAGTTC CGGTTAGCAG

651  TGACCTGCCT CAACCCTCCTG TCAATGCTGG CGGCGGCTCT GGTGGTGGTT
     ACTGGACGGA GTTGGAGGAC AGTTACGACC GCCGCCGAGA CCACCACCAA

701  CTGGTGGCGG CTCTGAGGGT GGTGGCTCTG AGGGTGGCGG TTCTGAGGGT
     GACCACCGCC GAGACTCCCA CCACCGAGAC TCCCACCGCC AAGACTCCCA
```

FIG. 35A-15

```
 751   GGCGGCTCTG  AGGGAGGCGG  TTCCGGTGGT  TTCCGGTGGT  CCGGTGATTT
       CCGCCGAGAC  TCCCTCCGCC  AAGGCCACCA  CCGAGACCAA  GGCCACTAAA

801   TGATTATGAA  AAGATGGCAA  ACGCTAATAA  GGGGGCTATG  ACCGAAAATG
       ACTAATACTT  TTCTACCGTT  TGCGATTATT  CCCCCGATAC  TGGCTTTTAC

851   CCGATGAAAA  CGCGCTACAG  TCTGACGCTA  AAGGCAAACT  TGATTCTGTC
       GGCTACTTTT  GCGCGATGTC  AGACTGCGAT  TTCCGTTTGA  ACTAAGACAG

901   GCTACTGATT  ACGGTGCTGC  TATCGATGGT  TTCATTGGTG  ACGTTTCCGG
       CGATGACTAA  TGCCACGACG  ATAGCTACCA  AAGTAACCAC  TGCAAAGGCC

951   CCTTGCTAAT  GGTAATGGTG  CTACTGGTGA  TTTTGCTGGC  TCTAATTCCC
       GGAACGATTA  CCATTACCAC  GATGACCACT  AAAACGACCG  AGATTAAGGG

XmnI
                                                      |----|
1001   AAATGGCTCA  AGTCGGTGAA  GGTGATAATT  CACCTTTAAT  GAATAATTTC
       TTTACCGAGT  TCAGCCACTT  CCACTATTAA  GTGGAAATTA  CTTATTAAAG

1051   CGTCAATATT  TACCTTCCAT  CCCTCAATCG  GTTGAATGTC  GCCCTTTGT
       GCAGTTATAA  ATGGAAGGTA  GGGAGTTAGC  CAACTTACAG  CGGGAAAACA
```

FIG. 35A-16

```
1101  CTTTGGCGCT GGTAAACCCT ATGAATTTTC TATTGATTGT GACAAAATAA
      GAAACCGCGA CCATTTGGGA TACTTAAAAG ATAACTAACA CTGTTTTATT

1151  ACTTATTCCG TGGTGTCTTT GCCTTTCTTT TATATGTTGC CACCTTTATG
      TGAATAAGGC ACCACAGAAA CGCAAAGAAA ATATACAACG GTGGAAATAC

HindIII
                                                  ┌──────
1201  TATGTATTTT CTACGTTTGC TAACATACTG CGTAATAAGG AGTCTTGATA
      ATACATAAAA GATGCAAACG ATTGTATGAC GCATTATTCC TCAGAACTAT HindI
      ┌────
1251  AGCTT
      TCGAA
```

FIG. 35A-17

M 7-II (ss-TAG):

```
    EcoRI
    ~~~~~~
  1 CGGGAATTCG GAGGCGGTTC CGGTGGTGGC TCTGGTTCCG GTGATTTGA
    GCCCTTAAGC CTCCGCCAAG GCCACCACCG AGACCAAGGC CACTAAAACT

51 TTATGAAAAG ATGGCAAACG CTAATAAGGG GGCTATGACC GAAAATGCCG
    AATACTTTTC TACCGTTTGC GATTATTCCC CCGATACTGG CTTTTACGGC

101 ATGAAAACGC GCTACAGTCT GACGCTAAAG GCAAACTTGA TTCTGTCGCT
    TACTTTTGCG CGATGTCAGA CTGCGATTTC CGTTTGAACT AAGACAGCGA

151 ACTGATTACG GTGCTGCTAT CGATGGTTTC ATTGGTGACG TTTCCGGCCT
    TGACTAATGC CACGACGATA GCTACCAAAG TAACCACTGC AAAGGCCGGA

201 TGCTAATGGT AATGGTGCTA CTGGTGATTT TGCTGGCTCT AATTCCCAAA
    ACGATTACCA TTACCACGAT GACCACTAAA ACGACCGAGA TTAAGGGTTT

Xmn I
                                                ~~~~~~
251 TGGCTCAAGT CGGTGACGGT GATAATTCAC CTTTAATGAA TAATTTCCGT
    ACCGAGTTCA GCCACTGCCA CTATTAAGTG GAAATTACTT ATTAAAGGCA
```

FIG. 35A-19

```
301  CAATATTTAC CTTCCCTCCC TCAATCGGTT GAATGTCGCC CTTTTGTCTT
     GTTATAAATG GAAGGGAGGG AGTTAGCCAA CTTACAGCGG GAAAACAGAA

351  TGGCGCTGGT AAACCATATG AATTTCTAT TGATTGTGAC AAAATAAACT
     ACCGCGACCA TTTGGTATAC TTAAAAGATA ACTAACACTG TTTTATTTGA

401  TATTCCGTGG TGTCTTTGCG TTTCTTTTAT ATGTTGCCAC CTTTATGTAT
     ATAAGGCACC ACAGAAACGC AAAGAAAATA TACAACGGTG GAAATACATA

HindIII
                                                -----
451  GTATTTTCTA CGTTTGCTAA CATACTGCGT AATAAGGAGT CTTGATAAGC
     CATAAAAGAT GCAAACGATT GTATGACGCA TTATTCCTCA GAACTATTCG Hi                                         
     -                                          
501  TT                                         
     AA                                         
```

FIG. 35A-20

```
M 8:
         SphI                                              HindIII
         ------                                            ------
     1   GCATGCCATA ACTTCGTATA ATGTACGCTA TACGAAGTTA TAAGCTT
         CGTACGGTAT TGAAGCATAT TACATGCGAT ATGCTTCAAT ATTCGAA
```

FIG. 35A-22

M10-11
1163 bp

```
M 10-II:
        BsrGI
        ~~~~~~~
  1  GGGGGTGTAC ATTCAAATAT GTATCCGCTC ATGAGACAAT AACCCTGATA
     CCCCCACATG TAAGTTTATA CATAGGCGAG TACTCTGTTA TTGGGACTAT

51  AATGCTTCAA TAATATTGAA AAAGGAAGAG TATGAGTATT CAACATTTCC
     TTACGAAGTT ATTATAACTT TTTCCTTCTC ATACTCATAA GTTGTAAAGG

101  GTGTCGCCCT TATTCCCTTT TTTGCGGCAT TTTGCCTTCC TGTTTTTGCT
     CACAGCGGGA ATAAGGGAAA AAACGCCGTA AAACGGAAGG ACAAAAACGA

151  CACCCAGAAA CGCTGGTGAA AGTAAAAGAT GCTGAGGATC AGTTGGGTGC
     GTGGGTCTTT GCGACCACTT TCATTTTCTA CGACTCCTAG TCAACCCACG

201  GCGAGTGGGT TACATCGAAC TGGATCTCAA CAGCGGTAAG ATCCTTGAGA
     CGCTCACCCA ATGTAGCTTG ACCTAGAGTT GTCGCCATTC TAGGAACTCT
                          XmnI
                          ~~~~~~~~~~~
251  GTTTTCGCCC CGAAGAACGT TTTCCAATGA TGAGCACTTT TAAAGTTCTG
     CAAAAGCGGG GCTTCTTGCA AAAGGTTACT ACTCGTGAAA ATTTCAAGAC
```

FIG. 35A-24

```
301  CTATGTGGCG  CGTATTATC   CCGTATTGAC  GCCGGGCAAG  AGCAACTCGG
     GATACACCGC  GCCATAATAG  GGCATAACTG  CGGCCCGTTC  TCGTTGAGCC

351  TCGCCGCATA  CACTATTCTC  AGAATGACTT  GGTTGAGTAC  TCACCAGTCA
     AGCGGCGTAT  GTGATAAGAG  TCTTACTGAA  CCAACTCATG  AGTGGTCAGT

401  CAGAAAAGCA  TCTTACGGAT  GGCATGACAG  TAAGAGAATT  ATGCAGTGCT
     GTCTTTTCGT  AGAATGCCTA  CCGTACTGTC  ATTCTCTTAA  TACGTCACGA

451  GCCATAACCA  TGAGTGATAA  CACTGCGGCC  AACTTACTTC  TGACAACGAT
     CGGTATTGGT  ACTCACTATT  GTGACGCCGG  TTGAATGAAG  ACTGTTGCTA

501  CGGAGGACCG  AAGGAGCTAA  CCGCTTTTTT  GCACAACATG  GGGGATCATG
     GCCTCCTGGC  TTCCTCGATT  GGCGAAAAAA  CGTGTTGTAC  CCCCTAGTAC

551  TAACTCGCCT  TGATCGTTGG  GAACCGGAGC  TGAATGAAGC  CATACCAAAC
     ATTGAGCGGA  ACTAGCAACC  CTTGGCCTCG  ACTTACTTCG  GTATGGTTTG

601  GACGAGCGTG  ACACCACGAT  GCCTGTAGCA  ATGGCAACAA  CGTTGCGCAA
     CTGCTCGCAC  TGTGGTGCTA  CGGACATCGT  TACCGTTGTT  GCAACGCGTT

651  ACTATTAACT  GGCGAACTAC  TTACTCTAGC  TTCCCGGCAA  CAGTTAATAG
     TGATAATTGA  CCGCTTGATG  AATGAGATCG  AAGGGCCGTT  GTCAATTATC
```

FIG. 35A-25

```
 701  ACTGGATGGA GGCGGATAAA GTTGCAGGAC CACTTCTGCG CTCGGCCCTT
      TGACCTACCT CCGCCTATTT CAACGTCCTG GTGAAGACGC GAGCCGGGAA

751  CCGGCTGGCT GGTTTATTGC TGATAAATCT GGAGCCGGTG AGCGTGGGTC
      GGCCGACCGA CCAAATAACG ACTATTTAGA CCTCGGCCAC TCGCACCCAG

801  TCGCGGTATC ATTGCAGCAC TGGGGCCAGA TGGTAAGCCC TCCCGTATCG
      AGCGCCATAG TAACGTCGTG ACCCCGGTCT ACCATTCGGG AGGGCATAGC

851  TAGTTATCTA CACGACGGGG AGTCAGGCAA CTATGGATGA ACGAAATAGA
      ATCAATAGAT GTGCTGCCCC TCAGTCCGTT GATACCTACT TGCTTTATCT

901  CAGATCGCTG AGATAGGTGC CTCACTGATT AAGCATTGGG TAACTGTCAG
      GTCTAGCGAC TCTATCCACG GAGTGACTAA TTCGTAACCC ATTGACAGTC

951  ACCAAGTTTA CTCATATATA CTTTAGATTG ATTTAAAACT TCATTTTAA
      TGGTTCAAAT GAGTATATAT GAAATCTAAC TAAATTTTGA AGTAAAAATT

1001  TTTAAAAGGA TCTAGGTGAA GATCCTTTTT GATAATCTCA TGACCAAAAT
      AAATTTTCCT AGATCCACTT CTAGGAAAAA CTATTAGAGT ACTGGTTTTA

1051  CCCTTAACGT GAGTTTTCGT TCCACTGAGC GTCAGACCCC GTAGAAAAGA
      GGGAATTGCA CTCAAAAGCA AGGTGACTCG CAGTCTGGGG CATCTTTCT
```

FIG. 35A-26

```
                                            FseI              PacI
                                         -------           ------
1101   TCAAAGGATC TTCTTGAGAT CCTTTTTGAT AATGGCCGGC CCCCCCCTT
       AGTTTCCTAG AAGAACTCTA GGAAAAACTA TTACCGGCCG GGGGGGGAA

PacI
       ------
1151   AATTAAGGGG GGG
       TTAATTCCCC CCC
```

FIG. 35A-27

M11-II:

```
         NheI
         ------
  1   GCTAGCACGC GCCCTGTAGC GGCGCATTAA GCGCGGCGGG TGTGGTGGTT
      CGATCGTGCG CGGGACATCG CCGCGTAATT CGCGCCGCCC ACACCACCAA

51   ACGCGCAGCG TGACCGCTAC ACTTGCCAGC GCCCTAGCGC CCGCTCCTTT
      TGCGCGTCGC ACTGGCGATG TGAACGGTCG CGGGATCGCG GGCGAGGAAA

101   CGCTTTCTTC CCTTCCTTTC TCGCCACGTT CGCCGGCTTT CCCCGTCAAG
      GCGAAAGAAG GGAAGGAAAG AGCGGTGCAA GCGGCCGAAA GGGGCAGTTC
                                BanII
                                ------
151   CTCTAAATCG GGGGCTCCCT TTAGGGTTCC GATTTAGTGC TTTACGGCAC
      GAGATTTAGC CCCCGAGGGA AATCCCAAGG CTAAATCACG AAATGCCGTG

201   CTCGACCCCA AAAACTTGA TTAGGGTGAT GGTTCTCGTA GTGGGCCATC
      GAGCTGGGGT TTTTGAACT AATCCCACTA CCAAGAGCAT CACCCGGTAG

251   GCCCTGATAG ACGGTTTTTC GCCCTTTGAC GTTGGAGTCC ACGTTCTTTA
      CGGGACTATC TGCCAAAAAG CGGGAAACTG CAACCTCAGG TGCAAGAAAT
```

FIG. 35A-29

```
301  ATAGTGGACT CTTGTTCCAA ACTGGAACAA CACTCAACCC TATCTCGGTC
     TATCACCTGA GAACAAGGTT TGACCTTGTT GTGAGTTGGG ATAGAGCCAG

351  TATTCTTTTG ATTTATAAGG GATTTTGCCG ATTTCGGCCT ATTGGTTAAA
     ATAAGAAAAC TAAATATTCC CTAAAACGGC TAAAGCCGGA TAACCAATTT

401  AAATGAGCTG ATTTAACAAA AATTTAACGC GAATTTTAAC AAAATATTAA
     TTTACTCGAC TAAATTGTTT TTAAATTGCG CTTAAAATTG TTTTATAATT

BsrGI
               ------
451  CGTTTACAAT TTCATGTACA
     GCAAATGTTA AAGTACATGT
```

FIG. 35A-30

M 12:
BglII
-------

1    AGATCTAATA AGATGATCTT CTTGAGATCG TTTTGGTCTG CGCGTAATCT
     TCTAGATTAT TCTACTAGAA GAACTCTAGC AAAACCAGAC GCGCATTAGA

51   CTTGCTCTGA AAACGAAAAA ACCGCCTTGC AGGGCGGTTT TTCGTAGGTT
     GAACGAGACT TTTGCTTTTT TGGCGGAACG TCCCGCCAAA AAGCATCCAA

101  CTCTGAGCTA CCAACTCTTT GAACCGAGGT AACTGGCTTG GAGGAGCGCA
     GAGACTCGAT GGTTGAGAAA CTTGGCTCCA TTGACCGAAC CTCCTCGCGT

151  GTCACTAAAA CTTGTCCTTT CAGTTTAGCC TTAACCGGCG CATGACTTCA
     CAGTGATTTT GAACAGGAAA GTCAAATCGG AATTGGCCGC GTACTGAAGT

201  AGACTAACTC CTCTAAAATCA ATTACCAGTG GCTGCTGCCA GTGGTGCTTT
     TCTGATTGAG GAGATTTAGT TAATGGTCAC CGACGACGGT CACCACGAAA

251  TGCATGTCTT TCCGGGTTGG ACTCAAGACG ATAGTTACCG GATAAGGCGC
     ACGTACAGAA AGGCCCAACC TGAGTTCTGC TATCAATGGC CTATTCCGCG

301  AGCGGTCGGA CTGAACGGGG GGTTCGTGCA TACAGTCCAG CTTGGAGCGA
     TCGCCAGCCT GACTTGCCCC CCAAGCACGT ATGTCAGGTC GAACCTCGCT

FIG. 35A-32

```
351  ACTGCCTACC  CGGAACTGAG  TGTCAGGCGT  GGAATGAGAC  AAACGCGGCC
     TGACGGATGG  GCCTTGACTC  ACAGTCCGCA  CCTTACTCTG  TTTGCGCCGG

AgeI
                 -------
401  ATAACAGCGG  AATGACACCG  GTAAACCGAA  AGGCAGGAAC  AGGAGAGCGC
     TATTGTCGCC  TTACTGTGGC  CATTTGGCTT  TCCGTCCTTG  TCCTCTCGCG

451  AGGAGGGAGC  CGCCAGGGGG  AAACGCCTGG  TATCTTTATA  GTCCTGTCGG
     TCCTCCCTCG  GCGGTCCCCC  TTTGCGGACC  ATAGAAATAT  CAGGACAGCC

501  GTTTCGCCAC  CACTGATTTG  AGCGTCAGAT  TTCGTGATGC  TTGTCAGGGG
     CAAAGCGGTG  GTGACTAAAC  TCGCAGTCTA  AAGCACTACG  AACAGTCCCC

551  GGCGGAGCCT  ATGGAAAAAC  GGCTTTGCCG  CGGCCCTCTC  ACTTCCCTGT
     CCGCCTCGGA  TACCTTTTTG  CCGAAACGGC  GCCGGGAGAG  TGAAGGGACA

601  TAAGTATCTT  CCTGGCATCT  TCCAGGAAAT  CTCCGCCCCG  TTCGTAAGCC
     ATTCATAGAA  GGACCGTAGA  AGGTCCTTTA  GAGGCGGGGC  AAGCATTCGG

651  ATTTCCGCTC  GCCGCAGTCG  AACGACCGAG  CGTAGCGAGT  CAGTGAGCGA
     TAAAGGCGAG  CGGCGTCAGC  TTGCTGGCTC  GCATCGCTCA  GTCACTCGCT
```

FIG. 35A-33

```
                                                             AgeI
                                                          / / / /
701  GGAAGCGGAA TATATCCTGT ATCACATATT CTGCTGACGC ACCGGTGCAG
     CCTTCGCCTT ATATAGGACA TAGTGTATAA GACGACTGCG TGGCCACGTC

XmnI
                       / / / / / /
751  CCTTTTTTCT CCTGCCACAT GAAGCACTTC ACTGACACCC TCATCAGTGC
     GGAAAAAAGA GGACGGTGTA CTTCGTGAAG TGACTGTGGG AGTAGTCACG

NheI
                       / / / /
801  CAACATAGTA AGCCAGTATA CACTCCGCTA GC
     GTTGTATCAT TCGGTCATAT GTGAGGCGAT CG
```

FIG. 35A-34

M13
49 bp

M13:

```
     BglII                       XmnI              BglII
     |----|                      |-------|         |----|
1  AGATCTCATA ACTTCGTATA ATGTATGCTA TACGAAGTTA TTCAGATCT
   TCTAGAGTAT TGAAGCATAT TACATACGAT ATGCTTCAAT AAGTCTAGA
```

FIG. 35A-36

M19:

```
     XbaI SphI                                              EcoRI
     ---- ----                                              -----
 1   TCTAGAGCAT GCGTAGGAGA AAATAAAATG AAACAAAGCA CTATTGCACT GAATTC
     AGATCTCGTA CGCATCCTCT TTTATTTTAC TTTGTTTCGT GATAACGTGA CTTAAG
             SapI
             ----
51   GGCACTCTTA CCGTTGCTCT TCACCCCTGT TACCAAAGCC
     CCGTGAGAAT GGCAACGAGA AGTGGGGACA ATGGTTTCGG
```

FIG. 35A-38

M 20:

```
     XbaI SphI
     ---- ----
  1  TCTAGAGCAT GCGTAGGAGA AAATAAAATG AAACAAAGCA CTATTGCACT
     AGATCTCGTA CGCATCCTCT TTTATTTTAC TTTGTTTCGT GATAACGTGA
                              SapI
                              ----
 51  GGCACTCTTA CCGTTGCTCT TCACCCCTGT TACCAAAGCC GACTACAAAG
     CCGTGAGAAT GGCAACGAGA AGTGGGGACA ATGGTTTCGG CTGATGTTTC
          MunI EcoRI
          ---- -----
101  ATGAAGTGCA ATTGGAATTC
     TACTTCACGT TAACCTTAAG
```

FIG. 35A-40

M21
96 bp

M 21:

```
     XbaI
     ------
 1.  TCTAGAGGTT GAGGTGATTT TATGAAAAAG AATATCGCAT TTCTTCTTGC
     AGATCTCCAA CTCCACTAAA ATACTTTTTC TTATAGCGTA AAGAAGAACG

NsiI             EcoRI
                                   --------         ------
51.  ATCTATGTTC GTTTTTCTA TTGCTACAAA TGCATACGCT GAATTC
     TAGATACAAG CAAAAAAGAT AACGATGTTT ACGTATGCGA CTTAAG
```

FIG. 35A-42

M 41:

```
        NheI
        ------
  1  GCTAGCATCG AATGGCGCAA AACCTTTCGC GGTATGGCAT GATAGCGCCC
     CGATCGTAGC TTACCGCGTT TTGGAAAGCG CCATACCGTA CTATCGCGGG

51  GGAAGAGAGT CAATTCAGGG TGGTGAATGT GAAACCAGTA ACGTTATACG
     CCTTCTCTCA GTTAAGTCCC ACCACTTACA CTTTGGTCAT TGCAATATGC

101  ATGTCGCAGA GTATGCCGGT GTCTCTTATC AGACCGTTTC CCGCGTGGTG
     TACAGCGTCT CATACGGCCA CAGAGAATAG TCTGGCAAAG GGCGCACCAC

151  AACCAGGCCA GCCACGTTTC TGCGAAAACG CGGGAAAAAG TGGAAGCGGC
     TTGGTCCGGT CGGTGCAAAG ACGCTTTTGC GCCCTTTTTC ACCTTCGCCG

201  GATGGCGGAG CTGAATTACA TTCCTAACCG CGTGGCACAA CAACTGGCGG
     CTACCGCCTC GACTTAATGT AAGGATTGGC GCACCGTGTT GTTGACCGCC

251  GCAAACAGTC GTTGCTGATT GGCGTTGCCA CCTCCAGTCT GGCCCTGCAC
     CGTTTGTCAG CAACGACTAA CCGCAACGGT GGAGGTCAGA CCGGGACGTG

301  GCGCCGTCGC AAATTGTCGC GGCGATTAAA TCTCGCGCCG ATCAACTGGG
     CGCGGCAGCG TTTAACAGCG CCGCTAATTT AGAGCGCGGC TAGTTGACCC
```

FIG. 35A-44

```
351  TGCCAGCGTG GTCGTGTCGA TGGTAGAACG AAGCGGCGTC GAAGCCTGTA
     ACGGTCGCAC CAGCACAGCT ACCATCTTGC TTCGCCGCAG CTTCGGACAT

401  AAGCGGCGGT GCACAATCTT CTCGCGCAAC GTGTCAGTGG GCTGATTATT
     TTCGCCGCCA CGTGTTAGAA GAGCGCGTTG CACAGTCACC CGACTAATAA

451  AACTATCCGC TGGATGACCA GGATGCTATT GCTGTGGAAG CTGCCTGCAC
     TTGATAGGCG ACCTACTGGT CCTACGATAA CGACACCTTC GACGGACGTG

501  TAATGTTCCG GCGTTATTTC TTGATGTCTC TGACCAGACA CCCATCAACA
     ATTACAAGGC CGCAATAAAG AACTACAGAG ACTGGTCTGT GGGTAGTTGT

551  GTATTATTTT CTCCCATGAG GACGGTACGC GACTGGGCGT GGAGCATCTG
     CATAATAAAA GAGGGTACTC CTGCCATGCG CTGACCCGCA CCTCGTAGAC

601  GTCGCATTGG GCCACCAGCA AATCGCGCTG TTAGCTGGCC CATTAAGTTC
     CAGCGTAACC CGGTGGTCGT TTAGCGCGAC AATCGACCGG GTAATTCAAG

651  TGTCTCGGCG CGTCTGGCGT TGGCTGGCTG GCATAAATAT CTCACTCGCA
     ACAGAGCCGC GCAGACCGCA ACCGACCGAC CGTATTTATA GAGTGAGCGT

701  ATCAAATTCA GCCGATAGCG GAACGGGAAG GCGACTGGAG TGCCATGTCC
     TAGTTTAAGT CGGCTATCGC CTTGCCCTTC CGCTGACCTC ACGGTACAGG
```

FIG. 35A-45

```
 751  GGTTTTCAAC AAACCATGCA AATGCTGAAT GAGGGCATCG TTCCCACTGC
      CCAAAAGTTG TTTGGTACGT TTACGACTTA CTCCCGTAGC AAGGGTGACG

801  GATGCTGGTT GCCAACGATC AGATGGCGCT GGGCGCAATG CGTGCCATTA
      CTACGACCAA CGGTTGCTAG TCTACCGCGA CCCGCGTTAC GCACGGTAAT

851  CCGAGTCCGG GCTGCGCGTT GGTGCGGACA TCTCGGTAGT GGGATACGAC
      GGCTCAGGCC CGACGCGCAA CCACGCCTGT AGAGCCATCA CCCTATGCTG

901  GATACCGAGG ACAGCTCATG TTATATCCCG CCGCTGACCA CCATCAAACA
      CTATGGCTCC TGTCGAGTAC AATATAGGGC GGCGACTGGT GGTAGTTTGT

951  GGATTTTCGC CTGCTGGGGC AAACCAGCGT GGACCGCTTG CTGCAACTCT
      CCTAAAAGCG GACGACCCCG TTTGGTCGCA CCTGGCGAAC GACGTTGAGA

1001  CTCAGGGCCA GGCGGTGAAG GGCAATCAGC TGTTGCCCGT CTCACTGGTG
      GAGTCCCGGT CCGCCACTTC CCGTTAGTCG ACAACGGGCA GAGTGACCAC

1051  AAAAGAAAAA CCACCCTGGC TCCCAATACG CAAACCGCCT CTCCCCGCGC
      TTTTCTTTTT GGTGGGACCG AGGGTTATGC GTTTGGCGGA GAGGGGCGCG

1101  GTTGGCCGAT TCACTGATGC AGCTGGCACG ACAGGTTTCC CGACTGGAAA
      CAACCGGCTA AGTGACTACG TCGACCGTGC TGTCCAAAGG GCTGACCTTT
```

FIG. 35A-46

```
1151  GCGGGCAGTG AGGCTACCCG ATAAAAGCGG CTTCCTGACA GGAGGCCGTT
      CGCCCGTCAC TCCGATGGGC TATTTTCGCC GAAGGACTGT CCTCCGGCAA

AflII
                              ------
1201  TTGTTTTTGCA GCCCACTTAA G
      AACAAAAACGT CGGGTGAATT C
```

FIG. 35A-47 pCAL0-1:
BglII
~~~~

```
  1  GATCTAGCAC CAGGGCGTTTA AGGGCACCAA TAACTGCCTT AAAAAAATTA
     CTAGATCGTG GTCCGCAAAT TCCCGTGGTT ATTGACGGAA TTTTTTTAAT

51  CGCCCCGCCC TGCCACTCAT CGCAGTACTG TTGTAATTCA TTAAGCATTC
     GCGGGGCGGG ACGGTGAGTA GCGTCATGAC AACATTAAGT AATTCGTAAG

101  TGCCGACATG GAAGCCATCA CAAACGGCAT GATGAACCTG AATCGCCAGC
     ACGGCTGTAC CTTCGGTAGT GTTTGCCGTA CTACTTGGAC TTAGCGGTCG

151  GGCATCAGCA CCTTGTCGCC TTGCGTATAA TATTTGCCCA TAGTGAAAAC
     CCGTAGTCGT GGAACAGCGG AACGCATATT ATAAACGGGT ATCACTTTTG

201  GGGGGCGAAG AAGTTGTCCA TATTGGCTAC GTTTAAATCA AAACTGGTGA
     CCCCCGCTTC TTCAACAGGT ATAACCGATG CAAATTTAGT TTTGACCACT

251  AACTCACCCA GGGATTGGCT GAGACGAAAA ACATATTCTC AATAAACCCT
     TTGAGTGGGT CCCTAACCGA CTCTGCTTTT TGTATAAGAG TTATTTGGGA

301  TTAGGGAAAT AGGCCAGGTT TTCACCGTAA CACGCCACAT CTTGCGAATA
     AATCCCTTTA TCCGGTCCAA AAGTGGCATT GTGCGGTGTA GAACGCTTAT
```

FIG. 35A-49

```
351  TATGTGTAGA AACTGCCGGA AATCGTCGTG GTATTCACTC CAGAGCGATG
     ATACACATCT TTGACGGCCT TTAGCAGCAC CATAAGTGAG GTCTCGCTAC

401  AAAACGTTTC AGTTTGCTCA TGGAAAACGG TGTAACAAGG GTGAACACTA
     TTTTGCAAAG TCAAACGAGT ACCTTTTGCC ACATTGTTCC CACTTGTGAT

451  TCCCATATCA CCAGCTCACC GTCTTTCATT GCCATACGGA ACTCCGGGTG
     AGGGTATAGT GGTCGAGTGG CAGAAAGTAA CGGTATGCCT TGAGGCCCAC

501  AGCATTCATC AGGCGGGCAA GAATGTGAAT AAAGGCCGA TAAAACTTGT
     TCGTAAGTAG TCCGCCCGTT CTTACACTTA TTTCCGGCCT ATTTGAACA

551  GCTTATTTTT CTTTACGGTC TTTAAAAAGG CCGTAATATC CAGCTGAACG
     CGAATAAAAA GAAATGCCAG AAATTTTTCC GGCATTATAG GTCGACTTGC

601  GTCTGGTTAT AGGTACATTG AGCAACTGAC TGAAATGCCT CAAAATGTTC
     CAGACCAATA TCCATGTAAC TCGTTGACTG ACTTTACGGA GTTTACAAG

651  TTTACGATGC CATTGGGATA TATCAACGGT GGTATATCCA GTGATTTTTT
     AAATGCTACG GTAACCCTAT ATAGTTGCCA CCATATAGGT CACTAAAAAA

701  TCTCCATTTT AGCTTCCTTA GCTCCTGAAA ATCTCGATAA CTCAAAAAAT
     AGAGGTAAAA TCGAAGGAAT CGAGGACTTT TAGAGCTATT GAGTTTTTTA
```

FIG. 35A-50

```
 751   ACGCCCGGTA GTGATCTTAT TTCATTATGG TGAAAGTTGG AACCTCACCC
       TGCGGGCCAT CACTAGAATA AAGTAATACC ACTTTCAACC TTGGAGTGGG
                  AatII
                  ------

801   GACGTCTAAT GTGAGTTAGC TCACTCATTA GGCACCCCAG GCTTTACACT
       CTGCAGATTA CACTCAATCG AGTGAGTAAT CCGTGGGGTC CGAAATGTGA

851   TTATGCTTCC GGCTCGTATG TTGTGTGGAA TTGTGAGCGG ATAACAATTT
       AATACGAAGG CCGAGCATAC AACACACCTT AACACTCGCC TATTGTTAAA
                                                  XbaI
                                                  ------

901   CACACAGGAA ACAGCTATGA CCATGATTAC GAATTTCTAG ACCCCCCCCC
       GTGTGTCCTT TGTCGATACT GGTACTAATG CTTAAAGATC TGGGGGGGGG
                  SphI                                HindIII
                  ------                              -------

951   CGCATGCCAT AACTTCGTAT AATGTACGCT ATACGAAGTT ATAAGCTTGA
       GCGTACGGTA TTGAAGCATA TTACATGCGA TATGCTTCAA TATTCGAACT

1001   CCTGTGAAGT GAAAAATGGC GCAGATTGTG CGACATTTTT TTTGTCTGCC
       GGACACTTCA CTTTTTACCG CGTCTAACAC GCTGTAAAAA AAACAGACGG
```

FIG. 35A-51

```
              PacI                             FseI                              BsrGI
              ~~~~~~                           ~~~~~~                            ~~~~~~
1051   GTTTAATTAA AGGGGGGGGG GGCCCGGCCT GGGGGGGGT GTACATGAAA
       CAAATTAATT TCCCCCCCCC CCGGGCCGGA CCCCCCCCA CATGTACTTT

1101   TTGTAAACGT TAATATTTTG TTAAAATTCG CGTTAAATTT TTGTTAAATC
       AACATTTGCA ATTATAAAAC AATTTTAAGC GCAATTTAAA AACAATTTAG

1151   AGCTCATTTT TTAACCAATA GGCCGAAATC GGCAAAATCC CTTATAAATC
       TCGAGTAAAA AATTGGTTAT CCGGCTTTAG CCGTTTTAGG GAATATTTAG

1201   AAAAGAATAG ACCGAGATAG GGTTGAGTGT TGTTCCAGTT TGGAACAAGA
       TTTTCTTATC TGGCTCTATC CCAACTCACA ACAAGGTCAA ACCTTGTTCT

1251   GTCCACTATT AAAGAACGTG GACTCCAACG TCAAAGGGCG AAAAACCGTC
       CAGGTGATAA TTTCTTGCAC CTGAGGTTGC AGTTTCCCGC TTTTTGGCAG

1301   TATCAGGGCG ATGGCCCACT ACGAGAACCA TCACCCTAAT CAAGTTTTTT
       ATAGTCCCGC TACCGGGTGA TGCTCTTGGT AGTGGGATTA GTTCAAAAAA

BanII
                                                                    ~~~~~~
1351   GGGGTCGAGG TGCCGTAAAG CACTAAATCG GAACCCTAAA GGGAGCCCCC
       CCCCAGCTCC ACGGCATTTC GTGATTTAGC CTTGGGATTT CCCTCGGGGG
```

FIG. 35A-52

```
1401  GATTTAGAGC  TTGACGGGGA  AAGCCGGCGA  ACGTGGCGAG  AAAGGAAGGG
      CTAAATCTCG  AACTGCCCCT  TTCGGCCGCT  TGCACCGCTC  TTTCCTTCCC

1451  AAGAAAGCGA  AAGGAGCGGG  CGCTAGGGCG  CTGGCAAGTG  TAGCCGTCAC
      TTCTTTCGCT  TTCCTCGCCC  GCGATCCCGC  GACCGTTCAC  ATCGCCAGTG

1501  GCTGCGCGTA  ACCACCACAC  CCGCCGCGCT  TAATGCGCCG  CTACAGGGCG
      CGACGCGCAT  TGGTGGTGTG  GGCGGCGCGA  ATTACGCGGC  GATGTCCCGC
             NheI

1551  CGTGCTAGCG  GAGTGTATAC  TGGCTTACTA  TGTTGGCACT  GATGAGGGTG
      GCACGATCGC  CTCACATATG  ACCGAATGAT  ACAACCGTGA  CTACTCCCAC
              XmnI                                         AgeI

1601  TCAGTGAAGT  GCTTCATGTG  GCAGGAGAAA  AAAGGCTGCA  CCGGTGCGTC
      AGTCACTTCA  CGAAGTACAC  CGTCCTCTTT  TTTCCGACGT  GGCCACGCAG

1651  AGCAGAATAT  GTGATACAGG  ATATATTCCG  CTTCCTCGCT  CACTGACTCG
      TCGTCTTATA  CACTATGTCC  TATATAAGGC  GAAGGAGCGA  GTGACTGAGC

1701  CTACGCTCGG  TCGTTCGACT  GCGGGCGAGC  GAAATGGCTT  ACGAACGGGG
```

FIG. 35A-53

```
         GATGCGAGCC AGCAAGCTGA CGCCGCTCGC CTTTACCGAA TGCTTGCCCC
1751     CGGAGATTTC CTGGAAGATG CCAGGAAGAT ACTTAACAGG GAAGTGAGAG
         GCCTCTAAAG GACCTTCTAC GGTCCTTCTA TGAATTGTCC CTTCACTCTC
1801     GGCCGCGGCA AAGCCGTTTT TCCATAGGCT CCGCCCCCCT GACAAGCATC
         CCGGCGCCGT TTCGGCAAAA AGGTATCCGA GGCGGGGGA CTGTTCGTAG
1851     ACGAAATCTG ACGCTCAAAT CAGTGGTGGC GAAACCCGAC AGGACTATAA
         TGCTTTAGAC TGCGAGTTTA GTCACCACCG CTTTGGGCTG TCCTGATATT
1901     AGATACCAGG CGTTTCCCCC TGGCGGCTCC CTCCTGCGCT CTCCTGTTCC
         TCTATGGTCC GCAAAGGGGG ACCGCCGAGG GAGGACGCGA GAGGACAAGG
              AgeI
              ~~~~~~~
1951     TGCCTTTTCGG TTTACCGGTG TCATTCCGCT GTTATGGCCG CGTTTGTCTC
         ACGGAAAGCC AAATGGCCAC AGTAAGGCGA CAATACCGGC GCAAACAGAG
2001     ATTCCACGCC TGACACTCAG TTCCGGGTAG GCAGTTCGCT CCAAGCTGGA
         TAAGGTGCGG ACTGTGAGTC AAGGCCCATC CGTCAAGCGA GGTTCGACCT
2051     CTGTATGCAC GAACCCCCCG TTCAGTCCGA CCGCTGCGCC TTATCCGGTA
         GACATACGTG CTTGGGGGGC AAGTCAGGCT GGCGACGCGG AATAGGCCAT

FIG. 35A-54
```

```
2101  ACTATCGTCT TGAGTCCAAC CCGGAAAGAC ATGCAAAAGC ACCACTGGCA
      TGATAGCAGA ACTCAGGTTG GGCCTTTCTG TACGTTTTCG TGGTGACCGT

2151  GCAGCCACTG GTAATTGATT TAGAGGAGTT AGTCTTGAAG TCATGCGCCG
      CGTCGGTGAC CATTAACTAA ATCTCCTCAA TCAGAACTTC AGTACGCGGC

2201  GTTAAGGCTA AACTGAAAGG ACAAGTTTTA GTGACTGCGC TCCTCCAAGC
      CAATTCCGAT TTGACTTTCC TGTTCAAAAT CACTGACGCG AGGAGGTTCG

2251  CAGTTACCTC GGTTCAAAGA GTTGGTAGCT CAGAGAACCT ACGAAAAACC
      GTCAATGGAG CCAAGTTTCT CAACCATCGA GTCTCTTGGA TGCTTTTTGG

2301  GCCCTGCAAG GCGGTTTTTT CGTTTTCAGA GCAAGAGATT ACGCGCAGAC
      CGGGACGTTC CGCCAAAAAA GCAAAAGTCT CGTTCTCTAA TGCGCGTCTG

BglII
                                        ~
2351  CAAAACGATC TCAAGAAGAT CATCTTATTA
      GTTTTGCTAG AGTTCTTCTA GTAGAATAAT
```

FIG. 35A-55 pCAL0-2:
BsrGI
-----

```
  1 GTACATGAAA TTGTAAACGT TAATATTTTG TTAAAATTCG CGTTAAATTT
    CATGTACTTT AACATTTGCA ATTATAAAAC AATTTTAAGC GCAATTTAAA

51 TTGTTAAATC AGCTCATTTT TTAACCAATA GGCCGAAATC GGCAAAATCC
    AACAATTTAG TCGAGTAAAA AATTGGTTAT CCGGCTTTAG CCGTTTTAGG

101 CTTATAAATC AAAAGAATAG ACCGAGATAG GGTTGAGTGT TGTTCCAGTT
    GAATATTTAG TTTTCTTATC TGGCTCTATC CCAACTCACA ACAAGGTCAA

151 TGGAACAAGA GTCCACTATT AAAGAACGTG GACTCCAACG TCAAAGGGCG
    ACCTTGTTCT CAGGTGATAA TTTCTTGCAC CTGAGGTTGC AGTTTCCCGC

201 AAAAACCGTC TATCAGGCCG ATGCCCACT ACGAGAACCA TCACCCTAAT
    TTTTTGGCAG ATAGTCCCGC TACCGGGTGA TGCTCTTGGT AGTGGGATTA

251 CAAGTTTTTT GGGGTCGAGG TGCCGTAAAG CACTAAATCG GAACCCTAAA
    GTTCAAAAAA CCCCAGCTCC ACGGCATTTC GTGATTTAGC CTTGGGATTT

BanII
    -----
301 GGGAGCCCCC GATTTAGAGC TTGACGGGGA AAGCCGGGCGA ACGTGGCGAG
```

FIG. 35A-57

```
                 CCCTCGGGGG CTAAATCTCG AACTGCCCCT TTCGGCCGCT TGCACCGCTC
351  AAAGGAAGGG AAGAAAGCGA AAGGAGCGGG CGCTAGGGCG CTGGCAAGTG
     TTTCCTTCCC TTCTTTCGCT TTCCTCGCCC GCGATCCCGC GACCGTTCAC
401  TAGCGGTCAC GCTGCGCGTA ACCACCACAC CCGCCGCGCT TAATGCGCCG
     ATCGCCAGTG CGACGCGCAT TGGTGGTGTG GGCGGCGCGA ATTACGGGC
              NheI
              ~~~~~~
451  CTACAGGGCG CGTGCTAGCG GAGTGTATAC TGGCTTACTA TGTTGGCACT
     GATGTCCCGC GCACGATCGC CTCACATATG ACCGAATGAT ACAACCGTGA
                           XmnI                     AgeI
                           ~~~~~~~~                 ~
501  GATGAGGGTG TCAGTGAAGT GCTTCATGTG GCAGGAGAAA AAAGGCTGCA
     CTACTCCCAC AGTCACTTCA CGAAGTACAC CGTCCTCTTT TTTCCGACGT
     AgeI
     ~~~~~
551  CCGGTGCGTC AGCAGAATAT GTGATACAGG ATATATTCCG CTTCCTCGCT
     GGCCACGCAG TCGTCTTATA CACTATGTCC TATATAAGGC GAAGGAGCGA
601  CACTGACTCG CTACGCTCGG TCGTTCGACT GCGGCGAGCG GAAATGGCTT
```

FIG. 35A-58

```
         GTGACTGAGC GATGCGAGCC AGCAAGCTGA CGCCGCTCGC CTTTACCGAA
651  ACGAACGGGG CGGAGATTTC CTGGAAGATG CCAGGAAGAT ACTTAACAGG
     TGCTTGCCCC GCCTCTAAAG GACCTTCTAC GGTCCTTCTA TGAATTGTCC
701  GAAGTGAGAG GGCCGCGGCA AAGCCGTTTT TCCATAGGCT CCGCCCCCCT
     CTTCACTCTC CCGGCGCCGT TTCGGCAAAA AGGTATCCGA GGCGGGGGGA
751  GACAAGCATC ACGAAATCTG ACGCTCAAAT CAGTGGTGGC GAAACCCGAC
     CTGTTCGTAG TGCTTTAGAC TGCGAGTTTA GTCACCACCG CTTTGGGCTG
801  AGGACTATAA AGATACCAGG CGTTTCCCCC TGGCGGCTCC CTCCTGCGCT
     TCCTGATATT TCTATGGTCC GCAAAGGGGG ACCGCCGAGG GAGGACGCGA
                             AgeI
                             - - - - - -
851  CTCCTGTTCC TGCCTTTCGG TTTACCGGTG TCATTCCGCT GTTATGGCCG
     GAGGACAAGG ACGGAAAGCC AAATGGCCAC AGTAAGGCGA CAATACCGGC
901  CGTTTGTCTC ATTCCACGCC TGACACTCAG TTCCGGGTAG GCAGTTCGCT
     GCAAACAGAG TAAGGTGCGG ACTGTGAGTC AAGGCCCATC CGTCAAGCGA
951  CCAAGCTGGA CTGTATGCAC GAACCCCCCG TTCAGTCCGA CCGCTGCGCC
     GGTTCGACCT GACATACGTG CTTGGGGGGC AAGTCAGGCT GGCGACGCGG
```

FIG. 35A-59

```
1001  TTATCCGGTA ACTATCGTCT TGAGTCCAAC CCGGAAAGAC ATGCAAAAGC
      AATAGGCCAT TGATAGCAGA ACTCAGGTTG GGCCTTTCTG TACGTTTTCG

1051  ACCACTGGCA GCAGCCACTG GTAATTGATT TAGAGGAGTT AGTCTTGAAG
      TGGTGACCGT CGTCGGTGAC CATTAACTAA ATCTCCTCAA TCAGAACTTC

1101  TCATGCGCCG GTTAAGGCTA AACTGAAAGG ACAAGTTTTA GTGACTGCGC
      AGTACGCGGC CAATTCCGAT TTGACTTTCC TGTTCAAAAT CACTGACGCG

1151  TCCTCCAAGC CAGTTACCTC GGTTCAAAGA GTTGGTAGCT CAGAGAACCT
      AGGAGGTTCG GTCAATGGAG CCAAGTTTCT CAACCATCGA GTCTCTTGGA

1201  ACGAAAAACC GCCCTGCAAG GCGGTTTTT CGTTTTCAGA GCAAGAGATT
      TGCTTTTTGG CGGGACGTTC CGCCAAAAAA GCAAAAGTCT CGTTCTCTAA

Bg1II
1251  ACGCGCAGAC CAAAACGATC TCAAGAAGAT CATCTTATTA GATCTAGCAC
      TGCGCGTCTG GTTTTGCTAG AGTTCTTCTA GTAGAATAAT CTAGATCGTG

1301  CAGGCGTTTA AGGGCACCAA TAACTGCCTT AAAAAAATTA CGCCCCGCCC
      GTCCGCAAAT TCCGTGGTT ATTGACGGAA TTTTTTTAAT GCGGGGCGGG
```

FIG. 35A-60

```
1351  TGCCACTCAT  CGCAGTACTG  TTGTAATTCA  TTAAGCATTC  TGCCGACATG
      ACGGTGAGTA  GCGTCATGAC  AACATTAAGT  AATTCGTAAG  ACGGCTGTAC

1401  GAAGCCATCA  CAAACGGCAT  GATGAACCTG  AATCGCCAGC  GGCATCAGCA
      CTTCGGTAGT  GTTTGCCGTA  CTACTTGGAC  TTAGCGGTCG  CCGTAGTCGT

1451  CCTTGTCGCC  TTGCGTATAA  TATTTGCCCA  TAGTGAAAAC  GGGGGCGAAG
      GGAACAGCGG  AACGCATATT  ATAAACGGGT  ATCACTTTTG  CCCCGCTTC

1501  AAGTTGTCCA  TATTGGCTAC  GTTTAAATCA  AAAACTGGTGA  AACTCACCCA
      TTCAACAGGT  ATAACCGATG  CAAATTTAGT  TTTGACCACT  TTGAGTGGGT

1551  GGGATTGGCT  GAGACGAAAA  ACATATTCTC  AATAAACCCT  TTAGGAAAT
      CCCTAACCGA  CTCTGCTTTT  TGTATAAGAG  TTATTTGGGA  AATCCCTTTA

1601  AGGCCAGGTT  TTCACCGTAA  CACGCCACAT  CTTGCGAATA  TATGTGTAGA
      TCCGGTCCAA  AAGTGGCATT  GTGCGGTGTA  GAACGCTTAT  ATACACATCT

1651  AACTGCCGGA  AATCGTCGTG  GTATTCACTC  CAGAGCGATG  AAAACGTTTC
      TTGACGGCCT  TTAGCAGCAC  CATAAGTGAG  GTCTCGCTAC  TTTTGCAAAG

1701  AGTTTGCTCA  TGGAAAACGG  TGTAACAAGG  GTGAACACTA  TCCCATATCA
      TCAAACGAGT  ACCTTTTGCC  ACATTGTTCC  CACTTGTGAT  AGGGTATAGT
```

FIG. 35A-61

```
1751  CCAGCTCACC GTCTTTCATT GCCATACGGA ACTCCGGGTG AGCATTCATC
      GGTCGAGTGG CAGAAAGTAA CGGTATGCCT TGAGGCCCAC TCGTAAGTAG

1801  AGGCGGGCAA GAATGTGAAT AAAGGCCGGA TAAAACTTGT GCTTATTTTT
      TCCGCCCGTT CTTACACTTA TTTCCGGCCT ATTTTGAACA CGAATAAAAA

1851  CTTTACGGTC TTTAAAAAGG CCGTAATATC CAGCTGAACG GTCTGGTTAT
      GAAATGCCAG AAATTTTTCC GGCATTATAG GTCGACTTGC CAGACCAATA

1901  AGTACATTG AGCAACTGAC TGAAATGCCT CAAAATGTTC TTTACGATGC
      TCCATGTAAC TCGTTGACTG ACTTTACGGA GTTTTACAAG AAATGCTACG

1951  CATTGGGATA TATCAACGGT GGTATATCCA GTGATTTTTT TCTCCATTTT
      GTAACCCTAT ATAGTTGCCA CCATATAGGT CACTAAAAAA AGAGGTAAAA

2001  AGCTTCCTTA GCTCCTGAAA ATCTCGATAA CTCAAAAAAT ACGCCCGTA
      TCGAAGGAAT CGAGGACTTT TAGAGCTATT GAGTTTTTTA TGCGGGCCAT

AatII
                                                    ,,,,
2051  GTGATCTTAT TTCATTATGG TGAAAGTTGG AACCTCACCC GACGTCTAAT
      CACTAGAATA AAGTAATACC ACTTTCAACC TTGGAGTGGG CTGCAGATTA

2101  GTGAGTTAGC TCACTCATTA GGCACCCCAG GCTTTACACT TTATGCTTCC
```

FIG. 35A-62

```
        CACTCAATCG AGTGAGTAAT CCGTGGGGTC CGAAATGTGA AATACGAAGG
2151    GGCTCGTATG TTGTGTGGAA TTGTGAGCGG ATAACAATTT CACACAGGAA
        CCGAGCATAC AACACACCTT AACACTCGCC TATTGTTAAA GTGTGTCCTT
                                  XbaI                    SphI
                                  -----                   -----
2201    ACAGCTATGA CCATGATTAC GAATTCCTAG ACCCCCCCCC CGCATGCCAT
        TGTCGATACT GGTACTAATG CTTAAGGATC TGGGGGGGGG GCGTACGGTA

HindIII
                                  -------
2251    AACTTCGTAT AATGTACGCT ATAAGCTTGA CCTGTGAAGT
        TTGAAGCATA TTACATGCGA TATTCGAACT GGACACTTCA
                                                         PacI
                                                         ----
2301    GAAAAATGGC GCAGATTGTG CGACATTTTT TTTGTCTGCC GTTTAATTAA
        CTTTTTACCG CGTCTAACAC GCTGTAAAAA AAACAGACGG CAAATTAATT
             FseI
             ----
2351    GGGGGGGGGC CGGCCATTAT CAAAAAGGAT CTCAAGAAGA TCCTTTGATC
        CCCCCCCCCG GCCGGTAATA GTTTTTCCTA GAGTTCTTCT AGGAAACTAG
```

FIG. 35A-63

```
2401  TTTTCTACGG GGTCTGACGC TCAGTGGAAC GAAAACTCAC GTTAAGGGAT
      AAAAGATGCC CCAGACTGCG AGTCACCTTG CTTTTGAGTG CAATTCCCTA

2451  TTTGGTCATG AGATTATCAA AAAGGATCTT CACCTAGATC CTTTTAAATT
      AAACCAGTAC TCTAATAGTT TTTCCTAGAA GTGGATCTAG GAAAATTTAA

2501  AAAAATGAAG TTTTAAATCA ATCTAAAGTA TATATGAGTA AACTTGGTCT
      TTTTTACTTC AAAATTTAGT TAGATTTCAT ATATACTCAT TTGAACCAGA

2551  GACAGTTACC CAATGCTTAA TCAGTGAGGC ACCTATCTCA GCGATCTGTC
      CTGTCAATGG GTTACGAATT AGTCACTCCG TGGATAGAGT CGCTAGACAG

2601  TATTTCGTTC ATCCATAGTT GCCTGACTCC CCGTCGTGTA GATAACTACG
      ATAAAGCAAG TAGGTATCAA CGGACTGAGG GGCAGCACAT CTATTGATGC

2651  ATACGGGAGG GCTTACCATC TGGCCCCAGT GCTGCAATGA TACCGCGAGA
      TATGCCCTCC CGAATGGTAG ACCGGGGTCA CGACGTTACT ATGGCGCTCT

2701  CCCACGCTCA CCGGCTCCAG ATTTATCAGC AATAAACCAG CCAGCCGGAA
      GGGTGCGAGT GGCCGAGGTC TAAATAGTCG TTATTTGGTC GGTCGGCCTT

2751  GGGCCGAGCG CAGAAGTGGT CCTGCAACTT TATCCGCCTC CATCCAGTCT
      CCCGGCTCGC GTCTTCACCA GGACGTTGAA ATAGGCGGAG GTAGGTCAGA
```

FIG. 35A-64

```
2801  ATTAACTGTT GCCGGGAAGC TAGAGTAAGT AGTTCGCCAG TTAATAGTTT
      TAATTGACAA CGGCCCTTCG ATCTCATTCA TCAAGCGGTC AATTATCAAA

2851  GCGCAACGTT GTTGCCATTG CTACAGGCAT CGTGGTGTCA CGCTCGTCGT
      CGCGTTGCAA CAACGGTAAC GATGTCCGTA GCACCACAGT GCGAGCAGCA

2901  TTGGTATGGC TTCATTCAGC TCCGGTTCCC AACGATCAAG GCGAGTTACA
      AACCATACCG AAGTAAGTCG AGGCCAAGGG TTGCTAGTTC CGCTCAATGT

2951  TGATCCCCCA TGTTGTGCAA AAAAGCGGTT AGCTCCTTCG GTCCTCCGAT
      ACTAGGGGGT ACAACACGTT TTTTCGCCAA TCGAGGAAGC CAGGAGGCTA

3001  CGTTGTCAGA AGTAAGTTGG CCGCAGTGTT ATCACTCATG GTTATGGCAG
      GCAACAGTCT TCATTCAACC GGCGTCACAA TAGTGAGTAC CAATACCGTC

3051  CACTGCATAA TTCTCTTACT GTCATGCCAT CCGTAAGATG CTTTTCTGTG
      GTGACGTATT AAGAGAATGA CAGTACGGTA GGCATTCTAC GAAAAGACAC

3101  ACTGGTGAGT ACTCAACCAA GTCATTCTGA GAATAGTGTA TGCGGCGACC
      TGACCACTCA TGAGTTGGTT CAGTAAGACT CTTATCACAT ACGCCGCTGG

3151  GAGTTGCTCT TGCCCGGCGT CAATACGGGA TAATACCCCG CCACATAGCA
      CTCAACGAGA ACGGGCCGCA GTTATGCCCT ATTATGGGGC GGTGTATCGT
```

FIG. 35A-65

```
                       XmnI
3201  GAACTTTAAA  AGTGCTCATC  ATTGGAAAAC  GTTCTTCGGG  GCGAAAACTC
      CTTGAAATTT  TCACGAGTAG  TAACCTTTTG  CAAGAAGCCC  CGCTTTTGAG

3251  TCAAGGATCT  TACCGCTGTT  GAGATCCAGT  TCGATGTAAC  CCACTCGCGC
      AGTTCCTAGA  ATGGCGACAA  CTCTAGGTCA  AGCTACATTG  GGTGAGCGCG

3301  ACCCAACTGA  TCCTCAGCAT  CTTTTACTTT  CACCAGCGTT  TCTGGGTGAG
      TGGGTTGACT  AGGAGTCGTA  GAAAATGAAA  GTGGTCGCAA  AGACCCACTC

3351  CAAAAACAGG  AAGGCAAAAT  GCCGCAAAAA  AGGGAATAAG  GGCGACACGG
      GTTTTTGTCC  TTCCGTTTTA  CGGCGTTTTT  TCCCTTATTC  CCGCTGTGCC

3401  AAATGTTGAA  TACTCATACT  CTTCCTTTTT  CAATATTATT  GAAGCATTTA
      TTTACAACTT  ATGAGTATGA  GAAGGAAAAA  GTTATAATAA  CTTCGTAAAT

BsrGI
3451  TCAGGGTTAT  TGTCTCATGA  GCGGATACAT  ATTTGAAT
      AGTCCCAATA  ACAGAGTACT  CGCCTATGTA  TAAACTTA
```

FIG. 35A-66 pCAL0-3:

```
      BglII
      ~~~~~~                                                          AatII
                                                                      ~~~~~~
  1   GATCTCATAA CTTCGTATAA TGTATGCTAT ACGAAGTTAT GACGTCTAAT
      CTAGAGTATT GAAGCATATT ACATACGATA TGCTTCAATA CTGCAGATTA

51   GTGAGTTAGC TCACTCATTA GGCACCCCAG GCTTTACACT TTATGCTTCC
      CACTCAATCG AGTGAGTAAT CCGTGGGGTC CGAAATGTGA AATACGAAGG

101   GGCTCGTATG TTGTGTGGAA TTGTGAGCGG ATAACAATTT CACACAGGAA
      CCGAGCATAC AACACACCTT AACACTCGCC TATTGTTAAA GTGTGTCCTT

XbaI                                       SphI
                           ~~~~~~                                     ~~~~~~
151   ACAGCTATGA CCATGATTAC GAATTTCTAG ACCCCCCCCC CGCATGCCAT
      TGTCGATACT GGTACTAATG CTTAAAGATC TGGGGGGGGG GCGTACGGTA

HindIII
                                       ~~~~~~
201   AACTTCGTAT AATGTACGCT ATACGAAGTT ATAAGCTTGA CCTGTGAAGT
      TTGAAGCATA TTACATGCGA TATGCTTCAA TATTCGAACT GGACACTTCA PacI
```

FIG. 35A-68

```
251  GAAAAATGGC GCAGATTGTG CGACATTTTT TTTGTCTGCC GTTTAATTAA
     CTTTTTACCG CGTCTAACAC GCTGTAAAAA AAACAGACGG CAAATTAATT
                 FseI
                 ~~~~~~~~~

301  GGGGGGGGGC CGGCCATTAT CAAAAAGGAT CTCAAGAAGA TCCTTTGATC
     CCCCCCCCCG GCCGGTAATA GTTTTTCCTA GAGTTCTTCT AGGAAACTAG

351  TTTTCTACGG GGTCTGACGC TCAGTGGAAC GAAAACTCAC GTTAAGGGAT
     AAAAGATGCC CCAGACTGCG AGTCACCTTG CTTTTGAGTG CAATTCCCTA

401  TTTGGTCATG AGATTATCAA AAAGGATCTT CACCTAGATC CTTTTAAATT
     AAACCAGTAC TCTAATAGTT TTTCCTAGAA GTGGATCTAG GAAAATTTAA

451  AAAAATGAAG TTTTAAATCA ATCTAAAGTA TATATGAGTA AACTTGGTCT
     TTTTTACTTC AAAATTTAGT TAGATTTCAT ATATACTCAT TTGAACCAGA

501  GACAGTTACC CAATGCTTAA TCAGTGAGGC ACCTATCTCA GCGATCTGTC
     CTGTCAATGG GTTACGAATT AGTCACTCCG TGGATAGAGT CGCTAGACAG

551  TATTTCGTTC ATCCATAGTT GCCTGACTCC CCGTCGTGTA GATAACTACG
     ATAAAGCAAG TAGGTATCAA CGGACTGAGG GGCAGCACAT CTATTGATGC
```

FIG. 35A-69

```
601  ATACGGGAGG GCTTACCATC TGGCCCCAGT GCTGCAATGA TACCGGAGA
     TATGCCCTCC CGAATGGTAG ACCGGGGTCA CGACGTTACT ATGGCGCTCT
651  CCCACGCTCA CCGGCTCCAG ATTTATCAGC AATAAACCAG CCAGCCGGAA
     GGGTGCGAGT GGCCGAGGTC TAAATAGTCG TTATTTGGTC GGTCGGCCTT
701  GGGCCGAGCG CAGAAGTGGT CCTGCAACTT TATCCGCCTC CATCCAGTCT
     CCCGGCTCGC GTCTTCACCA GGACGTTGAA ATAGGCGGAG GTAGGTCAGA
751  ATTAACTGTT GCCGGGAAGC TAGAGTAAGT AGTTCGCCAG TTAATAGTTT
     TAATTGACAA CGGCCCTTCG ATCTCATTCA TCAAGCGGTC AATTATCAAA
801  GCGCAACGTT GTTGCCATTG CTACAGGCAT CGTGGTGTCA CGCTCGTCGT
     CGCGTTGCAA CAACGGTAAC GATGTCCGTA GCACCACAGT GCGAGCAGCA
851  TTGGTATGGC TTCATTCAGC TCCGGTTCCC AACGATCAAG GCGAGTTACA
     AACCATACCG AAGTAAGTCG AGGCCAAGGG TTGCTAGTTC CGCTCAATGT
901  TGATCCCCCA TGTTGTGCAA AAAAGCGGTT AGCTCCTTCG GTCCTCCGAT
     ACTAGGGGGT ACAACACGTT TTTTCGCCAA TCGAGGAAGC CAGGAGGCTA
951  CGTTGTCAGA AGTAAGTTGG CCGCAGTGTT ATCACTCATG GTTATGGCAG
     GCAACAGTCT TCATTCAACC GGCGTCACAA TAGTGAGTAC CAATACCGTC
```

FIG. 35A-70

```
1001  CACTGCATAA  TTCTCTTACT  GTCATGCCAT  CCGTAAGATG  CTTTTCTGTG
      GTGACGTATT  AAGAGAATGA  CAGTACGGTA  GGCATTCTAC  GAAAAGACAC

1051  ACTGGTGAGT  ACTCAACCAA  GTCATTCTGA  GAATAGTGTA  TGCGGGCGACC
      TGACCACTCA  TGAGTTGGTT  CAGTAAGACT  CTTATCACAT  ACGCCCGCTGG

1101  GAGTTGCTCT  TGCCCGGCGT  CAATACGGGA  TAATACCGCG  CCACATAGCA
      CTCAACGAGA  ACGGGCCGCA  GTTATGCCCT  ATTATGGCGC  GGTGTATCGT
                                                XmnI
                                             ~~~~~~~~~
1151  GAACTTTAAA  AGTGCTCATC  ATTGGAAAAC  GTTCTTCGGG  GCGAAAACTC
      CTTGAAATTT  TCACGAGTAG  TAACCTTTTG  CAAGAAGCCC  CGCTTTTGAG

1201  TCAAGGATCT  TACCGCTGTT  GAGATCCAGT  TCGATGTAAC  CCACTCGCGC
      AGTTCCTAGA  ATGGCGACAA  CTCTAGGTCA  AGCTACATTG  GGTGAGCGCG

1251  ACCCAACTGA  TCCTCAGCAT  CTTTTACTTT  CACCAGCGTT  TCTGGGTGAG
      TGGGTTGACT  AGGAGTCGTA  GAAAATGAAA  GTGGTCGCAA  AGACCCACTC

1301  CAAAAACAGG  AAGGCAAAAT  GCCGCAAAAA  AGGGAATAAG  GGCGACACGG
      GTTTTTGTCC  TTCCGTTTTA  CGGCGTTTTT  TCCCTTATTC  CCGCTGTGCC

1351  AAATGTTGAA  TACTCATACT  CTTCCTTTTT  CAATATTATT  GAAGCATTTA
```

FIG. 35A-71

```
            TTTACAACTT ATGAGTATGA GAAGGAAAAA GTTATAATAA CTTCGTAAAT
                                                    BsrGI
                                                    ~~~~~~~
1401  TCAGGGTTAT TGTCTCATGA GCGGATACAT ATTTGAATGT ACATGAAATT
      AGTCCCAATA ACAGAGTACT CGCCTATGTA TAAACTTACA TGTACTTTAA

1451  GTAAACGTTA ATATTTTGTT AAAATTCGCG TTAAATTTTT GTTAAATCAG
      CATTTGCAAT TATAAAACAA TTTTAAGCGC AATTTAAAAA CAATTTAGTC

1501  CTCATTTTTT AACCAATAGG CCGAAATCGG CAAAATCCCT TATAAATCAA
      GAGTAAAAAA TTGGTTATCC GGCTTTAGCC GTTTTAGGGA ATATTTAGTT

1551  AAGAATAGAC CGAGATAGGG TTGAGTGTTG TTCCAGTTTG GAACAAGAGT
      TTCTTATCTG GCTCTATCCC AACTCACAAC AAGGTCAAAC CTTGTTCTCA

1601  CCACTATTAA AGAACGTGGA CTCCAACGTC AAAGGGCGAA AAACCGTCTA
      GGTGATAATT TCTTGCACCT GAGGTTGCAG TTTCCCGCTT TTTGGCAGAT

1651  TCAGGGCGAT GGCCCACTAC GAGAACCATC ACCCTAATCA AGTTTTTGG
      AGTCCCGCTA CCGGGTGATG CTCTTGGTAG TGGGATTAGT TCAAAAAACC
                                                 BanII
                                                 ~~~~~~~
```

FIG. 35A-72

```
1701  GGTCGAGGTG CCGTAAAGCA CTAAATCGGA ACCCTAAAGG GAGCCCCCGA
      CCAGCTCCAC GGCATTTCGT GATTTAGCCT TGGGATTTCC CTCGGGGGCT

1751  TTTAGAGCTT GACGGGGAAA GCCGGCGAAC GTGGCGAGAA AGGAAGGGAA
      AAATCTCGAA CTGCCCCTTT CGGCCGCTTG CACCGCTCTT TCCTTCCCTT

1801  GAAAGCGAAA GGAGCGGGCG CTAGGGCGCT GGCAAGTGTA GCGGTCACGC
      CTTTCGCTTT CCTCGCCCGC GATCCCGCGA CCGTTCACAT CGCCAGTGCG

1851  TGCGCGTAAC CACCACACCC GCCCGCTTTA ATGCCCCGCT ACAGGGCGCG
      ACGCGCATTG GTGGTGTGGG CGGGCGAAAT TACGGGGCGA TGTCCCGCGC
            NheI
            ~~~~~~~

1901  TGCTAGCGGA GTGTATACTG GCTTACTATG TTGGCACTGA TGAGGGTGTC
      ACGATCGCCT CACATATGAC CGAATGATAC AACCGTGACT ACTCCCACAG
                 XmnI                                    AgeI
                 ~~~~~~~                                 ~~~~~~~

1951  AGTGAAGTGC TTCATGTGGC AGGAGAAAAA AGGCTGCACC GGTGCGTCAG
      TCACTTCACG AAGTACACCG TCCTCTTTTT TCCGACGTGG CCACGCAGTC

2001  CAGAATATGT GATACAGGAT ATATTCCGCT TCCTCGCTCA CTGACTCGCT
      GTCTTATACA CTATGTCCTA TATAAGGCGA AGGAGCGAGT GACTGAGCGA
```

FIG. 35A-73

```
2051  ACGCTCGGTC GTTCGACTGC GGCGAGCGGA AATGGCTTAC GAACGGGGCG
      TGCGAGCCAG CAAGCTGACG CCGCTCGCCT TTACCGAATG CTTGCCCCGC

2101  GAGATTTCCT GGAAGATGCC AGGAAGATAC TTAACAGGGA AGTGAGAGGG
      CTCTAAAGGA CCTTCTACGG TCCTTCTATG AATTGTCCCT TCACTCTCCC

2151  CCGCGGCAAA GCCGTTTTC  CATAGGCTCC GCCCCCCTGA CAAGCATCAC
      GGCGCCGTTT CGGCAAAAAG GTATCCGAGG CGGGGGGACT GTTCGTAGTG

2201  GAAATCTGAC GCTCAAATCA GTGGTGGCGA AACCCGACAG GACTATAAAG
      CTTTAGACTG CGAGTTTAGT CACCACCGCT TTGGGCTGTC CTGATATTTC

2251  ATACCAGGCG TTTCCCCCTG GCGGCTCCCT CCTGCGCTCT CCTGTTCCTG
      TATGGTCCGC AAAGGGGGAC CGCCGAGGGA GGACGCGAGA GGACAAGGAC
                 AgeI
                 ------

2301  CCTTTCGGTT TACCGGTGTC ATTCCGCTGT TATGGCCGCG TTTGTCTCAT
      GGAAAGCCAA ATGGCCACAG TAAGGCGACA ATACCGGCGC AAACAGAGTA

2351  TCCACGCCTG ACACTCAGTT CCGGGTAGGC AGTTCGCTCC AAGCTGGACT
      AGGTGCGGAC TGTGAGTCAA GGCCCATCCG TCAAGCGAGG TTCGACCTGA
```

FIG. 35A-74

```
2401  GTATGCACGA  ACCCCCCGTT  CAGTCCGACC  GCTGCGCCTT  ATCCGGTAAC
      CATACGTGCT  TGGGGGGCAA  GTCAGGCTGG  CGACGCGGAA  TAGGCCATTG

2451  TATCGTCTTG  AGTCCAACCC  GGAAAGACAT  GCAAAAGCAC  CACTGGCAGC
      ATAGCAGAAC  TCAGGTTGGG  CCTTTCTGTA  CGTTTTCGTG  GTGACCGTCG

2501  AGCCACTGGT  AATTGATTTA  GAGGAGTTAG  TCTTGAAGTC  ATGCGCCGGT
      TCGGTGACCA  TTAACTAAAT  CTCCTCAATC  AGAACTTCAG  TACGCGGCCA

2551  TAAGGCTAAA  CTGAAAGGAC  AAGTTTTAGT  GACTGCGCTC  CTCCAAGCCA
      ATTCCGATTT  GACTTTCCTG  TTCAAAATCA  CTGACGCGAG  GAGGTTCGGT

2601  GTTACCTCGG  TTCAAAGAGT  TGGTAGCTCA  GAGAACCTAC  GAAAAACCGC
      CAATGGAGCC  AAGTTTCTCA  ACCATCGAGT  CTCTTGGATG  CTTTTTGGCG

2651  CCTGCAAGGC  GGTTTTTTCG  TTTTCAGAGC  AAGAGATTAC  GCGCAGACCA
      GGACGTTCCG  CCAAAAAAGC  AAAAGTCTCG  TTCTCTAATG  CGCGTCTGGT
                                         BglII

2701  AAACGATCTC  AAGAAGATCA  TCTTATTA
      TTTGCTAGAG  TTCTTCTAGT  AGAATAAT
```

FIG. 35A-75

M1: PCR using template
NoVspAatII: TAGACGTC

M2: synthesis
BloxA-A: TATGAGATCTCATAACTTCGTATAATGTACGCTATACG-
AAGTTAT

BloxA-B: TAATAACTTCGTATAGCATACATTATACGAAGTTATG-
AGATCTCA

M3: PCR, NoVspAatII as second oligo
XloxS-muta: CATTTTTTGCCCTCGTTATCTACGCATGCGATAACTTCGTA-
TAGCGTACATTATACGAAGTTATTCTAGACATGGTCATAGCTGTTTCCTG

M7-I: PCR
gIIINEW-fow: GGGGGGGAATTCGGTGGTGGTGGATCTGCGTGCGCTG-
AAACGGTTGAAAGTTG gIIINEW-rev: CCCCCCCAAGCTTATCAAGACTCCTTATTACG

M7-II: PCR
gIIIss-fow: GGGGGGGGGAATTCGGAGGCGGTTCCGGTGGTGGC

M7-III: PCR
gIIIsupernew-fow: GGGGGGGGGAATTCGAGCAGAAGCTGATCTCT-
GAGGAGGATCTGTAGGGTGGTGGCTCTGGTTCCGGTGATTTTG

FIG. 35A-76

M8: synthesis lox514-A: CCATAACTTCGTATAATGTACGCTATACGAAGTTATA lox514-B: AGCTTATAACTTCGTATAGCGTACATTATACGAAGT-
TATGGCATG

M9II: synthesis

M9II-fow: AGCTTGACCTGTGAAGTGAAAAATGGCGCAGATT-
GTGCGACATTTTTTTTGTCTGCCGTTTAATTAAAGGGGGGGT M9II-rev: GTACACCCCCCCCCAGGCCGGCCCCCCCCCCCTTTAA-
TTAAACGGCAGACAAAAAAAATGTCGCACAATCTGCG

M10II: assembly PCR with template bla-fow: GGGGGGGGTGTACATTCAAATATGTATCCGCTCATG bla-seq4: GGGTTACATCGAACTGGATCTC bla1-muta: CCAGTTCGATGTAACCCACTCGCGCACCCAACTGATC-
CTCAGCATCTTTTACTTTCACC blaII-muta: ACTCTAGCTTCCCGGCAACAGTTAATAGACTGGATG-
GAGGCGG bla-NEW: CTGTTGCCGGGAAGCTAGAGTAAG bla-rev: CCCCCCCTTAATTAAGGGGGGGGGGCCGGCCATTATCAAA-
AAGGATCTCAAGAAGATCC

M11II/III: PCR, site-directed mutagenesis

FIG. 35A-77 f1-fow: GGGGGGGGGCTAGCACGCGCCCTGTAGCGGCGCATTAA f1-rev: CCCCCCCTGTACATGAAATTGTAAACGTTAATATTTTG f1-t133.muta: GGGCGATGGCCCACTACGAGAACCATCACCCTAATC M12: assembly PCR using template p15-fow: GGGGGGGAGATCTAATAAGATGATCTTCTTGAG p15-NEWI: GAGTTGGTAGCTCAGAGAACCTACGAAAAACCGCCCTG-CAAGGCG p15-NEWII: GTAGGTTCTCTGAGCTACCAACTC p15-NEWIII: GTTTCCCCCTGGCGGCTCCCTCCTGCGCTCTCCTGTTCCT-GCC p15-NEWIV: AGGAGGGAGCCGCCAGGGGGAAAC p15-rev: GACATCAGCGCTAGCGGAGTGTATAC M13: synthesis BloxXB-A: GATCTCATAACTTCGTATAATGTATGCTATACGAAGTTA-TTCA BloxXB-B: GATCTGAATAACTTCGTATAGCATACATTATACGAAGTTA-TGAGA M14-Ext2: PCR, site-directed mutagenesis ColEXT2-fow: GGGGGGGAGATCTGACCAAAATCCCTTAACGTGAG Col-mutal: GGTATCTGCGCTCTGCTGTAGCCAGTTACCTTCGG

FIG. 35A-78

Col-rev: CCCCCCCGCTAGCCATGTGAGCAAAAGGCCAGCAA

M17: assembly PCR using template

CAT-1: GGGACGTCGGGTGAGGTTCCAAC

CAT-2: CCATACGGAACTCCGGGTGAGCATTCATC

CAT-3: CCGGAGTTCCGTATGG

CAT-4: ACGTTTAAATCAAAACTGG

CAT-5: CCAGTTTTGATTTAAACGTAGCCAATATGGACAACTTCTTC-GCCCCCGTTTTCACTATGGGCAAATATT

CAT-6: GGAAGATCTAGCACCAGGCGTTTAAG

M41: assembly PCR using template

LAC1: GAGGCCGGCCATCGAATGGCGCAAAAC

LAC2: CGCGTACCGTCCTCATGGGAGAAAATAATAC

LAC3: CCATGAGGACGGTACGCGACTGGGCGTGGAGCATCTGGTCGCA-TTGGGTCACCAGCAAATCCGCTGTTAGCTGGCCCATTAAG

LAC4: GTCAGCGGCGGGATATAACATGAGCTGTCCTCGGTATCGTCG

LAC5: GTTATATCCCGCCGCTGACCACCATCAAAC

LAC6: CATCAGTGAATCGGCCAACGCGCGGGGAGAGGCGGTTTGCGT4TTG-GGAGCCAGGGTGGTTTTTC

LAC7: GGTTAATTAACCTCACTGCCCGCTTTCCAGTCGGGAAACCTGTCGTGCC-AGCTGCATCAGTGAATCGGCCAAC

M41-MCS-fow: CTAGACTAGTGTTTAAACCGGACCGGGGGGGGGGCTT-AAGGGGGGGGGGGGG

FIG. 35A-79

M41-MCS-rev: CTAGCCCCCCCCCCCCTTAAGCCCCCCCCCGGTCCGGT-
TTAAACACTAGT

M41-fow: CTAGACTAGTGTTTAAACCGGACCGGGGGGGGGCTTAA-
GGGGGGGGGGGG

M41-rev: CCCCCCCTTAAGTGGGCTGCAAAACAAAACGGCCTCC-
TGTCAGGAAGCCGCTTTTATCGGGTAGCCTCACTGCCCGCTTCC

M41-A2: GTTGTTGTGCCACGCGGTTAGGAATGTAATTCAGCTCCGC

M41-B1: AACCGCGTGGCACAACAAC

M41-B2: CTTCGTTCTACCATCGACACGACCACGCTGGCACCCAGTTG

M41-C1: GTGTCGATGGTAGAACGAAG

M41-CII: CCACAGCAATAGCATCCTGGTCATCCAGCGGATAGTT-
AATAATCAGCCCACTGACACGTTGCGCGAG

M41-DI: GACCAGGATGCTATTGCTGTGG

M41-DII: CAGCGCGATTTGCTGGTGGCCCAATGCGACCAGATGC

M41-EI: CACCAGCAAATCGCGCTG

M41-EII: CCCGGACTCGGTAATGGCACGCATTGCGCCCAGCGCC

M41-FI: GCCATTACCGAGTCCGGG

<u>M42: synthesis</u>

Eco-H5-Hind-fow: AATTCCACCATCATCACCATTGACGTCTA

Eco-H5-Hind-rev: AGCTTAGACGTCAATGGTGATGATGGTGG

FIG. 35A-80

```
         MluI  Bsu36I                                                  StyI
           ~    ~                                                        ~
         HpaI  BstEII           BstXI          MscI            PspSII  BsiWI NspV
          ~     ~                 ~             ~               ~       ~     ~
126  CGCGTTAACC TCAGGTGACC AAGCCCCTGG CGGTACCAGG CCAAGGTCCC GTACGTTCGA
     GCGCAATTGG AGTCCACTGG TTCGGGGACC GCCATGGTCC GGTTCCAGGG CATGCAAGCT

PmlI                                   FseI          EcoO109I
                 ~                                      ~               ~
         NspVBsaBI      BamHI  KpnI              CCGGCCATTA  TCAAAAAGGA
          ~    ~          ~     ~                 ~
176  AGATTACCAT CACGTGGATC CGGTACCAGG CCGGCCATTA TCAAAAAGGA
     TCTAATGGTA GTGCACCTAG GCCATGGTCC GGCCGGTAAT AGTTTTTCCT

226  TCTCAAGAAG ATCCTTTGAT CTTTTCTACG GGGTCTGACG CTCAGTGGAA
     AGAGTTCTTC TAGGAAACTA GAAAAGATGC CCCAGACTGC GAGTCACCTT

276  CGAAAACTCA CGTTAAGGGA TTTTGGTCAT GAGATTATCA AAAAGGATCT
     GCTTTTGAGT GCAATTCCCT AAAACCAGTA CTCTAATAGT TTTTCCTAGA
```

FIG. 36B

```
326  TCACCTAGAT CCTTTTAAAT TAAAAATGAA GTTTTAAATC AATCTAAAGT
     AGTGGATCTA GGAAAATTTA ATTTTTACTT CAAAATTTAG TTAGATTTCA

376  ATATATGAGT AAACTTGGTC TGACAGTTAC CAATGCTTAA TCAGTGAGGC
     TATATACTCA TTTGAACCAG ACTGTCAATG GTTACGAATT AGTCACTCCG

426  ACCTATCTCA GCGATCTGTC TATTTCGTTC ATCCATAGTT GCCTGACTCC
     TGGATAGAGT CGCTAGACAG ATAAAGCAAG TAGGTATCAA CGGACTGAGG

476  CCGTCGTGTA GATAACTACG ATACGGGAGG GCTTACCATC TGGCCCCAGT
     GGCAGCACAT CTATTGATGC TATGCCCTCC CGAATGGTAG ACCGGGGTCA

526  GCTGCAATGA TACCGCGAGA CCCACGCTCA CCGGCTCCAG ATTTATCAGC
     CGACGTTACT ATGGCGCTCT GGGTGCGAGT GGCCGAGGTC TAAATAGTCG

576  AATAAACCAG CCAGCCGGAA GGGCCGAGCG CAGAAGTGGT CCTGCAACTT
     TTATTTGGTC GGTCGGCCTT CCCGGCTCGC GTCTTCACCA GGACGTTGAA

626  TATCCGCCTC CATCCAGTCT ATTAACTGTT GCCGGGAAGC TAGAGTAAGT
     ATAGGCGGAG GTAGGTCAGA TAATTGACAA CGGCCCTTCG ATCTCATTCA

676  AGTTCGCCAG TTAATAGTTT GCGCAACGTT GTTGCCATTG CTACAGGCAT
     TCAAGCGGTC AATTATCAAA CGCGTTGCAA CAACGGTAAC GATGTCCGTA
```

FIG. 36C

```
 726  CGTGGTGTCA CGCTCGTCGT TTGGTATGGC TTCATTCAGC TCCGGTTCCC
      GCACCACAGT GCGAGCAGCA AACCATACCG AAGTAAGTCG AGGCCAAGGG

776  AACGATCAAG GCGAGTTACA TGATCCCCCA TGTTGTGCAA AAAAGCGGTT
      TTGCTAGTTC CGCTCAATGT ACTAGGGGGT ACAACACGTT TTTTCGCCAA

826  AGCTCCTTCG GTCCTCCGAT CGTTGTCAGA AGTAAGTTGG CCGCAGTGTT
      TCGAGGAAGC CAGGAGGCTA GCAACAGTCT TCATTCAACC GGCGTCACAA

876  ATCACTCATG GTTATGGCAG CACTGCATAA TTTCTCTTACT GTCATGCCAT
      TAGTGAGTAC CAATACCGTC GTGACGTATT AAGAGAATGA CAGTACGGTA

926  CCGTAAGATG CTTTTCTGTG ACTGGTGAGT ACTCAACCAA GTCATTCTGA
      GGCATTCTAC GAAAAGACAC TGACCACTCA TGAGTTGGTT CAGTAAGACT

976  GAATAGTGTA TGCGGCGACC GAGTTGCTCT TGCCCGGCGT CAATACGGGA
      CTTATCACAT ACGCCGCTGG CTCAACGAGA ACGGGCCGCA GTTATGCCCT

1026  TAATACCGCG CCACATAGCA GAACTTTAAA AGTGCTCATC ATTGGAAAAC
      ATTATGGCGC GGTGTATCGT CTTGAAATTT TCACGAGTAG TAACCTTTTG

1076  GTTCTTCGGG GCGAAAACTC TCAAGGATCT TACCGCTGTT GAGATCCAGT
      CAAGAAGCCC CGCTTTTGAG AGTTCCTAGA ATGGCGACAA CTCTAGGTCA
```

FIG. 36D

```
1126  TCGATGTAAC CCACTCGTGC ACCCAACTGA TCTTCAGCAT CTTTTACTTT
      AGCTACATTG GGTGAGCACG TGGGTTGACT AGAAGTCGTA GAAAATGAAA
                 BssSI                 Eco57I
                 ~~~~                  ~~~~

1176  CACCAGCGTT TCTGGGTGAG CAAAAACAGG AAGGCAAAAT GCCGCAAAAA
      GTGGTCGCAA AGACCCACTC GTTTTTGTCC TTCCGTTTTA CGGCGTTTTT

1226  AGGGAATAAG GGCGACACGG AAATGTTGAA TACTCATACT CTTCCTTTTT
      TCCCTTATTC CCGCTGTGCC TTTACAACTT ATGAGTATGA GAAGGAAAAA

1276  CAATATTATT GAAGCATTTA TCAGGGTTAT TGTCTCATGA GCGGATACAT
      GTTATAATAA CTTCGTAAAT AGTCCCAATA ACAGAGTACT CGCCTATGTA
                                      PstI                XhoI
                                      ~~~~                ~~~~
                   EagI  BssSI         BbeI  AseI             BssHII
                   ~~~~  ~~~~          ~~~~  ~~~~             ~~~~

1326  ATTTGAATGT ACTCGGCCGC ACGAGCTGCA GGCGCCATTA ATGGCTCGAG
      TAAACTTACA TGAGCCGGCG TGCTCGACGT CCGCGGTAAT TACCGAGCTC

BsspEI BsrGI
      ~~~~
      BssHII
      ~~~~
```

FIG. 36E

1376  CGCGCTTCAG CGCTTTGTCT TCCGGATGTA CATGAAATT
      GCGCGAAGTC GCGAAACAGA AGGCCTACAT GTACTTTAA
      Eco57I         BbsI

FIG. 36F

```
              1              10
O_K3L_5  5'- G C C T G C A A G C G G A A G A C
                                   Bbsl
                                  E     D
Vk1 & Vk3 5'- G C C T G C A A G C G G A A G A C E     D
Vk2      5'- G C C T G C A A G C G G A A G A C
                                  E     D
Vk4      5'- G C C T G C A A G C G G A A G A C
```

*FIG. 37A*

|  | 50 |  |  | 60 |
|---|---|---|---|---|
|  |  |  |  | 3'- G G A |
|  |  |  |  |  |
|  |  |  |  | T |
| G |  |  |  | A C C T |
|  |  |  |  |  |
|  |  |  |  | T |
| G |  |  |  | A C C T |
|  |  |  |  | T |
| G |  |  |  | A C C T |

| | | | | |
|---|---|---|---|---|
| G C T |  |  | G C T | G C T |
| G A T | G A T | G A T | G A T | G A T |
| G A G |  |  | G A G | G A G |
| T T T |  |  | T T T | T T T |
| G G T | G G T | G G T | G G T | G G T |
| C A T |  |  | C A T | C A T |
| A T T |  |  | A T T | A T T |
| A A G |  |  | A A G | A A G |
| C T T |  |  | C T T | C T T |
| A T G |  |  | A T G | A T G |
| A A T | A A T | A A T | A A T | A A T |
|  |  | C C T | C C T | C C T |
| C A G |  |  | C A G | C A G |
| C G T |  |  | C G T | C G T |
| T C T | T C T | T C T | T C T | T C T |
| A C T |  |  | A C T | A C T |
| G T T |  |  | G T T | G T T |
| T G G |  |  | T G G | T G G |
| T A T | T A T |  | T A T | T A T |
| 50% Y |  |  | 80% P |  |

FIG. 37C

```
                   70                    80 81
         A A C C G G T A A G C T T T C G G  -5' O_K3L_3
              ┌─────────┐
              │   MscI  │
         F    G      Q
         T │T G G C C A│T T C G A A A G C C  -3'

```
                              60            70              80
                                    G   G   G   T   K   L
                              G G C G G C G G C A C G A A G T T A
                    ┌─────────────────────────────┐
                    │      gap   gap  │
                    │- G C T G C T G C T G C T│
                    │                 │
                    │ G A T G A T G A T G A T│
                    │ G A G G A G G A G G A G│
                    │ T T T T T T T T T T T T│
                    │ G G T G G T G G T G G T│
                    │ C A T C A T C A T C A T│
                    │ A T T A T T A T T A T T│
                    │ A A G A A G A A G A A G│
                    │ C T T C T T C T T C T T│
                    │ A T G A T G A T G A T G│
                    │ A A T A A T A A T A A T│
                    │ C C T C C T C C T C C T│
                    │ C A G C A G C A G C A G│
                    │ C G T C G T C G T C G T│
                    │ T C T T C T T C T T C T│
                    │ A C T A C T A C T A C T│
                    │ G T T G T T G T T G T T│
                    │                 T G G│
                    │ T A T T A T T A T T A T│  Variability
                    └─────────────────────────────┘
                         18              19      3.32E+05
                         18    18        19      5.98E+06
                         18    18    18  19      1.08E+08
```

| % soluble | κ1 | κ2 | κ3 | κ4 | λ1 | λ2 | λ3 |
|---|---|---|---|---|---|---|---|
| H1A | 61% | 58% | 52% | 42% | 90% | 61% | 60% |
| H1B | 39% | 48% | 66% | 48% | 47% | 39% | 36% |
| H2 | 47% | 57% | 46% | 49% | 37% | 36% | 45% |
| H3 | 85% | 67% | 76% | 61% | 80% | 71% | 83% |
| H4 | 69% | 52% | 51% | 44% | 45% | 33% | 42% |
| H5 | 49% | 49% | 46% | 67% | 54% | 46% | 47% |
| H6 | 90% | 58% | 54% | 47% | 45% | 50% | 51% |

| Total amount compared to H3κ2 | κ1 | κ2 | κ3 | κ4 | λ1 | λ2 | λ3 |
|---|---|---|---|---|---|---|---|
| H1A | 289% | 94% | 166% | 272% | 20% | 150% | 78% |
| H1B | 219% | 122% | 89% | 139% | 117% | 158% | 101% |
| H2 | 186% | 223% | 208% | 182% | 126% | 60% | 97% |
| H3 | 50% | 55% | 71% | 54% | 59% | 130% | 47% |
| H4 | 37% | 60% | 77% | 195% | 107% | 251% | |
| H5 | 98% | 201% | 167% | 83% | 93% | 128% | 115% |
| H6 | 65% | 117% | 89% | 109% | 299% | 215% | 278% |

*FIG. 40A*

| Soluble amount compared to H3κ2 | κ1 | κ2 | κ3 | κ4 | λ1 | λ2 | λ3 |
|---|---|---|---|---|---|---|---|
| H1A | 191% | 88% | 121% | 122% | 26% | 211% | 76% |
| H1B | 124% | 95% | 83% | 107% | 79% | 142% | 59% |
| H2 | 126% | 204% | 139% | 130% | 66% | 50% | 70% |
| H3 | 63% | - | 81% | 49% | 69% | 143% | 61% |
| H4 | 40% | 47% | 49% | 54% | 95% | 55% | 125% |
| H5 | 69% | 158% | 116% | 80% | 72% | 84% | 84% |
| H6 | 85% | 122% | 87% | 77% | 162% | 162% | 212% |

| McPC | |
|---|---|
| soluble | 38% |
| %H3k2 total | 117% |
| %H3k2 soluble | 69% |

FIG. 40B

PROTEIN(POLY)PEPTIDE LIBRARIES

This is a divisional of application Ser. No. 09/025,769 now U.S. Pat. No. 6,300,064, filed Feb. 18, 1998 which is a continuation of PCT/EP96/03647, filed Aug. 19, 1995.

FIELD OF THE INVENTION

The present invention relates to synthetic DNA sequences which encode one or more collections of homologous proteins/(poly)peptides, and methods for generating and applying libraries of these DNA sequences. In particular, the invention relates to the preparation of a library of human-derived antibody genes by the use of synthetic consensus sequences which cover the structural repertoire of antibodies encoded in the human genome. Furthermore, the invention relates to the use of a single consensus antibody gene as a universal framework for highly diverse antibody libraries.

BACKGROUND TO THE INVENTION

All current recombinant methods which use libraries of proteins/(poly)peptides, e.g. antibodies, to screen for members with desired properties, e.g. binding a given ligand, do not provide the possibility to improve the desired properties of the members in an easy and rapid manner. Usually a library is created either by inserting a random oligonucleotide sequence into one or more DNA sequences cloned from an organism, or a family of DNA sequences is cloned and used as the library. The library is then screened, e.g. using phage display, for members which show the desired property. The sequences of one or more of these resulting molecules are then determined. There is no general procedure available to improve these molecules further on.

Winter (EP 0 368 684 B1) has provided a method for amplifying (by PCR), cloning, and expressing antibody variable region genes. Starting with these genes he was able to create libraries of functional antibody fragments by randomizing the CDR3 of the heavy and/or the light chain. This process is functionally equivalent to the natural process of VJ and VDJ recombination which occurs during the development of B-cells in the immune system.

However the Winter invention does not provide a method for optimizing the binding affinities of antibody fragments further on, a process which would be functionally equivalent to the naturally occurring phenomenon of "affinity maturation", which is provided by the present invention. Furthermore, the Winter invention does not provide for artificial variable region genes, which represent a whole family of structurally similar natural genes, and which can be assembled from synthetic DNA oligonucleotides. Additionally, Winter does not enable the combinatorial assembly of portions of antibody variable regions, a feature which is provided by the present invention. Furthermore, this approach has the disadvantage that the genes of all antibodies obtained in the screening procedure have to be completely sequenced, since, except for the PCR priming regions, no additional sequence information about the library members is available. This is time and labor intensive and potentially leads to sequencing errors.

The teaching of Winter as well as other approaches have tried to create large antibody libraries having high diversity in the complementarity determining regions (CDRs) as well as in the frameworks to be able to find antibodies against as many different antigens as possible. It has been suggested that a single universal framework may be useful to build antibody libraries, but no approach has yet been successful.

Another problem lies in the production of reagents derived from antibodies. Small antibody fragments show exciting promise for use as therapeutic agents, diagnostic reagents, and for biochemical research. Thus, they are needed in large amounts, and the expression of antibody fragments, e.g. Fv, single-chain Fv (scFv), or Fab in the periplasm of E. coli (Skerra & Plückthun, 1988; Better et al., 1988) is now used routinely in many laboratories. Expression yields vary widely, however. While some fragments yield up to several mg of functional, soluble protein per liter and OD of culture broth in shake flask culture (Carter et al., 1992, Plückthun et al. 1996), other fragments may almost exclusively lead to insoluble material, often found in so-called inclusion bodies. Functional protein may be obtained from the latter in modest yields by a laborious and time-consuming refolding process. The factors influencing antibody expression levels are still only poorly understood. Folding efficiency and stability of the antibody fragments, protease lability and toxicity of the expressed proteins to the host cells often severely limit actual production levels, and several attempts have been tried to increase expression yields. For example, Knappik & Plückthun (1995) could show that expression yield depends on the antibody sequence. They identified key residues in the antibody framework which influence expression yields dramatically. Similarly, Ullrich et al. (1995) found that point mutations in the CDRs can increase the yields in periplasmic antibody fragment expression. Nevertheless, these strategies are only applicable to a few antibodies. Since the Winter invention uses existing repertoires of antibodies, no influence on expressibility of the genes is possible.

Furthermore, the findings of Knappik & Plückthun and Ullrich demonstrate that the knowledge about antibodies, especially about folding and expression is still increasing. The Winter invention does not allow to incorporate such improvements into the library design.

The expressibility of the genes is important for the library quality as well, since the screening procedure relies in most cases on the display of the gene product on a phage surface, and efficient display relies on at least moderate expression of the gene.

These disadvantages of the existing methodologies are overcome by the present invention, which is applicable for all collections of homologous proteins. It has the following novel and useful features illustrated in the following by antibodies as an example:

Artificial antibodies and fragments thereof can be constructed based on known antibody sequences, which reflect the structural properties of a whole group of homologous antibody genes. Therefore it is possible to reduce the number of different genes without any loss in the structural repertoire. This approach leads to a limited set of artificial genes, which can be synthesized de novo, thereby allowing introduction of cleavage sites and removing unwanted cleavages sites. Furthermore, this approach enables (i), adapting the codon usage of the genes to that of highly expressed genes in any desired host cell and (ii), analyzing all possible pairs of antibody light (L) and heavy (H) chains in terms of interaction preference, antigen preference or recombinant expression titer, which is virtually impossible using the complete collection of antibody genes of an organism and all combinations thereof.

The use of a limited set of completely synthetic genes makes it possible to create cleavage sites at the boundaries of encoded structural sub-elements. Therefore, each gene is built up from modules which represent structural sub-elements on the protein/(poly)peptide level. In the case of antibodies, the modules consist of "framework" and "CDR" modules. By creating separate framework and CDR modules, different combinatorial assembly possibilities are enabled. Moreover, if two or more artificial genes carry identical pairs of cleavage sites at the boundaries of each of the genetic sub-elements, pre-built libraries of sub-elements can be inserted in these genes simultaneously, without any additional information related to any particular gene sequence. This strategy enables rapid optimization of, for example, antibody affinity, since DNA cassettes encoding libraries of genetic sub-elements can be (i), pre-built, stored and reused and (ii), inserted in any of these sequences at the right position without knowing the actual sequence or having to determine the sequence of the individual library member.

Additionally, new information about amino acid residues important for binding, stability, or solubility and expression could be integrated into the library design by replacing existing modules with modules modified according to the new observations.

The limited number of consensus sequences used for creating the library allows to speed up the identification of binding antibodies after screening. After having identified the underlying consensus gene sequence, which could be done by sequencing or by using fingerprint restriction sites, just those part(s) comprising the random sequence(s) have to be determined. This reduces the probability of sequencing errors and of false-positive results.

The above mentioned cleavage sites can be used only if they are unique in the vector system where the artificial genes have been inserted. As a result, the vector has to be modified to contain none of these cleavage sites. The construction of a vector consisting of basic elements like resistance gene and origin of replication, where cleavage sites have been removed, is of general interest for many cloning attempts. Additionally, these vector(s) could be part of a kit comprising the above mentioned artificial genes and pre-built libraries.

The collection of artificial genes can be used for a rapid humanization procedure of non-human antibodies, preferably of rodent antibodies. First, the amino acid sequence of the non-human, preferably rodent antibody is compared with the amino acid sequences encoded by the collection of artificial genes to determine the most homologous light and heavy framework regions. These genes are then used for insertion of the genetic sub-elements encoding the CDRs of the non-human, preferably rodent antibody.

Surprisingly, it has been found that with a combination of only one consensus sequence for each of the light and heavy chains of a scFv fragment an antibody repertoire could be created yielding antibodies against virtually every antigen. Therefore, one aspect of the present invention is the use of a single consensus sequence as a universal framework for the creation of useful (poly)peptide libraries and antibody consensus sequences useful therefor.

DETAILED DESCRIPTION OF THE INVENTION

The present invention enables the creation of useful libraries of (poly)peptides. In a first embodiment, the invention provides for a method of setting up nucleic acid sequences suitable for the creation of said libraries. In a first step, a collection of at least three homologous proteins is identified and then analyzed. Therefore, a database of the protein sequences is established where the protein sequences are aligned to each other. The database is used to define subgroups of protein sequences which show a high degree of similarity in both the sequence and, if information is available, in the structural arrangement. For each of the subgroups a (poly)peptide sequence comprising at least one consensus sequence is deduced which represents the members of this subgroup; the complete collection of (poly)peptide sequences represent therefore the complete structural repertoire of the collection of homologous proteins. These artificial (poly)peptide sequences are then analyzed, if possible, according to their structural properties to identify unfavorable interactions between amino acids within said (poly)peptide sequences or between said or other (poly)peptide sequences, for example, in multimeric proteins. Such interactions are then removed by changing the consensus sequence accordingly. The (poly)peptide sequences are then analyzed to identify sub-elements such as domains, loops, helices or CDRs. The amino acid sequence is back-translated into a corresponding coding nucleic acid sequence which is adapted to the codon usage of the host planned for expressing said nucleic acid sequences. A set of cleavage sites is set up in a way that each of the sub-sequences encoding the sub-elements identified as described above, is flanked by two sites which do not occur a second time within the nucleic acid sequence. This can be achieved by either identifying a cleavage site already flanking a sub-sequence of by changing one or more nucleotides to create the cleavage site, and by removing that site from the remaining part of the gene. The cleavage sites should be common to all corresponding sub-elements or sub-sequences, thus creating a fully modular arrangement of the sub-sequences in the nucleic acid sequence and of the sub-elements in the corresponding (poly)peptide.

In a further embodiment, the invention provides for a method which sets up two or more sets of (poly)peptides, where for each set the method as described above is performed, and where the cleavage sites are not only unique within each set but also between any two sets. This method can be applied for the creation of (poly)peptide libraries comprising for example two ex-helical domains from two different proteins, where said library is screened for novel hetero-association domains.

In yet a further embodiment, at least two of the sets as described above, are derived from the same collection of proteins or at least a part of it. This describes libraries comprising for example, but not limited to, two domains from antibodies such as VH and VL, or two extracellular loops of transmembrane receptors.

In another embodiment, the nucleic acid sequences set up as described above, are synthesized. This can be achieved by any one of several methods well known to the practitioner skilled in the art, for example, by total gene synthesis or by PCR-based approaches.

In one embodiment, the nucleic acid sequences are cloned into a vector. The vector could be a sequencing vector, an expression vector or a display (e.g. phage display) vector, which are well known to those skilled in the art. Any vector could comprise one nucleic acid sequence, or two or more nucleic sequences, either in different or the same operon. In the last case, they could either be cloned separately or as contiguous sequences.

In one embodiment, the removal of unfavorable interactions as described above, leads to enhanced expression of the modified (poly)peptides.

In a preferred embodiment, one or more sub-sequences of the nucleic acid sequences are replaced by different sequences. This can be achieved by excising the sub-sequences using the conditions suitable for cleaving the cleavage sites adjacent to or at the end of the sub-sequence, for example, by using a restriction enzyme at the corresponding restriction site under the conditions well known to those skilled in the art, and replacing the sub-sequence by a different sequence compatible with the cleaved nucleic acid sequence. In a further preferred embodiment, the different sequences replacing the initial sub-sequence(s) are genomic or rearranged genomic sequences, for example in grafting CDRs from non-human antibodies onto consensus antibody sequences for rapid humanization of non-human antibodies. In the most preferred embodiment, the different sequences are random sequences, thus replacing the sub-sequence by a collection of sequences to introduce variability and to create a library. The random sequences can be assembled in various ways, for example by using a mixture of mononucleotides or preferably a mixture of trinucleotides (Virnekäs et al., 1994) during automated oligonucleotide synthesis, by error-prone PCR or by other methods well known to the practitioner in the art. The random sequences may be completely randomized or biased towards or against certain codons according to the amino acid distribution at certain positions in known protein sequences. Additionally, the collection of random sub-sequences may comprise different numbers of codons, giving rise to a collection of sub-elements having different lengths.

In another embodiment, the invention provides for the expression of the nucleic acid sequences from a suitable vector and under suitable conditions well known to those skilled in the art.

In a further preferred embodiment, the (poly)peptides expressed from said nucleic acid sequences are screened and, optionally, optimized. Screening may be performed by using one of the methods well known to the practitioner in the art, such as phage-display, selectively infective phage, polysome technology to screen for binding, assay systems for enzymatic activity or protein stability. (Poly)peptides having the desired property can be identified by sequencing of the corresponding nucleic acid sequence or by amino acid sequencing or mass spectrometry. In the case of subsequent optimization, the nucleic acid sequences encoding the initially selected (poly)peptides can optionally be used without sequencing. Optimization is performed by repeating the replacement of sub-sequences by different sequences, preferably by random sequences, and the screening step one or more times.

The desired property the (poly)peptides are screened for is preferably, but not exclusively, selected from the group of optimized affinity or specificity for a target molecule, optimized enzymatic activity, optimized expression yields, optimized stability and optimized solubility.

In one embodiment, the cleavage sites flanking the sub-sequences are sites recognized and cleaved by restriction enzymes, with recognition and cleavage sequences being either identical or different, the restricted sites either having blunt or sticky ends.

The length of the sub-elements is preferably, but not exclusively ranging between 1 amino acid, such as one residue in the active site of an enzyme or a structure-determining residue, and 150 amino acids, as for whole protein domains. Most preferably, the length ranges between 3 and 25 amino acids, such as most commonly found in CDR loops of antibodies.

The nucleic acid sequences could be RNA or, preferably, DNA.

In one embodiment, the (poly)peptides have an amino acid pattern characteristic of a particular species. This can for example be achieved by deducing the consensus sequences from a collection of homologous proteins of just one species, most preferably from a collection of human proteins. Since the (poly)peptides comprising consensus sequences are artificial, they have to be compared to the protein sequence(s) having the closest similarity to ensure the presence of said characteristic amino acid pattern.

In one embodiment, the invention provides for the creation of libraries of (poly)peptides comprising at least part of members or derivatives of the immunoglobulin superfamily, preferably of member or derivatives of the immunoglobulins. Most preferably, the invention provides for the creation of libraries of human antibodies, wherein said (poly)peptides are or are derived from heavy or light chain variable regions wherein said structural sub-elements are framework regions (FR) 1, 2, 3, or 4 or complementary determining regions (CDR) 1, 2, or 3. In a first step, a database of published antibody sequences of human origin is established where the antibody sequences are aligned to each other. The database is used to define subgroups of antibody sequences which show a high degree of similarity in both the sequence and the canonical fold of CDR loops (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed e.g. by total gene synthesis or by the use of synthetic genetic subunits. These genetic subunits correspond to structural sub-elements on the (poly)peptide level. On the DNA level, these genetic subunits are defined by cleavage sites at the start and the end of each of the sub-elements, which are unique in the vector system. All genes which are members of the collection of consensus sequences are constructed such that they contain a similar pattern of corresponding genetic sub-sequences. Most preferably, said (poly)peptides are or are derived from the HuCAL consensus genes: Vκ1, Vκ2, Vκ3, Vκ4, Vλ1, Vλ2, Vλ3, VH1A, VH1B, VH2, VH3, VH4, VH5, VH6, Cκ, Cλ, CH1 or any combination of said HuCAL consensus genes.

This collection of DNA molecules can then be used to create libraries of antibodies or antibody fragments, preferably Fv, disulphide-linked Fv, single-chain Fv (scFv), or Fab fragments, which may be used as sources of specificities against new target antigens. Moreover, the affinity of the antibodies can be optimized using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. Preferably, an scFv fragment library comprising the combination of HuCAL VH3 and HuCAL Vλ2 consensus genes and at least a random sub-sequence encoding the heavy chain CDR3 sub-element is screened for binding antibodies. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDRs) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are selected, collected and used as starting material for the next library. Here, one or more of the remaining genetic subunits are randomized as described above.

A further embodiment of the present invention relates to fusion proteins by providing for a DNA sequence which encodes both the (poly)peptide, as described above, as well as an additional moiety. Particularly preferred are moieties which have a useful therapeutic function. For example, the additional moiety may be a toxin molecule which is able to kill cells (Vitetta et al., 1993). There are numerous examples of such toxins, well known to the one skilled in the art, such as the bacterial toxins *Pseudomonas* exotoxin A, and diphtheria toxin, as well as the plant toxins ricin, abrin, modeccin, saporin, and gelonin. By fusing such a toxin for example to an antibody fragment, the toxin can be targeted to, for example, diseased cells, and thereby have a beneficial therapeutic effect. Alternatively, the additional moiety may be a cytokine, such as IL-2 (Rosenberg & Lotze, 1986), which has a particular effect (in this case a T-cell proliferative effect) on a family of cells. In a further embodiment, the additional moiety may confer on its (poly)peptide partner a means of detection and/or purification. For example, the fusion protein could comprise the modified antibody fragment and an enzyme commonly used for detection purposes, such as alkaline phosphatase (Blake et al., 1984). There are numerous other moieties which can be used as detection or purification tags, which are well known to the practitioner skilled in the art. Particularly preferred are peptides comprising at least five histidine residues (Hochuli et al., 1988), which are able to bind to metal ions, and can therefore be used for the purification of the protein to which they are fused (Lindner et al., 1992). Also provided for by the invention are additional moieties such as the commonly used C-myc and FLAG tags (Hopp et al., 1988; Knappik & Plückthun, 1994).

By engineering one or more fused additional domains, antibody fragments or any other (poly)peptide can be assembled into larger molecules which also fall under the scope of the present invention. For example, mini-antibodies (Pack, 1994) are dimers comprising two antibody fragments, each fused to a self-associating dimerization domain. Dimerization domains which are particularly preferred include those derived from a leucine zipper (Pack & Plückthun, 1992) or helix-turn-helix motif (Pack et al., 1993).

All of the above embodiments of the present invention can be effected using standard techniques of molecular biology known to anyone skilled in the art.

In a further embodiment, the random collection of sub-sequences (the library) is inserted into a singular nucleic acid sequence encoding one (poly)peptide, thus creating a (poly)peptide library based on one universal framework. Preferably a random collection of CDR sub-sequences is inserted into a universal antibody framework, for example into the HuCAL H3κ2 single-chain Fv fragment described above.

In further embodiments, the invention provides for nucleic acid sequence(s), vector(s) containing the nucleic acid sequence(s), host cell(s) containing the vector(s), and (poly)peptides, obtainable according to the methods described above.

In a further preferred embodiment, the invention provides for modular vector systems being compatible with the modular nucleic acid sequences encoding the (poly)peptides. The modules of the vectors are flanked by restriction sites unique within the vector system and essentially unique with respect to the restriction sites incorporated into the nucleic acid sequences encoding the (poly)peptides, except for example the restriction sites necessary for cloning the nucleic acid sequences into the vector. The list of vector modules comprises origins of single-stranded replication, origins of double-stranded replication for high- and low copy number plasmids, promotor/operator, repressor or terminator elements, resistance genes, potential recombination sites, gene III for display on filamentous phages, signal sequences, purification and detection tags, and sequences of additional moieties. The vectors are preferably, but not exclusively, expression vectors or vectors suitable for expression and screening of libraries.

In another embodiment, the invention provides for a kit, comprising one or more of the list of nucleic acid sequence(s), recombinant vector(s), (poly)peptide(s), and vector(s) according to the methods described above, and suitable host cell(s) for producing the (poly)peptide(s).

In a preferred embodiment, the invention provides for the creation of libraries of human antibodies. In a first step, a database of published antibody sequences of human origin is established. The database is used to define subgroups of antibody sequences which show a high degree of similarity in both the sequence and the canonical fold (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed by the use of synthetic genetic subunits. These genetic subunits correspond to structural sub-elements on the protein level. On the DNA level, these genetic subunits are defined by cleavage sites at the start and the end of each of the subelements, which are unique in the vector system. All genes which are members of the collection of consensus sequences are constructed such that they contain a similar pattern of said genetic subunits.

This collection of DNA molecules can then be used to create libraries of antibodies which may be used as sources of specificities against new target antigens. Moreover, the affinity of the antibodies can be optimised using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDR's) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are eluted, collected and used as starting material for the next library.

Here, one or more of the remaining genetic subunits are randomised as described above.

DEFINITIONS

Protein:

The term protein comprises monomeric polypeptide chains as well as homo- or heteromultimeric complexes of two or more polypeptide chains connected either by covalent interactions (such as disulphide bonds) or by non-covalent interactions (such as hydrophobic or electrostatic interactions).

Analysis of Homologous Proteins:

The amino acid sequences of three or more proteins are aligned to each other (allowing for introduction of gaps) in a way which maximizes the correspondence between identical or similar amino acid residues at all positions. These aligned sequences are termed homologous if the percentage of the sum of identical and/or similar residues exceeds a defined threshold. This threshold is commonly regarded by those skilled in the art as being exceeded when at least 15% of the amino acids in the aligned genes are identical, and at least 30% are similar. Examples for families of homologous proteins are: immunoglobulin superfamily, scavenger receptor superfamily, fibronectin superfamilies (e.g. type II and III), complement control protein superfamily, cytokine receptor superfamily, cystine knot proteins, tyrosine kinases, and numerous other examples well known to one of ordinary skill in the art.

Consensus Sequence:

Using a matrix of at least three aligned amino acid sequences, and allowing for gaps in the alignment, it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

Removing Unfavorable Interactions:

The consensus sequence is per se in most cases artificial and has to be analyzed in order to change amino acid residues which, for example, would prevent the resulting molecule to adapt a functional tertiary structure or which would block the interaction with other (poly)peptide chains in multimeric complexes. This can be done either by (i) building a three-dimensional model of the consensus sequence using known related structures as a template, and identifying amino acid residues within the model which may interact unfavorably with each other, or (ii) analyzing the matrix of aligned amino acid sequences in order to detect combinations of amino acid residues within the sequences which frequently occur together in one sequence and are therefore likely to interact with each other. These probable interaction-pairs are then tabulated and the consensus is compared with these "interaction maps". Missing or wrong interactions in the consensus are repaired accordingly by introducing appropriate changes in amino acids which minimize unfavorable interactions.

Identification of Structural Sub-Elements:

Structural sub-elements are stretches of amino acid residues within a protein/(poly)peptide which correspond to a defined structural or functional part of the molecule. These can be loops (e.g. CDR loops of an antibody) or any other secondary or functional structure within the protein/(poly) peptide (domains, α-helices, β-sheets, framework regions of antibodies, etc.). A structural sub-element can be identified using known structures of similar or homologous (poly) peptides, or by using the above mentioned matrices of aligned amino acid sequences. Here the variability at each position is the basis for determining stretches of amino acid residues which belong to a structural sub-element (e.g. hypervariable regions of an antibody).

Sub-Sequence:

A sub-sequence is defined as a genetic module which is flanked by unique cleavage sites and encodes at least one structural sub-element. It is not necessarily identical to a structural sub-element.

Cleavage Site:

A short DNA sequence which is used as a specific target for a reagent which cleaves DNA in a sequence-specific manner (e.g. restriction endonucleases).

Compatible Cleavage Sites:

Cleavage sites are compatible with each other, if they can be efficiently ligated without modification and, preferably, also without adding an adapter molecule.

Unique Cleavage Sites:

A cleavage site is defined as unique if it occurs only once in a vector containing at least one of the genes of interest, or if a vector containing at least one of the genes of interest could be treated in a way that only one of the cleavage sites could be used by the cleaving agent.

Corresponding (Poly)Peptide Sequences:

Sequences deduced from the same part of one group of homologous proteins are called corresponding (poly)peptide sequences.

Common Cleavage Sites:

A cleavage site in at least two corresponding sequences, which occurs at the same functional position (i.e. which flanks a defined sub-sequence), which can be hydrolyzed by the same cleavage tool and which yields identical compatible ends is termed a common cleavage site.

Excising Genetic Sub-Sequences:

A method which uses the unique cleavage sites and the corresponding cleavage reagents to cleave the target DNA at the specified positions in order to isolate, remove or replace the genetic sub-sequence flanked by these unique cleavage sites.

Exchanging Genetic Sub-Sequences:

A method by which an existing sub-sequence is removed using the flanking cleavage sites of this sub-sequence, and a new sub-sequence or a collection of sub-sequences, which contain ends compatible with the cleavage sites thus created, is inserted.

Expression of Genes:

The term expression refers to in vivo or in vitro processes, by which the information of a gene is transcribed into mRNA and then translated into a protein/(poly)peptide. Thus, the term expression refers to a process which occurs inside cells, by which the information of a gene is transcribed into mRNA and then into a protein. The term expression also includes all events of post-translational modification and transport, which are necessary for the (poly)peptide to be functional.

Screening of Protein (Poly)Peptide Libraries:

Any method which allows isolation of one or more proteins/(poly)peptides having a desired property from other proteins/(poly)peptides within a library.

Amino Acid Pattern Characteristic for a Species:

A (poly)peptide sequence is assumed to exhibit an amino acid pattern characteristic for a species if it is deduced from a collection of homologous proteins from just this species.

Immunoglobulin Superfamily (IgSF):

The IgSF is a family of proteins comprising domains being characterized by the immunoglobulin fold. The IgSF comprises for example T-cell receptors and the immunoglobulins (antibodies).

Antibody Framework:

A framework of an antibody variable domain is defined by Kabat et al. (1991) as the part of the variable domain which serves as a scaffold for the antigen binding loops of this variable domain.

Antibody CDR:

The CDRs (complementarity determining regions) of an antibody consist of the antigen binding loops, as defined by Kabat et al. (1991). Each of the two variable domains of an antibody Fv fragment contain three CDRs.

HuCAL:

Acronym for Human Combinatorial Antibody Library. Antibody Library based on modular consensus genes according to the invention (see Example 1).

Antibody Fragment:

Any portion of an antibody which has a particular function, e.g. binding of antigen. Usually, antibody fragments are smaller than whole antibodies. Examples are Fv, disulphide-linked Fv, single-chain Fv (scFv), or Fab fragments. Additionally, antibody fragments are often engineered to include new functions or properties.

Universal Framework:

One single framework which can be used to create the full variability of functions, specificities or properties which is originally sustained by a large collection of different frameworks, is called universal framework.

Binding of an Antibody to its Target:

The process which leads to a tight and specific association between an antibody and a corresponding molecule or ligand is called binding. A molecule or ligand or any part of a molecule or ligand which is recognized by an antibody is called the target.

Replacing Genetic Sub-Sequences

A method by which an existing sub-sequence is removed using the flanking cleavage sites of this sub-sequence, and a new sub-sequence or collection of sub-sequences, which contains ends compatible with the cleavage sites this creates, is inserted inserted.

Assembling of Genetic Sequences:

Any process which is used to combine synthetic or natural genetic sequences in a specific manner in order to get longer genetic sequences which contain at least parts of the used synthetic or natural genetic sequences.

Analysis of Homologous Genes:

The corresponding amino acid sequences of two or more genes are aligned to each other in a way which maximizes the correspondence between identical or similar amino acid residues at all positions. These aligned sequences are termed homologous if the percentage of the sum of identical and/or similar residues exceeds a defined threshold. This threshold is commonly regarded by those skilled in the art as being exceeded when at least 15 percent of the amino acids in the aligned genes are identical, and at least 30 percent are similar.

LEGENDS TO FIGURES AND TABLES

FIG. 1: Flow chart outlining the process of construction of a synthetic human antibody library based on consensus sequences.

FIGS. 2A–2G: Alignment of consensus sequences designed for each subgroup (amino acid residues are shown with their standard one-letter abbreviation). (2A–2B) kappa sequences, (2C–2D) lambda sequences and (2E–2G), heavy chain sequences. The positions are numbered according to Kabat (1991). In order to maximize homology in the alignment, gaps (–) have been introduced in the sequence at certain positions.

FIGS. 3A–3K: Gene sequences of the synthetic V kappa consensus genes. The corresponding amino acid sequences (see FIGS. 2A–2B) as well as the unique cleavage sites are also shown.

FIGS. 4A–4I: Gene sequences of the synthetic V lambda consensus genes. The corresponding amino acid sequences (see FIGS. 2C–2D) as well as the unique cleavage sites are also shown.

FIGS. 5A–5U: Gene sequences of the synthetic V heavy chain consensus genes. The corresponding amino acid sequences (see FIGS. 2E–2G) as well as the unique cleavage sites are also shown.

FIGS. 6A–6G: Oligonucleotides used for construction of the consensus genes. The oligos are named according to the corresponding consensus gene, e.g. the gene Vκ1 was constructed using the six oligonucleotides O1K1 to O1K6. The oligonucleotides used for synthesizing the genes encoding the constant domains Cκ (OCLK1 to 8) and CH1 (OCH1 to 8) are also shown.

FIGS. 7A–7D: Sequences of the synthetic genes encoding the constant domains Cκ (7A–7B) and CH1 (7C–7D). The corresponding amino acid sequences as well as unique cleavage sites introduced in these genes are also shown.

FIGS. 7E–7H: Functional map and sequence of module M24 comprising the synthetic Cλ gene segment (huCL lambda).

FIGS. 7I–7J: Oligonucleotides used for synthesis of module M24.

FIGS. 8A–8E: Sequence and restriction map of the synthetic gene encoding the consensus single-chain fragment VH3-Vκ2. The signal sequence (amino acids 1 to 21) was derived from the *E. coli* phoA gene (Skerra & Plückthun, 1988). Between the phoA signal sequence and the VH3 domain, a short sequence stretch encoding 4 amino acid residues (amino acid 22 to 25) has been inserted in order to allow detection of the single-chain fragment in Western blot or ELISA using the monoclonal antibody M1 (Knappik & Plückthun, 1994). The last 6 basepairs of the sequence were introduced for cloning purposes (EcoRI site).

Figure 9:
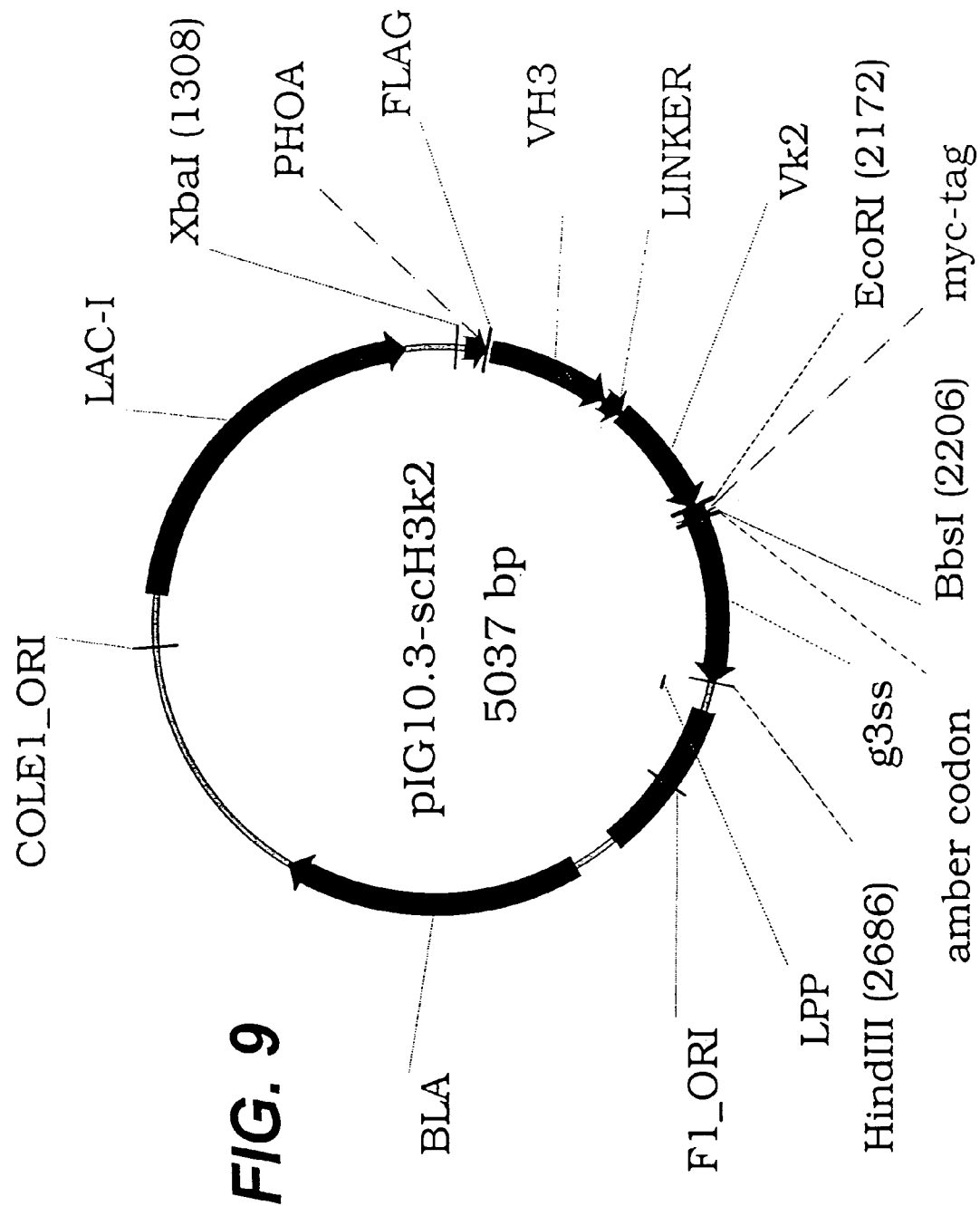

FIG. 9: Plasmid map of the vector pIG10.3 used for phage display of the H3κ2 scFv fragment. The vector is derived from pIG10 and contains the gene for the lac operon repressor, lacI, the artificial operon encoding the H3κ2-gene3ss fusion under control of the lac promoter, the 1pp terminator of transcription, the single-strand replication origin of the *E. coli* phage f1 (F1_ORI), a gene encoding β-lactamase (bla) and the ColEI derived origin of replication.

FIGS. 10A–10B: Sequencing results of independent clones from the initial library, translated into the corresponding amino acid sequences. (A) Amino acid sequence of the VH3 consensus heavy chain CDR3 (position 93 to 102, Kabat numbering). (B) Amino acid sequences of 12 clones of the 10-mer library. (C) Amino acid sequences of 11 clones of the 15-mer library, *: single base deletion.

Figure 11:
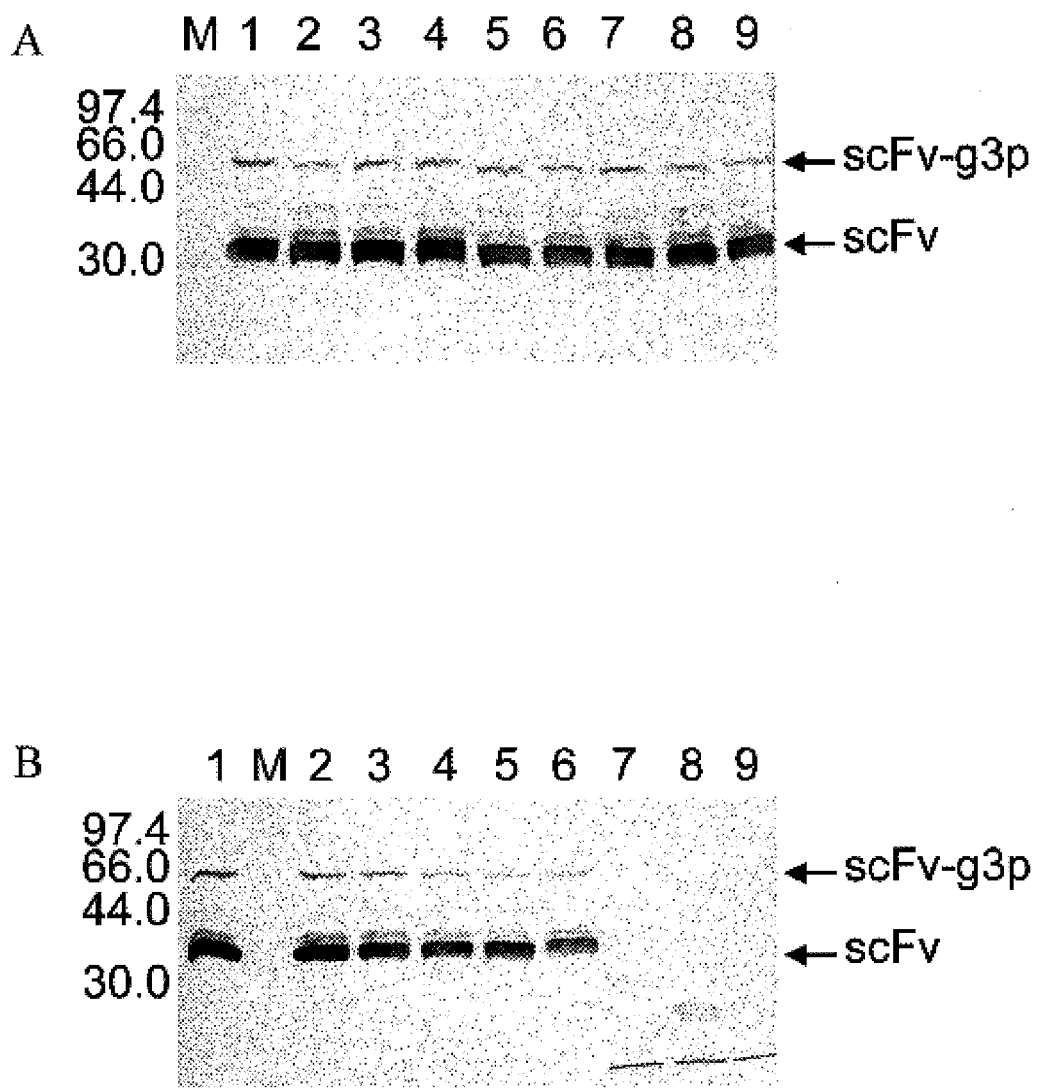

FIG. 11: Expression test of individual library members. (A) Expression of 9 independent clones of the 10-mer library. (B) Expression of 9 independent clones of the 15-mer library. The lane designated with M contains the size marker. Both the gp3-scFv fusion and the scFv monomer are indicated.

Figure 12:
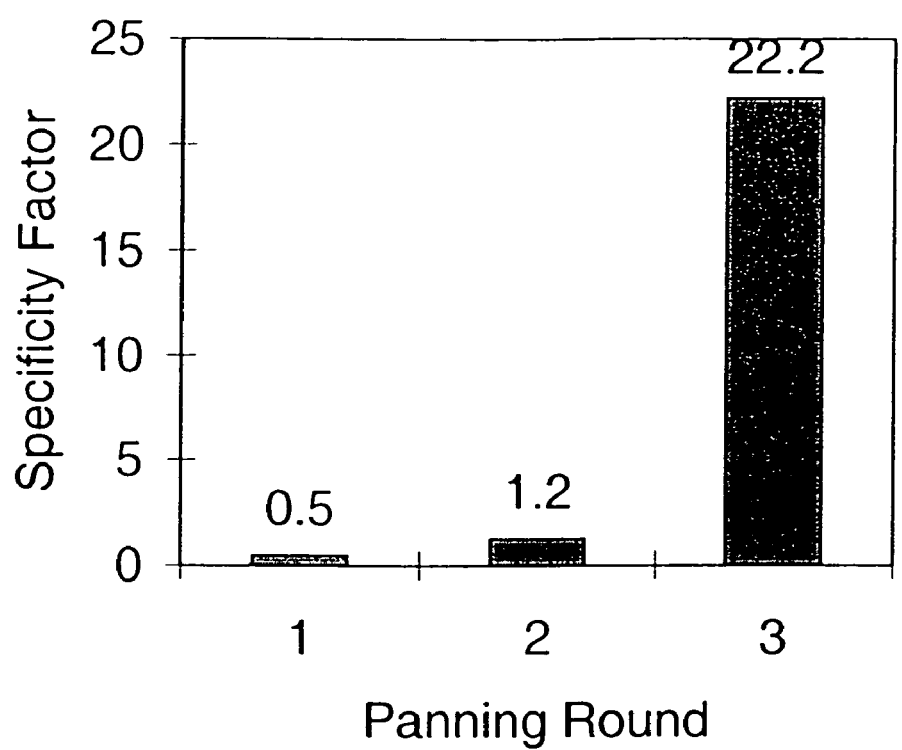

FIG. 12: Enrichment of specific phage antibodies during the panning against FITC-BSA. The initial as well as the subsequent fluorescein-specific sub-libraries were panned against the blocking buffer and the ratio of the phage eluted from the FITC-BSA coated well vs. that from the powder milk coated well from each panning round is presented as the "specificity factor".

Figure 13:
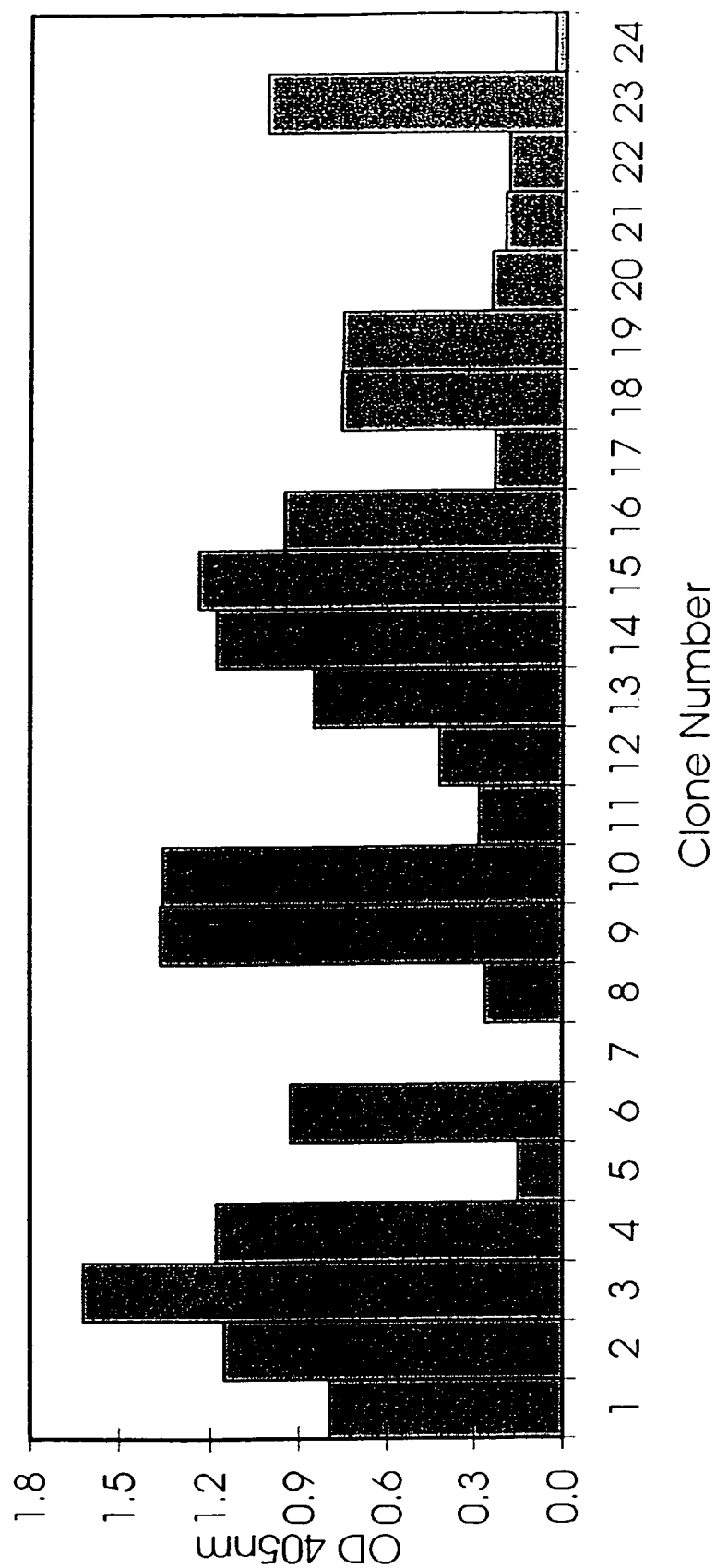

FIG. 13: Phage ELISA of 24 independent clones after the third round of panning tested for binding on FITC-BSA.

Figure 14:
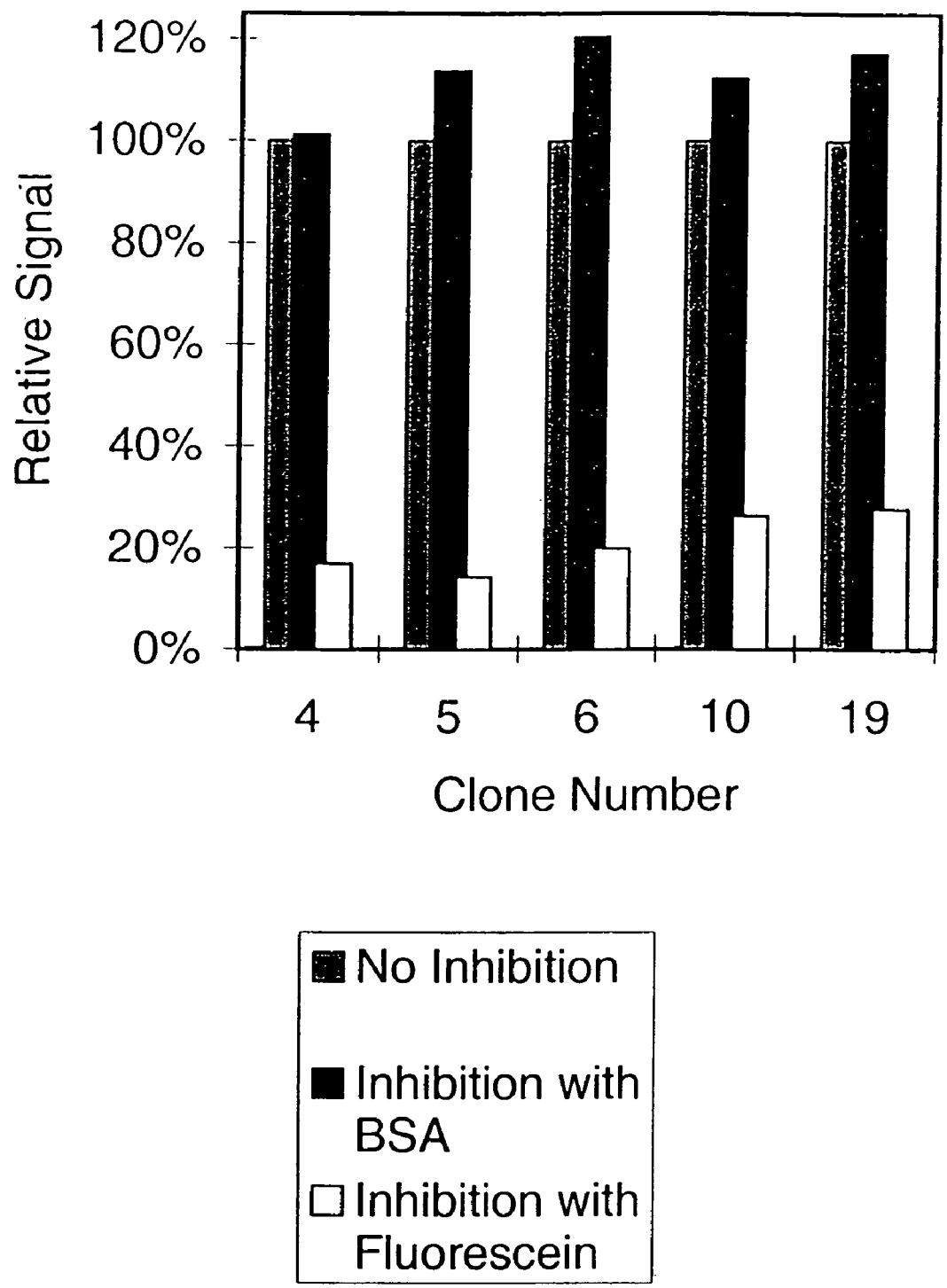

FIG. 14: Competition ELISA of selected FITC-BSA binding clones. The ELISA signals (OD.sub.405 nm) of scFv binding without inhibition are taken as 100%.

FIG. 15: Sequencing results of the heavy chain CDR3s of independent clones after 3 rounds of panning against FITC-BSA, translated into the corresponding amino acid sequences (SEQ ID NOS 203–218 respectively) (position 93 to 102, Kabat numbering).

Figure 16:
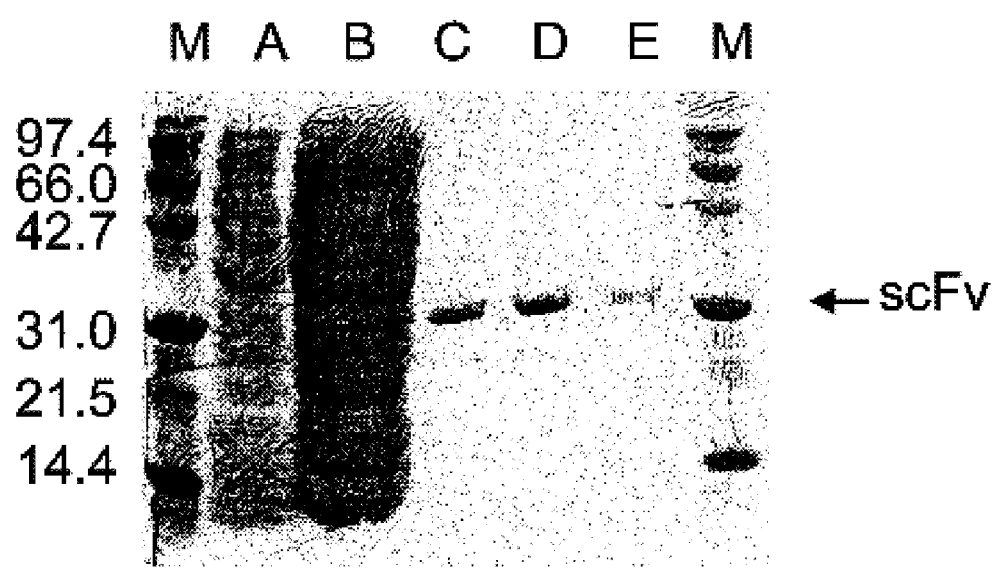

FIG. 16: Coomassie-Blue stained SDS-PAGE of the purified anti-fluorescein scFv fragments: M: molecular weight marker, A: total soluble cell extract after induction, B: fraction of the flow-through, C, D and E: purified scFv fragments 1HA-3E4, 1HA-3E5 and 1HA-3E10, respectively.

Figure 17:
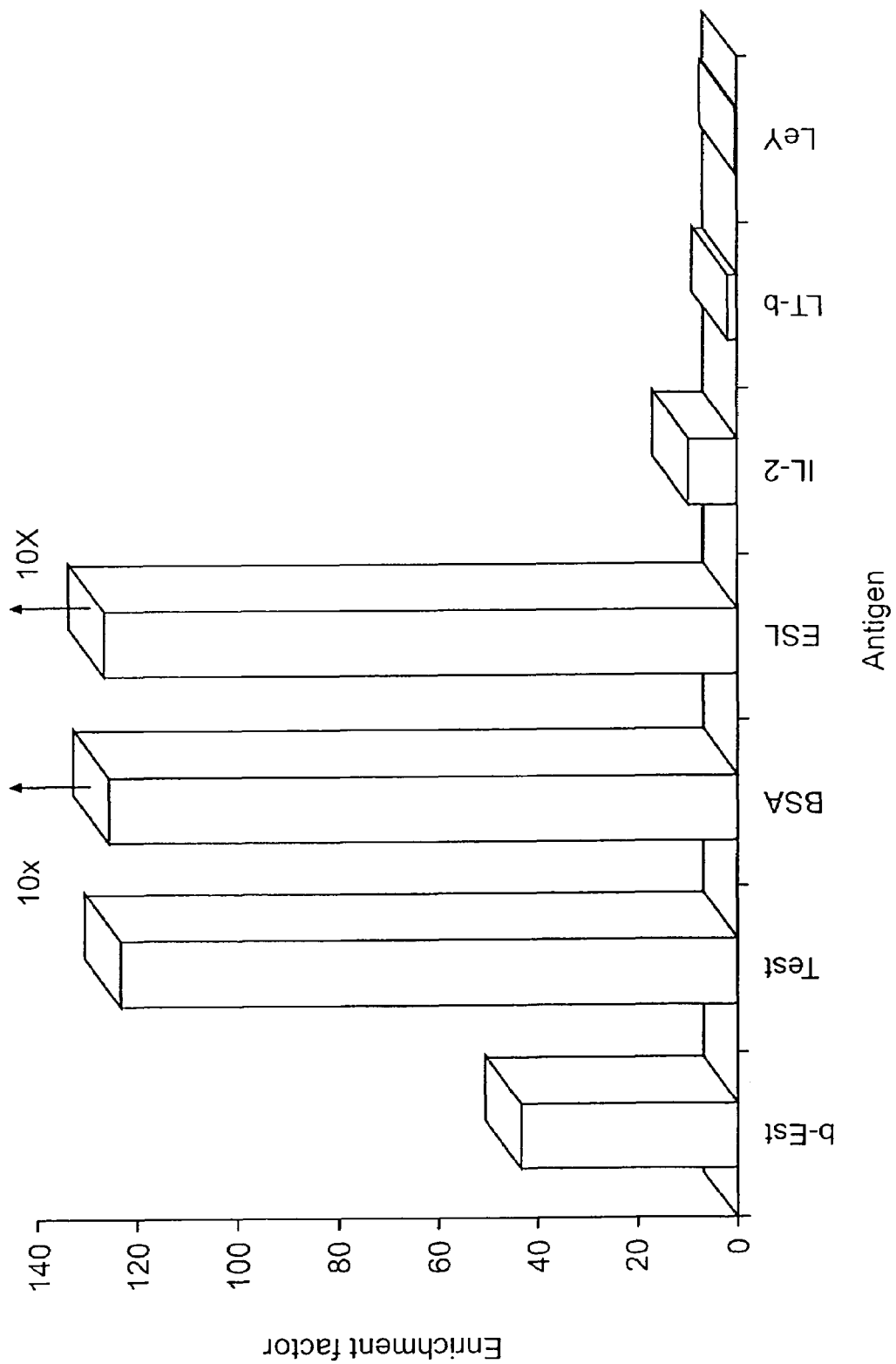

FIG. 17: Enrichment of specific phage antibodies during the panning against β-estradiol-BSA, testosterone-BSA, BSA, ESL-1, interleukin-2, lymphotoxin-β and, LeY-BSA after three rounds of panning.

Figure 18:
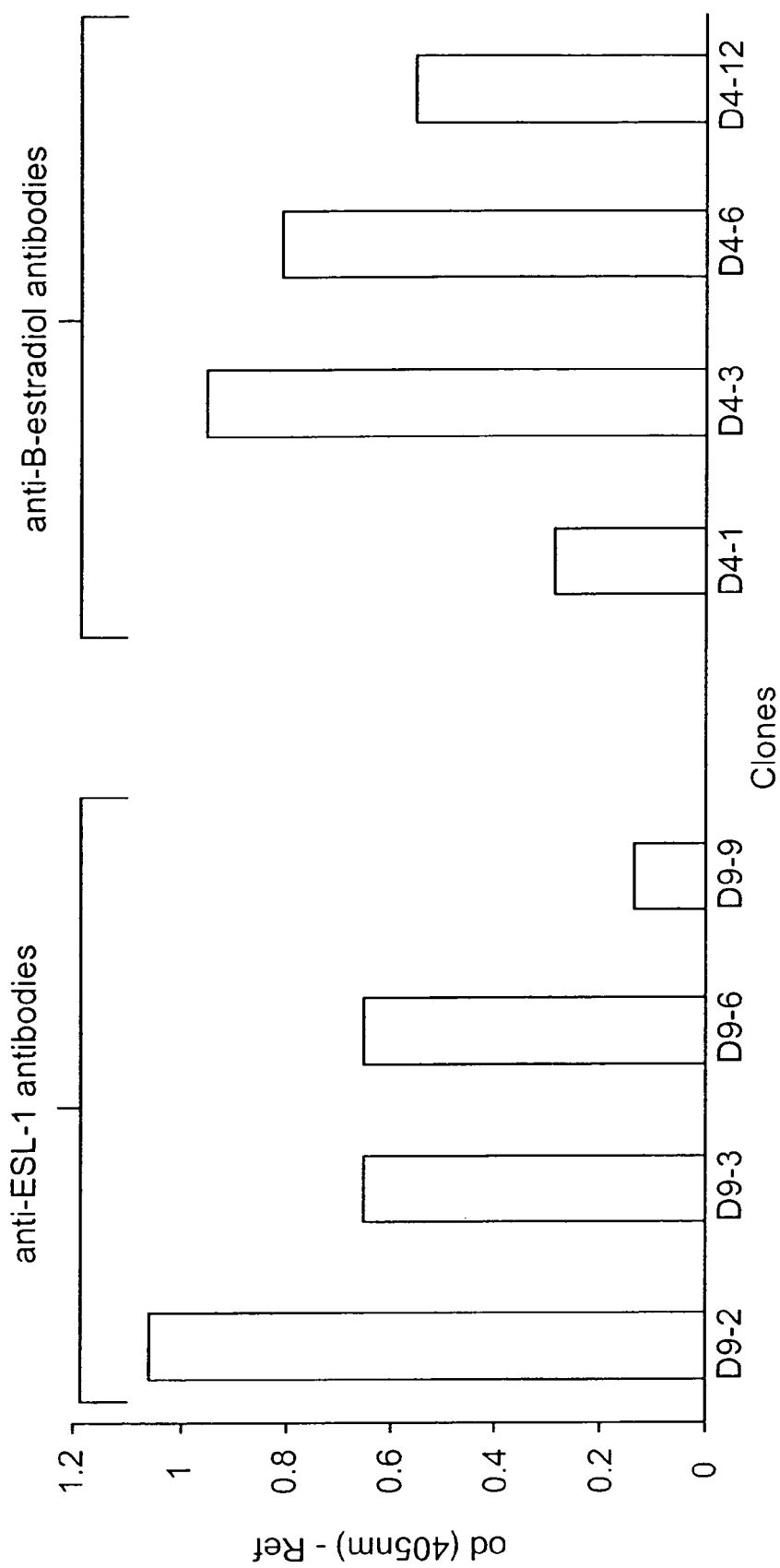

FIG. 18: ELISA of selected ESL-1 and .beta.-estradiol binding clones.

Figure 19:
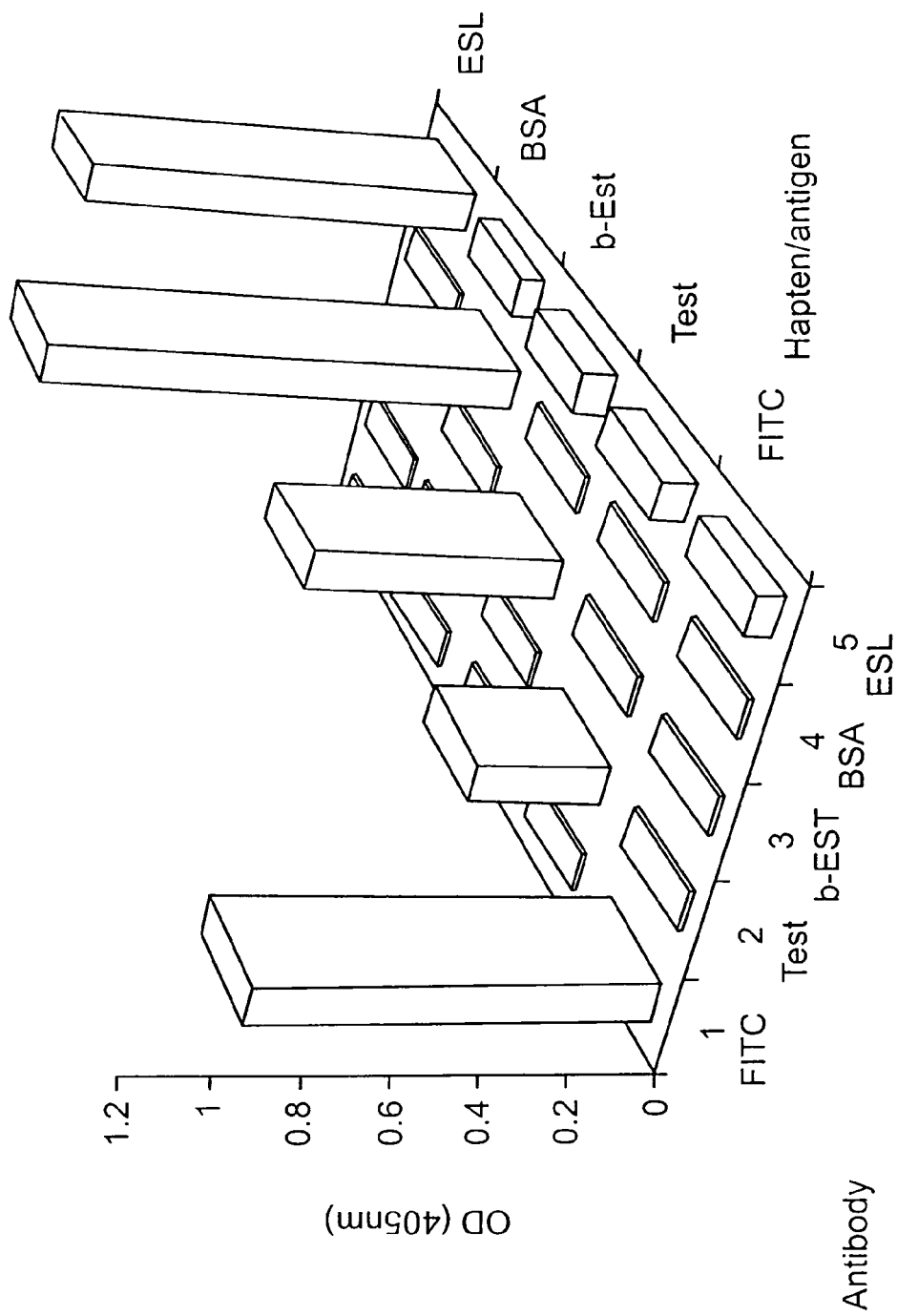

FIG. 19: Selectivity and cross-reactivity of HuCAL antibodies: in the diagonal specific binding of HuCAL antibodies can be seen, off-diagonal signals show non-specific cross-reactivity.

Figure 20:
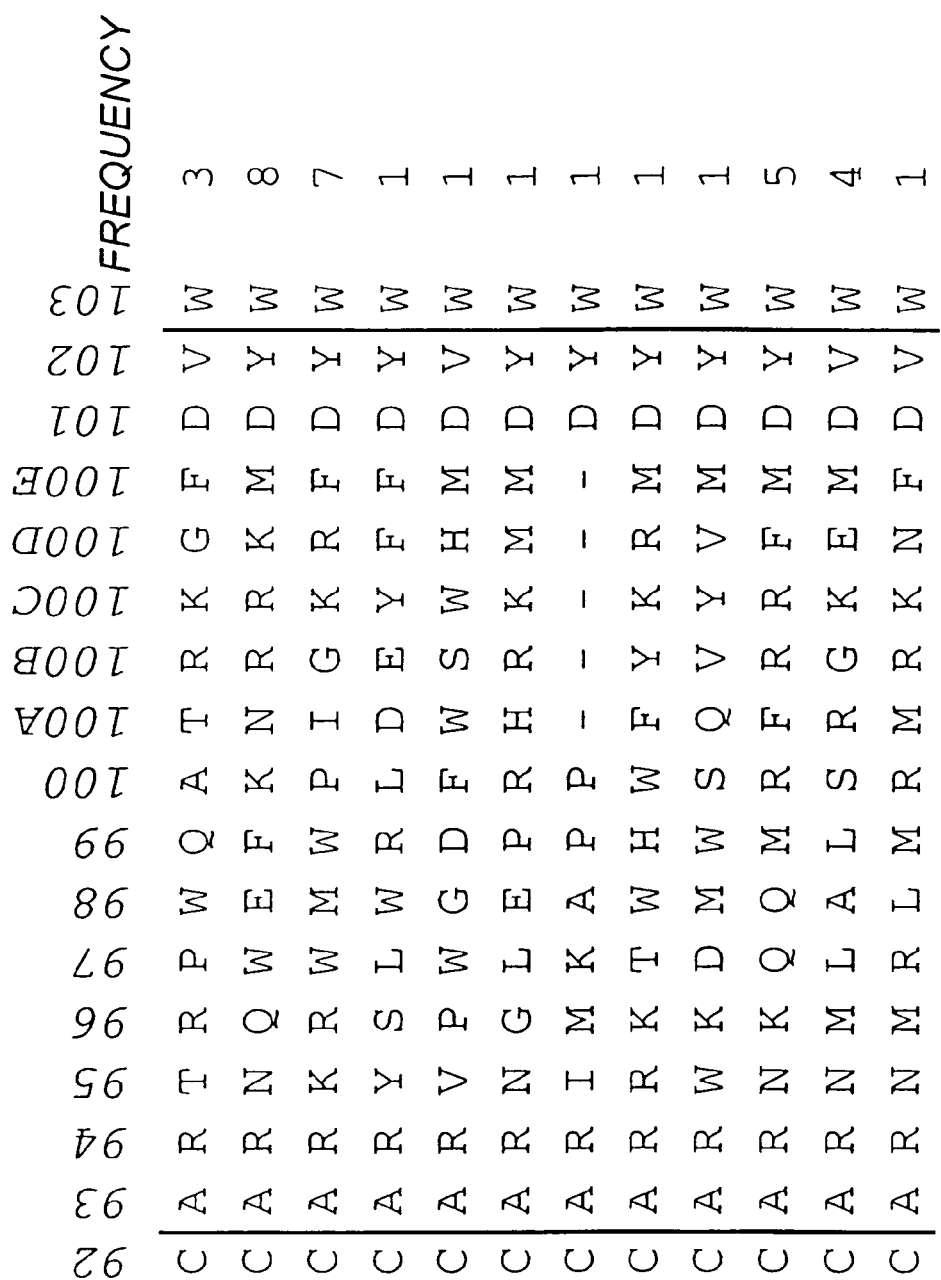

FIG. 20: Sequencing results of the heavy chain CDR3s of independent clones after 3 rounds of panning against β-estradiol-BSA, translated into the corresponding amino acid sequences (SEQ ID NOS 219–230 respectively) (position 93 to 102, Kabat numbering). One clone is derived from the 10mer library.

Figure 35:
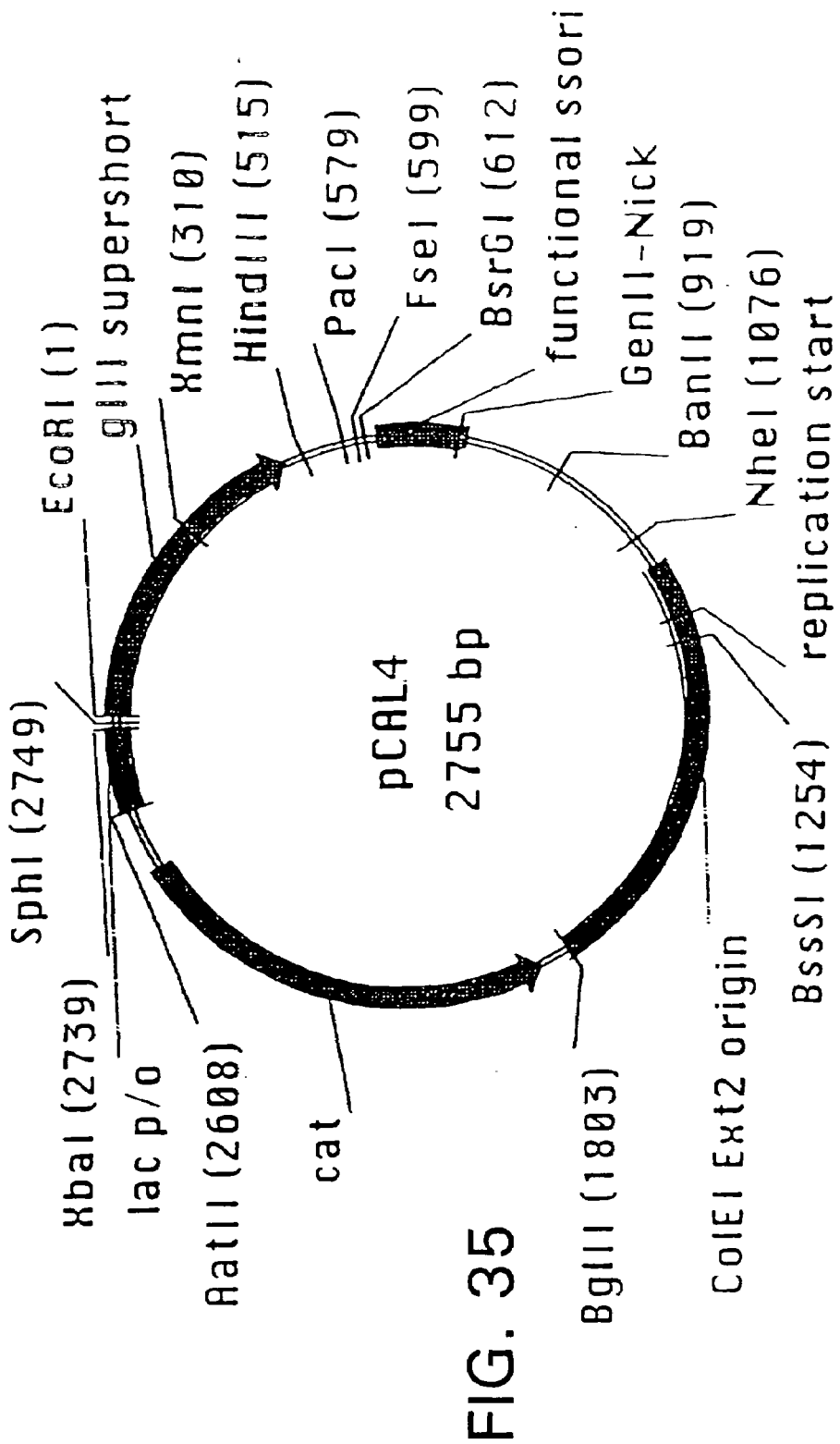
Figures 9, 35A:
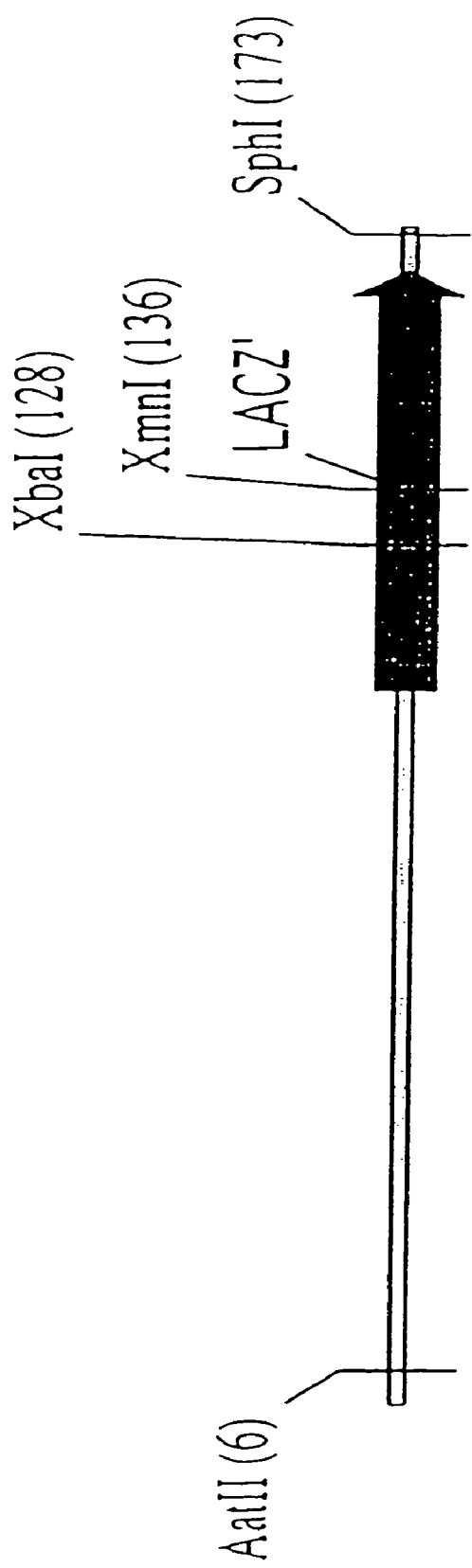
Figures 11, 35A:
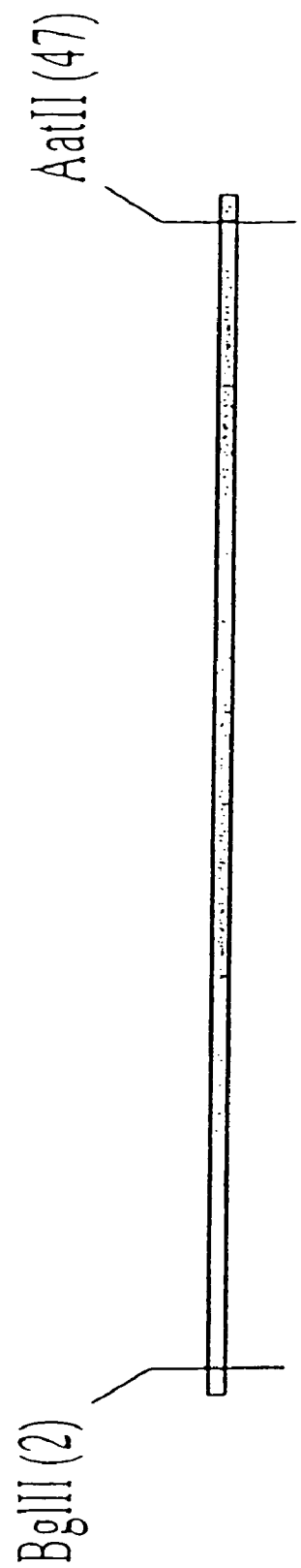
Figures 13, 35A:
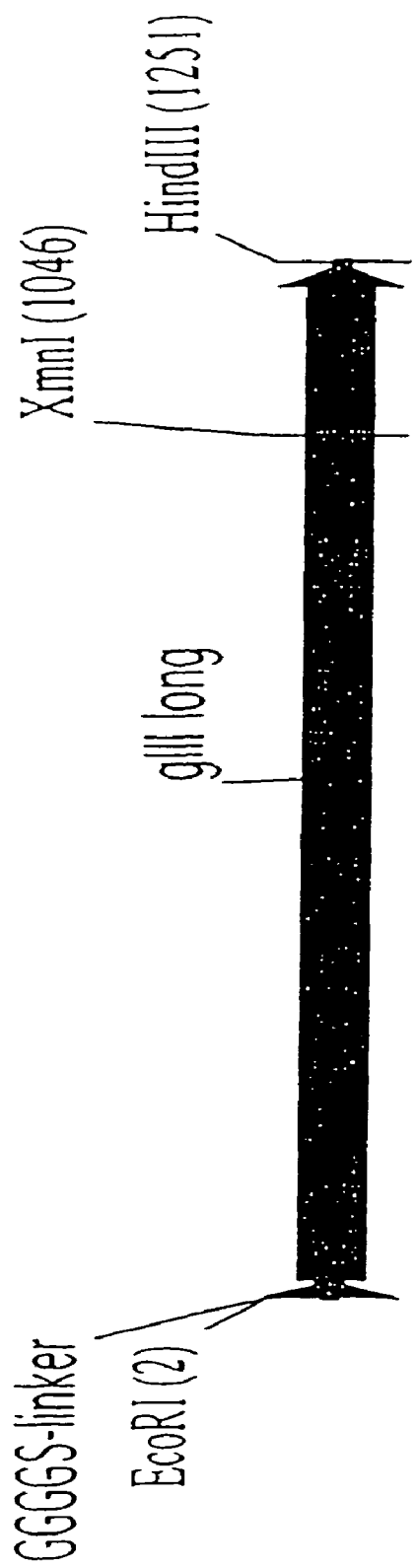
Figures 18, 35A:
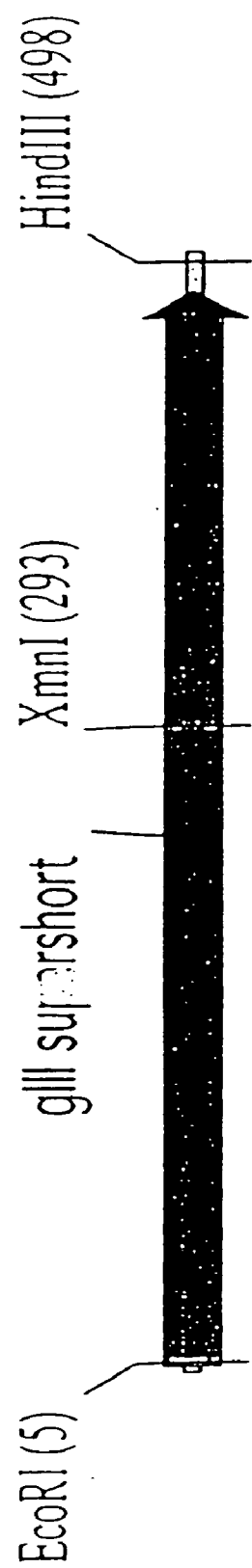
Figures 21, 35A:
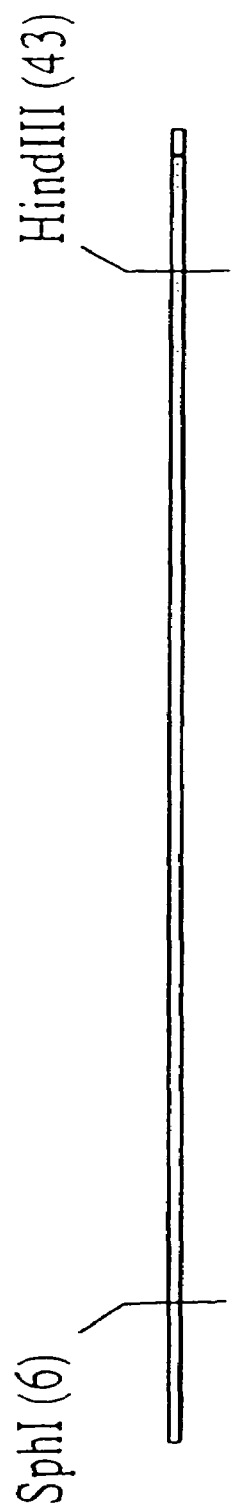

FIG. 21: Sequencing results of the heavy chain CDR3s of independent clones after 3 rounds of panning against testosterone-BSA, translated into the corresponding amino acid sequences (SEQ ID NOS 231–236 respectively) (position 93 to 102, Kabat numbering).

FIG. 22: Sequencing results of the heavy chain CDR3s of independent clones after 3 rounds of panning against lymphotoxin-.beta., translated into the corresponding amino acid sequences (SEQ ID NOS 237–244 respectively) (position 93 to 102, Kabat numbering). One clone comprises a 14mer CDR, presumably introduced by incomplete coupling of the trinucleotide mixture during oligonucleotide synthesis.

Figures 23, 35A:
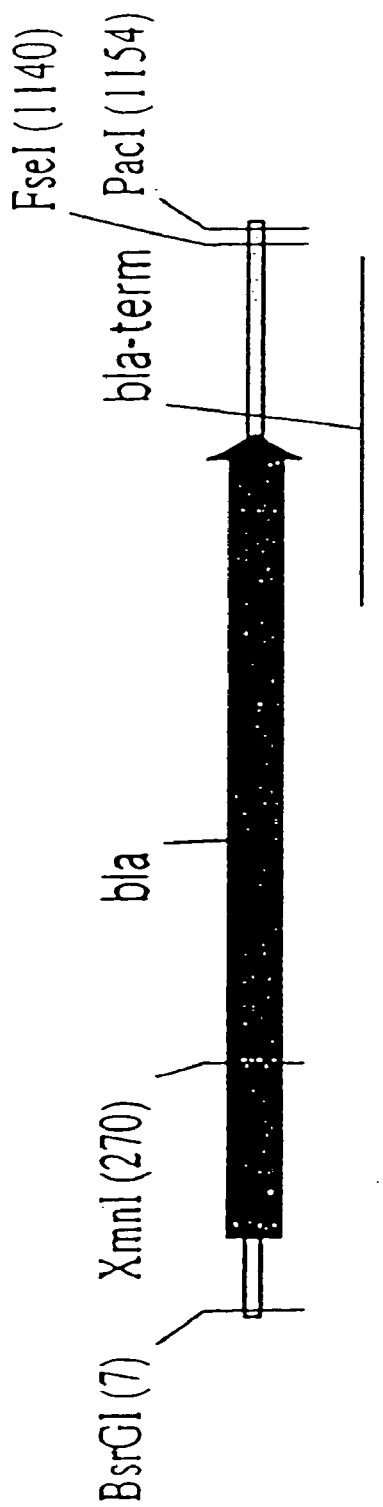

FIG. 23: Sequencing results of the heavy chain CDR3s of independent clones after 3 rounds of panning against ESL-1, translated into the corresponding amino acid sequences (SEQ ID NOS 245–256 respectively) (position 93 to 102, Kabat numbering). Two clones are derived from the 10mer library. One clone comprises a 16mer CDR, presumably introduced by chain elongation during oligonucleotide synthesis using trinucleotides.

FIG. 24: Sequencing results of the heavy chain CDR3s of independent clones after 3 rounds of panning against BSA, translated into the corresponding amino acid sequences (SEQ ID NOS 257–262 respectively) (position 93 to 102, Kabat numbering).

Figure 25A:
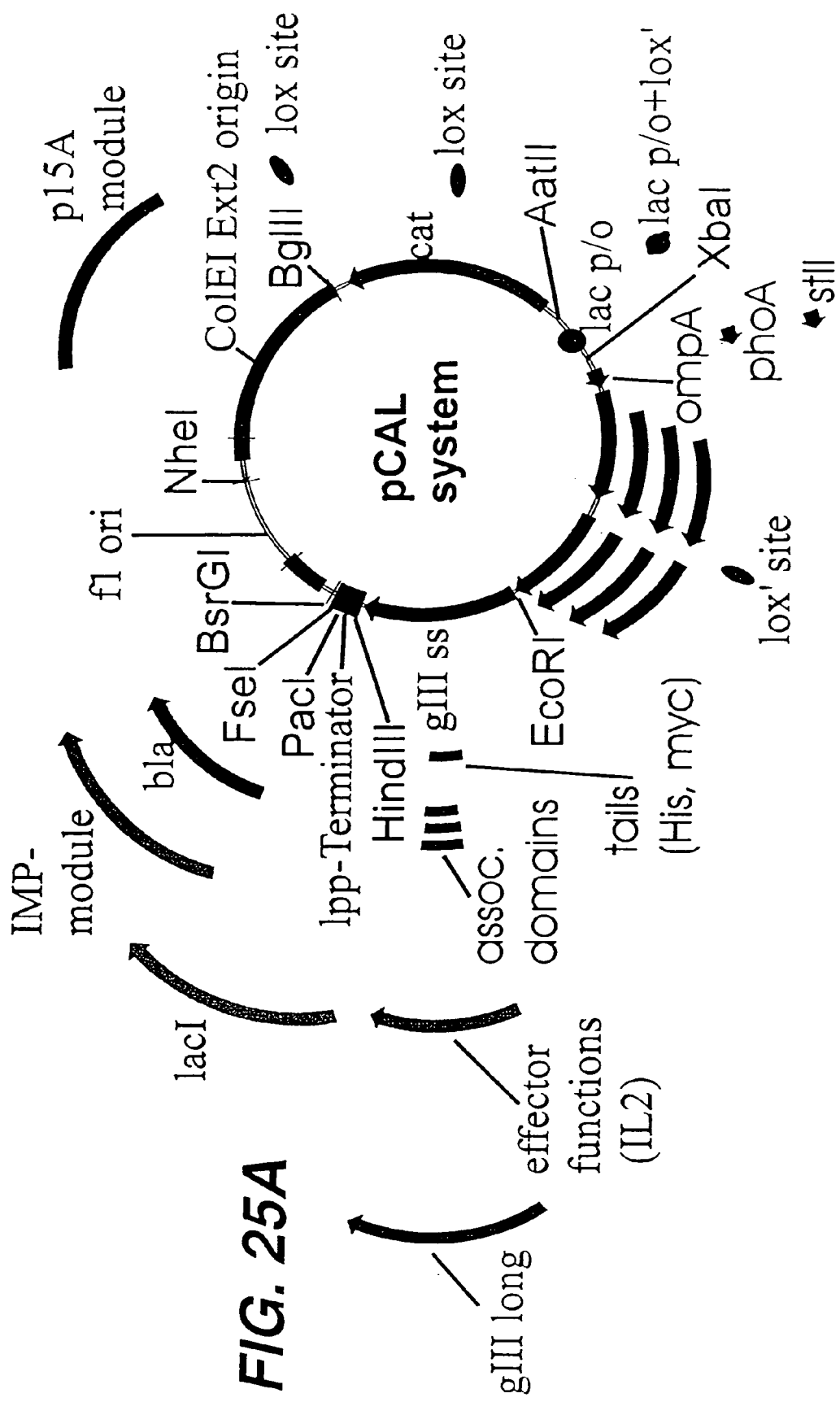

FIG. 25A: Schematic representation of the modular pCAL vector system.

FIGS. 25B–25C: List of restriction sites already used in or suitable for the modular HuCAL genes and pCAL vector system.

FIGS. 26A–26D: List of the modular vector elements for the pCAL vector series: shown are only those restriction sites which are part of the modular system.

Figure 27A:
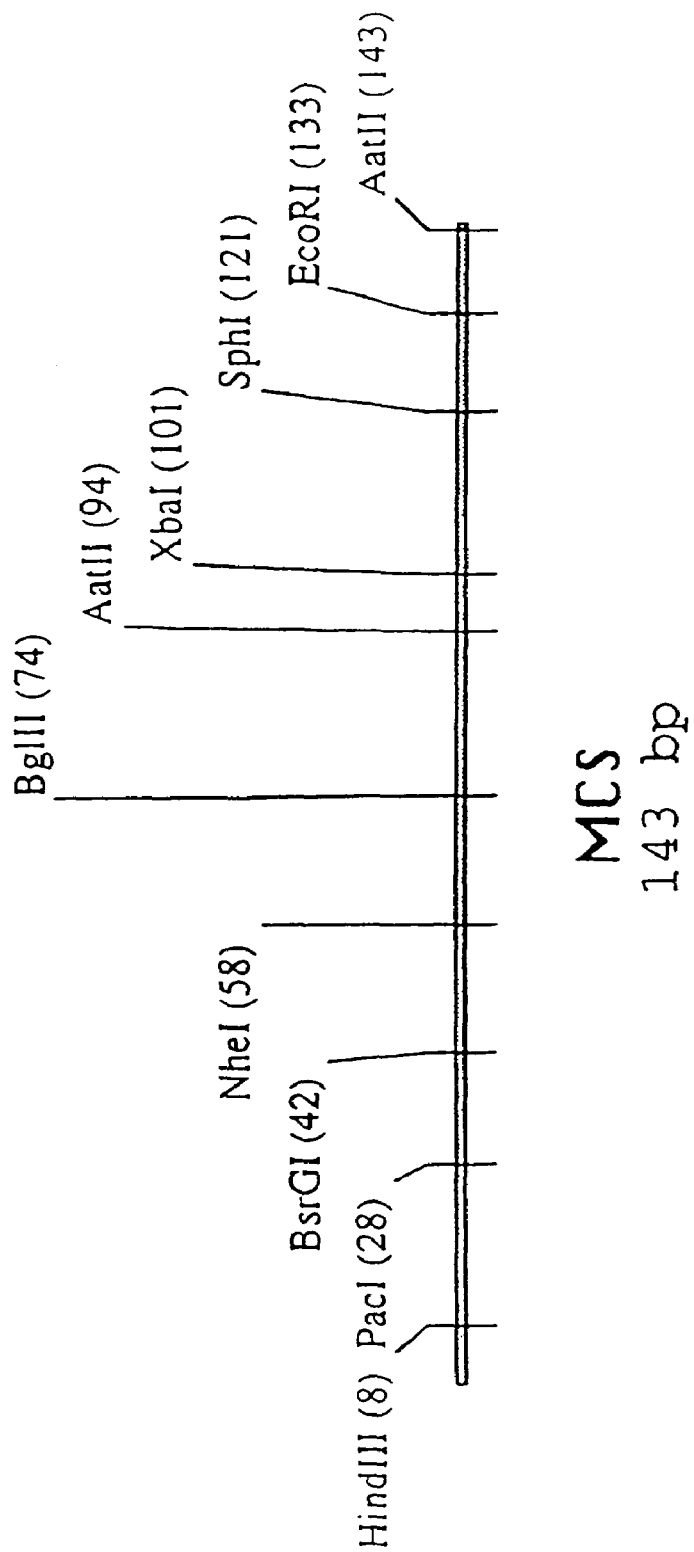
Figure 28A:
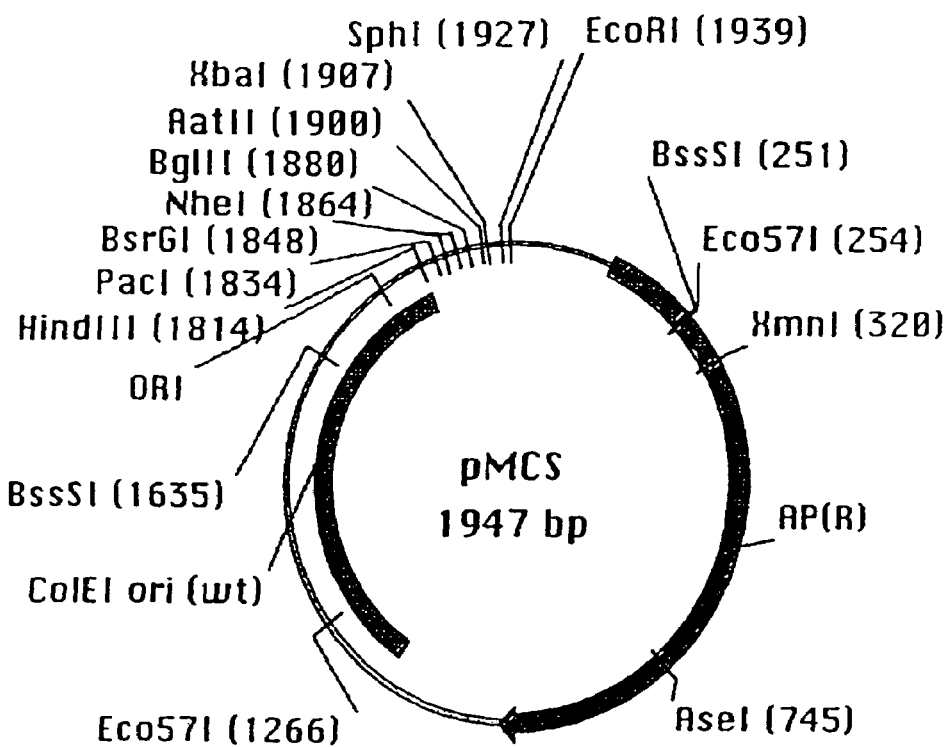

FIGS. 27A–27B: Functional map and sequence of the multi-cloning site module (MCS).

FIGS. 28A–28G: Functional map and sequence of the pMCS cloning vector series.

FIGS. 29A–29B: Functional map and sequence of the pCAL module M1 (see FIGS. 26A–26D).

Figure 30A:
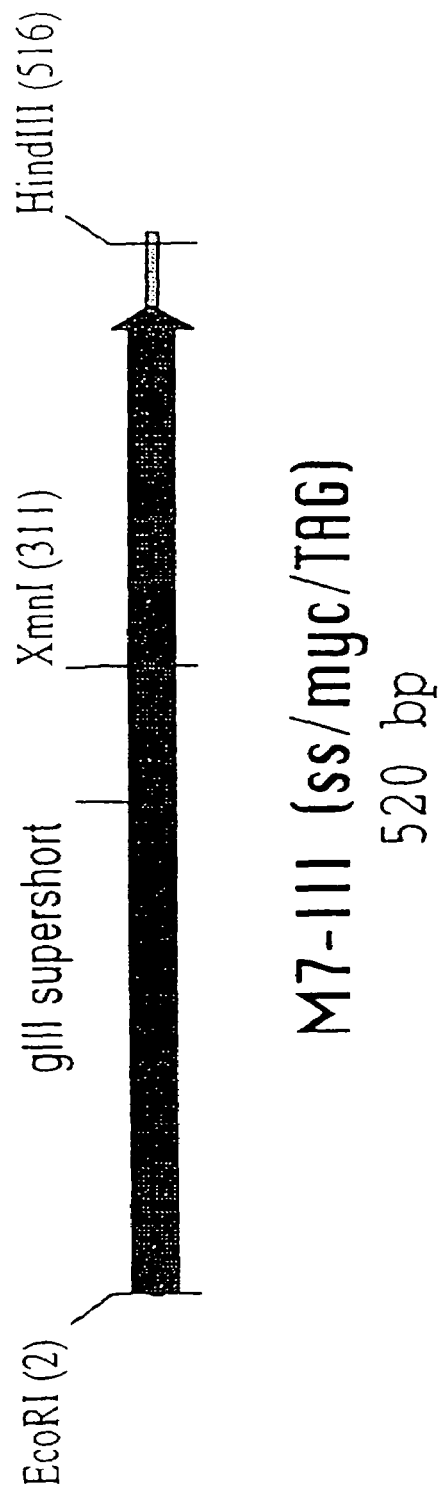

FIGS. 30A–30C: Functional map and sequence of the pCAL module M7-III (see FIGS. 26A–26D).

Figure 31A:
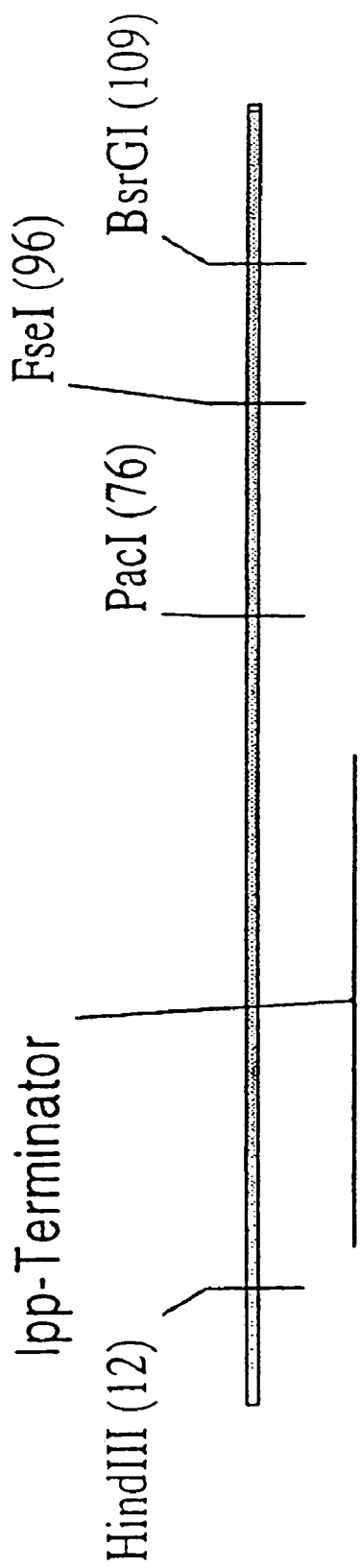
Figure 33A:
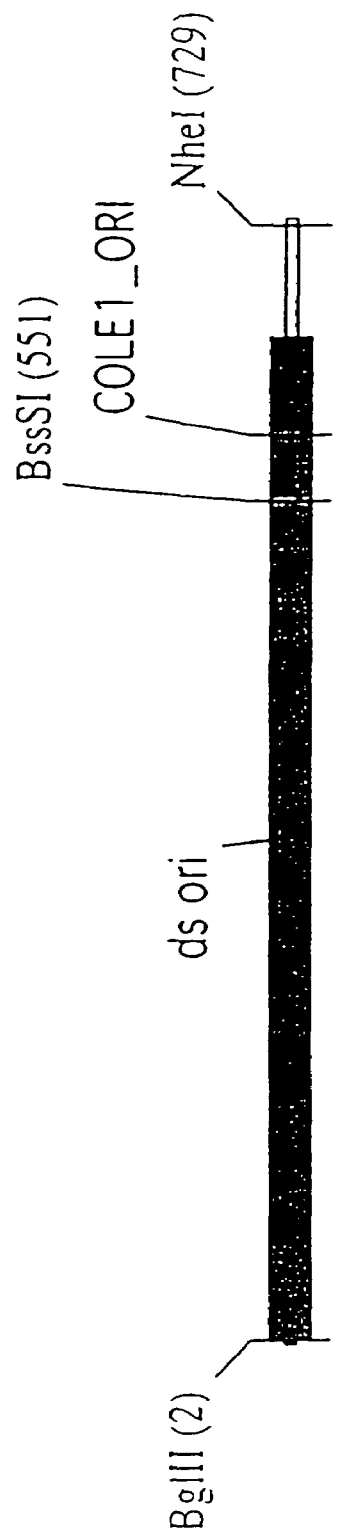
Figure 34A:
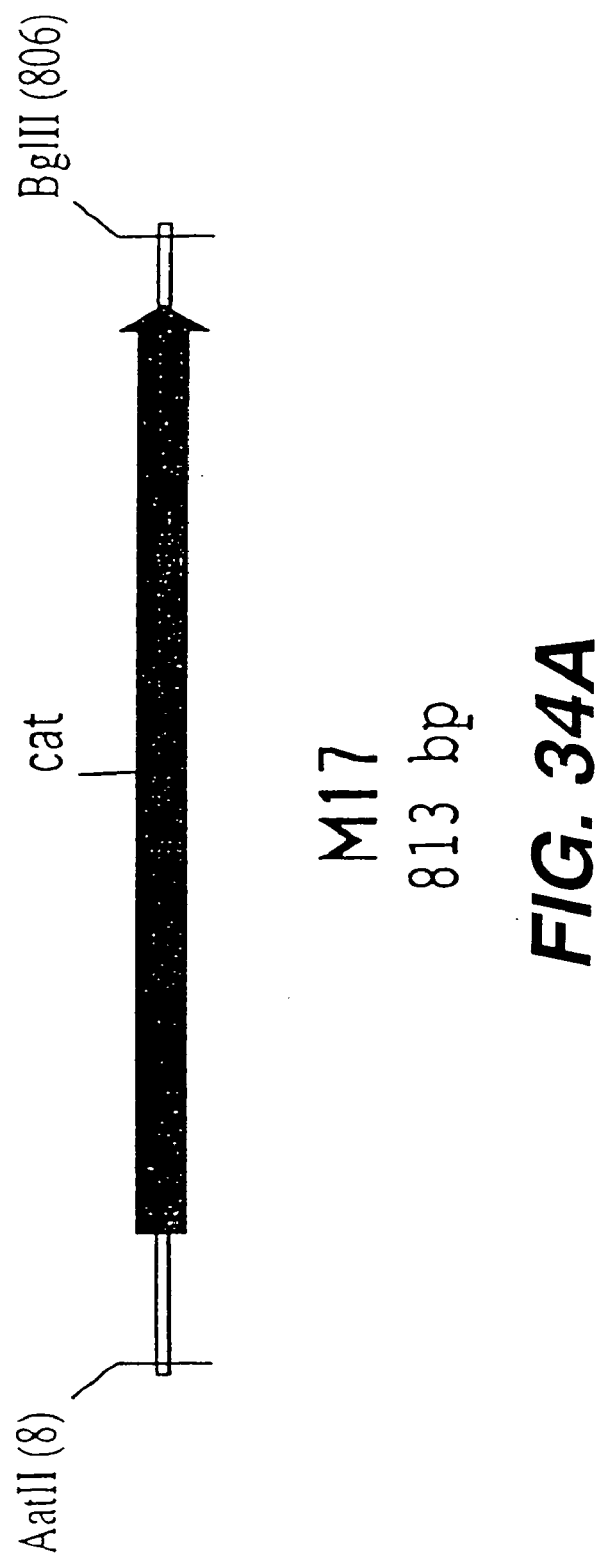

FIGS. 31A–31B: Functional map and sequence of the pCAL module M9-II (see FIGS. 26A–26D).

FIGS. 32A–32C: Functional map and sequence of the pCAL module M11-II (see FIGS. 26A–26D).

FIGS. 33A–33D: Functional map and sequence of the pCAL module M14-Ext2 (see FIGS. 26A–26D).

FIGS. 34A–34D: Functional map and sequence of the pCAL module M17 (see FIGS. 26A–26D).

FIGS. 35 to 35A-8: functional map and sequence module vector pCAL4.

FIGS. 35A-9 to 35A-75: Functional maps and sequences of additional pCAL modules (M2, M3, M7I, M7II, M8, M10II, M11II, M12, M13, M19, M20, M21, M41) and of low-copy number plasmid vectors (pCALO1 to pCALO3).

FIGS. 35A-76 to 35A-80: List of oligonucleotides and primers used for synthesis of pCAL vector modules.

FIGS. 36A–36F: Functional map and sequence of the β-lactamase cassette for replacement of CDRs for CDR library cloning.

FIGS. 37A–37D: Oligo and primer design for Vκ CDR3 libraries.

FIGS. 38A–38D: Oligo and primer design for Vλ CDR3 libraries.

Figures 28, 35A:
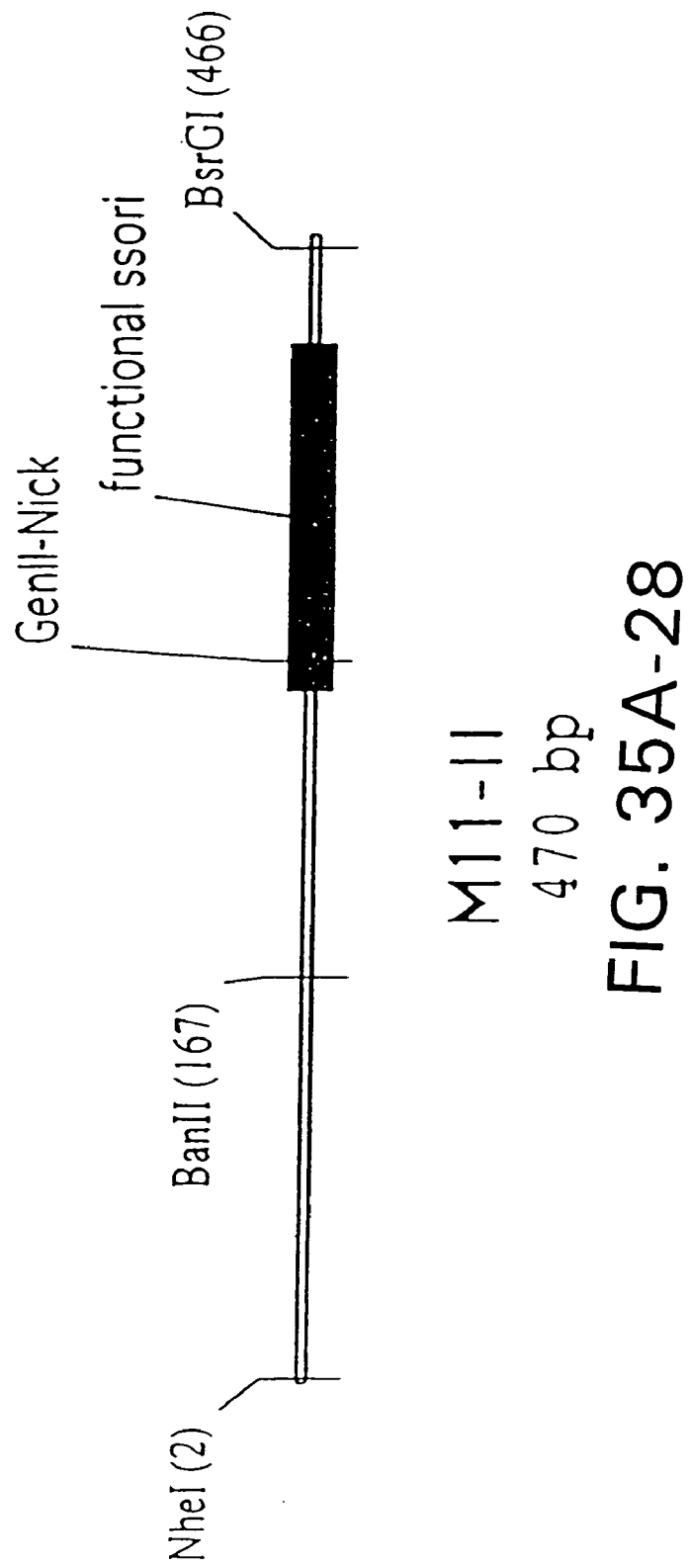
Figures 31, 35A:
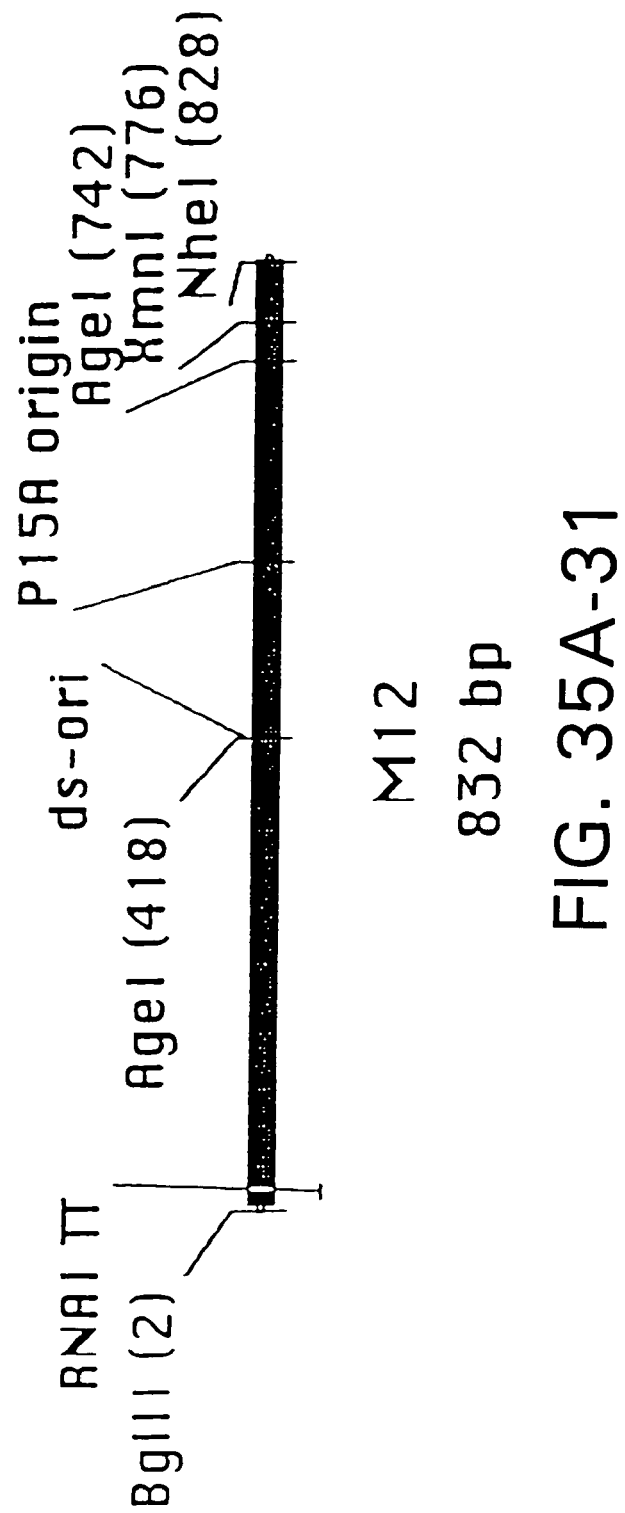
Figures 35, 35A:
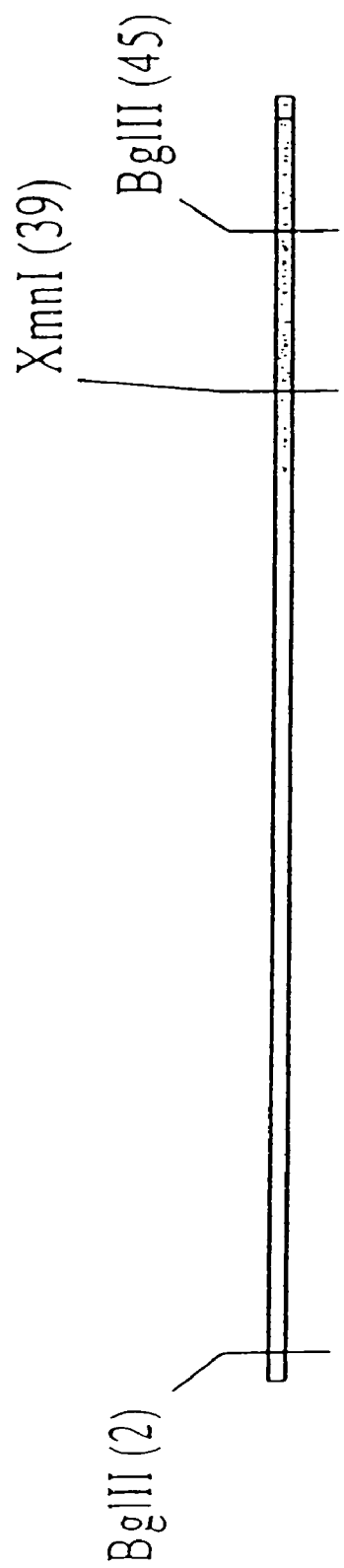
Figures 35, 35A, 36, 37:
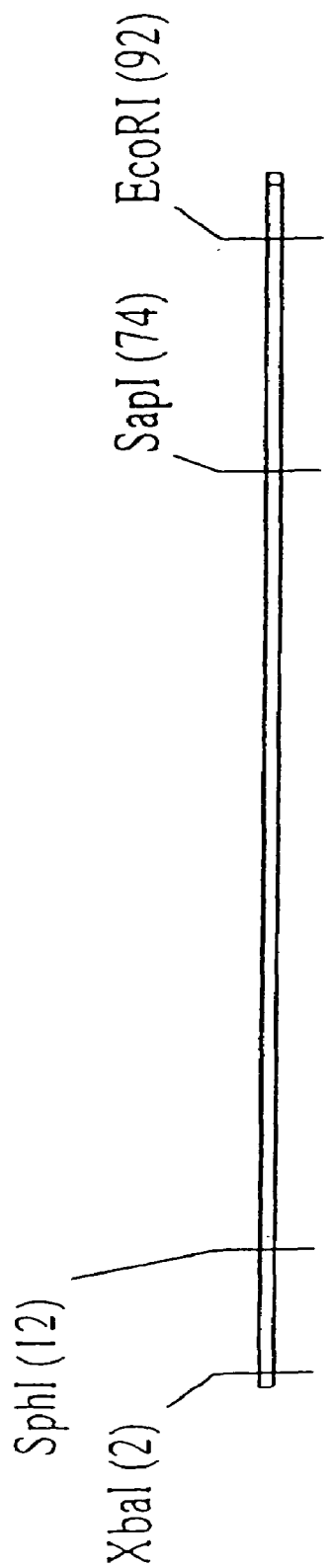
Figures 35, 35A, 36, 37, 38, 39:
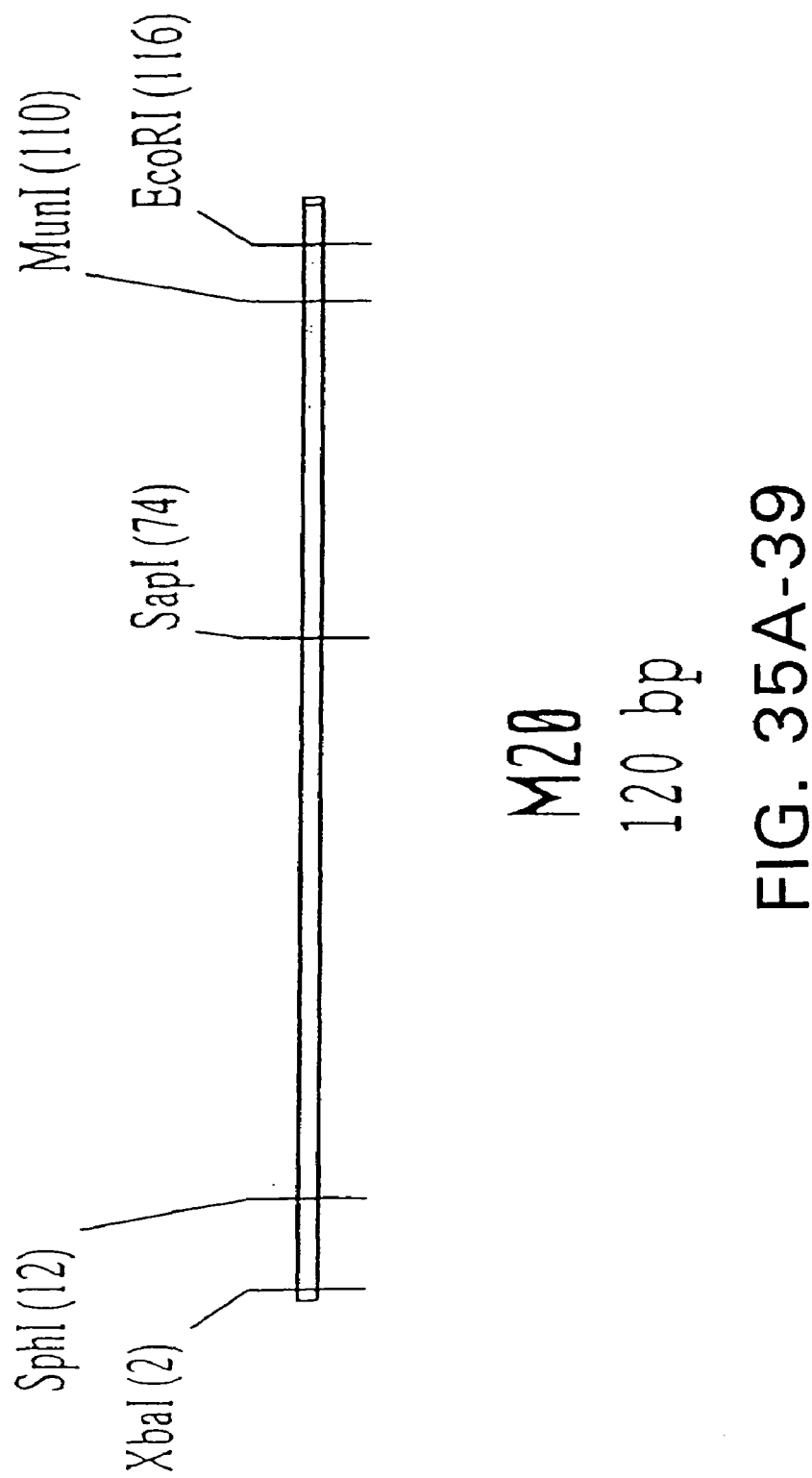
Figures 35, 35A, 36, 37, 38, 39, 40, 41:
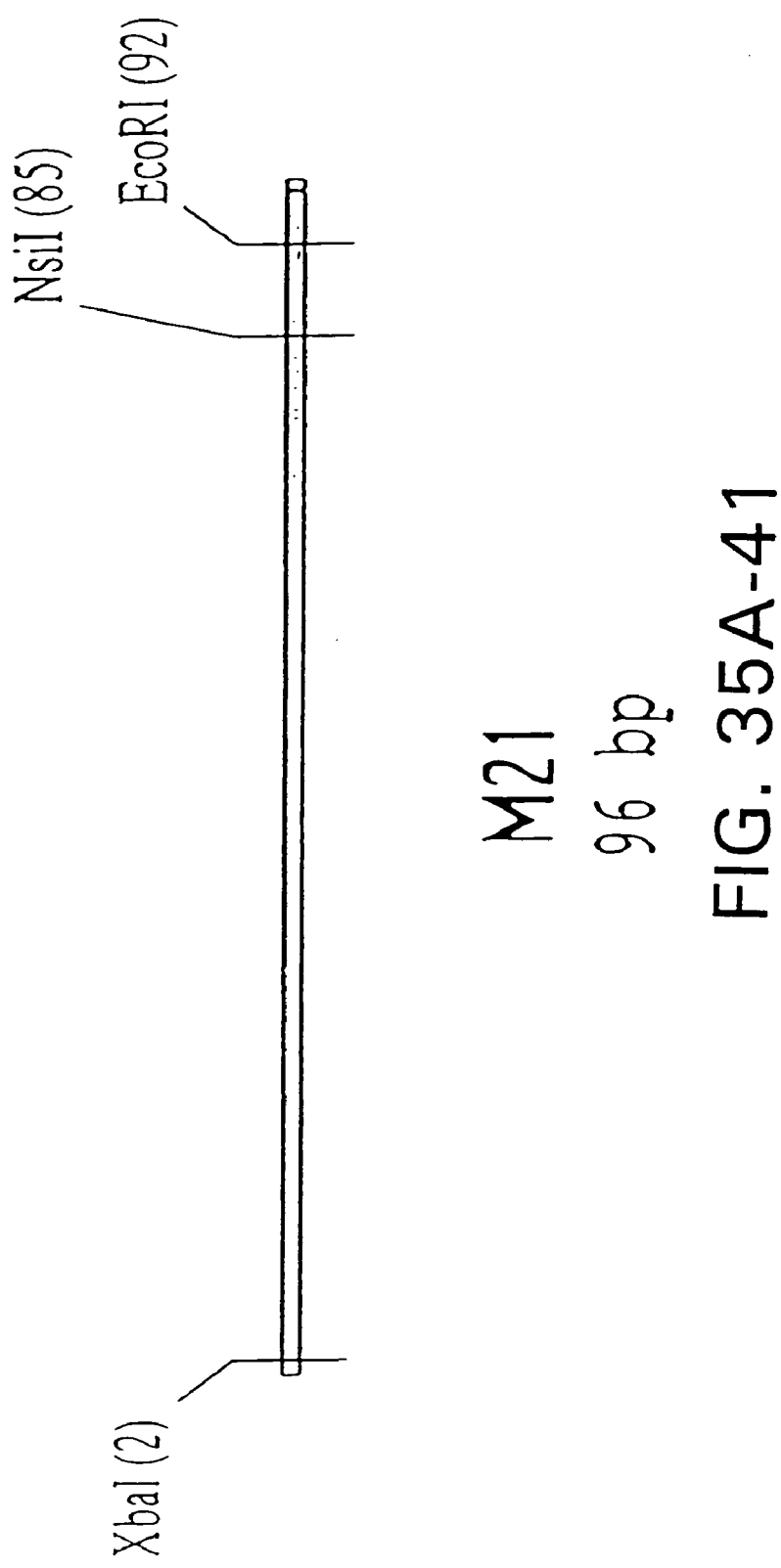
Figures 35, 35A, 36, 37, 38, 39, 40, 41, 42, 43:
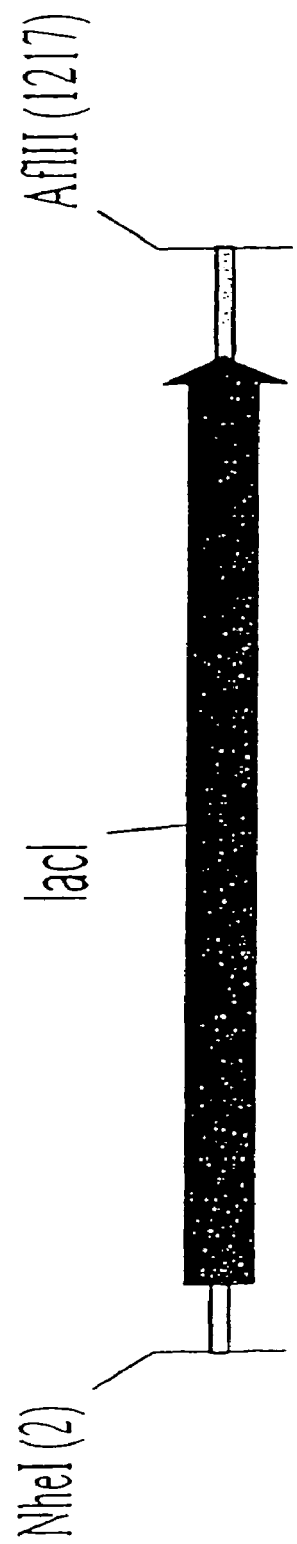
Figures 35, 35A, 36, 37, 38, 39, 40, 41, 42, 43, 44, 45, 46, 47, 48:
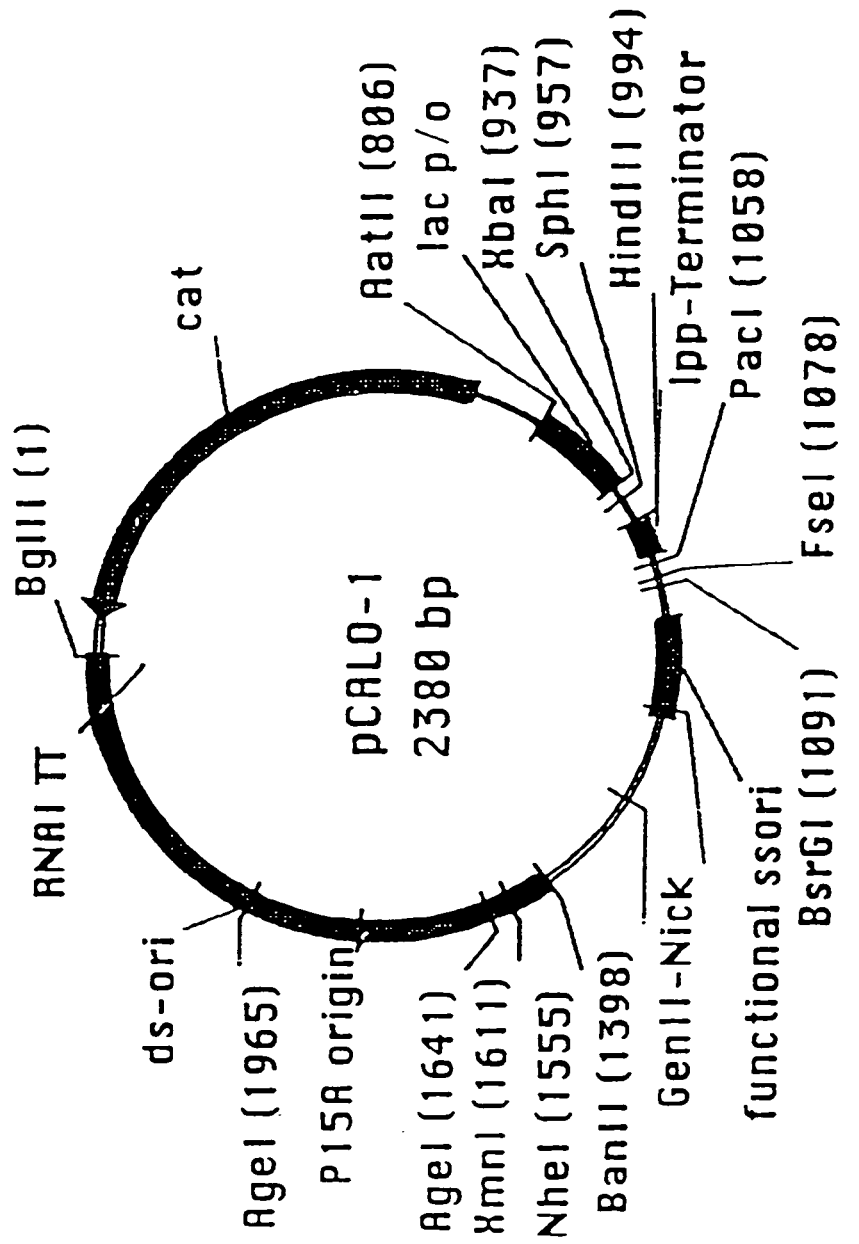
Figures 35, 35A, 36, 37, 38, 39, 40, 41, 42, 43, 44, 45, 46, 47, 48, 49, 50, 51, 52, 53, 54, 55, 56:
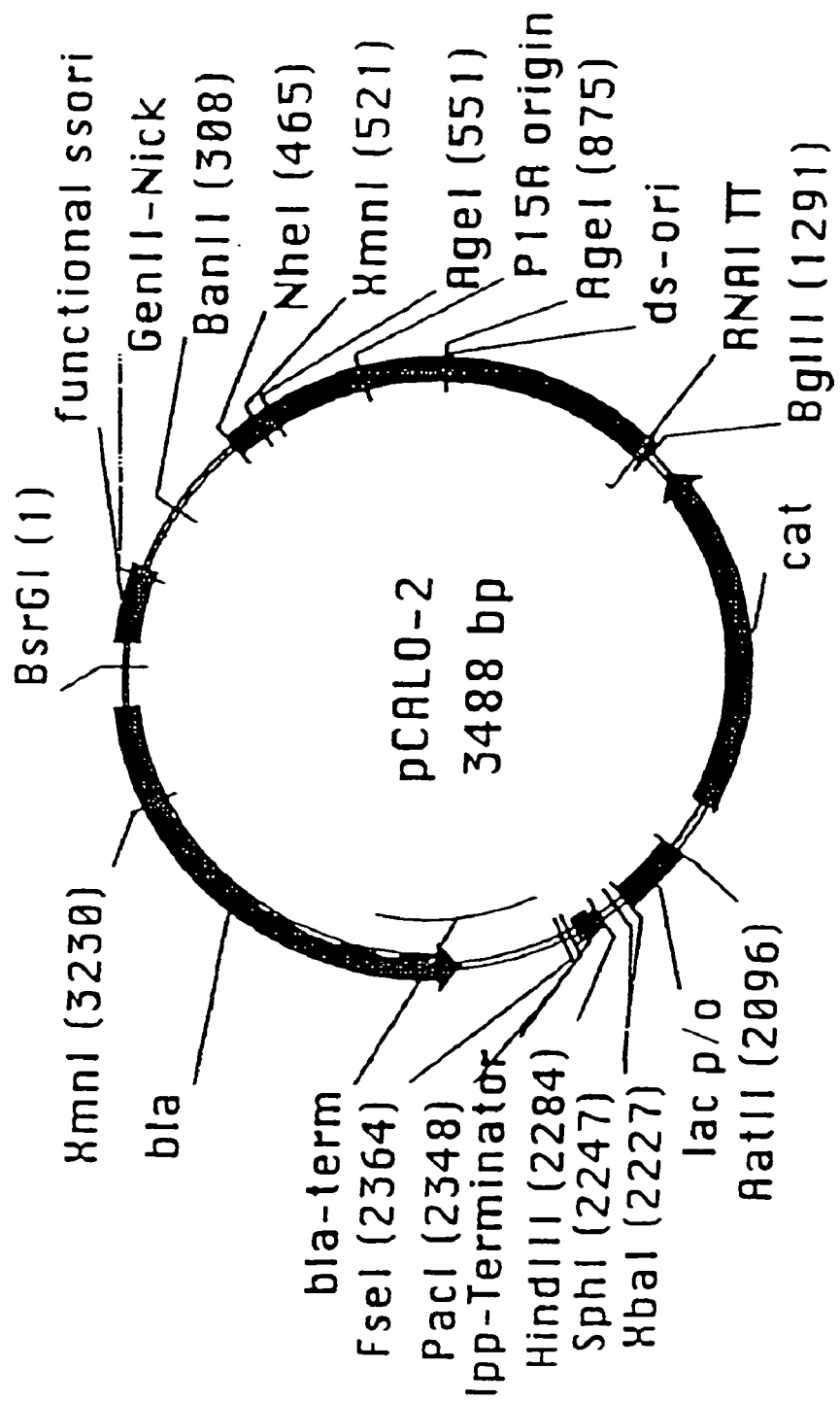
Figures 35, 35A, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67:
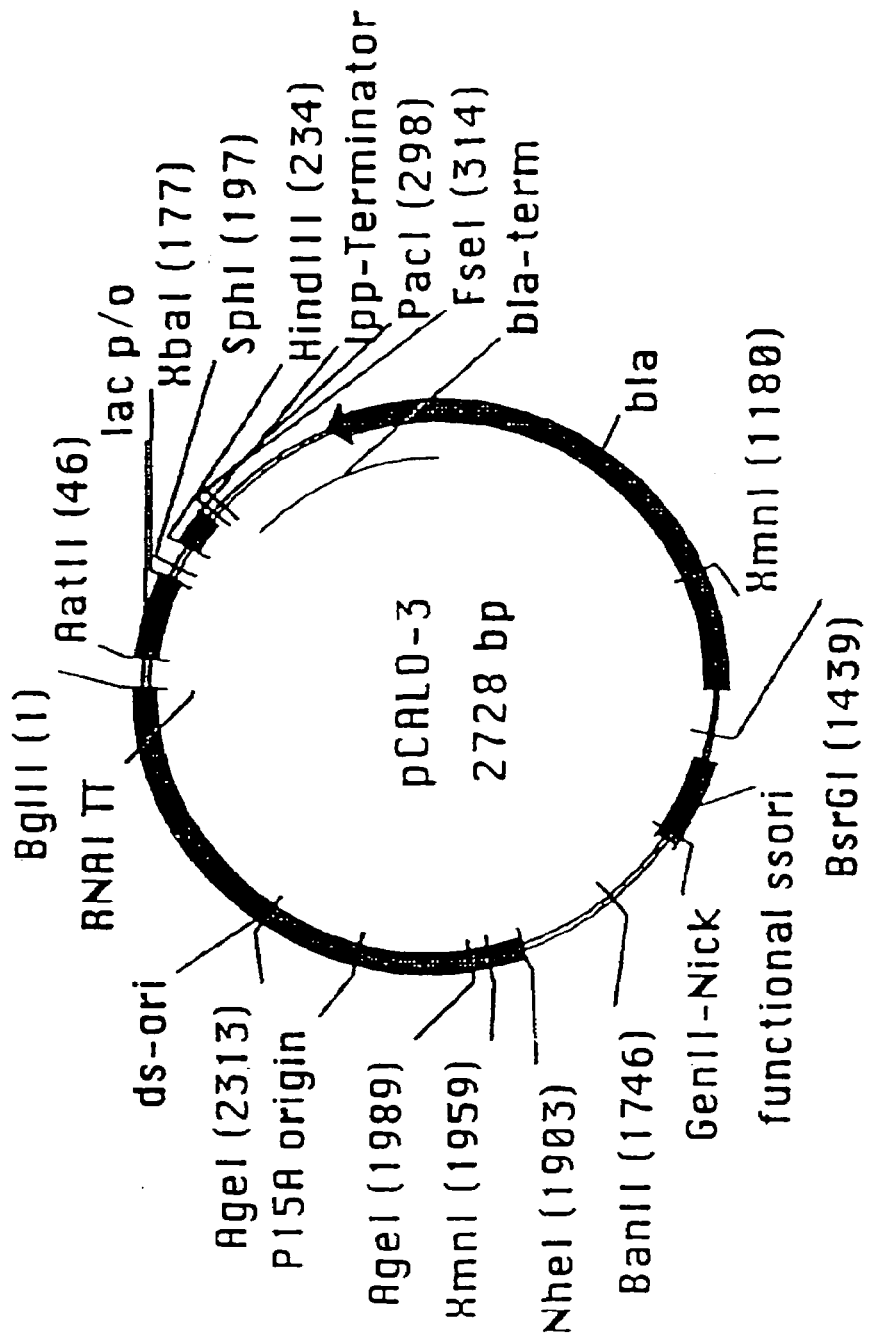
Figure 36A:
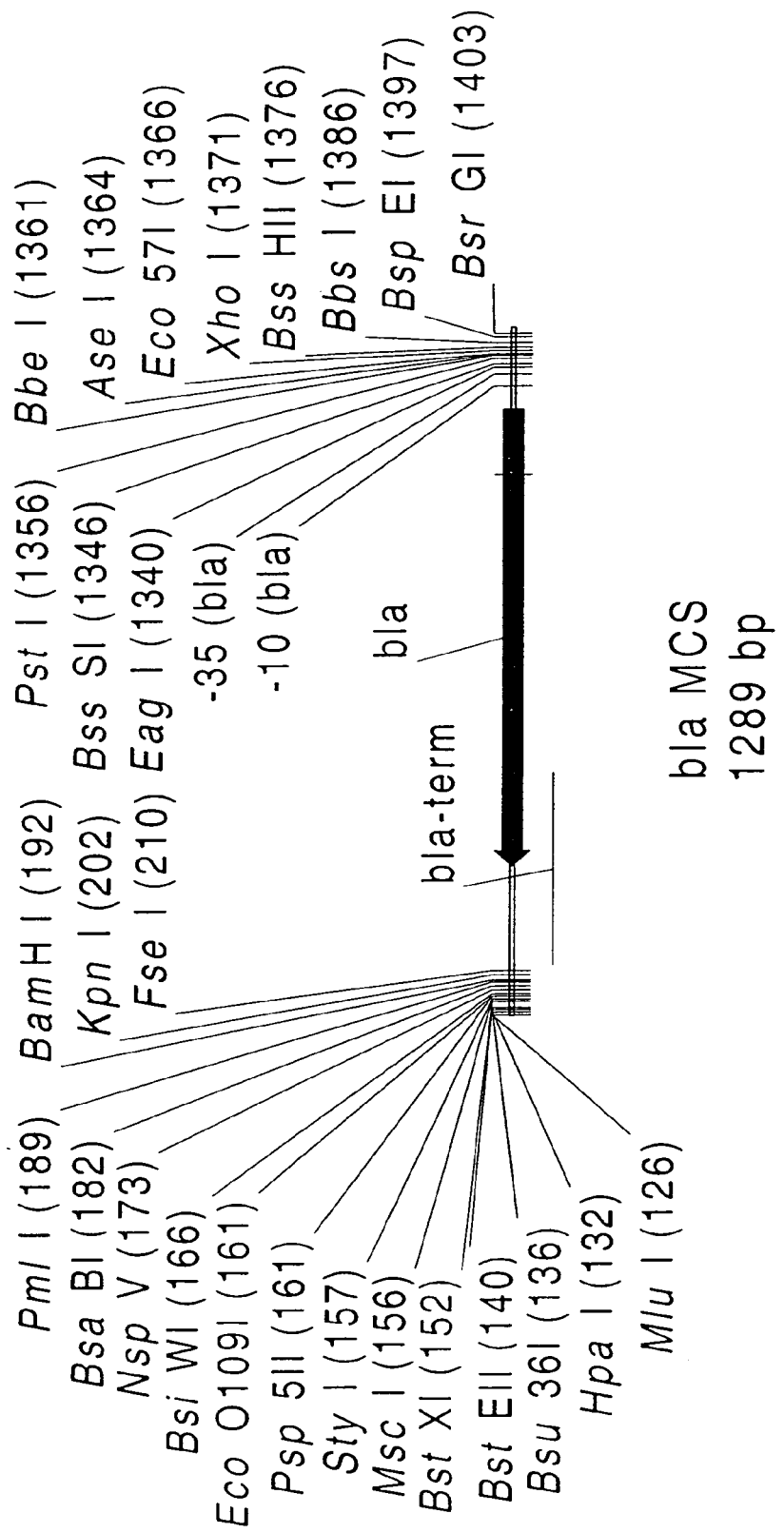
Figure 37B:
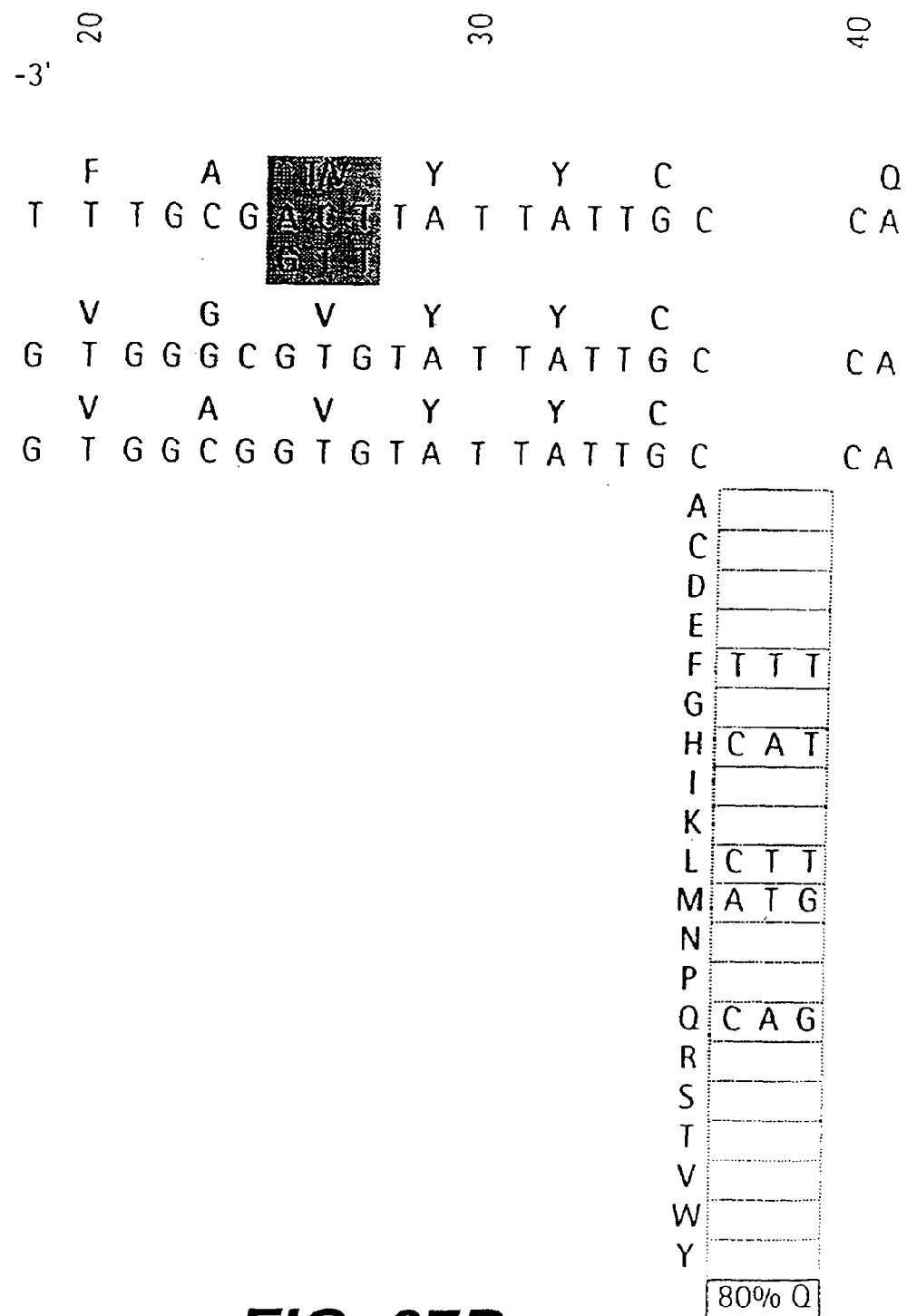
Figure 38B:
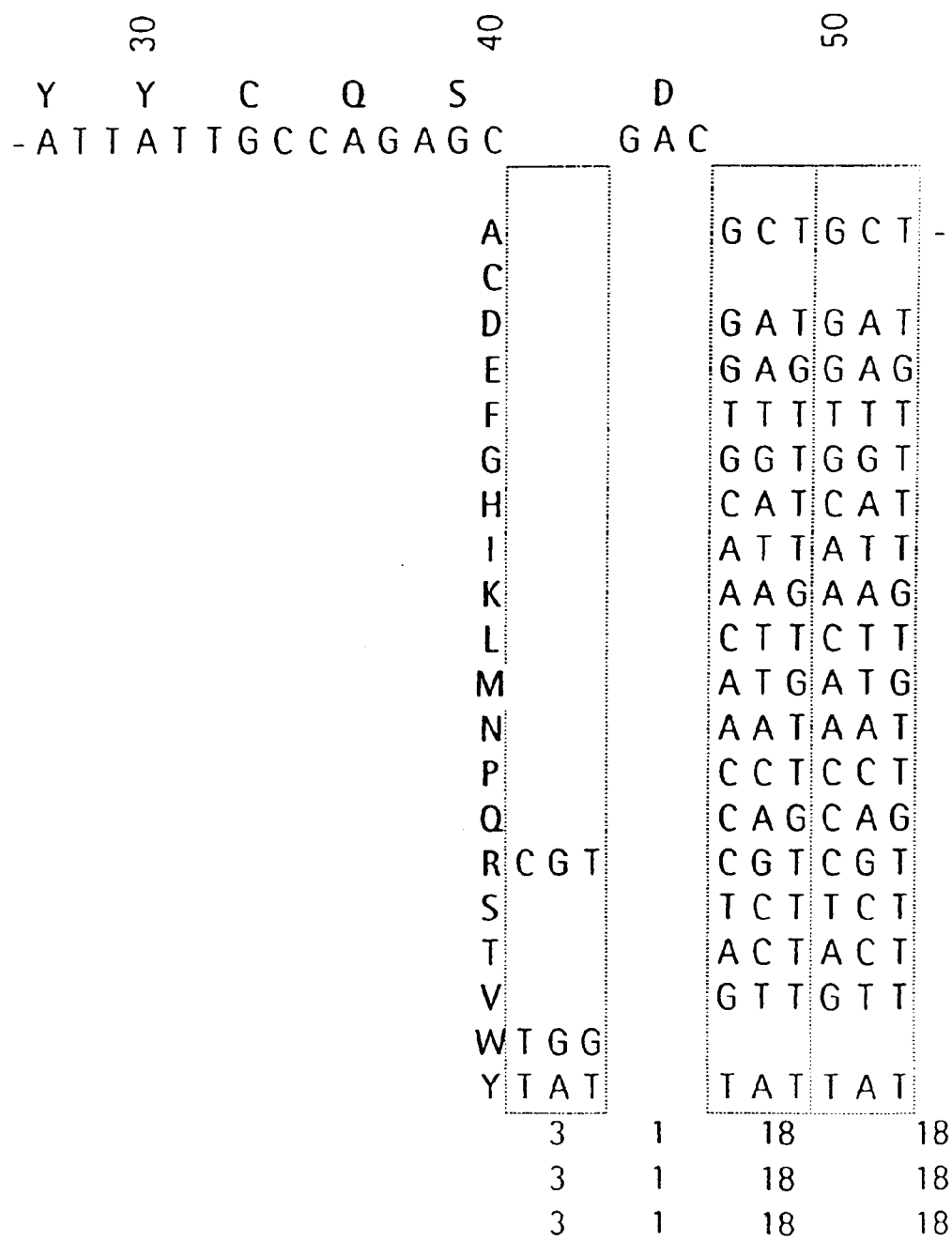
Figure 39:
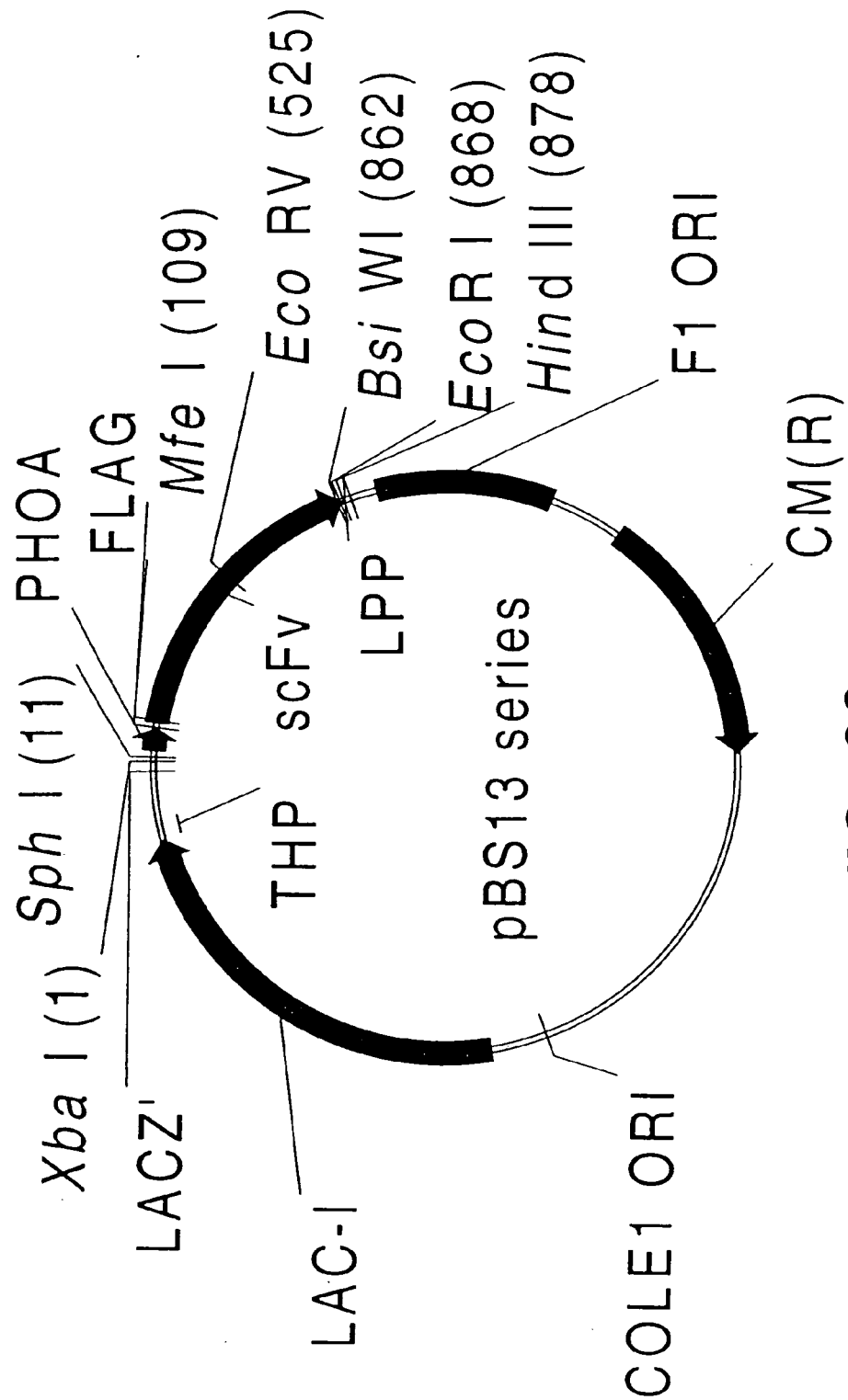

FIG. 39: Functional map of the pBS13 expression vector series.

FIGS. 40A–40B: Expression of all 49 HuCAL scFvs obtained by combining each of the 7 VH genes with each of the 7 VL genes (pBS 13, 30° C.): Values are given for the percentage of soluble vs. insoluble material, the total and the soluble amount compared to the combination H3P2, which was set to 100%. In addition, the corresponding values for the McPC603 scFv are given.

TABLE 1

Summary of human immunoglobulin germline sequences used for computing the germline membership of rearranged sequences. (A) kappa sequences, (B) lambda sequences and (C), heavy chain sequences. (1) The germline name used in the various calculations, (2) the references number for the corresponding sequence (see appendix for sequence related citations), (3) the family where each sequence belongs to and (4), the various names found in literature for germline genes with identical amino acid sequences.

TABLE 2

Rearranged human sequences used for the calculation of consensus sequences. (A) kappa sequences, (B) lambda sequences and (C), heavy chain sequences. The table summarized the name of the sequence (1), the length of the sequence in amino acids (2), the germline family (3) as well as the computed germline counterpart (4). The number of amino acid exchanges between the rearranged sequence and the germline sequence is tabulated in (5), and the percentage of different amino acids is given in (6). Column (7) gives the references number for the corresponding sequence (see appendix for sequence related citations).

TABLE 3

Assignment of rearranged V sequences to their germline counterparts. (A) kappa sequences, (B) lambda sequences and (C), heavy chain sequences. The germline genes are tabulated according to their family (1), and the number of rearranged genes found for every germline gene is given in (2).

TABLE 4

Computation of the consensus sequence of the rearranged V kappa sequences. (A) (SEQ ID NO: 14), V kappa subgroup 1, (B) (SEQ ID NO: 15), V kappa subgroup 2, (C) (SEQ ID NO: 16), V kappa subgroup 3 and (D) (SEQ ID NO: 17), V kappa subgroup 4. The number of each amino acid found at each position is tabulated together with the statistical analysis of the data. (1) Amino acids are given with their standard one-letter abbreviations (and B means D or N, Z means E or Q and X means any amino acid). The statistical analysis summarizes the number of sequences found at each position (2), the number of occurrences of the most common amino acid (3), the amino acid residue which is most common at this position (4), the relative frequency of the occurrence of the most common amino acid (5) and the number of different amino acids found at each position (6).

TABLE 5

Computation of the consensus sequence of the rearranged V lambda sequences. (A) (SEQ ID NO: 18), V lambda subgroup 1, (B) (SEQ ID NO: 19), V lambda subgroup 2, and (C) (SEQ ID NO: 20), V lambda subgroup 3. The number of each amino acid found at each position is tabulated together with the statistical analysis of the data. Abbreviations are the same as in Table 4.

TABLE 6

Computation of the consensus sequence of the rearranged V heavy chain sequences. (A) (SEQ ID NO: 21), V heavy chain subgroup 1A, (B) (SEQ ID NO: 22), V heavy chain subgroup 1B, (C) (SEQ ID NO: 23), V heavy chain subgroup 2, (D) (SEQ ID NO: 24), V heavy chain subgroup 3, (E) (SEQ ID NO: 25), V heavy chain subgroup 4, (F) (SEQ ID NO: 26), V heavy chain subgroup 5, and (G) (SEQ ID NO: 27), V heavy chain subgroup 6. The number of each amino acid found at each position is tabulated together with the statistical analysis of the data. Abbreviations are the same as in Table 4.

EXAMPLES

Example 1

Design of a Synthetic Human Combinatorial Antibody Library (HuCAL)

The following example describes the design of a fully synthetic human combinatorial antibody library (HuCAL), based on consensus sequences of the human immunoglobulin repertoire, and the synthesis of the consensus genes. The general procedure is outlined in FIG. 1.

1.1 Sequence Database 1.1.1 Collection and Alignment of Human Immunoglobulin Sequences In a first step, sequences of variable domains of human immunoglobulins have been collected and divided into three sub bases: V heavy chain (VH), V kappa (Vκ) and V lambda (Vλ). For each sequence, the gene sequence was then translated into the corresponding amino acid sequence. Subsequently, all amino acid sequences were aligned according to Kabat et al. (1991). In the case of Vλ sequences, the numbering system of Chuchana et al. (1990) was used. Each of the three main databases was then divided into two further sub bases: the first sub base contained all sequences derived from rearranged V genes, where more than 70 positions of the sequence were known. The second sub base contained all germline gene segments (without the D- and J-minigenes; pseudogenes with internal stop codons were also removed). In all cases, where germline sequences with identical amino acid sequence but different names were found, only one sequence was used (see Table 1). The final databases of rearranged sequences contained 386, 149 and 674 entries for Vκ, Vλ and VH, respectively. The final databases of germline sequences contained 48, 26 and 141 entries for Vκ, Vλ and VH, respectively.

1.1.2 Assignment of Sequences to Subgroups

The sequences in the three germline databases where then grouped according to sequence homology (see also Tomlinson et al., 1992, Williams & Winter, 1993, and Cox et al., 1994). In the case of Vκ, 7 families could be established. Vλ was divided into 8 families and VH into 6 families. The VH germline genes of the VH7 family (Van Dijk et al., 1993) were grouped into the VH1 family, since the genes of the two families are highly homologous. Each family contained different numbers of germline genes, varying from 1 (for example VH6) to 47 (VH3).

1.2 Analysis of Sequences 1.2.1 Computation of Germline Membership

For each of the 1209 amino acid sequences in the databases of rearranged genes, the nearest germline counterpart, i.e. the germline sequence with the smallest number of amino acid differences was then calculated. After the germline counterpart was found, the number of somatic mutations which occurred in the rearranged gene and which led to amino acid exchanges could be tabulated. In 140 cases, the germline counterpart could not be calculated exactly, because more than one germline gene was found with an identical number of amino acid exchanges. These rearranged sequences were removed from the database. In a few cases, the number of amino acid exchanges was found to be unusually large (>20 for VL and >25 for VH), indicating either heavily mutated rearranged genes or derivation from germline genes not present in the database. Since it was not possible to distinguish between these two possibilities, these sequences were also removed from the database. Finally, 12 rearranged sequences were removed from the database because they were found to have very unusual CDR lengths and composition or unusual amino acids at canonical positions (see below). In summary, 1023 rearranged sequences out of 1209 (85%) could be clearly assigned to their germline counterparts (see Table 2).

After this calculation, every rearranged gene could be arranged in one of the families established for the germline genes. Now the usage of each germline gene, i.e. the number of rearranged genes which originate from each germline gene, could be calculated (see Table 2). It was found that the usage was strongly biased towards a subset of germline genes, whereas most of the germline genes were not present as rearranged genes in the database and therefore apparently not used in the immune system (Table 3). This observation had already been reported in the case of Vκ (Cox, et al., 1994). All germline gene families, where no or only very few rearranged counterparts could be assigned, were removed from the database, leaving 4 Vκ, 3 Vλ, and 6 VH families.

1.2.2 Analysis of CDR Conformations

The conformation of the antigen binding loops of antibody molecules, the CDRs, is strongly dependent on both the length of the CDRs and the amino acid residues located at the so-called canonical positions (Chothia & Lesk, 1987). It has been found that only a few canonical structures exist, which determine the structural repertoire of the immunoglobulin variable domains (Chothia et al., 1989). The canonical amino acid positions can be found in CDR as well as framework regions. The 13 used germline families defined above (7 VL and 6 VH) were now analyzed for their canonical structures in order to define the structural repertoire encoded in these families.

In 3 of the 4 Vκ families (Vκ1, 2 and 4), one different type of CDR1 conformation could be defined for every family. The family Vκ3 showed two types of CDR1 conformation: one type which was identical to Vκ1 and one type only found in Vκ3. All Vκ CDR2s used the same type of canonical structure. The CDR3 conformation is not encoded in the germline gene segments. Therefore, the 4 Vκ families defined by sequence homology and usage corresponded also to 4 types of canonical structures found in Vκ germline genes.

The 3 Vκ families defined above showed 3 types of CDR1 conformation, each family with one unique type. The Vκ1 family contained 2 different CDR1 lengths (13 and 14 amino acids), but identical canonical residues, and it is thought that both lengths adopt the same canonical conformation (Chothia & Lesk, 1987). In the CDR2 of the used Vλ germlines, only one canonical conformation exists, and the CDR3 conformation is not encoded in the germline gene segments. Therefore, the 3 Vλ families defined by sequence homology and usage corresponded also to 3 types of canonical structures.

The structural repertoire of the human VH sequences was analyzed in detail by Chothia et al., 1992. In total, 3 conformations of CDR1 (H1-1, H1-2 and H1-3) and 6 conformations of CDR2 (H2-1, H2-2, H2-3, H2-4, H2-5 and H2-x) could be defined. Since the CDR3 is encoded in the D- and J-minigene segments, no particular canonical residues are defined for this CDR.

All the members of the VH1 family defined above contained the CDR1 conformation H1-1, but differed in their CDR2 conformation: the H2-2 conformation was found in 6 germline genes, whereas the conformation H2-3 was found in 8 germline genes. Since the two types of CDR2 conformations are defined by different types of amino acid at the framework position 72, the VH1 family was divided into two subfamilies: VH1A with CDR2 conformation H2-2 and VH1B with the conformation H2-3. The members of the VH2 family all had the conformations H1-3 and H2-1 in CDR1 and CDR2, respectively. The CDR1 conformation of the VH3 members was found in all cases to be H1-1, but 4 different types were found in CDR2 (H2-1, H2-3, H2-4 and H2-x). In these CDR2 conformations, the canonical framework residue 71 is always defined by an arginine. Therefore, it was not necessary to divide the VH3 family into subfamilies, since the 4 types of CDR2 conformations were defined solely by the CDR2 itself. The same was true for the VH4 family. Here, all 3 types of CDR1 conformations were found, but since the CDR1 conformation was defined by the CDR itself (the canonical framework residue 26 was found to be glycine in all cases), no subdivisions were necessary. The CDR2 conformation of the VH4 members was found to be H2-1 in all cases. All members of the VH5 family were found to have the conformation H1-1 and H2-2, respectively. The single germline gene of the VH6 family had the conformations H1-3 and H2-5 in CDR1 and CDR2, respectively.

In summary, all possible CDR conformations of the Vκ and Vλ genes were present in the 7 families defined by sequence comparison. From the 12 different CDR conformations found in the used VH germline genes, 7 could be covered by dividing the family VH1 into two subfamilies, thereby creating 7 VH families. The remaining 5 CDR conformations (3 in the VH3 and 2 in the VH4 family) were defined by the CDRs themselves and could be created during the construction of CDR libraries. Therefore, the structural repertoire of the used human V genes could be covered by 49 (7×7) different frameworks.

1.2.3 Computation of Consensus Sequences

The 14 databases of rearranged sequences (4 Vκ, 3 Vλ, and 7 VH) were used to compute the HuCAL consensus sequences of each subgroup (4 HuCAL-Vκ, 3 HuCAL-Vλ, 7 HuCAL-VH, see Table 4, 5 and 6). This was done by counting the number of amino acid residues used at each position (position variability) and subsequently identifying the amino acid residue most frequently used at each position. By using the rearranged sequences instead of the used germline sequences for the calculation of the consensus, the consensus was weighted according to the frequency of usage. Additionally, frequently mutated and highly conserved positions could be identified. The consensus sequences were cross-checked with the consensus of the germline families to see whether the rearranged sequences were biased at certain positions towards amino acid residues which did not occur in the collected germline sequences, but this was found not to be the case. Subsequently, the number of differences of each of the 14 consensus sequences to each of the germline sequences found in each specific family was calculated. The overall deviation from the most homologous germline sequence was found to be 2.4 amino acid residues (s.d.=2.7), ensuring that the "artificial" consensus sequences can still be considered as truly human sequences as far as immunogenicity is concerned.

1.3 Structural Analysis

So far, only sequence information was used to design the consensus sequences. Since it was possible that during the calculation certain artificial combinations of amino acid residues have been created, which are located far away in the sequence but have contacts to each other in the three dimensional structure, leading to destabilized or even misfolded frameworks, the 14 consensus sequences were analyzed according to their structural properties.

It was rationalized that all rearranged sequences present in the database correspond to functional and therefore correctly folded antibody molecules. Hence, the most homologous rearranged sequence was calculated for each consensus sequence. The positions where the consensus differed from the rearranged sequence were identified as potential "artificial residues" and inspected.

The inspection itself was done in two directions. First, the local sequence stretch around each potentially "artificial residue" was compared with the corresponding stretch of all the rearranged sequences. If this stretch was found to be truly artificial, i.e. never occurred in any of the rearranged sequences, the critical residue was converted into the second most common amino acid found at this position and analyzed again. Second, the potentially "artificial residues" were analyzed for their long range interactions. This was done by collecting all available structures of human antibody variable domains from the corresponding PDB files and calculating for every structure the number and type of interactions each amino acid residue established to each side-chain. These "interaction maps" were used to analyze the probable side-chain/side-chain interactions of the potentially "artificial residues". As a result of this analysis, the following residues were exchanged (given is the name of the gene, the position according to Kabat's numbering scheme, the amino acid found at this position as the most abundant one and the amino acid which was used instead):

VH2: $S_{65}T$

Vκ1: $N_{34}A$,

Vλ3: $G_9A$, $D_{60}A$, $R_{77}S$

Vκ3: $V_{78}T$ 1.4 Design of CDR Sequences

The process described above provided the complete consensus sequences derived solely from the databases of rearranged sequences. It was rationalized that the CDR1 and CDR2 regions should be taken from the databases of used germline sequences, since the CDRs of rearranged and mutated sequences are biased towards their particular antigens. Moreover, the germline CDR sequences are known to allow binding to a variety of antigens in the primary immune response, where only CDR3 is varied. Therefore, the consensus CDRs obtained from the calculations described above were replaced by germline CDRs in the case of VH and Vκ. In the case of Vλ, a few amino acid exchanges were introduced in some of the chosen germline CDRs in order to avoid possible protease cleavage sites as well as possible structural constraints.

The CDRs of following germline genes have been chosen:

| HuCAL gene | CDR1 | CDR2 |
|---|---|---|
| HuCAL-VH1A | VH1-12-1 | VH1-12-1 |
| HuCAL-VH1B | VH1-13-16 | VH1-13-6, -7, -8, -9 |
| HuCAL-VH2 | VH2-31-10, -11, -12, -13 | VH2-31-3, -4 |
| HuCAL-VH3 | VH3-13-8, -9, -10 | VH3-13-8, -9, -10 |
| HuCAL-VH4 | VH4-11-7 to -14 | VH4-11-8, -9, -11, -12, -14, -16 |
| | | VH4-31-17, -18, -19, -20 |
| HuCAL-VH5 | VH5-12-1, -2 | VH5-12-1, -2 |

-continued

| HuCAL gene | CDR1 | CDR2 |
|---|---|---|
| HuCAL-VH6 | VH6-35-1 | VH6-35-1 |
| HuCAL-Vκ1 | Vκ1-14, -15 | Vκ1-2, -3, -4, -5, -7, -8, -12, -13, -18, -19 |
| HuCAL-Vκ2 | Vκ2-6 | Vκ2-6 |
| HuCAL-Vκ3 | Vκ3-1, -4 | Vκ3-4 |
| HuCAL-Vκ4 | Vκ4-1 | Vκ4-1 |
| HuCAL-Vλ1 | HUMLV117, DPL5 | DPL5 |
| HuCAL-Vλ2 | DPL11, DPL12 | DPL12 |
| HuCAL-Vλ3 | DPL23 | HUMLV318 |

In the case of the CDR3s, any sequence could be chosen since these CDRs were planned to be the first to be replaced by oligonucleotide libraries. In order to study the expression and folding behavior of the consensus sequences in *E. coli*, it would be useful to have all sequences with the same CDR3, since the influence of the CDR3s on the folding behavior would then be identical in all cases. The dummy sequences QQHYTTPP (see, for instance, positions 89–96 of SEQ ID NO: 28 and positions 88–95 of SEQ ID NO: 34) and ARWGGDGFYAMDY (positions 97–109 of SEQ ID NOS 35 & 36) were selected for the VL chains (kappa and lambda) and for the VH chains, respectively. These sequences are known to be compatible with antibody folding in *E. coli* (Carter et al., 1992).

1.5 Gene Design

The final outcome of the process described above was a collection of 14 HuCAL amino acid sequences, which represent the frequently used structural antibody repertoire of the human immune system (see FIG. 2). These sequences were back-translated into DNA sequences. In a first step, the back-translation was done using only codons which are known to be frequently used in *E. coli*. These gene sequences were then used for creating a database of all possible restriction endonuclease sites, which could be introduced without changing the corresponding amino acid sequences. Using this database, cleavage sites were selected which were located at the flanking regions of all subelements of the genes (CDRs and framework regions) and which could be introduced in all HuCAL VH, Vκ or Vλ genes simultaneously at the same position. In a few cases it was not possible to find cleavage sites for all genes of a subgroup. When this happened, the amino acid sequence was changed, if this was possible according to the available sequence and structural information. This exchange was then analyzed again as described above. In total, the following 6 amino acid residues were exchanged during this design (given is the name of the gene, the position according to Kabat's numbering scheme, the amino acid found at this position as the most abundant one and the amino acid which was used instead):

VH2: $T_3Q$

VH6: $S_{42}G$

Vκ3: $E_1D$, $I_{58}V$

Vκ4: $K_{24}R$

Vλ3: $T_{22}S$

In one case (5'-end of VH framework 3) it was not possible to identify a single cleavage site for all 7 VH genes. Two different type of cleavage sites were used instead: BstEII for HuCAL VH1A, VH1B, VH4 and VH5, and NspV for HuCAL VH2, VH3, VH4 and VH6.

Several restriction endonuclease sites were identified, which were not located at the flanking regions of the sub-elements but which could be introduced in every gene of a given group without changing the amino acid sequence. These cleavage sites were also introduced in order to make the system more flexible for further improvements. Finally, all but one remaining restriction endonuclease sites were removed in every gene sequence. The single cleavage site, which was not removed was different in all genes of a subgroup and could be therefore used as a "fingerprint" site to ease the identification of the different genes by restriction digest. The designed genes, together with the corresponding amino acid sequences and the group-specific restriction endonuclease sites are shown in FIGS. 3, 4 and 5, respectively.

1.6 Gene Synthesis and Cloning

The consensus genes were synthesized using the method described by Prodromou & Pearl, 1992, using the oligonucleotides shown in FIG. 6. Gene segments encoding the human constant domains Cκ, Cλ and CH1 were also synthesized, based on sequence information given by Kabat et al., 1991 (see FIG. 6 and FIG. 7). Since for both the CDR3 and the framework 4 gene segments identical sequences were chosen in all HuCAL Vκ, Vλ and VH genes, respectively, this part was constructed only once, together with the corresponding gene segments encoding the constant domains. The PCR products were cloned into pCR-Script KS(+) (Stratagene, Inc.) or pZErO-1 (Invitrogen, Inc.) and verified by sequencing.

Example 2

Cloning and Testing of a HuCAL-Based Antibody Library

A combination of two of the synthetic consensus genes was chosen after construction to test whether binding antibody fragments can be isolated from a library based on these two consensus frameworks. The two genes were cloned as a single-chain Fv (scFv) fragment, and a VH-CDR3 library was inserted. In order to test the library for the presence of functional antibody molecules, a selection procedure was carried out using the small hapten fluorescein bound to BSA (FITC-BSA) as antigen.

2.1 Cloning of the HuCAL VH3-Vk2 scFv Fragment

In order to test the design of the consensus genes, one randomly chosen combination of synthetic light and heavy gene (HuCAL-Vκ2 and HuCAL-VH3) was used for the construction of a single-chain antibody (scFv) fragment. Briefly, the gene segments encoding the VH3 consensus gene and the CH1 gene segment including the CDR3-framework 4 region, as well as the Vκ2 consensus gene and the Cκ gene segment including the CDR3-framework 4 region were assembled yielding the gene for the VH3-CH1 Fd fragment and the gene encoding the Vκ2-Cκ light chain, respectively. The CH1 gene segment was then replaced by an oligonucleotide (SEQ ID NOS 2 & 3, respectively) cassette encoding a 20-mer peptide linker (SEQ ID NO: 1) with the sequence AGGGSGGGGSGGGGSGGGGS. The two oligonucleotides encoding this linker were 5'-TCAGCGGGTGGCGGTTCTGGCGGCG-GTGGGAGCGGTG GCGGTGGTTCTGGCGGTGGTG-GTTCCGATATCGGTCCACGTACGG-3' and 5'-AATTC-CGTACGTGGACCGATATCGGAACCACCACCGCCAGA ACCACCGCCACCGCTCCCACCGCCGCCA-GAACCGCCACCCGC-3', respectively. Finally, the HuCAL-Vκ2 gene was inserted via EcoRV and BsiWI into the plasmid encoding the HuCAL-VH3-linker fusion, leading to the final gene HuCAL-VH3-Vκ2, which encoded the two consensus sequences in the single-chain format VH-linker-VL. The complete coding sequence is shown in FIG. 8.

2.2 Construction of a Monovalent Phage-Display Phagemid Vector pIG10.3

Phagemid pIG10.3 (FIG. 9) was constructed in order to create a phage-display system (Winter et al., 1994) for the H3κ2 scFv gene. Briefly, the EcoRI/HindIII restriction fragment in the phagemid vector pIG10 (Ge et al., 1995) was replaced by the c-myc followed by an amber codon (which encodes an glutamate in the amber-suppresser strain XL1 Blue and a stop codon in the non-suppresser strain JM83) and a truncated version of the gene III (fusion junction at codon 249, see Lowman et al., 1991) through PCR mutagenesis.

2.3 Construction of H-CDR3 Libraries

Heavy chain CDR3 libraries of two lengths (10 and 15 amino acids) were constructed using trinucleotide codon containing oligonucleotides (Virnekas et al., 1994) as templates and the oligonucleotides complementing the flanking regions as primers. To concentrate only on the CDR3 structures that appear most often in functional antibodies, we kept the salt-bridge of $R_{H94}$ and $D_{H101}$ in the CDR3 loop. For the 15-mer library, both phenylalanine and methionine were introduced at position 100 since these two residues were found to occur quite often in human CDR3s of this length (not shown). For the same reason, valine and tyrosine were introduced at position 102. All other randomized positions contained codons for all amino acids except cystein, which was not used in the trinucleotide mixture.

The CDR3 libraries of lengths 10 and 15 were generated from the PCR fragments using oligonucleotide templates (SEQ ID NOS 4 & 5, respectively) O3HCDR103T (5'-GATACGGCCGTGTATTATTGCGCGCGT (TRI)$_6$ GAT-TATTGGGGCCAAGGCACCCTG-3') and O3HCDR153T (5'-GATACGGCCGTGTATTATTGCGCGCGT(TRI)$_6$ (TTT/ATG)GAT(GTT/TAT)TGGGGCCAAGGCAC-CCTG-3'), and primers (SEQ ID NOS 6 & 7, respectively) O3HCDR35 (5'-GATACGGCCGTGTATTATTGC-3') and O3HCDR33 (5'-CAGGGTGCCTTGGCCCC-3'), where TRI are trinucleotide mixtures representing all amino acids without cystein, (TTT/ATG) and (GTT/TAT) are trinucleotide mixtures encoding the amino acids phenylalanine/methionine and valine/tyrosine, respectively. The potential diversity of these libraries was $4.7 \times 10^7$ and $3.4 \times 10^{10}$ for 10-mer and 15-mer library, respectively. The library cassettes were first synthesized from PCR amplification of the oligo templates in the presence of both primers: 25 pmol of the oligo template O3HCDR103T or O3HCDR153T, 50 pmol each of the primers O3HCDR35 and O3HCDR33, 20 nmol of dNTP, 10× buffer and 2.5 units of Pfu DNA polymerase (Stratagene) in a total volume of 100 ml for 30 cycles (1 minute at 92° C., 1 minute at 62° C. and 1 minute at 72° C.). A hot-start procedure was used. The resulting mixtures were phenol-extracted, ethanol-precipitated and digested overnight with EagI and StyI. The vector pIG10.3-sCH3κ2cat, where the EagI-StyI fragment in the vector pIG10.3-sCH3κ2 encoding the H-CDR3 was replaced by the chloramphenicol acetyltransferase gene (cat) flanked with these two sites, was similarly digested. The digested vector (35 µg) was gel-purified and ligated with 100 µg of the library cassette overnight at 16° C. The ligation mixtures were isopropanol precipitated, air-dried and the pellets were redissolved in 100 ml of ddH2O. The ligation was mixed with 1 ml of freshly prepared electrocompetent XL 1 Blue on ice. 20 rounds of electroporation were performed and the transformants were diluted in SOC medium, shaken at 37° C. for 30 minutes and plated out on large LB plates (Amp/Tet/Glucose) at 37° C. for 6–9 hrs. The number of transformants (library size) was $3.2 \times 10^7$ and $2.3 \times 10^7$ for the 10-mer and the 15-mer library, respectively. The colonies were suspended in 2xYT medium (Amp/Tet/Glucose) and stored as glycerol culture. In order to test the quality of the initial library, phagemids from 24 independent colonies (12 from the 10-mer and 12 from the 15-mer library, respectively) were isolated and analyzed by restriction digestion and sequencing. The restriction analysis of the 24 phagemids indicated the presence of intact vector in all cases. Sequence analysis of these clones (see FIG. 10) indicated that 22 out of 24 contained a functional sequence in their heavy chain CDR3 regions. 1 out of 12 clones of the 10-mer library had a CDR3 of length 9 instead of 10, and 2 out of 12 clones of the 15-mer library had no open reading frame, thereby leading to a non-functional scFv; one of these two clones contained two consecutive inserts, but out of frame (data not shown). All codons introduced were presented in an even distribution.

Expression levels of individual library members were also measured. Briefly, 9 clones from each library were grown in 2xYT medium containing Amp/Tet/0.5% glucose at 37° C. overnight. Next day, the cultures were diluted into fresh medium with Amp/Tet. At an $OD_{600nm}$ of 0.4, the cultures were induced with 1 mM of IPTG and shaken at RT overnight. Then the cell pellets were suspended in 1 ml of PBS buffer+1 mM of EDTA. The suspensions were sonicated and the supernatants were separated on an SDS-PAGE under reducing conditions, blotted on nylon membrane and detected with anti-FLAG M1 antibody (see FIG. 11). From the nine clones of the 10-mer library, all express the scFv fragments. Moreover, the gene III scFv fusion proteins were present in all cases. Among the nine clones from the 15-mer library analyzed, 6/9 (67%) led to the expression of both scFv and the gene III/scFv fusion proteins. More importantly, all clones expressing the scFvs and gene III/scFv fusions gave rise to about the same level of expression.

2.4 Biopanning

Phages displaying the antibody libraries were prepared using standard protocols. Phages derived from the 10-mer library were mixed with phages from the 15-mer library in a ratio of 20:1 ($1 \times 10^{10}$ cfu/well of the 10-mer and $5 \times 10^8$ cfu/well of the 15-mer phages, respectively). Subsequently, the phage solution was used for panning in ELISA plates (Maxisorp, Nunc) coated with FITC-BSA (Sigma) at concentration of 100 µg/ml in PBS at 4° C. overnight. The antigen-coated wells were blocked with 3% powder milk in PBS and the phage solutions in 1% powder milk were added to each well and the plate was shaken at RT for 1 hr. The wells were then washed with PBST and PBS (4 times each with shaking at RT for 5 minutes). The bound phages were eluted with 0.1 M triethylamine (TEA) at RT for 10 minutes. The eluted phage solutions were immediately neutralized with ½ the volume of 1 M Tris.Cl, pH 7.6. Eluted phage solutions (ca. 450 µl) were used to infect 5 ml of XL1 Blue cells at 37° C. for 30 min. The infected cultures were then plated out on large LB plates (Amp/Tet/Glucose) and allowed to grow at 37° C. until the colonies were visible. The colonies were suspended in 2xYT medium and the glycerol cultures were made as above described. This panning round was repeated twice, and in the third round elution was carried out with addition of fluorescein in a concentration of 100 µg/ml in PBS. The enrichment of specific phage antibodies was monitored by panning the initial as well as the subsequent fluorescein-specific sub-libraries against the blocking buffer (FIG. 12). Antibodies with specificity against fluorescein were isolated after 3 rounds of panning.

2.5 ELISA Measurements

One of the criteria for the successful biopanning is the isolation of individual phage clones that bind to the targeted antigen or hapten. We undertook the isolation of anti-FITC phage antibody clones and characterized them first in a phage ELISA format. After the 3rd round of biopanning (see above), 24 phagemid containing clones were used to inoculate 100 µl of 2xYT medium (Amp/Tet/Glucose) in an ELISA plate (Nunc), which was subsequently shaken at 37° C. for 5 hrs. 100 µl of 2xYT medium (Amp/Tet/1 mM IPTG) were added and shaking was continued for 30 minutes. A further 100 µl of 2xYT medium (Amp/Tet) containing the helper phage ($1 \times 10^9$ cfu/well) was added and shaking was done at RT for 3 hrs. After addition of kanamycin to select for successful helper phage infection, the shaking was continued overnight. The plates were then centrifuged and the supernatants were pipetted directly into ELISA wells coated with 100 µl FITC-BSA (100 µg/ml) and blocked with milk powder. Washing was performed similarly as during the panning procedure and the bound phages were detected with anti-M13 antibody-POD conjugate (Pharmacia) using soluble POD substrate (Boehringer-Mannheim). Of the 24 clones screened against FITC-BSA, 22 were active in the ELISA (FIG. 13). The initial libraries of similar titer gave rise to no detectable signal.

Specificity for fluorescein was measured in a competitive ELISA. Periplasmic fractions of five FITC specific scFvs were prepared as described above. Western blotting indicated that all clones expressed about the same amount of scFv fragment (data not shown). ELISA was performed as described above, but additionally, the periplasmic fractions were incubated 30 min at RT either with buffer (no inhibition), with 10 mg/ml BSA (inhibition with BSA) or with 10 mg/ml fluorescein (inhibition with fluorescein) before adding to the well. Binding scFv fragment was detected using the anti-FLAG antibody M1. The ELISA signal could only be inhibited, when soluble fluorescein was added, indicating binding of the scFvs was specific for fluorescein (FIG. 14).

2.6 Sequence Analysis

The heavy chain CDR3 region of 20 clones were sequenced in order to estimate the sequence diversity of fluorescein binding antibodies in the library (FIG. 15). In total, 16 of 20 sequences (80%) were different, showing that the constructed library contained a highly diverse repertoire of fluorescein binders. The CDR3s showed no particular sequence homology, but contained on average 4 arginine residues. This bias towards arginine in fluorescein binding antibodies had already been described by Barbas et al., 1992.

2.7 Production

E. coli JM83 was transformed with phagemid DNA of 3 selected clones and cultured in 0.5 L 2xYT medium. Induction was carried out with 1 mM IPTG at $OD_{600nm}=0.4$ and growth was continued with vigorous shaking at RT overnight. The cells were harvested and pellets were suspended in PBS buffer and sonicated. The supernatants were separated from the cell debris via centrifugation and purified via the BioLogic system (Bio-Rad) by with a POROS®MC 20 column (IMAC, PerSeptive Biosystems, Inc.) coupled with an ion-exchange chromatography column. The ion-exchange column was one of the POROS®HS, CM or HQ or PI 20 (PerSeptive Biosystems, Inc.) depended on the theoretical pI of the scFv being purified. The pH of all the buffers was adjusted to one unit lower or higher than the pI of the scFv being purified throughout. The sample was loaded onto the first IMAC column, washed with 7 column volumes of 20 mM sodium phosphate, 1 M NaCl and 10 mM imidazole. This washing was followed by 7 column volumes of 20 mM sodium phosphate and 10 mM imidazole. Then 3 column volumes of an imidazole gradient (10 to 250 mM) were applied and the eluent was connected directly to the ion-exchanger. Nine column volumes of isocratic washing with 250 mM imidazole was followed by 15 column volumes of 250 mM to 100 mM and 7 column volumes of an imidazole/NaCl gradient (100 to 10 mM imidazole, 0 to 1 M NaCl). The flow rate was 5 ml/min. The purity of scFv fragments was checked by SDS-PAGE Coomassie staining (FIG. 16). The concentration of the fragments was determined from the absorbance at 280 nm using the theoretically determined extinction coefficient (Gill & von Hippel, 1989). The scFv fragments could be purified to homogeneity (see FIG. 16). The yield of purified fragments ranged from 5 to 10 mg/L/OD.

Example 3

HuCAL H3κ2 Library Against a Collection of Antigens

In order to test the library used in Example 2 further, a new selection procedure was carried out using a variety of antigens comprising β-estradiol, testosterone, Lewis-Y epitope (LeY), interleukin-2 (IL-2), lymphotoxin-β(LT-β), E-selectin ligand-1 (ESL-1), and BSA.

3.1 Biopanning

The library and all procedures were identical to those described in Example 2. The ELISA plates were coated with β-estradiol-BSA (100 µg/ml), testosterone-BSA (100 µg/ml), LeY-BSA (20 µg/ml) IL-2 (20 µg/ml), ESL-1 (20 µg/ml) and BSA (100 µg/ml), LT-β (denatured protein, 20 µg/ml). In the first two rounds, bound phages were eluted with 0.1 M triethylamine (TEA) at RT for 10 minutes. In the case of BSA, elution after three rounds of panning was carried out with addition of BSA in a concentration of 100 µg/ml in PBS. In the case of the other antigens, third round elution was done with 0.1 M triethylamine. In all cases except LeY, enrichment of binding phages could be seen (FIG. 17). Moreover, a repetition of the biopanning experiment using only the 15-mer library resulted in the enrichment of LeY-binding phages as well (data not shown).

3.2. ELISA Measurements

Clones binding to β-estradiol, testosterone, LeY, LT-β, ESL-1 and BSA were further analyzed and characterized as described in Example 2 for FITC. ELISA data for anti-β-estradiol and anti-ESL-1 antibodies are shown in FIG. 18. In one experiment, selectivity and cross-reactivity of binding scFv fragments were tested. For this purpose, an ELISA plate was coated with FITC, testosterone, β-estradiol, BSA, and ESL-1, with 5 wells for each antigen arranged in 5 rows, and 5 antibodies, one against each of the antigens, were screened against each of the antigens. FIG. 19 shows the specific binding of the antibodies to the antigen it was selected for, and the low cross-reactivity with the other four antigens.

3.3 Sequence Analysis

The sequencing data of several clones against β-estradiol (34 clones), testosterone (12 clones), LT-β (23 clones), ESL-1 (34 clones), and BSA (10 clones) are given in FIGS. 20 to 24.

Example 4

Vector Construction

To be able to take advantage of the modularity of the consensus gene repertoire, a vector system had to be constructed which could be used in phage display screening of HuCAL libraries and subsequent optimization procedures. Therefore, all necessary vector elements such as origins of single-stranded or double-stranded replication, promotor/operator, repressor or terminator elements, resistance genes, potential recombination sites, gene III for display on filamentous phages, signal sequences, or detection tags had to be made compatible with the restriction site pattern of the modular consensus genes. FIG. 25 shows a schematic representation of the pCAL vector system and the arrangement of vector modules and restriction sites therein. FIG. 25a shows a list of all restriction sites which are already incorporated into the consensus genes or the vector elements as part of the modular system or which are not yet present in the whole system. The latter could be used in a later stage for the introduction of or within new modules.

4.1 Vector Modules

A series of vector modules was constructed where the restriction sites flanking the gene sub-elements of the HuCAL genes were removed, the vector modules themselves being flanked by unique restriction sites. These modules were constructed either by gene synthesis or by mutagenesis of templates. Mutagenesis was done by add-on PCR, by site-directed mutagenesis (Kunkel et al., 1991) or multisite oligonucleotide-mediated mutagenesis (Sutherland et al., 1995; Perlak, 1990) using a PCR-based assembly method.

FIG. 26 contains a list of the modules constructed. Instead of the terminator module M9 (HindIII-Ipp-PacI), a larger cassette M9II was prepared to introduce FseI as additional restriction site. M9II can be cloned via HindIII/BsrGI.

All vector modules were characterized by restriction analysis and sequencing. In the case of module M11-II, sequencing of the module revealed a two-base difference in positions 164/65 compared to the sequence database of the template. These two different bases (CA→GC) created an additional BanII site. Since the same two-base difference occurs in the f1 origin of other bacteriophages, it can be assumed that the two-base difference was present in the template and not created by mutagenesis during cloning. This BanII site was removed by site-directed mutagenesis, leading to module M11-III. The BssSI site of module M14 could initially not be removed without impact on the function of the ColE1 origin, therefore M14-Ext2 was used for cloning of the first pCAL vector series. FIGS. 29 to 34 are showing the functional maps and sequences of the modules used for assembly of the modular vector pCAL4 (see below). The functional maps and sequences of additional modules can be found in FIGS. 35A-9 to 35A-75. FIGS. 35A-76 to 35A-80 contain lists of oligonucleotides and primers used for the synthesis of the modules.

4.2 Cloning Vector pMCS

To be able to assemble the individual vector modules, a cloning vector pMCS containing a specific multi-cloning site (MCS) was constructed. First, an MCS cassette (FIG. 27) was made by gene synthesis. This cassette contains all those restriction sites in the order necessary for the sequential introduction of all vector modules and can be cloned via the 5'-HindIII site and a four base overhang at the 3'-end compatible with an AatII site. The vector pMCS (FIG. 28) was constructed by digesting pUC19 with AatII and HindIII, isolating the 2174 base pair fragment containing the bla gene and the ColE1 origin, and ligating the MCS cassette.

4.3 Cloning of Modular Vector pCAL4

This was cloned step by step by restriction digest of pMCS and subsequent ligation of the modules M1 (via AatII/XbaI), M7III (via EcoRI/HindIII), and M9II (via HindIII/BsrGI), and M11-II (via BsrGI/NheI). Finally, the bla gene was replaced by the cat gene module M17 (via AatII/BglII), and the wild type ColE1 origin by module M14-Ext2 (via BglII/NheI). FIG. 35 is showing the functional map and the sequence of pCAL4.

4.4 Cloning of Low-Copy Number Plasmid Vectors pCALO

A series of low-copy number plasmid vectors was constructed in a similar way using the p15A module M12 instead of the ColE1 module M14-Ext2. FIGS. 35A-9 to 35A-75 show the functional maps and sequences of the vectors pCALO1 to pCALO3.

Example 5

Construction of a HuCAL scFv Library 5.1. Cloning of All 49 HuCAL scFv Fragments All 49 combinations of the 7 HuCAL-VH and 7 HuCAL-VL consensus genes were assembled as described for the HuCAL VH3-Vκ2 scFv in Example 2 and inserted into the vector pBS12, a modified version of the pLisc series of antibody expression vectors (Skerra et al., 1991).

5.2 Construction of a CDR Cloning Cassette

For replacement of CDRs, a universal β-lactamase cloning cassette was constructed having a multi-cloning site at the 5'-end as well as at the 3'-end. The 5'-multi-cloning site comprises all restriction sites adjacent to the 5'-end of the HuCAL VH and VL CDRs, the 3'-multi-cloning site comprises all restriction sites adjacent to the 3' end of the HuCAL VH and VL CDRs. Both 5'- and 3'-multi-cloning site were prepared as cassettes via add-on PCR using synthetic oligonucleotides as 5'- and 3'-primers using wild type β-lactamase gene as template. FIG. 36 shows the functional map and the sequence of the cassette bla-MCS.

5.3. Preparation of VL-CDR3 Library Cassettes

The VL-CDR3 libraries comprising 7 random positions were generated from the PCR fragments using oligonucleotide templates Vκ1&Vκ3, Vκ2 and Vκ4 and primers O_K3L_5 and O_K3L_3 (FIG. 37) for the Vκ genes, and Vλ and primers (SEQ ID NO: 8) O_L3L_5 (5'-GCA-GAAGGCGAACGTCC-3') and O_L3LA_3 (FIG. 38) for the Vλ genes. Construction of the cassettes was performed as described in Example 2.3.

5.4 Cloning of HuCAL scFv Genes with VL-CDR3 Libraries

Each of the 49 single-chains was subcloned into pCAL4 via XbaI/EcoRI and the VL-CDR3 replaced by the β-lactamase cloning cassette via BbsI/MscI, which was then replaced by the corresponding VL-CDR3 library cassette synthesized as described above. This CDR replacement is described in detail in Example 2.3 where the cat gene was used.

5.5 Preparation of VH-CDR3 Library Cassette

The VH-CDR3 libraries were designed and synthesized as described in Example 2.3.

5.6 Cloning of HuCAL scFv Genes with VL- and VH-CDR3 Libraries

Each of the 49 single-chain VL-CDR3 libraries was digested with BssHII/StyI to replace VH-CDR3. The "dummy" cassette digested with BssHII/StyI was inserted, and was then replaced by a corresponding VH-CDR3 library cassette synthesized as described above.

Example 6

Expression Tests

Expression and toxicity studies were performed using the scFv format VH-linker-VL. All 49 combinations of the 7 HuCAL-VH and 7 HuCAL-VL consensus genes assembled as described in Example 5 were inserted into the vector pBS13, a modified version of the pLisc series of antibody expression vectors (Skerra et al., 1991). A map of this vector is shown in FIG. 39.

*E. coli* JM83 was transformed 49 times with each of the vectors and stored as glycerol stock. Between 4 and 6 clones were tested simultaneously, always including the clone H3κ2, which was used as internal control throughout. As additional control, the McPC603 scFv fragment (Knappik & Plückthun, 1995) in pBS13 was expressed under identical conditions. Two days before the expression test was performed, the clones were cultivated on LB plates containing 30 μg/ml chloramphenicol and 60 mM glucose. Using this plates an 3 ml culture (LB medium containing 90 μg chloramphenicol and 60 mM glucose) was inoculated overnight at 37° C. Next day the overnight culture was used to inoculate 30 ml LB medium containing chloramphenicol (30 μg/ml). The starting $OD_{600nm}$ was adjusted to 0.2 and a growth temperature of 30.degree. C. was used. The physiology of the cells was monitored by measuring every 30 minutes for 8 to 9 hours the optical density at 600 nm. After the culture reached an $OD_{600nm}$ of 0.5, antibody expression was induced by adding IPTG to a final concentration of 1 mM. A 5 ml aliquot of the culture was removed after 2 h of induction in order to analyze the antibody expression. The cells were lysed and the soluble and insoluble fractions of the crude extract were separated as described in Knappik & Pluckthun, 1995. The fractions were assayed by reducing SDS-PAGE with the samples normalized to identical optical densities. After blotting and immunostaining using the α-FLAG antibody M1 as the first antibody (see Ge et al., 1994) and an Fc-specific anti-mouse antiserum conjugated to alkaline phosphatase as the second antibody, the lanes were scanned and the intensities of the bands of the expected size (appr. 30 kDa) were quantified densitometrically and tabulated relative to the control antibody (see FIG. 40).

Example 7

Optimization of Fluorescein Binders 7.1. Construction of L-CDR3 and H-CDR2 Library Cassettes A L-CDR3 library cassette was prepared from the oligonucleotide (SEQ ID NO: 9) template CDR3L (5'-TG- GAAGCTGAAGACGTGGGCGTGTATTATT GCCAG-CAG(TR5)(TRI)₄CCG(TRI)TTTGGCCAGGGTACGAAAGTT-3') and primer (SEQ ID NO: 10) 5'-AATTTCGTACCCTGGCC-3' for synthesis of the complementary strand, where (TRI) was a trinucleotide mixture representing all amino acids except Cys, (TR5) comprised a trinucleotide mixture representing the 5 codons for Ala, Arg, His, Ser, and Tyr.

A H-CDR2 library cassette was prepared from the oligonucleotide template CDRsH (SEQ ID NOS 11 & 12, respectively) (5'-AGGGTCTCG AGTGGGTGAGC(TRI)ATT (TRI)₂₋₃(6)₂(TRI)ACC(TRI)TATGCG GATAGCGTGAAAGGCCGTTTTAC-CATTTCACGTGATAATTCGAAAAA CACCA-3'), and primer (SEQ ID NO: 13) 5'-TGGTGTTTTTCGAAT-TATCA-3' for synthesis of the complementary strand, where (TRI) was a trinucleotide mixture representing all amino acids except Cys, (6) comprised the incorporation of (A/G) (A/C/G) T, resulting in the formation of 6 codons for Ala, Asn, Asp, Gly, Ser, and Thr, and the length distribution being obtained by performing one substoichiometric coupling of the (TRI) mixture during synthesis, omitting the capping step normally used in DNA synthesis.

DNA synthesis was performed on a 40 nmole scale, oligos were dissovled in TE buffer, purified via gel filtration using spin columns (S-200), and the DNA concentration determined by OD measurement at 260 nm (OD 1.0=40 µg/ml). 10 nmole of the oligonucleotide templates and 12 nmole of the corresponding primers were mixed and annealed at 80° C. for 1 min, and slowly cooled down to 37° C. within 20 to 30 min. The fill-in reaction was performed for 2 h at 37° C. using Klenow polymerase (2.0 µl) and 250 nmole of each dNTP. The excess of dNTPs was removed by gel filtration using Nick-Spin columns (Pharmacia), and the double-stranded DNA digested with BbsI/MscI (L-CDR3), or XhoI/SfuI (H-CDR2) over night at 37° C. The cassettes were purified via Nick-Spin columns (Pharmacia), the concentration determined by OD measurement, and the cassettes aliquoted (15 pmole) for being stored at –80° C.

7.2 Library Cloning:

DNA was prepared from the collection of FITC binding clones obtained in Example 2 (approx. 10⁴ to clones). The collection of scFv fragments was isolated via XbaI/EcoRI digest. The vector pCAL4 (100 fmole, 10 µg) described in Example 4.3 was similarly digested with XbaI/EcoRI, gel-purified and ligated with 300 fmole of the scFv fragment collection over night at 16° C. The ligation mixture was isopropanol precipitated, air-dried, and the pellets were redissolved in 100 µl of dd H₂O. The ligation mixture was mixed with 1 ml of freshly prepared electrocompetent SCS 101 cells (for optimization of L-CDR3), or XL1 Blue cells (for optimization of H-CDR2) on ice. One round of electroporation was performed and the transformants were eluted in SOC medium, shaken at 37° C. for 30 minutes, and an aliquot plated out on LB plates (Amp/Tet/Glucose) at 37° C. for 6–9 hrs. The number of transformants was 5×10⁴.

Vector DNA (100 µg) was isolated and digested (sequence and restriction map of sCH3κ2 see FIG. 8) with BbsI/MscI for optimization of L-CDR3, or XhoI/NspV for optimization of H-CDR2. 10 µg of purified vector fragments (5 pmole) were ligated with 15 pmole of the L-CDR3 or H-CDR2 library cassettes over night at 16° C. The ligation mixtures were isopropanol precipitated, air-dried, and the pellets were redissolved in 100 µl of dd H₂O. The ligation mixtures were mixed with 1 ml of freshly prepared electrocompetent XL1 Blue cells on ice. Electroporation was performed and the transformants were eluted in SOC medium and shaken at 37° C. for 30 minutes. An aliquot was plated out on LB plates (Amp/Tet/Glucose) at 37° C. for 6–9 hrs. The number of transformants (library size) was greater than 10⁸ for both libraries. The libraries were stored as glycerol cultures.

7.3. Biopanning

This was performed as described for the initial H3κ2H-CDR3 library in Example 2.1. Optimized scFvs binding to FITC could be characterized and analyzed as described in Example 2.2 and 2.3, and further rounds of optimization could be made if necessary.

REFERENCES

Barbas III, C. F., Bain, J. D., Hoekstra, D. M. & Lerner, R. A., PNAS 89, 4457–4461 (1992).

Better, M., Chang, P., Robinson, R. & Horwitz, A. H., Science 240, 1041–1043 (1988).

Blake, M. S., Johnston, K. H., Russel-Jones, G. J. & Gotschlich, E. C., Anal. Biochem. 136, 175–179 (1984).

Carter, P., Kelly, R. F., Rodrigues, M. L., Snedecor, B., Covrrubias, M., Velligan, M. D., Wong, W. L. T., Rowland, A. M., Kotts, C. E., Carver, M. E., Yang, M., Bourell, J. H., Shepard, H. M. & Henner, D., Bio/Technology 10, 163–167 (1992).

Chothia, C. & Lesk, A. M., J. Biol. Chem. 196, 910–917 (1987).

Chothia, C., Lesk, A. M., Gherardi, E., Tomlinson, I. A., Walter, G., Marks, J. D., Llewelyn, M. B. & Winter, G., J. Mol. Biol. 227, 799–817 (1992).

Chothia, C., Lesk, A. M., Tramontano, A., Levitt, M., Smith-Gill, S. J., Air, G., Sheriff, S., Padlan, E. A., Davies, D., Tulip, W. R., Colman, P. M., Spinelli, S., Alzari, P. M. & Poljak, R. J., Nature 342, 877–883 (1989).

Chuchana, P., Blancher, A., Brockly, F., Alexandre, D., Lefranc, G. & Lefranc, M.-P., Eur. J. Immunol. 20, 1317–1325 (1990).

Cox, J. P. L., Tomlinson, I. M. & Winter, G., Eur. J. Immunol. 24, 827–836 (1994).

Ge, L., Knappik, A., Pack, P., Freund, C. & Plückthun, A., In: Antibody Engineering. Borrebaeck, C. A. K. (Ed.). p. 229–266 (1995), Oxford University Press, New York, Oxford.)

Ghi, S. C. & von Hippel, P. H., Anal. Biochem. 182, 319.326 (1989).

Hochuli, E., Bannwarth, W., Döbeli, H., Gentz, R. & Stüber, D., Bio/Technology 6, 1321–1325 (1988).

Hopp, T. P., Prickett, K. S., Price, V. L., Libby, R. T., March, C. J., Cerretti, D. P., Urdal, D. L. & Conlon, P. J. Bio/Technology 6, 1204–1210 (1988).

Kabat, E. A., Wu, T. T., Perry, H. M., Gottesmann, K. S. & Foeller, C., Sequences of proteins of immunological interest, NIH publication 91–3242 (1991).

Knappik, A. & Plückthun, A., Biotechniques 17, 754–761 (1994).

Knappik, A. & Plückthun, A., Protein Engineering 8, 81–89 (1995).

Kunkel, T. A., Bebenek, K. & McClary, J., Methods in Enzymol 204, 125–39 (1991).

Lindner, P., Guth, B., Wülfing, C., Krebber, C., Steipe, B., Müller, F. & Plückthun, A., Methods: A Companion to Methods Enzymol. 4, 41–56 (1992).

Lowman, H. B., Bass, S. H., Simpson, N. and Wells, J. A., Biochemistry 30, 10832–10838 (1991).

Pack, P. & Plückthun, A., Biochemistry 31, 1579–1584 (1992).

Pack, P., Kujau, M., Schroeckh, V., Knüpfer, U., Wenderoth, R., Riesenberg D. & Plückthun, A., Bio/Technology 11, 1271–1277 (1993).
Pack, P., Ph.D. thesis, Ludwig-Maximilians-Universität München (1994).
Perlak, F. J., Nuc. Acids Res. 18, 7457–7458 (1990).
Plückthun, A., Krebber, A., Krebber, C., Horn, U., Knüpfer, U., Wenderoth, R., Nieba, L., Proba, K. & Riesenberg, D., A practical approach. Antibody Engineering (Ed. J. McCafferty). IRL Press, Oxford, pp. 203–252 (1996).
Prodromou, C. & Pearl, L. H., Protein Engineering 5, 827–829 (1992).
Rosenberg, S. A. & Lotze, M. T., Ann. Rev. Immunol. 4, 681–709 (1986).
Skerra, A. & Plückthun, A., Science 240, 1038–1041 (1988).
Skerra, A., Pfitzinger, I. & Plückthun, A., Bio/Technology 9, 273–278 (1991).
Sutherland, L., Davidson, J., Glass, L. L., & Jacobs, H. T., BioTechniques 18, 458–464, 1995.
Tomlinson, I. M., Walter, G., Marks, J. D., Llewelyn, M. B. & Winter, G., J. Mol. Biol. 227, 776–798 (1992).
Ullrich, H. D., Patten, P. A., Yang, P. L., Romesberg, F. E. & Schultz, P. G., Proc. Natl. Acad. Sci. USA 92, 11907–11911 (1995).
Van Dijk, K. W., Mortari, F., Kirkham, P. M., Schroeder Jr., H. W. & Milner, E. C. B., Eur. J. Immunol. 23, 832–839 (1993).
Virnekäs, B., Ge, L., Plückthun, A., Schneider, K. C., Wellnhofer, G. & Moroney, S. E., Nucleic Acids Research 22, 5600–5607 (1994).
Vitetta, E. S., Thorpe, P. E. & Uhr, J., Immunol. Today 14, 253–259 (1993).
Williams, S. C. & Winter, G., Eur. J. Immunol. 23, 1456–1461 (1993).
Winter, G., Griffiths, A. D., Hawkins, R. E. & Hoogenboom, H. R., Ann. Rev. Immunol. 12, 433–455 (1994).

TABLE 1A

Human kappa germline gene segments

| Used Name[1] | Reference[2] | Family[3] | Germline genes[4] |
|---|---|---|---|
| Vk1-1 | 9 | 1 | O8; O18; DPK1 |
| Vk1-2 | 1 | 1 | L14; DPK2 |
| Vk1-3 | 2 | 1 | L15(1); HK101; HK146; HK189 |
| Vk1-4 | 9 | 1 | L11 |
| Vk1-5 | 2 | 1 | A30 |
| Vk1-6 | 1 | 1 | LFVK5 |
| Vk1-7 | 1 | 1 | LFVK431 |
| Vk1-8 | 1 | 1 | L1; HK137 |
| Vk1-9 | 1 | 1 | A20; DPK4 |
| Vk1-10 | 1 | 1 | L18; Va" |
| Vk1-11 | 1 | 1 | L4; L18; Va'; V4a |
| Vk1-12 | 2 | 1 | L5; L19(1); Vb; Vb4; DPK5; L19(2); Vb"; DPK6 |
| Vk1-13 | 2 | 1 | L15(2); HK134; HK166; DPK7 |
| Vk1-14 | 8 | 1 | L8; Vd; DPK8 |
| Vk1-15 | 8 | 1 | L9; Ve |
| Vk1-16 | 1 | 1 | L12(1); HK102; V1 |
| Vk1-17 | 2 | 1 | L12(2) |
| Vk1-18 | 1 | 1 | O12a(V3b) |
| Vk1-19 | 6 | 1 | O2; O12; DPK9 |
| Vk1-20 | 2 | 1 | L24; Ve"; V13; DPK10 |
| Vk1-21 | 1 | 1 | O4; O14 |
| Vk1-22 | 2 | 1 | L22 |
| Vk1-23 | 2 | 1 | L23 |
| Vk2-1 | 1 | 2 | A2; DPK12 |
| Vk2-2 | 6 | 2 | O1; O11(1); DPK13 |
| Vk2-3 | 6 | 2 | O12(2); V3a |
| Vk2-4 | 2 | 2 | L13 |
| Vk2-5 | 1 | 2 | DPK14 |

TABLE 1A-continued

Human kappa germline gene segments

| Used Name[1] | Reference[2] | Family[3] | Germline genes[4] |
|---|---|---|---|
| Vk2-6 | 4 | 2 | A3; A19; DPK15 |
| Vk2-7 | 4 | 2 | A29; DPK27 |
| Vk2-8 | 4 | 2 | A13 |
| Vk2-9 | 1 | 2 | A23 |
| Vk2-10 | 4 | 2 | A7; DPK17 |
| Vk2-11 | 4 | 2 | A17; DPK18 |
| Vk2-12 | 4 | 2 | A1; DPK19 |
| Vk3-1 | 11 | 3 | A11; humkv305; DPK20 |
| Vk3-2 | 1 | 3 | L20; Vg" |
| Vk3-3 | 2 | 3 | L2; L16; humkv328; humkv328h2; humkv328h5; DPK21 |
| Vk3-4 | 11 | 3 | A27; humkv325; VkRF; DPK22 |
| Vk3-5 | 2 | 3 | L25; DPK23 |
| Vk3-6 | 2 | 3 | L10(1) |
| Vk3-7 | 7 | 3 | L10(2) |
| Vk3-8 | 7 | 3 | L6; Vg |
| Vk4-1 | 3 | 4 | B3; VkIV; DPK24 |
| Vk5-1 | 10 | 5 | B2; EV15 |
| Vk6-1 | 12 | 6 | A14; DPK25 |
| Vk6-2 | 12 | 6 | A10; A26; DPK26 |
| Vk7-1 | 5 | 7 | B1 |

TABLE 1B

Human lambda germline gene segments

| Used Name[1] | Reference[2] | Family[3] | Germilne genes[4] |
|---|---|---|---|
| DPL1 | 1 | 1 | |
| DPL2 | 1 | 1 | HUMLV1L1 |
| DPL3 | 1 | 1 | HUMLV122 |
| DPL4 | 1 | 1 | VLAMBDA 1.1 |
| HUMLV117 | 2 | 1 | |
| DPL5 | 1 | 1 | HUMLV117D |
| DPL6 | 1 | 1 | |
| DPL7 | 1 | 1 | IGLVIS2 |
| DPL8 | 1 | 1 | HUMLV1042 |
| DPL9 | 1 | 1 | HUMLV101 |
| DPL10 | 1 | 2 | |
| VLAMBDA 2.1 | 3 | 2 | |
| DPL11 | 1 | 2 | |
| DPL12 | 1 | 2 | |
| DPL13 | 1 | 2 | |
| DPL14 | 1 | 2 | |
| DPL16 | 1 | 3 | Humlv418; IGLV3S1 |
| DPL23 | 1 | 3 | VI III.1 |
| Humlv318 | 4 | 3 | |
| DPL18 | 1 | 7 | 4A; HUMIGLVA |
| DPL19 | 1 | | |
| DPL21 | 1 | 8 | VL8.1 |
| HUMLV801 | 5 | 8 | |
| DPL22 | 1 | 9 | |
| DPL24 | 1 | unassigned | VLAMBDA N.2 |
| gVLX-4.4 | 6 | 10 | |

TABLE 1C

Human heavy chain germline gene segments

| Used Name[1] | Reference[2] | Family[3] | Germline genes[4] |
|---|---|---|---|
| VH1-12-1 | 19 | 1 | DP10; DA-2; DA-6 |
| VH1-12-8 | 22 | 1 | RR.VH1.2 |
| VH1-12-2 | 6 | 1 | hv1263 |
| VH1-12-9 | 7 | 1 | YAC-7; RR.VH1.1; 1-69 |
| VH1-12-3 | 19 | 1 | DP3 |
| VH1-12-4 | 19 | 1 | DP21; 4d275a; VH7a |
| VH1-12-5 | 18 | 1 | 1-4.1b; V1-4.1b |

TABLE 1C-continued

Human heavy chain germline gene segments

| Used Name[1] | Reference[2] | Family[3] | Germline genes[4] |
|---|---|---|---|
| VH1-12-6 | 21 | 1 | 1D37; VH7b; 7-81; YAC-10 |
| VH1-12-7 | 19 | 1 | DP14; VH1GRR; V1-18 |
| VH1-13-1 | 10 | 1 | 71-5; DP2 |
| VH1-13-2 | 10 | 1 | E3-10 |
| VH1-13-3 | 19 | 1 | DP1 |
| VH1-13-4 | 12 | 1 | V35 |
| VH1-13-5 | 8 | 1 | V1-2b |
| VH1-13-6 | 18 | 1 | 1-2; DP75 |
| VH1-13-7 | 21 | 1 | V1-2 |
| VH1-13-8 | 19 | 1 | DP8 |
| VH1-13-9 | 3 | 1 | 1-1 |
| VH1-13-10 | 19 | 1 | DP12 |
| VH1-13-11 | 15 | 1 | V13C |
| VH1-13-12 | 18 | 1 | 1-3b; DP25; V1-3b |
| VH1-13-13 | 3 | 1 | 1-92 |
| VH1-13-14 | 18 | 1 | 1-3; V1-3 |
| VH1-13-15 | 19 | 1 | DP15; V1-8 |
| VH1-13-16 | 3 | 1 | 21-2; 3-1; DP7; V1-46 |
| VH1-13-17 | 16 | 1 | HG3 |
| VH1-13-18 | 19 | 1 | DP4; 7-2; V1-45 |
| VH1-13-19 | 27 | 1 | COS 5 |
| VH1-1X-1 | 19 | 1 | DP5; 1-24P |
| VH2-21-1 | 18 | 2 | II-5b |
| VH2-31-1 | 2 | 2 | VH2S12-1 |
| VH2-31-2 | 2 | 2 | VH2S12-7 |
| VH2-31-3 | 2 | 2 | VH2S12-9; DP27 |
| VH2-31-4 | 2 | 2 | VH2S12-10 |
| VH2-31-5 | 14 | 2 | V2-26; DP26; 2-26 |
| VH2-31-6 | 15 | 2 | VF2-26 |
| VH2-31-7 | 19 | 2 | DP28; DA-7 |
| VH2-31-14 | 7 | 2 | YAC-3; 2-70 |
| VH2-31-8 | 2 | 2 | VH2S12-5 |
| VH2-31-9 | 2 | 2 | VH2S12-12 |
| VH2-31-10 | 18 | 2 | II-5; V2-5 |
| VH2-31-11 | 2 | 2 | VH2S12-2; VH2S12-8 |
| VH2-31-12 | 2 | 2 | VH2S12-4; VH2S12-6 |
| VH2-31-13 | 2 | 2 | VH2S12-14 |
| VH3-11-1 | 13 | 3 | v65-2; DP44 |
| VH3-11-2 | 19 | 3 | DP45 |
| VH3-11-3 | 3 | 3 | 13-2; DP48 |
| VH3-11-4 | 19 | 3 | DP52 |
| VH3-11-5 | 14 | 3 | v3-13 |
| VH3-11-6 | 19 | 3 | DP42 |
| VH3-11-7 | 3 | 3 | 8-1B; YAC-5; 3-66 |
| VH3-11-8 | 14 | 3 | V3-53 |
| VH3-13-1 | 3 | 3 | 22-28; DP35; V3-11 |
| VH3-13-5 | 19 | 3 | DP59; VH19; V3-35 |
| VH3-13-6 | 25 | 3 | fl-p1; DP61 |
| VH3-13-7 | 19 | 3 | DP46; GL-SJ2; COS 8; hv3005; hv3005f3; 3d21b; 56p1 |
| VH3-13-8 | 24 | 3 | VH26 |
| VH3-13-9 | 5 | 3 | vh26c |
| VH3-13-10 | 19 | 3 | DP47; VH26; 3-23 |
| VH3-13-11 | 3 | 3 | 1-91 |
| VH3-13-12 | 19 | 3 | DP58 |
| VH3-13-13 | 3 | 3 | 1-9III; DP49; 3-30; 3d28.1 |
| VH3-13-14 | 24 | 3 | 3019B9; DP50, 3-33; 3d277 |
| VH3-13-15 | 27 | 3 | COS 3 |
| VH3-13-16 | 19 | 3 | DP51 |
| VH3-13-17 | 16 | 3 | H11 |
| VH3-13-18 | 19 | 3 | DP53; COS 6; 3-74; DA-8 |
| VH3-13-19 | 19 | 3 | DP54; VH3-11; V3-7 |
| VH3-13-20 | 14 | 3 | V3-64; YAC-6 |
| VH3-13-21 | 14 | 3 | V3-48 |
| VH3-13-22 | 14 | 3 | V3-43; DP33 |
| VH3-13-23 | 14 | 3 | V3-33 |
| VH3-13-24 | 14 | 3 | V3-21; DP77 |
| VH3-13-25 | 14 | 3 | V3-20; DP32 |
| VH3-13-26 | 14 | 3 | V3-9; DP31 |
| VH3-14-1 | 3 | 3 | 12-2; DP29; 3-72; DA-3 |
| VH3-14-4 | 7 | 3 | YAC-9; 3-73; MTGL |
| VH3-14-2 | 4 | 3 | VHD26 |
| VH3-14-3 | 19 | 3 | DP30 |
| VH3-1X-1 | 1 | 3 | LSG8.1; LSG9.1; LSG10.1; HUM12IGVH; HUM13IGVH |
| VH3-1X-2 | 1 | 3 | LSG11.1; HUM4IGVH |
| VH3-1X-3 | 3 | 3 | 9-1; DP38; LSG7.1; RCG1.1; LSG1.1; LSG3.1; LSG5.1; HUM15IGVH; HUM2IGVH; HUM9IGVH |
| VH3-1X-4 | 1 | 3 | LSG4.1 |
| VH3-1X-5 | 1 | 3 | LSG2.1 |
| VH3-1X-6 | 1 | 3 | LSG6.1; HUM10IGVH |
| VH3-1X-7 | 18 | 3 | 3-15; V3-15 |
| VH3-1X-8 | 1 | 3 | LSG12.1; HUM5IGVH |
| VH3-1X-9 | 14 | 3 | V3-49 |
| VH4-11-1 | 22 | 4 | Tou-VH4.21 |
| VH4-11-2 | 17 | 4 | VH4.21; DPG3; VH5; 4d76; V4-34 |
| VH4-11-3 | 23 | 4 | 4.44 |
| VH4-11-4 | 23 | 4 | 4.44.3 |
| VH4-11-5 | 23 | 4 | 4.36 |
| VH4-11-6 | 23 | 4 | 4.37 |
| VH4-11-7 | 18 | 4 | IV-4; 4.35; V4-4 |
| VH4-11-8 | 17 | 4 | VH4.11; 3d197d; DP71; 58p2 |
| VH4-11-9 | 20 | 4 | H7 |
| VH4-11-10 | 20 | 4 | H8 |
| VH4-11-11 | 20 | 4 | H9 |
| VH4-11-12 | 17 | 4 | VH4.16 |
| VH4-11-13 | 23 | 4 | 4.38 |
| VH4-11-14 | 17 | 4 | VH4.15 |
| VH4-11-15 | 11 | 4 | 58 |
| VH4-11-16 | 10 | 4 | 71-4; V4-59 |
| VH4-21-1 | 11 | 4 | 11 |
| VH4-21-2 | 17 | 4 | VH4.17; VH4.23; 4d255; 4.40; DP69 |
| VH4-21-3 | 17 | 4 | VH4.19; 79; V4-4b |
| VH4-21-4 | 19 | 4 | DP70; 4d68; 4.41 |
| VH4-21-5 | 19 | 4 | DP67; VH4-4B |
| VH4-21-6 | 17 | 4 | VH4.22; VHSP; VH-JA |
| VH4-21-7 | 17 | 4 | VH4.13; 1-9II; 12G-1; 3d28d; 4.42; DP68; 4-28 |
| VH4-21-8 | 26 | 4 | hv4005; 3d24d |
| VH4-21-9 | 17 | 4 | VH4.14 |
| VH4-31-1 | 23 | 4 | 4.34; 3d230d; DP78 |
| VH4-31-2 | 23 | 4 | 4.34.2 |
| VH4-31-3 | 19 | 4 | DP64; 3d216d |
| VH4-31-4 | 19 | 4 | DP65; 4-31; 3d277d |
| VH4-31-5 | 23 | 4 | 4.33; 3d75d |
| VH4-31-6 | 20 | 4 | H10 |
| VH4-31-7 | 20 | 4 | H11 |
| VH4-31-8 | 23 | 4 | 4.31 |
| VH4-31-9 | 23 | 4 | 4.32 |
| VH4-31-10 | 20 | 4 | 3d277d |
| VH4-31-11 | 20 | 4 | 3d216d |
| VH4-31-12 | 20 | 4 | 3d279d |
| VH4-31-13 | 17 | 4 | VH4.18; 4d154; DP79 |
| VH4-31-14 | 8 | 4 | V4-39 |
| VH4-31-15 | 11 | 4 | 2-1; DP79 |
| VH4-31-16 | 23 | 4 | 4.30 |
| VH4-31-17 | 17 | 4 | VH4.12 |
| VH4-31-18 | 10 | 4 | 71-2; DP66 |
| VH4-31-19 | 23 | 4 | 4.39 |
| VH4-31-20 | 8 | 4 | V4-61 |
| VH5-12-1 | 9 | 5 | VH251; DP73; VHVCW; 51-R1; VHVLB; VHVCH; VHVTT; VHVAU; VHVBLK; VhAU; V5-51 |
| VH5-12-2 | 17 | 5 | VHJB |
| VH5-12-3 | 3 | 5 | 1-v; DP80; 5-78 |
| VH5-12-4 | 9 | 5 | VH32; VHVRG; VHVMW; 5-2R1 |
| VH6-35-1 | 4 | 6 | VHVI; VH6; VHVIIS; VHVITE; VHVUB; VHVICH; VHVICW; VHVIBLK; VHVIMW; DP74; 6-1G1; V6-1 |

TABLE 2A

| | | | rearranged human kappa sequences | | | |
|---|---|---|---|---|---|---|
| Name[1] | aa[2] | Computed family[3] | Germline gene[4] | Diff. to germline[5] | % diff. to germline[6] | Reference[7] |
| III-3R | 108 | 1 | O8 | 1 | 1.1% | 70 |
| No.86 | 109 | 1 | O8 | 3 | 3.2% | 80 |
| AU | 108 | 1 | O8 | 6 | 6.3% | 103 |
| ROY | 108 | 1 | O8 | 6 | 6.3% | 43 |
| IC4 | 108 | 1 | O8 | 6 | 6.3% | 70 |
| HIV-B26 | 106 | 1 | O8 | 3 | 3.2% | 8 |
| GRI | 108 | 1 | O8 | 8 | 8.4% | 30 |
| AG | 106 | 1 | O8 | 8 | 8.6% | 116 |
| REI | 108 | 1 | O8 | 9 | 9.5% | 86 |
| CLL PATIENT 16 | 88 | 1 | O8 | 2 | 2.3% | 122 |
| CLL PATIENT 14 | 87 | 1 | O8 | 2 | 2.3% | 122 |
| CLL PATIENT 15 | 88 | 1 | O8 | 2 | 2.3% | 122 |
| GM4672 | 108 | 1 | O8 | 11 | 11.6% | 24 |
| HUM.YFC51.1 | 108 | 1 | O8 | 12 | 12.6% | 110 |
| LAY | 108 | 1 | O8 | 12 | 12.6% | 48 |
| HIV-b13 | 106 | 1 | O8 | 9 | 9.7% | 8 |
| MAL-NaCl | 108 | 1 | O8 | 13 | 13.7% | 102 |
| STRAb SA-1A | 108 | 1 | O2 | 0 | 0.0% | 120 |
| HuVHCAMP | 108 | 1 | O8 | 13 | 13.7% | 100 |
| CRO | 108 | 1 | O2 | 10 | 10.5% | 30 |
| Am107 | 108 | 1 | O2 | 12 | 12.6% | 108 |
| WALKER | 107 | 1 | O2 | 4 | 4.2% | 57 |
| III-2R | 109 | 1 | A20 | 0 | 0.0% | 70 |
| FOG1-A4 | 107 | 1 | A20 | 4 | 4.2% | 41 |
| HK137 | 95 | 1 | L1 | 0 | 0.0% | 10 |
| CEA4-8A | 107 | 1 | O2 | 7 | 7.4% | 41 |
| Va' | 95 | 1 | L4 | 0 | 0.0% | 90 |
| TR1.21 | 108 | 1 | O2 | 4 | 4.2% | 92 |
| HAU | 108 | 1 | O2 | 6 | 6.3% | 123 |
| HK102 | 95 | 1 | L12(1) | 0 | 0.0% | 9 |
| H20C3K | 108 | 1 | L12(2) | 3 | 3.2% | 125 |
| CHEB | 108 | 1 | O2 | 7 | 7.4% | 5 |
| HK134 | 95 | 1 | L15(2) | 0 | 0.0% | 10 |
| TEL9 | 108 | 1 | O2 | 9 | 9.5% | 73 |
| TR1.32 | 103 | 1 | O2 | 3 | 3.2% | 92 |
| RF-KES1 | 97 | 1 | A20 | 4 | 4.2% | 121 |
| WES | 108 | 1 | L5 | 10 | 10.5% | 61 |
| DILp1 | 95 | 1 | O4 | 1 | 1.1% | 70 |
| SA-4B | 107 | 1 | L12(2) | 8 | 8.4% | 120 |
| HK101 | 95 | 1 | L15(1) | 0 | 0.0% | 9 |
| TR1.23 | 108 | 1 | O2 | 5 | 5.3% | 92 |
| HF2-1/17 | 108 | 1 | A30 | 0 | 0.0% | 4 |
| 2E7 | 108 | 1 | A30 | 1 | 1.1% | 62 |
| 33.C9 | 107 | 1 | L12(2) | 7 | 7.4% | 126 |
| 3D6 | 105 | 1 | L12(2) | 2 | 2.1% | 34 |
| I-2a | 108 | 1 | L8 | 8 | 8.4% | 70 |
| RF-KL1 | 97 | 1 | L8 | 4 | 4.2% | 121 |
| TNF-E7 | 108 | 1 | A30 | 9 | 9.5% | 41 |
| TR1.22 | 108 | 1 | O2 | 7 | 7.4% | 92 |
| HIV-B35 | 106 | 1 | O2 | 2 | 2.2% | 8 |
| HIV-b22 | 106 | 1 | O2 | 2 | 2.2% | 8 |
| HIV-b27 | 106 | 1 | O2 | 2 | 2.2% | 8 |
| HIV-B8 | 107 | 1 | O2 | 10 | 10.8% | 8 |
| HIV-b8 | 107 | 1 | O2 | 10 | 10.8% | 8 |
| RF-SJ5 | 95 | 1 | A30 | 5 | 5.3% | 113 |
| GAL(1) | 108 | 1 | A30 | 6 | 6.3% | 64 |
| R3.5H5G | 108 | 1 | O2 | 6 | 6.3% | 70 |
| HIV-b14 | 106 | 1 | A20 | 2 | 2.2% | 8 |
| TNF-E1 | 105 | 1 | L5 | 8 | 8.4% | 41 |
| WEA | 108 | 1 | A30 | 8 | 8.4% | 37 |
| EU | 108 | 1 | L12(2) | 5 | 5.3% | 40 |
| FOG1-G8 | 108 | 1 | L8 | 11 | 11.6% | 41 |
| 1X7RG1 | 108 | 1 | L1 | 8 | 8.4% | 70 |
| BLI | 108 | 1 | L8 | 3 | 3.2% | 72 |
| KUE | 108 | 1 | L12(2) | 11 | 11.6% | 32 |
| LUNm01 | 108 | 1 | L12(2) | 10 | 10.5% | 6 |
| HIV-b1 | 106 | 1 | A20 | 4 | 4.3% | 8 |
| HIV-s4 | 103 | 1 | O2 | 2 | 2.2% | 8 |
| CAR | 107 | 1 | L12(2) | 11 | 11.7% | 79 |
| BR | 107 | 1 | L12(2) | 11 | 11.6% | 50 |
| CLL PATIENT 10 | 88 | 1 | O2 | 0 | 0.0% | 122 |
| CLL PATIENT 12 | 88 | 1 | O2 | 0 | 0.0% | 122 |
| KING | 108 | 1 | L12(2) | 12 | 12.6% | 30 |
| V13 | 95 | 1 | L24 | 0 | 0.0% | 46 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| CLL PATIENT 11 | 87 | 1 | O2 | 0 | 0.0% | 122 |
| CLL PATIENT 13 | 87 | 1 | O2 | 0 | 0.0% | 122 |
| CLL PATIENT 9 | 88 | 1 | O12 | 1 | 1.1% | 122 |
| HIV-B2 | 106 | 1 | A20 | 9 | 9.7% | 8 |
| HIV-b2 | 106 | 1 | A20 | 9 | 9.7% | 8 |
| CLL PATIENT 5 | 88 | 1 | A20 | 1 | 1.1% | 122 |
| CLL PATIENT 1 | 88 | 1 | L8 | 2 | 2.3% | 122 |
| CLL PATIENT 2 | 88 | 1 | L8 | 0 | 0.0% | 122 |
| CLL PATIENT 7 | 88 | 1 | L5 | 0 | 0.0% | 122 |
| CLL PATIENT 8 | 88 | 1 | L5 | 0 | 0.0% | 122 |
| HIV-b5 | 105 | 1 | L5 | 11 | 12.0% | 8 |
| CLL PATIENT 3 | 87 | 1 | L8 | 1 | 1.1% | 122 |
| CLL PATIENT 4 | 88 | 1 | L9 | 0 | 0.0% | 122 |
| CLL PATIENT 18 | 85 | 1 | L9 | 6 | 7.1% | 122 |
| CLL PATIENT 17 | 86 | 1 | L12(2) | 7 | 8.1% | 122 |
| HIV-b20 | 107 | 3 | A27 | 11 | 11.7% | 8 |
| 2C12 | 108 | 1 | L12(2) | 20 | 21.1% | 68 |
| 1B11 | 108 | 1 | L12(2) | 20 | 21.1% | 68 |
| 1H1 | 108 | 1 | L12(2) | 21 | 22.1% | 68 |
| 2A12 | 108 | 1 | L12(2) | 21 | 22.1% | 68 |
| CUR | 109 | 3 | A27 | 0 | 0.0% | 66 |
| GLO | 109 | 3 | A27 | 0 | 0.0% | 16 |
| RF-TS1 | 96 | 3 | A27 | 0 | 0.0% | 121 |
| GAR' | 109 | 3 | A27 | 0 | 0.0% | 67 |
| FLO | 109 | 3 | A27 | 0 | 0.0% | 66 |
| PIE | 109 | 3 | A27 | 0 | 0.0% | 91 |
| HAH 14.1 | 109 | 3 | A27 | 1 | 1.0% | 51 |
| HAH 14.2 | 109 | 3 | A27 | 1 | 1.0% | 51 |
| HAH 16.1 | 109 | 3 | A27 | 1 | 1.0% | 51 |
| NOV | 109 | 3 | A27 | 1 | 1.0% | 52 |
| 33.F12 | 108 | 3 | A27 | 1 | 1.0% | 126 |
| 8E10 | 110 | 3 | A27 | 1 | 1.0% | 25 |
| TH3 | 109 | 3 | A27 | 1 | 1.0% | 25 |
| HIC(R) | 108 | 3 | A27 | 0 | 0.0% | 51 |
| SON | 110 | 3 | A27 | 1 | 1.0% | 67 |
| PAY | 109 | 3 | A27 | 1 | 1.0% | 66 |
| GOT | 109 | 3 | A27 | 1 | 1.0% | 67 |
| mAbA6H4C5 | 109 | 3 | A27 | 1 | 1.0% | 12 |
| BOR' | 109 | 3 | A27 | 2 | 2.1% | 84 |
| RF-SJ3 | 96 | 3 | A27 | 2 | 2.1% | 121 |
| SIE | 109 | 3 | A27 | 2 | 2.1% | 15 |
| ESC | 109 | 3 | A27 | 2 | 2.1% | 98 |
| HEW' | 110 | 3 | A27 | 2 | 2.1% | 98 |
| YES8c | 109 | 3 | A27 | 3 | 3.1% | 33 |
| TI | 109 | 3 | A27 | 3 | 3.1% | 114 |
| mAb113 | 109 | 3 | A27 | 3 | 3.1% | 71 |
| HEW | 107 | 3 | A27 | 0 | 0.0% | 94 |
| BRO | 106 | 3 | A27 | 0 | 0.0% | 94 |
| ROB | 106 | 3 | A27 | 0 | 0.0% | 94 |
| NG9 | 96 | 3 | A27 | 4 | 4.2% | 11 |
| NEU | 109 | 3 | A27 | 4 | 4.2% | 66 |
| WOL | 109 | 3 | A27 | 4 | 4.2% | 2 |
| 35G6 | 109 | 3 | A27 | 4 | 4.2% | 59 |
| RF-SJ4 | 109 | 3 | A11 | 0 | 0.0% | 88 |
| KAS | 109 | 3 | A27 | 4 | 4.2% | 84 |
| BRA | 106 | 3 | A27 | 1 | 1.1% | 94 |
| HAH | 106 | 3 | A27 | 1 | 1.1% | 94 |
| HIC | 105 | 3 | A27 | 0 | 0.0% | 94 |
| FS-2 | 109 | 3 | A27 | 6 | 6.3% | 87 |
| JH' | 107 | 3 | A27 | 6 | 6.3% | 38 |
| EV1-15 | 109 | 3 | A27 | 6 | 6.3% | 83 |
| SCA | 108 | 3 | A27 | 6 | 6.3% | 65 |
| mAb112 | 109 | 3 | A27 | 6 | 6.3% | 71 |
| SIC | 103 | 3 | A27 | 3 | 3.3% | 94 |
| SA-4A | 109 | 3 | A27 | 6 | 6.3% | 120 |
| SER | 108 | 3 | A27 | 6 | 6.3% | 98 |
| GOL' | 109 | 3 | A27 | 7 | 7.3% | 82 |
| BSG10K | 105 | 3 | A27 | 9 | 9.7% | 125 |
| HG2B10K | 110 | 3 | A27 | 9 | 9.4% | 125 |
| Taykv322 | 105 | 3 | A27 | 5 | 5.4% | 52 |
| CLL PATIENT 24 | 89 | 3 | A27 | 1 | 1.1% | 122 |
| HIV-b24 | 107 | 3 | A27 | 7 | 7.4% | 8 |
| HIV-b6 | 107 | 3 | A27 | 7 | 7.4% | 8 |
| Taykv310 | 99 | 3 | A27 | 1 | 1.1% | 52 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| KA3D1 | 108 | 3 | L6 | 0 | 0.0% | 85 |
| 19.E7 | 107 | 3 | L6 | 0 | 0.0% | 126 |
| rsv61 | 109 | 3 | A27 | 12 | 12.5% | 7 |
| Taykv320 | 98 | 3 | A27 | 1 | 1.2% | 52 |
| Vh | 96 | 3 | L10(2) | 0 | 0.0% | 89 |
| LS8 | 108 | 3 | L6 | 1 | 1.1% | 109 |
| LS1 | 108 | 3 | L6 | 1 | 1.1% | 109 |
| LS2S3-3 | 107 | 3 | L6 | 2 | 2.1% | 99 |
| LS2 | 108 | 3 | L6 | 1 | 1.1% | 109 |
| LS7 | 108 | 3 | L6 | 1 | 1.1% | 109 |
| LS2S3-4d | 107 | 3 | L6 | 2 | 2.1% | 99 |
| LS2S3-4a | 107 | 3 | L6 | 2 | 2.1% | 99 |
| LS4 | 108 | 3 | L6 | 1 | 1.1% | 109 |
| LS6 | 108 | 3 | L6 | 1 | 1.1% | 109 |
| LS2S3-10a | 107 | 3 | L6 | 2 | 2.1% | 99 |
| LS2S3-8c | 107 | 3 | L6 | 2 | 2.1% | 99 |
| LS5 | 108 | 3 | L6 | 1 | 1.1% | 109 |
| LS2S3-5 | 107 | 3 | L6 | 3 | 3.2% | 99 |
| LUNm03 | 109 | 3 | A27 | 13 | 13.5% | 6 |
| IARC/BL41 | 108 | 3 | A27 | 13 | 13.7% | 55 |
| slkv22 | 99 | 3 | A27 | 3 | 3.5% | 13 |
| POP | 108 | 3 | L6 | 4 | 4.2% | 111 |
| LS2S3-10b | 107 | 3 | L6 | 3 | 3.2% | 99 |
| LS2S3-8f | 107 | 3 | L6 | 3 | 3.2% | 99 |
| LS2S3-12 | 107 | 3 | L6 | 3 | 3.2% | 99 |
| HIV-B30 | 107 | 3 | A27 | 11 | 11.7% | 8 |
| HIV-B20 | 107 | 3 | A27 | 11 | 11.7% | 8 |
| HIV-b3 | 108 | 3 | A27 | 11 | 11.7% | 8 |
| HIV-s6 | 104 | 3 | A27 | 9 | 9.9% | 8 |
| YSE | 107 | 3 | L2/L16 | 1 | 1.1% | 72 |
| POM | 109 | 3 | L2/L16 | 9 | 9.4% | 53 |
| Humkv328 | 95 | 3 | L2/L16 | 1 | 1.1% | 19 |
| CLL | 109 | 3 | L2/L16 | 3 | 3.2% | 47 |
| LES | 96 | 3 | L2/L16 | 3 | 3.2% | 38 |
| HIV-s5 | 104 | 3 | A27 | 11 | 12.1% | 8 |
| HIV-s7 | 104 | 3 | A27 | 11 | 12.1% | 8 |
| slkv1 | 99 | 3 | A27 | 7 | 8.1% | 13 |
| Humka31es | 95 | 3 | L2/L16 | 4 | 4.2% | 18 |
| slkv12 | 101 | 3 | A27 | 8 | 9.2% | 13 |
| RF-TS2 | 95 | 3 | L2/L16 | 3 | 3.2% | 121 |
| II-1 | 109 | 3 | L2/L16 | 4 | 4.2% | 70 |
| HIV-s3 | 105 | 3 | A27 | 13 | 14.3% | 8 |
| RF-TMC1 | 96 | 3 | L6 | 10 | 10.5% | 121 |
| GER | 109 | 3 | L2/L16 | 7 | 7.4% | 75 |
| GF4/1.1 | 109 | 3 | L2/L16 | 8 | 8.4% | 36 |
| mAb114 | 109 | 3 | L2/L16 | 6 | 6.3% | 71 |
| HIV-loop13 | 109 | 3 | L2/L16 | 7 | 7.4% | 8 |
| bkv16 | 86 | 3 | L6 | 1 | 1.2% | 13 |
| CLL PATIENT 29 | 86 | 3 | L6 | 1 | 1.2% | 122 |
| slkv9 | 98 | 3 | L6 | 3 | 3.5% | 13 |
| bkv17 | 99 | 3 | L6 | 1 | 1.2% | 13 |
| slkv14 | 99 | 3 | L6 | 1 | 1.2% | 13 |
| slkv16 | 101 | 3 | L6 | 2 | 2.3% | 13 |
| bkv33 | 101 | 3 | L6 | 4 | 4.7% | 13 |
| slkv15 | 99 | 3 | L6 | 2 | 2.3% | 13 |
| bkv6 | 100 | 3 | L6 | 3 | 3.5% | 13 |
| R6B8K | 108 | 3 | L2/L16 | 12 | 12.6% | 125 |
| AL 700 | 107 | 3 | L2/L16 | 9 | 9.5% | 117 |
| slkv11 | 100 | 3 | L2/L16 | 3 | 3.5% | 13 |
| slkv4 | 97 | 3 | L6 | 4 | 4.8% | 13 |
| CLL PATIENT 26 | 87 | 3 | L2/L16 | 1 | 1.1% | 122 |
| AL Se124 | 103 | 3 | L2/L16 | 9 | 9.5% | 117 |
| slkv13 | 100 | 3 | L2/l16 | 6 | 7.0% | 13 |
| bkv7 | 100 | 3 | L2/L16 | 5 | 5.8% | 13 |
| bkv22 | 100 | 3 | L2/L16 | 6 | 7.0% | 13 |
| CLL PATIENT 27 | 84 | 3 | L2/L16 | 0 | 0.0% | 122 |
| bkv35 | 100 | 3 | L6 | 8 | 9.3% | 13 |
| CLL PATIENT 25 | 87 | 3 | L2/L16 | 4 | 4.6% | 122 |
| slkv3 | 86 | 3 | L2/L16 | 7 | 8.1% | 13 |
| slkv7 | 99 | 1 | O2 | 7 | 8.1% | 13 |
| HuFd79 | 111 | 3 | L2/L16 | 24 | 24.2% | 21 |
| RAD | 99 | 3 | A27 | 9 | 10.3% | 78 |
| CLL PATIENT 28 | 83 | 3 | L2/L16 | 4 | 4.8% | 122 |
| REE | 104 | 3 | L2/L16 | 25 | 27.2% | 95 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| FR4 | 99 | 3 | A27 | 8 | 9.2% | 77 |
| MD3.3 | 92 | 3 | L6 | 1 | 1.3% | 54 |
| MD3.1 | 92 | 3 | L6 | 0 | 0.0% | 54 |
| GA3.6 | 92 | 3 | L6 | 2 | 2.6% | 54 |
| M3.5N | 92 | 3 | L6 | 3 | 3.8% | 54 |
| WEI' | 82 | 3 | A27 | 0 | 0.0% | 65 |
| MD3.4 | 92 | 3 | L2/L16 | 1 | 1.3% | 54 |
| MD3.2 | 91 | 3 | L6 | 3 | 3.8% | 54 |
| VER | 97 | 3 | A27 | 19 | 22.4% | 20 |
| CLL PATIENT 30 | 78 | 3 | L6 | 3 | 3.8% | 122 |
| M3.1N | 92 | 3 | L2/L16 | 1 | 1.3% | 54 |
| MD3.6 | 91 | 3 | L2/L16 | 0 | 0.0% | 54 |
| MD3.8 | 91 | 3 | L2/L16 | 0 | 0.0% | 54 |
| GA3.4 | 92 | 3 | L6 | 7 | 9.0% | 54 |
| M3.6N | 92 | 3 | A27 | 0 | 0.0% | 54 |
| MD3.10 | 92 | 3 | A27 | 0 | 0.0% | 54 |
| MD3.13 | 91 | 3 | A27 | 0 | 0.0% | 54 |
| MD3.7 | 93 | 3 | A27 | 0 | 0.0% | 54 |
| MD3.9 | 93 | 3 | A27 | 0 | 0.0% | 54 |
| GA3.1 | 93 | 3 | A27 | 6 | 7.6% | 54 |
| bkv32 | 101 | 3 | A27 | 5 | 5.7% | 13 |
| GA3.5 | 93 | 3 | A27 | 5 | 6.3% | 54 |
| GA3.7 | 92 | 3 | A27 | 7 | 8.9% | 54 |
| MD3.12 | 92 | 3 | A27 | 2 | 2.5% | 54 |
| M3.2N | 90 | 3 | L6 | 6 | 7.8% | 54 |
| MD3.5 | 92 | 3 | A27 | 1 | 1.3% | 54 |
| M3.4N | 91 | 3 | L2/L16 | 8 | 10.3% | 54 |
| M3.8N | 91 | 3 | L2/l16 | 7 | 9.0% | 54 |
| M3.7N | 92 | 3 | A27 | 3 | 3.8% | 54 |
| GA3.2 | 92 | 3 | A27 | 9 | 11.4% | 54 |
| GA3.8 | 93 | 3 | A27 | 4 | 5.1% | 54 |
| GA3.3 | 92 | 3 | A27 | 8 | 10.1% | 54 |
| M3.3N | 92 | 3 | A27 | 5 | 6.3% | 54 |
| B6 | 83 | 3 | A27 | 8 | 11.3% | 78 |
| E29.1 KAPPA | 78 | 3 | L2/L16 | 0 | 0.0% | 22 |
| SCW | 108 | 1 | O8 | 12 | 12.6% | 31 |
| REI-based CAMPATH-9 | 107 | 1 | O8 | 14 | 14.7% | 39 |
| RZ | 107 | 1 | O8 | 14 | 14.7% | 50 |
| B1 | 108 | 1 | O8 | 14 | 14.7% | 14 |
| AND | 107 | 1 | O2 | 13 | 13.7% | 69 |
| 2A4 | 109 | 1 | O2 | 12 | 12.6% | 23 |
| KA | 108 | 1 | O8 | 19 | 20.0% | 107 |
| MEV | 109 | 1 | O2 | 14 | 14.7% | 29 |
| DEE | 106 | 1 | O2 | 13 | 14.0% | 76 |
| OU(IOC) | 108 | 1 | O2 | 18 | 18.9% | 60 |
| HuRSV19VK | 111 | 1 | O8 | 21 | 21.0% | 115 |
| SP2 | 108 | 1 | O2 | 17 | 17.9% | 93 |
| BJ26 | 99 | 1 | O8 | 21 | 24.1% | 1 |
| N1 | 112 | 1 | O8 | 24 | 24.2% | 106 |
| BMA O310EUClV2 | 106 | 1 | L12(1) | 21 | 22.3% | 105 |
| CLL PATIENT 6 | 71 | 1 | A20 | 0 | 0.0% | 122 |
| BJ19 | 85 | 1 | O8 | 16 | 21.9% | 1 |
| GM 607 | 113 | 2 | A3 | 0 | 0.0% | 58 |
| R5A3K | 114 | 2 | A3 | 1 | 1.0% | 125 |
| R1C8K | 114 | 2 | A3 | 1 | 1.0% | 125 |
| VK2.R149 | 113 | 2 | A3 | 2 | 2.0% | 118 |
| TR1.6 | 109 | 2 | A3 | 4 | 4.0% | 92 |
| TR1.37 | 104 | 2 | A3 | 5 | 5.0% | 92 |
| FS-1 | 113 | 2 | A3 | 6 | 6.0% | 87 |
| TR1.8 | 110 | 2 | A3 | 6 | 6.0% | 92 |
| NIM | 113 | 2 | A3 | 8 | 8.0% | 28 |
| Inc | 112 | 2 | A3 | 11 | 11.0% | 35 |
| TEW | 107 | 2 | A3 | 6 | 6.4% | 96 |
| CUM | 114 | 2 | O1 | 7 | 6.9% | 44 |
| HRF1 | 71 | 2 | A3 | 4 | 5.6% | 124 |
| CLL PATIENT 19 | 87 | 2 | A3 | 0 | 0.0% | 122 |
| CLL PATIENT 20 | 87 | 2 | A3 | 0 | 0.0% | 122 |
| Mu | 112 | 2 | A3 | 16 | 16.2% | 26 |
| FR | 113 | 2 | A3 | 20 | 20.0% | 101 |
| MAL-Urine | 83 | 1 | O2 | 6 | 8.6% | 102 |
| Taykv306 | 73 | 3 | A27 | 1 | 1.6% | 52 |
| Taykv312 | 75 | 3 | A27 | 1 | 1.6% | 52 |
| HIV-b29 | 93 | 3 | A27 | 14 | 17.5% | 8 |
| 1-185-37 | 110 | 3 | A27 | 0 | 0.0% | 119 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| 1-187-29 | 110 | 3 | A27 | 0 | 0.0% | 119 |
| TT117 | 110 | 3 | A27 | 9 | 9.4% | 63 |
| HIV-loop8 | 108 | 3 | A27 | 16 | 16.8% | 8 |
| rsv23L | 108 | 3 | A27 | 16 | 16.8% | 7 |
| HIV-b7 | 107 | 3 | A27 | 14 | 14.9% | 8 |
| HIV-b11 | 107 | 3 | A27 | 15 | 16.0% | 8 |
| HIV-LC1 | 107 | 3 | A27 | 19 | 20.2% | 8 |
| HIV-LC7 | 107 | 3 | A27 | 20 | 21.3% | 8 |
| HIV-LC22 | 107 | 3 | A27 | 21 | 22.3% | 8 |
| HIV-LC13 | 107 | 3 | A27 | 21 | 22.3% | 8 |
| HIV-LC3 | 107 | 3 | A27 | 21 | 22.3% | 8 |
| HIV-LC5 | 107 | 3 | A27 | 21 | 22.3% | 8 |
| HIV-LC28 | 107 | 3 | A27 | 21 | 22.3% | 8 |
| HIV-b4 | 107 | 3 | A27 | 22 | 23.4% | 8 |
| CLL PATIENT 31 | 87 | 3 | A27 | 15 | 17.2% | 122 |
| HIV-loop2 | 108 | 3 | L2/L16 | 17 | 17.9% | 8 |
| HIV-loop35 | 108 | 3 | L2/l16 | 17 | 17.9% | 8 |
| HIV-LC11 | 107 | 3 | A27 | 23 | 24.5% | 8 |
| HIV-LC24 | 107 | 3 | A27 | 23 | 24.5% | 8 |
| HIV-b12 | 107 | 3 | A27 | 24 | 25.5% | 8 |
| HIV-LC25 | 107 | 3 | A27 | 24 | 25.5% | 8 |
| HIV-b21 | 107 | 3 | A27 | 24 | 25.5% | 8 |
| HIV-LC26 | 107 | 3 | A27 | 26 | 27.7% | 8 |
| G3D10k | 108 | 1 | L12(2) | 12 | 12.6% | 125 |
| TT125 | 108 | 1 | L5 | 8 | 8.4% | 63 |
| HIV-s2 | 103 | 3 | A27 | 28 | 31.1% | 8 |
| 265-695 | 108 | 1 | L5 | 7 | 7.4% | 3 |
| 2-115-19 | 108 | 1 | A30 | 2 | 2.1% | 119 |
| rsv13L | 107 | 1 | O2 | 20 | 21.1% | 7 |
| HIV-b18 | 106 | 1 | O2 | 14 | 15.1% | 8 |
| RF-KL5 | 98 | 3 | L6 | 36 | 36.7% | 97 |
| ZM1-1 | 113 | 2 | A17 | 7 | 7.0% | 3 |
| HIV-s8 | 103 | 1 | O8 | 16 | 17.8% | 8 |
| K-EV15 | 95 | 5 | B2 | 0 | 0.0% | 112 |
| RF-TS3 | 100 | 2 | A23 | 0 | 0.0% | 121 |
| HF-21/28 | 111 | 2 | A17 | 1 | 1.0% | 17 |
| RPMI6410 | 113 | 2 | A17 | 1 | 1.0% | 42 |
| JC11 | 113 | 2 | A17 | 1 | 1.0% | 49 |
| O-81 | 114 | 2 | A17 | 5 | 5.0% | 45 |
| FK-001 | 113 | 4 | B3 | 0 | 0.0% | 81 |
| CD5+.28 | 101 | 4 | B3 | 1 | 1.0% | 27 |
| LEN | 114 | 4 | B3 | 1 | 1.0% | 104 |
| UC | 114 | 4 | B3 | 1 | 1.0% | 111 |
| CD5+.5 | 101 | 4 | B3 | 1 | 1.0% | 27 |
| CD5+.26 | 101 | 4 | B3 | 1 | 1.0% | 27 |
| CD5+.12 | 101 | 4 | B3 | 2 | 2.0% | 27 |
| CD5+.23 | 101 | 4 | B3 | 2 | 2.0% | 27 |
| CD5+.7 | 101 | 4 | B3 | 2 | 2.0% | 27 |
| VJI | 113 | 4 | B3 | 3 | 3.0% | 56 |
| LOC | 113 | 4 | B3 | 3 | 3.0% | 72 |
| MAL | 113 | 4 | B3 | 3 | 3.0% | 72 |
| CD5+.6 | 101 | 4 | B3 | 3 | 3.0% | 27 |
| H2F | 113 | 4 | B3 | 3 | 3.0% | 70 |
| PB17IV | 114 | 4 | B3 | 4 | 4.0% | 74 |
| CD5+.27 | 101 | 4 | B3 | 4 | 4.0% | 27 |
| CD5+.9 | 101 | 4 | B3 | 4 | 4.0% | 27 |
| CD5−.28 | 101 | 4 | B3 | 5 | 5.0% | 27 |
| CD5−.26 | 101 | 4 | B3 | 6 | 5.9% | 27 |
| CD5+.24 | 101 | 4 | B3 | 6 | 5.9% | 27 |
| CD5+.10 | 101 | 4 | B3 | 6 | 5.9% | 27 |
| CD5−.19 | 101 | 4 | B3 | 6 | 5.9% | 27 |
| CD5−.18 | 101 | 4 | B3 | 7 | 6.9% | 27 |
| CD5−.16 | 101 | 4 | B3 | 8 | 7.9% | 27 |
| CD5−.24 | 101 | 4 | B3 | 8 | 7.9% | 27 |
| CD5−.17 | 101 | 4 | B3 | 10 | 9.9% | 27 |
| MD4.1 | 92 | 4 | B3 | 0 | 0.0% | 54 |
| MD4.4 | 92 | 4 | B3 | 0 | 0.0% | 54 |
| MD4.5 | 92 | 4 | B3 | 0 | 0.0% | 54 |
| MD4.6 | 92 | 4 | B3 | 0 | 0.0% | 54 |
| MD4.7 | 92 | 4 | B3 | 0 | 0.0% | 54 |
| MD4.2 | 92 | 4 | B3 | 1 | 1.3% | 54 |
| MD4.3 | 92 | 4 | B3 | 5 | 6.3% | 54 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| CLL PATIENT 22 | 87 | 2 | A17 | 2 | 2.3% | 122 |
| CLL PATIENT 23 | 84 | 2 | A17 | 2 | 2.4% | 122 |

TABLE 2B rearranged human lambda sequences

| Name[1] | aa[2] | Computed family[3] | Germline gene[4] | Diff. to germline[5] | % diff. to germline[6] | Reference[7] |
|---|---|---|---|---|---|---|
| WAH | 110 | 1 | DPL3 | 7 | 7% | 68 |
| 1B9/F2 | 112 | 1 | DPL3 | 7 | 7% | 9 |
| DIA | 112 | 1 | DPL2 | 7 | 7% | 36 |
| mAb67 | 89 | 1 | DPL3 | 0 | 0% | 29 |
| HiH2 | 110 | 1 | DPL3 | 12 | 11% | 3 |
| NIG-77 | 112 | 1 | DPL2 | 9 | 9% | 72 |
| OKA | 112 | 1 | DPL2 | 7 | 7% | 84 |
| KOL | 112 | 1 | DPL2 | 12 | 11% | 40 |
| T2:C5 | 111 | 1 | DPL5 | 0 | 0% | 6 |
| T2:C14 | 110 | 1 | DPL5 | 0 | 0% | 6 |
| PR-TS1 | 110 | 1 | DPL5 | 0 | 0% | 55 |
| 4G12 | 111 | 1 | DPL5 | 1 | 1% | 35 |
| KIM46L | 112 | 1 | HUMLV117 | 0 | 0% | 8 |
| Fog-B | 111 | 1 | DPL5 | 3 | 3% | 31 |
| 9F2L | 111 | 1 | DPL5 | 3 | 3% | 79 |
| mAb111 | 110 | 1 | DPL5 | 3 | 3% | 48 |
| PHOX15 | 111 | 1 | DPL5 | 4 | 4% | 49 |
| BL2 | 111 | 1 | DPL5 | 4 | 4% | 74 |
| NIG-64 | 111 | 1 | DPL5 | 4 | 4% | 72 |
| RF-SJ2 | 100 | 1 | DPL5 | 6 | 6% | 78 |
| AL EZI | 112 | 1 | DPL5 | 7 | 7% | 41 |
| ZIM | 112 | 1 | HUMLV117 | 7 | 7% | 18 |
| RF-SJ1 | 100 | 1 | DPL5 | 9 | 9% | 78 |
| IGLV1.1 | 98 | 1 | DPL4 | 0 | 0% | 1 |
| NEW | 112 | 1 | HUMLV117 | 11 | 10% | 42 |
| CB-201 | 87 | 1 | DPL2 | 1 | 1% | 62 |
| MEM | 109 | 1 | DPL2 | 6 | 6% | 50 |
| H210 | 111 | 2 | DPL10 | 4 | 4% | 45 |
| NOV | 110 | 2 | DPL10 | 8 | 8% | 25 |
| NEI | 111 | 2 | DPL10 | 8 | 8% | 24 |
| ALMC | 110 | 2 | DPL11 | 6 | 6% | 28 |
| MES | 112 | 2 | DPL11 | 8 | 8% | 84 |
| FOG1-A3 | 111 | 2 | DPL11 | 9 | 9% | 27 |
| AL NOV | 112 | 2 | DPL11 | 7 | 7% | 28 |
| HMST-1 | 110 | 2 | DPL11 | 4 | 4% | 82 |
| HBW4-1 | 108 | 2 | DPL12 | 9 | 9% | 52 |
| WH | 110 | 2 | DPL11 | 11 | 11% | 34 |
| 11-50 | 110 | 2 | DPL11 | 7 | 7% | 82 |
| HBp2 | 110 | 2 | DPL12 | 8 | 8% | 3 |
| NIG-84 | 113 | 2 | DPL11 | 12 | 11% | 73 |
| VIL | 112 | 2 | DPL11 | 9 | 9% | 58 |
| TRO | 111 | 2 | DPL12 | 10 | 10% | 61 |
| ES492 | 108 | 2 | DPL11 | 15 | 15% | 76 |
| mAb216 | 89 | 2 | DPL12 | 1 | 1% | 7 |
| BSA3 | 109 | 3 | DPL16 | 0 | 0% | 49 |
| THY-29 | 110 | 3 | DPL16 | 0 | 0% | 27 |
| PR-TS2 | 108 | 3 | DPL16 | 0 | 0% | 55 |
| E29.1 LAMBDA | 107 | 3 | DPL16 | 1 | 1% | 13 |
| mAb63 | 109 | 3 | DPL16 | 2 | 2% | 29 |
| TEL14 | 110 | 3 | DPL16 | 6 | 6% | 49 |
| 6H-3C4 | 108 | 3 | DPL16 | 7 | 7% | 39 |
| SH | 109 | 3 | DPL16 | 7 | 7% | 70 |
| AL GIL | 109 | 3 | DPL16 | 8 | 8% | 23 |
| H6-3C4 | 108 | 3 | DPL16 | 8 | 8% | 83 |
| V-lambda-2.DS | 111 | 2 | DPL11 | 3 | 3% | 15 |
| 8.12 ID | 110 | 2 | DPL11 | 3 | 3% | 81 |
| DSC | 111 | 2 | DPL11 | 3 | 3% | 56 |
| PV11 | 110 | 2 | DPL11 | 1 | 1% | 56 |
| 33.H11 | 110 | 2 | DPL11 | 4 | 4% | 81 |
| AS17 | 111 | 2 | DPL11 | 7 | 7% | 56 |
| SD6 | 110 | 2 | DPL11 | 7 | 7% | 56 |

TABLE 2B-continued rearranged human lambda sequences

| Name[1] | aa[2] | Computed family[3] | Germline gene[4] | Diff. to germline[5] | % diff. to germline[6] | Reference[7] |
|---|---|---|---|---|---|---|
| KS3 | 110 | 2 | DPL11 | 9 | 9% | 56 |
| PV6 | 110 | 2 | DPL12 | 5 | 5% | 56 |
| NGD9 | 110 | 2 | DPL11 | 7 | 7% | 56 |
| MUC1-1 | 111 | 2 | DPL11 | 11 | 10% | 27 |
| A30c | 111 | 2 | DPL10 | 6 | 6% | 56 |
| KS6 | 110 | 2 | DPL12 | 6 | 6% | 56 |
| TEL13 | 111 | 2 | DPL11 | 11 | 10% | 49 |
| AS7 | 110 | 2 | DPL12 | 6 | 6% | 56 |
| MCG | 112 | 2 | DPL12 | 12 | 11% | 20 |
| U266L | 110 | 2 | DPL12 | 13 | 12% | 77 |
| PR-SJ2 | 110 | 2 | DPL12 | 14 | 13% | 55 |
| BOH | 112 | 2 | DPL12 | 11 | 10% | 37 |
| TOG | 111 | 2 | DPL11 | 19 | 18% | 53 |
| TEL16 | 111 | 2 | DPL11 | 19 | 18% | 49 |
| No.13 | 110 | 2 | DPL10 | 14 | 13% | 52 |
| BO | 112 | 2 | DPL12 | 18 | 17% | 80 |
| WIN | 112 | 2 | DPL12 | 17 | 16% | 11 |
| BUR | 104 | 2 | DPL12 | 15 | 15% | 46 |
| NIG-58 | 110 | 2 | DPL12 | 20 | 19% | 69 |
| WEIR | 112 | 2 | DPL11 | 26 | 25% | 21 |
| THY-32 | 111 | 1 | DPL8 | 8 | 8% | 27 |
| TNF-H9G1 | 111 | 1 | DPL8 | 9 | 9% | 27 |
| mAb61 | 111 | 1 | DPL3 | 1 | 1% | 29 |
| LV1L1 | 98 | 1 | DPL2 | 0 | 0% | 54 |
| HA | 113 | 1 | DPL3 | 14 | 13% | 63 |
| LA1L1 | 111 | 1 | DPL2 | 3 | 3% | 54 |
| RHE | 112 | 1 | DPL1 | 17 | 16% | 22 |
| K1B12L | 113 | 1 | DPL8 | 17 | 16% | 79 |
| LOC | 113 | 1 | DPL2 | 15 | 14% | 84 |
| NIG-51 | 112 | 1 | DPL2 | 12 | 11% | 67 |
| NEWM | 104 | 1 | DPL8 | 23 | 22% | 10 |
| MD3-4 | 106 | 3 | DPL23 | 14 | 13% | 4 |
| COX | 112 | 1 | DPL2 | 13 | 12% | 84 |
| HiH10 | 106 | 3 | DPL23 | 13 | 12% | 3 |
| VOR | 112 | 1 | DPL2 | 16 | 15% | 16 |
| AL POL | 113 | 1 | DPL2 | 16 | 15% | 57 |
| CD4-74 | 111 | 1 | DPL2 | 19 | 18% | 27 |
| AMYLOID MOL | 102 | 3 | DPL23 | 15 | 15% | 30 |
| OST577 | 108 | 3 | Humlv318 | 10 | 10% | 4 |
| NIG-48 | 113 | 1 | DPL3 | 42 | 40% | 66 |
| CARR | 108 | 3 | DPL23 | 18 | 17% | 19 |
| mAb60 | 108 | 3 | DPL23 | 14 | 13% | 29 |
| NIG-68 | 99 | 3 | DPL23 | 25 | 26% | 32 |
| KERN | 107 | 3 | DPL23 | 26 | 25% | 59 |
| ANT | 106 | 3 | DPL23 | 17 | 16% | 19 |
| LEE | 110 | 3 | DPL23 | 18 | 17% | 85 |
| CLE | 94 | 3 | DPL23 | 17 | 17% | 19 |
| VL8 | 98 | 8 | DPL21 | 0 | 0% | 81 |
| MOT | 110 | 3 | Humlv318 | 23 | 22% | 38 |
| GAR | 108 | 3 | DPL23 | 26 | 25% | 33 |
| 32.B9 | 98 | 8 | DPL21 | 5 | 5% | 81 |
| PUG | 108 | 3 | Humlv318 | 24 | 23% | 19 |
| T1 | 115 | 8 | HUMLV801 | 52 | 50% | 6 |
| RF-TS7 | 96 | 7 | DPL18 | 4 | 4% | 60 |
| YM-1 | 116 | 8 | HUMLV801 | 51 | 49% | 75 |
| K6H6 | 112 | 8 | HUMLV801 | 20 | 19% | 44 |
| K5C7 | 112 | 8 | HUMLV801 | 20 | 19% | 44 |
| K5B8 | 112 | 8 | HUMLV801 | 20 | 19% | 44 |
| K5G5 | 112 | 8 | HUMLV801 | 20 | 19% | 44 |
| K4B8 | 112 | 8 | HUMLV801 | 19 | 18% | 44 |
| K6F5 | 112 | 8 | HUMLV801 | 17 | 16% | 44 |
| HIL | 108 | 3 | DPL23 | 22 | 21% | 47 |
| KIR | 109 | 3 | DPL23 | 20 | 19% | 19 |
| CAP | 109 | 3 | DPL23 | 19 | 18% | 84 |
| 1B8 | 110 | 3 | DPL23 | 22 | 21% | 43 |
| SHO | 108 | 3 | DPL23 | 19 | 18% | 19 |
| HAN | 108 | 3 | DPL23 | 20 | 19% | 19 |
| cML23 | 96 | 3 | DPL2J | 3 | 3% | 12 |
| PR-SJ1 | 96 | 3 | DPL23 | 7 | 7% | 55 |
| BAU | 107 | 3 | DPL23 | 9 | 9% | 5 |
| TEX | 99 | 3 | DPL23 | 8 | 8% | 19 |
| X(PET) | 107 | 3 | DPL23 | 9 | 9% | 51 |
| DOY | 106 | 3 | DPL23 | 9 | 9% | 19 |
| COT | 106 | 3 | DPL23 | 13 | 12% | 19 |

TABLE 2B-continued rearranged human lambda sequences

| Name[1] | aa[2] | Computed family[3] | Germline gene[4] | Diff. to germline[5] | % diff. to germline[6] | Reference[7] |
|---|---|---|---|---|---|---|
| Pag-1 | 111 | 3 | Humlv318 | 5 | 5% | 31 |
| DIS | 107 | 3 | Humlv318 | 2 | 2% | 19 |
| WIT | 108 | 3 | Humlv318 | 7 | 7% | 19 |
| I.RH | 108 | 3 | Humlv318 | 12 | 11% | 19 |
| S1-1 | 108 | 3 | Humlv318 | 12 | 11% | 52 |
| DEL | 108 | 3 | Humlv318 | 14 | 13% | 17 |
| TYR | 108 | 3 | Humlv318 | 11 | 10% | 19 |
| J.RH | 109 | 3 | Humlv318 | 13 | 12% | 19 |
| THO | 112 | 2 | DPL13 | 38 | 36% | 26 |
| LBV | 113 | 1 | DPL3 | 38 | 36% | 2 |
| WLT | 112 | 1 | DPL3 | 33 | 31% | 14 |
| SUT | 112 | 2 | DPL12 | 37 | 35% | 65 |

TABLE 2C rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| 21/28 | 119 | 1 | VH1-13-12 | 0 | 0.0% | 31 |
| 8E10 | 123 | 1 | VH1-13-12 | 0 | 0.0% | 31 |
| MUC1-1 | 118 | 1 | VH1-13-6 | 4 | 4.1% | 42 |
| gF1 | 98 | 1 | VH1-13-12 | 10 | 10.2% | 75 |
| VHGL 1.2 | 98 | 1 | VH1-13-6 | 2 | 2.0% | 26 |
| HV1L1 | 98 | 1 | VH1-13-6 | 0 | 0.0% | 81 |
| RF-TS7 | 104 | 1 | VH1-13-6 | 3 | 3.1% | 96 |
| E55 1.A15 | 106 | 1 | VH1-13-15 | 1 | 1.0% | 26 |
| HA1L1 | 126 | 1 | VH1-13-6 | 7 | 7.1% | 81 |
| UC | 123 | 1 | VH1-13-6 | 5 | 5.1% | 115 |
| WIL2 | 123 | 1 | VH1-13-6 | 6 | 6.1% | 55 |
| R3.5H5G | 122 | 1 | VH1-13-6 | 10 | 10.2% | 70 |
| N89P2 | 123 | 1 | VH1-13-16 | 11 | 11.2% | 77 |
| mAb113 | 126 | 1 | VH1-13-6 | 10 | 10.2% | 71 |
| LS2S3-3 | 125 | 1 | VH1-12-7 | 5 | 5.1% | 98 |
| LS2S3-12a | 125 | 1 | VH1-12-7 | 5 | 5.1% | 98 |
| LS2S3-5 | 125 | 1 | VH1-12-7 | 5 | 5.1% | 98 |
| L52S3-12e | 125 | 1 | VH1-12-7 | 5 | 5.1% | 98 |
| LS2S3-4 | 125 | 1 | VH1-12-7 | 5 | 5.1% | 98 |
| LS2S3-10 | 125 | 1 | VH1-12-7 | 5 | 5.1% | 98 |
| LS2S3-12d | 125 | 1 | VH1-12-7 | 6 | 6.1% | 98 |
| LS2S3-8 | 125 | 1 | VH1-12-7 | 5 | 5.1% | 98 |
| LS2 | 125 | 1 | VH1-12-7 | 6 | 6.1% | 113 |
| LS4 | 105 | 1 | VH1-12-7 | 6 | 6.1% | 113 |
| LS5 | 125 | 1 | VH1-12-7 | 6 | 6.1% | 113 |
| LS1 | 125 | 1 | VH1-12-7 | 6 | 6.1% | 113 |
| LS6 | 125 | 1 | VH1-12-7 | 6 | 6.1% | 113 |
| LS8 | 125 | 1 | VH1-12-7 | 7 | 7.1% | 113 |
| THY-29 | 122 | 1 | VH1-12-7 | 0 | 0.0% | 42 |
| 1B9/F2 | 122 | 1 | VH1-12-7 | 10 | 10.2% | 21 |
| 51P1 | 122 | 1 | VH1-12-1 | 0 | 0.0% | 105 |
| NEI | 127 | 1 | VH1-12-1 | 0 | 0.0% | 55 |
| AND | 127 | 1 | VH1-12-1 | 0 | 0.0% | 55 |
| L7 | 127 | 1 | VH1-12-1 | 0 | 0.0% | 54 |
| L22 | 124 | 1 | VH1-12-1 | 0 | 0.0% | 54 |
| L24 | 127 | 1 | VH1-12-1 | 0 | 0.0% | 54 |
| L26 | 116 | 1 | VH1-12-1 | 0 | 0.0% | 54 |
| L33 | 119 | 1 | VH1-12-1 | 0 | 0.0% | 54 |
| L34 | 117 | 1 | VH1-12-1 | 0 | 0.0% | 54 |
| L36 | 118 | 1 | VH1-12-1 | 0 | 0.0% | 54 |
| L39 | 120 | 1 | VH1-12-1 | 0 | 0.0% | 54 |
| L41 | 120 | 1 | VH1-12-1 | 0 | 0.0% | 54 |
| L42 | 125 | 1 | VH1-12-1 | 0 | 0.0% | 54 |
| VHGL 1.8 | 101 | 1 | VH1-12-1 | 0 | 0.0% | 26 |
| 783c | 127 | 1 | VH1-12-1 | 0 | 0.0% | 22 |
| X17115 | 127 | 1 | VH1-12-1 | 0 | 0.0% | 37 |
| L25 | 124 | 1 | VH1-12-1 | 0 | 0.0% | 54 |
| L17 | 120 | 1 | VH1-12-1 | 1 | 1.0% | 54 |
| L30 | 127 | 1 | VH1-12-1 | 1 | 1.0% | 54 |
| L37 | 120 | 1 | VH1-12-1 | 1 | 1.0% | 54 |
| TNF-E7 | 116 | 1 | VH1-12-1 | 2 | 2.0% | 42 |
| mAb111 | 122 | 1 | VH1-12-1 | 7 | 7.1% | 71 |
| III-2R | 122 | 1 | VH1-12-9 | 3 | 3.1% | 70 |
| KAS | 121 | 1 | VH1-12-1 | 7 | 7.1% | 79 |
| YES8c | 122 | 1 | VH1-12-1 | 8 | 8.2% | 34 |
| RF-TS1 | 123 | 1 | VH1-12-1 | 8 | 8.2% | 82 |
| BOR | 121 | 1 | VH1-12-8 | 7 | 7.1% | 79 |
| VHGL 1.9 | 101 | 1 | VH1-12-1 | 8 | 8.2% | 26 |
| mAb410.30F305 | 117 | 1 | VH1-12-9 | 5 | 5.1% | 52 |
| EV1-15 | 127 | 1 | VH1-12-8 | 10 | 10.2% | 78 |
| mAb112 | 122 | 1 | VH1-12-1 | 11 | 11.2% | 71 |
| EU | 117 | 1 | VH1-12-1 | 11 | 11.2% | 28 |
| H210 | 127 | 1 | VH1-12-1 | 12 | 12.2% | 66 |
| TRANSGENE | 104 | 1 | VH1-12-1 | 0 | 0.0% | 111 |
| CLL2-1 | 93 | 1 | VH1-12-1 | 0 | 0.0% | 30 |
| CLL10 13-3 | 97 | 1 | VH1-12-1 | 0 | 0.0% | 29 |
| LS7 | 99 | 1 | VH1-12-7 | 4 | 4.1% | 113 |
| ALL7-1 | 87 | 1 | VH1-12-7 | 0 | 0.0% | 30 |
| CLL3-1 | 91 | 1 | VH1-12-7 | 1 | 1.0% | 30 |
| ALL56-1 | 85 | 1 | VH1-13-8 | 0 | 0.0% | 30 |
| ALL1-1 | 87 | 1 | VH1-13-6 | 1 | 1.0% | 30 |
| ALL4-1 | 94 | 1 | VH1-13-8 | 0 | 0.0% | 30 |
| ALL56 15-4 | 85 | 1 | VH1-13-8 | 5 | 5.1% | 29 |
| CLL4-1 | 88 | 1 | VH1-13-1 | 1 | 1.0% | 30 |
| Au92.1 | 98 | 1 | VH1-12-5 | 0 | 0.0% | 49 |
| RF-TS3 | 120 | 1 | VH1-12-5 | 1 | 1.0% | 82 |
| Au4.1 | 98 | 1 | VH1-12-5 | 1 | 1.0% | 49 |
| HP1 | 121 | 1 | VH1-13-6 | 13 | 13.3% | 110 |
| BLI | 127 | 1 | VH1-13-15 | 5 | 5.1% | 72 |
| No.13 | 127 | 1 | VH1-12-2 | 19 | 19.4% | 76 |
| TR1.23 | 122 | 1 | VH1-13-2 | 23 | 23.5% | 88 |
| S1-1 | 125 | 1 | VH1-12-2 | 18 | 18.4% | 76 |
| TR1.10 | 119 | 1 | VH1-13-12 | 14 | 14.3% | 88 |
| E55 1.A2 | 102 | 1 | VH1-13-15 | 3 | 3.1% | 26 |
| SP2 | 119 | 1 | VH1-13-6 | 15 | 15.3% | 89 |
| TNF-H9G1 | 111 | 1 | VH1-13-18 | 2 | 2.0% | 42 |
| G3D10H | 127 | 1 | VH1-13-16 | 19 | 19.4% | 127 |
| TR1.9 | 118 | 1 | VH1-13-12 | 14 | 14.3% | 88 |
| TR1.8 | 121 | 1 | VH1-12-1 | 24 | 24.5% | 88 |
| LUNm01 | 127 | 1 | VH1-13-6 | 22 | 22.4% | 9 |
| K1B12H | 127 | 1 | VH1-12-7 | 23 | 23.5% | 127 |
| L3B2 | 99 | 1 | VH1-13-6 | 2 | 2.0% | 46 |
| ss2 | 100 | 1 | VH1-13-6 | 2 | 2.0% | 46 |
| No.86 | 124 | 1 | VHI-12-1 | 20 | 20.4% | 76 |
| TR1.6 | 124 | 1 | VH1-12-1 | 19 | 19.4% | 88 |
| ss7 | 99 | 1 | VH1-12-7 | 3 | 3.1% | 46 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| s5B7 | 102 | 1 | VH1-12-1 | 0 | 0.0% | 46 |
| s6A3 | 97 | 1 | VH1-12-1 | 0 | 0.0% | 46 |
| ss6 | 99 | 1 | VH1-12-1 | 0 | 0.0% | 46 |
| L2H7 | 103 | 1 | VH1-13-12 | 0 | 0.0% | 46 |
| s6BG8 | 93 | 1 | VH1-13-12 | 0 | 0.0% | 46 |
| s6C9 | 107 | 1 | VH1-13-12 | 0 | 0.0% | 46 |
| HIV-b4 | 124 | 1 | VH1-13-12 | 21 | 21.4% | 12 |
| HIV-b12 | 124 | 1 | VH1-13-12 | 21 | 21.4% | 12 |
| L3G5 | 98 | 1 | VH1-13-6 | 1 | 1.0% | 46 |
| 22 | 115 | 1 | VH1-13-6 | 11 | 11.2% | 118 |
| L2A12 | 99 | 1 | VH1-13-15 | 3 | 3.1% | 46 |
| PHOX15 | 124 | 1 | VH1-12-7 | 20 | 20.4% | 73 |
| LUNm03 | 127 | 1 | VH1-1X-1 | 18 | 18.4% | 9 |
| CEA4-8A | 129 | 1 | VH1-12-7 | 1 | 1.0% | 42 |
| M60 | 121 | 2 | VH2-31-3 | 3 | 3.0% | 103 |
| HiH10 | 127 | 2 | VH2-31-5 | 9 | 9.0% | 4 |
| COR | 119 | 2 | VH2-31-2 | 11 | 11.0% | 91 |
| 2-115-19 | 124 | 2 | VH2-31-11 | 8 | 8.1% | 124 |
| OU | 125 | 2 | VH2-31-14 | 20 | 25.6% | 92 |
| HE | 120 | 2 | VH2-31-13 | 19 | 19.0% | 27 |
| CLL33 40-1 | 78 | 2 | VH2-31-5 | 2 | 2.0% | 29 |
| E55 3.9 | 88 | 3 | VH3-11-5 | 7 | 7.2% | 26 |
| MTFC3 | 125 | 3 | VH3-14-4 | 21 | 21.0% | 131 |
| MTFC11 | 125 | 3 | VH3-14-4 | 21 | 21.0% | 131 |
| MTFJ1 | 114 | 3 | VH3-14-4 | 21 | 21.0% | 131 |
| MTFJ2 | 114 | 3 | VH3-14-4 | 21 | 21.0% | 131 |
| MTFUJ4 | 100 | 3 | VH3-14-4 | 21 | 21.0% | 131 |
| MTFUJ5 | 100 | 3 | VH3-14-4 | 21 | 21.0% | 131 |
| MTFUJ2 | 100 | 3 | VH3-14-4 | 22 | 22.0% | 131 |
| MTFC8 | 125 | 3 | VH3-14-4 | 23 | 23.0% | 131 |
| TD e Vq | 113 | 3 | VH3-14-4 | 0 | 0.0% | 16 |
| rMTF | 114 | 3 | VH3-14-4 | 5 | 5.0% | 131 |
| MTFUJ6 | 100 | 3 | VH3-14-4 | 10 | 10.0% | 131 |
| RF-KES | 107 | 3 | VH3-14-4 | 9 | 9.0% | 85 |
| N51P8 | 126 | 3 | VH3-14-1 | 9 | 9.0% | 77 |
| TEI | 119 | 3 | VH3-13-8 | 21 | 21.4% | 20 |
| 33.H11 | 115 | 3 | VH3-13-19 | 10 | 10.2% | 129 |
| SB1/D8 | 101 | 3 | VH3-1X-8 | 14 | 14.0% | 2 |
| 38P1 | 119 | 3 | VH3-11-3 | 0 | 0.0% | 104 |
| BRO'IGM | 119 | 3 | VH3-11-3 | 13 | 13.4% | 19 |
| NIE | 119 | 3 | VH3-13-7 | 15 | 15.3% | 87 |
| 3D6 | 126 | 3 | VH3-13-26 | 5 | 5.1% | 35 |
| ZM1-1 | 112 | 3 | VH3-11-3 | 8 | 8.2% | 5 |
| E55 3.15 | 110 | 3 | VH3-13-26 | 0 | 0.0% | 26 |
| gF9 | 108 | 3 | VH3-13-8 | 15 | 15.3% | 75 |
| THY-32 | 120 | 3 | VH3-13-26 | 3 | 3.1% | 42 |
| RF-KL5 | 100 | 3 | VH3-13-26 | 5 | 5.1% | 96 |
| OST577 | 122 | 3 | VH3-13-13 | 6 | 6.1% | 5 |
| BO | 113 | 3 | VH3-13-19 | 15 | 15.3% | 10 |
| TT125 | 121 | 3 | VH3-13-10 | 15 | 15.3% | 64 |
| 2-115-58 | 127 | 3 | VH3-13-10 | 11 | 11.2% | 124 |
| KOL | 126 | 3 | VH3-13-14 | 16 | 16.3% | 102 |
| mAb60 | 118 | 3 | VH3-13-17 | 14 | 14.3% | 45 |
| RF-AN | 106 | 3 | VH3-13-26 | 8 | 8.2% | 85 |
| BUT | 115 | 3 | VH3-11-6 | 13 | 13.4% | 119 |
| KOL-based CAMPATH-9 | 118 | 3 | VH3-13-13 | 16 | 16.3% | 41 |
| B1 | 119 | 3 | VH3-13-19 | 13 | 13.3% | 53 |
| N98P1 | 127 | 3 | VH3-13-1 | 13 | 13.3% | 77 |
| TT117 | 107 | 3 | VH3-13-10 | 12 | 12.2% | 64 |
| WEA | 114 | 3 | VH3-13-12 | 15 | 15.3% | 40 |
| HIL | 120 | 3 | VH3-13-14 | 14 | 14.3% | 23 |
| s5A10 | 97 | 3 | VH3-13-14 | 0 | 0.0% | 46 |
| s5D11 | 98 | 3 | VH3-13-7 | 0 | 0.0% | 46 |
| s6C8 | 100 | 3 | VH3-13-7 | 0 | 0.0% | 46 |
| s6H12 | 98 | 3 | VH3-13-7 | 0 | 0.0% | 46 |
| VH10.7 | 119 | 3 | VH3-13-14 | 16 | 16.3% | 128 |
| HIV-loop2 | 126 | 3 | VH3-13-7 | 16 | 16.3% | 12 |
| HIV-loop35 | 126 | 3 | VH3-13-7 | 16 | 16.3% | 12 |
| TRO | 122 | 3 | VH3-13-1 | 13 | 13.3% | 61 |
| SA-4B | 123 | 3 | VH3-13-1 | 15 | 15.3% | 125 |
| L2B5 | 98 | 3 | VH3-13-13 | 0 | 0.0% | 46 |
| s6E11 | 95 | 3 | VH3-13-13 | 0 | 0.0% | 46 |
| s6H7 | 100 | 3 | VH3-13-13 | 0 | 0.0% | 46 |
| ss1 | 102 | 3 | VH3-13-13 | 0 | 0.0% | 46 |
| ss8 | 94 | 3 | VH3-13-13 | 0 | 0.0% | 46 |
| DOB | 120 | 3 | VH3-13-26 | 21 | 21.4% | 116 |
| THY-33 | 115 | 3 | VH3-13-15 | 20 | 20.4% | 42 |
| NOV | 118 | 3 | VH3-13-19 | 14 | 14.3% | 38 |
| rsv13H | 120 | 3 | VH3-13-24 | 20 | 20.4% | 11 |
| L3G11 | 98 | 3 | VH3-13-20 | 2 | 2.0% | 46 |
| L2E8 | 99 | 3 | VH3-13-19 | 0 | 0.0% | 46 |
| L2D10 | 101 | 3 | VH3-13-10 | 1 | 1.0% | 46 |
| L2E7 | 98 | 3 | VH3-13-10 | 1 | 1.0% | 46 |
| L3A10 | 100 | 3 | VH3-13-24 | 0 | 0.0% | 46 |
| L2E5 | 97 | 3 | VH3-13-2 | 1 | 1.0% | 46 |
| BUR | 119 | 3 | VH3-13-7 | 21 | 21.4% | 67 |
| s4D5 | 107 | 3 | VH3-11-3 | 1 | 1.0% | 46 |
| 19 | 116 | 3 | VH3-13-16 | 4 | 4.1% | 118 |
| s5D4 | 99 | 3 | VH3-13-1 | 0 | 0.0% | 46 |
| s6A8 | 100 | 3 | VH3-13-1 | 0 | 0.0% | 46 |
| HIV-loop13 | 123 | 3 | VH3-13-12 | 17 | 17.3% | 12 |
| TR1.32 | 112 | 3 | VH3-11-8 | 18 | 18.6% | 88 |
| L2B10 | 97 | 3 | VH3-11-3 | 1 | 1.0% | 46 |
| TR1.5 | 114 | 3 | VH3-11-8 | 21 | 21.6% | 88 |
| s6H9 | 101 | 3 | VH3-13-25 | 0 | 0.0% | 46 |
| 8 | 112 | 3 | VH3-13-1 | 6 | 6.1% | 118 |
| 23 | 115 | 3 | VH3-13-1 | 6 | 6.1% | 118 |
| 7 | 115 | 3 | VH3-13-1 | 4 | 4.1% | 118 |
| TR1.3 | 120 | 3 | VH3-11-8 | 20 | 20.6% | 88 |
| 18/2 | 125 | 3 | VH3-13-10 | 0 | 0.0% | 32 |
| 18/9 | 125 | 3 | VH3-13-10 | 0 | 0.0% | 31 |
| 30P1 | 119 | 3 | VH3-13-10 | 0 | 0.0% | 106 |
| HF2-1/17 | 125 | 3 | VH3-13-10 | 0 | 0.0% | 8 |
| A77 | 109 | 3 | VH3-13-10 | 0 | 0.0% | 44 |
| B19.7 | 108 | 3 | VH3-13-10 | 0 | 0.0% | 44 |
| M43 | 119 | 3 | VH3-13-10 | 0 | 0.0% | 103 |
| 1/17 | 125 | 3 | VH3-13-10 | 0 | 0.0% | 31 |
| 18/17 | 125 | 3 | VH3-13-10 | 0 | 0.0% | 31 |
| E54 3.4 | 109 | 3 | VH3-13-10 | 0 | 0.0% | 26 |
| LAMBDA-VH26 | 98 | 3 | VH3-13-10 | 1 | 1.0% | 95 |
| E54 3.8 | 111 | 3 | VH3-13-10 | 1 | 1.0% | 26 |
| GL16 | 106 | 3 | VH3-13-10 | 1 | 1.0% | 44 |
| 4G12 | 125 | 3 | VH3-13-10 | 1 | 1.0% | 56 |
| A73 | 106 | 3 | VH3-13-10 | 2 | 2.0% | 44 |
| AL1.3 | 111 | 3 | VH3-13-10 | 3 | 3.1% | 117 |
| 3.A290 | 118 | 3 | VH3-13-10 | 2 | 2.0% | 108 |
| Ab18 | 127 | 3 | VH3-13-8 | 2 | 2.0% | 100 |
| E54 3.3 | 105 | 3 | VH3-13-10 | 3 | 3.1% | 26 |
| 35G6 | 121 | 3 | VH3-13-10 | 3 | 3.1% | 57 |
| A95 | 107 | 3 | VH3-13-10 | 5 | 5.1% | 44 |
| Ab25 | 128 | 3 | VH3-13-10 | 5 | 5.1% | 100 |
| N87 | 126 | 3 | VH3-13-10 | 4 | 4.1% | 77 |
| ED8.4 | 99 | 3 | VH3-13-10 | 6 | 6.1% | 2 |
| RF-KL1 | 122 | 3 | VH3-13-10 | 6 | 6.1% | 82 |
| AL1.1 | 112 | 3 | VH3-13-10 | 2 | 2.0% | 117 |
| AL3.11 | 102 | 3 | VH3-13-10 | 1 | 1.0% | 117 |
| 32.B9 | 127 | 3 | VH3-13-8 | 6 | 6.1% | 129 |
| TK1 | 109 | 3 | VH3-13-10 | 2 | 2.0% | 117 |
| POP | 123 | 3 | VH3-13-10 | 8 | 8.2% | 115 |
| 9F2H | 127 | 3 | VH3-13-10 | 9 | 9.2% | 127 |
| VD | 115 | 3 | VH3-13-10 | 9 | 9.2% | 10 |
| Vh38Cl.10 | 121 | 3 | VH3-13-10 | 8 | 8.2% | 74 |
| Vh38Cl.9 | 121 | 3 | VH3-13-10 | 8 | 8.2% | 74 |
| Vh38Cl.8 | 121 | 3 | VH3-13-10 | 8 | 8.2% | 74 |
| 63P1 | 120 | 3 | VH3-11-8 | 0 | 0.0% | 104 |
| 60P2 | 117 | 3 | VH3-11-8 | 0 | 0.0% | 104 |
| AL3.5 | 90 | 3 | VH3-13-10 | 2 | 2.0% | 117 |
| GF4/1.1 | 123 | 3 | VH3-13-10 | 10 | 10.2% | 39 |
| Ab21 | 126 | 3 | VH3-13-10 | 12 | 12.2% | 100 |
| TD d Vp | 118 | 3 | VH3-13-17 | 2 | 2.0% | 16 |
| Vh38Cl.4 | 119 | 3 | VH3-13-10 | 8 | 8.2% | 74 |
| Vh38Cl.5 | 119 | 3 | VH3-13-10 | 8 | 8.2% | 74 |
| AL3.4 | 104 | 3 | VH3-13-10 | 1 | 1.0% | 117 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| FOG1-A3 | 115 | 3 | VH3-13-19 | 2 | 2.0% | 42 |
| HA3D1 | 117 | 3 | VH3-13-21 | 1 | 1.0% | 81 |
| E54 3.2 | 112 | 3 | VH3-13-24 | 0 | 0.0% | 26 |
| mAb52 | 128 | 3 | VH3-13-12 | 2 | 2.0% | 51 |
| mAb53 | 128 | 3 | VH3-13-12 | 2 | 2.0% | 51 |
| mAb56 | 128 | 3 | VH3-13-12 | 2 | 2.0% | 51 |
| mAb57 | 128 | 3 | VH3-13-12 | 2 | 2.0% | 51 |
| mAb58 | 128 | 3 | VH3-13-12 | 2 | 2.0% | 51 |
| mAb59 | 128 | 3 | VH3-13-12 | 2 | 2.0% | 51 |
| mAb105 | 128 | 3 | VH3-13-12 | 2 | 2.0% | 51 |
| mAb107 | 128 | 3 | VH3-13-12 | 2 | 2.0% | 51 |
| E55 3.14 | 110 | 3 | VH3-13-19 | 0 | 0.0% | 26 |
| F13-28 | 106 | 3 | VH3-13-19 | 1 | 1.0% | 94 |
| mAb55 | 127 | 3 | VH3-13-18 | 4 | 4.1% | 51 |
| YSE | 117 | 3 | VH3-13-24 | 6 | 6.1% | 72 |
| E55 3.23 | 106 | 3 | VH3-13-19 | 2 | 2.0% | 26 |
| RF-TS5 | 101 | 3 | VH3-13-1 | 3 | 3.1% | 85 |
| N42P5 | 124 | 3 | VH3-13-2 | 7 | 7.1% | 77 |
| FOG1-H6 | 110 | 3 | VH3-13-16 | 7 | 7.1% | 42 |
| O-81 | 115 | 3 | VH3-13-19 | 11 | 11.2% | 47 |
| HIV-s8 | 122 | 3 | VH3-13-12 | 11 | 11.2% | 12 |
| mAb114 | 125 | 3 | VH3-13-19 | 12 | 12.2% | 71 |
| 33.F12 | 116 | 3 | VH3-13-2 | 4 | 4.1% | 129 |
| 4B4 | 119 | 3 | VH3-1X-3 | 0 | 0.0% | 101 |
| M26 | 123 | 3 | VH3-1X-3 | 0 | 0.0% | 103 |
| VHGL 3.1 | 100 | 3 | VH3-1X-3 | 0 | 0.0% | 26 |
| E55 3.13 | 113 | 3 | VH3-1X-3 | 1 | 1.0% | 26 |
| SB5/D6 | 101 | 3 | VH3-1X-6 | 3 | 3.0% | 2 |
| RAY4 | 101 | 3 | VH3-1X-6 | 3 | 3.0% | 2 |
| 82-D V-D | 106 | 3 | VH3-1X-3 | 5 | 5.0% | 112 |
| MAL | 129 | 3 | VH3-1X-3 | 5 | 5.0% | 72 |
| LOC | 123 | 3 | VH3-1X-6 | 5 | 5.0% | 72 |
| LSF2 | 101 | 3 | VH3-1X-6 | 11 | 11.0% | 2 |
| HIB RC3 | 100 | 3 | VH3-1X-6 | 11 | 11.0% | 1 |
| 56P1 | 119 | 3 | VH3-13-7 | 0 | 0.0% | 104 |
| M72 | 122 | 3 | VH3-13-7 | 0 | 0.0% | 103 |
| M74 | 121 | 3 | VH3-13-7 | 0 | 0.0% | 103 |
| E54 3.5 | 105 | 3 | VH3-13-7 | 0 | 0.0% | 26 |
| 2E7 | 123 | 3 | VH3-13-7 | 0 | 0.0% | 63 |
| 2P1 | 117 | 3 | VH3-13-7 | 0 | 0.0% | 104 |
| RF-SJ2 | 127 | 3 | VH3-13-7 | 1 | 1.0% | 83 |
| PR-TS1 | 114 | 3 | VH3-13-7 | 1 | 1.0% | 85 |
| KIM46H | 127 | 3 | VH3-13-13 | 0 | 0.0% | 18 |
| E55 3.6 | 108 | 3 | VH3-13-7 | 2 | 2.0% | 26 |
| E55 3.10 | 107 | 3 | VH3-13-13 | 1 | 1.0% | 26 |
| 3.B6 | 114 | 3 | VH3-13-13 | 1 | 1.0% | 108 |
| E54 3.6 | 110 | 3 | VH3-13-13 | 1 | 1.0% | 26 |
| FL2-2 | 114 | 3 | VH3-13-13 | 1 | 1.0% | 80 |
| RF-SJ3 | 112 | 3 | VH3-13-7 | 2 | 2.0% | 85 |
| E55 3.5 | 105 | 3 | VH3-13-14 | 1 | 1.0% | 26 |
| BSA3 | 121 | 3 | VH3-13-13 | 1 | 1.0% | 73 |
| HMST-1 | 119 | 3 | VH3-13-7 | 3 | 3.1% | 130 |
| RF-TS2 | 126 | 3 | VH3-13-13 | 4 | 4.1% | 82 |
| E55 3.12 | 109 | 3 | VH3-13-15 | 0 | 0.0% | 26 |
| 19.E7 | 126 | 3 | VH3-13-14 | 3 | 3.1% | 129 |
| 11-50 | 119 | 3 | VH3-13-13 | 6 | 6.1% | 130 |
| E29.1 | 120 | 3 | VH3-13-15 | 2 | 2.0% | 25 |
| E55 3.16 | 108 | 3 | VH3-13-7 | 6 | 6.1% | 26 |
| TNF-E1 | 117 | 3 | VH3-13-7 | 7 | 7.1% | 42 |
| AF-SJ1 | 127 | 3 | VH3-13-13 | 6 | 6.1% | 83 |
| FOG1-A4 | 116 | 3 | VH3-13-7 | 8 | 8.2% | 42 |
| TNF-A1 | 117 | 3 | VH3-13-15 | 4 | 4.1% | 42 |
| PR-SJ2 | 107 | 3 | VH3-13-14 | 8 | 8.2% | 85 |
| HN.14 | 124 | 3 | VH3-13-13 | 10 | 10.2% | 33 |
| CAM' | 121 | 3 | VH3-13-7 | 12 | 12.2% | 65 |
| HIV-B8 | 125 | 3 | VH3-13-7 | 9 | 9.2% | 12 |
| HIV-b27 | 125 | 3 | VH3-13-7 | 9 | 9.2% | 12 |
| HIV-b8 | 125 | 3 | VH3-13-7 | 9 | 9.2% | 12 |
| HIV-s4 | 125 | 3 | VH3-13-7 | 9 | 9.2% | 12 |
| HIV-B26 | 125 | 3 | VH3-13-7 | 9 | 9.2% | 12 |
| HIV-B35 | 125 | 3 | VH3-13-7 | 10 | 10.2% | 12 |
| HIV-b18 | 125 | 3 | VH3-13-7 | 10 | 10.2% | 12 |
| HIV-b22 | 125 | 3 | VH3-13-7 | 11 | 11.2% | 12 |
| HIV-b13 | 125 | 3 | VH3-13-7 | 12 | 12.2% | 12 |
| 333 | 117 | 3 | VH3-14-4 | 24 | 24.0% | 24 |
| 1H1 | 120 | 3 | VH3-14-4 | 24 | 24.0% | 24 |
| 1B11 | 120 | 3 | VH3-14-4 | 23 | 23.0% | 24 |
| CLL30 2-3 | 86 | 3 | VH3-13-19 | 1 | 1.0% | 29 |
| GA | 110 | 3 | VH3-13-7 | 19 | 19.4% | 36 |
| JeB | 99 | 3 | VH3-13-14 | 3 | 3.1% | 7 |
| GAL | 110 | 3 | VH3-13-19 | 10 | 10.2% | 126 |
| K6H6 | 119 | 3 | VH3-1X-6 | 18 | 18.0% | 60 |
| K4B8 | 119 | 3 | VH3-1X-6 | 18 | 18.0% | 60 |
| K5B8 | 119 | 3 | VH3-1X-6 | 18 | 18.0% | 60 |
| K5C7 | 119 | 3 | VH3-1X-6 | 19 | 19.0% | 60 |
| K5G5 | 119 | 3 | VH3-1X-6 | 19 | 19.0% | 60 |
| K6F5 | 119 | 3 | VH3-1X-6 | 19 | 19.0% | 60 |
| AL3.16 | 98 | 3 | VH3-13-10 | 1 | 1.0% | 117 |
| N86P2 | 98 | 3 | VH3-13-10 | 3 | 3.1% | 77 |
| N54P6 | 95 | 3 | VH3-13-16 | 7 | 7.1% | 77 |
| LAMBDA HT112-1 | 126 | 4 | VH4-11-2 | 0 | 0.0% | 3 |
| HY18 | 121 | 4 | VH4-11-2 | 0 | 0.0% | 43 |
| mAb63 | 126 | 4 | VH4-11-2 | 0 | 0.0% | 45 |
| FS-3 | 105 | 4 | VH4-11-2 | 0 | 0.0% | 86 |
| FS-5 | 111 | 4 | VH4-11-2 | 0 | 0.0% | 86 |
| FS-7 | 107 | 4 | VH4-11-2 | 0 | 0.0% | 86 |
| FS-8 | 110 | 4 | VH4-11-2 | 0 | 0.0% | 86 |
| PR-TS2 | 105 | 4 | VH4-11-2 | 0 | 0.0% | 85 |
| RF-TMC | 102 | 4 | VH4-11-2 | 0 | 0.0% | 85 |
| mAb216 | 122 | 4 | VH4-11-2 | 1 | 1.0% | 15 |
| mAb410.7.F91 | 122 | 4 | VH4-11-2 | 1 | 1.0% | 52 |
| mAbA6H4C5 | 124 | 4 | VH4-11-2 | 1 | 1.0% | 15 |
| Ab44 | 127 | 4 | VH4-11-2 | 2 | 2.1% | 100 |
| 6H-3C4 | 124 | 4 | VH4-11-2 | 3 | 3.1% | 59 |
| FS-6 | 108 | 4 | VH4-11-2 | 6 | 6.2% | 86 |
| FS-2 | 114 | 4 | VH4-11-2 | 6 | 6.2% | 84 |
| H1G1 | 126 | 4 | VH4-11-2 | 7 | 7.2% | 62 |
| FS-4 | 105 | 4 | VH4-11-2 | 8 | 8.2% | 86 |
| SA-4A | 123 | 4 | VH4-11-2 | 9 | 9.3% | 125 |
| LES-C | 119 | 4 | VH4-11-2 | 10 | 10.3% | 99 |
| DI | 78 | 4 | VH4-11-9 | 16 | 16.5% | 58 |
| Ab26 | 126 | 4 | VH4-31-4 | 8 | 8.1% | 100 |
| TS2 | 124 | 4 | VH4-11-12 | 15 | 15.2% | 110 |
| 265-695 | 115 | 4 | VH4-11-7 | 16 | 16.5% | 5 |
| WAH | 129 | 4 | VH4-31-13 | 19 | 19.2% | 93 |
| 268-D | 122 | 4 | VH4-11-8 | 22 | 22.7% | 6 |
| 58P2 | 118 | 4 | VH4-11-8 | 0 | 0.0% | 104 |
| mAb67 | 128 | 4 | VH4-11-8 | 1 | 1.0% | 45 |
| 4.L39 | 115 | 4 | VH4-11-8 | 2 | 2.1% | 108 |
| mF7 | 111 | 4 | VH4-31-13 | 3 | 3.0% | 75 |
| 33.C9 | 122 | 4 | VH4-21-5 | 7 | 7.1% | 129 |
| Pag-1 | 124 | 4 | VH4-11-16 | 5 | 5.2% | 50 |
| B3 | 123 | 4 | VH4-21-3 | 8 | 8.2% | 53 |
| IC4 | 120 | 4 | VH4-11-8 | 6 | 6.2% | 70 |
| C6B2 | 127 | 4 | VH4-31-12 | 4 | 4.0% | 48 |
| N78 | 118 | 4 | VH4-11-9 | 11 | 11.3% | 77 |
| B2 | 109 | 4 | VH4-11-8 | 12 | 12.4% | 53 |
| WRD2 | 123 | 4 | VH4-11-12 | 6 | 6.2% | 90 |
| mAb426.4.2F20 | 126 | 4 | VH4-11-8 | 2 | 2.1% | 52 |
| E54 4.58 | 115 | 4 | VH4-11-8 | 1 | 1.0% | 26 |
| WRD6 | 123 | 4 | VH4-11-12 | 10 | 10.3% | 90 |
| mAb426.12.3F1.4 | 122 | 4 | VH4-11-9 | 4 | 4.1% | 52 |
| E54 4.2 | 108 | 4 | VH4-21-6 | 2 | 2.0% | 26 |
| WIL | 127 | 4 | VH4-31-13 | 0 | 0.0% | 90 |
| COF | 126 | 4 | VH4-31-13 | 0 | 0.0% | 90 |
| LAR | 122 | 4 | VH4-31-13 | 2 | 2.0% | 90 |
| WAT | 125 | 4 | VH4-31-13 | 4 | 4.0% | 90 |
| mAb61 | 123 | 4 | VH4-31-13 | 5 | 5.1% | 45 |
| WAG | 127 | 4 | VH4-31-4 | 0 | 0.0% | 90 |
| RF-SJ4 | 108 | 4 | VH4-31-12 | 2 | 2.0% | 85 |
| E54 4.4 | 110 | 4 | VH4-11-7 | 0 | 0.0% | 26 |
| E55 4.A1 | 108 | 4 | VH4-11-7 | 0 | 0.0% | 26 |
| PR-SJ1 | 103 | 4 | VH4-11-7 | 1 | 1.0% | 85 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| E54 4.23 | 111 | 4 | VH4-11-7 | 1 | 1.0% | 26 |
| CLL7 7-2 | 97 | 4 | VH4-11-12 | 0 | 0.0% | 29 |
| 37P1 | 95 | 4 | VH4-11-12 | 0 | 0.0% | 104 |
| ALL52 30-2 | 91 | 4 | VH4-31-12 | 4 | 4.0% | 29 |
| EBV-21 | 98 | 5 | VH5-12-1 | 0 | 0.0% | 13 |
| CB-4 | 98 | 5 | VH5-12-1 | 0 | 0.0% | 13 |
| CLL-12 | 98 | 5 | VH5-12-1 | 0 | 0.0% | 13 |
| L3-4 | 98 | 5 | VH5-12-1 | 0 | 0.0% | 13 |
| CLL11 | 98 | 5 | VH5-12-1 | 0 | 0.0% | 17 |
| CORD3 | 98 | 5 | VH5-12-1 | 0 | 0.0% | 17 |
| CORD4 | 98 | 5 | VH5-12-1 | 0 | 0.0% | 17 |
| CORD8 | 98 | 5 | VH5-12-1 | 0 | 0.0% | 17 |
| CORD9 | 98 | 5 | VH5-12-1 | 0 | 0.0% | 17 |
| CD + 1 | 98 | 5 | VH5-12-1 | 0 | 0.0% | 17 |
| CD + 3 | 98 | 5 | VH5-12-1 | 0 | 0.0% | 17 |
| CD + 4 | 98 | 5 | VH5-12-1 | 0 | 0.0% | 17 |
| CD − 1 | 98 | 5 | VH5-12-1 | 0 | 0.0% | 17 |
| CD − 5 | 98 | 5 | VH5-12-1 | 0 | 0.0% | 17 |
| VERG14 | 98 | 5 | VH5-12-1 | 0 | 0.0% | 17 |
| PBL1 | 98 | 5 | VH5-12-1 | 0 | 0.0% | 17 |
| PBL10 | 98 | 5 | VH5-12-1 | 0 | 0.0% | 17 |
| STRAb SA-1A | 127 | 5 | VH5-12-1 | 0 | 0.0% | 125 |
| DOB' | 122 | 5 | VH5-12-1 | 0 | 0.0% | 97 |
| VERG5 | 98 | 5 | VH5-12-1 | 0 | 0.0% | 17 |
| PBL2 | 98 | 5 | VH5-12-1 | 1 | 1.0% | 17 |
| Tu16 | 119 | 5 | VH5-12-1 | 1 | 1.0% | 49 |
| PBL12 | 98 | 5 | VH5-12-1 | 1 | 1.0% | 17 |
| CD + 2 | 98 | 5 | VH5-12-1 | 1 | 1.0% | 17 |
| CORD10 | 98 | 5 | VH5-12-1 | 1 | 1.0% | 17 |
| PBL9 | 98 | 5 | VH5-12-1 | 1 | 1.0% | 17 |
| CORD2 | 98 | 5 | VH5-12-1 | 2 | 2.0% | 17 |
| PBL6 | 98 | 5 | VH5-12-1 | 2 | 2.0% | 17 |
| CORD5 | 98 | 5 | VH5-12-1 | 2 | 2.0% | 17 |
| CD − 2 | 98 | 5 | VH5-12-1 | 2 | 2.0% | 17 |
| CORD1 | 98 | 5 | VH5-12-1 | 2 | 2.0% | 17 |
| CD − 3 | 98 | 5 | VH5-12-1 | 3 | 3.1% | 17 |
| VERG4 | 98 | 5 | VH5-12-1 | 3 | 3.1% | 17 |
| PBL13 | 98 | 5 | VH5-12-1 | 3 | 3.1% | 17 |
| PBL7 | 98 | 5 | VH5-12-1 | 3 | 3.1% | 17 |
| HAN | 119 | 5 | VH5-12-1 | 3 | 3.1% | 97 |
| VERG3 | 98 | 5 | VH5-12-1 | 3 | 3.1% | 17 |
| PBL3 | 98 | 5 | VH5-12-1 | 3 | 3.1% | 17 |
| VERG7 | 98 | 5 | VH5-12-1 | 3 | 3.1% | 17 |
| PBL5 | 94 | 5 | VH5-12-1 | 0 | 0.0% | 17 |
| CD − 4 | 98 | 5 | VH5-12-1 | 4 | 4.1% | 17 |
| CLL10 | 98 | 5 | VH5-12-1 | 4 | 4.1% | 17 |
| PBL11 | 98 | 5 | VH5-12-1 | 4 | 4.1% | 17 |
| CORD6 | 98 | 5 | VH5-12-1 | 4 | 4.1% | 17 |
| VERG2 | 98 | 5 | VH5-12-1 | 5 | 5.1% | 17 |
| 83P2 | 119 | 5 | VH5-12-1 | 0 | 0.0% | 103 |
| VERG9 | 98 | 5 | VH5-12-1 | 6 | 6.1% | 17 |
| CLL6 | 98 | 5 | VH5-12-1 | 6 | 6.1% | 17 |
| PBL8 | 98 | 5 | VH5-12-1 | 7 | 7.1% | 17 |
| Ab2022 | 120 | 5 | VH5-12-1 | 3 | 3.1% | 100 |
| CAV | 127 | 5 | VH5-12-4 | 0 | 0.0% | 97 |
| HOW' | 120 | 5 | VH5-12-4 | 0 | 0.0% | 97 |
| PET | 127 | 5 | VH5-12-4 | 0 | 0.0% | 97 |
| ANG | 121 | 5 | VH5-12-4 | 0 | 0.0% | 97 |
| KER | 121 | 5 | VH5-12-4 | 0 | 0.0% | 97 |
| 5.M13 | 118 | 5 | VH5-12-4 | 0 | 0.0% | 107 |
| Au2.1 | 118 | 5 | VH5-12-4 | 1 | 1.0% | 49 |
| WS1 | 126 | 5 | VH5-12-1 | 9 | 9.2% | 110 |
| TD Vn | 98 | 5 | VH5-12-4 | 1 | 1.0% | 16 |
| TEL13 | 116 | 5 | VH5-12-4 | 9 | 9.2% | 73 |
| E55 5.237 | 112 | 5 | VH5-12-4 | 2 | 2.0% | 26 |
| VERG1 | 98 | 5 | VH5-12-1 | 10 | 10.2% | 17 |
| CD4-74 | 117 | 5 | VH5-12-1 | 10 | 10.2% | 42 |
| 257-D | 125 | 5 | VH5-12-1 | 11 | 11.2% | 6 |
| CLL4 | 98 | 5 | VH5-12-1 | 11 | 11.2% | 17 |
| CLL8 | 98 | 5 | VH5-12-1 | 11 | 11.2% | 17 |
| Ab2 | 124 | 5 | VH5-12-1 | 12 | 12.2% | 120 |
| Vh3B3ex | 98 | 5 | VH5-12-1 | 12 | 12.2% | 120 |
| CLL3 | 98 | 5 | VH5-12-2 | 11 | 11.2% | 17 |
| Au59.1 | 122 | 5 | VH5-12-1 | 12 | 12.2% | 49 |
| TEL16 | 117 | 5 | VH5-12-1 | 12 | 12.2% | 73 |
| M61 | 104 | 5 | VH5-12-1 | 0 | 0.0% | 103 |
| TuO | 99 | 5 | VH5-12-1 | 5 | 5.1% | 49 |
| P2-51 | 122 | 5 | VH5-12-1 | 13 | 13.3% | 121 |
| P2-54 | 122 | 5 | VH5-12-1 | 11 | 11.2% | 121 |
| P1-56 | 119 | 5 | VH5-12-1 | 9 | 9.2% | 121 |
| P2-53 | 122 | 5 | VH5-12-1 | 10 | 10.2% | 121 |
| P1-51 | 123 | 5 | VH5-12-1 | 19 | 19.4% | 121 |
| P1-54 | 123 | 5 | VH5-12-1 | 3 | 3.1% | 121 |
| P3-69 | 127 | 5 | VH5-12-1 | 4 | 4.1% | 121 |
| P3-9 | 119 | 5 | VH5-12-1 | 4 | 4.1% | 121 |
| 1-185-37 | 125 | 5 | VH5-12-4 | 0 | 0.0% | 124 |
| 1-187-29 | 125 | 5 | VH5-12-4 | 0 | 0.0% | 124 |
| P1-58 | 128 | 5 | VH5-12-4 | 10 | 10.2% | 121 |
| P2-57 | 118 | 5 | VH5-12-4 | 3 | 3.1% | 121 |
| P2-55 | 123 | 5 | VH5-12-1 | 5 | 5.1% | 121 |
| P2-56 | 123 | 5 | VH5-12-1 | 20 | 20.4% | 121 |
| P2-52 | 122 | 5 | VH5-12-1 | 11 | 11.2% | 121 |
| P3-60 | 122 | 5 | VH5-12-1 | 8 | 8.2% | 121 |
| P1-57 | 123 | 5 | VH5-12-1 | 4 | 4.1% | 121 |
| P1-55 | 122 | 5 | VH5-12-1 | 14 | 14.3% | 121 |
| MD3-4 | 128 | 5 | VH5-12-4 | 12 | 12.2% | 5 |
| P1-52 | 121 | 5 | VH5-12-1 | 11 | 11.2% | 121 |
| CLL5 | 98 | 5 | VH5-12-1 | 13 | 13.3% | 17 |
| CLL7 | 98 | 5 | VH5-12-1 | 14 | 14.3% | 17 |
| L2F10 | 100 | 5 | VH5-12-1 | 1 | 1.0% | 46 |
| L386 | 98 | 5 | VH5-12-1 | 1 | 1.0% | 46 |
| VH6.A12 | 119 | 6 | VH6-35-1 | 13 | 12.9% | 122 |
| s5A9 | 102 | 6 | VH6-35-1 | 1 | 1.0% | 46 |
| s6G4 | 99 | 6 | VH6-35-1 | 1 | 1.0% | 46 |
| ss3 | 99 | 6 | VH6-35-1 | 1 | 1.0% | 46 |
| 6-1G1 | 101 | 6 | VH6-35-1 | 0 | 0.0% | 14 |
| F19L16 | 107 | 6 | VH6-35-1 | 0 | 0.0% | 68 |
| L16 | 120 | 6 | VH6-35-1 | 0 | 0.0% | 69 |
| M71 | 121 | 6 | VH6-35-1 | 0 | 0.0% | 103 |
| ML1 | 120 | 6 | VH6-35-1 | 0 | 0.0% | 69 |
| F19ML1 | 107 | 6 | VH6-35-1 | 0 | 0.0% | 68 |
| 15P1 | 127 | 6 | VH6-35-1 | 0 | 0.0% | 104 |
| VH6.N1 | 121 | 6 | VH6-35-1 | 0 | 0.0% | 122 |
| VH6.N11 | 123 | 6 | VH6-35-1 | 0 | 0.0% | 122 |
| VH6.N12 | 123 | 6 | VH6-35-1 | 0 | 0.0% | 122 |
| VH6.N2 | 125 | 6 | VH6-35-1 | 0 | 0.0% | 122 |
| VH6.N5 | 125 | 6 | VH6-35-1 | 0 | 0.0% | 122 |
| VH6.N6 | 127 | 6 | VH6-35-1 | 0 | 0.0% | 122 |
| VH6.N7 | 126 | 6 | VH6-35-1 | 0 | 0.0% | 122 |
| VH6.N8 | 123 | 6 | VH6-35-1 | 0 | 0.0% | 122 |
| VH6.N9 | 123 | 6 | VH6-35-1 | 0 | 0.0% | 122 |
| VH6.N10 | 123 | 6 | VH6-35-1 | 0 | 0.0% | 122 |
| VH6.A3 | 123 | 6 | VH6-35-1 | 0 | 0.0% | 122 |
| VH6.A1 | 124 | 6 | VH6-35-1 | 0 | 0.0% | 122 |
| VH6.A4 | 120 | 6 | VH6-35-1 | 0 | 0.0% | 122 |
| E55 6.16 | 116 | 6 | VH6-35-1 | 0 | 0.0% | 26 |
| E55 6.17 | 120 | 6 | VH6-35-1 | 0 | 0.0% | 26 |
| E55 6.6 | 120 | 6 | VH6-35-1 | 0 | 0.0% | 26 |
| VHGL 6.3 | 102 | 6 | VH6-35-1 | 0 | 0.0% | 26 |
| CB-201 | 118 | 6 | VH6-35-1 | 0 | 0.0% | 109 |
| VH6.N4 | 122 | 6 | VH6-35-1 | 0 | 0.0% | 122 |
| E54 6.4 | 109 | 6 | VH6-35-1 | 1 | 1.0% | 26 |
| VH6.A6 | 126 | 6 | VH6-35-1 | 1 | 1.0% | 122 |
| E55 6.14 | 120 | 6 | VH6-35-1 | 1 | 1.0% | 26 |
| E54 6.6 | 107 | 6 | VH6-35-1 | 1 | 1.0% | 26 |
| E55 6.10 | 112 | 6 | VH6-35-1 | 1 | 1.0% | 26 |
| E54 6.1 | 107 | 6 | VH6-35-1 | 2 | 2.0% | 26 |
| E55 6.13 | 120 | 6 | VH6-35-1 | 2 | 2.0% | 26 |
| E55 6.3 | 120 | 6 | VH6-35-1 | 2 | 2.0% | 26 |
| E55 6.7 | 116 | 6 | VH6-35-1 | 2 | 2.0% | 26 |
| E55 6.2 | 120 | 6 | VH6-35-1 | 2 | 2.0% | 26 |
| E55 6.X | 111 | 6 | VH6-35-1 | 2 | 2.0% | 26 |
| E55 6.11 | 111 | 6 | VH6-35-1 | 3 | 3.0% | 26 |
| VH6.A11 | 118 | 6 | VH6-35-1 | 3 | 3.0% | 122 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| A10 | 107 | 6 | VH6-35-1 | 3 | 3.0% | 68 |
| E55 6.1 | 120 | 6 | VH6-35-1 | 4 | 4.0% | 26 |
| FK-001 | 124 | 6 | VH6-35-1 | 4 | 4.0% | 65 |
| VH6.A5 | 121 | 6 | VH6-35-1 | 4 | 4.0% | 122 |
| VH6.A7 | 123 | 6 | VH6-35-1 | 4 | 4.0% | 122 |
| HBp2 | 119 | 6 | VH6-35-1 | 4 | 4.0% | 4 |
| Au46.2 | 123 | 6 | VH6-35-1 | 5 | 5.0% | 49 |
| A431 | 106 | 6 | VH6-35-1 | 5 | 5.0% | 68 |
| VH6.A2 | 120 | 6 | VH6-35-1 | 5 | 5.0% | 122 |
| VH6.A9 | 125 | 6 | VH6-35-1 | 8 | 7.9% | 122 |
| VH6.A8 | 118 | 6 | VH6-35-1 | 10 | 9.9% | 122 |
| VH6-FF3 | 118 | 6 | VH6-35-1 | 2 | 2.0% | 123 |
| VH6.A10 | 126 | 6 | VH6-35-1 | 12 | 11.9% | 122 |
| VH6-EB10 | 117 | 6 | VH6-35-1 | 3 | 3.0% | 123 |
| VH6-E6 | 119 | 6 | VH6-35-1 | 6 | 5.9% | 123 |
| VH6-FE2 | 121 | 6 | VH6-35-1 | 6 | 5.9% | 123 |
| VH6-EE6 | 116 | 6 | VH6-35-1 | 6 | 5.9% | 123 |
| VH6-FD10 | 118 | 6 | VH6-35-1 | 6 | 5.9% | 123 |
| VH6-EX8 | 113 | 6 | VH6-35-i | 6 | 5.9% | 123 |
| VH6-FG9 | 121 | 6 | VH6-35-1 | 8 | 7.9% | 123 |
| VH6-E5 | 116 | 6 | VH6-35-1 | 9 | 8.9% | 123 |
| VH6-EC8 | 122 | 6 | VH6-35-1 | 9 | 8.9% | 123 |
| VH6-E10 | 120 | 6 | VH6-35-1 | 10 | 9.9% | 123 |
| VH6-FF11 | 122 | 6 | VH6-35-1 | 11 | 10.9% | 123 |
| VH6-FD2 | 115 | 6 | VH6-35-1 | 11 | 10.9% | 123 |
| CLL10 17-2 | 88 | 6 | VH6-35-1 | 4 | 4.0% | 29 |
| VH6-BB11 | 94 | 6 | VH6-35-1 | 4 | 4.0% | 123 |
| VH6-B4I | 93 | 6 | VH6-35-1 | 7 | 6.9% | 123 |
| JU17 | 102 | 6 | VH6-35-1 | 3 | 3.0% | 114 |
| VH6-BD9 | 96 | 6 | VH6-35-1 | 11 | 10.9% | 123 |
| VH6-BB9 | 94 | 6 | VH6-35-1 | 12 | 11.9% | 123 |

TABLE 3A assignment of rearranged V kappa sequences to their germline counterparts

| Family[1] | Name | Rearranged[2] | Sum |
|---|---|---|---|
| 1 | Vk1-1 | 28 | |
| 1 | Vk1-2 | 0 | |
| 1 | Vk1-3 | 1 | |
| 1 | Vk1-4 | 0 | |
| 1 | Vk1-5 | 7 | |
| 1 | Vk1-6 | 0 | |
| 1 | Vk1-7 | 0 | |
| 1 | Vk1-8 | 2 | |
| 1 | Vk1-9 | 9 | |
| 1 | Vk1-10 | 0 | |
| 1 | Vk1-11 | 1 | |
| 1 | Vk1-12 | 7 | |
| 1 | Vk1-13 | 1 | |
| 1 | Vk1-14 | 7 | |
| 1 | Vk1-15 | 2 | |
| 1 | Vk1-16 | 2 | |
| 1 | Vk1-17 | 16 | |
| 1 | Vk1-18 | 1 | |
| 1 | Vk1-19 | 33 | |
| 1 | Vk1-20 | 1 | |
| 1 | Vk1-21 | 1 | |
| 1 | Vk1-22 | 0 | |
| 1 | Vk1-23 | 0 | 119 entries |
| 2 | Vk2-1 | 0 | |
| 2 | Vk2-2 | 1 | |
| 2 | Vk2-3 | 0 | |
| 2 | Vk2-4 | 0 | |
| 2 | Vk2-5 | 0 | |
| 2 | Vk2-6 | 16 | |
| 2 | Vk2-7 | 0 | |
| 2 | Vk2-8 | 0 | |

TABLE 3A-continued assignment of rearranged V kappa sequences to their germline counterparts

| Family[1] | Name | Rearranged[2] | Sum |
|---|---|---|---|
| 2 | Vk2-9 | 1 | |
| 2 | Vk2-10 | 0 | |
| 2 | Vk2-11 | 7 | |
| 2 | Vk2-12 | 0 | 25 entries |
| 3 | Vk3-1 | 1 | |
| 3 | Vk3-2 | 0 | |
| 3 | Vk3-3 | 35 | |
| 3 | Vk3-4 | 115 | |
| 3 | Vk3-5 | 0 | |
| 3 | Vk3-6 | 0 | |
| 3 | Vk3-7 | 1 | |
| 3 | Vk3-8 | 40 | 192 entries |
| 4 | Vk4-1 | 33 | 33 entries |
| 5 | Vk5-1 | 1 | 1 entry |
| 6 | Vk6-1 | 0 | |
| 6 | Vk6-2 | 0 | 0 entries |
| 7 | Vk7-1 | 0 | 0 entries |

TABLE 3B assignment of rearranged V lambda sequences to their germline counterparts

| Family[1] | Name | Rearranged[2] | Sum |
|---|---|---|---|
| 1 | DPL1 | 1 | |
| 1 | DPL2 | 14 | |
| 1 | DPL3 | 6 | |
| 1 | DPL4 | 1 | |
| 1 | HUMLV117 | 4 | |
| 1 | DPL5 | 13 | |
| 1 | DPL6 | 0 | |
| 1 | DPL7 | 0 | |
| 1 | DPL8 | 3 | |
| 1 | DPL9 | 0 | 42 entries |
| 2 | DPL10 | 5 | |
| 2 | VLAMBDA 2.1 | 0 | |
| 2 | DPL11 | 23 | |
| 2 | DPL12 | 15 | |
| 2 | DPL13 | 0 | |
| 2 | DPL14 | 0 | 43 entries |
| 3 | DPL16 | 10 | |
| 3 | DPL23 | 19 | |
| 3 | Humlv318 | 9 | 38 entries |
| 7 | DPL18 | 1 | |
| 7 | DPL19 | 0 | 1 entries |
| 8 | DPL21 | 2 | |
| 8 | HUMLV801 | 6 | 8 entries |
| 9 | DPL22 | 0 | 0 entries |
| unassigned | DPL24 | 0 | 0 entries |
| 10 | gVLX-4.4 | 0 | 0 entries |

TABLE 3C assignment of rearranged V heavy chain sequences to their germline counterparts

| Family[1] | Name | Rearranged[2] | Sum |
|---|---|---|---|
| 1 | VH1-12-1 | 38 | |
| 1 | VH1-12-8 | 2 | |
| 1 | VH1-12-2 | 2 | |
| 1 | VH1-12-9 | 2 | |
| 1 | VH1-12-3 | 0 | |
| 1 | VH1-12-4 | 0 | |
| 1 | VH1-12-5 | 3 | |
| 1 | VH1-12-6 | 0 | |
| 1 | VH1-12-7 | 23 | |
| 1 | VH1-13-1 | 1 | |
| 1 | VH1-13-2 | 1 | |

TABLE 3C-continued assignment of
rearranged V heavy chain sequences to their germline counterparts

| Family[1] | Name | Rearranged[2] | Sum |
|---|---|---|---|
| 1 | VH1-13-3 | 0 | |
| 1 | VH1-13-4 | 0 | |
| 1 | VH1-13-5 | 0 | |
| 1 | VH1-13-6 | 17 | |
| 1 | VH1-13-7 | 0 | |
| 1 | VH1-13-8 | 3 | |
| 1 | VH1-13-9 | 0 | |
| 1 | VH1-13-10 | 0 | |
| 1 | VH1-13-11 | 0 | |
| 1 | VH1-13-12 | 10 | |
| 1 | VH1-13-13 | 0 | |
| 1 | VH1-13-14 | 0 | |
| 1 | VH1-13-15 | 4 | |
| 1 | VH1-13-16 | 2 | |
| 1 | VH1-13-17 | 0 | |
| 1 | VH1-13-18 | 1 | |
| 1 | VH1-13-19 | 0 | |
| 1 | VH1-1X-1 | 1 | 110 entries |
| 2 | VH2-21-1 | 0 | |
| 2 | VH2-31-1 | 0 | |
| 2 | VH2-31-2 | 1 | |
| 2 | VH2-31-3 | 1 | |
| 2 | VH2-31-4 | 0 | |
| 2 | VH2-31-5 | 2 | |
| 2 | VH2-31-6 | 0 | |
| 2 | VH2-31-7 | 0 | |
| 2 | VH2-31-14 | 1 | |
| 2 | VH2-31-8 | 0 | |
| 2 | VH2-31-9 | 0 | |
| 2 | VH2-31-10 | 0 | |
| 2 | VH2-31-11 | 1 | |
| 2 | VH2-31-12 | 0 | |
| 2 | VH2-31-13 | 1 | 7 entries |
| 3 | VH3-11-1 | 0 | |
| 3 | VH3-11-2 | 0 | |
| 3 | VH3-11-3 | 5 | |
| 3 | VH3-11-4 | 0 | |
| 3 | VH3-11-5 | 1 | |
| 3 | VH3-11-6 | 1 | |
| 3 | VH3-11-7 | 0 | |
| 3 | VH3-11-8 | 5 | |
| 3 | VH3-13-1 | 9 | |
| 3 | VH3-13-2 | 3 | |
| 3 | VH3-13-3 | 0 | |
| 3 | VH3-13-4 | 0 | |
| 3 | VH3-13-5 | 0 | |
| 3 | VH3-13-6 | 0 | |
| 3 | VH3-13-7 | 32 | |
| 3 | VH3-13-8 | 4 | |
| 3 | VH3-13-9 | 0 | |
| 3 | VH3-13-10 | 46 | |
| 3 | VH3-13-11 | 0 | |
| 3 | VH3-13-12 | 11 | |
| 3 | VH3-13-13 | 17 | |
| 3 | VH3-13-14 | 8 | |
| 3 | VH3-13-15 | 4 | |
| 3 | VH3-13-16 | 3 | |
| 3 | VH3-13-17 | 2 | |
| 3 | VH3-13-18 | 1 | |
| 3 | VH3-13-19 | 13 | |
| 3 | VH3-13-20 | 1 | |
| 3 | VH3-13-21 | 1 | |
| 3 | VH3-13-22 | 0 | |
| 3 | VH3-13-23 | 0 | |
| 3 | VH3-13-24 | 4 | |
| 3 | VH3-13-25 | 1 | |
| 3 | VH3-13-26 | 6 | |
| 3 | VH3-14-1 | 1 | |
| 3 | VH3-14-4 | 15 | |
| 3 | VH3-14-2 | 0 | |
| 3 | VH3-14-3 | 0 | |
| 3 | VH3-1X-1 | 0 | |
| 3 | VH3-1X-2 | 0 | |
| 3 | VH3-1X-3 | 6 | |
| 3 | VH3-1X-4 | 0 | |
| 3 | VH3-1X-5 | 0 | |
| 3 | VH3-1X-6 | 11 | |
| 3 | VH3-1X-7 | 0 | |
| 3 | VH3-1X-8 | 1 | |
| 3 | VH3-1X-9 | 0 | 212 entries |
| 4 | VH4-11-1 | 0 | |
| 4 | VH4-11-2 | 20 | |
| 4 | VH4-11-3 | 0 | |
| 4 | VH4-11-4 | 0 | |
| 4 | VH4-11-5 | 0 | |
| 4 | VH4-11-6 | 0 | |
| 4 | VH4-11-7 | 5 | |
| 4 | VH4-11-8 | 7 | |
| 4 | VH4-11-9 | 3 | |
| 4 | VH4-11-10 | 0 | |
| 4 | VH4-11-11 | 0 | |
| 4 | VH4-11-12 | 4 | |
| 4 | VH4-11-13 | 0 | |
| 4 | VH4-11-14 | 0 | |
| 4 | VH4-11-15 | 0 | |
| 4 | VH4-11-16 | 1 | |
| 4 | VH4-21-1 | 0 | |
| 4 | VH4-21-2 | 0 | |
| 4 | VH4-21-3 | 1 | |
| 4 | VH4-21-4 | 1 | |
| 4 | VH4-21-5 | 1 | |
| 4 | VH4-21-6 | 1 | |
| 4 | VH4-21-7 | 0 | |
| 4 | VH4-21-8 | 0 | |
| 4 | VH4-21-9 | 0 | |
| 4 | VH4-31-1 | 0 | |
| 4 | VH4-31-2 | 0 | |
| 4 | VH4-31-3 | 0 | |
| 4 | VH4-31-4 | 2 | |
| 4 | VH4-31-5 | 0 | |
| 4 | VH4-31-6 | 0 | |
| 4 | VH4-31-7 | 0 | |
| 4 | VH4-31-8 | 0 | |
| 4 | VH4-31-9 | 0 | |
| 4 | VH4-31-10 | 0 | |
| 4 | VH4-31-11 | 0 | |
| 4 | VH4-31-12 | 4 | |
| 4 | VH4-31-13 | 7 | |
| 4 | VH4-31-14 | 0 | |
| 4 | VH4-31-15 | 0 | |
| 4 | VH4-31-16 | 0 | |
| 4 | VH4-31-17 | 0 | |
| 4 | VH4-31-18 | 0 | |
| 4 | VH4-31-19 | 0 | |
| 4 | VH4-31-20 | 0 | 57 entries |
| 5 | VH5-12-1 | 82 | |
| 5 | VH5-12-2 | 1 | |
| 5 | VH5-12-3 | 0 | |
| 5 | VH5-12-4 | 14 | 97 entries |
| 6 | VH6-35-1 | 74 | 74 entries |

TABLE 4A

Analysis of V kappa subgroup 1

Framework I

| amino acid[1] | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| A |  | 1 |  |  |  |  |  |  | 1 |  |  |  | 102 |  | 1 |  |
| B |  |  | 1 |  |  | 1 |  |  |  |  |  |  |  |  |  |  |
| C |  |  |  |  |  |  |  |  |  |  |  |  |  | 1 |  |  |
| D | 64 |  |  |  |  |  |  |  |  |  |  |  |  |  |  |  |
| E | 8 |  | 14 |  |  |  |  |  |  |  |  |  |  |  | 1 |  |
| F |  |  |  |  |  |  |  | 1 |  | 6 |  |  |  | 1 |  |  |
| G |  |  |  |  |  |  |  |  |  |  |  |  |  |  |  | 105 |
| H |  |  |  |  |  |  |  |  |  |  |  |  |  |  |  |  |
| I |  | 65 |  |  |  |  |  |  |  |  |  |  |  |  | 4 |  |
| K |  |  | 1 |  |  |  |  |  |  |  |  |  |  |  |  |  |
| L |  | 6 |  | 21 |  |  |  |  |  |  |  | 96 |  | 1 |  |  |
| M | 1 |  |  | 66 |  |  |  |  |  |  |  |  |  |  |  |  |
| N |  |  |  |  |  |  |  |  |  |  |  |  |  |  |  |  |
| P |  |  |  |  |  |  |  | 103 |  | 1 |  | 2 |  |  | 1 |  |
| Q |  |  | 62 |  |  | 88 |  |  |  |  | 1 |  |  |  |  |  |
| R |  |  |  |  |  |  |  |  |  |  |  |  |  |  |  |  |
| S |  |  |  |  |  |  | 89 |  | 102 | 80 |  | 103 |  | 103 |  |  |
| T |  | 1 |  |  | 88 |  |  |  |  | 18 |  |  |  |  |  |  |
| V |  | 1 | 9 |  |  |  |  |  |  |  | 8 |  | 2 |  | 98 |  |
| W |  |  |  |  |  |  |  |  |  |  |  |  |  |  |  |  |
| X | 1 |  |  |  |  |  |  |  |  |  |  |  |  |  |  |  |
| Y |  |  |  |  |  |  |  |  |  |  |  |  |  |  |  |  |
| — |  |  |  |  |  |  |  |  |  |  |  |  |  |  |  |  |
| unknown (?) |  |  |  |  |  |  |  |  |  |  |  |  |  |  |  |  |
| not sequenced | 31 | 31 | 18 | 18 | 17 | 16 | 16 | 2 | 1 |  |  |  |  |  |  |  |
| sum of seq[2] | 74 | 74 | 87 | 87 | 88 | 89 | 89 | 103 | 104 | 105 | 105 | 105 | 105 | 105 | 105 | 105 |
| oomcaa[3] | 64 | 65 | 62 | 66 | 88 | 88 | 89 | 103 | 102 | 80 | 96 | 103 | 102 | 103 | 98 | 105 |
| mcaa[4] | D | I | Q | M | T | Q | S | P | S | S | L | S | A | S | V | G |
| rel. oomcaa[5] | 86% | 88% | 71% | 76% | 100% | 99% | 100% | 100% | 98% | 76% | 91% | 98% | 97% | 98% | 93% | 100% |
| pos occupied[6] | 4 | 5 | 5 | 2 | 1 | 2 | 1 | 1 | 3 | 4 | 3 | 2 | 3 | 3 | 5 | 1 |

Framework I / CDRI

| amino acid[1] | 17 | 18 | 19 | 20 | 21 | 22 | 23 | 24 | 25 | 26 | 27 | A | B | C | D |
|---|---|---|---|---|---|---|---|---|---|---|---|---|---|---|---|
| A |  |  | 1 | 1 |  | 1 |  |  | 103 |  |  |  |  |  |  |
| B |  |  |  |  |  |  |  |  |  |  | 1 |  |  |  |  |
| C |  |  |  |  |  |  | 105 |  |  |  |  |  |  |  |  |
| D | 101 |  |  |  |  |  |  |  |  |  |  |  |  |  |  |
| E | 2 |  |  |  |  |  |  | 1 | 1 |  | 2 |  |  |  |  |
| F |  |  |  |  | 2 |  |  |  |  |  |  |  |  |  |  |
| G |  |  |  |  |  |  |  |  |  | 1 |  |  |  |  |  |
| H |  |  |  |  |  |  |  |  |  |  | 1 |  |  |  |  |
| I |  |  | 6 | 4 | 101 | 1 |  |  |  |  |  |  |  |  |  |
| K |  |  |  |  |  |  |  | 2 |  |  | 1 |  |  |  |  |
| L |  |  |  |  |  |  |  | 1 |  |  |  |  |  |  |  |
| M |  |  |  |  |  |  |  |  |  |  |  |  |  |  |  |
| N |  |  |  |  |  |  |  |  |  |  | 1 |  |  |  |  |
| P |  |  |  |  |  |  |  |  |  |  |  |  |  |  |  |
| Q |  |  |  |  |  |  |  | 20 |  |  | 100 |  |  |  |  |
| R |  | 94 |  |  |  |  |  | 81 |  |  |  |  |  |  |  |
| S |  | 5 |  |  | 1 |  |  |  |  |  | 102 |  |  |  |  |
| T |  | 6 |  | 99 |  | 103 |  |  | 1 | 1 |  |  |  |  |  |
| V |  |  | 98 |  | 2 |  |  |  |  |  |  |  |  |  |  |
| W |  |  |  |  |  |  |  |  |  |  |  |  |  |  |  |
| X | 1 |  |  |  |  |  |  |  |  |  |  |  |  |  |  |
| Y | 1 |  |  |  |  |  |  |  |  |  |  |  |  |  |  |
| — |  |  |  |  |  |  |  |  |  |  |  | 105 | 105 | 105 | 105 |
| unknown (?) |  |  |  |  |  |  |  |  |  |  |  |  |  |  |  |
| not sequenced |  |  |  |  |  |  |  |  |  |  |  |  |  |  |  |
| sum of seq[2] | 105 | 105 | 105 | 105 | 105 | 105 | 105 | 105 | 105 | 105 | 105 | 105 | 105 | 105 | 105 |
| oomcaa[3] | 101 | 94 | 98 | 99 | 101 | 103 | 105 | 81 | 103 | 102 | 100 | 105 | 105 | 105 | 105 |
| mcaa[4] | D | R | V | T | I | T | C | R | A | S | Q | — | — | — | — |
| rel. oomcaa[5] | 96% | 90% | 93% | 94% | 96% | 98% | 100% | 77% | 98% | 97% | 95% | 100% | 100% | 100% | 100% |
| pos occupied[6] | 4 | 3 | 3 | 4 | 3 | 3 | 1 | 5 | 3 | 4 | 5 | 1 | 1 | 1 | 1 |

CDRI / Framework II

| amino acid[1] | E | F | 28 | 29 | 30 | 31 | 32 | 33 | 34 | 35 | 36 | 37 | 38 | 39 | 40 |
|---|---|---|---|---|---|---|---|---|---|---|---|---|---|---|---|
| A |  |  |  |  | 1 | 1 |  | 1 | 42 |  |  |  |  |  |  |
| B |  |  |  |  |  |  |  |  |  |  |  |  | 1 | 1 |  |
| C |  |  |  |  |  |  | 1 |  |  |  |  |  |  |  |  |

TABLE 4A-continued

Analysis of V kappa subgroup 1

| amino acid[1] | 27 | 28 | 29 | 30 | 31 | 32 | 33 | 34 | 35 | 36 | 37 | 38 | 39 | 40 |
|---|---|---|---|---|---|---|---|---|---|---|---|---|---|---|
| D |  | 25 |  | 1 | 5 | 7 |  |  |  |  | 1 |  |  |  |
| E |  |  |  |  |  | 1 |  |  |  |  | 2 |  |  |  |
| F |  |  | 1 | 1 |  | 7 |  |  |  | 6 |  |  |  |  |
| G |  | 25 |  | 7 | 3 |  |  | 4 |  |  |  |  |  |  |
| H |  |  |  | 1 | 2 | 2 |  | 1 |  | 2 |  |  |  |  |
| I |  |  | 98 | 1 | 4 |  |  | 1 |  |  |  |  |  |  |
| K |  |  |  |  | 7 |  |  |  |  |  |  |  | 95 |  |
| L |  |  |  | 2 | 1 |  | 101 |  |  |  |  |  |  |  |
| M |  |  |  |  |  |  |  |  |  |  |  |  |  |  |
| N |  | 6 |  | 16 | 42 |  |  | 50 |  |  |  |  |  |  |
| P |  |  |  |  |  |  |  |  |  |  |  |  |  | 102 |
| Q |  |  |  |  |  |  |  |  |  | 98 | 103 | 2 |  |  |
| R |  |  |  | 16 | 3 | 2 |  |  |  |  |  | 3 |  | 1 |
| S |  | 41 | 2 | 57 | 32 | 3 | 1 | 1 |  |  |  |  |  | 1 |
| T |  | 7 |  |  | 4 |  |  | 4 |  |  |  | 1 |  |  |
| V |  |  | 1 | 4 | 1 |  | 1 |  |  |  |  |  |  |  |
| W |  |  |  |  |  | 21 |  |  | 104 |  |  |  |  |  |
| X |  |  |  |  |  |  |  | 1 |  |  |  |  |  |  |
| Y |  |  |  | 1 |  | 60 |  |  |  | 98 |  |  |  |  |
| — | 105 | 105 |  |  |  |  |  |  |  |  |  |  |  |  |
| unknown (?) |  |  |  |  |  |  |  |  |  |  |  |  | 3 |  |
| not sequenced |  |  |  |  | 1 | 1 | 1 | 1 | 1 | 1 | 1 | 1 | 1 | 1 |
| sum of seq[2] | 105 | 105 | 105 | 105 | 105 | 104 | 104 | 104 | 104 | 104 | 104 | 104 | 104 | 104 |
| oomcaa[3] | 105 | 105 | 41 | 98 | 57 | 42 | 60 | 101 | 50 | 104 | 98 | 98 | 103 | 95 | 102 |
| mcaa[4] | — | — | S | I | S | N | Y | L | N | W | Y | Q | Q | K | P |
| rel. oomcaa[5] | 100% | 100% | 39% | 93% | 54% | 40% | 58% | 97% | 48% | 100% | 94% | 94% | 99% | 91% | 98% |
| pos occupied[6] | 1 | 1 | 6 | 4 | 12 | 11 | 9 | 4 | 8 | 1 | 2 | 5 | 2 | 4 | 3 |

| | Framework II | | | | | | | | | CDR II | | | | | | |
|---|---|---|---|---|---|---|---|---|---|---|---|---|---|---|---|---|
| amino acid[1] | 41 | 42 | 43 | 44 | 45 | 46 | 47 | 48 | 49 | 50 | 51 | 52 | 53 | 54 | 55 | 56 |
| A |  |  | 94 |  |  |  |  |  |  | 50 | 95 |  |  |  |  | 3 |
| B |  |  |  |  |  |  |  |  |  |  |  |  |  |  |  |  |
| C |  |  |  |  |  |  |  |  |  |  |  |  |  |  |  |  |
| D |  |  |  |  |  |  |  |  |  | 21 | 1 | 1 | 1 |  |  | 1 |
| E | 1 | 3 |  |  | 1 | 1 |  |  |  | 1 |  | 1 |  |  | 33 |  |
| F |  |  |  |  |  | 1 |  |  | 3 |  |  | 1 |  |  |  |  |
| G | 100 |  | 1 |  |  |  |  |  |  | 9 | 2 |  |  |  |  | 2 |
| H |  |  |  |  |  |  |  |  | 2 |  |  |  |  |  | 1 |  |
| I |  | 1 |  |  |  | 1 |  | 100 |  |  |  |  | 1 |  |  | 3 |
| K |  | 95 |  |  | 86 |  |  |  |  | 16 |  |  | 2 |  | 5 | 1 |
| L |  | 1 |  |  |  | 89 | 103 |  |  |  |  |  |  | 101 |  |  |
| M |  |  |  |  |  |  |  |  | 2 |  |  |  |  |  |  |  |
| N |  |  |  |  | 10 |  |  |  |  | 2 |  | 1 | 25 |  |  | 6 |
| P |  |  |  | 104 |  |  |  |  |  | 1 |  |  |  |  | 1 | 1 |
| Q |  | 1 |  |  | 1 |  |  |  |  |  |  |  |  |  | 62 |  |
| R |  |  |  |  | 3 | 3 |  |  |  |  |  |  | 1 | 1 | 2 | 1 |
| S |  |  |  |  | 1 |  |  |  | 5 | 1 | 1 | 99 | 41 | 2 |  | 68 |
| T |  | 3 |  |  | 1 |  |  |  |  | 1 | 4 | 1 | 31 |  |  | 19 |
| V |  |  | 9 |  |  | 9 |  |  |  |  | 1 |  | 1 |  |  |  |
| W |  |  |  |  |  |  |  |  |  |  |  |  |  |  |  |  |
| X |  |  |  |  | 1 |  |  |  |  |  |  |  | 1 |  |  |  |
| Y |  |  |  |  |  |  |  | 92 | 1 |  |  |  |  |  |  |  |
| — |  |  |  |  |  |  |  |  |  |  |  |  |  |  |  |  |
| unknown (?) | 3 |  |  |  |  |  |  |  |  |  |  |  |  |  |  |  |
| not sequenced | 1 | 1 | 1 | 1 | 1 | 1 | 2 | 3 | 3 | 2 | 1 | 1 | 1 | 1 | 1 |  |
| sum of seq[2] | 104 | 104 | 104 | 104 | 104 | 104 | 103 | 102 | 102 | 103 | 104 | 104 | 104 | 104 | 104 | 105 |
| oomcaa[3] | 100 | 95 | 94 | 104 | 86 | 89 | 103 | 100 | 92 | 50 | 95 | 99 | 41 | 101 | 62 | 68 |
| mcaa[4] | G | K | A | P | K | L | L | I | Y | A | A | S | S | L | Q | S |
| rel. oomcaa[5] | 96% | 91% | 90% | 100% | 83% | 86% | 100% | 98% | 90% | 49% | 91% | 95% | 39% | 97% | 60% | 65% |
| pos occupied[6] | 2 | 6 | 3 | 1 | 8 | 6 | 1 | 2 | 4 | 10 | 6 | 6 | 9 | 3 | 6 | 10 |

| | Framework III | | | | | | | | | | | | | | | |
|---|---|---|---|---|---|---|---|---|---|---|---|---|---|---|---|---|
| amino acid[1] | 57 | 58 | 59 | 60 | 61 | 62 | 63 | 64 | 65 | 66 | 67 | 68 | 69 | 70 | 71 | 72 |
| A |  |  |  |  |  |  |  |  |  | 2 | 1 | 1 | 1 |  |  | 3 |
| B |  |  | 1 |  |  |  |  |  |  |  |  |  |  |  |  |  |
| C |  |  |  |  |  |  |  |  |  |  |  |  |  |  |  |  |
| D |  |  |  |  |  |  |  |  |  |  |  |  |  | 67 |  |  |
| E |  |  |  |  |  |  |  |  |  |  | 1 |  |  | 30 |  |  |
| F |  | 1 |  |  |  | 103 |  |  |  |  | 3 |  |  |  | 102 | 1 |
| G | 105 |  | A |  |  |  | 105 | 4 | 101 |  | 102 |  |  |  |  |  |
| H |  |  |  |  |  |  |  |  |  |  |  |  | 3 |  |  |  |
| I |  | 4 |  |  | 1 | 3 |  |  |  |  |  |  |  |  |  |  |
| K |  |  |  | 1 |  |  |  |  |  |  |  |  |  |  | 1 |  |

TABLE 4A-continued

Analysis of V kappa subgroup 1

| | | | | | | | | | | | | | | | | |
|---|---|---|---|---|---|---|---|---|---|---|---|---|---|---|---|---|
| L | | | | | | | 1 | | | | | | | | | |
| M | | | | | | | | | | | | | 1 | | | |
| N | | | | | | | | | | | | | | | | |
| P | | | 101 | 2 | | | | | | | | | | | | |
| Q | | | | | | | | 1 | | | | | | | | |
| R | | | | | 103 | | 1 | | 1 | 1 | | | 2 | | | |
| S | | | 2 | 103 | | | 98 | | 96 | | 100 | | | | | 2 |
| T | | | 1 | | 1 | | 2 | | 3 | | | | 101 | | | 98 |
| V | | 99 | | | | 1 | | | | | | | | 1 | 1 | |
| W | | | | | | | | | | | | | | | | |
| X | | 1 | | | | | | | 1 | | 1 | | 2 | | | |
| Y | | | | | | | | | | | | 1 | | 1 | 1 | |
| — | | | | | | | | | | | | | | | | |
| unknown (?) | | | | | | | | | | | | | | | | |
| not sequenced | | | | | | | | | | | | | | | 1 | 1 |
| sum of seq² | 105 | 105 | 105 | 105 | 105 | 105 | 105 | 105 | 105 | 105 | 105 | 105 | 105 | 105 | 104 | 104 |
| oomcaa³ | 105 | 99 | 101 | 103 | 103 | 103 | 98 | 105 | 96 | 101 | 100 | 102 | 101 | 67 | 102 | 98 |
| mcaa⁴ | G | V | P | S | R | F | S | G | S | G | S | G | T | D | F | T |
| rel. oomcaa⁵ | 100% | 94% | 96% | 98% | 98% | 98% | 93% | 100% | 91% | 96% | 95% | 97% | 96% | 64% | 98% | 94% |
| pos occupied⁶ | 1 | 4 | 4 | 2 | 3 | 3 | 5 | 1 | 5 | 4 | 4 | 4 | 4 | 7 | 3 | 4 |

Framework III

| amino acid¹ | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|
| A | | | | 1 | | | | 2 | | | | | 101 | 1 | | |
| B | | | 1 | | | | 3 | | 2 | | | | | | | |
| C | | | | | | | | | | | | | | | | 102 |
| D | | | | 1 | | | | | 16 | 101 | | | | | | |
| E | | | | | | | | | 83 | | | | | | | |
| F | 21 | | | | | | | | | | | 73 | | | 7 | |
| G | | | | | 4 | | | | 1 | | | | 2 | | | |
| H | | | | | | | | | | | | | | | 1 | |
| I | | | 99 | 5 | | | | | | | | 17 | | | | |
| K | | | | | | | | | | | | | | 1 | | |
| L | 81 | | | | | 103 | 1 | | | | | 1 | | | | |
| M | | | | | | | | | | | | | | 1 | | |
| N | | | | 7 | 4 | | | | | | | | | 1 | | |
| P | | | | | | | | | 97 | | | | | 1 | | |
| Q | | | | | | | 97 | | | | | | | | | |
| R | | | | 2 | 1 | | 2 | | | | | | | | | |
| S | | 1 | | 86 | 94 | | | | 4 | | | 1 | | 1 | | |
| T | | 102 | | 2 | 1 | | | | | | | | 97 | | | |
| V | 2 | | 4 | | | 1 | | | | | | 11 | 1 | | | |
| W | | | | | | | | | | | | | | | | |
| X | | | 1 | | | | | | 1 | 2 | | | | | | |
| Y | | | | | | | | | | | | | | 101 | 93 | |
| — | | | | | | | | | | | | | | | | |
| unknown (?) | | | | | | | | | | | | | | | 1 | |
| not sequenced | 1 | 1 | 1 | 1 | 1 | 1 | 2 | 2 | 2 | 2 | 2 | 2 | 3 | 2 | 3 | 3 |
| sum of seq² | 104 | 104 | 104 | 104 | 104 | 104 | 103 | 103 | 103 | 103 | 103 | 103 | 102 | 103 | 102 | 102 |
| oomcaa³ | 81 | 102 | 99 | 86 | 94 | 103 | 97 | 97 | 83 | 101 | 73 | 101 | 97 | 101 | 93 | 102 |
| mcaa⁴ | L | T | I | S | S | L | Q | P | E | D | F | A | T | Y | Y | C |
| rel. oomcaa⁵ | 78% | 98% | 95% | 83% | 90% | 99% | 94% | 94% | 81% | 98% | 71% | 98% | 95% | 98% | 91% | 100% |
| pos occupied⁶ | 3 | 3 | 3 | 7 | 5 | 2 | 4 | 3 | 5 | 2 | 5 | 2 | 6 | 3 | 3 | 1 |

CDR III

| amino acid¹ | 89 | 90 | 91 | 92 | 93 | 94 | 95 | A | B | C | D | E | F | 96 | 97 |
|---|---|---|---|---|---|---|---|---|---|---|---|---|---|---|---|
| A | | 1 | 7 | 1 | | 5 | 1 | | | | | | | 1 | |
| B | 2 | 3 | | | | | | | | | | | | | |
| C | | | | | | | | | | | | | | | |
| D | | | | 23 | 5 | 1 | | | | | | | | 1 | |
| E | | | | 1 | 1 | | 1 | 1 | | | | | | | |
| F | | | 3 | | | 13 | | | | | | | | 6 | |
| G | | | 1 | | 1 | 2 | 1 | | 1 | | | | | 2 | 1 |
| H | 4 | 6 | 7 | 3 | 1 | | | | | | | | | 2 | 1 |
| I | | | | 4 | 1 | 2 | 1 | | | | | | | 5 | |
| K | | 7 | | 1 | | | | | | | | | | 1 | 1 |
| L | 7 | | 6 | 2 | | 18 | 2 | | | | | | | 18 | 1 |
| M | | | | | | | | | | | | | | | 1 |
| N | | | 6 | 31 | 19 | 1 | | | | | | | | 1 | |
| P | | | | | | 1 | 82 | 6 | | | | | | 6 | |
| Q | 90 | 86 | 1 | 2 | | | | | | | | | | 1 | |
| R | | | 1 | | 2 | 2 | | | | | | | | 6 | |
| S | | | 27 | 3 | 58 | 5 | 10 | | | | | | | 2 | 2 |

TABLE 4A-continued

Analysis of V kappa subgroup 1

| amino acid[1] | | | | | | | | | | | | | | | |
|---|---|---|---|---|---|---|---|---|---|---|---|---|---|---|---|
| T | | | 3 | 1 | 15 | 25 | | | | | | | | 2 | 82 |
| V | | | | | 5 | | | | | | | | | 2 | |
| W | | | | | 1 | | | | | | | | | 15 | |
| X | | | | | | | | | | | | | | | |
| Y | | | 42 | 32 | 1 | 23 | | | | | | | | 16 | |
| — | | | | | | | 3 | 82 | 88 | 89 | 89 | 89 | 89 | 4 | 1 |
| unknown (?) | | | | | | | | | | | | | | | |
| not sequenced | 2 | 2 | 1 | 1 | 1 | 1 | 4 | 16 | 16 | 16 | 16 | 16 | 16 | 16 | 16 |
| sum of seq[2] | 103 | 103 | 104 | 104 | 104 | 104 | 101 | 89 | 89 | 89 | 89 | 89 | 89 | 89 | 89 |
| oomcaa[3] | 90 | 86 | 42 | 32 | 58 | 25 | 82 | 82 | 88 | 89 | 89 | 89 | 89 | 18 | 82 |
| mcaa[4] | Q | Q | Y | Y | S | T | P | — | — | — | — | — | — | L | T |
| rel. oomcaa[5] | 87% | 83% | 40% | 31% | 56% | 24% | 81% | 92% | 99% | 100% | 100% | 100% | 100% | 20% | 92% |
| pos occupied[6] | 4 | 5 | 11 | 12 | 10 | 14 | 8 | 3 | 2 | 1 | 1 | 1 | 1 | 17 | 1 |

| | Framework IV | | | | | | | | | | | |
|---|---|---|---|---|---|---|---|---|---|---|---|---|
| amino acid[1] | 98 | 99 | 100 | 101 | 102 | 103 | 104 | 105 | 106 | A | 107 | 108 | sum |
| A | | | | | | | | | | | | | 627 |
| B | | | 1 | | | | | 1 | | | | | 19 |
| C | | | | | | | | | | | | | 209 |
| D | | | | | | | | 15 | | | | | 459 |
| E | | | 2 | | | | | 65 | | | | | 258 |
| F | 86 | | | | | | | | 2 | | | | 451 |
| G | | 87 | 29 | 87 | | | | | | | | 2 | 894 |
| H | | | | | | | | | | | | | 40 |
| I | | | | | | | 1 | | 72 | | | | 606 |
| K | | | | | | | 77 | | | | 79 | | 480 |
| L | 1 | | | | | | 22 | 4 | 2 | | | | 793 |
| M | | | | | | | | | 5 | | | | 77 |
| N | | | | | | | | | 1 | | | 2 | 232 |
| P | | | 7 | | | | | | | | | 1 | 620 |
| Q | | | 48 | | | | | 1 | | | | | 865 |
| R | | | | | | | 6 | | | | 2 | 70 | 413 |
| S | | | | | | | | | | | | | 1636 |
| T | | | | | 87 | 3 | | | | | 2 | | 1021 |
| V | | | | | | | 1 | 63 | | 3 | | | 440 |
| W | | | | | | | | | | | | | 141 |
| X | | | | | | | | | | | | | 14 |
| Y | | | | | | | | | | | | | 564 |
| — | | | | | | | | | | 85 | | 1 | 1250 |
| unknown (?) | | | | | | | | | | | | | 7 |
| not sequenced | 18 | 18 | 18 | 18 | 18 | 18 | 19 | 19 | 20 | 20 | 20 | 31 | 589 |
| sum of seq[2] | 87 | 87 | 87 | 87 | 87 | 87 | 86 | 86 | 85 | 85 | 85 | 74 | |
| oomcaa[3] | 86 | 87 | 48 | 87 | 87 | 77 | 63 | 65 | 72 | 85 | 79 | 70 | |
| mcaa[4] | F | G | G | G | T | K | V | E | I | — | K | R | |
| rel. oomcaa[5] | 99% | 100% | 55% | 100% | 100% | 89% | 73% | 76% | 85% | 100% | 93% | 95% | |
| pos occupied[6] | 2 | 1 | 5 | 1 | 1 | 4 | 3 | 5 | 6 | 1 | 4 | 4 | |

TABLE 4B

Analysis of V kappa subgroup 2

| | Framework I | | | | | | | | | | | | | |
|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 |
| A | | | | | | | | | | | | | | | |
| B | | | | | | | | | | | | | | | |
| C | | | | | | | | | | | | | | | |
| D | 14 | | | | | | | | | | | | | | |
| E | 3 | | | | | | | | | | | | | | |
| F | | | | | | | | | 1 | 1 | | | | | |
| G | | | | | | | | | | | | | | | |
| H | | | | | | | | | | | | | | | |
| I | | 8 | | | | | | | | | | | | | |
| K | | | | | | | | | | | | | | | |
| L | | 3 | | 1 | | | | | 17 | | 18 | | | | 6 |
| M | | | | | 15 | | | | | | | | | | |
| N | | | | | | | | | | | | | | | |
| P | | | | | | | | | 18 | | | 18 | | | 15 |
| Q | | | | | | 18 | | | | | | | | | |
| R | | | | | | | | | | | | | | | |
| S | | | | | | | 18 | | | 17 | | | | | |

TABLE 4B-continued

Analysis of V kappa subgroup 2

| amino acid[1] | | | | | | | | | | | | | | | |
|---|---|---|---|---|---|---|---|---|---|---|---|---|---|---|---|
| T | | | | 17 | | | | | | | | | 21 | | |
| V | | 6 | 17 | 1 | | | | | | | | | 18 | | |
| W | | | | | | | | | | | | | | | |
| X | | | | | | | | | | | | | | | |
| Y | | | | | | | | | | | | | | | |
| — | | | | | | | | | | | | | | | |
| unknown (?) | | | | 1 | | | | | | | | | | | |
| not sequenced | 5 | 5 | 5 | 5 | 4 | 4 | 4 | 4 | 4 | 4 | 4 | 4 | 4 | 1 | 1 |
| sum of seq[2] | 17 | 17 | 17 | 17 | 18 | 18 | 18 | 18 | 18 | 18 | 18 | 18 | 18 | 21 | 21 |
| oomcaa[3] | 14 | 8 | 17 | 15 | 17 | 18 | 18 | 18 | 17 | 17 | 18 | 18 | 18 | 21 | 15 |
| mcaa[4] | D | I | V | M | T | Q | S | P | L | S | L | P | V | T | P |
| rel. oomcaa[5] | 82% | 47% | 100% | 88% | 94% | 100% | 100% | 100% | 94% | 94% | 100% | 100% | 100% | 100% | 71% |
| pos occupied[6] | 2 | 3 | 1 | 3 | 1 | 1 | 1 | 1 | 2 | 2 | 1 | 1 | 1 | 1 | 2 |

| | Framework I | | | | | | CDRI | | | | | | | | |
|---|---|---|---|---|---|---|---|---|---|---|---|---|---|---|---|
| amino acid[1] | 16 | 17 | 18 | 19 | 20 | 21 | 22 | 23 | 24 | 25 | 26 | 27 | A | B | C | D |
| A | | | | 22 | | | | | | | | | | | | |
| B | | | | | | | | | | | | | | | | |
| C | | | | | | | | 22 | | | | | | | | |
| D | | | | | | | | | | | | | | | | 1 |
| E | | 15 | | | | | | | | | | | | | | |
| F | | | | | | | | | | | | | | | | |
| G | 22 | | | | | | | | | | | | | | | |
| H | | | | | | | | | | | | | | | | 16 |
| I | | | | | | | 22 | | | | | | | | | |
| K | | | | | | | | | | 1 | | | | | | |
| L | | | | | | | | | | | | | 1 | 22 | 13 | |
| M | | | | | | | | | | | | | | | 1 | |
| N | | | | | | | | | | | | | | | | |
| P | | | 22 | | | | | | | | | | | | | |
| Q | | 7 | | | | | | 1 | | | | 21 | | | | |
| R | | | | | | | | | 21 | | | | | | | |
| S | | | | | 22 | | 21 | | | 22 | 22 | | 22 | | | |
| T | | | | | | | | | | | | | | | | |
| V | | | | | | | | | | | | | | | 8 | |
| W | | | | | | | | | | | | | | | | 1 |
| X | | | | | | | | | | | | | | | | |
| Y | | | | | | | | | | | | | | | | 4 |
| unknown (?) | | | | | | | | | | | | | | | | |
| not sequenced | | | | | | | | | | | | | | | | |
| sum of seq[2] | 22 | 22 | 22 | 22 | 22 | 22 | 22 | 22 | 22 | 22 | 22 | 22 | 22 | 22 | 22 | 22 |
| oomcaa[3] | 22 | 15 | 22 | 22 | 22 | 22 | 21 | 22 | 21 | 22 | 22 | 21 | 22 | 22 | 13 | 16 |
| mcaa[4] | G | E | P | A | S | I | S | C | R | S | S | Q | S | L | L | H |
| rel. oomcaa[5] | 100% | 68% | 100% | 100% | 100% | 100% | 95% | 100% | 95% | 100% | 100% | 95% | 100% | 100% | 59% | 73% |
| pos occupied[6] | 1 | 2 | 1 | 1 | 1 | 1 | 2 | 1 | 2 | 1 | 1 | 2 | 1 | 1 | 3 | 4 |

| | CDRI | | | | | | | | Framework II | | | | | |
|---|---|---|---|---|---|---|---|---|---|---|---|---|---|---|
| amino acid[1] | E | F | 28 | 29 | 30 | 31 | 32 | 33 | 34 | 35 | 36 | 37 | 38 | 39 | 40 |
| A | | | | | | | | | | | | | | | |
| B | | | | | | | | | | | | | | | |
| C | | | | | | | | | | | | | | | |
| D | | | 9 | | 1 | 1 | | | | 11 | | | | | |
| E | | | | | | | | | | | | | | | |
| F | | | | 2 | | | | | | | | 7 | | | |
| G | 1 | | | 22 | | | | | | | | | | | |
| H | | | | | | | 1 | | | 1 | | | | | |
| I | | | | | | | | | | | | | | | |
| K | | | | | | 1 | | | | | | | | 15 | |
| L | | | | | | | | | 22 | | | | 16 | | |
| M | | | | | | | | | | | | | | | |
| N | | | 10 | | 7 | 12 | | | | 9 | | | | | |
| P | | | | | | | | | | | | | | | 22 |
| Q | | | | | | | | | | | | 6 | 22 | | |
| R | 2 | | | | | | | | | | | | | 7 | |
| S | 19 | | 1 | | | | | | | | | | | | |
| T | | | | | | | 8 | | | | | | | | |
| V | | | | | | | | | | | | | | | |
| W | | | | | | | | | | 22 | | | | | |
| X | | | 1 | | 1 | | | 1 | | | | | | | |
| Y | | | 1 | | 11 | 21 | | | | | 15 | | | | |
| — | | 22 | | | | | | | | | | | | | |
| unknown (?) | | | | | | | | | | | | | | | |

TABLE 4B-continued

Analysis of V kappa subgroup 2

| | | | | | | | | | | | | | | | |
|---|---|---|---|---|---|---|---|---|---|---|---|---|---|---|---|
| not sequenced | | | | | | | | | | | | | | | |
| sum of seq[2] | 22 | 22 | 22 | 22 | 22 | 22 | 22 | 22 | 22 | 22 | 22 | 22 | 22 | 22 | 22 |
| oomcaa[3] | 19 | 22 | 10 | 22 | 11 | 12 | 21 | 22 | 11 | 22 | 15 | 16 | 22 | 15 | 22 |
| mcaa[4] | S | — | N | G | Y | N | Y | L | D | W | Y | L | Q | K | P |
| rel. oomcaa[5] | 86% | 100% | 45% | 100% | 50% | 55% | 95% | 100% | 50% | 100% | 68% | 73% | 100% | 68% | 100% |
| pos occupied[6] | 3 | 1 | 5 | 1 | 5 | 4 | 2 | 1 | 4 | 1 | 2 | 2 | 1 | 2 | 1 |

| | Framework II | | | | | | | | | CDR II | | | | | |
|---|---|---|---|---|---|---|---|---|---|---|---|---|---|---|---|
| amino acid[1] | 41 | 42 | 43 | 44 | 45 | 46 | 47 | 48 | 49 | 50 | 51 | 52 | 53 | 54 | 55 | 56 |
| A | | | | | | | | | | | | | | | 14 | |
| B | | | | | | | | | | | | | | | | |
| C | | | | | | | | | | | | | | | | |
| D | | | | | | | | | | | | | | | 7 | |
| E | | | | | 1 | | | | | | | | | | | |
| F | | | | | | | | | | | | | | | | |
| G | 22 | | | | | | | | | | | 12 | | | 1 | |
| H | | | | | | | | | | | | | | | | |
| I | | | | | | | 1 | | 22 | | | | | | | |
| K | | | | | | | | | | | 5 | | | | | |
| L | | | | | | 14 | | 21 | | 14 | 1 | | | | | |
| M | | | | | | | | | | | | | | | | |
| N | | | | | | | | | | | | | | 18 | | |
| P | | | | | 21 | | | | | | | | | | | |
| Q | | 22 | | | | 12 | | | | 1 | | | | | | |
| R | | | | | | 8 | 7 | | | 1 | | | | | 22 | |
| S | | | 21 | | | | | | | | | 2 | 22 | 2 | | 22 |
| T | | | | | | | | | | | | | | 1 | | |
| V | | | | | | | 1 | | | | 6 | | | | | |
| W | | | | | | | | | | | | | | | | |
| X | | | | | | | | | | | | | | | | |
| Y | | | | | | | | | 21 | | | | | 1 | | |
| — | | | | | | | | | | | | | | | | |
| unknown (?) | | | | | | | | | | | | | | | | |
| not sequenced | | | 1 | 1 | 1 | | | | 1 | 1 | 1 | | | | | |
| sum of seq[2] | 22 | 22 | 21 | 21 | 21 | 22 | 22 | 22 | 21 | 21 | 21 | 22 | 22 | 22 | 22 | 22 |
| oomcaa[3] | 22 | 22 | 21 | 21 | 12 | 14 | 21 | 22 | 21 | 14 | 12 | 22 | 18 | 22 | 14 | 22 |
| mcaa[4] | G | Q | S | P | Q | L | I | L | Y | L | L | S | N | R | A | S |
| rel. oomcaa[5] | 100% | 100% | 100% | 100% | 57% | 64% | 95% | 100% | 100% | 67% | 57% | 100% | 82% | 100% | 64% | 100% |
| pos occupied[6] | 1 | 1 | 1 | 1 | 3 | 3 | 2 | 1 | 1 | 4 | 4 | 1 | 4 | 1 | 3 | 1 |

| | Framework III | | | | | | | | | | | | | | | |
|---|---|---|---|---|---|---|---|---|---|---|---|---|---|---|---|---|
| amino acid[1] | 57 | 58 | 59 | 60 | 61 | 62 | 63 | 64 | 65 | 66 | 67 | 68 | 69 | 70 | 71 | 72 |
| A | | | | | | | | | | | | | | | | |
| B | | | | | | | | | | | | | | | | |
| C | | | | | | | | | | | | | | | | |
| D | | | | 22 | | | | 1 | | | | 1 | | | 22 | |
| E | | | | | | | | | | | | | | | | |
| F | | | | | | 21 | | | | | | | | | 22 | |
| G | 22 | | | | | | | 21 | | 22 | | 21 | | | | |
| H | | | | | | | | | | | | | | | | |
| I | | | | | | | | | | | | | | | | |
| K | | | | | | | | | | | | | | | | |
| L | | | | | | | | | | | | | | | | |
| M | | | | | | | | | | | | | | | | |
| N | | | | | | | | | | | | | | | | |
| P | | | 22 | | | | | | | | | | | | | |
| Q | | | | | | | | | | | | | | | | |
| R | | | | | 20 | | | | 1 | | | | | | | |
| S | | | | | 1 | | 22 | | 21 | | 22 | | | | | |
| T | | | | | 1 | | | | | | | | | 22 | | 21 |
| V | | 22 | | | | 1 | | | | | | | | | | |
| W | | | | | | | | | | | | | | | | |
| X | | | | | | | | | | | | | | | | |
| Y | | | | | | | | | | | | | | | | |
| — | | | | | | | | | | | | | | | | |
| unknown (?) | | | | | | | | | | | | | | | | 1 |
| not sequenced | | | | | | | | | | | | | | | | |
| sum of seq[2] | 22 | 22 | 22 | 22 | 22 | 22 | 22 | 22 | 22 | 22 | 22 | 22 | 22 | 22 | 22 | 22 |
| oomcaa[3] | 22 | 22 | 22 | 22 | 20 | 21 | 22 | 21 | 21 | 22 | 22 | 21 | 22 | 22 | 22 | 21 |
| mcaa[4] | G | V | P | D | R | F | S | G | S | G | S | G | T | D | F | T |
| rel. oomcaa[5] | 100% | 100% | 100% | 100% | 91% | 95% | 100% | 95% | 95% | 100% | 100% | 95% | 100% | 100% | 100% | 95% |
| pos occupied[6] | 1 | 1 | 1 | 1 | 3 | 2 | 1 | 2 | 2 | 1 | 1 | 2 | 1 | 1 | 1 | 1 |

TABLE 4B-continued

Analysis of V kappa subgroup 2

Framework III

| amino acid[1] | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|
| A | | | | | | | | 20 | | | | | | | | |
| B | | | | | | | | | | | | | | | | |
| C | | | | | | | | | | | | | | | | 21 |
| D | | | | | | | | | | 1 | 21 | | | | | |
| E | | | | | | | 19 | | 20 | | | | | | | |
| F | | | | | | | | | | | | | | | | |
| G | | | | | | | 1 | | | | | | 21 | | | |
| H | | | | | | | | | | | | | | | | |
| I | | | 1 | 21 | | | | | | | | | | 1 | | |
| K | | 19 | | | | | | | | | | | | | | |
| L | 21 | 1 | | | | | | | | | | | | 1 | | |
| M | | | | | | | | | | | | | | | | |
| N | | | | | | | | | | | | | | | | |
| P | | | | | | | | 1 | | | | | | | | |
| Q | | | | | | | | 1 | | | | | | | | |
| R | | | | | | 20 | | | | | | | | | | |
| S | | | | 20 | 1 | | | | | | | | | | | |
| T | | | | 1 | | | | | | | | | | | | |
| V | | | | | | | 21 | | | | | 21 | | 19 | | |
| W | | | | | | | | | | | | | | | | |
| X | | | | | | | | | | | | | | | | |
| Y | | | | | | | | | | | | | | 21 | 21 | |
| — | | | | | | | | | | | | | | | | |
| unknown (?) | | | | | | | | | | | | | | | | |
| not sequenced | 1 | 1 | 1 | 1 | 1 | 1 | 1 | 1 | 1 | 1 | 1 | 1 | 1 | 1 | 1 | 1 |
| sum of seq[2] | 21 | 21 | 21 | 21 | 21 | 21 | 21 | 21 | 21 | 21 | 21 | 21 | 21 | 21 | 21 | 21 |
| oomcaa[3] | 21 | 19 | 21 | 20 | 20 | 21 | 19 | 20 | 20 | 21 | 21 | 21 | 19 | 21 | 21 | 21 |
| mcaa[4] | L | K | I | S | R | V | E | A | E | D | V | G | V | Y | Y | C |
| rel. oomcaa[5] | 100% | 90% | 100% | 95% | 95% | 100% | 90% | 95% | 95% | 100% | 100% | 100% | 90% | 100% | 100% | 100% |
| pos occupied[6] | 1 | 3 | 1 | 2 | 2 | 1 | 3 | 2 | 2 | 1 | 1 | 1 | 3 | 1 | 1 | 1 |

CDR III

| amino acid[1] | 89 | 90 | 91 | 92 | 93 | 94 | 95 | A | B | C | D | E | F | 96 | 97 |
|---|---|---|---|---|---|---|---|---|---|---|---|---|---|---|---|
| A | | | 14 | | | 1 | | | | | | | | | |
| B | | 1 | | | 1 | | | | | | | | | | |
| C | | | | | | | | | | | | | | | |
| D | | | | | | | | | | | | | | | |
| E | | | | | | | | | | | | | | | |
| F | | | | | | | | | | | | | | 1 | |
| G | | | 6 | | | 1 | | 2 | | | | | | | |
| H | | | 1 | | 7 | | | | | | | | | | |
| I | | | | | | 1 | | | | | | | | 3 | |
| K | | | | | | | | | | | | | | | |
| L | | | | 12 | | | 2 | | | | | | | 2 | |
| M | | | | | | | | | | | | | | | |
| N | | | | | | | | | | | | | | | |
| P | | | | | 2 | 16 | 1 | | | | | | | 1 | |
| Q | | 20 | | | 13 | | | | | | | | | 1 | |
| R | | | | 1 | | | | | | | | | | | |
| S | | | | | | 3 | 2 | | | | | | | | |
| T | | | | 8 | | 7 | | | | | | | | | 17 |
| V | | | | | | | | | | | | | | | |
| W | | | | | | 6 | | | | | | | | 2 | |
| X | | | | | | | | | | | | | | | |
| Y | | | | | | | | | | | | | | 7 | |
| — | | | | | | | 14 | 17 | 17 | 17 | 17 | 17 | | | |
| unknown (?) | | | | | | | | | | | | | | | |
| not sequenced | 1 | 1 | 1 | 1 | 1 | 1 | 2 | 5 | 5 | 5 | 5 | 5 | 5 | 5 | 5 |
| sum of seq[2] | 21 | 21 | 21 | 21 | 21 | 21 | 20 | 17 | 17 | 17 | 17 | 17 | 17 | 17 | 17 |
| oomcaa[3] | 21 | 20 | 14 | 12 | 13 | 7 | 16 | 14 | 17 | 17 | 17 | 17 | 17 | 7 | 17 |
| mcaa[4] | M | Q | A | L | Q | T | P | — | — | — | — | — | — | Y | T |
| rel. oomcaa[5] | 100% | 95% | 67% | 57% | 62% | 33% | 80% | 82% | 100% | 100% | 100% | 100% | 100% | 41% | 100% |
| pos occupied[6] | 1 | 2 | 3 | 3 | 3 | 7 | 3 | 3 | 1 | 1 | 1 | 1 | 1 | 7 | 1 |

Framework IV

| amino acid[1] | 98 | 99 | 100 | 101 | 102 | 103 | 104 | 105 | 106 | A | 107 | 108 | sum |
|---|---|---|---|---|---|---|---|---|---|---|---|---|---|
| A | | | | | | | | | | | | | 71 |
| B | | | | | | | | | | 1 | | | 3 |
| C | | | | | | | | | | | | | 43 |

TABLE 4B-continued

Analysis of V kappa subgroup 2

| amino acid | | | | | | | | | | | | | |
|---|---|---|---|---|---|---|---|---|---|---|---|---|---|
| D | | | | | | | | | | | | | 112 |
| E | | | | | | | | 13 | | | | | 71 |
| F | 17 | | | | | | | | | | | | 72 |
| G | | 17 | 2 | 16 | | | | 1 | | | | | 233 |
| H | | | | | | | | | | | | | 26 |
| I | | | | | | | | | 14 | | | | 94 |
| K | | | | | | 12 | | | | | 13 | | 66 |
| L | | | | | | | 11 | | | | | | 219 |
| M | | | | | | | | | | | | | 37 |
| N | | | | | | | | | | | | | 56 |
| P | | | | | | | | | | | | | 159 |
| Q | | | 14 | | | | | | | | | | 159 |
| R | | | | | | | 4 | | | | | 12 | 126 |
| S | | | | | | | | | | | | | 325 |
| T | | | | | 16 | | | | | | | | 140 |
| V | | | | | | | 5 | | | | | | 146 |
| W | | | | | | | | | | | | | 31 |
| X | | | | | | | | | | | | | 3 |
| Y | | | | | | | | | | | | | 123 |
| — | | | | | | | | | | 13 | | | 134 |
| unknown (?) | | | | | | | | | | | | | 2 |
| not sequenced | 5 | 5 | 6 | 6 | 6 | 6 | 6 | 7 | 8 | 9 | 9 | 10 | 211 |
| sum of seq[2] | 17 | 17 | 16 | 16 | 16 | 16 | 16 | 15 | 14 | 13 | 13 | 12 | |
| oomcaa[3] | 17 | 17 | 14 | 16 | 16 | 12 | 11 | 13 | 14 | 13 | 13 | 12 | |
| mcaa[4] | F | G | Q | G | T | K | L | E | I | — | K | R | |
| rel. oomcaa[5] | 100% | 100% | 88% | 100% | 100% | 75% | 69% | 87% | 100% | 100% | 100% | 100% | |
| pos occupied[6] | 1 | 1 | 2 | 1 | 1 | 2 | 2 | 3 | 1 | 1 | 1 | 1 | |

TABLE 4C

Analysis of V kappa subgroup 3

Framework I

| amino acid[1] | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| A | | 5 | | | | | 2 | | 27 | | | | | | 1 |
| B | 1 | | | | | | | | | | | | 2 | | |
| C | | | | | | | | | | | | | 2 | | |
| D | 2 | | | | | | | | 14 | | | | | | |
| E | 76 | | 27 | | | | | | | | | | | | |
| F | | 1 | | | | | | | | | | | | 1 | |
| G | 1 | | | | | | | | 82 | | | | | | 1 |
| H | | | | | | | | | | 1 | | | | | |
| I | | 75 | | | | | | | | | | | | | |
| K | 3 | | | | | | | | | | | | | | |
| L | | 4 | 1 | 104 | | | 1 | | | | 150 | | 129 | | 1 |
| M | 5 | | | 13 | | | | | | | | | | 5 | |
| N | | | | | | | | | | | | | | | 147 |
| P | | | | | | | 124 | | | | | | | | |
| Q | | | | | | 123 | | | | | | | | | |
| R | | | | | 1 | | | | | | | | | | |
| S | | | | | | | | 119 | | 3 | 1 | 150 | 1 | 141 | |
| T | | 2 | | 117 | | | | | | 147 | | | | 5 | 1 |
| V | | 1 | 89 | 1 | | | 1 | | | | 1 | | 22 | | 1 |
| W | | | | | | | | | | | | | | | |
| X | | | | | | | | | | | | | | | |
| Y | | | | | | | | | | | | | | | |
| — | | | | | | | | | | | | | | | |
| unknown (?) | | | | | | | | | | | | | | | |
| not sequenced | | | | | | | | | | | | | | | |
| sum of seq[2] | 88 | 88 | 117 | 118 | 118 | 123 | 123 | 124 | 126 | 149 | 151 | 152 | 152 | 152 | 152 |
| oomcaa[3] | 76 | 75 | 89 | 104 | 117 | 123 | 119 | 124 | 82 | 147 | 150 | 150 | 129 | 141 | 147 |
| mcaa[4] | E | I | V | L | T | Q | S | P | G | T | L | S | L | S | P |
| rel. oomcaa[5] | 86% | 85% | 76% | 88% | 99% | 100% | 97% | 100% | 65% | 99% | 99% | 99% | 85% | 93% | 97% |
| pos occupied[6] | 6 | 6 | 3 | 3 | 2 | 1 | 4 | 1 | 4 | 3 | 2 | 2 | 3 | 4 | 6 |

| | Framework I | | | | | | | | CDRI | | | | | |
|---|---|---|---|---|---|---|---|---|---|---|---|---|---|---|
| amino acid[1] | 16 | 17 | 18 | 19 | 20 | 21 | 22 | 23 | 24 | 25 | 26 | 27 | A | B | C |
| A | | | | 178 | 2 | | | | | 166 | 1 | | | | |
| B | | | | | | | | | | | | | | | |
| C | | | | | | | | 181 | | | 1 | | | | |

TABLE 4C-continued

Analysis of V kappa subgroup 3

| amino acid | | | | | | | | | | | | | | | |
|---|---|---|---|---|---|---|---|---|---|---|---|---|---|---|---|
| D | | 6 | | | | | | | | | | | | | |
| E | | 146 | 1 | | | | | | | | | 1 | | | |
| F | | | | | 7 | 1 | | | | | | | | | |
| G | 152 | 1 | 1 | | | | | | | 1 | 1 | | 1 | | |
| H | | | | | | | | | | | | | 17 | | |
| I | | | 1 | | 5 | 2 | | | | | | | | | |
| K | | | 1 | | | | | | 5 | | | | | | |
| L | | | | | | 173 | | | | | | 1 | 1 | | |
| M | | | | | | | | | | | | | | | |
| N | | | | | | | | | | | | | 9 | | |
| P | | | | | | | | | | | | | | | |
| Q | | | | | | | | | | | | 159 | | | |
| R | | | 175 | | | | | | 176 | | 1 | 1 | 10 | | |
| S | | | | | | | 180 | | | | 7 | 175 | 87 | | |
| T | | | 1 | | 174 | | | | 7 | 2 | | | 1 | | |
| V | | | 1 | 4 | 1 | | | | 1 | | | | 1 | | |
| W | | | | | | | | 1 | | | | | | | |
| X | | | | | | | | | | | | | | | |
| Y | | | | | | | 1 | | | | | 1 | | | |
| — | | | | | | | | | | | | | 72 | 182 | 182 |
| unknown (?) | | | | | | | | | | | 1 | | | | |
| not sequenced | | | | | | | | | | | | | | | |
| sum of seq² | 152 | 153 | 181 | 182 | 182 | 182 | 182 | 181 | 182 | 182 | 181 | 181 | 182 | 182 | 182 |
| oomcaa³ | 152 | 146 | 175 | 178 | 174 | 173 | 180 | 181 | 176 | 166 | 175 | 159 | 87 | 182 | 182 |
| mcaa⁴ | G | E | R | A | T | L | S | C | R | A | S | Q | S | — | — |
| rel. oomcaa⁵ | 100% | 95% | 97% | 98% | 96% | 95% | 99% | 100% | 97% | 91% | 97% | 88% | 48% | 100% | 100% |
| pos occupied⁶ | 1 | 3 | 7 | 2 | 4 | 3 | 3 | 1 | 3 | 5 | 6 | 6 | 8 | 1 | 1 |

| | CDR I | | | | | | | | | | Framework II | | | | | |
|---|---|---|---|---|---|---|---|---|---|---|---|---|---|---|---|---|
| amino acid¹ | D | E | F | 28 | 29 | 30 | 31 | 32 | 33 | 34 | 35 | 36 | 37 | 38 | 39 | 40 |
| A | | | | | | | 1 | 1 | | | 181 | | | | | |
| B | | | | | | | | | | | | | | | | |
| C | | | | | | | | | | | | | | | | |
| D | | | | | 1 | 1 | 2 | 1 | | | | | | | | |
| E | | | | | | | | 1 | | | | | | | 1 | |
| F | | | | 1 | | | | 7 | | | | | 1 | | | |
| G | | | | | 2 | 7 | 3 | 1 | | | 2 | | | 12 | 1 | 1 |
| H | | | | | 1 | | | 2 | | | | | 1 | | | |
| I | | | | 24 | 4 | | 1 | 1 | | | | | | | | |
| K | | | | | | | 1 | 1 | | | | | | | 153 | |
| L | | | | 8 | 1 | | | 1 | 176 | | | | | 3 | | |
| M | | | | | | | | | | | | | | | | |
| N | | | | | 3 | 12 | 25 | 32 | | | | | | | | |
| P | | | | | | | 1 | | | | | | | | | 170 |
| Q | | | | | | | 1 | 1 | | | | | 183 | 167 | 1 | |
| R | | | | | 10 | 3 | 18 | 16 | | 1 | | | 1 | | 27 | 5 |
| S | | | | 72 | 86 | 151 | 118 | 4 | | | | | | | | 5 |
| T | | | | 1 | 1 | 3 | 8 | 1 | | | | | | | 1 | |
| V | | | | 76 | 68 | | 1 | | | 7 | | | | 3 | | 2 |
| W | | | | | 5 | | | | | | | 185 | | | | |
| X | | | | | | | | | | | | | | | | |
| Y | | | | | 1 | 1 | 115 | | | | | | 183 | | | |
| — | 182 | 182 | 182 | | | | | | | | | | | | | |
| unknown (?) | | | | | | | | | | | | 1 | | | | |
| not sequenced | | | | | | | | | | | | | | | | |
| sum of seq² | 182 | 182 | 182 | 182 | 182 | 181 | 181 | 182 | 183 | 184 | 185 | 185 | 185 | 185 | 184 | 184 |
| oomcaa³ | 182 | 182 | 182 | 76 | 86 | 151 | 118 | 115 | 176 | 181 | 185 | 183 | 183 | 167 | 153 | 170 |
| mcaa⁴ | — | — | — | V | S | S | S | Y | L | A | W | Y | Q | Q | K | P |
| rel. oomcaa⁵ | 100% | 100% | 100% | 42% | 47% | 83% | 65% | 63% | 96% | 98% | 100% | 99% | 99% | 90% | 83% | 92% |
| pos occupied⁶ | 1 | 1 | 1 | 6 | 11 | 10 | 13 | 12 | 2 | 3 | 1 | 3 | 2 | 4 | 6 | 6 |

| | Framework II | | | | | | | | | CDR II | | | | | | |
|---|---|---|---|---|---|---|---|---|---|---|---|---|---|---|---|
| amino acid¹ | 41 | 42 | 43 | 44 | 45 | 46 | 47 | 48 | 49 | 50 | 51 | 52 | 53 | 54 | 55 | 56 |
| A | | | 176 | | | | | | | 4 | 147 | | | | 176 | 1 |
| B | | | | | | | | | | | | | | | | |
| C | | | | | | | | | | | | 1 | | | | |
| D | | | | | | | | | | 43 | | | | | 2 | |
| E | | 1 | | | | | | | | | | | | | | |
| F | | | | | | 1 | | | 4 | | | | | | | |
| G | 184 | | | | | | | | | 125 | 1 | | | | 2 | 10 |
| H | | | | | | | | | 9 | | 1 | | | | | |
| I | | | | | | | | 178 | | | | | | 7 | | 1 |
| K | | | | | 1 | | | | | | | | | | | |

TABLE 4C-continued

Analysis of V kappa subgroup 3

| amino acid | | | | | | | | | | | | | | | | |
|---|---|---|---|---|---|---|---|---|---|---|---|---|---|---|---|---|
| L |  | 2 | 1 |  |  | 179 | 174 | 1 |  |  |  |  |  |  |  |  |
| M |  |  |  |  |  | 3 |  |  |  |  |  |  |  | 1 |  |  |
| N |  |  |  | 1 |  |  |  |  |  | 1 |  |  | 53 |  | 2 | 2 |
| P |  |  | 5 | 184 |  |  |  |  |  |  |  |  | 2 |  | 2 | 2 |
| Q |  | 181 |  |  |  |  |  |  | 1 |  |  |  |  |  |  |  |
| R |  |  |  |  | 182 |  |  |  |  |  | 1 |  | 4 | 180 |  |  |
| S |  |  |  |  |  |  |  |  | 3 | 6 | 4 | 179 | 74 | 1 |  | 5 |
| T |  |  | 3 |  |  |  |  |  |  | 11 | 2 |  | 44 |  |  | 164 |
| V |  |  |  |  | 3 | 9 |  |  |  | 3 | 19 |  |  |  | 3 |  |
| W |  |  |  |  |  |  |  |  | 1 |  |  |  | 1 |  |  |  |
| X |  |  |  |  |  |  |  |  |  |  |  |  |  |  |  |  |
| Y |  |  |  |  |  |  |  |  | 165 |  |  |  |  |  |  |  |
| — |  |  |  |  |  |  |  |  |  |  |  |  |  |  |  |  |
| unknown (?) |  |  |  |  |  |  |  |  |  |  |  |  |  |  |  |  |
| not sequenced |  |  |  | 1 |  |  |  |  |  |  |  |  |  |  |  |  |
| sum of seq[2] | 184 | 184 | 184 | 185 | 185 | 183 | 183 | 183 | 183 | 183 | 183 | 183 | 183 | 183 | 185 | 185 |
| oomcaa[3] | 184 | 181 | 176 | 184 | 182 | 179 | 174 | 178 | 165 | 125 | 147 | 179 | 74 | 180 | 176 | 164 |
| mcaa[4] | G | Q | A | P | R | L | L | I | Y | G | A | S | S | R | A | T |
| rel. oomcaa[5] | 100% | 98% | 96% | 99% | 98% | 98% | 95% | 97% | 90% | 68% | 80% | 98% | 40% | 98% | 95% | 89% |
| pos occupied[6] | 1 | 3 | 3 | 2 | 3 | 3 | 2 | 3 | 4 | 6 | 7 | 6 | 4 | 5 | 5 | 7 |

Framework III

| amino acid[1] | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|
| A |  |  |  | 68 |  |  |  |  |  | 3 |  | 5 | 3 | 1 |  | 3 |
| B |  |  |  |  |  |  |  |  |  |  |  |  |  |  |  |  |
| C |  |  |  |  |  |  |  |  |  |  |  |  |  |  |  |  |
| D | 4 |  |  | 112 |  |  |  | 1 |  |  |  |  | 1 | 152 |  |  |
| E |  |  |  |  |  |  |  |  |  |  | 1 |  | 1 | 30 |  |  |
| F |  |  |  |  |  | 183 |  |  |  |  |  |  |  |  | 183 |  |
| G | 179 |  |  |  |  |  |  | 184 | 3 | 178 |  | 177 |  |  |  |  |
| H |  |  |  | 1 |  |  |  |  |  |  |  |  |  |  |  |  |
| I |  | 168 |  |  |  | 1 |  |  |  |  |  |  |  |  |  | 1 |
| K |  |  |  |  | 1 |  |  |  |  |  |  |  |  |  |  |  |
| L |  |  |  |  |  |  | 1 |  |  |  |  |  |  |  |  |  |
| M |  |  |  |  |  |  |  |  |  |  | 1 |  |  |  |  |  |
| N |  |  |  | 1 |  |  |  |  |  |  |  |  |  |  |  | 1 |
| P |  |  | 177 |  |  |  |  |  |  |  |  |  |  |  |  |  |
| Q |  |  |  |  |  |  |  |  |  |  |  |  | 1 |  |  |  |
| R |  |  |  |  | 182 |  | 2 |  | 1 |  |  |  | 2 |  |  |  |
| S |  |  | 7 |  |  |  | 180 |  | 179 |  |  | 185 | 3 |  |  | 7 |
| T |  | 2 | 1 |  | 2 |  | 3 |  | 2 |  |  | 1 | 177 |  |  | 172 |
| V |  | 15 |  | 3 |  |  |  |  |  |  | 1 | 1 |  |  |  |  |
| W |  |  |  |  |  |  |  |  |  |  |  |  | 1 |  |  |  |
| X |  |  |  |  |  |  |  |  |  |  |  |  |  |  |  |  |
| Y | 2 |  |  |  |  |  |  |  |  |  |  |  |  |  | 1 |  |
| — |  |  |  |  |  |  |  |  |  |  |  |  |  |  |  |  |
| unknown (?) |  |  |  |  |  |  |  |  |  |  |  |  | 1 |  |  |  |
| not sequenced |  |  |  |  |  |  |  |  |  |  |  |  |  |  |  |  |
| sum of seq[2] | 185 | 185 | 185 | 185 | 185 | 185 | 185 | 185 | 185 | 185 | 185 | 185 | 185 | 184 | 184 | 184 |
| oomcaa[3] | 179 | 168 | 177 | 112 | 182 | 183 | 180 | 184 | 179 | 178 | 185 | 177 | 177 | 152 | 183 | 172 |
| mcaa[4] | G | I | P | D | R | F | S | G | S | G | S | G | T | D | F | T |
| rel. oomcaa[5] | 97% | 91% | 96% | 61% | 98% | 99% | 97% | 99% | 97% | 96% | 100% | 96% | 96% | 83% | 99% | 93% |
| pos occupied[6] | 3 | 3 | 3 | 5 | 3 | 3 | 3 | 2 | 4 | 5 | 1 | 5 | 4 | 4 | 2 | 5 |

Framework III

| amino acid[1] | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|
| A |  |  |  |  |  |  |  |  | 3 |  |  | 174 |  |  |  |  |
| B |  |  |  |  |  | 1 |  |  |  |  |  |  |  |  |  |  |
| C |  |  |  |  |  |  |  |  |  |  | 2 |  |  |  | 1 | 182 |
| D |  |  |  | 1 |  |  |  | 3 |  | 182 |  |  |  |  |  |  |
| E |  |  |  |  |  | 149 |  | 175 |  |  |  |  |  |  |  |  |
| F | 2 |  |  | 1 |  |  |  |  |  |  | 178 |  | 2 | 1 | 4 |  |
| G |  |  |  | 3 |  |  |  |  |  | 1 |  | 2 |  |  |  |  |
| H |  |  |  |  |  |  |  |  |  |  |  |  | 1 |  |  |  |
| I |  | 3 | 178 |  |  |  |  |  |  | 1 | 1 |  | 9 |  |  |  |
| K |  |  |  |  |  |  |  |  | 1 |  |  |  |  |  |  |  |
| L | 182 |  |  |  | 178 |  | 1 |  |  |  | 1 |  | 7 |  | 1 |  |
| M |  |  |  |  |  |  |  |  |  |  |  | 1 | 5 |  |  |  |
| N |  |  | 1 | 5 |  |  |  |  |  |  |  |  |  |  |  |  |
| P |  |  |  |  |  |  | 149 |  |  |  |  |  |  |  |  |  |
| Q |  |  |  |  |  |  | 34 |  |  |  |  |  |  |  |  | 1 |
| R |  |  | 1 | 111 |  |  |  |  |  |  | 3 |  |  |  |  |  |
| S |  | 2 | 169 | 65 |  |  | 34 |  |  |  | 1 |  |  |  | 2 |  |

TABLE 4C-continued

Analysis of V kappa subgroup 3

| amino acid[1] | | | | | | | | | | | | | | | | |
|---|---|---|---|---|---|---|---|---|---|---|---|---|---|---|---|---|
| T | | 179 | | 8 | 4 | | | | | | | 1 | | | | |
| V | | | 4 | | | 6 | | | | | 1 | 3 | 159 | | | |
| W | | | | | | | | | | | | | | | | |
| X | | | | | | | | | | | | | | | | |
| Y | | | 1 | | | | | | | | | | 1 | 183 | 176 | |
| — | | | | | | | | | | | | | | | | |
| unknown (?) | | | | | | | | | | | | | | | | |
| not sequenced | | | | | | | | | | | | | | | | |
| sum of seq[2] | 184 | 184 | 184 | 184 | 184 | 184 | 184 | 184 | 182 | 184 | 184 | 184 | 184 | 184 | 184 | 183 |
| oomcaa[3] | 182 | 179 | 178 | 169 | 111 | 178 | 149 | 149 | 175 | 182 | 178 | 174 | 159 | 183 | 176 | 182 |
| mcaa[4] | L | T | I | S | R | L | E | P | E | D | F | A | V | Y | Y | C |
| rel. oomcaa[5] | 99% | 97% | 97% | 92% | 60% | 97% | 81% | 81% | 96% | 99% | 97% | 95% | 86% | 99% | 96% | 99% |
| pos occupied[6] | 2 | 3 | 4 | 5 | 5 | 2 | 3 | 3 | 4 | 3 | 6 | 6 | 7 | 2 | 5 | 2 |

| | CDR III | | | | | | | | | | | | | |
|---|---|---|---|---|---|---|---|---|---|---|---|---|---|---|
| amino acid[1] | 89 | 90 | 91 | 92 | 93 | 94 | 95 | A | B | C | D | E | F | 96 | 97 |
| A | | | | 1 | 8 | 3 | 3 | | | | | | | | |
| B | | | | | | | | | | | | | | | |
| C | | | 2 | | | 1 | | | | | | | | 2 | |
| D | | | | 8 | 5 | | | | | | | | | | 1 |
| E | | 2 | | 2 | | | | | | | | | | 1 | |
| F | | | 5 | | 2 | | | | | | | | | 7 | |
| G | | | 1 | 104 | 15 | | 1 | 1 | 2 | | | | | 1 | |
| H | 1 | 7 | 4 | 1 | | | | 1 | | | | | | 2 | |
| I | | | | | 1 | | | 1 | | | | | | 4 | |
| K | | | | | 2 | | | 1 | | | | | | 1 | |
| L | | 1 | | | | 2 | 7 | 5 | | | | | | 42 | |
| M | | | | 1 | | | 1 | 2 | | | | | | | |
| N | | | | 28 | 71 | | | | | | | | | 1 | |
| P | | | | | | 1 | 139 | 24 | | | | | | 7 | 2 |
| Q | 181 | 155 | 1 | | 1 | | 3 | 1 | | | | | | 3 | |
| R | | 1 | 34 | 2 | 3 | | 2 | 2 | | | | | | 19 | |
| S | | | 2 | 33 | 58 | 102 | 15 | 2 | | | | | | 1 | 8 |
| T | | 8 | | 2 | 13 | 1 | 1 | 2 | | | | | | 1 | 154 |
| V | | 7 | | | | | 3 | 1 | | | | | | 2 | |
| W | | | | | | 69 | | | | | | | | 24 | |
| X | | | | | | | | | | | | | | | |
| Y | 1 | 2 | 134 | 1 | 1 | | | | | | | | | 43 | |
| — | | | | | 3 | 3 | 7 | 127 | 167 | 169 | 169 | 169 | 169 | 8 | 1 |
| unknown (?) | | | | | | | | | | | | | | | |
| not sequenced | | | | | | | 14 | 14 | 14 | 14 | 14 | 14 | 14 | 17 | |
| sum of seq[2] | 183 | 183 | 183 | 183 | 183 | 182 | 182 | 169 | 169 | 169 | 169 | 169 | 169 | 169 | 166 |
| oomcaa[3] | 181 | 155 | 134 | 104 | 71 | 102 | 139 | 127 | 167 | 169 | 169 | 169 | 169 | 43 | 154 |
| mcaa[4] | Q | Q | Y | G | N | S | P | — | — | — | — | — | — | Y | T |
| rel. oomcaa[5] | 99% | 85% | 73% | 57% | 39% | 56% | 76% | 75% | 99% | 100% | 100% | 100% | 100% | 25% | 93% |
| pos occupied[6] | 3 | 8 | 8 | 11 | 13 | 8 | 11 | 12 | 2 | 1 | 1 | 1 | 1 | 18 | 5 |

| | Framework IV | | | | | | | | | | | | |
|---|---|---|---|---|---|---|---|---|---|---|---|---|---|
| amino acid[1] | 98 | 99 | 100 | 101 | 102 | 103 | 014 | 105 | 106 | A | 107 | 108 | sum |
| A | | | | 1 | | | | | | | | | 1345 |
| B | | | | | | | | | | | | | 2 |
| C | | | | | | | | | | | | | 375 |
| D | | | | | | | | | 23 | | | | 564 |
| E | | | | | | 3 | | | 141 | | | | 759 |
| F | 166 | | | | | | | | 6 | | | | 765 |
| G | | 166 | 41 | 166 | | | | | | | | 1 | 1804 |
| H | | | | | | | | | 1 | | | | 64 |
| I | | | | | | | | | 143 | | | | 803 |
| K | | | | 1 | | | 152 | | | | 157 | | 489 |
| L | | | | | | | | 54 | 1 | | | 2 | 1596 |
| M | | | | | | | | | 3 | | | | 36 |
| N | | | | | 1 | | | | | | 3 | | 255 |
| P | | | 9 | | 1 | | 1 | | | | | | 1147 |
| Q | | | 114 | | | | 1 | | 1 | | | | 1314 |
| R | | | | | | | 9 | | | 2 | | 4 | 134 1326 |
| S | | | | | 2 | | | | | | | | 2629 |
| T | | | | | 162 | 1 | | | | | | 1 | 1593 |
| V | | | | | | | | 111 | | 11 | | | 646 |
| W | | | | | | | | | | | | | 287 |
| X | | | | | | | | | | | | | |
| Y | | | | | | 1 | | | | | | | 1014 |
| — | | 1 | 1 | 1 | 1 | 1 | 1 | 1 | 1 | 166 | 1 | 1 | 2151 |
| unknown (?) | | | | | | | | | | | | | 4 |

TABLE 4C-continued

Analysis of V kappa subgroup 3

| | | | | | | | | | | | | | |
|---|---|---|---|---|---|---|---|---|---|---|---|---|---|
| not sequenced | 16 | 16 | 16 | 16 | 16 | 15 | 16 | 16 | 16 | 17 | 17 | 45 | 337 |
| sum of seq[2] | 167 | 167 | 167 | 167 | 167 | 168 | 167 | 167 | 167 | 166 | 166 | 138 | |
| oomcaa[3] | 166 | 166 | 114 | 166 | 162 | 152 | 111 | 141 | 143 | 166 | 157 | 134 | |
| mcaa[4] | F | G | Q | G | T | K | V | E | I | — | K | R | |
| rel. oomcaa[5] | 99% | 99% | 68% | 99% | 97% | 90% | 66% | 84% | 86% | 100% | 95% | 97% | |
| pos occupied[6] | 2 | 2 | 6 | 2 | 5 | 7 | 4 | 5 | 7 | 1 | 5 | 4 | |

TABLE 4D

Analysis of V kappa subgroup 4

Framework I

| amino acid[1] | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| A | | | | | | | | | | | | 24 | | | | | 1 | | 26 |
| B | | | | | | | | | | | | | | | | | | | |
| C | | | | | | | | | | 1 | | | | | | 1 | | | |
| D | 25 | | | | | | | | 26 | | | | | | | | | | |
| E | | | | | | | | | | | | | | | | 25 | | | |
| F | | | | | | | | | | | | | | | | | | | |
| G | | | | | | | | | | | | | 1 | | | 24 | | | |
| H | | | | | | | | | | | | | | | | | | | |
| I | | 26 | | | | | | | | | | | | | | | | | |
| K | | | | | | 1 | | | | | | | | | | | | | |
| L | | | | 1 | | | | | | | | 26 | | | | 26 | | | |
| M | | | | 24 | | | | | | | | | | | | | | | |
| N | 1 | | | | | | | | | | | | | | | | | | |
| P | | | | | | | | | 26 | | | | 1 | | | | | | |
| Q | | | 1 | | 25 | | | | | | | | | | | | | | |
| R | | | | | | | | | | | | | | | | | | 26 | |
| S | | | | | | | 26 | | | 25 | | | | | 26 | 1 | | | |
| T | | | | | 26 | | | | | | | | | | | | | | |
| V | | 25 | 1 | | | | | | | | | 26 | | | | | | | |
| W | | | | | | | | | | | | | | | | | | | |
| X | | | | | | | | | | | | | | | | | | | |
| Y | | | | | | | | | | | | | | | | | | | |
| — | | | | | | | | | | | | | | | | | | | |
| unknown (?) | | | | | | | | | | | | | | | | | | | |
| not sequenced | 7 | 7 | 7 | 7 | 7 | 7 | 7 | 7 | 7 | 7 | 7 | 7 | 7 | 7 | 7 | 7 | 7 | 7 | 7 |
| sum of seq[2] | 26 | 26 | 26 | 26 | 26 | 26 | 26 | 26 | 26 | 26 | 26 | 26 | 26 | 26 | 26 | 26 | 26 | 26 | 26 |
| oomcaa[3] | 25 | 26 | 25 | 24 | 26 | 25 | 26 | 26 | 26 | 25 | 26 | 24 | 26 | 26 | 26 | 24 | 25 | 26 | 26 |
| mcaa[4] | D | I | V | M | T | Q | S | P | D | S | L | A | V | S | L | G | E | R | A |
| rel. oomcaa[5] | 96% | 100% | 96% | 92% | 100% | 96% | 100% | 100% | 100% | 96% | 100% | 92% | 100% | 100% | 100% | 92% | 96% | 100% | 100% |
| pos occupied[6] | 2 | 1 | 2 | 3 | 1 | 2 | 1 | 1 | 1 | 2 | 1 | 3 | 1 | 1 | 1 | 3 | 2 | 1 | 1 |

Framework I / CDRI

| amino acid[1] | 20 | 21 | 22 | 23 | 24 | 25 | 26 | 27 | A | B | C | D | E | F | 28 | 29 | 30 | 31 |
|---|---|---|---|---|---|---|---|---|---|---|---|---|---|---|---|---|---|---|
| A | | | | | 1 | | | | | 1 | | | | | | | | |
| B | | | | | | | | | | | | | | | | | | |
| C | | | | 33 | | | | | | | | | | | | | | |
| D | | | | | | | | | | 1 | | 1 | | | | | 1 | |
| E | | | | | | | | | | | | | | | | | | |
| F | | | | | | | | | | | | | | | | | | |
| G | | | | | | | | | | | | | | | | | | |
| H | | | | | | | | | | | | | | | | | | |
| I | | 26 | | | | | | | | 1 | | | | | | | | |
| K | | | | | | 33 | | | | | | | | | | 2 | 30 | |
| L | | | | | | | | | | 2 | 31 | | | | | | | |
| M | | | | | | | | | | | | | | | | | | |
| N | | | 26 | | | | | | | | | | | | 30 | 31 | 1 | 33 |
| P | | | | | | | 1 | | | | | | | 1 | | | | |
| Q | | | | | | | | 32 | | | | | | | | | 1 | |
| R | | | | | | | | | 1 | | | | | | | | 1 | 1 |
| S | | | | | 31 | 33 | | | 33 | | | | 32 | 32 | | 1 | | |
| T | 26 | | | | | | | | | | | | | 1 | | | | |
| V | | | | | | | | | | 28 | 2 | | | | | | | |
| W | | | | | | | | | | | | | | | | | | |
| X | | | | | | | | | | | | | | | | | | |
| Y | | | | | | | | | | | | | | | 32 | | | |

TABLE 4D-continued

Analysis of V kappa subgroup 4

| | | | | | | | | | | | | | | | | | | |
|---|---|---|---|---|---|---|---|---|---|---|---|---|---|---|---|---|---|---|
| unknown (?) | | | | | | | | | | | | | | | | | | |
| not sequenced | | | | | | | | | | | | | | | | | | |
| sum of seq² | 26 | 26 | 26 | 33 | 33 | 33 | 33 | 33 | 33 | 33 | 33 | 33 | 33 | 33 | 33 | 33 | 33 | 33 |
| oomcaa³ | 26 | 26 | 26 | 33 | 33 | 31 | 33 | 32 | 33 | 28 | 31 | 32 | 32 | 32 | 30 | 31 | 30 | 33 |
| mcaa⁴ | T | I | N | C | K | S | S | Q | S | V | L | Y | S | S | N | N | K | N |
| rel. oomcaa⁵ | 100% | 100% | 100% | 100% | 100% | 94% | 100% | 97% | 100% | 85% | 94% | 97% | 97% | 97% | 91% | 94% | 91% | 100% |
| pos occupied⁶ | 1 | 1 | 1 | 1 | 1 | 3 | 1 | 2 | 1 | 5 | 2 | 2 | 2 | 2 | 3 | 3 | 4 | 1 |

| | CDRI | | | Framework II | | | | | | | | | | | | | |
|---|---|---|---|---|---|---|---|---|---|---|---|---|---|---|---|---|---|
| amino acid¹ | 32 | 33 | 34 | 35 | 36 | 37 | 38 | 39 | 40 | 41 | 42 | 43 | 44 | 45 | 46 | 47 | 48 | 49 |
| A | | | 32 | | | | | | | 2 | | | | | | | | |
| B | | | | | | | | | | | | | | | | | | |
| C | | | | | | | | | | | | | | | | | | |
| D | | | | | | | | | | | | | | | | | | |
| E | | | | | | | | | | | 1 | | | | | | | |
| F | | | | | | | | | | | | | | | | | | |
| G | | | | | | | | | | | 32 | | | | | | | |
| H | | | | | | 2 | | | | | | | | | | | | |
| I | | | | | | | | | | | | | | | | | | 32 |
| K | | | | | | | | | 33 | | | | | 32 | | | | |
| L | | 33 | | | | | | | | | | | | | 29 | 33 | | |
| M | | | | | | | | | | | | | | | | | 1 | |
| N | | | | | | | | | | | | | | | | | | |
| P | | | | | | | | | | | 31 | | 31 | 33 | | | | |
| Q | | | | | | | | 32 | 33 | | | 32 | | | | | | |
| R | | | | | | | | | 1 | | | 1 | | | 1 | | | |
| S | | | | | | | | | | | | | 2 | | | | | |
| T | | | 1 | | | | | | | | | | | | | | | |
| V | | | | | | | | | | | | | | | 4 | | | |
| W | | | | 33 | | | | | | | | | | | | | | |
| X | | | | | | | | | | | | | | | | | | |
| Y | 33 | | | | | 31 | | | | | | | | | | | | 33 |
| unknown (?) | | | | | | | | | | | | | | | | | | |
| not sequenced | | | | | | | | | | | | | | | | | | |
| sum of seq² | 33 | 33 | 33 | 33 | 33 | 33 | 33 | 33 | 33 | 33 | 33 | 33 | 33 | 33 | 33 | 33 | 33 | 33 |
| oomcaa³ | 33 | 33 | 32 | 33 | 31 | 32 | 33 | 33 | 31 | 32 | 32 | 31 | 33 | 32 | 29 | 33 | 32 | 33 |
| mcaa⁴ | Y | L | A | W | Y | Q | Q | K | P | G | Q | P | P | K | L | L | I | Y |
| rel. oomcaa⁵ | 100% | 100% | 97% | 100% | 94% | 97% | 100% | 100% | 94% | 97% | 97% | 94% | 100% | 97% | 88% | 100% | 97% | 100% |
| pos occupied⁶ | 1 | 1 | 2 | 1 | 2 | 2 | 1 | 1 | 2 | 2 | 2 | 2 | 1 | 2 | 2 | 1 | 2 | 1 |

| | CDR II | | | | | | | Framework III | | | | | | | | | |
|---|---|---|---|---|---|---|---|---|---|---|---|---|---|---|---|---|---|
| amino acid¹ | 50 | 51 | 52 | 53 | 54 | 55 | 56 | 57 | 58 | 59 | 60 | 61 | 62 | 63 | 64 | 65 | 66 | 67 |
| A | | 30 | | | | | | | | | | | | | | | | |
| B | | | | | | | | | | | | | | | | | | |
| C | | | | | | | | | | | | | | | | | | |
| D | | | | | | | | | | | 33 | | | | | | | |
| E | | | | | 32 | | | | | | | | | | | | | |
| F | | | | | | | | | | | | | 33 | | | | | |
| G | | | | | | | | | 33 | | | | | 1 | 33 | | 33 | |
| H | | | | | | | | | | | | | | | | | | |
| I | | | | 1 | | | | | | | | | | | | | | |
| K | | | | | | | | | | | | | | | | | | |
| L | | | | | | | | | | | | | | | | | | |
| M | | | | | | | | | | | | | | | | | | |
| N | | | | 2 | | | | | | | | | | | | | | |
| P | | | 1 | | | | | | | | | 33 | 1 | | | | | |
| Q | | | | | | | | | | | | | | | | | | |
| R | | | | | | 33 | | | | | | | 32 | | | | | |
| S | | 1 | 31 | 1 | | | 33 | | | | | | | 32 | | 33 | | 33 |
| T | | 2 | 1 | 29 | | | | | | | | | | | | | | |
| V | | | | | | | 1 | | | 33 | | | | | | | | |
| W | 33 | | | | | | | | | | | | | | | | | |
| X | | | | | | | | | | | | | | | | | | |
| Y | | | | | | | | | | | | | | | | | | |
| unknown(?) | | | | | | | | | | | | | | | | | | |
| not sequenced | | | | | | | | | | | | | | | | | | |
| sum of seq² | 33 | 33 | 33 | 33 | 33 | 33 | 33 | 33 | 33 | 33 | 33 | 33 | 33 | 33 | 33 | 33 | 33 | 33 |
| oomcaa³ | 33 | 30 | 31 | 29 | 33 | 32 | 33 | 33 | 33 | 33 | 33 | 33 | 32 | 33 | 32 | 33 | 33 | 33 |
| mcaa⁴ | W | A | S | T | R | E | S | G | V | P | D | R | F | S | G | S | G | S |
| rel. oomcaa⁵ | 100% | 91% | 94% | 88% | 100% | 97% | 100% | 100% | 100% | 100% | 100% | 100% | 97% | 100% | 97% | 100% | 100% | 100% |
| pos occupied⁶ | 1 | 3 | 3 | 4 | 1 | 2 | 1 | 1 | 1 | 1 | 1 | 1 | 2 | 1 | 2 | 1 | 1 | 1 |

TABLE 4D-continued

Analysis of V kappa subgroup 4

| | Framework III | | | | | | | | | | | | | | | | | |
|---|---|---|---|---|---|---|---|---|---|---|---|---|---|---|---|---|---|---|
| amino acid[1] | 68 | 69 | 70 | 71 | 72 | 73 | 74 | 75 | 76 | 77 | 78 | 79 | 80 | 81 | 82 | 83 | 84 | 85 |
| A | | | | | | | | | | | | | 33 | | | | 32 | |
| B | | | | | | | | | | | | | | | | | | |
| C | | | | | | | | | | | | | | | | | | |
| D | | | 32 | | | | | | | | | | | | | 33 | | |
| E | | | | | | | | | | | | | | 33 | | | | |
| F | | | | 32 | | | | | | | | | | | | | | |
| G | 33 | | 1 | | | | | | | | | | | | | | 1 | |
| H | | | | | | | | | | | | | | | | | | |
| I | | | | | | | | 33 | | | | | | | | | | |
| K | | | | | | | | | | | | | | | | | | |
| L | | | | | | 33 | | | | | 32 | | | | | | | |
| M | | | | | | | | | | | 1 | | | | | | | |
| N | | | | | | | | | 2 | 1 | | | | | | | | |
| P | | | | | | | | | | | | | | | | | | |
| Q | | | | | | | | | | | | | 32 | | | | | |
| R | | | | | | | | | | | | | 1 | | | | | |
| S | | | | | | | | | 30 | 32 | | | | | | | | |
| T | | 33 | | | 33 | | 33 | | 1 | | | | | | | | | |
| V | | | | 1 | | | | | | | | | | | | | 33 | 33 |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 33 | 33 | 32 | 32 | 33 | 33 | 33 | 33 | 30 | 32 | 32 | 32 | 33 | 33 | 33 | 33 | 32 | 33 |
| mcaa[4] | G | T | D | F | T | L | T | I | S | S | L | Q | A | E | D | V | A | V |
| rel. oomcaa[5] | 100% | 100% | 97% | 97% | 100% | 100% | 100% | 100% | 91% | 97% | 97% | 97% | 100% | 100% | 100% | 100% | 97% | 100% |
| pos occupied[6] | 1 | 1 | 2 | 2 | 1 | 1 | 1 | 1 | 3 | 2 | 2 | 2 | 1 | 1 | 1 | 1 | 2 | 1 |

| | Framework III | | | CDR III | | | | | | | | | | | | | |
|---|---|---|---|---|---|---|---|---|---|---|---|---|---|---|---|---|---|
| amino acid[1] | 86 | 87 | 88 | 89 | 90 | 91 | 92 | 93 | 94 | 95 | A | B | C | D | E | F | 96 | 97 |
| A | | | | | | | | | 1 | | | | | | | | | |
| B | | | | | | | | | | | | | | | | | | |
| C | | | 33 | | | | | | | | | | | | | | | |
| D | | | | | | | 1 | 1 | | | | | | | | | | |
| E | | | | | | | | | | | | | | | | | | |
| F | | 1 | | | | | 1 | | | | | | | | | | | |
| G | | | | | | | | 2 | | | | | | | | | | |
| H | | 1 | | 3 | | | | | | | | | | | | | | |
| I | | | | | | | | | 2 | | | | | | | | | |
| K | | | | | | | | | | | | | | | | | | |
| L | | | | | 1 | | 2 | | 1 | 3 | | | | | | | 1 | |
| M | | | | | | | | | | | | | | | | | | 1 |
| N | | | | | | | | 4 | 4 | | | | | | | | | |
| P | | | | | | | | | 1 | 29 | 1 | | | | | | 4 | |
| Q | | | | 30 | 32 | | | | | 1 | | | | | | | 1 | |
| R | | | | | | | | 1 | | | 1 | | | | | | 2 | |
| S | | | | | | 2 | | 23 | 2 | | | | | | | | 1 | 2 |
| T | | | | | | | | 2 | 22 | | | | | | | | | 12 |
| V | | | | | | | | | | | | | | | | | | |
| W | | | | | | | | | | | | | | | | | 2 | |
| X | | | | | | | | | | | | | | | | | | |
| Y | 33 | 31 | | | | 31 | 29 | | | | | | | | | | 1 | |
| — | | | | | | | | | | | 13 | 15 | 15 | 15 | 15 | 15 | 3 | |
| unknown (?) | | | | | | | | | | | | | | | | | | |
| not sequenced | | | | | | | | | | | 18 | 18 | 18 | 18 | 18 | 18 | 18 | 18 |
| sum of seq[2] | 33 | 33 | 33 | 33 | 33 | 33 | 33 | 33 | 33 | 33 | 15 | 15 | 15 | 15 | 15 | 15 | 15 | 15 |
| oomcaa[3] | 33 | 31 | 33 | 30 | 32 | 31 | 29 | 23 | 22 | 29 | 13 | 15 | 15 | 15 | 15 | 15 | 4 | 12 |
| mcaa[4] | Y | Y | C | Q | Q | Y | Y | S | T | P | — | — | — | — | — | — | P | |
| rel. oomcaa[5] | 100% | 94% | 100% | 91% | 97% | 94% | 88% | 70% | 67% | 88% | 87% | 100% | 100% | 100% | 100% | 100% | 27% | |
| pos occupied[6] | 1 | 3 | 1 | 2 | 2 | 2 | 4 | 6 | 7 | 3 | 3 | 1 | 1 | 1 | 1 | 1 | 8 | 3 |

| | Framework IV | | | | | | | | | | | |
|---|---|---|---|---|---|---|---|---|---|---|---|---|
| amino acid[1] | 98 | 99 | 100 | 101 | 102 | 103 | 104 | 105 | 106 | A | 107 | 108 | sum |
| A | | | | | | | | | | | | | 183 |
| B | | | | | | | | | | | | | |
| C | | | | | | | | | | | | | 68 |

TABLE 4D-continued

Analysis of V kappa subgroup 4

| amino acid | | | | | | | | | | | | | total |
|---|---|---|---|---|---|---|---|---|---|---|---|---|---|
| D | | | | | | | | | | | | | 154 |
| E | | | | | | | | | 14 | | | | 105 |
| F | 15 | | | | | | | | | | | | 82 |
| G | | 15 | 4 | 15 | | | | | | | | | 228 |
| H | | | | | | | | | | | | | 6 |
| I | | | | | | | | | 14 | | | | 135 |
| K | | | | | | 14 | | | | | 13 | | 158 |
| L | | | | | | | | 4 | | | | | 258 |
| M | | | | | | | | | | | | | 27 |
| N | | | | | | | | | | 1 | | | 136 |
| P | | | | | | | 1 | | | | | | 195 |
| Q | | | 11 | | | | 1 | | | | | | 264 |
| R | | | | | | 1 | | 1 | | | 1 | 11 | 116 |
| S | | | | | | | | | | 1 | | | 499 |
| T | | | | | 14 | | | | | | | | 236 |
| V | | | | | | | | 9 | | | | | 196 |
| W | | | | | | | | | 1 | | | | 69 |
| X | | | | | | | | | | | | | |
| Y | | | | | | | | | | | | | 254 |
| — | | | | | | | | | | | 15 | | 106 |
| unknown (?) | | | | | | | | | | | | | |
| not sequenced | 18 | 18 | 18 | 18 | 18 | 18 | 18 | 18 | 18 | 18 | 18 | 22 | 518 |
| sum of seq[2] | 15 | 15 | 15 | 15 | 15 | 15 | 15 | 15 | 15 | 15 | 15 | 11 | |
| oomcaa[3] | 15 | 15 | 11 | 15 | 14 | 14 | 14 | 9 | 14 | 15 | 13 | 11 | |
| mcaa[4] | F | G | Q | G | T | K | V | E | I | — | K | R | |
| rel. oomcaa[5] | 100% | 100% | 73% | 100% | 93% | 93% | 60% | 93% | 93% | 100% | 87% | 100% | |
| pos occupied[6] | 1 | 1 | 2 | 1 | 2 | 2 | 4 | 2 | 2 | 1 | 3 | 1 | |

TABLE 5A

Analysis of V lambda subgroup 1

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | | | | | | | 19 | | 18 | 20 | | | | | |
| B | | | | | | | | | | | | | | | | | | | |
| C | | | | | | | | | | | | | | | | | | | |
| D | | | | | | | | | | | | | | | | | | | |
| E | | | | | | | | | | | | | | | | | | 1 | |
| F | | | | | | | | | | | | | | | | | | | |
| G | | | | | | | | | | | | | 22 | | | 42 | | | |
| H | 2 | | | | | | | | | | | | | | | | | | |
| I | | | 1 | | | | | | | | 1 | | | | | | | | |
| K | | | | | | | | | | | | | | | | | | 14 | |
| L | | | 1 | 41 | | | | | | | 1 | | | | | | | | |
| M | | | | | | | | | | | | | | | | | | | |
| N | | | | | | | | | | | | | | | | | | | |
| P | | | | | | | 41 | 41 | | | | | | 1 | 41 | | | | |
| Q | 22 | | 1 | | | 41 | | | | | | | | | | 42 | | | |
| R | | | | | | | | | | | | | | | | | | 25 | |
| S | | 39 | | | | | | | 41 | | | 41 | | | 1 | | | 1 | |
| T | | | | | 41 | | | | | | | | 19 | | | | | 1 | |
| V | | 1 | 38 | | | | | | | | 20 | | 1 | 1 | | | | | 42 |
| W | | | | | | | | | | | | | | | | | | | |
| X | | | | | | | | | | | | | | | | | | | |
| Y | | | | | | | | | | | | | | | | | | | |
| Z | 16 | | | | | | | | | | | | | | | | | | |
| — | | | | | | | | | | | 41 | | | | | | | | |
| unknown (?) | | | | | | | | | | | | | | | | | | | |
| not sequenced | 2 | 2 | 1 | 1 | 1 | 1 | 1 | 1 | 1 | 1 | 1 | 1 | 1 | 1 | | | | | |
| sum of seq[2] | 40 | 40 | 41 | 41 | 41 | 41 | 41 | 41 | 41 | 41 | 41 | 41 | 41 | 41 | 42 | 42 | 42 | 42 | 42 |
| oomcaa[3] | 22 | 39 | 38 | 41 | 41 | 41 | 41 | 41 | 41 | 41 | 20 | 41 | 22 | 20 | 41 | 42 | 42 | 25 | 42 |
| mcaa[4] | Q | S | V | L | T | Q | P | P | S | — | V | S | G | A | P | G | Q | R | V |
| rel. oomcaa[5] | 55% | 98% | 93% | 100% | 100% | 100% | 100% | 100% | 100% | 100% | 49% | 100% | 54% | 49% | 98% | 100% | 100% | 60% | 100% |
| pos occupied[6] | 3 | 2 | 4 | 1 | 1 | 1 | 1 | 1 | 1 | 1 | 4 | 1 | 3 | 4 | 2 | 1 | 1 | 5 | 1 |

| | Framework I | | | | CDRI | | | | | | | | | | |
|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 |

TABLE 5A-continued

Analysis of V lambda subgroup 1

| amino acid[1] | | | | | | | | | | | | | | | | | | |
|---|---|---|---|---|---|---|---|---|---|---|---|---|---|---|---|---|---|---|
| A | 2 | | | | | | | 1 | | | 2 | 2 | | | 1 | | | |
| B | | | | | | | | | | | | | | | | | | |
| C | | | 42 | | | | | | | | | | | | | | | |
| D | | | | | | | | | | 3 | | 3 | 1 | | 3 | | | 1 |
| E | | | | | | | | | | | | 1 | | | | | | |
| F | | | | | 1 | | | | 1 | | | | | | 1 | 1 | | |
| G | | | | | | 42 | 3 | 1 | | | 2 | 39 | 4 | 2 | | | | |
| H | | | | | | | | | | | | | 2 | | 2 | | | 2 |
| I | 1 | 41 | | | | | | | 1 | 37 | | | 1 | | | | | 1 |
| K | | | | | | | | | 1 | | | 1 | | | | | | |
| L | | 1 | | | | | | | | 1 | | | | | | | | |
| M | | | | | | | | | | | 1 | | | | | | | |
| N | | | | | | | 2 | 1 | 37 | | | 13 | 31 | 2 | | 1 | | 9 |
| P | | | | | | | | | | | | | | | 1 | | | |
| Q | | | | | | | | | | | | | | | 1 | | | |
| R | | | | | | 1 | 1 | | | | | 5 | | | | | | |
| S | 1 | | 42 | | 38 | | 34 | 34 | 38 | | | 13 | 1 | 1 | 3 | | | 19 |
| T | 38 | | | | 3 | | 4 | 3 | 2 | | 1 | | 1 | | 7 | | | 2 |
| V | | | | | | | | | | 1 | | | | | 2 | 40 | | |
| W | | | | | | | | | | | | | | | | | | |
| X | | | | | | | | | | | | | | | | | | |
| Y | | | | | | | | | | | | | 4 | 1 | 20 | | | 7 |
| Z | | | | | | | | | | | | | | | | | | |
| — | | | | | | | | | | | | | 36 | | | | | |
| unknown (?) | | | | | | | | | | | | | | | | | | |
| not sequenced | | | | | | | | | | | | | | 1 | 1 | 1 | | 1 |
| sum of seq[2] | 42 | 42 | 42 | 42 | 42 | 42 | 42 | 42 | 42 | 42 | 42 | 42 | 42 | 42 | 41 | 41 | 41 | 41 |
| oomcaa[3] | 38 | 41 | 42 | 42 | 38 | 42 | 34 | 34 | 38 | 37 | 37 | 39 | 13 | 31 | 36 | 20 | 40 | 19 |
| mcaa[4] | T | I | S | C | S | G | S | S | S | N | I | G | N | N | — | Y | V | S |
| rel. oomcaa[5] | 90% | 98% | 100% | 100% | 90% | 100% | 81% | 81% | 90% | 88% | 88% | 93% | 31% | 74% | 88% | 49% | 98% | 46% |
| pos occupied[6] | 4 | 2 | 1 | 1 | 3 | 1 | 4 | 6 | 4 | 4 | 5 | 3 | 8 | 7 | 5 | 10 | 2 | 7 |

| | Framework II | | | | | | | | | | | | | | CDR II | | | |
|---|---|---|---|---|---|---|---|---|---|---|---|---|---|---|---|---|---|---|
| amino acid[1] | 35 | 36 | 37 | 38 | 39 | 40 | 41 | 42 | 43 | 44 | 45 | 46 | 47 | 48 | 49 | 50 | 51 | 52 | 53 |
| A | | | | | | | | 4 | 40 | | | | | | | | | | 1 |
| B | | | | | | | | | | | | | | | | | | | |
| C | | | | | | | | | | | | | | | | | | | |
| D | | | | | | | 1 | | | | | | | | | 13 | 10 | 8 | |
| E | | | | | | | | | | | 2 | | | | | 5 | | | 1 |
| F | | 1 | | | 4 | | | | | | | | | | 1 | | | | |
| G | | | | | | 39 | | | | | | | | | | 1 | | | |
| H | | | 1 | 1 | 6 | 1 | | | | | | | | | 1 | | | | 1 |
| I | | | | | | | | | | | | | | 40 | | 1 | | | |
| K | | | | | | | | 1 | | | 35 | | | | | 1 | 1 | | 18 |
| L | | | | 1 | 31 | | | | | | | 41 | 40 | | | | | | 1 |
| M | | | | | | | | 1 | | | | | 1 | | | | | | 1 |
| N | | | | | | | | | | | 1 | | | | | 3 | 28 | 30 | 2 |
| P | | | | | | | 42 | 1 | | | 42 | | | | | | | | |
| Q | | | 39 | 34 | | | | | | | | | | | | | | | 15 |
| R | | | 2 | | 1 | | 1 | | | | | 4 | | | | 7 | | | 2 |
| S | | | | | | | | | 1 | | | | | | | 9 | 2 | 3 | 1 |
| T | | | | | | | | 36 | 1 | | | | | | | 1 | | | |
| V | | | | 1 | 5 | | | | | | | 1 | 2 | 1 | | | | | |
| W | 42 | | | | | | | | | | | | | | | | | | |
| X | | | | | | | | | | | | | | | | | | | |
| Y | | 40 | | | | | | | | | | | | | 40 | 1 | 1 | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 42 | 42 | 42 | 42 | 42 | 42 | 42 | 42 | 42 | 42 | 42 | 42 | 42 | 42 | 42 | 42 | 42 | 42 | 42 |
| oomcaa[3] | 42 | 40 | 39 | 34 | 31 | 42 | 39 | 36 | 40 | 42 | 35 | 41 | 40 | 40 | 40 | 13 | 28 | 30 | 18 |
| mcaa[4] | W | Y | Q | Q | L | P | G | T | A | P | K | L | L | I | Y | D | N | N | K |
| rel. oomcaa[5] | 100% | 95% | 93% | 81% | 74% | 100% | 93% | 86% | 95% | 100% | 83% | 98% | 95% | 95% | 95% | 31% | 67% | 71% | 43% |
| pos occupied[6] | 1 | 3 | 3 | 4 | 5 | 1 | 4 | 4 | 3 | 1 | 4 | 2 | 2 | 3 | 3 | 10 | 5 | 4 | 9 |

| | CDR II | | | | | | | Framework III | | | | | | | | | |
|---|---|---|---|---|---|---|---|---|---|---|---|---|---|---|---|---|---|
| amino acid[1] | 54 | 55 | 56 | A | B | C | D | E | 57 | 58 | 59 | 60 | 61 | 62 | 63 | 64 | 65 | 66 | A |
| A | | 1 | | | | | | | | | | | | | | 5 | | | |
| B | | | | | | | | | | | | | | | | | | | |
| C | | | | | | | | | | | | | | | | | | | |
| D | | | | | | | | | | | | 38 | | | | | | | |

TABLE 5A-continued

Analysis of V lambda subgroup 1

| amino acid[1] | | | | | | | | | | | | | | | | | | | |
|---|---|---|---|---|---|---|---|---|---|---|---|---|---|---|---|---|---|---|---|
| E | | | | | | | | | | | | | | | | | | | |
| F | | | | | | | | | | | | | | | | | | | |
| G | | | | | | 41 | | | | | 2 | | | 38 | | 36 | | | |
| H | | | | | | | | | | | 1 | | | | | | | | |
| I | | | | | | | 17 | | | | | 3 | | | | | | | |
| K | | | | | | | | | | | | | | | | | | 38 | |
| L | 1 | | 1 | | | | | | | 1 | | | | | | | | | |
| M | | | | | | | | | | | | | | | | | | | |
| N | | | | | | | | | | | | | | | | | | | |
| P | | 38 | | | | | | | | 38 | | | | | | | | | |
| Q | | | | | | | | | | | | | | | | | | | |
| R | 40 | | | | | | | | | | | 42 | | | 42 | | 4 | | |
| S | | 2 | 40 | | | | | | | 2 | | | 42 | | 42 | | | | |
| T | | | | | | | | | | | | | | 1 | | | | | |
| V | | | | | | | 24 | | | | 1 | | | | | | | | |
| W | 1 | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | 41 | 41 | 41 | 41 | 42 | | | | | | | | | | | 42 | |
| unknown (?) | | | | | | | | | | | | | | | | | | | |
| not sequenced | | 1 | 1 | | | | | 1 | 1 | 1 | 1 | | | | | | | | |
| sum of seq[2] | 42 | 41 | 41 | 41 | 41 | 41 | 41 | 42 | 41 | 41 | 41 | 41 | 42 | 42 | 42 | 42 | 42 | 42 | 42 |
| oomcaa[3] | 40 | 38 | 40 | 41 | 41 | 41 | 41 | 42 | 41 | 24 | 38 | 38 | 42 | 38 | 42 | 36 | 42 | 38 | 42 |
| mcaa[4] | R | P | S | — | — | — | — | — | G | V | P | D | R | F | S | G | S | K | — |
| rel. oomcaa[5] | 95% | 93% | 98% | 100% | 100% | 100% | 100% | 100% | 100% | 59% | 93% | 93% | 100% | 90% | 100% | 86% | 100% | 90% | 100% |
| pos occupied[6] | 3 | 3 | 2 | 1 | 1 | 1 | 1 | 1 | 1 | 2 | 3 | 3 | 1 | 3 | 1 | 3 | 1 | 2 | 1 |

| | Framework III | | | | | | | | | | | | | | | | | | |
|---|---|---|---|---|---|---|---|---|---|---|---|---|---|---|---|---|---|---|---|
| amino acid[1] | B | 67 | 68 | 69 | 70 | 71 | 72 | 73 | 74 | 75 | 76 | 77 | 78 | 79 | 80 | 81 | 82 | 83 | 84 |
| A | | | 1 | 3 | | 41 | | | 24 | | | | | | 2 | | | | 38 |
| B | | | | | | | | | | | | | | | | | | | |
| C | | | | | | | | | | | | | | | | | | | |
| D | | | 1 | | | | | | | | | | | | 1 | 41 | | | |
| E | | | | | | | | | | | | | | 1 | | 24 | | 42 | |
| F | | | | | | | | | | | | | | | | | | | |
| G | | | 40 | | | | | | 17 | | 1 | 42 | | 1 | 15 | | | | |
| H | | | | | | | | | | | | | | 1 | | | | | |
| I | | | | | | | | | | 41 | | | | | | | | | |
| K | | | | | | | | | | | | | | | | | | | |
| L | | | | | | | 42 | | | | | | 41 | | | | | | |
| M | | | | | | | | | | | | | | | | | | | |
| N | | | | | | | | | | | | | | | | | 1 | | |
| P | | | | | | | | | | | | | | | 2 | | | | |
| Q | | | | | | | | | | | | | | | 31 | | | | |
| R | | | | | | | | | | | | | | | 8 | | | | |
| S | | | 42 | | 1 | 42 | | 24 | | | 20 | | | | 20 | | | | 1 |
| T | | | | 38 | | | 18 | | | | 21 | | | | 17 | | | | 3 |
| V | | | | | 1 | | | | 1 | 1 | | | 1 | | 1 | | | | |
| W | | | | | | | | | | | | | 1 | | 2 | | | | |
| X | | | | | | | | | | | | | | | | | | | |
| Y | | | | | | | | | | | | | | | | | | | |
| Z | | | | | | | | | | | | | | | | | | | |
| — | 42 | | | | | | | | | | | | | | | | | | |
| unknown (?) | | | | | | | | | | | | | | | | | | | |
| not sequenced | | | | | | | | | | | | | | | | | | | |
| sum of seq[2] | 42 | 42 | 42 | 42 | 42 | 42 | 42 | 42 | 42 | 42 | 42 | 42 | 42 | 42 | 42 | 42 | 42 | 42 | 42 |
| oomcaa[3] | 42 | 42 | 40 | 38 | 42 | 41 | 24 | 42 | 24 | 41 | 21 | 42 | 41 | 31 | 20 | 24 | 41 | 42 | 38 |
| mcaa[4] | — | S | G | T | A | S | L | A | I | T | G | L | Q | S | E | D | E | A |
| rel. oomcaa[5] | 100% | 100% | 95% | 90% | 100% | 98% | 57% | 100% | 57% | 98% | 50% | 100% | 98% | 74% | 48% | 57% | 98% | 100% | 90% |
| pos occupied[6] | 1 | 1 | 3 | 3 | 1 | 2 | 2 | 1 | 3 | 2 | 3 | 1 | 2 | 5 | 5 | 4 | 2 | 1 | 3 |

| | Framework III | | | | CDR III | | | | | | | | | | | |
|---|---|---|---|---|---|---|---|---|---|---|---|---|---|---|---|---|---|
| amino acid[1] | 85 | 86 | 87 | 88 | 89 | 90 | 91 | 92 | 93 | 94 | 95 | A | B | C | D | E | F | 96 |
| A | 1 | | | | 22 | 15 | | | 1 | | | | 16 | | | | | 4 |
| B | | | | | | | | | | | | | | | | | | |
| C | | | | 42 | | | | | | | | | | | | | | |
| D | 37 | | | | | | | 39 | 17 | | | 7 | | | | | | |
| E | 1 | | | | | | | | | | | | 1 | | | | | 1 |

TABLE 5A-continued

Analysis of V lambda subgroup 1

| | | | | | | | | | | | | | | | | | | | |
|---|---|---|---|---|---|---|---|---|---|---|---|---|---|---|---|---|---|---|---|
| F | | | 2 | | | | | | 1 | | | | | | | | | | |
| G | | | | 14 | | | | 1 | | | | 17 | 1 | | | | | 5 | |
| H | 2 | | 1 | | | | | | | | | | | 1 | | | | | | |
| I | 1 | | | | | | | | | | | 1 | | | | | | | | |
| K | | | | | | | | | | | | 1 | | | | | | | | |
| L | | | | 1 | | | | | | 37 | | | | 1 | | | | | | |
| M | | | | | | | | | | | | | | | | | | | | |
| N | | | | | | 2 | 2 | | | | 9 | 1 | | | | | | | |
| P | | | | | | | | 1 | | | | | | | | | | | 6 |
| Q | | | | 3 | | | | | | | | | | | | | | | | |
| R | | | | | | | | 5 | 1 | 2 | | | | | | | | 2 | |
| S | | | | | 4 | | 17 | 35 | | 18 | | 1 | | | | | 1 | | |
| T | | | | | 22 | | 1 | 1 | | 1 | | | | | | | | | |
| V | | | | 1 | | | 1 | | 1 | | 2 | | | | | | | 9 | |
| W | | | | | | 38 | | | | | | | | | | | | 7 | |
| X | | | | | | | | | | | | | | | | | | | | |
| Y | | 42 | 39 | | | | 3 | | 1 | | | | | | | | | 3 | |
| Z | | | | | | | | | | | | | | | | | | | | |
| — | | | | | | | | | | | 2 | 4 | 35 | 39 | 38 | 38 | 1 | | |
| unknown (?) | | | | | | | | | | | | | | | | | | | | |
| not sequenced | | | | | 1 | 1 | 1 | 1 | 1 | 1 | 1 | 1 | 1 | 3 | 3 | 3 | 3 | 3 | |
| sum of seq[2] | 42 | 42 | 42 | 42 | 41 | 41 | 41 | 41 | 41 | 41 | 41 | 41 | 41 | 39 | 39 | 38 | 38 | 39 | |
| oomcaa[3] | 37 | 42 | 39 | 42 | 22 | 22 | 38 | 39 | 17 | 35 | 37 | 18 | 17 | 35 | 39 | 38 | 38 | 9 | |
| mcaa[4] | D | Y | Y | C | A | T | W | D | D | S | L | S | G | — | — | — | — | V | |
| rel. oomcaa[5] | 88% | 100% | 93% | 100% | 54% | 54% | 93% | 95% | 41% | 85% | 90% | 44% | 41% | 90% | 100% | 100% | 100% | 23% | |
| pos occupied[6] | 5 | 1 | 3 | 1 | 5 | 3 | 2 | 2 | 8 | 3 | 5 | 8 | 6 | 5 | 1 | 1 | 1 | 10 | |

| | Framework IV | | | | | | | | | | | | |
|---|---|---|---|---|---|---|---|---|---|---|---|---|---|
| amino acid[1] | 97 | 98 | 99 | 100 | 101 | 102 | 103 | 104 | 105 | 106 | A | 107 | 108 | sum |
| A | 1 | | | | | | | | | | | | | 285 |
| B | | | | | | | | | | | | | | |
| C | | | | | | | | | | | | | | 84 |
| D | | | | | | | | | | | | | | 224 |
| E | | | | | 1 | | | | | | | | | 81 |
| F | | 36 | | | | | | | | | | | | 87 |
| G | 1 | | 36 | 31 | 36 | | | | | | | 26 | | 559 |
| H | | | | | | | | | | | | | | 25 |
| I | 1 | | | | | | | | | | | | | 188 |
| K | | | | | | | | 30 | | | | | | 141 |
| L | 1 | | | | | | | | 25 | | | 34 | | 344 |
| M | 1 | | | | | | | | | | | | | 5 |
| N | | | | | | | 1 | | | | | | | 176 |
| P | | | | | | | | | | | | | 1 | 296 |
| Q | | | | | | | 3 | | | | | 1 | 18 | 251 |
| R | | | | | | | | 1 | | | | 2 | | 156 |
| S | | | | 1 | | | | | | | | 2 | | 720 |
| T | | | | 3 | | 36 | 1 | | 36 | | | | | 359 |
| V | 34 | | | | | | | 11 | | 36 | 1 | | | 282 |
| W | | | | | | | | | | | 1 | | | 92 |
| X | | | | | | | | | | | | | | |
| Y | | | | | | | | | | | | | | 202 |
| Z | | | | | | | | | | | | | | 16 |
| — | | | | | | | | | | | | | | 524 |
| unknown (?) | | | | | | | | | | | | | | |
| not sequenced | 3 | 4 | 4 | 6 | 6 | 6 | 6 | 6 | 6 | 6 | 6 | 10 | 22 | 141 |
| sum of seq[2] | 39 | 36 | 36 | 36 | 36 | 36 | 36 | 36 | 36 | 36 | 36 | 31 | 19 | |
| oomcaa[3] | 34 | 36 | 36 | 31 | 36 | 36 | 30 | 25 | 36 | 36 | 34 | 26 | 18 | |
| mcaa[4] | V | F | G | G | G | T | K | L | T | V | L | G | Q | |
| rel. oomcaa[5] | 87% | 100% | 100% | 86% | 100% | 100% | 83% | 69% | 100% | 100% | 94% | 84% | 95% | |
| pos occupied[6] | 6 | 1 | 1 | 4 | 1 | 1 | 5 | 2 | 1 | 1 | 3 | 4 | 2 | |

TABLE 5B

Analysis of V lambda subgroup 2

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | 35 | | | | | 30 | | | 6 | | 1 | 1 | | | | |
| B | | | | | | | | | | | | | | | | | | | |
| C | | | | | | | | | | | | | | | | | | | |

TABLE 5B-continued

Analysis of V lambda subgroup 2

| amino acid[1] | | | | | | | | | | | | | | | | | | | |
|---|---|---|---|---|---|---|---|---|---|---|---|---|---|---|---|---|---|---|---|
| D | | | | | | | | | | | | | | 1 | | | | | |
| E | | | | | | | | | | | | | | | | | | | |
| F | | | | | | | | | | | | | | | | | | | |
| G | | | | | | | | | | | | | 42 | | | 42 | | | |
| H | 2 | | | | | | | | | | | | | | | | 1 | | |
| I | | | 1 | | | | | | | | | | | | | | | | 28 |
| K | | | | | | | | | | | | | | | | | | | |
| L | | | | 40 | | | | | | | | | | | 3 | | | | 1 |
| M | | | | | | | | | | | | | | | | | | | |
| N | | | | | | | | | | | | | | | | | | | |
| P | | | | | | | 42 | 6 | | | | | | 40 | | | | | |
| Q | 22 | | 4 | | 41 | | | | | | | | | | | 42 | | | |
| R | | | | | | | | 6 | 1 | | | | | | | | | | |
| S | | 41 | | | | | | | 40 | | 42 | | | 42 | | | | 43 | |
| T | | | | | 42 | | | | 1 | | | | | | | | | | |
| V | | 1 | 2 | | | | | | | | | | 36 | | | | | | 14 |
| W | | | | | | | | | | | | | | | | | | | |
| X | | | | | | | | | | | | | | | | | | | |
| Y | | | | | | | | | | | | | | | | | | | |
| Z | 16 | | | | | | | | | | | | | | | | | | |
| — | | | | | | | | | | 42 | | | | | | | | | |
| unknown (?) | | | | | | 1 | | | | | | | | | | | | | |
| not sequenced | 3 | 1 | 1 | 3 | 1 | 1 | 1 | 1 | 1 | 1 | 1 | 1 | | | | | | | |
| sum of seq[2] | 40 | 42 | 42 | 40 | 42 | 42 | 42 | 42 | 42 | 42 | 42 | 42 | 43 | 43 | 43 | 43 | 43 | 43 | 43 |
| oomcaa[3] | 22 | 41 | 35 | 40 | 42 | 41 | 42 | 30 | 40 | 42 | 36 | 42 | 42 | 42 | 40 | 42 | 42 | 43 | 28 |
| mcaa[4] | Q | S | A | L | T | Q | P | A | S | — | V | S | G | S | P | G | Q | S | I |
| rel. oomcaa[5] | 55% | 98% | 83% | 100% | 100% | 98% | 100% | 71% | 95% | 100% | 86% | 100% | 98% | 98% | 93% | 98% | 98% | 100% | 65% |
| pos occupied[6] | 3 | 2 | 4 | 1 | 1 | 1 | 1 | 3 | 3 | 1 | 2 | 1 | 2 | 2 | 2 | 2 | 2 | 1 | 3 |

| | Framework I | | | | CDR I | | | | | | | | | | | | | |
|---|---|---|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 |
| A | | | | | 3 | 1 | | | | | | 1 | | | 1 | 1 | | |
| B | | | | | | | | | | | | | | | | | | |
| C | | | | 42 | | | | 1 | | | | | 1 | | | | | |
| D | | | | | | | | | 39 | | 1 | 4 | | 5 | | | | |
| E | | | | | | | | | | | | | | 1 | | | | |
| F | | 1 | | | | | | | | | 1 | | | | 4 | | | |
| G | | | | | | 43 | | 1 | | | 39 | 26 | | | | 1 | 1 | |
| H | | | | | | | | 1 | | | | | | | | 1 | 1 | |
| I | | 41 | | | 1 | | | | | 6 | | | | 4 | | | | |
| K | | | | | | | | | | | | | | 4 | | | | |
| L | | 1 | | | | | | | | | | | | | | | | |
| M | | | | | | | | | | | | | | | | | | |
| N | | | | | | | | 1 | 3 | 4 | | 1 | 4 | 3 | 28 | | | |
| P | | | | | | | | | 1 | | | | | | | | | |
| Q | | | | | | | | | | | | | | | | | | |
| R | | | | | | | | 1 | | | | 2 | | | | | | |
| S | | | 42 | | 3 | | 3 | 35 | 38 | | | 5 | 1 | 2 | 4 | 1 | | 42 |
| T | 43 | | | | 36 | | 39 | 3 | | | | | 1 | | 1 | | | |
| V | | | | | | | | | | 37 | | | | | | | 41 | |
| W | | | | | | | | | | | | | | | | | | |
| X | | | | | | | | | | | | | | | | | | |
| Y | | | | | | | | | 1 | | | 1 | | 37 | 29 | | | |
| Z | | | | | | | | | | | | | | | | | | |
| — | | | | | | | | | | | | | | | 1 | | | |
| unknown (?) | | | | | | | | | | | | | | | 1 | | | |
| not sequenced | | | 1 | 1 | | | | | | | | | | | | | 1 | 1 |
| sum of seq[2] | 43 | 43 | 42 | 42 | 43 | 43 | 43 | 43 | 43 | 43 | 43 | 43 | 43 | 43 | 43 | 43 | 42 | 42 |
| oomcaa[3] | 43 | 41 | 42 | 42 | 36 | 43 | 39 | 35 | 38 | 39 | 37 | 39 | 26 | 37 | 28 | 29 | 41 | 42 |
| mcaa[4] | T | I | S | C | T | G | T | S | D | V | G | Y | N | Y | V | S | | |
| rel. oomcaa[5] | 100% | 95% | 100% | 100% | 84% | 100% | 91% | 81% | 88% | 91% | 86% | 91% | 60% | 86% | 65% | 67% | 98% | 100% |
| pos occupied[6] | 1 | 3 | 1 | 1 | 4 | 1 | 3 | 7 | 4 | 2 | 2 | 5 | 7 | 5 | 7 | 6 | 2 | 1 |

| | Framework II | | | | | | | | | | | | | | | CDR II | | | |
|---|---|---|---|---|---|---|---|---|---|---|---|---|---|---|---|---|---|---|---|
| amino acid[1] | 35 | 36 | 37 | 38 | 39 | 40 | 41 | 42 | 43 | 44 | 45 | 46 | 47 | 48 | 49 | 50 | 51 | 52 | 53 |
| A | | | | | | 1 | 4 | | 40 | | | | | | | | | | |
| B | | | | | | | | | | | | | | | | | | | |
| C | | | | | | | | | | | | | | | | | | | |
| D | | | | 1 | | 2 | | | | | | | | | | 20 | 1 | 2 | 1 |
| E | | | | | | | | | | | | | | | | 20 | | | 2 |
| F | | 2 | | | | | | | | | | | | 7 | | | 1 | | |

TABLE 5B-continued

Analysis of V lambda subgroup 2

| amino acid | | | | | | | | | | | | | | | | | | | |
|---|---|---|---|---|---|---|---|---|---|---|---|---|---|---|---|---|---|---|---|
| G | | | | | 36 | | | | | | | | | | | 2 | 2 | | 1 |
| H | | | 2 | 34 | | | | | | | | | | | | | | | 1 |
| I | | | | | | 1 | | | | | 1 | 9 | 43 | | | | 1 | | |
| K | | | | | | 40 | | | | | 41 | | | | | | | 1 | 21 |
| L | | | 1 | 1 | | | | | | | | 38 | 6 | | | | | | |
| M | | | | | | | | | | | | | 26 | | | | | 1 | |
| N | | | | 2 | | | | | | | | | | | | 1 | | 8 | 12 |
| P | | | | | | 41 | | | | 43 | | | | | | | | | |
| Q | | 41 | 39 | | | | | | | 2 | | | | | | | | | |
| R | | | 1 | | | | 1 | | | | | | | | | | | 2 | |
| S | | | | | 1 | | | | | | | | | | | 2 | | 21 | 3 |
| T | | | | | | | 1 | | | | | | | | | | | 7 | |
| V | | | | | | 1 | | 3 | | | | 4 | 2 | | | | 39 | | |
| W | 43 | | | | | | | | | | | | | | | | | | |
| X | | | | | | | | | | | | | | | | | | | |
| Y | | 41 | | | 5 | | | | | | | | | | | 34 | | | 2 |
| Z | | | | | | | | | | | | | | | | | | | |
| — | | | | | | | | | | | | | | | | | | | |
| unknown (?) | | | 1 | 1 | | | | | | | | | | | | | | | |
| not sequenced | | | | | | | | | | | | | | | | | | | |
| sum of seq[2] | 43 | 43 | 43 | 43 | 43 | 43 | 43 | 43 | 43 | 43 | 43 | 43 | 43 | 43 | 43 | 43 | 43 | 43 | 43 |
| oomcaa[3] | 43 | 41 | 41 | 39 | 34 | 41 | 36 | 40 | 40 | 43 | 41 | 38 | 26 | 43 | 34 | 20 | 39 | 21 | 21 |
| mcaa[4] | W | Y | Q | Q | H | P | G | K | A | P | K | L | M | I | Y | D | V | S | K |
| rel. oomcaa[5] | 100% | 95% | 95% | 91% | 79% | 95% | 84% | 93% | 93% | 100% | 95% | 88% | 60% | 100% | 79% | 47% | 91% | 49% | 49% |
| pos occupied[6] | 1 | 2 | 2 | 3 | 5 | 3 | 4 | 4 | 2 | 1 | 2 | 3 | 4 | 1 | 3 | 4 | 4 | 8 | 8 |

| | CDR II | | | | | | | | Framework III | | | | | | | | | |
|---|---|---|---|---|---|---|---|---|---|---|---|---|---|---|---|---|---|---|
| amino acid[1] | 54 | 55 | 56 | A | B | C | D | E | 57 | 58 | 59 | 60 | 61 | 62 | 63 | 64 | 65 | 66 | A |
| A | | | | | | | | | | | | | | | | 2 | | | |
| B | | | | | | | | | | | | | | | | | | | |
| C | | | | | | | | | | | | | | | | | 1 | | |
| D | | | | | | | | | | | | 17 | | | | | | | |
| E | | | | | | | | | | | | | | 42 | | | | | |
| F | | | | | | | | | | | | | | 42 | | | | | |
| G | | | | | | | | | 43 | 1 | | | | | 41 | | | | |
| H | | | | | | | | | | | | 2 | | | | | | | |
| I | | | | | | | | | | 3 | | | | | | | | | |
| K | | | | | | | | | | | | | | | | | | 42 | |
| L | | | | | | | | | | | | 1 | | 1 | | | | | |
| M | | | | | | | | | | | | | | | | | | | |
| N | | | | | | | | | | | | 19 | | | | | | | |
| P | | 43 | | | | | | | | | 15 | | | | | | | | |
| Q | | | | | | | | | | | | | | | | | | | |
| R | 43 | | | | | | | | | | | | | 43 | | 43 | | 1 | |
| S | | | 43 | | | | | | | 28 | 2 | | | | 43 | | 42 | | |
| T | | | | | | | | | | | | | | | | | | | |
| V | | | | | | | | | | 39 | | | | | | | | | |
| W | | | | | | | | | | | | | | | | | | | |
| X | | | | | | | | | | | | | | | | | | | |
| Y | | | | | | | | | | | | 2 | | | | | | | |
| Z | | | | | | | | | | | | | | | | | | | |
| — | | | | 43 | 43 | 43 | 43 | 43 | | | | | | | | | | | 43 |
| unknown (?) | | | | | | | | | | | | | | | | | | | |
| not sequenced | | | | | | | | | | | | | | | | | | | |
| sum of seq[2] | 43 | 43 | 43 | 43 | 43 | 43 | 43 | 43 | 43 | 43 | 43 | 43 | 43 | 43 | 43 | 43 | 43 | 43 | 43 |
| oomcaa[3] | 43 | 43 | 43 | 43 | 43 | 43 | 43 | 43 | 43 | 39 | 28 | 19 | 43 | 42 | 43 | 41 | 42 | 42 | 43 |
| mcaa[4] | R | P | S | — | — | — | — | — | G | V | S | N | R | F | S | G | S | K | — |
| rel. oomcaa[5] | 100% | 100% | 100% | 100% | 100% | 100% | 100% | 100% | 100% | 91% | 65% | 44% | 100% | 98% | 100% | 95% | 98% | 98% | 100% |
| pos occupied[6] | 1 | 1 | 1 | 1 | 1 | 1 | 1 | 1 | 1 | 3 | 2 | 6 | 1 | 2 | 1 | 2 | 2 | 2 | 1 |

| | Framework III | | | | | | | | | | | | | | | | | |
|---|---|---|---|---|---|---|---|---|---|---|---|---|---|---|---|---|---|---|
| amino acid[1] | B | 67 | 68 | 69 | 70 | 71 | 72 | 73 | 74 | 75 | 76 | 77 | 78 | 79 | 80 | 81 | 82 | 83 | 84 |
| A | | | 3 | | 1 | 43 | | | | | | | | | 36 | | | | 43 |
| B | | | | | | | | | | | | | | | | | | | |
| C | | | | | | | | | | | | | | | | | | | |
| D | | | 1 | 2 | | | | | | | | | | | 3 | 42 | | | |
| E | | | | | | | | | | | | 1 | | | 38 | | 43 | | |
| F | | | | | | | | | | | | | | | | | | | |
| G | | | 39 | | | | | | | | | | 42 | | | 1 | | | |

TABLE 5B-continued

Analysis of V lambda subgroup 2

| amino acid | | | | | | | | | | | | | | | | | | | |
|---|---|---|---|---|---|---|---|---|---|---|---|---|---|---|---|---|---|---|---|
| H | | | | | | | | | | | | | | | | | | | |
| I | | | | | | | | | | 35 | | | | | | | | | |
| K | | | 1 | | | | | | | | | | | | | | | | |
| L | | | | | | | 43 | | | | | | 43 | | | | | | |
| M | | | | | | | | | | | | | | | | | | | |
| N | | | 38 | | | | | | | | | | | | | 1 | 1 | | |
| P | | | | | | | | | | | | | | | 2 | | | | |
| Q | | | | | | | | | | | | | | 41 | | | | | |
| R | | | | | | | | | | | | | | 2 | | | | | |
| S | | 42 | | | | 43 | | | | | 42 | | | | | | | | |
| T | | | 1 | 41 | | | | 43 | | | 1 | | | | 2 | | | | |
| V | | | | | | | | | 8 | | | | | | 3 | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | 43 | | | | | | | | | | | | | | | | | | |
| unknown (?) | | | 1 | | | | | | | | | | | | | | | | |
| not sequenced | | 1 | | | | | | | | | | | | | | | | | |
| sum of seq[2] | 43 | 42 | 43 | 43 | 43 | 43 | 43 | 43 | 43 | 43 | 43 | 43 | 43 | 43 | 43 | 43 | 43 | 43 | 43 |
| oomcaa[3] | 43 | 42 | 39 | 38 | 41 | 43 | 43 | 43 | 35 | 42 | 42 | 43 | 41 | 36 | 38 | 42 | 43 | 43 |
| mcaa[4] | — | S | G | N | T | A | S | L | T | I | S | G | L | Q | A | E | D | E | A |
| rel. oomcaa[5] | 100% | 100% | 91% | 88% | 95% | 100% | 100% | 100% | 100% | 81% | 98% | 98% | 100% | 95% | 84% | 88% | 98% | 100% | 100% |
| pos occupied[6] | 1 | 1 | 3 | 4 | 3 | 1 | 1 | 1 | 1 | 2 | 2 | 2 | 1 | 2 | 4 | 4 | 2 | 1 | 1 |

| | Framework III | | | | CDR III | | | | | | | | | | | | |
|---|---|---|---|---|---|---|---|---|---|---|---|---|---|---|---|---|---|
| amino acid[1] | 85 | 86 | 87 | 88 | 89 | 90 | 91 | 92 | 93 | 94 | 95 | A | B | C | D | E | F | 96 |
| A | | | | | 2 | 1 | | 21 | | 1 | | | | | | | | 1 |
| B | | | | | | | | | | | | | | | | | | |
| C | | | | 43 | 11 | | | | | | | | | | | | | |
| D | 39 | | | | | | | 3 | 1 | 2 | | | | | | | | 1 |
| E | | | | | | | 1 | 1 | | | | | | | | | | |
| F | | | 3 | | | | 3 | | | 1 | | 1 | | | | | | 5 |
| G | | | | | | | | 1 | 21 | 3 | 4 | | | | | | | 1 |
| H | 2 | | | | | | 1 | | | | | | | | | | | |
| I | | | | | | | | 1 | 1 | | 1 | 2 | | | | | | 1 |
| K | | | | | | | | | | | 3 | | | | | | | |
| L | | | | | | | | | | | | 1 | 1 | | | | | 6 |
| M | | | | | | | | | | | | | | | | | | 1 |
| N | 1 | | | | | | | | | 5 | 7 | 5 | | | | | | 1 |
| P | | | | | | | | | 1 | | | 4 | | | | | | |
| Q | | | | | | | | | | 3 | 1 | 2 | | | | | | |
| R | | | | | | | | 2 | | 3 | | 1 | | | | | | 5 |
| S | | | 1 | | 30 | 41 | | | 12 | 23 | 14 | 9 | | | | | | 1 |
| T | | | | | | | | 16 | 4 | 4 | 3 | 21 | | | | | | |
| V | | | | | | | | 1 | | | | | | | | | | 11 |
| W | | | | | | | | | | | | | | | | | | 5 |
| X | | | | | | | | | | | | | | | | | | |
| Y | | 43 | 39 | | | | 39 | | | 1 | 6 | | | | | | | 4 |
| Z | | | | | | | | | | | | | | | | | | |
| — | | | | | | | | | | | 1 | 3 | 36 | 42 | 43 | 43 | 43 | |
| unknown (?) | 1 | | | | | | | | | | 2 | | | | | | | |
| not sequenced | | | | | | 1 | | | | | | 1 | | | | | | |
| sum of seq[2] | 43 | 43 | 43 | 43 | 43 | 42 | 43 | 43 | 43 | 43 | 43 | 42 | 43 | 43 | 43 | 43 | 43 | 43 |
| oomcaa[3] | 39 | 43 | 39 | 43 | 30 | 41 | 39 | 21 | 21 | 23 | 14 | 21 | 36 | 42 | 43 | 43 | 43 | 11 |
| mcaa[4] | D | Y | Y | C | S | S | Y | A | G | S | S | T | — | — | — | — | — | V |
| rel. oomcaa[5] | 91% | 100% | 91% | 100% | 70% | 98% | 91% | 49% | 49% | 53% | 33% | 50% | 84% | 98% | 100% | 100% | 100% | 26% |
| pos occupied[6] | 3 | 1 | 3 | 1 | 3 | 2 | 3 | 7 | 7 | 8 | 11 | 6 | 5 | 2 | 1 | 1 | 1 | 13 |

| | Framework IV | | | | | | | | | | | | |
|---|---|---|---|---|---|---|---|---|---|---|---|---|---|
| amino acid[1] | 97 | 98 | 99 | 100 | 101 | 102 | 103 | 104 | 105 | 106 | A | 107 | 108 | sum |
| A | 1 | | | 1 | | | | | | | | | | 280 |
| B | | | | | | | | | | | | | | 99 |
| C | | | | | | | | | | | | | | 188 |
| D | | | | | | | | | | | | | | 107 |
| E | | | | | | | | | | | | | | 113 |
| F | | 42 | | | | | | | | | | | | 567 |
| G | | | 42 | 33 | 42 | | | | | | | 19 | | 48 |
| H | | | | | | | | | | | | | | 184 |
| I | 7 | | | | | | | | | 1 | | | | 189 |
| K | | | | | | | | | 36 | | | | | |

TABLE 5B-continued

Analysis of V lambda subgroup 2

| amino acid | | | | | | | | | | | | | |
|---|---|---|---|---|---|---|---|---|---|---|---|---|---|
| L | 5 | | | | | | | 28 | | 40 | | | 264 |
| M | 1 | | | | | | | | | | | | 29 |
| N | | | | | | | 1 | | | | | | 146 |
| P | | | | | | | | | | | | | 238 |
| Q | | | | | | | 1 | | | | | 14 | 250 |
| R | | | | 1 | | | 2 | | | | 4 | | 121 |
| S | | | | | | | | | 1 | | 2 | | 831 |
| T | | | | | 7 | 41 | | | 40 | | | | 398 |
| V | 28 | | | | | | | 14 | | 42 | 1 | | 327 |
| W | | | | | | | | | | | | | 48 |
| X | | | | | | | | | | | | | |
| Y | | | | | | | | | 1 | | | | 285 |
| Z | | | | | | | | | | | | | 16 |
| — | | | | | | | | | | | | | 555 |
| unknown (?) | | | | | | | | | | | | | 8 |
| not sequenced | 1 | 1 | 1 | 1 | 1 | 2 | 2 | 1 | 1 | 1 | 2 | 15 | 28 | 80 |
| sum of seq[2] | 42 | 42 | 42 | 42 | 42 | 41 | 41 | 42 | 42 | 42 | 41 | 25 | 14 | |
| oomcaa[3] | 28 | 42 | 42 | 33 | 42 | 41 | 36 | 28 | 40 | 42 | 40 | 19 | 14 | |
| mcaa[4] | V | F | G | G | G | T | K | L | T | V | L | G | Q | |
| rel. oomcaa[5] | 67% | 100% | 100% | 79% | 100% | 100% | 88% | 67% | 95% | 100% | 98% | 76% | 100% | |
| pos occupied[6] | 5 | 1 | 1 | 4 | 1 | 1 | 5 | 2 | 3 | 1 | 2 | 3 | 1 | |

TABLE 5C

Analysis of V lambda subgroup 3

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | | 1 | | 1 | 2 | 7 | | | | | 20 | 1 | | | 27 |
| B | | | | | | | | | | | | | | | | | | | |
| C | | | | | | | | | | | | | | | | | | | |
| D | | | | 5 | | | 10 | | | | | | | | | | | | |
| E | | | 20 | | | | | | | | | | | 1 | | 1 | | | |
| F | 1 | 1 | | | | | | | | | | 1 | | | 1 | | | | |
| G | | | | 1 | | | | | | | | | | | | 37 | | | |
| H | | | | | | | | | | | | | | | | | | | |
| I | | | | | | | | | | | | | | | | | | | |
| K | | | | | | | | | | | | | | | | | 2 | | |
| L | | | | 37 | | | | | | | 4 | | 1 | | 9 | | | | |
| M | | | | | | | | | | | | | | | | | | | |
| N | | | | | | | | | | | | | | | | | | | |
| P | | | | | | | 26 | 35 | 1 | | | | | | 27 | | | | 1 |
| Q | 4 | | 4 | | | 38 | | | | | | | | | | | 36 | | |
| R | | | | | | | | | | | | | | | | | | | |
| S | 13 | 14 | | | 1 | | 1 | | 28 | | | 37 | | 18 | | | | | |
| T | | | | | 36 | | | 1 | | | | | | | | | | 38 | |
| V | | | 8 | 1 | | | | | 2 | | 34 | | 36 | | | | | | 10 |
| W | | | | | | | | | | | | | | | | | | | |
| X | | | | | | | | | | | | | | | | | | | |
| Y | | 23 | | | | | | | | | | | | | | | | | |
| Z | | | | | | | | | | | | | | | | | | | |
| — | 20 | | | | | | | | | 38 | | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 20 | 23 | 20 | 37 | 36 | 38 | 26 | 35 | 28 | 38 | 34 | 37 | 36 | 20 | 27 | 37 | 36 | 38 | 27 |
| mcaa[4] | — | Y | E | L | T | Q | P | P | S | — | V | S | V | A | P | G | Q | T | A |
| rel. oomcaa[5] | 53% | 61% | 53% | 97% | 95% | 100% | 68% | 92% | 74% | 100% | 89% | 97% | 95% | 53% | 71% | 97% | 95% | 100% | 71% |
| pos occupied[6] | 4 | 3 | 5 | 2 | 3 | 1 | 4 | 3 | 4 | 1 | 2 | 2 | 3 | 2 | 4 | 2 | 2 | 1 | 3 |

| | Framework I | | | | CDRI | | | | | | | | | | | |
|---|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 |
| A | | | 1 | | | | | 5 | | | | | 1 | 1 | | | 21 | 3 |
| B | | | | | | | | | | | | | | | | | | |
| C | | | | 38 | | | | | | | | | | | | | | 5 |
| D | | | | | | 30 | 1 | | | | | | 10 | | | 3 | | 1 |
| E | | | | | | 2 | 2 | | | | | 1 | 3 | 6 | | | | |
| F | | | | | | | | | | | | | | 1 | | 2 | | |

TABLE 5C-continued

Analysis of V lambda subgroup 3

| amino acid[1] | | | | | | | | | | | | | | | | | | |
|---|---|---|---|---|---|---|---|---|---|---|---|---|---|---|---|---|---|---|
| G | | | | | 9 | 38 | | 1 | | | 23 | 4 | | | | 2 | | 9 |
| H | | | | | | | 1 | | | | | | | | | | | |
| I | | 38 | | | | | | | | 9 | | | 1 | | | | | |
| K | | | | | | | 7 | | | | | 2 | 13 | | | | | |
| L | | | | | | | | | | | 28 | | | | | | | |
| M | 1 | | | | | | | | | | | | | 1 | | | | |
| N | | | 2 | | | 4 | 9 | | | 1 | | 2 | | | | 1 | | 2 |
| P | | | 1 | | | | | | | | 3 | | | | | | | |
| Q | | | | 10 | | | | | | | | | 4 | | | | | |
| R | 25 | | | | | | 2 | | | | 10 | 1 | | | | | 1 | |
| S | 9 | | 1 | 19 | | | 10 | | | | | 11 | 2 | | | 8 | | 14 |
| T | 3 | | 33 | | | | 1 | | | | 1 | 4 | | | | | | |
| V | | | | | | | | | | | | | | | | 1 | 15 | |
| W | | | | | | | | | | | | | | | | | | |
| X | | | | | | | | | | | | | | | | | | |
| Y | | | | | | 1 | | | | | | 8 | | | 20 | 1 | 4 | |
| Z | | | | | | | | | | | | | | | | | | |
| — | | | | | | | | 38 | 38 | | | | | 37 | | | | |
| unknown (?) | | | | | | | | | | | | | | | | | | |
| not sequenced | | | | | | | | | | | | | 1 | 1 | | | | |
| sum of seq[2] | 38 | 38 | 38 | 38 | 38 | 38 | 38 | 38 | 38 | 38 | 38 | 38 | 38 | 37 | 37 | 37 | 38 | 38 |
| oomcaa[3] | 25 | 38 | 33 | 38 | 19 | 38 | 30 | 10 | 38 | 38 | 28 | 23 | 11 | 13 | 37 | 20 | 21 | 14 |
| mcaa[4] | R | I | T | C | S | G | D | S | — | — | L | G | S | K | — | Y | A | S |
| rel. oomcaa[5] | 66% | 100% | 87% | 100% | 50% | 100% | 79% | 26% | 100% | 100% | 74% | 61% | 29% | 35% | 100% | 54% | 55% | 37% |
| pos occupied[6] | 4 | 1 | 5 | 1 | 3 | 1 | 5 | 9 | 1 | 1 | 3 | 5 | 9 | 9 | 1 | 7 | 4 | 7 |

| | Framework II | | | | | | | | | | | | | | CDR II | | | |
|---|---|---|---|---|---|---|---|---|---|---|---|---|---|---|---|---|---|---|
| amino acid[1] | 35 | 36 | 37 | 38 | 39 | 40 | 41 | 42 | 43 | 44 | 45 | 46 | 47 | 48 | 49 | 50 | 51 | 52 | 53 |
| A | | | | | | | | | 23 | | | | | | | | 1 | | 1 |
| B | | | | | | | | | | | | | | | | | | | |
| C | | | | | | | | | | | | | | | | | | | |
| D | | | | | | | | | | | | | | | | 9 | 22 | 2 | 8 |
| E | | | | 1 | | | | | | | | | | | | 5 | 3 | | 3 |
| F | | 3 | | | | | | | | | | | | | 2 | | | 1 | |
| G | | | | | | 36 | | | | | | | | | | 9 | 2 | | |
| H | | | | | | | | 1 | | | | | | | 1 | 3 | | | 1 |
| I | | | | | | | | | | | 1 | | | 28 | | | | 1 | |
| K | | | | | 32 | | | | | | | | | | | 2 | 6 | 1 | 13 |
| L | | | | 2 | | | | | | | 6 | 33 | 1 | | | | | | |
| M | | | | | | | | | | | | 1 | | 1 | | | | | |
| N | | | | | | | | | | | | | | | | 1 | 19 | 9 | |
| P | | | | | | 36 | | 1 | | 38 | | | | | | | | | |
| Q | | | 37 | 35 | 1 | | 36 | | | | | | | | | 9 | | | 1 |
| R | | | 1 | | 4 | | 2 | | | | | | | | | 1 | 1 | | 1 |
| S | | | | 1 | 2 | | | 14 | | | | | | | | | 2 | 10 | 1 |
| T | | | | | | | | | | | | | | | | | | 4 | |
| V | | | | | | | | | 1 | | 31 | 4 | 37 | 9 | | | | | |
| W | 38 | | | | | | | | | | | | | | | | | | |
| X | | | | | | | | | | | | | | | | | | | |
| Y | | 35 | | | | | | | | | | | | | 35 | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 38 | 35 | 37 | 35 | 32 | 36 | 36 | 36 | 23 | 38 | 31 | 33 | 37 | 28 | 35 | 9 | 22 | 19 | 13 |
| mcaa[4] | W | Y | Q | Q | K | P | G | Q | A | P | V | L | V | I | Y | D | D | N | K |
| rel. oomcaa[5] | 100% | 92% | 97% | 92% | 84% | 95% | 95% | 95% | 61% | 100% | 82% | 87% | 97% | 74% | 92% | 24% | 58% | 50% | 34% |
| pos occupied[6] | 1 | 2 | 2 | 3 | 4 | 2 | 2 | 3 | 3 | 1 | 3 | 3 | 2 | 3 | 3 | 7 | 8 | 7 | 9 |

| | CDR II | | | | | | | Framework III | | | | | | | | | |
|---|---|---|---|---|---|---|---|---|---|---|---|---|---|---|---|---|---|
| amino acid[1] | 54 | 55 | 56 | A | B | C | D | E | 57 | 58 | 59 | 60 | 61 | 62 | 63 | 64 | 65 | 66 | A |
| A | | 1 | | | | | | | | | | | | | | | | | |
| B | | | | | | | | | | | | | | | | | | | |
| C | | | | | | | | | | | | | | | | | | | |
| D | | | | | | | | | | | | | 9 | | | | | | |
| E | | | | | | | | | | | | | 27 | | | | | | |
| F | | | | | | | | | | | | | | | 38 | | | | |
| G | | | | | | | | | 38 | | | | | | | 38 | | | |

TABLE 5C-continued

Analysis of V lambda subgroup 3

| amino acid[1] | B | | | | | | | | | | | | | | | | | | |
|---|---|---|---|---|---|---|---|---|---|---|---|---|---|---|---|---|---|---|---|
| H | | | | | | | | | | | | | | | | | | | |
| I | | | | | | | | | | | | | | | | | | | |
| K | | | | | | | | | 37 | | | | | | | | | | |
| L | | | | | | | | | | | | | | | | | | | |
| M | | | | | | | | | | | | | | | | | | | |
| N | | | | | | | | | | | | | | | | | | | 21 |
| P | | 37 | 1 | | | | | | | 36 | | | | | | | | | |
| Q | | | | | | | | | | | | | | | | | | | |
| R | 38 | | | | | | | | | | | | 38 | | | | | | |
| S | | 1 | 36 | | | | | | | 1 | | | 38 | | 38 | | 12 | |
| T | | | | | | | | | | | | | | | | | 5 | |
| V | | | | | | | | | | | | | | | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | 38 | 38 | 38 | 38 | 38 | | | | | | | | | | | 38 |
| unknown (?) | | | | | | | | | | | 1 | | | | | | | | |
| not sequenced | | | | | | | | | | 1 | 1 | 1 | | | | | | | |
| sum of seq[2] | 38 | 38 | 38 | 38 | 38 | 38 | 38 | 38 | 38 | 37 | 37 | 37 | 38 | 38 | 38 | 38 | 38 | 38 | 38 |
| oomcaa[3] | 38 | 37 | 36 | 38 | 38 | 38 | 38 | 38 | 38 | 37 | 36 | 27 | 38 | 38 | 38 | 38 | 38 | 21 | 38 |
| mcaa[4] | R | P | S | — | — | — | — | — | G | I | P | E | R | F | S | G | S | N | — |
| rel. oomcaa[5] | 100% | 97% | 95% | 100% | 100% | 100% | 100% | 100% | 100% | 100% | 97% | 73% | 100% | 100% | 100% | 100% | 100% | 55% | 100% |
| pos occupied[6] | 1 | 2 | 3 | 1 | 1 | 1 | 1 | 1 | 1 | 1 | 1 | 2 | 2 | 1 | 1 | 1 | 1 | 3 | 1 |

| | Framework III | | | | | | | | | | | | | | | | | | |
|---|---|---|---|---|---|---|---|---|---|---|---|---|---|---|---|---|---|---|---|
| amino acid[1] | B | 67 | 68 | 69 | 70 | 71 | 72 | 73 | 74 | 75 | 76 | 77 | 78 | 79 | 80 | 81 | 82 | 83 | 84 |
| A | | | | | 1 | 36 | 1 | | 1 | | | | 11 | 1 | 34 | | | | 38 |
| B | | | | | | | | | | | | | | | | | | | |
| C | | | | | | | | | | | | | | | | | | | |
| D | | | | | | | | | | | | | | | | 38 | | | |
| E | | | | | | | | | | | | | | | 10 | | 14 | 38 | |
| F | | | | | | | | | | | | | | | | | | | |
| G | | | 37 | | | | | | | | | 28 | | | 10 | | | | |
| H | | | | 1 | | | | | | | | | | | | | | | |
| I | | | | | | | 1 | | 1 | 37 | 1 | | | | | 1 | | | |
| K | | | | 1 | | | | | | | | | | | | | | | |
| L | | | | | | | 38 | | | | | | | | 2 | | | | |
| M | | | | | | | | | | | | | | | 10 | | | | |
| N | | | | 28 | | | | | | | 1 | | | | | | | | |
| P | | | | | | | | | | | | | | | | | | | |
| Q | | | 1 | | | | | | | | | | | 25 | | | | | |
| R | | | | | | | | | | | | 1 | 10 | 1 | | | | | |
| S | | 37 | | 2 | | | 11 | | | | | 23 | | | 1 | | | | |
| T | | 1 | | 6 | 37 | | 25 | | 36 | | 12 | | 13 | | 2 | | | | |
| V | | | | | | 2 | | | | 1 | | | 14 | 1 | 1 | 1 | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | 38 | | | | | | | | | | | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 38 | 37 | 37 | 28 | 37 | 36 | 25 | 38 | 36 | 37 | 23 | 28 | 14 | 25 | 34 | 14 | 38 | 38 | 38 |
| mcaa[4] | — | S | G | N | T | A | T | L | T | I | S | G | V | Q | A | E | D | E | A |
| rel. oomcaa[5] | 100% | 97% | 97% | 74% | 97% | 95% | 66% | 100% | 95% | 97% | 61% | 74% | 37% | 66% | 89% | 37% | 100% | 100% | 100% |
| pos occupied[6] | 1 | 2 | 2 | 5 | 2 | 2 | 4 | 1 | 3 | 2 | 5 | 2 | 3 | 5 | 4 | 6 | 1 | 1 | 1 |

| | Framework III | | | | CDR III | | | | | | | | | | | |
|---|---|---|---|---|---|---|---|---|---|---|---|---|---|---|---|---|---|
| amino acid[1] | 85 | 86 | 87 | 88 | 89 | 90 | 91 | 92 | 93 | 94 | 95 | A | B | C | D | E | F | 96 |
| A | | | | | | 13 | 3 | 2 | | | 1 | 2 | | | | | | 4 |
| B | | | | | | | | | | | | | | | | | | |
| C | | | | 38 | | | | | | | | | | | | | | |
| D | | 37 | | | | | | 32 | 1 | 1 | | 6 | | | | | | |
| E | | 1 | | | 1 | | | | | | | | 2 | | | | | 2 |
| F | | | | 2 | | | | | | 2 | | | | | | | | |
| G | | | | | | | | | | | 3 | 14 | 3 | | | 1 | | 3 |
| H | | | | | | | | | | | | | 12 | 1 | | | | |

TABLE 5C-continued

Analysis of V lambda subgroup 3

| amino acid | | | | | | | | | | | | | | | | | | sum |
|---|---|---|---|---|---|---|---|---|---|---|---|---|---|---|---|---|---|---|
| I | | | | | | | | | | | | | | | | | | |
| K | | | | | | | | | | | 1 | | | | | | | |
| L | | | 1 | | | | 1 | | 1 | | 1 | 1 | | | | | 4 | |
| M | | | | | | | | 1 | | | | | | | | | 1 | |
| N | | | | 10 | | | 2 | 1 | 2 | | 10 | 1 | | | | | | |
| P | | | | | | | | | 1 | | | | 3 | | | | 1 | |
| Q | | | | 25 | | | | | 1 | 1 | | | | | | | | |
| R | | | | | | 10 | | 1 | 2 | | | 2 | | | | | | |
| S | | | 1 | | 14 | 1 | | 28 | 26 | 13 | | 1 | | | | 1 | | |
| T | | | | | | 1 | | 3 | | 7 | 2 | | | | | | | |
| V | | | | | 11 | | | | | | | | | | | | 18 | |
| W | | | | | | 23 | | | | | | | | | | | 1 | |
| X | | | | | | | | | | | | | | | | | | |
| Y | 38 | 36 | | | | 1 | | 1 | | 1 | 3 | 1 | | | | | 3 | |
| Z | | | | | | | | | | | | | | | | | | |
| — | | | | | | | | | | 10 | 15 | 31 | 36 | 37 | 36 | | | |
| unknown (?) | | | | | | | | | | | | | | | | | | |
| not sequenced | | | | | | 1 | 1 | 1 | 1 | 2 | 1 | 1 | 1 | 1 | 1 | 1 | 1 | |
| sum of seq[2] | 38 | 38 | 38 | 38 | 38 | 38 | 38 | 37 | 37 | 37 | 37 | 36 | 37 | 37 | 37 | 37 | 37 | 37 |
| oomcaa[3] | 37 | 38 | 36 | 38 | 25 | 14 | 23 | 32 | 28 | 26 | 14 | 10 | 15 | 31 | 36 | 37 | 36 | 18 |
| mcaa[4] | D | Y | Y | C | Q | S | W | D | S | S | G | N | — | — | — | — | — | V |
| rel. oomcaa[5] | 97% | 100% | 95% | 100% | 66% | 37% | 61% | 86% | 76% | 70% | 38% | 28% | 41% | 84% | 97% | 100% | 97% | 49% |
| pos occupied[6] | 2 | 1 | 2 | 1 | 5 | 3 | 5 | 4 | 7 | 8 | 6 | 9 | 8 | 5 | 2 | 1 | 2 | 9 |

| | Framework IV | | | | | | | | | | | | |
|---|---|---|---|---|---|---|---|---|---|---|---|---|---|
| amino acid[1] | 97 | 98 | 99 | 100 | 101 | 102 | 103 | 104 | 105 | 106 | A | 107 | 108 | sum |
| A | | | | | | | | | | | | | | 265 |
| B | | | | | | | | | | | | | | 82 |
| C | | | | | | | | | | | | | 1 | 82 |
| D | | | | | | | | | | | | | | 225 |
| E | | | | | | | 2 | | | | | | | 145 |
| F | | 35 | | | | | | | | | | | | 90 |
| G | 1 | | 35 | 31 | 35 | | | | | | | 24 | | 461 |
| H | | | | | | | | | | | | | | 32 |
| I | 4 | | | | | | | | | | | | | 160 |
| K | | | | | | | 30 | | | | | | | 110 |
| L | 2 | | | | | | | 28 | | | 33 | | | 233 |
| M | 1 | | | | | | | | | | | | | 17 |
| N | | | | | | | | | | | | | | 126 |
| P | | | | | | | | | | | 1 | | | 249 |
| Q | | | | | | | | | | | | | 7 | 275 |
| R | | | | | | | | 2 | | | | | | 154 |
| S | | | | | | | | | | | 2 | | | 501 |
| T | | | | 4 | | 35 | | | 35 | | | | | 347 |
| V | 28 | | | | | | | 7 | | 35 | | | | 308 |
| W | | | | | | | | | | | | | | 62 |
| X | | | | | | | | | | | | | | |
| Y | | | | | | | | | | | | | | 211 |
| Z | | | | | | | | | | | | | | |
| — | 1 | | | | | | | | | | | | | 603 |
| unknown (?) | | | | | | | | | | | | | | 1 |
| not sequenced | 1 | 3 | 3 | 3 | 3 | 3 | 4 | 3 | 3 | 3 | 4 | 11 | 28 | 89 |
| sum of seq[2] | 37 | 35 | 35 | 35 | 35 | 35 | 34 | 35 | 35 | 35 | 34 | 27 | 7 | |
| oomcaa[3] | 28 | 35 | 35 | 31 | 35 | 35 | 30 | 28 | 35 | 35 | 33 | 24 | 7 | |
| mcaa[4] | V | F | G | G | G | T | K | L | T | V | L | G | Q | |
| rel. oomcaa[5] | 76% | 100% | 100% | 89% | 100% | 100% | 88% | 80% | 100% | 100% | 97% | 89% | 100% | |
| pos occupied[6] | 6 | 1 | 1 | 2 | 1 | 1 | 3 | 2 | 1 | 1 | 2 | 3 | 1 | |

TABLE 6A

Analysis of V heavy chain subgroup 1A

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | 1 | 14 | | | | 60 | | | | | | | 24 | 1 | | |
| B | | | | | | | | | | | | | | | | | | | |

TABLE 6A-continued

Analysis of V heavy chain subgroup 1A

| | | | | | | | | | | | | | | | | | | | |
|---|---|---|---|---|---|---|---|---|---|---|---|---|---|---|---|---|---|---|---|
| C | | | | | | | | | | | | | | | | | | | |
| D | | | | | | | | | | | | | | | | | | | |
| E | 1 | | | | 2 | 1 | | 2 | | 64 | | | | | | | | | |
| F | | | | | | | | | | | | | | | | | | | |
| G | | | | | | | | 58 | 1 | | | | | | | 64 | | | | |
| H | | | 2 | | | | | | | | | | | | | | | | | |
| I | | 2 | | | | | | | | | | | 57 | 64 | | | | | | 60 |
| K | | 2 | | | | | | | | | | | | | | | | | | |
| L | | | 2 | 59 | | | | | | | 3 | | | | | | | | | |
| M | | 1 | | | | | | | | | | | | | | | | | | |
| N | | | | | | | | | | | | | 6 | | | | | | | |
| P | | | | | | | | | | | | | | | 63 | | | | | |
| Q | 53 | | 56 | | 2 | 45 | | | | | | | | | | | | | | |
| R | | | | | | | | | | | | | 1 | | | | | | | 3 |
| S | | | | | | | 60 | | 3 | | | | | | 1 | | 40 | 63 | | |
| T | | | | | | | | | | | | | | | | | | | | 1 |
| V | 2 | 55 | | | 1 | 55 | | | | | 61 | | | | | | | | 64 | |
| W | | | | | | | | | | | | | | | | | | | | |
| X | | | | | | | | | | | | | | | | | | | | |
| Y | | | | | | | | | | | | | | | | | | | | |
| Z | 3 | | | | | | | | | | | | | | | | | | | |
| — | | | | | | | | | | | | | | | | | | | | |
| unknown (?) | | | | | | | | | | | | | | | | | | | | |
| not sequenced | 11 | 10 | 10 | 10 | 10 | 10 | 10 | 10 | 6 | 6 | 6 | 6 | 6 | 6 | 6 | 6 | 6 | 6 | 6 | 6 |
| sum of seq[2] | 59 | 60 | 60 | 60 | 60 | 60 | 60 | 60 | 64 | 64 | 64 | 64 | 64 | 64 | 64 | 64 | 64 | 64 | 64 | 64 |
| oomcaa[3] | 53 | 55 | 56 | 59 | 55 | 45 | 60 | 58 | 60 | 64 | 61 | 57 | 64 | 63 | 64 | 64 | 40 | 63 | 64 | 60 |
| mcaa[4] | Q | V | Q | L | V | Q | S | G | A | E | V | K | K | P | G | S | S | S | V | K |
| rel. oomcaa[5] | 90% | 92% | 93% | 98% | 92% | 75% | 100% | 97% | 94% | 100% | 95% | 89% | 100% | 98% | 100% | 63% | 98% | 100% | 94% |
| pos occupied[6] | 4 | 4 | 3 | 2 | 4 | 3 | 1 | 2 | 3 | 1 | 2 | 3 | 1 | 2 | 1 | 2 | 2 | 1 | 3 |

| | Framework I | | | | | | | | | | | CDR I | | | | | | |
|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | | | | 62 | | | | 1 | | | | | | | 41 | | | |
| B | | | | | | | | | | | | | | | | | | | |
| C | | | 63 | | | | | | | | | | | | | | | | |
| D | | | | | | | | 1 | | | | | | | | | | | |
| E | | | | | | | | | | | | | | | | | | | |
| F | | | | | | | | | 69 | | | | | | 3 | | 3 | | |
| G | | | | | | 1 | 69 | 41 | | 1 | | | | | 1 | 23 | | | |
| H | | | | | | | | | | | 1 | | | | | 1 | | | 1 |
| I | | | | | | | | | 1 | | | | | | | | 61 | 1 | |
| K | | | | 63 | | | | | | | | 1 | 1 | | | | | | |
| L | | | | | | | | | | | | | | | | 1 | 2 | | |
| M | | | | | | | | | | | | | | | | | 4 | | |
| N | | | | | | | | | | | | 2 | 5 | | | | | 4 | |
| P | | | | | | | | | | | | | | | | | 1 | | |
| Q | | | | | | | | | | | | | | | | | | | |
| R | | | | 1 | 1 | | | | | | | 1 | 1 | | | | | | |
| S | | 63 | | | | | 68 | | 1 | | | 40 | 60 | | 2 | | | 60 | |
| T | | 1 | | | 2 | | | | 68 | | | 25 | 3 | | | 3 | | 4 | |
| V | 64 | | | | | | | | | | | | | | | 1 | | | |
| W | | | | | | | | | | | | | | | | | | | 70 |
| X | | | | | | | | | | | | | | | | | | | |
| Y | | | | | | | | 27 | | | | | | | 64 | | | | |
| Z | | | | | | | | | | | | | | | | | | | |
| — | | | | | | | | | | | | 70 | 70 | | | | | | |
| unknown (?) | | | | | | | | | | | | | | | | | | | |
| not sequenced | 6 | 6 | 6 | 6 | 5 | 2 | 1 | | | | | | | | | | | | |
| sum of seq[2] | 64 | 64 | 64 | 64 | 65 | 68 | 69 | 70 | 70 | 70 | 70 | 70 | 70 | 70 | 70 | 70 | 70 | 70 | 70 |
| oomcaa[3] | 64 | 63 | 63 | 63 | 62 | 68 | 69 | 41 | 68 | 69 | 40 | 60 | 70 | 70 | 64 | 41 | 61 | 60 | 70 |
| mcaa[4] | V | S | C | K | A | S | G | G | T | F | S | S | — | — | Y | A | I | S | W |
| rel. oomcaa[5] | 100% | 98% | 98% | 98% | 95% | 100% | 100% | 59% | 97% | 99% | 57% | 86% | 100% | 100% | 91% | 59% | 87% | 86% | 100% |
| pos occupied[6] | 1 | 2 | 2 | 2 | 3 | 1 | 1 | 4 | 3 | 2 | 6 | 5 | 1 | 1 | 4 | 6 | 4 | 5 | 1 |

| | Framework II | | | | | | | | | | | | | CDR II | | | |
|---|---|---|---|---|---|---|---|---|---|---|---|---|---|---|---|---|---|
| amino acid[1] | 37 | 38 | 39 | 40 | 41 | 42 | 43 | 44 | 45 | 46 | 47 | 48 | 49 | 50 | 51 | 52 | A | B | C |
| A | | | | 70 | | | | | | | | | 1 | | | 5 | | | |
| B | | | | | | | | | | | | | | | | | | | |
| C | | | | | | | | | | | | | | | | | | | |

TABLE 6A-continued

Analysis of V heavy chain subgroup 1A

| amino acid[1] | | | | | | | | | | | | | | | | | | | |
|---|---|---|---|---|---|---|---|---|---|---|---|---|---|---|---|---|---|---|---|
| D | | | | | | | | | 1 | | | | | | | | | | |
| E | | | | | | | | | 69 | | | | | | | | | | |
| F | | | | | | | | | | | | | | | 2 | | | | |
| G | | | | 1 | 68 | | 69 | | | 1 | | 69 | 39 | | | 1 | | | |
| H | | | | | 1 | | | | | | | | | | | | | | |
| I | 1 | | | | | | | | | | | | | | 65 | 38 | | | |
| K | | | | | | | | | | | | | | | | | | | |
| L | | | | | 1 | | | 68 | | | 1 | | 1 | | | | | | |
| M | | | | | | | | | | | | 67 | | | | 2 | | | |
| N | | | | | | | | | | | | | | | | 4 | | | |
| P | | | | 68 | | | | 1 | | | | | | | | | 44 | | |
| Q | | | 69 | | | 69 | | | | | | | | | | | | | |
| R | | 70 | 1 | | | 1 | | 1 | | | | | | 4 | | | | | |
| S | | | | | | | 1 | | | | 1 | 1 | | | | 22 | | | |
| T | | | | | | | | | | | | | | | 1 | 2 | 4 | | |
| V | 69 | | | | | | | | | | | 1 | | | 2 | 2 | 16 | | |
| W | | | | | | | | 1 | | 67 | | | | 26 | | | | | |
| X | | | | | | | | | | | | | | | | | | | |
| Y | | | | | | | | | | 1 | | | | | | | | | |
| Z | | | | | | | | | | | | | | | | | | | |
| — | | | | | | | | | | | | | | | | | | 70 | 70 |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 69 | 70 | 69 | 70 | 68 | 68 | 69 | 69 | 68 | 69 | 67 | 67 | 69 | 39 | 65 | 38 | 44 | 70 | 70 |
| mcaa[4] | V | R | Q | A | P | G | Q | G | L | E | W | M | G | G | I | I | P | — | — |
| rel. oomcaa[5] | 99% | 100% | 99% | 100% | 97% | 97% | 99% | 99% | 97% | 99% | 96% | 96% | 99% | 56% | 93% | 54% | 63% | 100% | 100% |
| pos occupied[6] | 2 | 1 | 2 | 1 | 3 | 3 | 2 | 2 | 3 | 2 | 4 | 4 | 2 | 4 | 4 | 6 | 5 | 1 | 1 |

| | CDR II | | | | | | | | | | | | | | Framework III | | | | |
|---|---|---|---|---|---|---|---|---|---|---|---|---|---|---|---|---|---|---|---|
| amino acid[1] | 53 | 54 | 55 | 56 | 57 | 58 | 59 | 60 | 61 | 62 | 63 | 64 | 65 | 66 | 67 | 68 | 69 | 70 | 71 |
| A | | | | 1 | 34 | | 69 | | | | | | | | | | | | 43 |
| B | | | | | | | | | | | | | | | | | | | |
| C | | | | | | | | | | | | | | | | | | | |
| D | | | | 15 | | 1 | | | | | | | 2 | | | | | | |
| E | | | | | | | | | | | | | 1 | | | | | | |
| F | 3 | 39 | | | | | 1 | | | | 48 | | | | 3 | | 4 | | |
| G | | | 68 | 1 | | | | | | 3 | | | 67 | | | | | | |
| H | | | | | | 1 | | | | | | | | | | | | | |
| I | 34 | | | 4 | | | | | | | | | | | | 1 | 44 | | |
| K | | | | 1 | | 2 | 1 | | | 47 | | 1 | | 1 | | | | | |
| L | 2 | 4 | | 1 | 1 | | | | | | 22 | | | | 2 | | 1 | | 3 |
| M | 4 | | | | | | | | | | | | | | | | 21 | | |
| N | 3 | 22 | | 9 | | 59 | | | | 18 | | | | | | | | | |
| P | | | | 1 | 7 | | | | | | | | | | | | | | |
| Q | 1 | 1 | 1 | 1 | 1 | | | | 70 | | | 64 | | | | | | | |
| R | 1 | | | 2 | | | | | | 2 | | 1 | | 69 | | | | | |
| S | | 1 | 1 | | 1 | 2 | | 1 | | | | | | | | | | 5 | |
| T | 1 | 3 | | 34 | 26 | 4 | | | | | | 3 | | | | 66 | | 65 | 24 |
| V | 1 | | | | | | | | | | | | 1 | | 65 | 3 | | | |
| W | | | | | | | | | | | | | | | | | | | |
| X | | | | | | | | | | | | | | | | | | | |
| Y | 20 | | | | | 1 | 68 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 34 | 39 | 68 | 34 | 34 | 59 | 68 | 69 | 70 | 47 | 48 | 64 | 67 | 69 | 65 | 66 | 44 | 65 | 43 |
| mcaa[4] | I | F | G | T | A | N | Y | A | Q | K | F | Q | G | R | V | T | I | T | A |
| rel. oomcaa[5] | 49% | 56% | 97% | 49% | 49% | 84% | 97% | 99% | 100% | 67% | 69% | 91% | 96% | 99% | 93% | 94% | 63% | 93% | 61% |
| pos occupied[6] | 10 | 6 | 3 | 11 | 6 | 7 | 3 | 2 | 1 | 4 | 2 | 5 | 3 | 2 | 3 | 3 | 4 | 2 | 3 |

| | Framework III | | | | | | | | | | | | | | | |
|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | | | | | | 64 | | | 1 | | | | | 3 | | | | 1 |
| B | | | | | | | | | | | | | | | | | | | |
| C | | | | | | | | | | | | | | | | | | | |
| D | 70 | | | | | | | | | | 2 | | | | | | 26 | 70 | |

TABLE 6A-continued

Analysis of V heavy chain subgroup 1A

| amino acid | | | | | | | | | | | | | | | | | | | |
|---|---|---|---|---|---|---|---|---|---|---|---|---|---|---|---|---|---|---|---|
| E | | 33 | | | | | | | 64 | | | | | | | | 44 | | |
| F | | | | | | | | | | | | | | | | | | | |
| G | | | | | | | | | | | | | 1 | | | | | | |
| H | | | | | | | 1 | | | | 1 | | | | | | | | |
| I | | 1 | | | 1 | | | | | 3 | 1 | 1 | | | | | | | |
| K | | 8 | | | | | | | | | | | | | 3 | | | | |
| L | | | | | | | | | 3 | | 63 | | | 70 | | | | | |
| M | | | | | | | | | 67 | | | | | | | | | | 1 |
| N | | | | 4 | | | | | | | 1 | 16 | | | | | | | |
| P | | | | | | | | | | | | | | | | | | | |
| Q | | | | | | | 1 | | | 3 | | | | | | | | | |
| R | | 1 | | | 3 | | | | | | 23 | 1 | | | 62 | | | | |
| S | | | 70 | | 62 | | 1 | | | | 41 | 49 | | | | 67 | | | 1 |
| T | | 27 | | 67 | 1 | 69 | 2 | | | | 3 | 2 | | 4 | | | | | 67 |
| V | | | | 3 | | | 3 | | | 4 | | | | 1 | | | | | |
| W | | | | | | | | | | | | | | | | | | | |
| X | | | | | | | | | | | | | | | | | | | |
| Y | | | | | | | | | 68 | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 |
| oomcaa[3] | 70 | 33 | 70 | 67 | 62 | 69 | 64 | 68 | 67 | 64 | 63 | 41 | 49 | 70 | 62 | 67 | 44 | 70 | 67 |
| mcaa[4] | D | E | S | T | S | T | A | Y | M | E | L | S | S | L | R | S | E | D | T |
| rel. oomcaa[5] | 100% | 47% | 100% | 96% | 89% | 99% | 91% | 97% | 96% | 91% | 90% | 59% | 70% | 100% | 89% | 96% | 63% | 100% | 96% |
| pos occupied[6] | 1 | 5 | 1 | 2 | 4 | 2 | 4 | 3 | 2 | 4 | 3 | 6 | 6 | 1 | 4 | 2 | 2 | 1 | 4 |

| | Framework III | | | | | CDR III | | | | | | | | | | | | | |
|---|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 70 | | | | | 66 | 2 | 16 | | 1 | 1 | 1 | 4 | 1 | 2 | 2 | 1 | 1 | |
| B | | | | | | | | | | | | | | | | | | | |
| C | | | | | 70 | | | | 1 | 1 | | 16 | 2 | | 1 | 1 | 7 | 2 | 1 |
| D | | | | | | | 16 | 5 | 3 | | 3 | 5 | 4 | 3 | 4 | | | | 1 |
| E | | | | | | | 9 | | | | 2 | | | 1 | | | 1 | | |
| F | | 1 | 1 | 2 | | | | | 1 | 3 | | 2 | | 3 | 1 | 2 | | | 2 |
| G | | | | | | 2 | 14 | 13 | 20 | 10 | 14 | 5 | 20 | 15 | 16 | 3 | 3 | 4 | |
| H | | | | | | | | | | | | | | 1 | 1 | 1 | | | 1 |
| I | | 2 | | | | | | 2 | 5 | 2 | 2 | | 2 | 2 | 1 | 1 | | | |
| K | | | | | | 5 | | | 2 | 1 | | | 1 | | | | | | |
| L | | 2 | | | | 1 | 4 | 4 | 2 | 5 | 2 | 1 | 1 | | 4 | 2 | | | 1 |
| M | | 1 | | | | | 1 | | 2 | | 1 | | 1 | | | 1 | 1 | | |
| N | | | | | | | | 2 | 2 | 1 | 2 | 1 | 2 | 2 | 2 | 2 | | | |
| P | | | | | | | | 20 | 3 | | 1 | 3 | 2 | 2 | 2 | 4 | 2 | 1 | |
| Q | | | | | | | | 1 | | | 1 | | 1 | 1 | 1 | | | | |
| R | | | | | | 55 | 1 | 5 | 7 | 8 | 1 | 4 | | 2 | | 1 | | 16 | |
| S | | | | | | 1 | 1 | 5 | 5 | 5 | 5 | 21 | 5 | 11 | 8 | 4 | 3 | | |
| T | | | | | 1 | 3 | 3 | 5 | 4 | 1 | 3 | 4 | 2 | 5 | 2 | | 1 | | |
| V | | 64 | | | 3 | | 3 | 2 | 4 | 3 | 3 | 3 | 4 | 2 | 2 | 2 | 1 | 2 | |
| W | | | | | | | | 1 | 1 | 3 | 1 | 1 | | | 2 | | 3 | | |
| X | | | | | | | | | | | | | | | | | | | |
| Y | | | 69 | 68 | | 1 | | 2 | 3 | 20 | 5 | 4 | 9 | 1 | 2 | 11 | 20 | 10 | |
| Z | | | | | | | | | | | | | | | | | | | |
| — | | | | | | | 1 | 2 | 2 | 3 | 6 | 11 | 11 | 14 | 23 | 26 | 26 | | |
| unknown (?) | | | | | | | | | | | | | | | | | 1 | | |
| not sequenced | | | | | | 2 | 2 | 2 | 4 | 4 | 4 | 4 | 5 | 5 | 5 | 5 | 5 | | |
| sum of seq[2] | 70 | 70 | 70 | 70 | 70 | 70 | 70 | 68 | 68 | 68 | 66 | 66 | 66 | 66 | 65 | 65 | 65 | 65 | 65 |
| oomcaa[3] | 70 | 64 | 69 | 68 | 70 | 66 | 55 | 16 | 20 | 20 | 20 | 16 | 21 | 20 | 15 | 16 | 23 | 26 | 26 |
| mcaa[4] | A | V | Y | Y | C | A | R | A | P | G | Y | C | S | G | — | — | — | — | — |
| rel. oomcaa[5] | 100% | 91% | 99% | 97% | 100% | 94% | 79% | 24% | 29% | 29% | 30% | 24% | 32% | 30% | 23% | 25% | 35% | 40% | 40% |
| pos occupied[6] | 1 | 5 | 2 | 2 | 1 | 3 | 8 | 10 | 14 | 18 | 15 | 18 | 15 | 15 | 17 | 17 | 15 | 12 | 11 |

| | Framework IV | | | | | | | | | | | | | | |
|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | 1 | 1 | 1 | 2 | | 1 | | | | | | | | | | | | | 670 |
| B | | | | | | | | | | | | | | | | | | | |
| C | | | | | | | | | | | | | | | | | | | 165 |
| D | 1 | 14 | | | | 59 | | 1 | 1 | | | | | | | | | | 308 |
| E | | 1 | | | | | 1 | 1 | | | | | | | | | | | 297 |

TABLE 6A-continued

Analysis of V heavy chain subgroup 1A

| | | | | | | | | | | | | | | | | | | |
|---|---|---|---|---|---|---|---|---|---|---|---|---|---|---|---|---|---|---|
| F | 1 | | | | 28 | 2 | 2 | | | | | | | | | | | 226 |
| G | 15 | 1 | 1 | 7 | | | | | 58 | | 59 | 1 | 1 | | | | | 928 |
| H | | | | | | | | | | 1 | | | | | | | | 14 |
| I | 1 | | | | | 3 | | | | | | | | | 4 | | | 286 |
| K | | | | | | | | | 3 | | | 1 | | | | | | 325 |
| L | | | 1 | | 1 | | 3 | | 1 | | | | 40 | 1 | | | | 386 |
| M | | | | | 10 | | 1 | | | | | | 3 | | | | | 189 |
| N | 1 | 1 | 4 | | | | | | 1 | | | | | | | | | 176 |
| P | 4 | 1 | | 1 | | 1 | 5 | | | | | | | | | | 1 | 238 |
| Q | | | | | | | | | | 52 | | | | | | | | 494 |
| R | | | | | | | | | | 1 | | | | | | | | 351 |
| S | 2 | 1 | | 2 | | 1 | | | | | | 54 | 11 | 1 | 51 | | 53 | 51 | 972 |
| T | | 1 | 1 | | | | | | | | | | | | | 1 | | 736 |
| V | 1 | | | | | 15 | | 1 | | | | | 1 | 54 | | 54 | | 1 | 699 |
| W | | | 1 | 5 | 1 | | | 59 | | 1 | | | | | | | | | 243 |
| X | | | | | | | | | | | | | | | | | | |
| Y | 6 | 9 | 10 | 7 | 1 | | 34 | | 1 | | | | | | | | | 542 |
| Z | | | | | | | | | | | | | | | | | | 3 |
| — | 31 | 34 | 46 | 39 | 21 | 1 | 1 | | | | | | | | | | | 578 |
| unknown (?) | 1 | 1 | | 2 | 3 | | | | | | | | | | | | | 8 |
| not sequenced | 5 | 5 | 5 | 5 | 5 | 5 | 5 | 9 | 9 | 10 | 11 | 14 | 14 | 14 | 15 | 16 | 16 | 17 | 406 |
| sum of seq[2] | 65 | 65 | 65 | 65 | 65 | 65 | 65 | 61 | 61 | 60 | 59 | 56 | 56 | 56 | 55 | 54 | 54 | 53 | |
| oomcaa[3] | 31 | 34 | 46 | 39 | 28 | 59 | 34 | 59 | 58 | 52 | 59 | 54 | 40 | 54 | 51 | 54 | 53 | 51 | |
| mcaa[4] | — | — | — | — | F | D | Y | W | G | Q | G | T | L | V | T | V | S | S | |
| rel. oomcaa[5] | 48% | 52% | 71% | 60% | 43% | 91% | 52% | 97% | 95% | 87% | 100% | 96% | 71% | 96% | 93% | 100% | 98% | 96% | |
| pos occupied[6] | 11 | 10 | 8 | 7 | 6 | 6 | 9 | 3 | 4 | 7 | 1 | 3 | 5 | 3 | 2 | 1 | 2 | 3 | |

TABLE 6B

Analysis of V heavy chain subgroup 1B

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | | | | | 32 | | | | | | | 34 | | | |
| B | | | | | | | | | | | | | | | | | | | |
| C | | | | | | | | | | | | | | | | | | | |
| D | | | | | | | | | | | | | | | | | | | |
| E | | 1 | | | 5 | 1 | | | | 35 | | | | | | | | | |
| F | | | | | | | | | | | | | | | | | | | |
| G | | | | | | | | 27 | | | | | | | | 35 | | | |
| H | | | 1 | | | | | | | | | | | 1 | | | | | |
| I | | | | | | | | | | | | | | | | | | | |
| K | | 3 | 1 | | | | | | | | | 34 | 33 | | | | | | 33 |
| L | | | 3 | 26 | 1 | | | | | | | | | | | | | | |
| M | | | | 1 | 1 | | | | | | | | | | | | | | |
| N | | | | | | | | | | | | | | | | | | | |
| P | | | | | | | | | 1 | | | | | 33 | | | 1 | | |
| Q | 21 | | 20 | | | 26 | | | | | | | | | | | | | |
| R | 1 | | | | | | | | | | | 1 | 2 | | | | | | |
| S | | | | | | | 27 | | | | | | | | | 1 | 34 | | |
| T | | | | | | | | | 1 | | | | | 1 | | | | | 2 |
| V | 3 | 21 | | | 20 | | | | | | 35 | | | | | | | 35 | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | 15 | 15 | 15 | 13 | 13 | 13 | 13 | 13 | 6 | 5 | 5 | 5 | 5 | 5 | 5 | 5 | 5 | 5 | 5 |
| sum of seq[2] | 25 | 25 | 25 | 27 | 27 | 27 | 27 | 27 | 34 | 35 | 35 | 35 | 35 | 35 | 35 | 35 | 35 | 35 | 35 |
| oomcaa[3] | 21 | 21 | 20 | 26 | 20 | 26 | 27 | 27 | 32 | 35 | 35 | 34 | 33 | 33 | 35 | 34 | 34 | 35 | 33 |
| mcaa[4] | Q | V | Q | L | V | Q | S | G | A | E | V | K | K | P | G | A | S | V | K |
| rel. oomcaa[5] | 84% | 84% | 80% | 96% | 74% | 96% | 100% | 100% | 94% | 100% | 100% | 97% | 94% | 94% | 100% | 97% | 97% | 100% | 94% |
| pos occupied[6] | 3 | 3 | 4 | 2 | 4 | 2 | 1 | 1 | 3 | 1 | 1 | 2 | 2 | 3 | 1 | 2 | 2 | 1 | 2 |

| | Framework I | | | | | | | | | | | CDRI | | | | | | |
|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |

TABLE 6B-continued

Analysis of V heavy chain subgroup 1B

| amino acid¹ | | | | | | | | | | | | | | | | | | | |
|---|---|---|---|---|---|---|---|---|---|---|---|---|---|---|---|---|---|---|---|
| A | | | | | 30 | | | | | | | | 2 | | 6 | | | | |
| B | | | | | | | | | | | | | | | | | | | |
| C | | 35 | | | | | | | | | | | | | | | | | |
| D | | | | | | | | | | | | 1 | | | 5 | | 1 | | |
| E | | | | 3 | | | | | | | | 1 | | | | | | | |
| F | | | | | | | 2 | | 39 | | | | | 2 | 2 | | | | |
| G | | | | | 1 | 40 | | | | 1 | 14 | | | | 1 | | | | |
| H | | | | | | | | | | | | | | 3 | 1 | | 34 | | |
| I | 1 | | | | | | | 1 | | 1 | | | | | 9 | | | | |
| K | | | | 28 | | | | | | | | | | | | | | | |
| L | | | | | | | | | 1 | | 1 | | | | 5 | | | | |
| M | | | | | | | | | | | | | | | 23 | | | | |
| N | | | | | | | 1 | | | 1 | 3 | | | | 1 | 3 | | | |
| P | | | | | | | | | | | | | | 1 | | | | | |
| Q | | | | 2 | | | | | | 1 | | | | 1 | | 1 | | | |
| R | | | | 2 | | | | 2 | | | 2 | 15 | | 1 | | | | | |
| S | | 35 | | | | 40 | | 5 | | 2 | | | | 2 | 1 | | | | |
| T | | | | | 3 | | | 32 | | 34 | | | | | 1 | | | | |
| V | 34 | | | | 1 | | 1 | | | 1 | 1 | | | | 2 | 2 | | | |
| W | | | | | | | | | | | | | | | | | | | 40 |
| X | | | | | | | | | | | | | | | | | | | |
| Y | | | | | | | 36 | | | 1 | | | | 32 | 19 | | 1 | | |
| Z | | | | | | | | | | | | | | | | | | | |
| — | | | | | | | | | | | | 40 | 40 | | | | | | |
| unknown (?) | | | | | | | | | | | | | | | | | | | |
| not sequenced | 5 | 5 | 5 | 5 | 5 | | | | | | | | | | | | | | |
| sum of seq² | 35 | 35 | 35 | 35 | 35 | 40 | 40 | 40 | 40 | 40 | 40 | 40 | 40 | 40 | 40 | 40 | 40 | 40 | 40 |
| oomcaa³ | 34 | 35 | 35 | 28 | 30 | 40 | 40 | 36 | 32 | 39 | 34 | 15 | 40 | 40 | 32 | 19 | 23 | 34 | 40 |
| mcaa⁴ | V | S | C | K | A | S | G | Y | T | F | T | S | — | — | Y | Y | M | H | W |
| rel. oomcaa⁵ | 97% | 100% | 100% | 80% | 86% | 100% | 100% | 90% | 80% | 98% | 85% | 38% | 100% | 100% | 80% | 48% | 58% | 85% | 100% |
| pos occupied⁶ | 2 | 1 | 1 | 4 | 4 | 1 | 1 | 4 | 4 | 2 | 6 | 10 | 1 | 1 | 5 | 11 | 5 | 5 | 1 |

| | Framework II | | | | | | | | | | | | | | CDR II | | | | |
|---|---|---|---|---|---|---|---|---|---|---|---|---|---|---|---|---|---|---|---|
| amino acid¹ | 37 | 38 | 39 | 40 | 41 | 42 | 43 | 44 | 45 | 46 | 47 | 48 | 49 | 50 | 51 | 52 | A | B | C |
| A | | | | 39 | | | | 1 | | | | | 1 | | | 7 | | | |
| B | | | | | | | | | | | | | | | | | | | |
| C | | | | | | | | | | | | | | | | | | | |
| D | | 1 | | | | | | | | | | | | | 1 | | | | |
| E | | | | | | 1 | | | | 39 | | | | | | | | | |
| F | | | | | | | | 2 | | | | | | | 1 | 1 | | | |
| G | | 1 | | | | 39 | | 28 | | | | | 39 | 1 | | 1 | | | |
| H | | | | | | | | | | | | | | | | | | | |
| I | | | | | | | | | | | | 3 | | | 34 | | | | |
| K | | | | | 1 | | | | | | | | | | | | | | |
| L | 2 | | | 1 | | | | | 37 | | | | | | 1 | | | | |
| M | | | | | | | | | | | | 37 | | | 4 | | | | |
| N | | | | | | | | | | | | | | | | 35 | | | |
| P | | | | 1 | 34 | | | | 1 | | | | | | | 31 | | | |
| Q | | 1 | 39 | | | | 39 | | | 1 | | | | | | | | | |
| R | | 37 | 1 | | | | | 10 | | | | | | 4 | | | | | |
| S | | | | | 1 | | | 1 | | | | | | | | 2 | | | |
| T | | | | | 4 | | | | | | | | | | | 1 | | | |
| V | 38 | | | | | | | | | | | | | | 1 | 1 | | | |
| W | | | | | | | | | | | 40 | | | 33 | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | 40 | 40 |
| unknown (?) | | | | | | | | | | | | | | | | | | | |
| not sequenced | | | | | | | | | | | | | | | | | | | |
| sum of seq² | 40 | 40 | 40 | 40 | 40 | 40 | 40 | 40 | 40 | 40 | 40 | 40 | 40 | 40 | 40 | 40 | 40 | 40 | 40 |
| oomcaa³ | 38 | 37 | 39 | 39 | 34 | 39 | 39 | 28 | 37 | 39 | 40 | 37 | 39 | 33 | 34 | 35 | 31 | 40 | 40 |
| mcaa⁴ | V | R | Q | A | P | G | Q | G | L | E | W | M | G | W | I | N | P | — | — |
| rel. oomcaa⁵ | 95% | 93% | 98% | 98% | 85% | 98% | 98% | 70% | 93% | 98% | 100% | 93% | 98% | 83% | 85% | 88% | 78% | 100% | 100% |
| pos occupied⁶ | 2 | 4 | 2 | 2 | 4 | 2 | 2 | 4 | 3 | 2 | 1 | 2 | 2 | 4 | 4 | 5 | 4 | 1 | 1 |

| | CDR II | | | | | | | | | | | | | | Framework III | | | | |
|---|---|---|---|---|---|---|---|---|---|---|---|---|---|---|---|---|---|---|---|
| amino acid¹ | 53 | 54 | 55 | 56 | 57 | 58 | 59 | 60 | 61 | 62 | 63 | 64 | 65 | 66 | 67 | 68 | 69 | 70 | 71 |

TABLE 6B-continued

Analysis of V heavy chain subgroup 1B

| amino acid | | | | | | | | | | | | | | | | | | | |
|---|---|---|---|---|---|---|---|---|---|---|---|---|---|---|---|---|---|---|---|
| A | 1 | | 1 | 2 | | | 27 | 2 | | | | 1 | | 1 | | | | | 2 |
| B | | | | | | | | | | | | | | | | | | | |
| C | | | | | | | | | | | | | | | | | | | |
| D | | 1 | | 1 | | | | | | | | | 4 | | | | | | |
| E | 1 | 1 | | 2 | | 2 | | | 1 | | | | 1 | | | | | | 1 |
| F | 1 | | | | | | 4 | | | | 39 | | | | | | 3 | | |
| G | 9 | 1 | 39 | 15 | | 6 | | 1 | | | | | 34 | | | | | | |
| H | 2 | | | | | 1 | 1 | | | | | | | | | | | | |
| I | | | | | 1 | 1 | | | | | | | | | 1 | 1 | 13 | | |
| K | | 1 | | 2 | 2 | 8 | | | 36 | | 1 | | | | | | | | 1 |
| L | | | | | | | | | 1 | | 1 | | | | | | 1 | | |
| M | | | | | | | | | | | | | | | | | 23 | | |
| N | 20 | 12 | 1 | 17 | | 18 | | | 1 | | | | | | | | | | |
| P | | | | | | | | | | | | | | | | | | | |
| Q | | | | | | | | | 36 | | | 37 | | | | | | | |
| R | 3 | 1 | | | | 2 | | | 1 | | 2 | | | 37 | | | | | 34 |
| S | 1 | 20 | | 1 | | | 2 | 11 | | 1 | | | | | | 39 | | | 1 |
| T | | 3 | | | 35 | 2 | | 1 | | 1 | | | | | | | | 40 | 1 |
| V | | | | 1 | | | | | | | | | | | 38 | | | | |
| W | | | | | | | | | | | | | | 3 | | | | | |
| X | | | | | | | | | | | | | | | | | | | |
| Y | 2 | | | | | | 33 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 |
| oomcaa[3] | 20 | 20 | 39 | 17 | 35 | 18 | 33 | 27 | 36 | 36 | 39 | 37 | 34 | 37 | 38 | 39 | 23 | 40 | 34 |
| mcaa[4] | N | S | G | N | T | N | Y | A | Q | K | F | Q | G | R | V | T | M | T | R |
| rel. oomcaa[5] | 50% | 50% | 98% | 43% | 88% | 45% | 83% | 68% | 90% | 90% | 98% | 93% | 85% | 93% | 95% | 98% | 58% | 100% | 85% |
| pos occupied[6] | 9 | 8 | 2 | 8 | 4 | 8 | 4 | 4 | 4 | 5 | 2 | 3 | 4 | 2 | 3 | 2 | 4 | 1 | 6 |

| | Framework III |
|---|---|
| amino acid[1] | 72 | 73 | 74 | 75 | 76 | 77 | 78 | 79 | 80 | 81 | 82 | A | B | C | 83 | 84 | 85 | 86 | 87 |

| A | | | | 12 | | | 35 | | | | | | | | | 1 | 2 | | |
|---|---|---|---|---|---|---|---|---|---|---|---|---|---|---|---|---|---|---|---|
| B | | | | | | | | | | | | | | | | | | | |
| C | | | | | | | | | | | | | | | | | | | |
| D | 35 | | | | 1 | | | | | 4 | | | | | | 19 | 40 | | |
| E | | | | | | | | | | 35 | | | | | | 19 | | | |
| F | | | | | | 1 | | | | | | | | | 2 | | | | |
| G | | | | | | | | | | 1 | | 1 | 2 | | | | | | |
| H | 1 | | | | | | | | | | | | | | | | | | |
| I | | | | 22 | | 1 | | | | | | | | | | | | | |
| K | | | | | | | | | | | | | | | 1 | | | | |
| L | | | | | | | | | 2 | | 39 | | | 39 | | | | | |
| M | | 1 | | 1 | | | | | 37 | | 1 | | | | | | | | |
| N | 4 | | | | 7 | | | | | | | 1 | 2 | | | | | | |
| P | | | 3 | | | | | | | | | | | | | 1 | | | |
| Q | | | | | | | | | | | | | | | | | | | |
| R | | 1 | | | 4 | | | | | | | 2 | 16 | | 37 | | | | |
| S | | | 37 | | 27 | | | 1 | | | | 35 | 20 | | 1 | 36 | | | |
| T | | 38 | | 5 | 1 | 39 | | | | | | 1 | | | 1 | | | | 40 |
| V | | | | | | | 4 | | 1 | | | | | 1 | | | | | |
| W | | | | | | | | | | | | | | | | | | | |
| X | | | | | | | | | | | | | | | | | | | |
| Y | | | | | | | | 39 | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 |
| oomcaa[3] | 35 | 38 | 37 | 22 | 27 | 39 | 35 | 39 | 37 | 35 | 39 | 35 | 20 | 39 | 37 | 36 | 19 | 40 | 40 |
| mcaa[4] | D | T | S | I | S | T | A | Y | M | E | L | S | S | L | R | S | D | D | T |
| rel. oomcaa[5] | 88% | 95% | 93% | 55% | 68% | 98% | 88% | 98% | 93% | 88% | 98% | 88% | 50% | 98% | 93% | 90% | 48% | 100% | 100% |
| pos occupied[6] | 3 | 3 | 2 | 4 | 5 | 2 | 3 | 2 | 3 | 3 | 2 | 5 | 4 | 2 | 4 | 4 | 3 | 1 | 1 |

| | Framework III | | | | | CDR III | | | | | | | | | | | | |
|---|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 40 | | | | | 37 | 1 | 6 | | 1 | 1 | | 2 | 3 | 1 | 3 | | 1 | |

TABLE 6B-continued

| Analysis of V heavy chain subgroup 1B | | | | | | | | | | | | | | | | | | | |
|---|---|---|---|---|---|---|---|---|---|---|---|---|---|---|---|---|---|---|---|
| B | | | | | | | | | | | | | | | | | | | |
| C | | | | | 37 | | 1 | | | 3 | | | | 2 | 1 | | | | |
| D | | 1 | | | | | | 7 | | 5 | 2 | 3 | 1 | 5 | 4 | | 1 | | 2 |
| E | | | | | | | | 2 | | 1 | | | 1 | 1 | | 2 | | 1 | |
| F | | | 2 | 1 | | | | 1 | 1 | 3 | | | | 2 | 1 | 1 | 1 | 1 | |
| G | | | | | | 1 | 7 | 7 | 5 | 5 | 9 | 4 | 7 | 1 | 3 | | | 2 | 2 |
| H | | | | | | | 1 | | | | 2 | | | 1 | 1 | | | | |
| I | | 1 | | | | 1 | | 1 | 3 | 1 | 1 | 1 | 1 | 1 | 1 | 1 | | | |
| K | | | | | | 1 | | | 1 | | | | 1 | 1 | | 1 | | | 1 |
| L | | 2 | | | 1 | | 2 | 4 | 4 | 4 | 3 | | | 1 | 2 | 1 | 1 | | 2 |
| M | | 2 | | | | | | 2 | | 1 | 1 | | | | | | | | |
| N | | | | | | | | | 1 | | | 1 | | 1 | 1 | 1 | | | |
| P | | | | 1 | | | | 6 | 4 | | | | | 1 | 1 | | 3 | 2 | |
| Q | | | | | | | | | 1 | | | | | | | 1 | 2 | | 1 |
| R | | | | | | 1 | 31 | | 5 | 1 | 1 | 3 | | | | 1 | | | 1 |
| S | | | 1 | 1 | | | 1 | 3 | 3 | 1 | 4 | 3 | 6 | 3 | 2 | 2 | 1 | | 1 |
| T | | | | | | | 2 | 1 | 1 | 2 | 2 | 1 | 5 | 1 | 1 | 1 | | 1 | |
| V | | 33 | | | | 1 | | 7 | 1 | 1 | | 1 | 3 | 1 | 2 | | 1 | | |
| W | | | | | | | | 1 | | 1 | | 2 | 2 | | 1 | 1 | | | |
| X | | | | | | | | | | | | | | | | | | | |
| Y | | | 38 | 35 | | | | 5 | 5 | 4 | 2 | 3 | | 4 | 3 | 3 | 2 | 1 | |
| Z | | | | | | | | | | | | | | | | | | | |
| — | | | | | | | | 1 | 1 | 4 | 6 | 8 | 10 | 11 | 14 | 20 | 23 | 25 | |
| unknown (?) | | | | | | | | | | | | | | | | | | | |
| not sequenced | 1 | 1 | 1 | 1 | 1 | 1 | 3 | 3 | 3 | 3 | 3 | 3 | 4 | 4 | 4 | 4 | 4 | 4 | |
| sum of seq[2] | 40 | 39 | 39 | 39 | 39 | 39 | 39 | 37 | 37 | 37 | 37 | 37 | 37 | 36 | 36 | 36 | 36 | 36 | 36 |
| oomcaa[3] | 40 | 33 | 38 | 35 | 37 | 37 | 31 | 7 | 7 | 5 | 5 | 9 | 8 | 10 | 11 | 14 | 20 | 23 | 25 |
| mcaa[4] | A | V | Y | Y | C | A | R | D | G | D | G | G | — | — | — | — | — | — | — |
| rel. oomcaa[5] | 100% | 85% | 97% | 90% | 95% | 95% | 79% | 19% | 19% | 14% | 14% | 24% | 22% | 28% | 31% | 39% | 56% | 64% | 69% |
| pos occupied[6] | 1 | 5 | 2 | 4 | 3 | 3 | 8 | 10 | 12 | 18 | 13 | 13 | 12 | 12 | 17 | 14 | 13 | 10 | 9 |

| | Framework IV | | | | | | | | | | | | | | | | | | |
|---|---|---|---|---|---|---|---|---|---|---|---|---|---|---|---|---|---|---|---|
| amino acid[1] | G | H | I | J | K | 101 | 102 | 103 | 104 | 105 | 106 | 107 | 108 | 109 | 110 | 111 | 112 | 113 | sum |
| A | | | | 5 | | | | | | | | | | | | | | | 340 |
| B | | | | | | | | | | | | | | | | | | | |
| C | | | | | | | | | | | | | | | | | | | 79 |
| D | 2 | 1 | 2 | | | 27 | 2 | | | | | | | | | | | | 179 |
| E | 1 | | | | | | | | | 1 | | | | | | | | | 159 |
| F | | | | 2 | 15 | | 1 | | | | | | | | | | | | 130 |
| G | 1 | | 1 | 3 | | 1 | | | 27 | | 26 | | | | | 1 | | | 450 |
| H | | | | | | | 1 | | | | | | | | | | | | 51 |
| I | | | | 1 | | | 7 | | | | | | | | 3 | | | | 113 |
| K | | | 1 | | | | | | | 2 | | | | | | | | | 194 |
| L | | 1 | | | 2 | | | | | | | | 12 | | | 1 | | | 204 |
| M | 1 | | | | 4 | | | | | | | | 2 | | | | | | 144 |
| N | 3 | | 1 | | | 1 | 1 | | | | | | | | | | | | 138 |
| P | | | 1 | | | | 1 | | | 1 | | | | | | | | | 128 |
| Q | | | | | | | | | | 23 | | | | | | | | | 253 |
| R | | | | 1 | | | | | | | | | 1 | | | | | | 247 |
| S | | | | | | | 3 | | | | | | | | 1 | | 18 | 18 | 432 |
| T | | 1 | | 1 | | | | | | | | 21 | 6 | | 16 | | 1 | | 390 |
| V | 1 | 2 | 1 | | | 1 | 6 | | | | | | | 21 | | 18 | | | 342 |
| W | | 1 | | 4 | | | | 29 | | | | | | | | | | | 158 |
| X | | | | | | | | | | | | | | | | | | | |
| Y | 2 | 5 | 6 | 2 | | | 11 | | | | | | | | | | | | 294 |
| Z | | | | | | | | | | | | | | | | | | | |
| — | 25 | 25 | 23 | 18 | 11 | 6 | 3 | | | | | | | | | | | | 394 |
| unknown (?) | | | | | 3 | | | | | | | | | | | | | | 3 |
| not sequenced | 4 | 4 | 4 | 4 | 4 | 4 | 4 | 11 | 13 | 13 | 14 | 19 | 19 | 19 | 20 | 20 | 21 | 22 | 458 |
| sum of seq[2] | 36 | 36 | 36 | 36 | 36 | 36 | 36 | 29 | 27 | 27 | 26 | 21 | 21 | 21 | 20 | 20 | 19 | 18 | |
| oomcaa[3] | 25 | 25 | 23 | 18 | 15 | 27 | 11 | 29 | 27 | 23 | 26 | 21 | 12 | 21 | 16 | 18 | 18 | 18 | |
| mcaa[4] | — | — | — | — | F | D | Y | W | G | Q | G | T | L | V | T | V | S | S | |
| rel. oomcaa[5] | 69% | 69% | 64% | 50% | 42% | 75% | 31% | 100% | 100% | 85% | 100% | 100% | 57% | 100% | 80% | 90% | 95% | 100% | |
| pos occupied[6] | 8 | 7 | 8 | 8 | 5 | 5 | 10 | 1 | 1 | 4 | 1 | 1 | 4 | 1 | 3 | 3 | 2 | 1 | |

TABLE 6C

Analysis of V heavy chain subgroup 2

Framework I

| amino acid[1] | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| A | | | | | | | | | | 3 | | | | | | | | | |
| B | | | | | | | | | | | | | | | | | | | |
| C | | | | | | | | | | | | | | | | | | | |
| D | | | | | | | | | | | | | | | | | | | |
| E | 1 | | | | | 6 | | | | | | | | | | 2 | | | |
| F | | | | | | | | | | | | | | | | | | | |
| G | | | | | | | 6 | | | | | | | | | | | | |
| H | | | | | | | | | | | | | | | | | | | |
| I | | 1 | | | | | | | | | | | | | | | | | |
| K | | | | | 3 | | | | | | | | | 6 | | 1 | | | |
| L | | | | 6 | | | | | | | | 6 | | | | | | 6 | |
| M | | | | | | | | | | | | | | | | | | | |
| N | | | | | | | | 1 | | | | | | | | | | | |
| P | | | | | | | | 1 | | 6 | | | | | 6 | | 1 | | |
| Q | 2 | | | | | | | | | | | | | | | 4 | | | |
| R | | | | | | 2 | | | | | | | | | | | | | |
| S | | | | | | | | 4 | | | | | | | | | | | |
| T | | | | 6 | | | | | | 2 | | | | | 5 | | 5 | | 6 |
| V | | 5 | | | | | | | | 1 | | 6 | | | | | | | |
| W | | | | | | | | | | | | | | | | | | | |
| X | | | | | | | | | | | | | | | | | | | |
| Y | | | | | | | | | | | | | | | | | | | |
| Z | 3 | | | | | | | | | | | | | | | | | | |
| — | | | | | | | | | | | | | | | | | | | |
| unknown (?) | | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 1 | 1 | 1 |
| sum of seq[2] | 6 | 6 | 6 | 6 | 6 | 6 | 6 | 6 | 6 | 6 | 6 | 6 | 6 | 6 | 6 | 6 | 6 | 6 | 6 |
| oomcaa[3] | 3 | 5 | 6 | 6 | 3 | 6 | 4 | 6 | 6 | 3 | 6 | 6 | 6 | 6 | 5 | 4 | 6 | 6 | 6 |
| mcaa[4] | Z | V | T | L | K | E | S | G | P | A | L | V | K | P | T | Q | T | L | T |
| rel. oomcaa[5] | 50% | 83% | 100% | 100% | 50% | 100% | 67% | 100% | 100% | 50% | 100% | 100% | 100% | 100% | 83% | 67% | 83% | 100% | 100% |
| pos occupied[6] | 3 | 2 | 1 | 1 | 3 | 1 | 3 | 1 | 1 | 3 | 1 | 1 | 1 | 1 | 2 | 2 | 2 | 1 | 1 |

| | Framework I | | | | | | | | | | | CDR1 | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | 28 | 29 | 30 | 31 | A | B | 32 | 33 | 34 | 35 | 36 |
| A | | | | | | | | 1 | | | | 1 | | | 1 | | | | |
| B | | | | | | | | | | | | | | | | | | | |
| C | | | 7 | | | | | | | | | | | | | | | | |
| D | | | | | | | | | | | | | 1 | | | | | | |
| E | | | | | | | | | | | | | | | | | | | |
| F | | | | 3 | | | 6 | | 1 | | | | | | | | | | |
| G | | | | | | 7 | | | | | | | | 4 | | 3 | | 3 | |
| H | | | | | | | | | | | | | | | | | | | |
| I | | | | | | | | | | | | | | | 1 | | | | |
| K | | | | | | | | | | | | | | | | | | | |
| L | 6 | | | 2 | | | 1 | | 6 | | | | | | | | | | |
| M | | | | | | | | | | | | | | | 5 | | | | |
| N | | | | | | | | | | | | | 2 | | | | | | |
| P | | | | | | | | | | | | | | | | | | | |
| Q | | | | | | | | | | | | | | | | | | | |
| R | | | | | | | | | | | | | | | 2 | 1 | | | |
| S | | | | 1 | | 6 | | 6 | | | 6 | 2 | | 4 | | | | 4 | |
| T | | 6 | | 6 | | | | | | 1 | | 3 | | 1 | | | | | |
| V | | | | | 2 | | | | | | | | | | 2 | | 7 | | |
| W | | | | | | | | | | | | | | | | | | | 7 |
| X | | | | | | | | | | | | | | | | | | | |
| Y | | | | | 1 | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | 1 | 1 | | | | | | | | | | | | | | | | | |
| sum of seq[2] | 6 | 6 | 7 | 7 | 7 | 7 | 7 | 7 | 7 | 7 | 7 | 7 | 7 | 7 | 7 | 7 | 7 | 7 | 7 |
| oomcaa[3] | 6 | 6 | 7 | 6 | 3 | 6 | 7 | 6 | 6 | 6 | 6 | 3 | 4 | 4 | 5 | 3 | 7 | 4 | 7 |
| mcaa[4] | L | T | C | T | F | S | G | F | S | L | S | T | S | G | M | G | V | S | W |

TABLE 6C-continued

Analysis of V heavy chain subgroup 2

| amino acid[1] | Framework II | | | | | | | | | | | | | | CDR II | | | | |
|---|---|---|---|---|---|---|---|---|---|---|---|---|---|---|---|---|---|---|---|
| | 37 | 38 | 39 | 40 | 41 | 42 | 43 | 44 | 45 | 46 | 47 | 48 | 49 | 50 | 51 | 52 | A | B | C |
| A | | | | | | | | 6 | | | | | | 7 | | | | | |
| B | | | | | | | | | | | | | | | | | | | |
| C | | | | | | | | | | | | | | | | | | | |
| D | | | | | | | | | | | | | | | | | 2 | | |
| E | | | | | | | | | | | 7 | | | | | | 2 | | |
| F | | | | | | | | | | | | | | | | | 2 | | |
| G | | | | 1 | | 7 | | 1 | | | | | | | | | | | |
| H | | | | | | | | | | | | | 2 | | | | | | |
| I | 7 | | | | | | | | | | | | | | 6 | | | | |
| K | | | | | | | 6 | | | | | | | | | | | | |
| L | | | | | | | | | 7 | | | 7 | | 2 | 1 | 1 | | | |
| M | | | | | | | | | | | | | | | | | | | |
| N | | | | | | | | | | | | | | | | | | | |
| P | | | | 5 | 7 | | | | | | | | | | | | | | |
| Q | | | 6 | | | | | | | | | | | | | | | | |
| R | | 7 | 1 | | | | 1 | | | | | | | 2 | | | | | |
| S | | | | 1 | | | | | | | | | | | | | | | |
| T | | | | | | | | | | | | | | | | | | | |
| V | | | | | | | | | | | | | | | | | | | |
| W | | | | | | | | | | | | 7 | | 1 | | | | | |
| X | | | | | | | | | | | | | | | 1 | | | | |
| Y | | | | | | | | | | | | | | | 1 | 1 | | | |
| Z | | | | | | | | | | | | | | | | | | | |
| — | | | | | | | | | | | | | | | | | 6 | 7 | 7 |
| unknown (?) | | | | | | | | | | | | | | | | | | | |
| not sequenced | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 |
| oomcaa[3] | 7 | 7 | 6 | 5 | 7 | 7 | 6 | 6 | 7 | 7 | 7 | 7 | 7 | 2 | 6 | 2 | 6 | 7 | 7 |
| mcaa[4] | I | R | Q | P | P | G | K | A | L | E | W | L | A | H | I | D | — | — | — |
| rel. oomcaa[5] | 100% | 100% | 86% | 71% | 100% | 100% | 86% | 86% | 100% | 100% | 100% | 100% | 100% | 29% | 86% | 29% | 86% | 100% | 100% |
| pos occupied[6] | 1 | 1 | 2 | 3 | 1 | 1 | 2 | 2 | 1 | 1 | 1 | 1 | 1 | 4 | 2 | 5 | 2 | 1 | 1 |

| amino acid[1] | CDR II | | | | | | | | | | | | | | Framework III | | | | |
|---|---|---|---|---|---|---|---|---|---|---|---|---|---|---|---|---|---|---|---|
| | 53 | 54 | 55 | 56 | 57 | 58 | 59 | 60 | 61 | 62 | 63 | 64 | 65 | 66 | 67 | 68 | 69 | 70 | 71 |
| A | | | | | | | | | | | | | | | | | | | |
| B | | | | | | | | | | | | | | | | | | | |
| C | | | | | | | | | | | | | | | | | | | |
| D | | 3 | 6 | 5 | | | | | | | | | | | | | | | |
| E | | | | 1 | | | | | | | | | 1 | | | | | | |
| F | | | | | 1 | | 1 | | | | | | | | | | | | |
| G | | | | | | | | | | | | | | | | | | | |
| H | | | 1 | | | | 1 | | | | | | | | | | 6 | | |
| I | | | | | | | | | | | | | | | | | 6 | | |
| K | | | | 1 | 6 | | | | | | | 4 | | | | | | | 6 |
| L | | | | | | | | | | | | | 7 | | | 7 | | | |
| M | | | | | | | | | | | | | | | | | | | |
| N | | 3 | | | | | | | | | | | | | | | | | |
| P | | | | | | | | | | 2 | | | | | | | | | |
| Q | | | | | | | | | | | | | | | | | | | |
| R | | | | | | 2 | | | 1 | | | 2 | | 7 | | | | | 1 |
| S | 2 | | | | | 2 | | 6 | | 7 | | | 4 | | | 1 | | 5 | |
| T | | | | | | | | 4 | | | | | 3 | | | 6 | | 2 | |
| V | | | | | | | | | | | | | | | | | 1 | | |
| W | 4 | | | | | | 1 | | | | | | | | | | | | |
| X | 1 | 1 | | | | | | 1 | | | | | | | | | | | |
| Y | | | | | | 3 | 4 | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 |
| oomcaa[3] | 4 | 3 | 6 | 5 | 6 | 3 | 4 | 6 | 4 | 7 | 7 | 4 | 4 | 7 | 7 | 6 | 6 | 5 | 6 |
| mcaa[4] | W | D | D | D | K | Y | Y | S | T | S | L | K | S | R | L | T | I | S | K |
| rel. oomcaa[5] | 57% | 43% | 86% | 71% | 86% | 43% | 57% | 86% | 57% | 100% | 100% | 57% | 57% | 100% | 100% | 86% | 86% | 71% | 86% |

TABLE 6C-continued

Analysis of V heavy chain subgroup 2

| pos occupied[6] | 3 | 3 | 2 | 3 | 2 | 3 | 4 | 2 | 3 | 1 | 1 | 3 | 2 | 1 | 1 | 2 | 2 | 2 | 2 |
|---|---|---|---|---|---|---|---|---|---|---|---|---|---|---|---|---|---|---|---|

| | Framework III | | | | | | | | | | | | | | | | | | |
|---|---|---|---|---|---|---|---|---|---|---|---|---|---|---|---|---|---|---|---|
| amino acid[1] | 72 | 73 | 74 | 75 | 76 | 77 | 78 | 79 | 80 | 81 | 82 | A | B | C | 83 | 84 | 85 | 86 | 87 |
| A | | | | | | | | | | | | | | | | | 1 | | |
| B | | | | | | | | | | | | | | | | | | | |
| C | | | | | | | | | | | | | | | | | | | |
| D | 6 | 1 | | | | | | | | | | | | | 6 | | 7 | | |
| E | | | | | | | | | | | | | | | | | | | |
| F | | | | | | | | | 1 | | | | | | | | | | |
| G | | | | | | | | | | | | | | | | | | | |
| H | | | | | | | | | | | | | | | | | | | |
| I | | | | | | | | | | 2 | | 1 | | | | | | | |
| K | | | | 6 | | | | | | | | | | | | | | | |
| L | | | | | | | | | | 6 | | | | | | | | | |
| M | | | | | | | | | | | 7 | | | 5 | | | | | |
| N | 1 | | | | 5 | | | | | | | | 6 | | 1 | 7 | | | |
| P | | | | | | | | | | | | | | | | | | | |
| Q | | | | | | 7 | | | | | | | | | | | | | |
| R | | | | 1 | | | | | | | | | | | | | | | |
| S | | | 7 | | 2 | | | | | | | | | | | | | | |
| T | | 6 | | | | | | | | | 5 | | 5 | | | | 6 | | 7 |
| V | | | | | | | 7 | 7 | | | | | | 1 | | 6 | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | 1 | 1 | 1 | | | | | |
| unknown (?) | | | | | | | | | | | | | | | | | | | |
| not sequenced | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 |
| oomcaa[3] | 6 | 6 | 7 | 6 | 5 | 7 | 7 | 7 | 6 | 5 | 7 | 5 | 6 | 5 | 6 | 7 | 6 | 7 | 7 |
| mcaa[4] | D | T | S | K | N | Q | V | V | L | T | M | T | N | M | D | P | V | D | T |
| rel. oomcaa[5] | 86% | 86% | 100% | 86% | 71% | 100% | 100% | 100% | 86% | 71% | 100% | 71% | 86% | 71% | 86% | 100% | 86% | 100% | 100% |
| pos occupied[6] | 2 | 2 | 1 | 2 | 2 | 1 | 1 | 1 | 2 | 2 | 1 | 3 | 2 | 3 | 2 | 1 | 2 | 1 | 1 |

| | Framework III | | | | | CDR III | | | | | | | | | | | |
|---|---|---|---|---|---|---|---|---|---|---|---|---|---|---|---|---|---|
| amino acid[1] | 88 | 89 | 90 | 91 | 92 | 93 | 94 | 95 | 96 | 97 | 98 | 99 | 100 | A | B | C | D | E | F |
| A | 5 | | | | | 5 | | | | | | | 1 | 2 | 1 | | | | |
| B | | | | | | | | | | | | | | | | | | | |
| C | | | | | 7 | | | | | | | | | | | | | | |
| D | | | | | | | | | | | | | | | | | | | |
| E | | | | | | | | | | | | | 2 | | | 1 | | | |
| F | 2 | | | | | | | | | | | | | | | | | | |
| G | | | | | | | | | | 1 | 1 | | 1 | 2 | 1 | 1 | 1 | 1 | 1 |
| H | | | | | | | 1 | | 1 | | | | | | | | | | |
| I | | | | | | | | 3 | | | 2 | | | | | | | | |
| K | | | | | | | | | | | | 1 | | | | | | | |
| L | | | | | | | | | | | | | 1 | | 1 | | | | |
| M | | | | | | | | | | | | | 1 | | | | | | |
| N | | | | | | | | 1 | 2 | | | | | 1 | | | | | |
| P | | | | | | | | | 1 | 1 | | 1 | | 1 | | | | | |
| Q | | | | | | | 1 | | | | | | | | | | | | |
| R | | | | | | | 6 | 1 | | | 1 | | | 1 | | | | | |
| S | | | | | | | | | | 1 | | 1 | 1 | | | | | | |
| T | | 7 | | | | | | | | 1 | | 1 | 1 | | | | | | |
| V | | | | | | 2 | | 1 | 1 | 1 | | 1 | 1 | | | 1 | | | |
| W | | | | | | | | | | | 1 | | | | | | | | |
| X | | | | | | | | | | | | | | | | | | | |
| Y | | | 7 | 7 | | | | | | | 2 | | | | 1 | 2 | 1 | 1 | |
| Z | | | | | | | | | | | | | | | | | | | |
| — | | | | | | | | | | | | | 2 | 2 | 3 | 4 | 4 | | |
| unknown (?) | | | | | | | 1 | 1 | 1 | 1 | 1 | 1 | 1 | 1 | 1 | 1 | 1 | 1 | 1 |
| not sequenced | | | | | | | | | | | | | | | | | | | |
| sum of seq[2] | 7 | 7 | 7 | 7 | 7 | 7 | 7 | 6 | 6 | 6 | 6 | 6 | 6 | 6 | 6 | 6 | 6 | 6 | 6 |
| oomcaa[3] | 5 | 7 | 7 | 7 | 7 | 5 | 6 | 3 | 1 | 2 | 2 | 1 | 2 | 2 | 2 | 2 | 3 | 4 | 4 |
| mcaa[4] | A | T | Y | Y | C | A | R | I | H | N | I | G | E | A | — | — | — | — | — |
| rel. oomcaa[5] | 71% | 100% | 100% | 100% | 100% | 71% | 86% | 50% | 17% | 33% | 33% | 17% | 33% | 33% | 33% | 33% | 50% | 67% | 67% |
| pos | 2 | 1 | 1 | 1 | 1 | 2 | 2 | 4 | 6 | 4 | 5 | 6 | 5 | 5 | 4 | 5 | 3 | 3 | 3 |

TABLE 6C-continued

Analysis of V heavy chain subgroup 2

| amino acid[1] | G | H | I | J | K | 101 | 102 | 103 | 104 | 105 | 106 | 107 | 108 | 109 | 110 | 111 | 112 | 113 | sum |
|---|---|---|---|---|---|---|---|---|---|---|---|---|---|---|---|---|---|---|---|
| A | | | | | | | | | | | | | | | 1 | | | | 35 |
| B | | | | | | | | | | | | | | | | | | | |
| C | | | | | | | | | | | | | | | | | | | 16 |
| D | | | | | | | 6 | | | | | | | | | | | | 43 |
| E | | | | | | | | | | | | | | | | | | | 21 |
| F | | | | | 3 | | | | | | | | | | | | | | 18 |
| G | | | | | | | | | 6 | | 6 | | | | | | | | 55 |
| H | | | | | | | | | | | | | | | | | | | 6 |
| I | | | | | | | | | | | | | | | | | | | 29 |
| K | | | | | | | | | | 1 | | | 1 | | | | | | 42 |
| L | | | | | 1 | | 1 | | | | | | 3 | | | | | | 78 |
| M | | | | | 2 | | | | | | | | | | | | | | 20 |
| N | | | 1 | | | | | | | | | | | | | | | | 23 |
| P | | | | | | | 1 | | | | | | 1 | | | | | | 41 |
| Q | | | | | | | | | | | 3 | | | | | | | | 23 |
| R | | | | | | | | | | | 2 | | | | | | | | 41 |
| S | | | | | | | | | | | | | | | | | 6 | 3 | 82 |
| T | | | | | | | | | | | | 6 | 1 | | 5 | | | | 102 |
| V | | | | | | | | | 3 | | | | | 6 | | 6 | | | 68 |
| W | 1 | | | 1 | | | | 6 | | | | | | | | | | | 29 |
| X | | | | | | | | | | | | | | | | | | | 4 |
| Y | 1 | | 2 | | | | | | 1 | | | | | | | | | | 35 |
| Z | | | | | | | | | | | | | | | | | | | 3 |
| — | 4 | 6 | 5 | 3 | | | | | | | | | | | | | | | 56 |
| unknown (?) | | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 1 | 4 | 54 |
| sum of seq[2] | 6 | 6 | 6 | 6 | 6 | 6 | 6 | 6 | 6 | 6 | 6 | 6 | 6 | 6 | 6 | 6 | 6 | 3 | |
| oomcaa[3] | 4 | 6 | 5 | 3 | 3 | 6 | 3 | 6 | 6 | 3 | 6 | 6 | 3 | 6 | 5 | 6 | 6 | 3 | |
| mcaa[4] | — | — | — | — | F | D | V | W | G | Q | G | T | L | V | T | V | S | S | |
| rel. oomcaa[5] | 67% | 100% | 83% | 50% | 50% | 100% | 50% | 100% | 100% | 50% | 100% | 100% | 50% | 100% | 83% | 100% | 100% | 100% | |
| pos occupied[6] | 3 | 1 | 2 | 3 | 3 | 1 | 4 | 1 | 1 | 3 | 1 | 1 | 4 | 1 | 2 | 1 | 1 | 1 | |

TABLE 6D

Analysis of V heavy chain subgroup 3

| amino acid[1] | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| A | | | | | 1 | | 1 | | | 12 | | 1 | | 3 | 1 |
| B | | | 1 | | | 1 | | | | | | | 1 | | |
| C | | | | | | | | | | | | | | | |
| D | 1 | | | | | 1 | | | | 16 | | | | | |
| E | 110 | | 9 | | 15 | 166 | | | 9 | | | 4 | 8 | | 2 |
| F | | | | | | | | | | | | | | | |
| G | | | | | | | | 181 | 193 | 174 | | 1 | | 202 | |
| H | | | 5 | | | | | | | | | | 4 | | |
| I | | | | | | | | | | | | 9 | | | |
| K | | 5 | 3 | | | | | | | | | | 26 | | |
| L | | 1 | 5 | 176 | 43 | | | | | | 140 | | | 1 | |
| M | | 12 | | 1 | | | | | | | | | | | |
| N | | | | | | | | | | | 1 | | | | |
| P | | | | | | | | | | | | | 1 | 194 | |
| Q | 41 | | 138 | 1 | 3 | 12 | | | | | | | 162 | | |
| R | | | 6 | | | | | | | | | | 4 | | |
| S | | | | | | | 178 | | | | 2 | | | 8 | |
| T | | | | | | | 1 | | | | | | | | |
| V | 5 | 147 | | 1 | 118 | | | | | | 62 | 195 | | | |
| W | | | | | | | | | | | | | | 1 | |
| X | | | | | | | | | | | | | | | |
| Y | | | | | | | | | | | | | | | |
| Z | 8 | | | | | | | | | | | | | | |
| — | | | | | | | | | | | | | | | |
| unknown (?) | | | | | | | | | | | | | | | |
| not sequenced | 47 | 47 | 45 | 33 | 32 | 32 | 32 | 31 | 10 | 7 | 6 | 6 | 6 | 6 | 6 |

TABLE 6D-continued

Analysis of V heavy chain subgroup 3

| | | | | | | | | | | | | | | | |
|---|---|---|---|---|---|---|---|---|---|---|---|---|---|---|---|
| sum of seq[2] | 165 | 165 | 167 | 179 | 180 | 180 | 180 | 181 | 202 | 205 | 206 | 206 | 206 | 206 | 206 |
| oomcaa[3] | 110 | 147 | 138 | 176 | 118 | 166 | 178 | 181 | 193 | 174 | 140 | 195 | 162 | 194 | 202 |
| mcaa[4] | E | V | Q | L | V | E | S | G | G | G | L | V | Q | P | G |
| rel. oomcaa[5] | 67% | 89% | 83% | 98% | 66% | 92% | 99% | 100% | 96% | 85% | 68% | 95% | 79% | 94% | 98% |
| pos occupied[6] | 5 | 4 | 7 | 4 | 5 | 4 | 3 | 1 | 2 | 5 | 3 | 4 | 7 | 4 | 4 |

| | Framework I | | | | | | | | | | | | | | |
|---|---|---|---|---|---|---|---|---|---|---|---|---|---|---|---|
| amino acid[1] | 16 | 17 | 18 | 19 | 20 | 21 | 22 | 23 | 24 | 25 | 26 | 27 | 28 | 29 | 30 |
| A | | | | | | | | 183 | 192 | | 1 | | | | |
| B | | | | | | | | | | | | | | | |
| C | | | | | | 1 | 209 | | | | | | | | |
| D | | | | | | | | | | | | | | | 7 |
| E | 8 | | | | | | | 8 | | | 3 | | 1 | | |
| F | | 1 | 1 | | | 1 | | | | | | 201 | | 201 | |
| G | 134 | | | | | | | | 2 | | 207 | | | | 3 |
| H | | | | | | | | | | | | | | | 1 |
| I | | | | | | | | 2 | | | | 3 | 17 | 1 | |
| K | | | | 15 | | | | | | | | | | | 4 |
| L | | | 205 | | 201 | | | | | | | 6 | | 3 | |
| M | | | | 1 | | | | | | | | | 1 | | |
| N | | | | | | | | | | | | | 10 | | 10 |
| P | | | | | | | | 1 | | | | 2 | | | |
| Q | | | 1 | | | | | | | | | | | | |
| R | 62 | | | 191 | | | | | | | | | 15 | | 11 |
| S | | 206 | | | | 207 | | 4 | 2 | 209 | | | 15 | | 174 |
| T | 4 | 1 | | 2 | | | | 4 | 4 | | | 1 | 163 | | |
| V | | | | | 8 | | | 7 | 9 | | | | 1 | 6 | |
| W | | | | | | | | | | | | | | | |
| X | | | | | | | | | | | | | | | |
| Y | | | | | | | | | | | | | | | |
| Z | | | | | | | | | | | | | | | |
| — | | | | | | | | | | | | | | | |
| unknown (?) | | | | | | | | | | | | | | | |
| not sequenced | 4 | 4 | 4 | 4 | 3 | 3 | 3 | 3 | 3 | 3 | 1 | 1 | 2 | 1 | 2 |
| sum of seq[2] | 208 | 208 | 208 | 208 | 209 | 209 | 209 | 209 | 209 | 209 | 211 | 211 | 210 | 211 | 210 |
| oomcaa[3] | 134 | 206 | 205 | 191 | 201 | 207 | 209 | 183 | 192 | 209 | 207 | 201 | 163 | 201 | 174 |
| mcaa[4] | G | S | L | R | L | S | C | A | A | S | G | F | T | F | S |
| rel. oomcaa[5] | 64% | 99% | 99% | 92% | 96% | 99% | 100% | 88% | 92% | 100% | 98% | 95% | 78% | 95% | 83% |
| pos occupied[6] | 4 | 3 | 4 | 3 | 2 | 3 | 1 | 7 | 5 | 1 | 3 | 4 | 8 | 4 | 7 |

| | CDRI | | | | | | | Framework II | | | | | | | |
|---|---|---|---|---|---|---|---|---|---|---|---|---|---|---|---|
| amino acid[1] | 31 | A | B | 32 | 33 | 34 | 35 | 36 | 37 | 38 | 39 | 40 | 41 | 42 | 43 |
| A | 1 | | | 17 | 80 | | 1 | | 1 | | | 187 | | 1 | |
| B | | | | | | | | | | | | | | | |
| C | | | | | | | | | | | | 1 | | 1 | |
| D | 26 | | | 3 | 7 | 2 | | | | | | | | 1 | 1 |
| E | 1 | | | | 10 | | | | | | | | | 1 | 1 |
| F | | | | 5 | | | | | | | | | | | |
| G | 13 | | | | 31 | | 1 | | | | | 2 | | 209 | |
| H | | | | 4 | | | 88 | | | | | | | | |
| I | 1 | | | 1 | | 15 | | | 12 | | | | | | |
| K | 7 | | | | | | | | | | | 1 | | | 202 |
| L | 3 | | | | | 3 | | | 2 | 3 | 1 | 2 | 1 | | |
| M | | | | | | | 193 | | | | | | | | |
| N | 35 | | | 8 | 3 | | 34 | | | | | 4 | 191 | | |
| P | | | | 1 | | | 1 | | | | | | | | |
| Q | | | | | | | | | | | | 209 | 1 | | 1 |
| R | 7 | | | | | | | | | 207 | | 7 | | | 8 |
| S | 103 | | | 17 | 8 | | 72 | | | | | 3 | 14 | | |
| T | 9 | | | | 15 | | 10 | | | | | 4 | 5 | | |
| V | 2 | | | | 7 | 1 | | | 197 | | | 2 | | | |
| W | | | | | 30 | | | 212 | | | | | | | |
| X | 1 | | | | | | | | | | | | | | |
| Y | 1 | | | 154 | 19 | | 3 | | | | | | | | |
| Z | | | | | | | | | | | | | | | |
| — | | 210 | 210 | | | | | | | | | | | | |
| unknown (?) | | | | | | | | | | | | | | | |
| not sequenced | 2 | | | 2 | 2 | | | | 1 | 1 | 1 | | | | |
| sum of seq[2] | 210 | 210 | 210 | 210 | 210 | 212 | 212 | 212 | 211 | 211 | 211 | 212 | 212 | 212 | 212 |
| oomcaa[3] | 103 | 210 | 210 | 154 | 80 | 193 | 88 | 212 | 197 | 207 | 209 | 187 | 191 | 209 | 202 |
| mcaa[4] | S | — | — | Y | A | M | H | W | V | R | Q | A | P | G | K |
| rel. oomcaa[5] | 49% | 100% | 100% | 73% | 38% | 91% | 42% | 100% | 93% | 98% | 99% | 88% | 90% | 99% | 95% |
| pos occupied[6] | 14 | 1 | 1 | 9 | 10 | 4 | 9 | 1 | 3 | 3 | 3 | 9 | 5 | 4 | 4 |

TABLE 6D-continued

Analysis of V heavy chain subgroup 3

| | Framework II | | | | | | | CDR II | | | | | | | |
|---|---|---|---|---|---|---|---|---|---|---|---|---|---|---|---|
| amino acid[1] | 44 | 45 | 46 | 47 | 48 | 49 | 50 | 51 | 52 | A | B | C | 53 | 54 | 55 |
| A | 1 | | | | | 77 | 42 | | 1 | 2 | | 14 | | 7 | |
| B | | | 3 | | | | | | 1 | | | | | | |
| C | | | | | | | | | | | | | 1 | | |
| D | | | 1 | | | | | | | 7 | | | 94 | 8 | 3 |
| E | | | 198 | | | | | | 3 | 2 | 1 | | 2 | | 1 |
| F | | | | | | | 7 | 1 | 2 | 1 | | | | 1 | 8 |
| G | 207 | | | | | 33 | 11 | | 10 | 46 | | | 4 | 163 | 85 |
| H | | | | | | | 6 | | | 1 | | | | | |
| I | | | | | 3 | | 3 | 191 | | 1 | | | | | 1 |
| K | | | | | | | | 1 | 37 | 2 | 30 | | 3 | 1 | |
| L | | 211 | | | 5 | | 12 | 1 | | | | | | | |
| M | | | | | | | 1 | 1 | | | | | | | |
| N | | | | | | | 13 | | 7 | 9 | 2 | | 13 | 11 | 1 |
| P | | 1 | | | | | | | | 1 | | | 1 | | |
| Q | | | 7 | | | | 7 | | | 10 | | | | | |
| R | 1 | | | | | | 24 | 1 | 17 | 5 | 1 | | 2 | | 16 |
| S | 3 | | | 1 | | 102 | 11 | 9 | 118 | 43 | | 1 | 74 | 17 | 82 |
| T | | | | | | | 3 | 5 | 4 | 2 | | 13 | 12 | 3 | 3 |
| V | | | 3 | | 204 | | 49 | 2 | | 1 | | 6 | | | |
| W | | | | 210 | | | 1 | | 8 | 6 | | | | | |
| X | | | | | | | | | | | | | 4 | | 3 |
| Y | | | | 1 | | | 22 | | 5 | 58 | | | | | 8 |
| Z | | | | | | | | | | | | | | | |
| — | | | | | | | | | | | | | | | |
| unknown (?) | | | | | | | | | | | | | | | |
| not sequenced | | | | | | | | 14 | 178 | 178 | 2 | 1 | 1 | | |
| sum of seq[2] | 212 | 212 | 212 | 212 | 212 | 212 | 212 | 212 | 212 | 212 | 212 | 212 | 212 | 212 | 212 |
| oomcaa[3] | 207 | 211 | 198 | 210 | 204 | 102 | 49 | 191 | 118 | 58 | 178 | 178 | 94 | 163 | 85 |
| mcaa[4] | G | L | E | W | V | S | V | I | S | Y | — | — | D | G | G |
| rel. oomcaa[5] | 98% | 100% | 93% | 99% | 96% | 48% | 23% | 90% | 56% | 27% | 84% | 84% | 44% | 77% | 40% |
| pos occupied[6] | 4 | 2 | 5 | 3 | 3 | 15 | 9 | 11 | 19 | 5 | 5 | 12 | 9 | 12 | |

| | CDR II | | | | | | | | | | | Framework III | | | |
|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 |
| A | 9 | 1 | 2 | | 174 | 33 | | | | | | | 1 | | |
| B | 1 | 2 | | | | | | | | | | | | | |
| C | | | | | | | | | | | | | | | |
| D | 11 | | 17 | | | 160 | | | | | | | | | |
| E | 8 | 3 | 2 | | | 1 | | | 2 | | | | | | |
| F | 1 | | 3 | 2 | | | | | | | | 207 | | | |
| G | 5 | 1 | 5 | | 4 | 5 | | | | 212 | 1 | | | | |
| H | 1 | | 4 | | | | | | | | | | | | |
| I | 3 | 37 | 2 | | | | | 8 | | | | | 14 | 208 | |
| K | 1 | 61 | | | | | | | 199 | | 8 | | | | |
| L | 1 | 1 | 1 | | 1 | | | | | | | 1 | | 1 | |
| M | 8 | | 2 | | 1 | | | | | | | | | | |
| N | 51 | | 4 | | | 2 | | | 2 | | | | | | |
| P | 1 | 1 | | | 6 | 8 | 18 | | 1 | | | | | | |
| Q | 3 | 2 | | | | | | | 2 | | | 2 | | | |
| R | 5 | 4 | | | 5 | | | | 6 | | 201 | | | | |
| S | 48 | | 11 | | 4 | | 193 | | | | | 2 | 7 | | 211 |
| T | 42 | 97 | 5 | | 7 | | | 204 | | | | | 189 | | 1 |
| V | | 2 | | | 10 | 2 | | 204 | | | | 1 | | 3 | |
| W | | | 2 | | | | | | | | | | | | |
| X | 4 | | 1 | | | 1 | | | | | | | | | |
| Y | 9 | | 151 | 210 | | | 1 | | | | | 1 | 1 | | |
| Z | | | | | | | | | | | | | | | |
| — | | | | | | | | | | | | | | | |
| unknown (?) | | | | | | | | | | | | | | | |
| not sequenced | | | | | | | | | | | | | | | |
| sum of seq[2] | 212 | 212 | 212 | 212 | 212 | 212 | 212 | 212 | 212 | 212 | 212 | 212 | 212 | 212 | 212 |
| oomcaa[3] | 51 | 97 | 151 | 210 | 174 | 160 | 193 | 204 | 199 | 212 | 201 | 207 | 189 | 208 | 211 |
| mcaa[4] | N | T | Y | Y | A | D | S | V | K | G | R | F | T | I | S |
| rel. oomcaa[5] | 24% | 46% | 71% | 99% | 82% | 75% | 91% | 96% | 94% | 100% | 95% | 98% | 89% | 98% | 100% |
| pos occupied[6] | 19 | 12 | 15 | 2 | 9 | 8 | 3 | 2 | 6 | 1 | 4 | 5 | 5 | 3 | 2 |

| | Framework III | | | | | | | | | | | | | |
|---|---|---|---|---|---|---|---|---|---|---|---|---|---|---|
| amino acid[1] | 71 | 72 | 73 | 74 | 75 | 76 | 77 | 78 | 79 | 80 | 81 | 82 | A | B | C |

TABLE 6D-continued

Analysis of V heavy chain subgroup 3

| | | | | | | | | | | | | | | | |
|---|---|---|---|---|---|---|---|---|---|---|---|---|---|---|---|
| A | | | | 57 | | 1 | 8 | | | | | | | 1 | |
| B | | | | | | | | | | | 2 | | | | |
| C | | | | | | | | | | | | | | | |
| D | | 199 | 38 | | 2 | 2 | | | 1 | | | | 10 | | |
| E | | 6 | | | 4 | | | | | | 5 | | | | |
| F | | | | | | | | 13 | | | | | | | |
| G | | | | | | | | | | | | | 1 | 4 | |
| H | | | | | 1 | | | 1 | | | 2 | | 2 | | |
| I | | | 1 | | | | 2 | 2 | | | | 3 | 1 | 1 | |
| K | | | | | 186 | 6 | | | | | | | 3 | | |
| L | | | | | | | 188 | | 209 | | | 3 | 1 | | 212 |
| M | 1 | | | | 2 | | 10 | 3 | | 2 | | 205 | | | |
| N | | 5 | 170 | | 2 | 188 | | | | | 3 | | 181 | 10 | |
| P | | | | | | 1 | | | | | | | | | |
| Q | | | | | 7 | | | | | | 199 | | | | |
| R | 211 | | | | 1 | 1 | | | | | | | 2 | 8 | |
| S | | | | 153 | 8 | 10 | 56 | | 3 | | | | 6 | 186 | |
| T | | | | | | | 142 | | | | | 1 | 4 | 2 | |
| V | | | | 1 | | | | 11 | | 1 | | 1 | | | |
| W | | | | | | | | | | | | | | | |
| X | | 2 | 2 | | | 4 | | | | | | | 1 | | |
| Y | | | | | | | | | 194 | | | | | | |
| Z | | | | | | | | | | | | | | | |
| — | | | | | | | | | | | | | | | |
| unknown (?) | | | | | | | | | | | | | | | |
| not sequenced | | | 1 | 1 | | | | | | | | | | | |
| sum of seq[2] | 212 | 212 | 212 | 212 | 212 | 212 | 212 | 212 | 212 | 212 | 212 | 212 | 212 | 212 | 212 |
| oomcaa[3] | 211 | 199 | 170 | 153 | 186 | 188 | 142 | 188 | 194 | 209 | 299 | 205 | 181 | 186 | 212 |
| mcaa[4] | R | D | N | S | K | N | T | L | Y | L | Q | M | N | S | L |
| rel. oomcaa[5] | 100% | 94% | 81% | 73% | 88% | 89% | 67% | 89% | 92% | 99% | 94% | 97% | 85% | 88% | 100% |
| pos occupied[6] | 2 | 4 | 4 | 3 | 8 | 7 | 6 | 5 | 5 | 3 | 6 | 4 | 11 | 7 | 1 |

| | Framework III | | | | | | | | | | CDR III | | | | |
|---|---|---|---|---|---|---|---|---|---|---|---|---|---|---|---|
| amino acid[1] | 83 | 84 | 85 | 86 | 87 | 88 | 89 | 90 | 91 | 92 | 93 | 94 | 95 | 96 | 97 |
| A | | 149 | 1 | | 1 | 207 | | | | | 173 | 2 | 15 | 9 | 11 |
| B | | | | | | | | | | | | | | | |
| C | | | | | | | | | 1 | 210 | | 5 | 2 | | 1 |
| D | | 5 | 15 | 209 | | | | | | | 2 | 54 | 7 | 6 | |
| E | 1 | | 190 | | | | | | | | | 11 | 2 | 11 | |
| F | | | | | | | 1 | | 15 | | 1 | | 9 | 6 | |
| G | 1 | 1 | 6 | | | 4 | 1 | | | | 2 | 8 | 34 | 26 | 35 |
| H | | 1 | | | | | | | 1 | | | | 3 | 11 | |
| I | | 8 | | | | | 2 | | | | | 4 | 15 | 10 | |
| K | 30 | | | | | | | | | | 60 | 4 | 3 | 5 | |
| L | | | | | | 18 | | | | | 1 | 6 | 11 | 7 | |
| M | | | | 2 | | 1 | | | | | | | 6 | 1 | |
| N | | 1 | | 1 | | | | | | | 2 | 20 | 4 | 3 | |
| P | | 9 | | | | | | | | | 1 | 3 | 4 | 29 | 10 |
| Q | | | | 1 | | | | | | | | 5 | 3 | 9 | 2 |
| R | 177 | | | | | | | | | | 103 | 9 | 30 | 19 | |
| S | | 1 | | | 1 | | | | | | 3 | 9 | 8 | 11 | |
| T | 3 | 28 | | | 207 | | 1 | | | | 25 | 15 | 7 | 6 | 20 |
| V | | 9 | | | | | 187 | | | | 10 | 1 | 7 | 7 | 15 |
| W | | | | | | | | | 1 | | | 3 | 4 | 3 | |
| X | | | | 1 | | | | | | | | | | | |
| Y | | | | | | | 211 | 194 | | | | 12 | 9 | 8 | |
| Z | | | | | | | | | | | 1 | 3 | 4 | | |
| — | | | | | | | | | | | | | | | |
| unknown (?) | | | | | | | | | | | | | | | |
| not sequenced | | | | | 1 | 1 | 1 | 1 | 1 | 1 | 1 | 1 | 7 | 12 | 13 |
| sum of seq[2] | 212 | 212 | 212 | 212 | 211 | 211 | 211 | 211 | 211 | 211 | 211 | 211 | 205 | 200 | 199 |
| oomcaa[3] | 177 | 149 | 190 | 209 | 207 | 207 | 187 | 211 | 211 | 210 | 173 | 103 | 54 | 30 | 35 |
| mcaa[4] | R | A | E | D | T | A | V | Y | Y | C | A | R | D | R | G |
| rel. oomcaa[5] | 83% | 70% | 90% | 99% | 98% | 98% | 89% | 100% | 92% | 100% | 82% | 49% | 26% | 15% | 18% |
| pos occupied[6] | 5 | 10 | 4 | 4 | 4 | 2 | 7 | 1 | 4 | 2 | 5 | 14 | 18 | 20 | 21 |

| | CDR III | | | | | | | | | | | | | |
|---|---|---|---|---|---|---|---|---|---|---|---|---|---|---|
| amino acid[1] | 98 | 99 | 100 | A | B | C | D | E | F | G | H | I | J | K | 101 |
| A | 7 | 13 | 7 | 9 | 6 | 2 | 3 | 5 | 5 | | 9 | | 13 | | 2 |
| B | | | | | | | | | | | | | | | |
| C | 13 | 5 | | 1 | 2 | 11 | 3 | | 2 | | | | | 1 | |
| D | 11 | 7 | 10 | 4 | 2 | 3 | 10 | 3 | 3 | 1 | | 3 | 2 | | 146 |
| E | 6 | 3 | 1 | 13 | | 1 | 1 | | | | | | | | 1 |

TABLE 6D-continued

Analysis of V heavy chain subgroup 3

| | | | | | | | | | | | | | | | |
|---|---|---|---|---|---|---|---|---|---|---|---|---|---|---|---|
| F | 3 | 5 | 4 | 5 | 5 | 6 | 3 | 5 | 7 | 2 | | 1 | 1 | 65 | 1 |
| G | 34 | 17 | 35 | 17 | 14 | 23 | 10 | 5 | 1 | 5 | 3 | 2 | 32 | | 6 |
| H | 3 | 4 | 3 | 2 | 9 | 2 | | 1 | 3 | 1 | 2 | 8 | 1 | | |
| I | 6 | 11 | 4 | 4 | 3 | 1 | 3 | 10 | 3 | 3 | 2 | | 1 | 2 | |
| K | 2 | 11 | | | 3 | 1 | | | | | | | | | |
| L | 26 | 13 | 4 | 12 | 8 | 2 | 6 | 3 | 10 | 3 | | | | 2 | 1 |
| M | | 1 | 2 | | | | | | | | 1 | | | 32 | |
| N | 4 | 6 | 4 | 3 | 2 | 2 | 6 | | | | 2 | 5 | | | 2 |
| P | 6 | 5 | 5 | 6 | 9 | 8 | 2 | 3 | 2 | 1 | | 3 | | 9 | |
| Q | 4 | | 1 | 1 | 1 | 1 | 1 | | | | | 1 | | | |
| R | 4 | 10 | 9 | 7 | 5 | 5 | 2 | 3 | 1 | | 1 | | 2 | | 4 |
| S | 16 | 28 | 27 | 25 | 24 | 8 | 11 | 9 | 3 | | 2 | 3 | 1 | 1 | 1 |
| T | 6 | 12 | 9 | 17 | 17 | 1 | 2 | 5 | 1 | 9 | 3 | 1 | | | |
| V | 13 | 7 | 15 | 4 | 3 | 6 | 2 | 12 | | 1 | 1 | 1 | 1 | | |
| W | 6 | 5 | 6 | 7 | 2 | 4 | | | | 1 | | 6 | 10 | | |
| X | | | | 1 | | | | | | | | | | | 1 |
| Y | 16 | 14 | 17 | 5 | 8 | 18 | 20 | 13 | 20 | 25 | 28 | 32 | 28 | | |
| Z | | | | | | | | | | | | | | | |
| — | 12 | 21 | 35 | 54 | 73 | 87 | 102 | 110 | 126 | 135 | 134 | 120 | 91 | 71 | 21 |
| unknown (?) | | | | | | | 3 | 2 | 1 | 1 | | | 3 | 2 | |
| not sequenced | 14 | 14 | 14 | 14 | 15 | 19 | 21 | 22 | 23 | 23 | 23 | 25 | 25 | 26 | 25 |
| sum of seq[2] | 198 | 198 | 198 | 197 | 196 | 192 | 190 | 189 | 188 | 188 | 188 | 186 | 186 | 185 | 186 |
| oomcaa[3] | 34 | 28 | 35 | 54 | 73 | 87 | 102 | 110 | 126 | 135 | 134 | 120 | 91 | 71 | 146 |
| mcaa[4] | G | S | G | — | — | — | — | — | — | — | — | — | — | — | D |
| rel. oomcaa[5] | 17% | 14% | 18% | 27% | 37% | 45% | 54% | 58% | 67% | 72% | 71% | 65% | 49% | 38% | 78% |
| pos occupied[6] | 20 | 20 | 19 | 20 | 19 | 20 | 17 | 14 | 14 | 12 | 12 | 13 | 12 | 8 | 11 |

Framework IV

| amino acid[1] | 102 | 103 | 104 | 105 | 106 | 107 | 108 | 109 | 110 | 111 | 112 | 113 | sum |
|---|---|---|---|---|---|---|---|---|---|---|---|---|---|
| A | 1 | | 1 | | | 2 | | | | | | | 1767 |
| B | | | | 1 | | | | | | | | | 13 |
| C | | | | | | | | | | | | | 470 |
| D | 2 | | | | | | | | | | | | 1121 |
| E | | | | | 1 | | | | | | | | 832 |
| F | 2 | | | | | | | | | | | | 807 |
| G | | | 140 | | 130 | | 1 | | | | | | 2743 |
| H | 4 | | | | | | | | | | | | 179 |
| I | 15 | | | | | | | | 1 | 1 | | | 651 |
| K | | | | 13 | | | | | | | | | 933 |
| L | 10 | | | 1 | | | 91 | | | | | 2 | 1881 |
| M | | | | | | | 6 | | | | | | 496 |
| N | 1 | | | | | 1 | | | | | | | 844 |
| P | 17 | | | | | 1 | 1 | | | | | | 568 |
| Q | | | | 111 | | | | | | | | | 949 |
| R | | | | 8 | | | | | | | | | 1413 |
| S | 7 | 1 | | | | | | | | | 118 | 110 | 3009 |
| T | | | | | | 123 | 27 | | 122 | | | 1 | 1426 |
| V | 34 | | 1 | | | 1 | | 125 | | 119 | | | 1851 |
| W | | 158 | | | | | | | | | | | 686 |
| X | | | | | | | | | | | | | 26 |
| Y | 82 | | | | | | | | | | | | 1598 |
| Z | | | | | | | | | | | | | 8 |
| — | 9 | 2 | 2 | 2 | 2 | 2 | 2 | 2 | 2 | 2 | 1 | 1 | 2023 |
| unknown (?) | | | | | | | | | | | | | 12 |
| not sequenced | 27 | 50 | 67 | 75 | 78 | 81 | 83 | 84 | 86 | 89 | 92 | 97 | 1650 |
| sum of seq[2] | 184 | 161 | 144 | 136 | 133 | 130 | 128 | 127 | 125 | 122 | 119 | 114 | |
| oomcaa[3] | 82 | 158 | 140 | 111 | 120 | 123 | 91 | 125 | 122 | 119 | 118 | 110 | |
| mcaa[4] | Y | W | G | Q | G | T | L | V | T | V | S | S | |
| rel. oomcaa[5] | 45% | 98% | 97% | 82% | 98% | 95% | 71% | 98% | 98% | 98% | 99% | 96% | |
| pos occupied[6] | 12 | 3 | 4 | 6 | 3 | 6 | 6 | 2 | 3 | 3 | 2 | 4 | |

TABLE 6E

Analysis of V heavy chain subgroup 4

Framework I

| amino acid[1] | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A | | | | | | | | | 19 | | | | | 1 | | | 1 |
| B | | | | | | | | | | | | | | | | | |
| C | | | | | | | | | | | | | | | | | |

TABLE 6E-continued

Analysis of V heavy chain subgroup 4

| | | | | | | | | | | | | | | | | | |
|---|---|---|---|---|---|---|---|---|---|---|---|---|---|---|---|---|---|
| D | | | | | | | | | | | | | | | | | |
| E | | | | | 32 | | | | | | | | | | | 44 | |
| F | | | | | | | | | | | | | | | | | |
| G | | | | | | 54 | 1 | 53 | | | | | | | | 2 | |
| H | | | 4 | | 2 | | | | | | | | | | | | |
| I | | | | | | | | | | | | | 1 | 54 | | | |
| K | | | | | | | | | | | | 53 | 19 | | 1 | | |
| L | | 7 | | 54 | | | | | | | | | | | | | |
| M | | | | | | | | | | | | | | | | | |
| N | | | | | | | | | 33 | | | | | 51 | 1 | | |
| P | 52 | | 50 | | 51 | 20 | | | | | | | | | | 7 | |
| Q | 1 | | | | | | | | | | | | | | | | |
| R | | | | | | | 33 | | | | | | | | 52 | | |
| S | | | | | | | | | | 1 | | | | | | | 52 |
| T | | 47 | | | 1 | | | | | | | 34 | | | | | |
| V | | | | | | | 20 | | | | | | | | | | |
| W | | | | | | | | | | | | | | | | | |
| X | | | | | | | | | | | | | | | | | |
| Y | 1 | | | | | | | | | | | | | | | | |
| Z | | | | | | | | | | | | | | | | | |
| — | | | | | | | | | | | | | | | | | |
| unknown (?) | | | | | | | | | | | | | | | | | |
| not sequenced | 3 | 3 | 3 | 3 | 4 | 4 | 4 | 3 | 3 | 4 | 4 | 3 | 3 | 4 | 4 | 4 | 4 |
| sum of seq[2] | 54 | 54 | 54 | 54 | 53 | 53 | 53 | 54 | 54 | 53 | 53 | 54 | 54 | 53 | 53 | 53 | 53 |
| oomcaa[3] | 52 | 47 | 50 | 54 | 51 | 32 | 33 | 54 | 33 | 53 | 53 | 34 | 54 | 51 | 52 | 44 | 52 |
| mcaa[4] | Q | V | Q | L | Q | E | S | G | P | G | L | V | K | P | S | E | T |
| rel. oomcaa[5] | 96% | 87% | 93% | 100% | 96% | 60% | 62% | 100% | 61% | 100% | 100% | 63% | 100% | 96% | 98% | 83% | 98% |
| pos occupied[6] | 3 | 2 | 2 | 1 | 2 | 3 | 2 | 1 | 4 | 1 | 1 | 3 | 1 | 3 | 2 | 3 | 2 |

| | Framework I | | | | | | | | | | | | | CDRI | | | |
|---|---|---|---|---|---|---|---|---|---|---|---|---|---|---|---|---|---|
| amino acid[1] | 18 | 19 | 20 | 21 | 22 | 23 | 24 | 25 | 26 | 27 | 28 | 29 | 30 | 31 | A | B | 32 |
| A | | 1 | | | 22 | | | | | | | | | | | | 1 |
| B | | | | | | | | | | | | | | | | | |
| C | | | | | 53 | | | | | | | | | | | | |
| D | | | | | 1 | | | | | | | | | 4 | 1 | 1 | 1 |
| E | | | | | | | | | | | | | | | | | |
| F | | | | | | | | 1 | | | | 22 | | | | | 1 |
| G | | | | | | | | | 53 | 53 | | | | 21 | 3 | 4 | |
| H | | | | | | | | | | 1 | | | | | | | 2 |
| I | | | | | | 1 | | | | | 1 | 32 | | | | | |
| K | | 1 | | | | | | | | | | | | | | | |
| L | 53 | | 50 | | | | | | | | | | | | | | |
| M | | | | | | | | | | | | | | | | | |
| N | | | | | | | | | | | | | 1 | 1 | | 2 | 2 |
| P | | | 2 | | | | | | | | 3 | | | | | | |
| Q | | | | | | | | | | | | | | 1 | | | |
| R | | | | | | | | | 1 | | | | 3 | 2 | | 1 | |
| S | | 52 | | | | 2 | | 35 | | | | 51 | 1 | 52 | 25 | 5 | 9 | 1 |
| T | | | | 53 | | 29 | | | | | | | | | 2 | 1 | |
| V | | | 1 | | | | 55 | | 1 | | | 1 | | | | | |
| W | | | | | | | | | | | | | | | 1 | | |
| X | | | | | | | | | | | | | | | | | |
| Y | | | | | | | 19 | | | 1 | | | | | | | 48 |
| Z | | | | | | | | | | | | | | | | | |
| — | | | | | | | | | | | | | | 45 | 39 | | |
| unknown (?) | | | | | | | | | | | | | | | | | |
| not sequenced | 4 | 3 | 4 | 4 | 4 | 2 | 2 | 2 | 2 | 2 | 2 | 1 | 1 | 1 | | | 1 |
| sum of seq[2] | 53 | 54 | 53 | 53 | 53 | 55 | 55 | 55 | 55 | 55 | 55 | 56 | 56 | 56 | 56 | 56 | 56 |
| oomcaa[3] | 53 | 52 | 50 | 53 | 53 | 29 | 55 | 35 | 53 | 53 | 51 | 32 | 52 | 25 | 45 | 39 | 48 |
| mcaa[4] | L | S | L | T | C | T | V | S | G | G | S | I | S | S | — | — | Y |
| rel. oomcaa[5] | 100% | 96% | 94% | 100% | 100% | 53% | 100% | 64% | 96% | 96% | 93% | 57% | 93% | 45% | 80% | 70% | 86% |
| pos occupied[6] | 1 | 3 | 3 | 1 | 1 | 5 | 1 | 3 | 3 | 3 | 3 | 4 | 3 | 7 | 6 | 6 | 7 |

| | CDRI | | | | Framework II | | | | | | | | | | | | |
|---|---|---|---|---|---|---|---|---|---|---|---|---|---|---|---|---|---|
| amino acid[1] | 33 | 34 | 35 | 36 | 37 | 38 | 39 | 40 | 41 | 42 | 43 | 44 | 45 | 46 | 47 | 48 | 49 | 50 |
| A | | | | | | | | | | 8 | 1 | | | | | | 1 | |
| B | | | | | | | | | | | | | | | | | | |
| C | | 1 | | | | | | | | | | | | | | | | |
| D | | | 1 | | | | | | | | | | | | | | | |
| E | | | | | | | | | | | 1 | | | 56 | | | | 22 |
| F | 1 | | | | | 1 | | | | | | | | | | | | 1 |
| G | | | 8 | | | | | | | | 55 | | 55 | | | | 56 | 1 |
| H | | | | | | | 2 | | | | | | | | | | | |

TABLE 6E-continued

Analysis of V heavy chain subgroup 4

| amino acid[1] | | | | | | | | | | | | | | | | | | |
|---|---|---|---|---|---|---|---|---|---|---|---|---|---|---|---|---|---|---|
| I | | | | 51 | | | | | | | | | | | | 54 | | 1 |
| K | | | | | | | | | | | 54 | | | | | | | |
| L | | | | | 1 | | 1 | | | | | | 55 | | 2 | | | |
| M | | | | | | | | | | | | | | | | | | |
| N | | | 1 | | | | | | | | | | | | | | | |
| P | | | | | | | | 50 | 49 | | | | | 2 | | | | |
| Q | | | | | | 56 | | | | | | | | 1 | | | | 1 |
| R | | | | | | | 57 | | | | 3 | 2 | | | | | | 9 |
| S | | | 44 | | 1 | | | 3 | | | | | | | | | | 7 |
| T | | | 3 | | | | 1 | 1 | | | | | | | | | | |
| V | | | | | 3 | | | | | | | | | | | 1 | | |
| W | 2 | 56 | | 57 | | | | | | | | | | | 56 | | | |
| X | | | | | | | | | | | | | | | | | | |
| Y | 52 | | | | | | | | | | | | | | 1 | | | 15 |
| Z | | | | | | | | | | | | | | | | | | |
| — | | | | | | | | | | | | | | | | | | |
| unknown (?) | | | | | | | | | | | | | | | | | | |
| not sequenced | 1 | 1 | | | | | | | | | | | | | | | | |
| sum of seq[2] | 56 | 56 | 57 | 57 | 57 | 57 | 57 | 57 | 57 | 57 | 57 | 57 | 57 | 57 | 57 | 57 | 57 | 57 |
| oomcaa[3] | 52 | 56 | 44 | 57 | 51 | 57 | 56 | 50 | 49 | 55 | 54 | 55 | 55 | 56 | 56 | 54 | 56 | 22 |
| mcaa[4] | Y | W | S | W | I | R | Q | P | P | G | K | G | L | E | W | I | G | E |
| rel. oomcaa[5] | 93% | 100% | 77% | 100% | 89% | 100% | 98% | 88% | 86% | 96% | 95% | 96% | 96% | 98% | 98% | 95% | 98% | 39% |
| pos occupied[6] | 4 | 1 | 5 | 1 | 5 | 1 | 2 | 5 | 2 | 3 | 2 | 2 | 2 | 2 | 2 | 3 | 2 | 8 |

| | CDR II | | | | | | | | | | | | | | | | |
|---|---|---|---|---|---|---|---|---|---|---|---|---|---|---|---|---|---|
| amino acid[1] | 51 | 52 | A | B | C | 53 | 54 | 55 | 56 | 57 | 58 | 59 | 60 | 61 | 62 | 63 | 64 |
| A | | | | | | | | | | | 1 | | | | | | | |
| B | | | | | | | | | | | | | | | | | | |
| C | | | | | | | | | | | | | | | | | | |
| D | | 1 | | | | 1 | | | | | 2 | | | | | | | |
| E | | | | | | | | | | | | | | | | | | |
| F | | 1 | | | | | | | | | | | 3 | | | | | |
| G | | | | | | 1 | | 57 | 1 | | | | | | | | | |
| H | | | | | | 24 | | | | | 2 | | | | | | | |
| I | 54 | | | | | | | | 1 | 1 | | | | | | | | |
| K | | | | | | | | | | | | | | 1 | | | | 53 |
| L | | | | | | | | | | | | | | | 1 | | 55 | |
| M | | | | | | | | | | | | | | | | | | |
| N | | 21 | | | | | | | 2 | | | 40 | | 53 | | | | |
| P | | | | | | | | | | | | | | | 54 | | 1 | |
| Q | | | | | | | | | | | | | | | | | | |
| R | | 1 | | | | | | | 2 | | | | | | | | | 3 |
| S | | 1 | | | | | 52 | | 49 | | | 1 | | 2 | | 56 | | |
| T | | | | | | 8 | 5 | | 1 | 54 | 1 | | | | 1 | | | 1 |
| V | 3 | | | | | | | | 1 | 1 | | | | | | | | |
| W | | | | | | | | | | | | | | | | | | |
| X | | | | | | | | | | | | | | | | | | |
| Y | | 32 | | | | 23 | | | | | | 11 | 54 | | | | | |
| Z | | | | | | | | | | | | | | | | | | |
| — | | | 57 | 57 | 57 | | | | | | | | | | | | | |
| unknown (?) | | | | | | | | | | | | | | | | | | |
| not sequenced | | | | | | | | | | | | | | 1 | 1 | 1 | 1 | |
| sum of seq[2] | 57 | 57 | 57 | 57 | 57 | 57 | 57 | 57 | 57 | 57 | 57 | 57 | 57 | 56 | 56 | 56 | 56 | 57 |
| oomcaa[3] | 54 | 32 | 57 | 57 | 57 | 24 | 52 | 57 | 49 | 54 | 40 | 54 | 53 | 54 | 56 | 55 | 56 | 53 |
| mcaa[4] | I | Y | — | — | — | H | S | G | S | T | N | Y | N | P | S | L | K |
| rel. oomcaa[5] | 95% | 56% | 100% | 100% | 100% | 42% | 91% | 100% | 86% | 95% | 70% | 95% | 95% | 96% | 100% | 98% | 93% |
| pos occupied[6] | 2 | 6 | 1 | 1 | 1 | 5 | 2 | 1 | 7 | 4 | 6 | 2 | 3 | 3 | 1 | 2 | 3 |

| | CDR II | | Framework III | | | | | | | | | | | | | |
|---|---|---|---|---|---|---|---|---|---|---|---|---|---|---|---|---|
| amino acid[1] | 65 | 66 | 67 | 68 | 69 | 70 | 71 | 72 | 73 | 74 | 75 | 76 | 77 | 78 | 79 | 80 | 81 |
| A | | 1 | | 1 | | | 1 | | | | 1 | | | | | | |
| B | | | | | | | | | | | | | | | | | |
| C | | | | | | | | | | | | | | | | | |
| D | | | 1 | | | | | 55 | | | | | | | | 1 | |
| E | | | | | | | | 1 | | | | | | | | | 1 |
| F | | | | | | | | | 1 | | | | | 54 | | | |
| G | 1 | | | | | | | | | | | | | | | | |
| H | | | | | | | | | | | | | | | | | |
| I | | | 1 | 1 | 48 | | 3 | | | | | 51 | 3 | | 1 | | 46 |
| K | | | | | | | | | | 1 | | | | | | | |
| L | | | 1 | | | | 3 | | | | 1 | | 3 | 1 | | 55 | |
| M | | | | | 7 | | | | 2 | | | 1 | 54 | | | | 1 |
| N | | | | 2 | | | | | | | | | | | | | 3 |

TABLE 6E-continued

Analysis of V heavy chain subgroup 4

| amino acid[1] | | | | | | | | | | | | | | | | | |
|---|---|---|---|---|---|---|---|---|---|---|---|---|---|---|---|---|---|
| P | | | | | | | | | | | | | | | | | |
| Q | | | | | | | 1 | | | | | 54 | | | 1 | 1 |
| R | | 56 | | | | | | | | | 2 | | | | | 2 |
| S | 56 | | | 1 | | 56 | | 1 | 57 | | | | 1 | 57 | | 2 |
| T | | | | 51 | 1 | | | 52 | | | | | | | | 1 |
| V | | | 53 | | 2 | | 50 | | | 1 | | | | | | |
| W | | | | | | | | | | | | | | | | |
| X | | | | | | | | | | | | | | | | |
| Y | | | | | | | | | | | | | | | | |
| Z | | | | | | | | | | | | | | | | |
| unknown (?) | | | | | | | | | | | | | | | | |
| not sequenced | | | 1 | 1 | | | | | | | | | | | | |
| sum of seq[2] | 57 | 57 | 56 | 56 | 57 | 57 | 57 | 57 | 57 | 57 | 57 | 57 | 57 | 57 | 57 | 57 |
| oomcaa[3] | 56 | 56 | 53 | 51 | 48 | 56 | 50 | 55 | 52 | 57 | 51 | 54 | 54 | 54 | 57 | 55 | 46 |
| mcaa[4] | S | R | V | T | I | S | V | D | T | S | K | N | Q | F | S | L | K |
| rel. oomcaa[5] | 98% | 98% | 95% | 91% | 84% | 98% | 88% | 96% | 91% | 100% | 89% | 95% | 95% | 95% | 100% | 96% | 81% |
| pos occupied[6] | 2 | 2 | 4 | 5 | 3 | 2 | 4 | 3 | 5 | 1 | 6 | 2 | 2 | 4 | 1 | 3 | 8 |

| | Framework III | | | | | | | | | | | | CDR III | | |
|---|---|---|---|---|---|---|---|---|---|---|---|---|---|---|---|
| amino acid[1] | 82 | A | B | C | 83 | 84 | 85 | 86 | 87 | 88 | 89 | 90 | 91 | 92 | 93 | 94 | 95 |
| A | | | | | | 55 | 57 | | 57 | | | | | | 56 | | 3 |
| B | | | | | | | | | | | | | | | | | |
| C | | | | | | | | | | | | | | 57 | | | |
| D | | | | | | | | 57 | | | | | | | | | 6 |
| E | | | | | | | | | | | | | | | | | 6 |
| F | | | 1 | | | | | | | | | | | | | | |
| G | | 1 | | | | | | | | | | | | | | | 25 |
| H | | | | | | | | | | | | | | | | | 1 |
| I | | 1 | | 3 | | | | | | | | | | | | | |
| K | | 2 | | | | | | | | | | | | | | | 2 |
| L | 53 | | | 2 | | | | | | 1 | | | | | | | 2 |
| M | 1 | | | 1 | | | | | | 1 | | | | | | | |
| N | | 3 | 1 | | | | | | | | | | | | | | |
| P | | | | | | | | | | | | | | | | | |
| Q | | | | | | | | | | | | | | | | | |
| R | | 2 | | | | 1 | | | | | | | | | | 54 | 4 |
| S | 1 | 44 | 55 | | 1 | | | | 2 | | | | 1 | | | 1 | 1 |
| T | | 4 | | | 53 | | | | 55 | | | | | | | 1 | 1 |
| V | 2 | | | 54 | 1 | | | | | 55 | | | | | 1 | 1 | 4 |
| W | | | | | | | | | | | | | | | | | 1 |
| X | | | | | | | | | | | | | | | | | |
| Y | | | | | | | | | | | | 57 | 56 | | | | |
| Z | | | | | | | | | | | | | | | | | |
| unknown (?) | | | | | | | | | | | | | | | | | |
| not sequenced | | | | | | | | | | | | | | | | | 1 |
| sum of seq[2] | 57 | 57 | 57 | 57 | 57 | 57 | 57 | 57 | 57 | 57 | 57 | 57 | 57 | 57 | 57 | 57 | 56 |
| oomcaa[3] | 53 | 44 | 55 | 54 | 53 | 55 | 57 | 57 | 55 | 57 | 55 | 57 | 56 | 57 | 56 | 54 | 25 |
| mcaa[4] | L | S | S | V | T | A | A | D | T | A | V | Y | Y | C | A | R | G |
| rel. oomcaa[5] | 93% | 77% | 96% | 95% | 93% | 96% | 100% | 100% | 96% | 100% | 96% | 100% | 98% | 100% | 98% | 95% | 45% |
| pos occupied[6] | 4 | 7 | 3 | 3 | 3 | 3 | 1 | 1 | 2 | 1 | 3 | 1 | 2 | 1 | 2 | 4 | 12 |

| | CDR III | | | | | | | | | | | | | | |
|---|---|---|---|---|---|---|---|---|---|---|---|---|---|---|---|
| amino acid[1] | 96 | 97 | 98 | 99 | 100 | A | B | C | D | E | F | G | H | I | J | K | 101 |
| A | 3 | 3 | 2 | 5 | 4 | 2 | 2 | 4 | | 2 | 1 | | 1 | 1 | 12 | | |
| B | | | | | | | | | | | | | | | | | |
| C | | 1 | | | | 1 | | | | | | | | | | | |
| D | | 5 | 5 | 5 | 4 | 3 | 2 | 4 | 3 | 1 | | 1 | 2 | 1 | | | 41 |
| E | 1 | 1 | 2 | 1 | | | 1 | 3 | 1 | 2 | 1 | | | | | | |
| F | 4 | 1 | 1 | | 2 | 3 | 2 | 2 | | 1 | 1 | | | | | 31 | |
| G | 9 | 10 | 8 | 10 | 11 | 4 | 7 | 7 | 6 | 1 | 1 | 1 | 2 | 1 | 9 | | 2 |
| H | | | | 1 | | | | | | 1 | | | 1 | | | | |
| I | 1 | | 2 | 4 | 1 | 3 | 2 | 3 | | 1 | | | | | | 1 | |
| K | 1 | | | | | | 2 | 2 | | | | 1 | | | | | |
| L | 6 | 7 | 3 | 5 | 3 | 2 | 4 | 1 | 5 | 3 | 3 | | 1 | | | | |
| M | 1 | 4 | | 3 | 1 | | 2 | 1 | | | | | | | | 9 | |
| N | 3 | | | | | 2 | 1 | 1 | 5 | 1 | 1 | | | 2 | | | |
| P | 4 | 5 | 3 | 1 | 1 | 2 | 1 | 1 | 1 | | 2 | 3 | 2 | 1 | | | |
| Q | | 1 | 1 | | 1 | | | 1 | 1 | | | 3 | | | | | 1 |
| R | 12 | 2 | 5 | 5 | 3 | 2 | 3 | 1 | 2 | | | 2 | 1 | | | | |
| S | 4 | 8 | 8 | 1 | 2 | 5 | 7 | 4 | 2 | 1 | 1 | 1 | | | | | |
| T | 2 | 1 | 3 | 4 | 4 | 3 | 3 | | | 1 | 1 | 1 | | | | | |

TABLE 6E-continued

Analysis of V heavy chain subgroup 4

| | | | | | | | | | | | | | | | | | |
|---|---|---|---|---|---|---|---|---|---|---|---|---|---|---|---|---|---|
| V | 2 | 2 | 5 | 4 | 4 | 7 | 3 | 1 | 2 | 1 | | | | | | | |
| W | 2 | 1 | 2 | 2 | 4 | 5 | 1 | 1 | 2 | | 2 | 1 | | 3 | 2 | | |
| X | | | | | | | | | | | | | | | | | |
| Y | 1 | 4 | 5 | 3 | 6 | 4 | 2 | 3 | 4 | 8 | 4 | 8 | 3 | 5 | 8 | | 2 |
| Z | | | | | | | | | | | | | | | | | |
| — | | | 1 | 2 | 4 | 6 | 9 | 11 | 16 | 23 | 27 | 29 | 34 | 31 | 14 | 4 | |
| unknown (?) | | | | | | | | | | | 1 | | | 1 | 1 | 1 | |
| not sequenced | 1 | 1 | 1 | 1 | 2 | 3 | 3 | 6 | 7 | 8 | 9 | 9 | 10 | 11 | 11 | 11 | 11 |
| sum of seq[2] | 56 | 56 | 56 | 56 | 55 | 54 | 54 | 51 | 50 | 49 | 48 | 48 | 47 | 46 | 46 | 46 | 46 |
| oomcaa[3] | 12 | 10 | 8 | 10 | 11 | 7 | 9 | 11 | 16 | 23 | 27 | 29 | 34 | 31 | 14 | 31 | 41 |
| mcaa[4] | R | G | G | G | G | V | — | — | — | — | — | — | — | — | — | F | D |
| rel. oomcaa[5] | 21% | 18% | 14% | 18% | 20% | 13% | 17% | 22% | 32% | 47% | 56% | 60% | 72% | 67% | 30% | 67% | 89% |
| pos occupied[6] | 16 | 16 | 16 | 16 | 16 | 16 | 18 | 18 | 13 | 15 | 13 | 10 | 9 | 8 | 5 | 4 | 4 |

| | | Framework IV | | | | | | | | | | | |
|---|---|---|---|---|---|---|---|---|---|---|---|---|---|
| amino acid[1] | | 102 | 103 | 104 | 105 | 106 | 107 | 108 | 109 | 110 | 111 | 112 | 113 | sum |
| A | | | | | | | 1 | | 1 | | | | | 332 |
| B | | | | | | | | | | | | | | |
| C | | | | | | | | | | | | | | 113 |
| D | | | | | | | | | | | | | | 210 |
| E | | | | | | | | | | | | | | 176 |
| F | | | | | | | | | | | | | | 135 |
| G | | | | 41 | | 40 | 1 | | | | | | | 674 |
| H | | 1 | | | | | | | | 1 | | | | 45 |
| I | | 9 | | | | | | 1 | | | | | | 282 |
| K | | | | | 3 | | | | | | | | | 278 |
| L | | 4 | | | | | | | | 19 | | | | 540 |
| M | | | | | | | | | 9 | | | | | 43 |
| N | | | | | | | | 1 | | | | | | 204 |
| P | | 3 | | | 2 | | | | | | | | 2 | 281 |
| Q | | | | | 29 | | | | | | | | | 334 |
| R | | 1 | | | 4 | | | 1 | | | | | | 250 |
| S | | 1 | | | 1 | | | | | | | 36 | 33 | 986 |
| T | | | | | 1 | | 33 | 8 | | 34 | | | | 532 |
| V | | 12 | | | | | | | 36 | | 36 | | | 488 |
| W | | | 46 | | | | | | | | | | | 267 |
| X | | | | | | | | | | | | | | |
| Y | | 16 | | | | | | | | | | | | 455 |
| Z | | | | | | | | | | | | | | 1 |
| — | | | | | | | | | | | | | | 466 |
| unknown (?) | | | | | | | | | | | | | | 4 |
| not sequenced | | 10 | 11 | 16 | 17 | 17 | 20 | 20 | 21 | 21 | 21 | 21 | 22 | 426 |
| sum of seq[2] | | 47 | 46 | 41 | 40 | 40 | 37 | 37 | 36 | 36 | 36 | 36 | 35 | |
| oomcaa[3] | | 16 | 46 | 41 | 29 | 40 | 33 | 19 | 36 | 34 | 36 | 36 | 33 | |
| mcaa[4] | | Y | W | G | Q | G | T | L | V | T | V | S | S | |
| rel. oomcaa[5] | | 34% | 100% | 100% | 73% | 100% | 89% | 51% | 100% | 94% | 100% | 100% | 94% | |
| pos occupied[6] | | 8 | 1 | 1 | 6 | 1 | 5 | 4 | 1 | 3 | 1 | 1 | 2 | |

TABLE 6F

Analysis of V heavy chain subgroup 5

Framework I

| amino acid[1] | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A | | | | | 1 | | | 1 | | 89 | | 1 | | | 1 | | |
| B | | | | | | | | | | | | | | | | | |
| C | | | | | | 1 | | | | | | | | | | | |
| D | | | | | | | | | | 2 | | | | | | | |
| E | 88 | 1 | | | 2 | | | | 4 | 93 | | | | | | 92 | |
| F | | | | | | | | | | | | | | | | | 1 |
| G | | 1 | | | | | | 92 | | | | | | | 94 | | |
| H | | | | | | | | | | | | | | | | | |
| I | | | | | | | | | | | | | | | | | |
| K | | | | | | | | | | | | 94 | 94 | | | | |
| L | | | 1 | | 91 | | 2 | | | | | | | 3 | | | |
| M | | | | | | | | | | | | | | | | | |
| N | | | | | | | | | | | | | | | 94 | | |
| P | | | | 1 | | | | 1 | | | | | | | | 3 | |
| Q | 3 | | 92 | | 1 | 90 | | | | | | | | | | | |
| R | | | | | | 1 | | | | | | 1 | 1 | | | 1 | |

TABLE 6F-continued

Analysis of V heavy chain subgroup 5

| | | | | | | | | | | | | | | | | | |
|---|---|---|---|---|---|---|---|---|---|---|---|---|---|---|---|---|---|
| S | | | | | | | 92 | | | | | | | | | | 94 |
| T | | | | | | | | | | | | | | | | | |
| V | | 90 | | 89 | | | | | 1 | | 91 | | | | | | |
| W | | | | | | | | | | | | | | | | | |
| X | | | | | | | | | | | | | | | | | |
| Y | | | | | | | | | | | | | | | | | |
| Z | | | | | | | | | | | | | | | | | |
| — | | | | | | | | | | | | | | | | | |
| unknown (?) | | | | | | | | | | | | | | | | | |
| not sequenced | 5 | 5 | 5 | 5 | 4 | 4 | 4 | 4 | 2 | 2 | 2 | 2 | 2 | 2 | 2 | 2 | 2 |
| sum of seq[2] | 92 | 92 | 92 | 92 | 93 | 93 | 93 | 93 | 95 | 95 | 95 | 95 | 95 | 95 | 95 | 95 | 95 |
| oomcaa[3] | 88 | 90 | 92 | 91 | 89 | 90 | 92 | 92 | 89 | 93 | 91 | 94 | 94 | 94 | 94 | 92 | 94 |
| mcaa[4] | E | V | Q | L | V | Q | S | G | A | E | V | K | K | P | G | E | S |
| rel. oomcaa[5] | 96% | 98% | 100% | 99% | 96% | 97% | 99% | 99% | 94% | 98% | 96% | 99% | 99% | 99% | 99% | 97% | 99% |
| pos occupied[6] | 3 | 3 | 1 | 2 | 4 | 3 | 2 | 2 | 4 | 2 | 3 | 2 | 2 | 2 | 2 | 2 | 2 |

| | Framework I | | | | | | | | | | | | | CDRI | | | |
|---|---|---|---|---|---|---|---|---|---|---|---|---|---|---|---|---|---|
| amino acid[1] | 18 | 19 | 20 | 21 | 22 | 23 | 24 | 25 | 26 | 27 | 28 | 29 | 30 | 31 | A | B | 32 |
| A | | | | | | | 3 | 2 | | | | | 4 | | | | |
| B | | | | | | | | | | | | | | | | | |
| C | | | | | 96 | | | | | | 1 | | | 1 | | | |
| D | | | | | | | | | | | 2 | | | 2 | | | |
| E | | | | | | | | | 2 | | | | | 1 | | | |
| F | | | | | | | 3 | | | 6 | | 97 | | | | | 2 |
| G | | | | | | | 92 | | 93 | | | | | 1 | | | |
| H | | | | | | | | | | | | | | 1 | | | 4 |
| I | | | 96 | | | | | | | | | | | 4 | | | |
| K | | 77 | | | | 89 | | | | | 1 | | | | | | |
| L | 95 | | | | | | | | | | | | | | | | |
| M | | 1 | | | | 1 | | | | | | | | | | | |
| N | | | | | | 1 | | | | | 2 | | 4 | 14 | | | 2 |
| P | | | | | | | | 1 | | | | | | | | | |
| Q | | 1 | | | 4 | | | | | | | | | | | | |
| R | | 17 | | | | 1 | | | 1 | | 2 | | | | | | |
| S | | | | 94 | | 1 | 90 | | | | 84 | | 10 | 61 | | | 2 |
| T | | | | 2 | | | | | | | 5 | | 75 | 16 | | | |
| V | | | | | | | | | | | | | | | | | |
| W | | | | | | | | | | | | | | | | | |
| X | | | | | | | | | | | | | | | | | |
| Y | | | | | | | | | | 90 | | | | | | | 87 |
| Z | | | | | | | | | | | | | | | | | |
| — | | | | | | | | | | | | | | | 97 | 97 | |
| unknown (?) | | | | | | | | | | | | | | | | | |
| not sequenced | 2 | 1 | 1 | 1 | 1 | 1 | 1 | 1 | 1 | 1 | | | | | | | |
| sum of seq[3] | 95 | 96 | 96 | 96 | 96 | 96 | 96 | 96 | 96 | 96 | 97 | 97 | 97 | 97 | 97 | 97 | 97 |
| oomcaa[3] | 95 | 77 | 96 | 94 | 96 | 89 | 92 | 90 | 93 | 90 | 84 | 97 | 75 | 61 | 97 | 97 | 87 |
| mcaa[4] | L | K | I | S | C | K | G | S | G | Y | S | F | T | S | — | — | Y |
| rel. oomcaa[5] | 100% | 80% | 100% | 98% | 100% | 93% | 96% | 94% | 97% | 94% | 87% | 100% | 77% | 63% | 100% | 100% | 90% |
| pos occupied[6] | 1 | 4 | 1 | 2 | 1 | 5 | 3 | 4 | 3 | 2 | 7 | 1 | 5 | 8 | 1 | 1 | 5 |

| | CDRI | | | | Framework II | | | | | | | | | | | | |
|---|---|---|---|---|---|---|---|---|---|---|---|---|---|---|---|---|---|
| amino acid[1] | 33 | 34 | 35 | 36 | 37 | 38 | 39 | 40 | 41 | 42 | 43 | 44 | 45 | 46 | 47 | 48 | 49 | 50 |
| A | | | 8 | | 1 | | | | 1 | | | 1 | | | | | | |
| B | | | | | | | | | | | | | | | | | | |
| C | | | | | | | | | | | | | | | | | | |
| D | | | 1 | | | | | | | | | | | | | | | |
| E | | | | | | | | | | | 3 | | | 97 | | | | |
| F | | | | | | | | | | | | | | | | | | 1 |
| G | | | 72 | | | | | | | 97 | | 96 | | | | | 95 | |
| H | | | | | | 1 | | | | | | | | | | | | |
| I | | 93 | | | | | | | | | | | | | | 1 | | 75 |
| K | | | | | | | | 1 | | | 94 | | | | | | | |
| L | 1 | | | | 2 | | | | | | | | 94 | | | 2 | | 2 |
| M | | 1 | | | 1 | | 92 | | | | | | | | 89 | | | |
| N | | | | | | | | | | | | | | | | | | |
| P | | | | | 1 | | | 96 | | | | | 2 | | | | | |
| Q | | | | | | 97 | | | | | | | 1 | | | | | |
| R | 1 | | | | | 95 | 1 | | | | | | | | | 1 | 14 | |
| S | 2 | | 15 | | | | | | | | | | | | | | | 1 |
| T | | 2 | 1 | | | | 1 | | | | | | | | | 5 | 1 | 3 |
| V | | 1 | | | 93 | | 2 | | | | | | | | | 1 | | 1 |
| W | 93 | | 97 | | | | | | | | | | | 94 | | | | |
| X | | | | | | | | | | | | | | | | | | |

TABLE 6F-continued

Analysis of V heavy chain subgroup 5

| | | | | | | | | | | | | | | | | | | |
|---|---|---|---|---|---|---|---|---|---|---|---|---|---|---|---|---|---|---|
| Y | | | | | | | | | | | | | | | | 3 | | |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 |
| oomcaa[1] | 93 | 93 | 72 | 97 | 93 | 95 | 97 | 92 | 96 | 97 | 94 | 96 | 94 | 97 | 94 | 89 | 95 | 75 |
| mcaa[4] | W | I | G | W | V | R | Q | M | P | G | K | G | L | E | W | M | G | I |
| rel. oomcaa[5] | 96% | 96% | 74% | 100% | 96% | 98% | 100% | 95% | 99% | 100% | 97% | 99% | 97% | 100% | 97% | 92% | 98% | 77% |
| pos occupied[6] | 4 | 4 | 5 | 1 | 4 | 3 | 1 | 5 | 2 | 1 | 2 | 2 | 3 | 1 | 2 | 4 | 3 | 7 |

| | CDR II | | | | | | | | | | | | | | |
|---|---|---|---|---|---|---|---|---|---|---|---|---|---|---|---|
| amino acid[1] | 51 | 52 | A | B | C | 53 | 54 | 55 | 56 | 57 | 58 | 59 | 60 | 61 | 62 | 63 | 64 |
| A | | | 1 | | | 2 | 1 | | | 6 | | | | | 1 | | |
| B | | | | | | | | | | | | | | | | | |
| C | | 1 | | | | 1 | | | | | | | 1 | | | | |
| D | | 14 | | | | 8 | 93 | | 77 | | | | | | | | |
| E | | | | | | | 2 | | 3 | | | | | | | | 2 |
| F | | 2 | | | | | | | | | | 2 | | | | 91 | |
| G | | | | | | 69 | 1 | | 1 | | | | | | | | |
| H | | 3 | 1 | | | | | | | | | | | | | | |
| I | 92 | | | | | | | | | 4 | 1 | | | | | 1 | |
| K | | | | | | | | | | | 2 | | | | | | |
| L | 1 | | | | | | | | | | | | | 1 | | 4 | |
| M | 1 | | | | | | | | | | | | | | | | |
| N | | | | | | | | | 2 | | 14 | 2 | | | | | |
| P | | 1 | 93 | | | | | 1 | | | | | | 95 | 1 | | 1 |
| Q | | | | | | | | | | | | | | | | | 91 |
| R | | | | | | | 1 | | | | 78 | | | | | | 3 |
| S | | | 1 | | | 16 | | 96 | 2 | 2 | | | 95 | 1 | 95 | 1 | |
| T | 1 | 1 | | | | | | | | 85 | 2 | | 1 | | | | |
| V | 2 | | | | | | | | | | | 1 | | | | | |
| W | | | | | | | | | | | | | | | | | |
| X | | | | | | | | | | | | | | | | | |
| Y | | 76 | | | | | | | 12 | | | 92 | | | | | |
| Z | | | | | | | | | | | | | | | | | |
| — | | | | 97 | 97 | | | | | | | | | | | | |
| unknown (?) | | | | | | | | | | | | | | | | | |
| not sequenced | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 |
| oomcaa[3] | 92 | 76 | 93 | 97 | 97 | 69 | 93 | 96 | 77 | 85 | 78 | 92 | 95 | 95 | 95 | 91 | 91 |
| mcaa[4] | I | Y | P | — | — | G | D | S | D | T | R | Y | S | P | S | F | Q |
| rel. oomcaa[5] | 95% | 78% | 96% | 100% | 100% | 71% | 96% | 99% | 79% | 88% | 80% | 95% | 98% | 98% | 98% | 94% | 94% |
| pos occupied[6] | 5 | 6 | 5 | 1 | 1 | 6 | 4 | 2 | 6 | 4 | 5 | 4 | 3 | 3 | 3 | 4 | 4 |

| | CDR II | | Framework III | | | | | | | | | | | | | |
|---|---|---|---|---|---|---|---|---|---|---|---|---|---|---|---|---|
| amino acid[1] | 65 | 66 | 67 | 68 | 69 | 70 | 71 | 72 | 73 | 74 | 75 | 76 | 77 | 78 | 79 | 80 | 81 |
| A | | | | | | | 88 | | | | | | 1 | 91 | | | |
| B | | | | | | | | | | | | | | | | | |
| C | 1 | | | | | | | | | | | | | | | | |
| D | 2 | | | | | | | 97 | | | | | | | 1 | | |
| E | | | | | | | | | 2 | | | | | | | | 1 |
| F | | | 1 | | 3 | | | | | | | | | | 1 | | |
| G | 94 | | | | | | | | | | | | | | | | |
| H | | 15 | | | | | | | | | | | | | | | 3 |
| I | | | 3 | | 88 | | | | | 93 | | 91 | | | | | |
| K | | | | | | | | | | | | | | | | | |
| L | | | | | | 2 | | | | | | | | | | 96 | |
| M | | | | | 3 | | | | | | | 1 | | | | | |
| N | | | | | | | | | | | | | 7 | | | | |
| P | | | | | | | | | 1 | | | | | 1 | | | |
| Q | | 81 | | | | | | | 1 | | | | | | | | 93 |
| R | | 1 | | | 1 | | | | 1 | | | 1 | | | | | |
| S | | | | 1 | | 95 | | | | 96 | 1 | 87 | 2 | 1 | 1 | | |
| T | | | | 96 | | | | | | 4 | 2 | | 94 | 2 | | | |
| V | | | 93 | | 2 | | 9 | | | | | | | 2 | | 1 | |
| W | | | | | | | | | | | | | | | | | |
| X | | | | | | | | | | | | | | | | | |
| Y | | | | | | | | | | | | | | | 94 | | |
| Z | | | | | | | | | | | | | | | | | |
| — | | | | | | | | | | | | | | | | | |
| unknown (?) | | | | | | | | | | | | | | | | | |
| not sequenced | | | | | | | | | | | | | | | | | |

TABLE 6F-continued

Analysis of V heavy chain subgroup 5

| | | | | | | | | | | | | | | | | | |
|---|---|---|---|---|---|---|---|---|---|---|---|---|---|---|---|---|---|
| sum of seq[2] | 97 | 97 | 97 | 97 | 97 | 97 | 97 | 97 | 97 | 97 | 97 | 97 | 97 | 97 | 97 | 97 | 97 |
| oomcaa[3] | 94 | 81 | 93 | 96 | 88 | 95 | 88 | 97 | 93 | 96 | 91 | 87 | 94 | 91 | 94 | 96 | 93 |
| mcaa[4] | G | Q | V | T | I | S | A | D | K | S | I | S | T | A | Y | L | Q |
| rel. oomcaa[5] | 97% | 84% | 96% | 99% | 91% | 98% | 91% | 100% | 96% | 99% | 94% | 90% | 97% | 94% | 97% | 99% | 96% |
| pos occupied[6] | 3 | 3 | 3 | 2 | 5 | 2 | 2 | 1 | 4 | 2 | 4 | 4 | 3 | 5 | 4 | 2 | 3 |

| | Framework III | | | | | | | | | | | | | CDR III | | |
|---|---|---|---|---|---|---|---|---|---|---|---|---|---|---|---|---|
| amino acid[1] | 82 | A | B | C | 83 | 84 | 85 | 86 | 87 | 88 | 89 | 90 | 91 | 92 | 93 | 94 | 95 |
| A | | | | | 1 | 96 | | | | 93 | | | | | 92 | | 1 |
| B | | | | | | | | | | | | | | | | | |
| C | 1 | | | | | | | | | | | | | 95 | | | |
| D | | | | | | | | 96 | | | | | | | | | |
| E | | | | | | | 1 | | | | | | | | | | 1 |
| F | | | | | | | | | | | | 2 | 6 | | | | |
| G | | 3 | 1 | | | | | | | 4 | | | | | | | 1 |
| H | | | | | | | | | | | | | | | | | 10 |
| I | | | | | | | | | 2 | | 9 | | | | | | |
| K | | | | | 91 | | | | | | 1 | | | | | 1 | 1 |
| L | | | | 97 | | | | | | | 2 | | | | | | 11 |
| M | | | | | | | | | | | 84 | | | | | | |
| N | | 2 | 2 | | | | | | 2 | | | | | | | | |
| P | | | | | | | | | | | | | | | | | 5 |
| Q | | | | | | | | | | | | | | | 1 | | 3 |
| R | 1 | 1 | 3 | | 3 | | | | | | | | | | 92 | | 7 |
| S | | 90 | 91 | | | | 96 | | 5 | | | | | | 1 | | 1 |
| T | | 1 | | | 1 | 1 | 1 | | 88 | | 1 | | | 1 | | | 1 |
| V | | | | | | | | 1 | | | | | | 2 | | | 2 |
| W | 95 | | | | | | | | | | | | | | | | 1 |
| X | | | | | | | | | | | | | | | | | |
| Y | | | | | | | | | | | | 94 | 89 | | | | |
| Z | | | | | | | | | | | | | | | | | |
| — | | | | | | | | | | | | | | | | | |
| unknown (?) | | | | | | | | | | | | | | | | | |
| not sequenced | | | | | | | | | | | | 1 | 2 | 2 | 2 | 2 | 52 |
| sum of seq[2] | 97 | 97 | 97 | 97 | 97 | 97 | 97 | 97 | 97 | 97 | 97 | 96 | 95 | 95 | 95 | 95 | 45 |
| oomcaa[3] | 95 | 90 | 91 | 97 | 91 | 96 | 96 | 96 | 88 | 93 | 84 | 94 | 89 | 95 | 92 | 92 | 11 |
| mcaa[4] | W | S | S | L | K | A | S | D | T | A | M | Y | Y | C | A | R | L |
| rel. oomcaa[5] | 98% | 93% | 94% | 100% | 94% | 99% | 99% | 99% | 91% | 96% | 87% | 98% | 94% | 100% | 97% | 97% | 24% |
| pos occupied[6] | 3 | 5 | 4 | 1 | 5 | 2 | 2 | 2 | 4 | 2 | 5 | 2 | 2 | 1 | 3 | 4 | 13 |

| | CDR III | | | | | | | | | | | | | | | |
|---|---|---|---|---|---|---|---|---|---|---|---|---|---|---|---|---|
| amino acid[1] | 96 | 97 | 98 | 99 | 100 | A | B | C | D | E | F | G | H | I | J | K | 101 |
| A | 1 | 2 | | 3 | 4 | 3 | 2 | | 1 | | | 1 | | | 4 | | 2 |
| B | | | | | | | | | | | | | | | | | |
| C | | | 1 | 1 | 1 | | 2 | | | 1 | | | | | | | |
| D | 3 | 3 | 3 | 3 | 1 | 2 | 1 | 1 | 2 | | 2 | 1 | 1 | 2 | | | 37 |
| E | 1 | 1 | 2 | | | 1 | 1 | | | | 1 | | | 1 | | | |
| F | | | 1 | 3 | | | 3 | 2 | | 1 | | | | | | 26 | |
| G | 9 | 11 | 12 | 12 | 5 | 2 | 4 | 3 | 10 | 2 | 1 | | | | 5 | | |
| H | 1 | | 2 | | | 1 | 1 | | 1 | | | | | | | | |
| I | 3 | | 2 | 2 | 1 | 1 | 4 | 1 | 1 | | 1 | 1 | | | | | |
| K | 1 | | 1 | 3 | 1 | | | | | | | | 2 | | | | |
| L | 2 | 3 | 1 | 1 | 2 | 5 | | 1 | | 1 | | 1 | | | | | |
| M | | 2 | 1 | 1 | | 1 | 1 | 1 | 1 | | | | | | | 10 | |
| N | 1 | | 2 | | 1 | 2 | 2 | | | 1 | | | | | 2 | | |
| P | 1 | 4 | 3 | 1 | 2 | | | 1 | | 1 | 1 | 1 | | | | | |
| Q | 2 | | 1 | 1 | 4 | 2 | 1 | 2 | | | | | | | | | 3 |
| R | 9 | 2 | 2 | | 2 | 1 | | 2 | | | | | | | | | |
| S | 3 | 2 | 6 | 4 | 4 | 5 | 3 | 5 | 3 | 2 | 2 | | | 1 | | 1 | |
| T | 3 | 2 | 1 | 2 | 6 | 3 | 3 | 6 | 1 | | 1 | | | | | | |
| V | 4 | 4 | | 1 | | 1 | 2 | | | 1 | | | | | | | |
| W | | 2 | 1 | | | | | 1 | | | 2 | | 1 | | 1 | | |
| X | | | | | | | | | | | | | | | | | |
| Y | 1 | 6 | 3 | 6 | 9 | 8 | 7 | 2 | 1 | 2 | 6 | 8 | 9 | 9 | 10 | | 1 |
| Z | | | | | | | | | | | | | | | | | |
| — | | 1 | 1 | 2 | 8 | 10 | 16 | 23 | 30 | 30 | 31 | 32 | 30 | 22 | 7 | 2 | |
| unknown (?) | | | | | | | | | | 1 | | | 1 | 1 | 1 | | |
| not sequenced | 52 | 52 | 52 | 52 | 52 | 52 | 52 | 52 | 52 | 52 | 52 | 52 | 52 | 52 | 52 | 53 | 52 |
| sum of seq[2] | 45 | 45 | 45 | 45 | 45 | 45 | 45 | 45 | 45 | 45 | 45 | 45 | 45 | 45 | 45 | 44 | 45 |
| oomcaa[3] | 9 | 11 | 12 | 12 | 9 | 8 | 10 | 16 | 23 | 30 | 30 | 31 | 32 | 30 | 22 | 26 | 37 |
| mcaa[4] | G | G | G | G | Y | Y | — | — | — | — | — | — | — | — | — | F | D |
| rel. oomcaa[5] | 20% | 24% | 27% | 27% | 20% | 18% | 22% | 36% | 51% | 67% | 67% | 69% | 71% | 67% | 49% | 59% | 82% |
| pos occupied[6] | 16 | 14 | 18 | 16 | 15 | 16 | 15 | 14 | 11 | 11 | 9 | 8 | 4 | 6 | 6 | 4 | 5 |

TABLE 6F-continued

Analysis of V heavy chain subgroup 5

| | | Framework IV | | | | | | | | | | | | |
|---|---|---|---|---|---|---|---|---|---|---|---|---|---|---|
| amino acid[1] | 102 | 103 | 104 | 105 | 106 | 107 | 108 | 109 | 110 | 111 | 112 | 113 | sum |
| A | | | | | | | | | | | | 1 | 611 |
| B | | | | | | | | | | | | | |
| C | | | | | | | | | | | | | 205 |
| D | 1 | | | | | | | | | | | | 458 |
| E | | | | 1 | | | | | | | | | 404 |
| F | 2 | | | | | | | | | | | | 256 |
| G | | | 41 | | 41 | | | | | | | | 1065 |
| H | | | | | | | | | | | | | 44 |
| I | 9 | | | | | | | | 2 | | | | 588 |
| K | | | | 3 | | | | | | | | | 650 |
| L | 2 | | | | | | 25 | 1 | | | | | 549 |
| M | | | | | | | 8 | | | | | | 303 |
| N | | | | | | | | | | | | | 64 |
| P | 2 | | | | | 1 | | | | | 1 | | 414 |
| Q | | | | 34 | | | | | | | | | 612 |
| R | | | | 3 | | | | | | | | | 351 |
| S | 2 | | | | | | | | | | 40 | 39 | 1545 |
| T | 1 | | | | | 40 | 8 | | 39 | | | | 604 |
| V | 11 | | | | | | | 40 | | 41 | | | 594 |
| W | | 43 | | | | | | | | | | | 432 |
| X | | | | | | | | | | | | | |
| Y | 13 | | | | | | | | | | | | 738 |
| Z | | | | | | | | | | | | | |
| — | 2 | | | | | | | | | | | | 635 |
| unknown (?) | | | | | | | | | | | | | 4 |
| not sequenced | 52 | 54 | 56 | 56 | 56 | 56 | 56 | 56 | 56 | 56 | 56 | 57 | 1678 |
| sum of seq[3] | 45 | 43 | 41 | 41 | 41 | 41 | 41 | 41 | 41 | 41 | 41 | 40 | |
| oomcaa[3] | 13 | 43 | 41 | 34 | 41 | 40 | 25 | 40 | 39 | 41 | 40 | 39 | |
| mcaa[4] | Y | W | G | Q | G | T | L | V | T | V | S | S | |
| rel. oomcaa[5] | 29% | 100% | 100% | 83% | 100% | 98% | 61% | 98% | 95% | 100% | 98% | 98% | |
| pos occupied[6] | 10 | 1 | 1 | 4 | 1 | 2 | 3 | 2 | 2 | 1 | 2 | 2 | |

TABLE 6G

Analysis of V heavy chain subgroup 6

| | Framework I | | | | | | | | | | | | | | | | |
|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 |
| A | | | | | | | | | | | | 1 | | | | | |
| B | | | | | | | | | | | | | | | | | |
| C | | | | | | | | | | | | | | | | | |
| D | | | | | | | | | | | | | | | | | |
| E | | | | | | | | | | | | | | | | | |
| F | | | | | | | | | | | | | | | | | |
| G | | | | | | | | 52 | | 67 | | | | | | | |
| H | | | | | | | | | | | | | | | | | |
| I | | | | | | | | | | | | | | | | | |
| K | | | | | | | | | | | | | 68 | | | | |
| L | | | | | 52 | | | | | | 68 | 1 | | | | | |
| M | | | | | | | | | | | | | | | | | |
| N | | | | | | | | | | | | | | | | | |
| P | | | | | | | | | 68 | | | | | 67 | | | |
| Q | 52 | | 52 | | 51 | 52 | | | | | | | | | | 68 | |
| R | | | | | 1 | | | | | 1 | | | | | | | |
| S | | | | | | | 52 | | | | | | | 1 | 68 | | |
| T | | | | | | | | | | | | | | | | | 68 |
| V | | 52 | | | | | | | | | | 66 | | | | | |
| W | | | | | | | | | | | | | | | | | |
| X | | | | | | | | | | | | | | | | | |
| Y | | | | | | | | | | | | | | | | | |
| Z | | | | | | | | | | | | | | | | | |
| — | | | | | | | | | | | | | | | | | |
| unknown (?) | | | | | | | | | | | | | | | | | |
| not sequenced | 22 | 22 | 22 | 22 | 22 | 22 | 22 | 22 | 6 | 6 | 6 | 6 | 6 | 6 | 6 | 6 | 6 |
| sum of seq[2] | 52 | 52 | 52 | 52 | 52 | 52 | 52 | 52 | 68 | 68 | 68 | 68 | 68 | 68 | 68 | 68 | 68 |
| oomcaa[3] | 52 | 52 | 52 | 52 | 51 | 52 | 52 | 52 | 68 | 67 | 68 | 66 | 68 | 67 | 68 | 68 | 68 |
| mcaa[4] | Q | V | Q | L | Q | Q | S | G | P | G | L | V | K | P | S | Q | T |

TABLE 6G-continued

Analysis of V heavy chain subgroup 6

| rel. oomcaa[5] | 100% | 100% | 100% | 100% | 98% | 100% | 100% | 100% | 100% | 99% | 100% | 97% | 100% | 99% | 100% | 100% | 100% |
|---|---|---|---|---|---|---|---|---|---|---|---|---|---|---|---|---|---|
| pos occupied[6] | 1 | 1 | 1 | 1 | 2 | 1 | 1 | 1 | 1 | 2 | 1 | 3 | 1 | 2 | 1 | 1 | 1 |

| | Framework I | | | | | | | | | | | | | CDRI | | | |
|---|---|---|---|---|---|---|---|---|---|---|---|---|---|---|---|---|---|
| amino acid[1] | 18 | 19 | 20 | 21 | 22 | 23 | 24 | 25 | 26 | 27 | 28 | 29 | 30 | 31 | A | B | 32 |
| A | | | | 1 | | 67 | | | | | | | | | | | 66 |
| B | | | | | | | | | | | | | | | | | |
| C | | | | | 68 | | | | | | | | | | | | |
| D | | | | | | | | | | 68 | | | | 1 | | | |
| E | | | | | | | | | | | | | | | | | |
| F | | | | | | | | | | | | | 2 | | | | 1 |
| G | | | | | | 1 | | | 69 | | | | | | | 3 | 1 |
| H | | | | | | | | | | | | | | | | | |
| I | | | | | | | 64 | | | | | | | | 2 | | |
| K | | | | | | | | | | | | | | | 3 | | |
| L | 67 | 1 | 68 | | | | | | | | | | | | | | |
| M | | | | | | | | | | | | | | | | | |
| N | | | | | | | | | | | 1 | | | | 2 | 66 | |
| P | | 1 | | | | | | | | | | | | | | | |
| Q | | | | | | | | | | | | | | | | | |
| R | | | | | | | | | | | | | | | 2 | 1 | |
| S | | 66 | | | 1 | | | 1 | 69 | | 69 | | | 68 | 66 | | 67 |
| T | | | | 67 | | | | | | | | | | | 2 | 1 | 4 |
| V | 1 | | | | | 1 | 4 | | | | | 70 | | | | | 6 |
| W | | | | | 1 | | | | | | | | | | | | |
| X | | | | | | | | | | | | | | | | | |
| Y | | | | | | | | | | | | | | 1 | | | |
| Z | | | | | | | | | | | | | | | | | |
| — | | | | | | | | | | | | | | | | | |
| unknown (?) | | | | | | | | | | | | | | 1 | | | |
| not sequenced | 6 | 6 | 6 | 5 | 5 | 5 | 5 | 5 | 5 | 5 | 5 | 4 | 4 | | | | |
| sum of seq[2] | 68 | 68 | 68 | 69 | 69 | 69 | 69 | 69 | 69 | 69 | 69 | 70 | 70 | 74 | 74 | 74 | 74 |
| oomcaa[3] | 67 | 66 | 68 | 67 | 68 | 67 | 64 | 69 | 69 | 68 | 69 | 70 | 68 | 66 | 66 | 67 | 66 |
| mcaa[4] | L | S | L | T | C | A | I | S | G | D | S | V | S | S | N | S | A |
| rel. oomcaa[5] | 99% | 97% | 100% | 97% | 99% | 97% | 93% | 100% | 100% | 99% | 100% | 100% | 97% | 89% | 89% | 91% | 89% |
| pos occupied[6] | 2 | 3 | 1 | 3 | 2 | 3 | 3 | 1 | 1 | 2 | 1 | 1 | 2 | 5 | 6 | 3 | 4 |

| | CDRI | | | | Framework II | | | | | | | | | | | | |
|---|---|---|---|---|---|---|---|---|---|---|---|---|---|---|---|---|---|
| amino acid[1] | 33 | 34 | 35 | 36 | 37 | 38 | 39 | 40 | 41 | 42 | 43 | 44 | 45 | 46 | 47 | 48 | 49 | 50 |
| A | 67 | | | | | | | | | 1 | | | | | | | | |
| B | | | | | | | | | | | | | | | | | | |
| C | | | | | | | | | | | | | | | | | | |
| D | | | 1 | | | | | | | | | | | | | | | |
| E | | | | | | | | | | | | | | | 74 | | | |
| F | 1 | | | | 1 | | | | | | | | | | | | | |
| G | 2 | | | | | | | | | | | 74 | | | | | 74 | 1 |
| H | | | 1 | | | | | | | | | | | | | | | |
| I | | | 1 | | 70 | | | | | | | | | | | | | |
| K | | | | | | | | 1 | | | 1 | | | | | | | |
| L | | | | | | | | 1 | | | | | | 74 | | 74 | | |
| M | | | | | | | | | | | | | | | | | | |
| N | | | 70 | | | | | | | | | | | | | | | |
| P | | | | | | | | | | | 73 | | | | | | | |
| Q | | | | | | 72 | | | | | | | | | | | | |
| R | | | | | | | 74 | | | | 73 | | | | | | | 73 |
| S | 3 | | 1 | | | | | | 74 | 1 | 73 | | | | | | | |
| T | 1 | | | | | | | | | | | | | | | | | |
| V | | | | | 2 | | | | | | | | | | | | | |
| W | | 74 | | 74 | | | | | | | | | | | 74 | | | |
| X | | | | | | | | | | | | | | | | | | |
| Y | | | | | | | 1 | | | | | | | | | | | |
| Z | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 | 74 |
| oomcaa[3] | 67 | 74 | 70 | 74 | 70 | 74 | 72 | 74 | 73 | 73 | 73 | 74 | 74 | 74 | 74 | 74 | 74 | 73 |
| mcaa[4] | A | W | N | W | I | R | Q | S | P | S | R | G | L | E | W | L | G | R |
| rel. oomcaa[5] | 91% | 100% | 95% | 100% | 95% | 100% | 97% | 100% | 99% | 99% | 99% | 100% | 100% | 100% | 100% | 100% | 100% | 99% |
| pos occupied[6] | 5 | 1 | 5 | 1 | 4 | 1 | 3 | 1 | 2 | 2 | 2 | 1 | 1 | 1 | 1 | 1 | 1 | 2 |

CDR II

TABLE 6G-continued

Analysis of V heavy chain subgroup 6

| amino acid[1] | 51 | 52 | A | B | C | 53 | 54 | 55 | 56 | 57 | 58 | 59 | 60 | 61 | 62 | 63 | 64 |
|---|---|---|---|---|---|---|---|---|---|---|---|---|---|---|---|---|---|
| A | 1 |  |  |  |  | 1 |  |  |  |  |  |  | 73 | 1 |  |  |  |
| B |  |  |  |  |  |  |  |  |  |  |  |  |  |  |  |  |  |
| C |  |  |  |  |  |  |  |  |  |  |  | 1 |  |  |  |  |  |
| D |  |  |  |  |  |  |  |  |  |  | 68 |  |  | 1 |  |  |  |
| E |  |  |  |  |  |  |  |  | 1 | 3 |  |  |  | 7 |  |  | 1 |
| F |  | 2 | 1 |  |  | 1 |  |  | 7 |  |  |  |  |  |  |  |  |
| G |  |  |  |  |  |  | 1 |  |  | 1 |  |  |  |  | 1 |  |  |
| H |  |  | 1 |  |  |  |  |  | 1 |  |  |  |  |  |  |  |  |
| I |  |  |  |  |  |  |  |  |  |  |  |  |  | 1 |  |  |  |
| K |  |  |  | 1 |  |  | 66 |  |  | 1 |  |  |  |  |  |  | 67 |
| L |  |  |  |  |  |  |  |  | 1 |  |  |  |  | 5 |  | 2 |  |
| M |  |  |  |  |  |  |  |  |  |  |  |  |  |  |  |  |  |
| N |  |  |  |  |  |  | 1 |  | 2 | 65 | 1 |  |  |  |  |  | 1 |
| P |  |  |  |  |  |  |  |  |  |  |  |  | 1 | 1 |  |  |  |
| Q |  |  |  |  |  |  |  |  |  |  |  |  |  |  |  |  | 2 |
| R |  |  |  | 72 |  |  | 1 | 1 |  | 1 |  |  |  |  |  |  | 3 |
| S |  |  |  | 1 |  | 72 |  |  | 2 | 2 | 1 | 1 |  |  | 73 |  |  |
| T | 73 |  |  |  |  |  | 5 |  |  | 4 |  |  |  |  |  |  |  |
| V |  |  |  |  |  |  |  |  |  |  |  |  |  | 58 |  | 72 |  |
| W |  |  |  |  |  |  |  | 73 |  |  |  |  |  |  |  |  |  |
| X |  |  |  |  |  |  |  |  |  |  |  |  |  |  |  |  |  |
| Y |  | 72 | 72 |  |  |  |  |  |  | 60 | 1 |  | 72 |  |  |  |  |
| Z |  |  |  |  |  |  |  |  |  |  |  |  |  |  |  |  |  |
| — |  |  |  |  | 74 |  |  |  |  |  |  |  |  |  |  |  |  |
| unknown (?) |  |  |  |  |  |  |  |  |  |  |  |  |  |  |  |  |  |
| not sequenced |  |  |  |  |  |  |  |  |  |  |  |  |  |  |  |  |  |
| sum of seq[2] | 74 | 74 | 74 | 74 | 74 | 74 | 74 | 74 | 74 | 74 | 74 | 74 | 74 | 74 | 74 | 74 | 74 |
| oomcaa[3] | 73 | 72 | 72 | 72 | 74 | 72 | 66 | 73 | 60 | 65 | 68 | 72 | 73 | 58 | 73 | 72 | 67 |
| mcaa[4] | T | Y | Y | R | — | S | K | W | Y | N | D | Y | A | V | S | V | K |
| rel. oomcaa[5] | 99% | 97% | 97% | 97% | 100% | 97% | 89% | 99% | 81% | 88% | 92% | 97% | 99% | 78% | 99% | 97% | 91% |
| pos occupied[6] | 2 | 2 | 3 | 3 | 1 | 3 | 5 | 2 | 7 | 6 | 5 | 3 | 2 | 7 | 2 | 2 | 5 |

| | CDR II | | Framework III | | | | | | | | | | | | | |
|---|---|---|---|---|---|---|---|---|---|---|---|---|---|---|---|---|---|
| amino acid[1] | 65 | 66 | 67 | 68 | 69 | 70 | 71 | 72 | 73 | 74 | 75 | 76 | 77 | 78 | 79 | 80 | 81 |
| A |  |  |  | 2 |  |  | 6 |  |  | 1 |  |  |  |  |  |  |  |
| B |  |  |  |  |  |  |  |  |  |  |  |  |  |  |  |  |  |
| C |  |  |  |  |  |  |  |  |  |  |  |  |  |  |  |  |  |
| D |  |  |  |  |  | 2 |  | 73 |  |  |  |  |  |  |  |  |  |
| E |  |  |  |  |  |  |  |  |  |  | 2 |  |  |  |  |  |  |
| F |  |  |  |  |  |  |  |  |  |  |  |  |  |  | 71 |  |  |
| G | 8 |  |  |  |  |  |  |  |  |  |  |  |  |  |  |  |  |
| H |  |  |  |  |  |  |  | 1 |  |  |  |  |  |  |  |  | 2 |
| I |  |  | 65 | 2 | 71 |  |  |  | 1 |  |  |  |  | 1 |  |  |  |
| K |  |  |  |  |  |  | 1 |  |  |  |  | 70 |  |  |  |  |  |
| L |  |  | 4 |  |  |  |  |  | 1 |  |  |  | 1 |  |  | 74 |  |
| M |  |  | 1 |  |  |  |  |  |  |  |  |  |  |  |  |  |  |
| N |  |  |  |  |  | 69 |  |  |  |  |  |  | 74 |  |  |  |  |
| P |  |  |  |  |  |  | 66 |  |  |  |  |  |  |  |  |  |  |
| Q |  | 1 |  |  |  |  |  |  |  |  |  |  |  | 72 |  |  | 71 |
| R |  | 73 |  |  |  |  |  |  |  |  |  |  |  | 1 |  |  | 1 |
| S | 66 |  |  | 1 |  | 2 | 1 |  |  | 73 |  |  |  |  | 74 |  |  |
| T |  |  |  | 69 | 1 |  |  |  | 71 | 1 | 2 |  |  |  |  |  |  |
| V |  |  | 4 |  | 2 |  | 1 |  |  |  |  |  |  | 2 |  |  |  |
| W |  |  |  |  |  |  |  |  |  |  |  |  |  |  |  |  |  |
| X |  |  |  |  |  |  |  |  |  |  |  |  |  |  |  |  |  |
| Y |  |  |  |  |  |  |  |  |  |  |  |  |  |  |  |  |  |
| Z |  |  |  |  |  |  |  |  |  |  |  |  |  |  |  |  |  |
| — |  |  |  |  |  |  |  |  |  |  |  |  |  |  |  |  |  |
| unknown (?) |  |  |  |  |  |  |  |  |  |  |  |  |  |  |  |  |  |
| not sequenced |  |  |  |  |  |  |  |  |  |  |  |  |  |  |  |  |  |
| sum of seq[2] | 74 | 74 | 74 | 74 | 74 | 74 | 74 | 74 | 74 | 74 | 74 | 74 | 74 | 74 | 74 | 74 | 74 |
| oomcaa[3] | 66 | 73 | 65 | 69 | 71 | 69 | 66 | 73 | 71 | 73 | 70 | 74 | 72 | 71 | 74 | 74 | 71 |
| mcaa[4] | S | R | I | T | I | N | P | D | T | S | K | N | Q | F | S | L | Q |
| rel. oomcaa[5] | 89% | 99% | 88% | 93% | 96% | 93% | 89% | 99% | 96% | 99% | 95% | 100% | 97% | 96% | 100% | 100% | 96% |
| pos occupied[6] | 2 | 2 | 4 | 4 | 3 | 4 | 4 | 2 | 4 | 2 | 3 | 1 | 3 | 3 | 1 | 1 | 3 |

| | Framework III | | | | | | | | | | | | CDR III | | |
|---|---|---|---|---|---|---|---|---|---|---|---|---|---|---|---|
| amino acid[1] | 82 | A | B | C | 83 | 84 | 85 | 86 | 87 | 88 | 89 | 90 | 91 | 92 | 93 | 94 | 95 |
| A |  |  |  |  |  | 1 |  |  |  | 74 |  |  |  |  | 69 |  | 11 |
| B |  |  |  |  |  |  |  |  |  |  |  |  |  |  |  |  |  |
| C |  |  |  |  |  |  |  |  |  |  |  |  |  | 73 |  |  |  |

TABLE 6G-continued

Analysis of V heavy chain subgroup 6

| | | | | | | | | | | | | | | | | | |
|---|---|---|---|---|---|---|---|---|---|---|---|---|---|---|---|---|---|
| D | | 3 | | | | | | 73 | | | | | | | | | 19 |
| E | | | | | | | 73 | | | | | | | | | | 10 |
| F | | | 1 | | | | | | | | | | 3 | | 1 | | 1 |
| G | | | | | | | | 1 | | | | | | | 1 | | 16 |
| H | | 1 | | | | | | | | | | | | | | | |
| I | | | | | | | | | | | 2 | | | | | | |
| K | | 4 | | | | | | | | | | | | | | 1 | 1 |
| L | 72 | | | | | | | | | | | | | | | | 1 |
| M | 1 | | | 1 | | | | | | | 2 | | | | | | |
| N | | 63 | | | | | | | | | | | 1 | | | | 1 |
| P | | | | | 70 | | | | | | | | | | | | |
| Q | | | | | | | | | | | | | | | | | 1 |
| R | | 1 | | | | | | | | | | | 1 | | | 69 | 1 |
| S | | 1 | 73 | | 1 | 3 | | | | | | | | | | 3 | 5 |
| T | | 1 | | | 73 | | | | 74 | | | 1 | | | | | 1 |
| V | 1 | | | 73 | | | | | | | 70 | | | | 3 | 1 | 4 |
| W | | | | | | | | | | | | | | | | | 1 |
| X | | | | | | | | | | | | | | | | | |
| Y | | | | | | | | | | | | | 73 | 70 | | | |
| Z | | | | | | | | | | | | | | | | | |
| — | | | | | | | | | | | | | | | | | |
| unknown (?) | | | | | | | | | | | | | | | | | |
| not sequenced | | | | | | 1 | | | | | | | | | | | |
| sum of seq[2] | 74 | 74 | 74 | 74 | 74 | 73 | 74 | 74 | 74 | 74 | 74 | 74 | 74 | 74 | 74 | 74 | 73 |
| oomcaa[3] | 72 | 63 | 73 | 73 | 73 | 70 | 73 | 73 | 74 | 74 | 70 | 73 | 70 | 73 | 69 | 69 | 19 |
| mcaa[4] | L | N | S | V | T | P | E | D | T | A | V | Y | Y | C | A | R | D |
| rel. oomcaa[5] | 97% | 85% | 99% | 99% | 99% | 96% | 99% | 99% | 100% | 100% | 95% | 99% | 95% | 99% | 93% | 93% | 26% |
| pos occupied[6] | 3 | 7 | 2 | 2 | 2 | 2 | 2 | 2 | 1 | 1 | 3 | 2 | 3 | 2 | 4 | 4 | 14 |

| | CDR III | | | | | | | | | | | | | | | |
|---|---|---|---|---|---|---|---|---|---|---|---|---|---|---|---|---|
| amino acid[1] | 96 | 97 | 98 | 99 | 100 | A | B | C | D | E | F | G | H | I | J | K | 101 |
| A | 1 | 3 | 12 | 4 | 3 | 2 | 5 | | 8 | | | | | | 10 | 1 | |
| B | | | | | | | | | | | | | | | | | |
| C | | 1 | | 1 | | | 1 | | 1 | 1 | | | | | | | |
| D | 4 | 3 | 7 | 4 | 3 | 1 | 6 | 1 | 1 | 1 | | | | | | | 62 |
| E | 4 | 2 | 1 | 2 | 2 | 1 | 2 | | | | | | | 1 | | | |
| F | 1 | 1 | | 1 | 2 | 3 | | 2 | | | 1 | | | | | 38 | 4 |
| G | 4 | 15 | 15 | 11 | 8 | 6 | 2 | 5 | 1 | 8 | 6 | 1 | | | 17 | | |
| H | 1 | | 1 | | | 1 | 1 | 1 | 1 | | | | 1 | 1 | 1 | | |
| I | 1 | 2 | | 2 | | | 5 | 1 | | | | | | | | | |
| K | 1 | 1 | 1 | 1 | 1 | | | | 1 | | | | | | | | |
| L | 8 | 4 | 2 | 3 | 2 | 1 | | | | | 1 | 5 | | | | 8 | |
| M | 1 | | | | 1 | | | 5 | | | | | | | | 11 | |
| N | 3 | 1 | 2 | 1 | 1 | 1 | 3 | | 2 | | 1 | | 1 | 3 | | | |
| P | 10 | 4 | | 5 | 3 | | 5 | 1 | | 1 | | | | | | | |
| Q | 1 | 1 | 1 | | | | | 1 | | | | | | | | | 1 |
| R | 7 | 8 | 1 | 8 | 8 | 3 | | 1 | 1 | 5 | | | | | | | 1 |
| S | 5 | 5 | 7 | 6 | 7 | 3 | 4 | 2 | | | | | 1 | 1 | | | |
| T | 1 | 4 | 3 | 4 | 4 | 6 | 3 | 1 | | | 1 | | | | | 2 | |
| C | 5 | 1 | 9 | | | 4 | | 9 | 4 | 1 | 1 | | | | | | |
| W | 6 | 8 | | 3 | 2 | 4 | | | | | | | | 4 | 4 | | |
| X | | | | | | | | | | | | | | | | | |
| Y | 6 | 4 | 2 | 2 | 2 | 6 | 6 | 2 | 4 | 2 | 1 | 8 | 8 | 12 | 12 | | |
| Z | | | | | | | | | | | | | | | | | |
| — | 2 | 3 | 7 | 14 | 23 | 25 | 33 | 41 | 47 | 53 | 54 | 57 | 56 | 50 | 28 | 12 | 4 |
| unknown (?) | | | | | | | | | | | 6 | 1 | 5 | | | | |
| not sequenced | 1 | 2 | 2 | 1 | 1 | 1 | 1 | 1 | 1 | 1 | 1 | 1 | 1 | 1 | 1 | 1 | 1 |
| sum of seq[2] | 72 | 71 | 71 | 72 | 72 | 72 | 72 | 72 | 72 | 72 | 72 | 72 | 72 | 72 | 72 | 72 | 72 |
| oomcaa[3] | 10 | 15 | 15 | 14 | 23 | 25 | 33 | 41 | 47 | 53 | 54 | 57 | 56 | 50 | 28 | 38 | 62 |
| mcaa[4] | P | G | G | — | — | — | — | — | — | — | — | — | — | — | — | F | D |
| rel. oomcaa[5] | 14% | 21% | 21% | 19% | 32% | 35% | 46% | 57% | 65% | 74% | 75% | 79% | 78% | 69% | 39% | 53% | 86% |
| pos occupied[6] | 20 | 19 | 15 | 17 | 16 | 16 | 13 | 14 | 11 | 8 | 8 | 4 | 5 | 7 | 6 | 6 | 5 |

| | Framework IV | | | | | | | | | | | |
|---|---|---|---|---|---|---|---|---|---|---|---|---|
| amino acid[1] | 102 | 103 | 104 | 105 | 106 | 107 | 108 | 109 | 110 | 111 | 112 | 113 | sum |
| A | | | | | | | | | 2 | | | | 494 |
| B | | | | | | | | | | | | | 147 |
| C | | | | | | | | | | | | | 403 |
| D | | | | | | | | | | 1 | | | 186 |
| E | | | | | | | | | | | | | 186 |
| F | | 2 | | | | | | | | | 2 | | 150 |
| G | | | | 49 | | 50 | | | | | | | 571 |
| H | | 2 | | | | | | | | | | | 18 |

TABLE 6G-continued

Analysis of V heavy chain subgroup 6

| | | | | | | | | | | | | |
|---|---|---|---|---|---|---|---|---|---|---|---|---|
| I | 9 | | | | 3 | | 1 | | | | | 304 |
| K | | | | 1 | | 1 | | | | | | 293 |
| L | 5 | | | | | 26 | | | | | | 632 |
| M | | | | | | 8 | | | | | | 31 |
| N | | | | | | | | | | | | 436 |
| P | 4 | | | 6 | | | | | | | 1 | 387 |
| Q | | | | 40 | | | | | | | | 539 |
| R | | | | 2 | | | | | | | | 495 |
| S | 4 | | 1 | | 1 | | | | 43 | | 46 | 1271 |
| T | | | | | 45 | 4 | | 45 | | | | 640 |
| V | 21 | | | | | 2 | 46 | | 48 | | | 647 |
| W | | 65 | | | | 5 | | | | | | 398 |
| X | | | | | | | | | | | | |
| Y | 19 | | | | | | | | | | | 518 |
| Z | | | | | | | | | | | | |
| — | 2 | | | | | | | | | | | 585 |
| unknown (?) | | | | | | | | | | | | 13 |
| not sequenced | 5 | 8 | 23 | 24 | 23 | 24 | 25 | 25 | 28 | 25 | 28 | 26 | 580 |
| sum of seq[2] | 68 | 65 | 50 | 49 | 50 | 49 | 48 | 48 | 45 | 48 | 45 | 47 | |
| oomcaa[3] | 21 | 65 | 49 | 40 | 50 | 45 | 26 | 46 | 45 | 48 | 43 | 46 | |
| mcaa[4] | V | W | G | Q | G | T | L | V | T | V | S | S | |
| rel. oomcaa[5] | 31% | 100% | 98% | 82% | 100% | 92% | 54% | 96% | 100% | 100% | 96% | 98% | |
| pos occupied[6] | 9 | 1 | 2 | 4 | 1 | 3 | 7 | 3 | 1 | 1 | 2 | 2 | |

Appendix to Tables 1A–C

A. References of Rearranged Sequences

References of Rearranged Human Kappa Sequences Used for Alignment

1 Alescio-Zonta, L. & Baglioni, C. (1970) Eur. J. Biochem., 15, 450–463.
2 Andrews, D. W. & Capra, J. D. (1981) Biochemistry, 20, 5816–5822.
3 Andris, J. S., Ehrlich, P. H., Ostberg, L. & Capra, J. D. (1992) J. Immunol., 149, 4053–4059.
4 Atkinson, P. M., Lampman, G. W., Furie, B. C., Naparstek, Y., Schwartz, R. S., Stollar, B. D. & Furie, B. (1985) J. Clin. Invest., 75, 1138–1143.
5 Aucouturier, P., Bauwens, M., Khamlichi, A. A., Denoroy, L. Spinelli, S., Touchard, G., Preud'homme, J.-L & Cogne, M. (1993) J. Immunol., 150, 3561–3568.
6 Avila, M. A., Vazques, J., Danielsson, L, Fernandez De Cossio, M. E. & Borrebaeck, C. A. K. (1993) Gene, 127, 273–274.
7 Barbas Iii, C. F., Crowe, Jr., J. E., Cababa, D., Jones, T. M., Zebedee, S. L., Murphy, B. R., Chanock, R. M. & Burton, D. R. (1992) Proc. Natl. Acad. Sci. Usa, 89, 10164–10168.
8 Barbas, CF., Iii, et al. (1993) J-Mol-Biol., 230, 812–23.
9 Bentley, D. L. & Rabbitts, T. H. (1980) Nature, 288, 730–733.
10 Bentley, D. L. & Rabbitts, T. H. (1983) Cell, 32, 181–189.
11 Bentley, D. L. (1984) Nature, 307, 77–80.
12 Bhat, N. M., Bieber, M. M., Chapman, C. J., Stevenson, F. K. & Teng, N. N. H. (1993) J. Immunol., 151, 5011–5021.
13 Blaison, G., Kuntz, J.-L & Pasquali, J.-L (1991) Eur. J. Immunol., 21, 1221–1227.
14 Braun, H., Leibold, W., Barnikol, H. U. & Hilschmann, N. (1971) Z. Physiol. Chem., 352, 647–651; (1972) Z. Physiol. Chem., 353, 1284–1306.
15 Capra, J. D. & Kehoe, J. M. (1975) Adv. Immunology, 20, 1–40.; Andrews, D. W. & Capra, J. D. (1981) Proc. Nat. Acad. Sci. Usa, 78, 3799–3803.
16 Capra, J. D. & Kehoe, J. M. (1975) Adv. Immunology, 20, 1–40.; Ledford, D. K., Goni, F., Pizzolato, M., Franklin, E. C., Solomon, A. & Frangione, B. (1983) J. Immunol., 131, 1322–1325.
17 Chastagner, P., Theze, J. & Zouali, M. (1991) Gene, 101, 305–306.
18 Chen, P. P., Robbins, D. L, Jirik, F. R., Kipps, T. J. & Carson, D. A. (1987) J. Exp. Med, 166, 1900–1905.
19 Chen, P. P., Robbins, D. L, Jirik, F. R., Kipps, T. J. & Carson, D. A. (1987) J. Exp. Med, 166, 1900–1905; Liu, M.-F., Robbins, D. L., Crowley, J. J., Sinha, S., Kozin, F., Kipps, T. J., Carson, D. A. & Chen. P. P. (1989) J. Immunol., 142, 688–694.
20 Chersi, A. & Natali, P. G. (1978) Immunochemistry, 15, 585–589.
21 Co, M. S., Deschamps, M., Whitley, R. J. & Queen, C. (1991) Proc. Natl. Acad. Sci. Usa, 88, 2869–2873.
22 Cuisinier, A.-M., Fumoux, F., Fougereau, M. & Tonnelle, C. (1992) Mol. Immunol., 29, 1363–1373.
23 Davidson, A., Manheimer-Lory, A., Aranow, C., Peterson, R., Hannigan, N. & Diamond, B. (1990) J. Clin. Invest., 85, 1401–1409.
24 Denomme, G. A., Mahmoudi, M., Edwards. J. Y., Massicotte, H., Cairns, E. & Bell, D. A. (1993) Hum. Antibod. Hybridomas, 4, 98–103.
25 Dersimonian, H., Mcadam, K. P. W. J., Mackworth-Young, C. & Stollar, B. D. (1989) J. Immunol., 142, 4027–4033.
26 Dreyer, W. J., Gray, W. R. & Hood, L. (1967) Cold Spring Harbor Symp. Quantitative Biol., 32, 353–367.
27 Ebeling, S. B., Schutte, M. E. M. & Logtenberg, T. (1993) Eur. J. Immunol., 23, 1405–1408.
28 Eulitz, M. & Kley, H.-P. (1977) Immunochem., 14, 289–297.
29 Eulitz, M. & Linke, R. P. (1982) Z. Physiol. Chem., 363, 1347–1358.
30 Eulitz, M., Breuer, M., Eblen, A., Weiss, D. T. & Solomon, A. (1990) In Amyloid And Amyloidosis, Eds. J. B. Natvig, O. Forre, G. Husby, A. Husebekk, B. Skogen, K. Sletten & P. Westermark, Kluwer Academic 31 Eulitz, M., Gotze, D. & Hilschmann, N. (1972) Z. Physiol. Chem., 353, 487–491; Eulitz, M. & Hilschmann, N. (1974) Z. Physiol. Chem., 355, 842–866.

32 Eulitz, M., Kley, H. P. & Zeitler, H. J. (1979) Z. Physiol. Chem., 360, 725–734.

33 Ezaki, I., Kanda, H., Sakai, K., Fukui, N., Shingu, M., Nobunaga, M. & Watanabe, T. (1991) Arthritis And Rheumatism, 34, 343–350.

34 Felgenhauer, M., Kohl, J. & Ruker, F. (1990) Nucl. Acids Res., 18, 4927.

35 Ferri, G., Stoppini, M., Iadarola, P., Bellotti, V. & Merlini, G. (1989) Biochim. Biophys. Acta, 995, 103–108.

36 Gillies, S. D. Dorai, H., Wesolowski, J., Majeau, G., Young, D., Boyd, J., Gardner, J. & James, K. (1989) Bio/Tech., 7.799–804.

37 Goni, F. & Frangione, B. (1983) Proc. Nat. Acad. Sci. Usa, 80, 48374841.

38 Goni, F. R., Chen, P. P., Mcginnis, D., Arjonilla, M. L., Fernandez, J., Carson, D., Solomon, A, Mendez, E. & Frangione, B. (1989) J. Immunol., 142, 3158–3163.

39 Gorman, S. D., Clark, M. R., Routledge, E. G., Cobbold, S. P. & Waldmann, H. (1991) Proc. Natl. Acad. Sci. Usa, 88, 4181–4185.

40 Gottlieb, P. D., Cunningham, B. A., Rutishauser, U. & Edelman, G. M. (1970) Biochemistry, 9, 3155–3161.

41 Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. & Winter, G. (1993) Embo J., 12, 725–734.

42 Hieter, P. A., Max, E. E., Seidman, J. G., Maizel, J. V., Jr. & Leder, P. (1980) Cell, 22, 197–207; Klobeck, H. G, Meindl, A., Combriato, G., Solomon, A. & Zachau, H. G. (1985) Nucl. Acids Res., 13, 6499–6513; Weir, L. & Leder, P. (1986)

43 Hilschmann, N. & Craig, L. C. (1965) Proc. Nat. Acad. Sci. Usa, 53, 1403–1409; Hilschmann, N. (1967) Z. Physiol. Chem., 348, 1077–1080.

44 Hilschmann, N. & Craig, L. C. (1965) Proc. Nat. Acad. Sci. Usa, 53, 1403–1409; Hilschmann, N. (1967) Z. Physiol. Chem., 348, 1718–1722; Hilschmann, N. (1969) Naturwissenschaften, 56, 195–205.

45 Hirabayashi, Y., Munakata, Y., Sasaki, T. & Sano, H. (19921 Nucl. Acids Res., 20, 2601.

46 Jaenichen, H.-R., Pech, M., Lindenmaier, W., Wildgruber, N. & Zachau, H. G. (1984) Nuc. Acids Res., 12, 5249–5263.

47 Jirik, F. R., Sorge, J., Fong, S., Heitzmann, J. G., Curd, J. G., Chen, P. P., Goldfien, R. & Carson, D. A (1986) Proc. Nat. Acad. Sci. Usa, 83, 2195–2199.

48 Kaplan, A. P. & Metzger, H. (1969) Biochemistry, 8, 3944–3951.; Klapper, D. G. & Capra, J. D. (1976) Ann. Immunol. (Inst. Pasteur), 127c, 261–271.

49 Kennedy, M. A. (1991) J. Exp. Med., 173, 1033–1036.

50 Kim, H. S. & Deutsch, H. F. (1988) Immunol., 64, 573–579.

51 Kipps, T. J., Tomhave, E., Chen, P. P. & Carson, D. A. (1988) J. Exp. Med., 167, 840–852.

52 Kipps, T. J., Tomhave, E., Chen, P. P. & Fox, R. I. (1989) J. Immunol., 142, 4261–4268.

53 Klapper, D. G. & Capra, J. D. (1976) Ann. Immunol. (Inst. Pasteur), 127c, 261–271.

54 Klein, U., Kuppers, R. & Rajewsky, K. (1993) Eur. J. Immunol., 23, 3272–3277.

55 Klobeck, H. G, Meindl, A., Combriato, G., Solomon, A. & Zachau, H. G. (1985) Nucl. Acids Res., 13, 6499–6513.

56 Klobeck, H. G., Bornkammm, G. W., Combriato, G., Mocikat, R., Pohlenz, H. D. & Zachau, H. G. (1985) Nucl. Acids Res., 13, 6515–6529.

57 Klobeck, H. G., Combriato, G. & Zachau, H. G. (1984) Nuc. Acids Res., 12, 6995–7006.

58 Klobeck, H. G., Solomon, A. & Zachau, H. G. (1984) Nature, 309, 73–76.

59 Knight, G. B., Agnello, V., Bonagura, V., Barnes, J. L., Panka, D. J. & Zhang, Q.-X. (1993) J. Exp. Med., 178, 1903–1911.

60 Kohler, H., Shimizu, A., Paul, C. & Putnam, F. W. (1970) Science, 169, 56–59. (Kaplan, A. P. & Metzger, H. (1969) Biochemistry, 8, 3944–3951.)

61 Kratzin, H., Yang, C. Y., Krusche, J. U. & Hilschmann, N. (1980) Z. Physiol. Chem., 361, 1591–1598.

62 Kunicki, T. J., Annis, D. S., Gorski, J. & Nugent, D. J. (1991) J. Autoimmunity, 4, 433–446.

63 Larrick, J. W., Wallace, E. F., Coloma, M. J., Bruderer, U., Lang, A. B. & Fry, K. E. (1992) Immunological Reviews, 130, 69–85.

64 Laure, C. J., Watanabe, S. & Hilschmann, N. (1973) Z. Physiol. Chem., 354, 1503–1504.

65 Ledford, D. K., Goni, F., Pizzolato, M., Franklin, E. C., Solomon, A. & Frangione, B. (1983) J. Immunol., 131, 1322–1325.

66 Ledford, D. K., Goni, F., Pizzolato, M., Franklin, E. C., Solomon, A. & Frangione, B. (1983) J. Immunol., 131, 1322–1325.

67 Ledford, D. K., Goni, F., Pizzolato, M., Franklin, E. C., Solomon, A. & Frangione, B. (1983) J. Immunol., 131, 1322–1325. Pons-Estel, B., Goni, F., Solomon, A. & Frangione, B. (1984) J. Exp. Med., 160, 893.

68 Levy, S., Mendel, E., Kon, S., Avnur, Z. & Levy, R. (1988) J. Exp. Med., 168, 475–489.

69 Liepnieks, J. J., Dwulet, F. E. & Benson, M. D. (1990) Mol. Immunol., 27, 481–485.

70 Manheimer-Lory, A., Katz, J. B., Pillinger, M., Ghossein, C., Smith, A. & Diamond, B. (1991) J. Exp. Med., 174, 1639–1652.

71 Mantovani, L, Wilder, R. L. & Casali, P. (1993) J. Immunol., 151, 473–488.

72 Mariette, X., Tsapis, A. & Brouet, J.-C. (1993) Eur. J. Immunol., 23, 846–851.

73 Marks, J. D., Hoogenboom, H. R., Bonnert, T. P., Mccafferty, J., Griffiths, A. D. & Winter, G. (1991) J. Mol. Biol., 222, 581–597.

74 Marsh, P., Mills, F. & Gould, H. (1985) Nuc. Acids Res., 13, 6531–6544.

75 Middaugh, C. R. & Litman, G. W. (1987) J. Biol. Chem., 262, 3671–3673.

76 Milstein, C. & Deverson, E. V. (1971) Biochem., 123, 945–958.

77 Milstein, C. (1969) Febs Letters, 2, 301–304.

78 Milstein, C. (1969) Febs Letters, 2, 301–304.

79 Milstein, C. P. & Deverson, E. V. (1974) Eur. J. Biochem., 49, 377–391.

80 Moran, M. J., Andris, J. S., Matsumato, Y.-I., Capra, J. D. & Hersh, E. M. (1993) Mol. Immunol., 30, 1543–1551.

81 Nakatani, T., Nomura, N., Horigome, K., Ohtsuka, H. & Noguchi, H. (1989) Bio/Tech., 7, 805–810.

82 Newkirk, M., Chen, P. P., Carson, D., Posnett, D. & Capra, J. D. (1986) Mol. Immunol., 23, 239–244.

83 Newkirk, M. M., Gram, H., Heinrich, G. F., Ostberg, L., Capra, J. D. & Wasserman, R. L. (1988) J. Clin. Invest., 81, 1511–1518.

84 Newkirk, M. M., Mageed, R. A., Jefferis, R., Chen, P. P. & Capra, J. D. (1987) J. Exp. Med., 166, 550–564.

85 Olee, B. T., Lu, E. W., Huang, D.-F., Soto-Gil, R. W., Deftos, M., Kozin, F., Carson, D. A. & Chen, P. P. (1992) J. Exp. Med., 175, 831–842.

86 Palm, W. & Hilschmann, N. (1973) Z. Physiol. Chem., 354, 1651–1654; (1975) Z. Physiol. Chem., 356, 167–191.

87 Pascual, V., Victor, K., Lelsz, D., Spellerberg, M. B., Hamblin, T. J., Thompson, K. M., Randen, I., Natvig, J., Capra, J. D. & Stevenson, F. K. (1991) J. Immunol., 146, 4385–4391.

88 Pascual, V., Victor, K., Randen, I., Thompson, K., Steinitz, M., Forre, O., Fu, S.-M., Natvig, J. B. & Capra, J. D. (1992) Scand. J. Immunol., 36, 349–362.

89 Pech, M. & Zachau, H. G. (1984) Nuc. Acids Res., 12, 9229–9236.

90 Pech, M., Jaenichen, H.-R., Pohlenz, H.-D., Neumaier, P. S., Klobeck, H.-G. & Zachau, H. G. (1984) J. Mol. Biol., 176, 189–204.

91 Pons-Estel, B., Goni, F., Solomon, A & Frangione, B. (1984) J. Exp. Med., 160, 893–904.

92 Portolano, S., Mclachlan, S. M. & Rapoport, B. (1993) J. Immunol., 151, 2839–2851.

93 Portolano, S., Seto, P., Chazenbalk, G. D., Nagayama, Y., Mclachlan, S. M. & Rapoport, B. (1991) Biochem. Biophys. Res. Commun., 179, 372–377.

94 Pratt, L. F., Rassenti, L, Larrick. J., Robbins, B., Banks, P. M. & Kipps, T. J. (1989) J. Immunol., 143,699–705.

95 Prelli, F., Tummolo, D., Solomon, A & Frangione, B. (1986) J. Immunol., 136, 4169–4173.

96 Putnam, F. W., Whitley, E. J., Jr., Paul, C. & Davidson, J. N. (1973) Biochemistry, 12, 3763–3780.

97 Randen, I., Pascual, V., Victor, K., Thompson, K. M., Forre, O., Capra, J. D. & Natvig, J. B. (1993) Eur. J. Immunol., 23, 1220–1225.

98 Rassenti, L. Z., Pratt, L. F., Chen, P. P., Carson, D. A. & Kipps, T. J. (1991) J. Immunol., 147, 1060–1066.

99 Reidl, L. S., Friedman, D. F., Goldman, J., Hardy, R. R., Jefferies, L. C. & Silberstein, L. E. (1991) J. Immunol., 147, 3623–3631.

100 Riechmann, L., Clark, M., Waldmann, H. & Winter, G. (1988) Nature, 332, 323–327.

101 Riesen, W., Rudikoff, S., Oriol, R. & Potter, M. (1975) Biochemistry, 14, 1052–1057; Riesen, W. F., Braun, D. G. & Jaton, J. C. (1976) Proc. Nat. Acad. Sci. Usa, 73, 2096–2100; Riesen, W. F. & Jaton, J. C. (1976) Biochemistry, 15, 3829.

102 Rodilla Sala, E., Kratzin, D. H., Pick, A. I. & Hilschmann, N. (1990) In Amyloid And Amyloidosis, Eds. J. B. Natvig, O. Forre, G. Husby, A. Husebekk, B. Skogen, K. Sletten & P. Westermark, Kluwer Academic 103 Schiechl, H. & Hilschmann, N. (1971) Z. Physiol. Chem., 352, 111–115; (1972) Z. Physiol. Chem., 353, 345–370.

104 Schneider, M. & Hilschmann, N. (1974) Z. Physiol. Chem., 355, 1164–1168.

105 Shearman, C. W., Pollock, D., White, G., Hehir, K., Moore, G. P., Kanzy, E. J. & Kurrle, R. (1991) J. Immunol., 147, 4366–4373.

106 Shinoda, T. (1973) J. Biochem., 73, 433–446.

107 Shinoda, T. (1975) J. Biochem., 77, 1277–1296.

108 Shinoda, T., Takenawa, T., Hoshi, A. & Isobe, T. (1990) In Amyloid And Amyloidosis, Eds. J. B. Natvig, O. Forre, G. Husby, A. Husebekk, B. Skogen, K. Sletten & P. Westermark, Kluwer Academic Publishers, Dordrecht/Boston/London, Pp. 157-

109 Silberstein, L. E., Litwin, S. & Carmack, C. E. (1989) J. Exp. Med., 169, 1631–1643.

110 Sims, M. J., Hassal, D. G., Brett, S., Rowan, W., Lockyer, M. J., Angel, A., Lewis, A. P., Hale, G., Waldmann, H. & Crowe, J. S. (1993) J. Immunol., 151, 2296–2308.

111 Spatz, L. A., Wong, K. K., Williams, M., Desai, R., Golier, J., Berman, J. E., Alt, F. W. & Latov, N. (1990) J. Immunol., 144, 2821–2828.

112 Stavnezer, J., Kekish, O., Batter, D., Grenier, J., Balazs, I., Henderson, E. & Zegers, B. J. M. (1985) Nucl. Acids Res., 13, 3495–3514.

113 Straubinger, B., Thiebe, R., Pech, M. & Zachau, H. G. (1988) Gene, 69, 209–214.

114 Suter, L, Barnikol, H. U., Watanabe, S. & Hilschmann, N. (1969) Z. Physiol. Chem., 350, 275–278; (1972) Z. Physiol. Chem., 353, 189–208.

115 Tempest, P. R., Bremner, P., Lambert, M., Taylor, G., Furze, J. M., Carr, F. J. & Harris, W. J. (1991) Bio/Tech., 9, 266–271.

116 Titani, K., Shinoda, T. & Putnam, F. W. (1969) J. Biol. Chem., 244, 3550–3560.

117 Toft, K. G., Olstad, O. K., Sletten, K. & Westermark, P. (1990) In Amyloid And Amyloidosis, Eds. J. B. Natvig, O. Forre, G. Husby, A. Husebekk, B. Skogen, K. Sletten & P. Westermark, Kluwer Academic.

118 Van Es, J. H., Aanstoot, H., Gmelig-Meyling, F. H. J., Derksen, R. H. W. M. & Logtenberg, T. (1992) J. Immunol., 149, 2234–2240.

119 Victor, K. D., Pascual, V., Lefvert, A. K. & Capra, J. D. (1992) Mol. Immunol., 29, 1501–1506.

120 Victor, K. D., Pascual, V., Williams, C. L., Lennon, V. A. & Capra, J. D. (1992) Eur. J. Immunol., 22, 2231–2236.

121 Victor, K. D., Randen, I., Thompson, K., Forre, O., Natvig, J. B., Fu, S. M. & Capra, J. D. (1991) J. Clin. Invest., 87, 1603–1613.

122 Wagner, S. D. & Luzzatto, L. (1993) Eur. J. Immunol., 23, 391–397.

123 Watanabe, S. & Hilschmann, N. (1970) Z. Physiol. Chem., 351, 1291–1295.

124 Weisbart, R. H., Wong, A. L., Noritake, D., Kacena, A., Chan, G., Ruland, C., Chin, E., Chen, I. S. Y. & Rosenblatt, J. D. (1991) J. Immunol., 147, 2795–2801.

125 Weng, N.-P., Yu-Lee, L.-Y., Sanz, I., Patten, B. M. & Marcus, D. M. (1992) J. Immunol., 149, 2518–2529.

126 Winkler, T. H., Fehr, H. & Kalden, J. R. (1992) Eur J. Immunol., 22, 1719–1728.

References of Rearranged Human Lambda Sequences Used for Alignment

1 Alexandre, D., Chuchana, P., Brockly, F., Blancher, A., Lefranc, G. & Lefranc, M.-P. (1989) Nuc. Acids Res., 17, 3975.

2 Anderson, M. L. M., Brown, L., Mckenzie, E., Kellow, J. E. & Young, B. D. (1985) Nuc. Acids Res, 13, 2931–2941.

3 Andris, J. S., Brodeur, B. R. & Capra, J. D. (1993) Mol. Immunol., 30, 1601–1616.

4 Andris, J. S., Ehrlich, P. H., Ostberg, L. & Capra, J. D. (1992) J. Immunol., 149, 4053–4059.

5 Baczko, K., Braun, D. G., Hess, M. & Hilschmann, N. (1970) Z. Physiol. Chem., 351, 763–767; Baczko, K., Braun, D. G. & Hilschmann, N. (1974) Z. Physiol. Chem., 355, 131–154.

6 Berinstein, N., Levy, S. & Levy, R. (1989) Science, 244, 337–339.

7 Bhat, N. M., Bieber, M. M., Chapman, C. J., Stevenson, F. K. & Teng, N. N. H. (1993) J. Immunol., 151, 5011–5021.

8 Cairns, E., Kwong, P. C., Misener, V., Ip, P., Bell, D. A. & Siminovitch, K. A. (1989) J. Immunol., 143, 685–691.

9 Carroll, W. L., Yu, M., Link, M. P. & Korsmeyer, S. J. (1989) J. Immunol., 143, 692–698.

10 Chen, B. L. & Poljak, R. J. (1974) Biochemistry, 13, 1295–1302.

11 Chen, B. L., Chiu, Y. Y. H., Humphrey, R. L. & Polijak, R. J. (1978) Biochim. Biophys. Acta, 537, 9–21.

12 Combriato, G. & Klobeck, H. G. (1991) Eur. J. Immunol., 21, 1513–1522.

13 Cuisinier, A.-M., Fumoux, F., Fougereau, M. & Tonnelle, C. (1992) Mol. Immunol., 29, 1363–1373.

14 Dwulet, F. E., Strako, K. & Benson, M. D. (1985) Scand. J. Immunol., 22, 653–660.

15 Elahna, P., Livneh, A., Manheimer-Lory, A. J. & Diamond, B. (1991) J. Immunol., 147, 2771–2776.

16 Engelhard, M., Hess, M. & Hilschmann, N. (1974) Z. Physiol. Chem., 355, 85–88; Engelhard, M. & Hilschmann, N. (1975) Z. Physiol. Chem., 356, 1413–1444.

17 Eulitz, M. (1974) Eur. J. Biochem., 50, 49–69.

18 Eulitz, M., Breuer, M. & Linke, R. P. (1987) Biol. Che. Hoppe-Seyler, 368, 863–870.

19 Eulitz, M., Murphy, C., Weiss, D. T. & Solomon, A. (1991) J. Immunol., 146, 3091–3096.

20 Fett, J. W. & Deutsch, H. F. (1974) Biochemistry, 13, 4102–4114.

21 Fett, J. W. & Deutsch, H. F. (1976) Immunochem., 13, 149–155.; Jabusch, J. R. & Deutsch, H. F. (1982) Mol. Immunol., 19, 901–906.

22 Furey, W. Jr., Wang, B. C., Yoo, C. S. & Sax, M. (1983) J. Mol. Biol., 167, 661–692.

23 Fykse, E.-M., Sletten, K., Husby, G. & Cornwell, G. G., Iii (1988) Biochem. J., 256, 973–980.

24 Garver, F. A. & Hilschmann, N. (1971) Febs Letters, 16, 128–132; (1972) Eur. J. Biochem., 26, 10–32.

25 Gawinowicz, M. A., Merlini, G., Birken, S., Osserman, E. F. & Kabat, E. A. (1991) J. Immunol., 147, 915–920.

26 Ghiso, J., Solomon, A. & Frangione, B. (1986) J. Immunol., 136, 716–719.

27 Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. & Winter, G. (1993) Embo J., 12, 725–734.

28 Gullasken, N., Idso, H., Nilsen, R., Sletten, K., Husby, G. & Cornwell, G. G. (1990) In Amyloid And Amyloidosis, Eds. J. B. Natvig, O. Forre, G. Husby, A. Husebekk, B. Skogen, K. Sletten & P. Westermark, Kluwer Academic 29 Harindranath, N., Goldfarb, I. S., Ikematsu, H., Burastero, S. E., Wilder, R. L, Notkins, A. L. & Casali, P. (1991) Int. Immunol., 3, 865–875.

30 Holm, E., Sletten, K. & Husby, G. (1986) Biochem. J., 239, 545–551.

31 Hughes-Jones, N. C., Bye, J. M., Beale, D. & Coadwell, J. (1990) Biochem. J., 268, 135–140.

32 Kametani, F., Yoshimura, K., Tonoike, H., Hoshi, A., Shinoda, T. & Isobe, T. (1985) Biochem. Biophys. Res. Commun., 126, 848–852.

33 Kiefer, C. R., Mcguire, B. S., Jr., Osserman, E. F. & Garver, F. A. (1983) J. Immunol., 131, 1871–1875.

34 Kiefer, C. R., Patton, H. M., Jr., Mcquire, B. S., Jr & Garver, F. A. (1980) J. Immunol., 124, 301–306.

35 Kishimoto, T., Okajima, H., Okumoto, T. & Taniguchi, M. (1989) Nucl. Acids Res., 17, 4385.

36 Klafki, H.-W., Kratzin, H. D., Pick, A. I., Eckart, K. & Hilschmann, N. (1990) In Amyloid And Amyloidosis, Eds. J. B. Natvig, O. Forre, G. Husby, A. Husebekk, B. Skogen, K. Sletten & P. Westermark, Kluwer Academic 37 Kohler, H., Rudofsky, S. & Kluskens, L. (1975) J. Immunology, 114, 415–421.

38 Kojima, M., Odani, S. & Ikenaka, T. (1980) Mol. Immunol., 17, 1407–1414.

39 Komori, S., Yamasaki, N., Shigeta, M., Isojima, S. & Watanabe, T. (1988) Clin. Exp. Immunol., 71, 508–516.

40 Kratzin, H. D., Palm, W., Stangel, M., Schmidt, W. E., Friedrich, J. & Hilschmann, N. (1989) Biol. Chem. Hoppe-Seyler, 370, 263–272.

41 Kratzin, H. D., Pick, A. I., Stangel, M. & Hilschmann, N. (1990) In Amyloid And Amyloidosis, Eds. J. B. Natvig, O. Forre, G. Husby, A. Husebekk, B. Skogen, K. Sletten & P. Westermark, Kluwer Academic Publishers, Dordrecht/Boston/London, Pp. 181-

42 Langer, B., Steinmetz-Kayne, M. & Hilschmann, N. (1968) Z. Physiol. Chem., 349, 945–951.

43 Larrick. J. W., Danielsson, L., Brenner, C. A., Wallace, E. F., Abrahamson, M., Fry, K. E. & Borrebaeck, C. A. K. (1989) Bio/Tech., 7, 934–938.

44 Levy, S., Mendel, E., Kon, S., Avnur, Z. & Levy, R. (1988) J. Exp. Med., 168, 475–489.

45 Lewis, A. P., Lemon, S. M., Barber, K. A., Murphy, P., Parry, N. R., Peakman, T. C., Sims, M. J., Worden, J. & Crowe, J. S. (1993) J. Immunol., 151, 2829–2838.

46 Liu, V. Y. S., Low, T. L. K, Infante, A. & Putnam, F. W. (1976) Science, 193, 1017–1020; Infante, A. & Putnam, F. W. 11979) J. Biol. Chem., 254, 9006–9016.

47 Lopez De Castro, J. A., Chiu, Y. Y. H. & Poljak, R. J. (1978) Biochemistry, 17, 1718–1723.

48 Mantovani, L., Wilder, R. L. & Casali, P. (1993) J. Immunol., 151, 473–488.

49 Marks, J. D., Hoogenboom, H. R., Bonnert, T. P., Mccafferty, J., Griffiths, A. D. & Winter, G. (1991) J. Mol. Biol., 222, 581–597.

50 Mihaesco, E., Roy, J.-P., Congy, N., Peran-Rivat, L. & Mihaesco, C. (1985) Eur. J. Biochem., 150, 349–357.

51 Milstein, C., Clegg, J. B. & Jarvis, J. M. (1968) Biochem. J., 110, 631–652.

52 Moran, M. J., Andris, J. S., Matsumato, Y.-I., Capra, J. D. & Hersh, E. M. (1993) Mol. Immunol., 30, 1543–1551.

53 Nabeshima, Y. & Ikenaka, T. (1979) Mol. Immunol., 16, 439–444.

54 Olee, B. T., Lu, E. W., Huang, D.-F., Soto-Gil, R. W., Deftos, M., Kozin, F., Carson, D. A. & Chen, P. P. (1992) J. Exp. Med., 175, 831–842.

55 Pascual, V., Victor, K., Randen, I., Thompson, K., Steinitz, M., Forre, O., Fu, S.-M., Natvig, J. B. & Capra, J. D. (1992) Scand. J. Immunol., 36.349–362.

56 Paul, E., Iliev, A. A., Livneh, A. & Diamond, B. (1992) J. Immunol., 149, 3588–3595.

57 Pick, A. I., Kratzin, H. D., Barnikol-Watanabe, S. & Hilschmann, N. (1990) In Amyloid And Amyloidosis, Eds. J. B. Natvig, O. Forre, G. Husby, A. Husebekk, B. Skogen, K. Sletten a P. Westermark, Kluwer Academic 58 Ponstingl. H. & Hilschmann, N. (1969) Z. Physiol. Chem., 350, 1148–1152; (1971) Z. Physiol. Chem., 352, 859–877.

59 Ponstingl, H., Hess, M. & Hilschmann, N. (1968) Z. Physiol. Chem., 349, 867–871; (1971) Z. Physiol. Chem., 352.247–266.

60 Randen, I., Pascual, V., Victor, K., Thompson, K. M., Forre, O., Capra, J. D. & Natvig, J. B. (1993) Eur. J. Immunol., 23, 1220–1225.

61 Scholz, R. & Hilschmann, N. (1975) Z. Physiol. Chem., 356, 1333–1335.

62 Settmacher, U., Jahn, S., Siegel, P., Von Baehr, R. & Hansen, A. (1993) Mol. Immunol., 30, 953–954.

63 Shinoda, T., Titani, K. & Putnam, F. W. (1970) J. Biol. Chem., 245, 4475–4487.

64 Sletten, K., Husby, G. & Natvig, J. B. (1974) Scand J. Immunol., 3, 833–836.; Sletten, K., Natvig, J. B., Husby, G. & Juul, J. (1981) Biochem J., 195, 561–572.

65 Solomon, A, Frangione, B. & Franklin, E. C. (1982) J. Clin. Invest., 70, 453–460.; Frangione, B., Moloshok, T. & Solomon, A (1983) J. Immunol., 131, 2490–2493.

66 Takahashi, N., Takayasu, T., Isobe, T., Shinoda, T., Okuyama, T. & Shimizu, A (1979) J. Biochem., 86, 1523–1535.

67 Takahashi, N., Takayasu, T., Shinoda, T., Ito, S., Okuyama, T. & Shimizu, A. (1980) Biomed. Res., 1, 321–333.

68 Takahashi, Y., Takahashi, N., Tetaert, D. & Putnam, F. W. (1983) Proc. Nat. Acad. Sci. Usa, 80, 3686–3690.

69 Takayasu, T., Takahashi, N., Shinoda, T., Okuyama, T. & Tomioka, H. (1980) J. Biochem., 89, 421–436.

70 Titani, K., Wikler, M., Shinoda, T. & Putnam, F. W. (1970) J. Biol. Chem., 245, 2171–2176.

71 Toft, K. G., Sletten, K. & Husby, G. (1985) Biol. Chem. Hoppe-Seyler, 366, 617–625.

72 Tonoike, H., Kametani, F., Hoshi, A, Shinoda, T. & Isobe, T. (1985) Biochem. Biophys. Res. Commun., 126, 1228–1234.

73 Tonoike, H., Kametani, F., Hoshi, A., Shinoda, T. & Isobe, T. (1985) Febs Letters, 185, 139–141.

74 Tsujimoto, Y. & Croce, C. M. (1984) Nucl. Acids Res., 12, 8407–8414.

75 Tsunetsugu-Yokota, Y., Minekawa, T., Shigemoto, K., Shirasawa, T. & Takemori, T. (1992) Mol. Immunol., 29, 723–728.

76 Tveteraas, T., Sletten, K. & Westermark, P. (1985) Biochem. J., 232, 183–190.

77 Vasicek, T. J. & Leder, P. (1990) J. Exp. Med., 172, 609–620.

78 Victor, K. D., Randen, I., Thompson, K., Forre, O., Natvig, J. B., Fu, S. M. & Capra, J. D. (1991) J. Clin. Invest., 87, 1603–1613.

79 Weng, N.-P., Yu-Lee, L.-Y., Sanz, I., Patten, B. M. & Marcus, D. M. (1992) J. Immunol., 149, 2518–2529.

80 Wikler, M. & Putnam, F. W. (1970) J. Biol. Chem., 245, 4488–4507.

81 Winkler, T. H., Fehr, H. & Kalden, J. R. (1992) Eur. J. Immunol., 22, 1719–1728.

82 Yago, K., Zenita, K., Ohwaki, I., Harada, Y., Nozawa, S., Tsukazaki, K., Iwamori, M., Endo, N., Yasuda, N., Okuma, M. & Kannagi, R. (1993) Mol. Immunol., 30, 1481–1489.

83 Yamasaki, N., Komori, S. & Watanabe, T. (1987) Mol. Immunol., 24, 981–985.

84 Zhu, D., Kim, H. S. & Deutsch, H. F. (1983) Mol. Immunol., 20, 1107–1116.

85 Zhu, D., Zhang, H., Zhu, N. & Luo, X. (1986) Scientia Sinica, 29, 746–755.

References of Rearranged Human Heavy Chain Sequences Used for Alignment

1 Adderson, E. E., Azmi, F. H., Wilson, P. M., Shackelford, P. G. & Carroll, W. L. (1993) J. Immunol., 151, 800–809.

2 Adderson, E. E., Shackelford, P. G., Quinn, A. & Carroll, W. L. (1991) J. Immunol., 147, 1667–1674.

3 Akahori, Y., Kurosawa, Y., Kamachi, Y., Torii, S. & Matsuoka, H. (1990) J. Clin. Invest., 85, 1722–1727.

4 Andris, J. S., Brodeur, B. R. & Capra, J. D. (1993) Mol. Immunol., 30, 1601–1616.

5 Andris, J. S., Ehrlich, P. H., Ostberg, L. & Capra, J. D. (1992) J. Immunol., 149, 4053–4059.

6 Andris, J. S., Johnson, S., Zolla-Pazner, S. & Capra, J. D. (1991) Proc. Natl. Acad. Sci. Usa, 88, 7783–7787.

7 Anker, R., Conley, M. E. & Pollok, B. A. (1989) J. Exp. Med., 169, 2109–2119.

8 Atkinson, P. M., Lampman, G. W., Furie, B. C., Naparstek, Y., Schwartz, R. S., Stollar, B. D. & Furie, B. (1985) J. Clin. Invest., 75, 1138–1143.; Lampman, G. W., Furie, B., Schwartz, R. S., Stollar, B. D. & Furie, B. C. (1989)

9 Avila, M. A., Vazques, J., Danielsson, L., Fernandez De Cossio, M. E. & Borrebaeck, C. A. K. (1993) Gene, 127, 273–274.

10 Bakkus, M. H. C., Heirman, C., Van Riet, I., Van Camp, B. & Thielemans, K. (1992) Blood, 80, 2326–2335.

11 Barbas Iii, C. F., Crowe, Jr., J. E., Cababa, D., Jones, T. M., Zebedee, S. L., Murphy, B. R., Chanock, R. M. & Burton, D. R. (1992) Proc. Natl. Acad. Sci. Usa, 89, 10164–10168.

12 Barbas, C. F., Iii, Collet, T. A., Amberg, W., Roben, P., Binley, J. M., Hoekstra, D., Cababa, D., Jones, T. M., Williamson, R. A., Pilkington, G. R., Haigwood, N. L., Cabezas, E., Satterthwait, A. C., Sanz, I. & Burton, D. R. (1993) J. Mol. Biol., 230, 812–823.

13 Berman, J. E., Humphries, C. G., Barth, J., Alt, F. W. & Tucker, P. W. (1991) J. Exp. Med., 173, 1529–1535.

14 Berman, J. E., Mellis, S. J., Pollock, R., Smith, C. L., Suh, H., Heinke, B., Kowal, C., Surti, U., Chess, L, Cantor, C. R & Alt, F. W. (1988) Embo J., 7, 727–738.

15 Bhat, N. M., Bieber, M. M., Chapman, C. J., Stevenson, F. K. & Teng, N. N. H. (1993) J. Immunol., 151, 5011–5021.

16 Bird, J., Galili, N., Link, M., Stites, D. & Sklar, J. (1988) J. Exp. Med., 168, 229–245.

17 Cai, J., Humphries, C., Richardson, A. & Tucker, P. W. (1992) J. Exp. Med., 176, 1073–1081.

18 Cairns, E., Kwong, P. C., Misener, V., Ip, P., Bell, D. A. & Siminovitch, K. A. (1989) J. Immunol., 143, 685–691.

19 Capra, J. D. & Hopper, J. E. (1976) Immunochemistry, 13, 995–999; Hopper, J. E., Noyes, C., Heinrikson, R. & Kessel, J. W. (1976) J. Immunol., 116, 743–746.

20 Capra, J. D. & Kehoe, J. M. (1974) Proc. Nat. Acad. Sci. Usa, 71, 845–848.

21 Carroll, W. L., Yu, M., Link, M. P. & Korsmeyer, S. J. (1989) J. Immunol., 143, 692–698.

22 Chen, P. P., Liu, M.-F., Glass, C. A., Sinha, S., Kipps, T. J. & Carson, D. A. (1989) Arthritis & Rheumatism, 32, 72–76; Kipps, T. J., Tomhave, E., Pratt, L. F., Duffy, S., Chen, P. P. & Carson, D. A. (1989) Proc. Natl. Acad. Sci. Usa, 86, 5913–5917.

23 Chiu, Y. Y. H., Lopez De Castro, J. A. Poljak, R. J. (1979) Biochemistry, 18, 553–560.

24 Cleary, M. L., Meeker, T. C., Levy, S., Lee, E., Trela, M., Sklar, J. & Levy, R. (1986) Cell, 44, 97–106.

25 Cuisinier, A.-M., Fumoux, F., Fougereau, M. & Tonnelle, C. (1992) Mol. Immunol., 29, 1363–1373.

26 Cuisinier, A.-M., Gauthier, L., Boubli, L., Fougereau, M. & Tonnelle, C. (1993) Eur. J. Immunol., 23, 110–118.

27 Cunningham, B. A., Gottlieb, P. D., Pflumm, M. N. & Edelman, G. M. (1971) Progress in Immunology (B. Amos, Ed.), Academic Press, N. Y., Pp. 3–24.

28 Cunningham, B. A., Rutishauser, U., Gall, W. E., Gottlieb, P. D., Waxdal, M. J. & Edelman, G. M. (1970) Biochemistry, 9, 3161–3170.

29 Deane, M. & Norton, J. D. (1990) Eur. J. Immunol., 20, 2209–2217.

30 Deane, M. & Norton, J. D. (1991) Leukemia, 5, 646–650.

31 Dersimonian, H., Schwartz, R. S., Barrett, K. J. & Stollar, B. D. (1987) J. Immunol., 139, 2496–2501.

32 Dersimonian, H., Schwartz, R. S., Barrett, K. J. & Stollar, B. D. (1987) J. Immunol., 139, 2496–2501; Chen, P. P., Liu, M.-F., Sinha, S. & Carson, D. A. (1988) Arth. Rheum., 31, 1429–1431.

33 Desai, R., Spatz, L., Matsuda, T., Ilyas, A. A., Berman, J. E., Alt, F. W., Kabat, E. A. & Latov, N. (1990) J. Neuroimmunol., 26, 35–41.

34 Ezaki, I., Kanda, H., Sakai, K., Fukui, N., Shingu, M., Nobunaga, M. & Watanabe, T. (1991) Arthritis And Rheumatism, 34, 343–350.

35 Felgenhauer, M., Kohl, J. & Ruker, F. (1990) Nucl. Acids Res., 18, 4927.

36 Florent, G., Lehman, D. & Putnam, F. W. (1974) Biochemistry, 13, 2482–2498.

37 Friedlander, R. M., Nussenzweig, M. C. & Leder, P. (1990) Nucl. Acids Res., 18, 4278.

38 Gawinowicz, M. A., Merlini, G., Birken, S., Osserman, E. F. & Kabat, E. A. (1991) J. Immunol., 147,915–920.

39 Gillies, S. D., Dorai, H., Wesolowski, J., Majeau, G., Young, D., Boyd, J., Gardner, J. & James, K. (1989) Bio/Tech., 7, 799–804.

40 Goni F. & Frangione, B. (1983) Proc. Nat. Acad. Sci. Usa, 80, 4837–4841.

41 Gorman, S. D., Clark, M. R., Routledge, E. G., Cobbold, S. P. & Waldmann, H. (1991) Proc. Natl. Acad. Sci. Usa, 88, 4181–4185.

42 Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. & Winter, G. (1993) Embo J., 12, 725–734.

43 Grillot-Courvalin, C., Brouet, J.-C., Piller, F., Rassenti, L. Z., Labaume, S., Silverman, G. J., Silberstein, L. & Kipps, T. J. (1992) Eur. J. Immunol., 22, 1781–1788.

44 Guillaume, T., Rubinstein, D. B., Young, F., Tucker, L., Logtenberg, T., Schwartz, R. S. & Barrett, K. L. (1990) J. Immunol., 145, 1934–1945; Young, F., Tucker, L., Rubinstein, D., Guillaume, T., Andre-Schwartz, J., Barrett, K. J., Schwartz, R. S. & Logtenberg, T. (1990)

45 Harindranath, N., Goldfarb, I. S., Ikematsu, H., Burastero, S. E., Wilder, R. L., Notkins, A. L. & Casali, P. (1991) Int. Immunol., 3, 865–875.

46 Hillson, J. L., Oppliger, I. R., Sasso, E. H., Milner, E. C. B. & Wener, M. H. (1992) J. Immunol., 149, 3741–3752.

47 Hirabayashi, Y., Munakata, Y., Sasaki, T. & Sano, H. (1992) Nucl. Acids Res., 20, 2601.

48 Hoch, S. & Schwaber, J. (1987) J. Immunol., 139, 1689–1693.

49 Huang, C., Stewart, A. K., Schwartz, R. S. & Stollar, B. D. (1992) J. Clin. Invest., 89, 1331–1343.

50 Hughes-Jones, N. C, Bye, J. M., Beale, D. & Coadwell, J. (1990) Biochem J., 268, 135–140.

51 Ikematsu, H., Harindranath, N., Ueki, Y., Notkins, A. L. & Casali, P. (1993) J. Immunol., 150, 1325–1337.

52 Ikematsu, H., Kasaian, M. T., Schettino, E. W. & Casali, P. (1993) J. Immunol., 151, 3604–3616.

53 Kelly, P. J., Pascual, V., Capra, J. D. & Lipsky, P. E. (1992) J. Immunol., 148, 1294–1301.

54 Kipps, T. J. & Duffy, S. F. (1991) J. Clin. Invest., 87, 2087–2096.

55 Kipps, T. J., Tomhave, E., Pratt, L. F., Duffy, S., Chen, P. P. & Carson, D. A. (1989) Proc. Natl. Acad. Sci. Usa, 86, 5913–5917.

56 Kishimoto, T., Okajima, H., Okumoto, T. & Taniguchi, M. (1989) Nucl. Acids Res., 17, 4385.

57 Knight, G. B., Agnello, V., Bonagura, V., Barnes, J. L., Panka, D. J. & Zhang, Q. X. (1993) J. Exp. Med., 178, 1903–1911.

58 Kohler, H., Shimizu, A, Paul, C., Moore, V. & Putnam, F. W. (1970) Nature, 227, 1318–1320; Florent, G., Lehman, D. & Putnam, F. W. (1974) Biochemistry, 13, 2482–2498

59 Komori, S., Yamasaki, N., Shigeta, M., Isojima, S. & Watanabe, T. (1988) Clin. Exp. Immunol., 71, 508–516.

60 Kon, S., Levy, S. & Levy, R. (1987) Proc. Natl. Acad. Sci. Usa, 84, 5053–5057.

61 Kratzin, H., Altevogt, P., Ruban, E., Kortt, A., Staroscik, K. & Hilschmann, N. (1975) Z. Physiol. Chem., 356, 1337–1342; Kratzin, H., Altevogt, P., Kortt, A, Ruban, E. & Hilschmann, N. (1978) Z. Physiol. Chem., 359, 1717–1745.

62 Kudo, A., Ishihara, T., Nishimura, Y. & Watanabe, T. (1985) Gene, 33, 181–189.

63 Kunicki, T. J., Annis, D. S., Gorski, J. & Nugent, D. J. (1991) J. Autoimmunity, 4, 433–446.

64 Larrick, J. W., Wallace, E. F., Coloma, M. J., Bruderer, U., Lang, A. B. & Fry, K. E. (1992) Immunological Reviews, 130, 69–85.

65 Lehman, D. W. & Putnam, F. W. (1980) Proc. Nat. Acad. Sci. Usa, 77, 3239–3243.

66 Lewis, A. P., Lemon, S. M., Barber. K. A., Murphy, P., Parry, N. R., Peakman, T. C., Sims, M. J., Worden, J. & Crowe, J. S. (1993) J. Immunol., 151, 2829–2838.

67 Liu, V. Y. S., Low, T. L. K., Infante, A. & Putnam, F. W. (1976) Science, 193, 1017–1020.

68 Logtenberg, T., Young, F. M., Van Es, J., Gmelig-Meyling, F. H. J., Berman, J. E. & Alt, F. W. (1989) J. Autoimmunity, 2, 203–213.

69 Logtenberg, T., Young, F. M., Van Es, J. H., Gmelig-Meyling, F. H. J. & Alt, F. W. (1989) J. Exp. Med., 170, 1347–1355.

70 Manheimer-Lory, A., Katz, J. B., Pillinger, M., Ghossein, C., Smith, A. & Diamond, B. (1991) J. Exp. Med., 174, 1639–1652.

71 Mantovani, L., Wilder, R. L. & Casali, P. (1993) J. Immunol., 151, 473–488.

72 Mariette, X., Tsapis, A. & Brouet, J.-C. (1993) Eur. J. Immunol., 23, 846–851.

73 Marks, J. D., Hoogenboom, H. R., Bonnert, T. P., Mccafferty, J., Griffiths, A. D. & Winter, G. (1991) J. Mol. Biol., 222, 581–597.

74 Meeker, T. C., Grimaldi, J., O'rourke, R., Loeb, J. Juliusson, G. & Einhorn, S. (1988) J. Immol., 141, 3994–3998.

75 Milili, M., Fougereau, M., Guglielmi, P. & Schiff, C. (1991) Mol. Immunol., 28, 753–761.

76 Moran, M. J., Andris, J. S., Matsumato, Y.-I., Capra, J. D. & Hersh, E. M. (1993) Mol. Immunol., 30, 1543–1551.

77 Mortari, F., Wang, J.-Y. & Schroeder, Jr., H. W. (1993) J. Immunol., 150, 1348–1357.

78 Newkirk, M. M., Gram, H., Heinrich, G. F., Ostberg, L, Capra, J. D. & Wasserman, R. L. (1988) J. Clin. Invest., 81, 1511–1518.

79 Newkirk, M. M., Mageed, R. A., Jefferis, R., Chen, P. P. & Capra, J. D. (1987) J. Exp. Med., 166, 550–564.

80 Nickerson, K. G., Berman, J., Glickman, E., Chess, L. & Alt, F. W. (1989) J. Exp. Med., 169, 1391–1403.

81 Olee, B. T., Lu, E. W., Huang, D.-F., Soto-Gil, R. W., Deftos, M., Kozin, F., Carson, D. A. & Chen, P. P. (1992) J. Exp. Med., 175, 831–842.

82 Pascual, V., Randen, I., Thompson, K., Sioud, M. Forre, O., Natvig, J. & Capra, J. D. (1990) J. Clin. Invest., 86, 1320–1328.

83 Pascual, V., Randen, I., Thompson, K., Sioud, M. Forre, O., Natvig, J. & Capra, J. D. (1990) J. Clin. Invest., 86, 1320–1328; Randen, I., Brown, D., Thompson, K. M., Hughes-Jones, N., Pascual, V., Victor, K., Capra, J. D., Forre, O. & Natvig, J. B. (1992)

84 Pascual, V., Victor, K., Lelsz, D., Spellerberg, M. B., Hamblin, T. J., Thompson, K. M., Randen, I., Natvig, J., Capra, J. D. & Stevenson, F. K. (1991) J. Immunol., 146, 4385–4391.

85 Pascual, V., Victor, K., Randen, I., Thompson, K., Steinitz, M., Forre, O., Fu, S.-M., Natvig, J. B. & Capra, J. D. (1992) Scand J. Immunol., 36, 349–362.

86 Pascual, V., Victor. K., Spellerberg, M., Hamblin, T. J., Stevenson, F. K. & Capra. J. D. (1992) J. Immunol., 149, 2337–2344.

87 Ponstingl, H., Schwarz, J., Reichel, W. & Hilschmann, N. (1970) Z. Physiol. Chem., 351, 1591–1594.; Ponstingl, H. & Hilschmann, N. (1976) Z. Physiol. Chem., 357, 1571–1604.

88 Portolano, S., Mclachlan, S. M. & Rapoport, B. (1993) J. Immunol., 151, 2839–2851.

89 Portolano, S., Seto, P., Chazenbalk, G. D., Nagayama, Y., Mclachlan, S. M. & Rapoport, B. (1991) Biochem. Biophys. Res. Commun., 179, 372–377.

90 Pratt, L. F., Szubin, R., Carson, D. A. & Kipps, T. J. (1991) J. Immunol., 147, 2041–2046.

91 Press, E. M. & Hogg, N. M. (1970) Biochem J., 117, 641–660.

92 Putnam, F. W., Shimizu, A, Paul., C., Shinoda, T. & Kohler, H. (1971) Ann. N.Y. Acad. Sci., 190, 83–103.

93 Putnam, F. W., Takahashi, N., Tetaert, D., Debuire, B. & Lin, L. C. (1981) Proc. Nat. Acad. Sci. Usa; 78, 6168–6172.; Takahashi, N., Tetaert, D., Debuire, B., Lin, L. & Putnam, F. W. (1982) Proc. Nat. Acad. Sci. Usa, 79, 2850–2854.

94 Raaphorst, F. M., Timmers, E., Kenter, M. J. H., Van Tol, M. J. D., Vossen, J. M. & Schuurman, R. K. B. (1992) Eur. J. Immunol., 22, 247–251.

95 Rabbitts, T. H., Bentley, D. L., Dunnick, W., Forster, A., Matthyssens, G. & Milstein, C. (1980) Cold Spring Harb. Symp. Quanti. Biol., 45, 867–878; Matthyssens, G. & Rabbitts, T. H. (1980) Proc. Nat. Acad. Sci. Usa, 77, 6561–6565.

96 Randen, I., Pascual, V., Victor, K., Thompson, K. M., Forre, O., Capra, J. D. & Natvig, J. B. (1993) Eur J. Immunol., 23, 1220–1225.

97 Rassenti, L. Z. & Kipps, T. J. (1993) J. Exp. Med., 177, 1039–1046.

98 Reidl, L. S., Friedman, D. F., Goldman, J., Hardy, R. R., Jefferies, L. C. & Silberstein, L. E. (1991) J. Immunol., 147, 3623–3631.

99 Roudier, J., Silverman, G. J., Chen, P. P., Carson, D. A. & Kipps, T. J. (1990) J. Immunol., 144, 1526–1530.

100 Sanz, I., Casali, P., Thomas, J. W., Notkins, A. L. & Capra, J. D. (1989) J. Immunol., 142, 4054–4061.

101 Sanz, I., Dang, H., Takei, M., Talal, N. & Capra, J. D. (1989) J. Immunol., 142, 883–887.

102 Schmidt, W. E., Jung, H.-D., Palm, W. & Hilschmann, N. (1983) Z. Physiol. Chem., 364, 713–747.

103 Schroeder, H. W., Jr. & Wang, J. Y. (1990) Proc. Natl. Acad. Sci. Usa, 87, 6146–6150.

104 Schroeder, H. W., Jr., Hillson, J. L. & Perlmutter, R. M. (1987) Science, 238, 791–793.

105 Schroeder, H. W., Jr., Hillson, J. L. & Perlmutter, R. M. (1987) Science, 238, 791–793; Chen, P. P., Liu, M.-F., Glass, C. A, Sinha, S., Kipps, T. J. & Carson, D. A. (1989) Arthritis & Rheumatism, 32, 72–76.

106 Schroeder, H. W., Jr., Hillson, J. L. & Perlmutter, R. M. (1987) Science, 238, 791–793; Chen, P. P., Liu, M.-F., Sinha, S. & Carson, D. A. (1988) Arth. Rheum., 31, 1429–1431.

107 Schutte, M. E., Ebeling, S. B., Akkermans, K. E., Gmelig-Meyling, F. H. & Logtenberg, T. (1991) Eur. J. Immunol., 21, 1115–1121.

108 Schutte, M. E., Ebeling, S. B., Akkermans, K. E., Gmelig-Meyling, F. H. J. & Logtenberg, T. (1991) Eur. J. Immunol., 21, 1115–1121.

109 Settmacher, U., Jahn, S., Siegel, P., Von Baehr, R. & Hansen, A. (1993) Mol. Immunol., 30, 953–954.

110 Shen, A., Humphries, C, Tucker, P. & Blattner, F. (1987) Proc. Natl. Acad. Sci. Usa, 84, 8563–8567.

111 Shimizu, A., Nussenzweig, M. C., Mizuta, T.-R., Leder, P. & Honjo, T. (1989) Proc. Natl. Acad. Sci. Usa, 86, 8020–8023.

112 Shin, E. K., Matsuda, F., Fujikura, J., Akamizu, T., Sugawa, H., Mori, T. & Honjo, T. (1993) Eur. J. Immunol., 23, 2365–2367.

113 Silberstein, L. E., Litwin, S. & Carmack, C. E. (1989) J. Exp. Med., 169, 1631–1643.

114 Singal, D. P., Frame, B., Joseph, S., Blajchman, M. A. & Leber, B. F. (1993) Immunogenet., 38, 242.

115 Spatz, L. A., Wong, K. K., Williams, M., Desai, R., Golier, J., Berman, J. E., Alt, F. W. & Latov, N. (1990) J. Immunol., 144, 2821–2828.

116 Steiner, L. A., Garcia-Pardo, A. & Margolies, M. N. (1979) Biochemistry, 18, 4068–4080.

117 Stewart, A. K., Huang, C., Stollar, B. D. & Schwartz, R. S. (1993) J. Exp. Med., 177, 409–418.

118 Thomas, J. W. (1993) J. Immunol., 150, 1375–1382.

119 Torano, A. & Putnam, F. W. (1978) Proc. Nat. Acad. Sci. Usa, 75, 966–969.

120 Van Der Heijden, R. W. J., Bunschoten, H., Pascual, V., Uytdehaag, F. G. C. M., Osterhaus, A. D. M. E. & Capra, J. D. (1990) J. Immunol., 144, 2835–2839.

121 Van Der Stoep, N., Van Der Linden, J. & Logtenberg, T. (1993) J. Exp. Med., 177, 99–107.

122 Van Es, J. H., Gmelig-Meyling, F. H. J. & Logtenberg, T. (1992) Eur. J. Immunol., 22, 2761–2764.

123 Varade, W. S., Marin, E., Kittelberger, A. M. & Insel, R. A. (1993) J. Immunol., 150, 4985–4995.

124 Victor, K. D., Pascual, V., Lefvert, A. K. & Capra, J. D. (1992) Mol. Immunol., 29, 1501–1506.

125 Victor, K. D., Pascual, V., Williams, C. L., Lennon, V. A. & Capra, J. D. (1992) Eur. J. Immunol., 22, 2231–2236.

126 Watanabe, S., Barnikol, H. U., Horn, J., Bertram, J. & Hilschmann, N. (1973) Z. Physiol. Chem., 354, 1505–1509.

127 Weng, N.-P., Yu-Lee, L.-Y., Sanz, I., Patten, B. M. & Marcus, D. M. (1992) J. Immunol., 149, 2518–2529.

128 White, M. B., Word, C. J., Humphries, C. G., Blattner, F. R. & Tucker, P. W. (1990) Mol. Cell. Biol., 10, 3690–3699.

129 Winkler, T. H., Fehr, H. & Kalden, J. R. (1992) Eur. J. Immunol., 22, 1719–1728.

130 Yago, K., Zenita, K., Ohwaki, I., Harada, Y., Nozawa, S., Tsukazaki, K., Iwamori, M., Endo, N., Yasuda, N., Okuma, M. & Kannagi, R. (1993) Mol. Immunol., 30, 1481–1489.

131 Zelenetz, A. D., Chen, T. T. & Levy, R. (1992) J. Exp. Med., 176, 1137–1148.

B. References of Germline Sequences

References of Human Germline Kappa Sequences
1. Cox, J. P. L, Tomlinson, I. M. & Winter, G. (1994) Eur. J. Immunol., 24, 827–836.
2. Huber, C., Et. Al. (1993) Eur. J. Immunol., 23, 2868.
3. Klobeck, H. G., Bornkammm, G. W., Combriato, G., Mocikat, R., Pohlenz, H. D. & Zachau, H. G. (1985) Nucl. Acids Res., 13, 6515–6529.
4. Lautner-Rieske, A., Huber, C., Meindl, A., Pargent, W., Schäble, K. F., Thiebe, R., Zocher, I. & Zachau, H. G. (1992) Eur. J. Immunol. 22, 1023.
5. Lorenz, W., Schäble, K. F., Thiebe, R., Stavnezer, J. & Zachau, H. G. (1988) Mol. Immunol., 25, 479.
6. Pargent, W., Meindl, A, Thiebe, R., Mitzel, S. & Zachau, H. G. (1991) Eur. J. Immunol., 21, 1821–1827.
7. Pech, M. & Zachau, H. G. (1984) Nuc. Acids Res., 12, 9229–9236.
8. Pech, M., Jaenichen, H.-R., Pohlenz, H.-D., Neumaier, P. S., Klobeck, H.-G. & Zachau, H. G. (1984) J. Mol. Biol., 176, 189–204.
9. Scott, M. G., Crimmins, D. L., Mccourt, D. W., Chung, G., Schäble, K. F., Thiebe, R., Quenzel, E.-M., Zachau, H. G. & Nahm, M. H. (1991) J. Immunol., 147, 4007–4013.
10. Stavnezer, J., Kekish, O., Batter, D., Grenier, J., Balazs, I., Henderson, E. & Zegers, B. J. M. (1985) Nucl. Acids Res., 13, 3495–3514.
11. Straubinger, B. Huber, E., Lorenz, W., Osterholzer, E., Pargent, W., Pech, M., Pohlenz, H.-D., Zimmer, F.-J. & Zachau, H. G. (1988) J. Mol. Biol., 199, 23–34.
12. Straubinger, B., Thiebe, R., Huber, C., Osterholzer, E. & Zachau, H. G. (1988) Biol. Chem. Hoppe-Seyer, 369, 601–607.

References of Human Germline Lambda Sequences
1. Williams, S. C. & Winter, G. (1993) Eur. J. Immunol., 23, 1456–1461.
2. Siminovitch, K. A., Misener, V., Kwong, P. C., Song, Q.-L. & Chen, P. P. (1989) J. Clin. Invest., 84, 1675–1678.
3. Brockly, F., Alexandre, D., Chuchana, P., Huck, S., Lefranc, G. & Lefranc, M.-P. (1989) Nuc. Acids. Res., 17, 3976.
4. Daley, M. D., Peng, H.-Q., Misener, V., Liu, X.-Y., Chen, P. P. & Siminovitch, K. A. (1992) Mol. Immunol., 29, 1515–1518.
5. Deftos, M., Soto-Gil, R., Quan, M., Olee, T. & Chen, P. P. (1994) Scand. J. Immunol., 39, 95.
6. Stiernholm, N. B. J., Kuzniar, B. & Berinstein, N. L. (1994) J. Immunol., 152, 4969–4975.
7. Combriato, G. & Klobeck, H. G. (1991) Eur. J. Immunol., 21, 1513–1522.
8. Anderson, M. L. M., Szajnert, M. F., Kaplan, J. C., Mccoll, L. & Young, B. D. (1984) Nuc. Acids Res., 12, 6647–6661.

References of Human Germline Heavy Chain Sequences
1. Adderson, E. E., Azmi, F. H., Wilson, P. M., Shackelford, P. G. & Carroll, W. L. (1993) J. Immunol., 151, 800–809.
2. Andris, J. S., Brodeur, B. R. & Capra, J. D. (1993) Mol. Immunol., 30, 1601–1616.
3. Berman, J. E., Mellis, S. J., Pollock, R., Smith, C. L., Suh, H., Heinke, B., Kowal, C., Surti, U., Chess, L, Cantor. C. R. & Alt, F. W. (1988) Embo J., 7, 727–738.
4. Buluwela, L. & Rabbitts, T. H. (1988) Eur. J. Immunol., 18, 1843–1845.; Buluwela, L., Albertson, D. G., Sherrington, P., Rabbitts, P. H., Spurr, N. & Rabbitts, T. H. (1988) Embo J., 7, 2003–2010.
5. Chen, P. P., Liu, M.-F., Sinha, S. & Carson, D. A. (1988) Arth. Rheum., 31, 1429–1431.
6. Chen, P. P., Liu, M.-F., Glass, C. A., Sinha, S., Kipps, T. J. & Carson, D. A. (1989) Arthritis & Rheumatism, 32, 72–76.
7. Cook, G. P. et al. (1994) Nature Genetics 7, 162–168.
8. Haino, M. et al., (1994). J. Biol. Chem. 269, 2619–2626
9. Humphries, C. G., Shen, A, Kuziel, W. A., Capra, J. D., Blattner, F. R. & Tucker, P. W. (1988) Nature, 331, 446–449.
10. Kodaira, M., Kinashi, T., Umemura, I., Matsuda, F., Noma, T., Ono, Y. & Honjo, T. (1986) J. Mol. Biol., 190, 529–541.
11. Lee, K. H., Matsuda, F., Kinashi, T., Kodaira, M. & Honjo, T. (1987) J. Mol. Biol., 195,761–768.
12. Matsuda, F., Lee, K. H., Nakai, S., Sato, T., Kodaira, M., Zong, S. Q., Ohno, H., Fukuhara, S. & Honjo, T. (1988) Embo J., 7, 1047–1051.
13. Matsuda, F., Shin, E. K., Hirabayashi, Y., Nagaoka, H., Yoshida, M. C., Zong, S. Q. & Honjo, T. (1990) Embo J., 9, 2501–2506.
14. Matsuda, F., Shin, E. K., Nagaoka, H., Matsumura, R., Haino, M., Fukita, Y., Taka-Ishi, S., Imai, T., Riley, J. H., Anand, R. Et, Al. (1993) Nature Genet. 3, 88–94
15. Nagaoka, H., Ozawa, K., Matsuda, F., Hayashida, H., Matsumura, R., Haino, M., Shin, E. K., Fukita, Y., Imai, T., Anand, R., Yokoyama, K., Eki, T., Soeda, E. & Honjo, T. (1993). (Temporal)
16. Rechavi, G., Bienz, B., Ram, D., Ben-Neriah, Y., Cohen, J. B., Zakut, R. & Givol, D. (1982) Proc. Nat. Acad. Sci. Usa, 79, 4405–4409.
17. Sanz, I., Kelly, P., Williams, C., Scholl, S., Tucker, P. & Capra, J. D. (1989) Embo J., 8, 3741–3748.
18. Shin, E. K., Matsuda, F., Fujikura, J., Akamizu, T., Sugawa, H., Mori, T. & Honjo, T. (1993) Eur. J. Immunol., 23, 2365–2367.
19. Tomlinson, Im., Walter, G., Marks, Jd., Llewelyn, Mb. & Winter. G. (1992) J. Mol. Biol. 227, 776–798.
20. Van Der Maarel. S., Van Dijk, K. W., Alexander, C. M., Sasso, E. H., Bull, A. & Milner, E. C. B. (1993) J. Immunol., 150, 2858–2868.
21. Van Dijk, K. W., Mortari, F., Kirkham, P. M., Schroeder, Jr., H. W. & Milner, E. C. B. (1993) Eur. J. Immunol., 23, 832–839.
22. Van Es, J. H., Aanstoot, H., Gmelig-Meyling, F. H. J., Derksen, R. H. W. M. & Logtenberg, T. (1992) J. Immunol., 149, 2234–2240.
23. Weng, N.-P., Snyder, J. G., Yu-Lee, L-Y. & Marcus, D. M. (1992) Eur J. Immunol., 22, 1075–1082.
24. Winkler, T. H., Fehr, H. & Kalden, J. R. (1992) Eur J. Immunol., 22, 1719–1728.
25. Olee, T., Yang, P. M., Siminovitch, K. A., Olsen, N. J., Hillson, J. L., Wu, J., Kozin, F., Carson, D. A. & Chen, P. P. (1991) J. Clin. Invest 88, 193–203.
26. Chen, P. P. & Yang, P. M. (1990) Scand. J. Immunol. 31, 593–599.
27. Tomlinson, M., Walter, G., Cook&Winter, G. (Unpublished).

SEQUENCE LISTING

<160> NUMBER OF SEQ ID NOS: 372

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 1

Ala Gly Gly Gly Ser Gly Gly Gly Ser Gly Gly Gly Ser Gly
 1               5                  10                  15

Gly Gly Gly Ser
            20

<210> SEQ ID NO 2
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcagcgggtg gcggttctgg cggcggtggg agcggtggcg gtggttctgg cggtggtggt      60
tccgatatcg gtccacgtac gg                                               82

<210> SEQ ID NO 3
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aattccgtac gtggaccgat atcggaacca ccaccgccag aaccaccgcc accgctccca      60
ccgccgccag aaccgccacc cgc                                              83

<210> SEQ ID NO 4
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (28)..(30)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (31)..(33)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (34)..(36)
<223> OTHER INFORMATION: region represents a variable trinucleotide
      combination capable of coding any natural occurring amino acid
      other than Cys
<220> FEATURE:
<221> NAME/KEY: modified_base

```
<222> LOCATION: (37)..(39)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (40)..(42)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (43)..(45)
<223> OTHER INFORMATION: region represents a variable trinucleotide
      combination capable of coding any natural occurring amino acid
      other than Cys

<400> SEQUENCE: 4
gatacggccg tgtattattg cgcgcgtnnn nnnnnnnnn nnnnngatta ttggggccaa    60
ggcaccctg                                                           69

<210> SEQ ID NO 5
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (28)..(30)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (31)..(33)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (34)..(36)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (37)..(39)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (40)..(42)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (43)..(45)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (46)..(48)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (49)..(51)
<223> OTHER INFORMATION: region represents a variable trinucleotide
      combination capable of coding any natural occurring amino acid
      other than Cys
```

```
<220> FEATURE:
<221> NAME/KEY: modified_base
<222> LOCATION: (52)..(54)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (55)..(57)
<223> OTHER INFORMATION: region represents a variable trinucleotide
      combination capable of coding any natural occurring amino acid
      other than Cys

<400> SEQUENCE: 5
gatacggccg tgtattattg cgcgcgtnnn nnnnnnnnn nnnnnnnnn nnnnnnnwtk      60 gatkwttggg gccaaggcac cctg                                           84

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatacggccg tgtattattg c                                              21

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagggtgcct tggcccc                                                   17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcagaaggcg aacgtcc                                                   17

<210> SEQ ID NO 9
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (42)..(44)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (45)..(47)
<223> OTHER INFORMATION: region represents a variable trinucleotide
      combination capable of coding any natural occurring amino acid
      other than Cys
<220> FEATURE:
```

```
<221> NAME/KEY: modified_base
<222> LOCATION: (48)..(50)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (51)..(53)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (57)..(59)
<223> OTHER INFORMATION: region represents a variable trinucleotide
      combination capable of coding any natural occurring amino acid
      other than Cys

<400> SEQUENCE: 9
tggaagctga agacgtgggc gtgtattatt gccagcagbv tnnnnnnnnn nnnccgnnnt    60
ttggccaggg tacgaaagtt                                                80

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aactttcgta ccctggcc                                                  18

<210> SEQ ID NO 11
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (21)..(23)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (27)..(29)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (30)..(32)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (33)..(35)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (42)..(44)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (48)..(50)
<223> OTHER INFORMATION: region represents a variable trinucleotide
```

-continued combination capable of coding any natural occurring amino acid
other than Cys

<400> SEQUENCE: 11
agggtctcga gtgggtgagc nnnattnnnn nnnnnrvtrv tnnnaccnnn tatgcggata    60
gcgtgaaagg ccgttttacc atttcacgtg ataattcgaa aaacacca    108

<210> SEQ ID NO 12
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (21)..(23)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (27)..(29)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (30)..(31)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (39)..(41)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (45)..(47)
<223> OTHER INFORMATION: region represents a variable trinucleotide
      combination capable of coding any natural occurring amino acid
      other than Cys

<400> SEQUENCE: 12
agggtctcga gtgggtgagc nnnattnnnn nnrvtrvtnn naccnnntat gcggatagcg    60
tgaaaggccg ttttaccatt tcacgtgata attcgaaaaa cacca    105

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggtgttttt cgaattatca    20

<210> SEQ ID NO 14
<211> LENGTH: 108
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr

```
                 20                  25                  30
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Thr Pro Leu
                 85                  90                  95

Thr Phe Gly Gly Gly Thr Lys Val Glu Ile Lys Arg
             100                 105

<210> SEQ ID NO 15
<211> LENGTH: 113
<212> TYPE: PRT
<213> ORGANISM: Homo sapiens

<400> SEQUENCE: 15

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Tyr Thr Phe Gly Gln Gly Thr Lys Leu Glu Ile Lys
             100                 105                 110

Arg

<210> SEQ ID NO 16
<211> LENGTH: 109
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Asn Ser Pro
                 85                  90                  95

Tyr Thr Phe Gly Gln Gly Thr Lys Val Glu Ile Lys Arg
             100                 105

<210> SEQ ID NO 17
```

```
<211> LENGTH: 114
<212> TYPE: PRT
<213> ORGANISM: Homo sapiens

<400> SEQUENCE: 17

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys Arg

<210> SEQ ID NO 18
<211> LENGTH: 112
<212> TYPE: PRT
<213> ORGANISM: Homo sapiens

<400> SEQUENCE: 18

Gln Ser Val Leu Thr Gln Pro Pro Ser Val Ser Gly Ala Pro Gly Gln
 1               5                  10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Thr Trp Asp Asp Ser Leu
                85                  90                  95

Ser Gly Val Val Phe Gly Gly Gly Thr Lys Leu Thr Val Leu Gly Gln
            100                 105                 110

<210> SEQ ID NO 19
<211> LENGTH: 112
<212> TYPE: PRT
<213> ORGANISM: Homo sapiens

<400> SEQUENCE: 19

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
```

```
                65                  70                  75                  80
Gln Ala Glu Asp Glu Ala Asp Tyr Tyr Cys Ser Ser Tyr Ala Gly Ser
                    85                  90                  95

Ser Thr Val Val Phe Gly Gly Gly Thr Lys Leu Thr Val Leu Gly Gln
                100                 105                 110

<210> SEQ ID NO 20
<211> LENGTH: 108
<212> TYPE: PRT
<213> ORGANISM: Homo sapiens

<400> SEQUENCE: 20

Tyr Glu Leu Thr Gln Pro Pro Ser Val Ser Val Ala Pro Gly Gln Thr
  1               5                  10                  15

Ala Arg Ile Thr Cys Ser Gly Asp Ser Leu Gly Ser Lys Tyr Ala Ser
                20                  25                  30

Trp Tyr Gln Gln Lys Pro Gly Gln Ala Pro Val Leu Val Ile Tyr Asp
            35                  40                  45

Asp Asn Lys Arg Pro Ser Gly Ile Pro Glu Arg Phe Ser Gly Ser Asn
    50                  55                  60

Ser Gly Asn Thr Ala Thr Leu Thr Ile Ser Gly Val Gln Ala Glu Asp
 65                  70                  75                  80

Glu Ala Asp Tyr Tyr Cys Gln Ser Trp Asp Ser Ser Gly Asn Val Val
                85                  90                  95

Phe Gly Gly Gly Thr Lys Leu Thr Val Leu Gly Gln
                100                 105

<210> SEQ ID NO 21
<211> LENGTH: 119
<212> TYPE: PRT
<213> ORGANISM: Homo sapiens

<400> SEQUENCE: 21

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ala Pro Gly Tyr Cys Ser Gly Phe Asp Tyr Trp Gly Gln Gly
                100                 105                 110

Thr Leu Val Thr Val Ser Ser
            115

<210> SEQ ID NO 22
<211> LENGTH: 117
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
  1               5                  10                  15
```

```
Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Asp Gly Gly Phe Asp Tyr Trp Gly Gln Gly Thr Leu
            100                 105                 110

Val Thr Val Ser Ser
        115

<210> SEQ ID NO 23
<211> LENGTH: 120
<212> TYPE: PRT
<213> ORGANISM: Homo sapiens

<400> SEQUENCE: 23

Glx Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Asp Trp Asp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile His Asn Ile Gly Glu Ala Phe Asp Val Trp Gly Gln
            100                 105                 110

Gly Thr Leu Val Thr Val Ser Ser
        115                 120

<210> SEQ ID NO 24
<211> LENGTH: 117
<212> TYPE: PRT
<213> ORGANISM: Homo sapiens

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Val Ile Ser Tyr Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Asp Arg Gly Gly Ser Gly Asp Tyr Trp Gly Gln Gly Thr Leu
            100                 105                 110
Val Thr Val Ser Ser
        115

<210> SEQ ID NO 25
<211> LENGTH: 118
<212> TYPE: PRT
<213> ORGANISM: Homo sapiens

<400> SEQUENCE: 25

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Glu Ile Tyr His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Arg Gly Gly Gly Val Phe Asp Tyr Trp Gly Gln Gly Thr
            100                 105                 110

Leu Val Thr Val Ser Ser
        115

<210> SEQ ID NO 26
<211> LENGTH: 119
<212> TYPE: PRT
<213> ORGANISM: Homo sapiens

<400> SEQUENCE: 26

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Gly Gly Gly Tyr Tyr Phe Asp Tyr Trp Gly Gln Gly
            100                 105                 110

Thr Leu Val Thr Val Ser Ser
        115

<210> SEQ ID NO 27
<211> LENGTH: 119
<212> TYPE: PRT
<213> ORGANISM: Homo sapiens

<400> SEQUENCE: 27
```

-continued

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Phe Asp Val Trp Gly Gln Gly
            100                 105                 110

Thr Leu Val Thr Val Ser Ser
            115

<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 29
<211> LENGTH: 114
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 29

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Val Glu Ile Lys
            100                 105                 110

Arg Thr

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 30

Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln His Tyr Thr Thr Pro
                 85                  90                  95

Pro Thr Phe Gly Gln Gly Thr Lys Val Glu Ile Lys Arg Thr
            100                 105                 110

<210> SEQ ID NO 31
<211> LENGTH: 115
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 31

Asp Ile Val Met Thr Gln Ser Pro Asp Ser Leu Ala Val Ser Leu Gly
  1               5                  10                  15

Glu Arg Ala Thr Ile Asn Cys Arg Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Thr Thr Pro Pro Thr Phe Gly Gln Gly Thr Lys Val Glu Ile
            100                 105                 110

Lys Arg Thr
        115
```

```
<210> SEQ ID NO 32
<211> LENGTH: 109
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 32

Gln Ser Val Leu Thr Gln Pro Pro Ser Val Ser Gly Ala Pro Gly Gln
  1               5                  10                  15

Arg Val Thr Ile Ser Cys Ser Gly Ser Ser Asn Ile Gly Ser Asn
             20                  25                  30

Tyr Val Ser Trp Tyr Gln Gln Leu Pro Gly Thr Ala Pro Lys Leu Leu
         35                  40                  45

Ile Tyr Asp Asn Asn Gln Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Gln His Tyr Thr Thr Pro
                 85                  90                  95

Pro Val Phe Gly Gly Gly Thr Lys Leu Thr Val Leu Gly
            100                 105

<210> SEQ ID NO 33
<211> LENGTH: 110
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 33

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Gln His Tyr Thr Thr
                 85                  90                  95

Pro Pro Val Phe Gly Gly Gly Thr Lys Leu Thr Val Leu Gly
            100                 105                 110

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 34

Ser Tyr Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
             20                  25                  30
```

```
Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Gln His Tyr Thr Thr Pro Pro Val
                 85                  90                  95

Phe Gly Gly Gly Thr Lys Leu Thr Val Leu Gly
            100                 105

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 35

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                 90                  95

Ala Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 36

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                 90                  95
```

```
Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 37

Gln Val Gln Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Val Gly Val Gly Trp Ile Arg Gln Pro Pro Gly Lys Ala Leu Glu
             35                  40                  45

Trp Leu Ala Leu Ile Asp Trp Asp Asp Lys Tyr Tyr Ser Thr Ser
     50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Trp Gly Gly Asp Gly Phe Tyr Ala Met Asp Tyr Trp Gly
            100                 105                 110

Gln Gly Thr Leu Val Thr Val Ser Ser
        115                 120

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 38

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 39
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 39

Gln Val Gln Leu Gln Glu Ser Gly Pro Gly Leu Val Lys Pro Ser Glu
  1               5                  10                  15

Thr Leu Ser Leu Thr Cys Thr Val Ser Gly Ser Ile Ser Ser Tyr
             20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Trp Gly Gly Asp Gly Phe Tyr Ala Met Asp Tyr Trp Gly Gln Gly
                100                 105                 110

Thr Leu Val Thr Val Ser Ser
            115

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 40

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 41
<211> LENGTH: 123
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 41
```

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
        115                 120
```

<210> SEQ ID NO 42
<211> LENGTH: 327
<212> TYPE: DNA
<213> ORGANISM: Artificial Sequence
<220> FEATURE:
<223> OTHER INFORMATION: Description of Artificial Sequence: Synthetic V
      kappa consensus gene
<220> FEATURE:
<221> NAME/KEY: CDS
<222> LOCATION: (1)..(327)

<400> SEQUENCE: 42

```
gat atc cag atg acc cag agc ccg tct agc ctg agc gcg agc gtg ggt        48
Asp Ile Gln Met Thr Gln Ser Pro Ser Ser Leu Ser Ala Ser Val Gly
 1               5                  10                  15 gat cgt gtg acc att acc tgc aga gcg agc cag ggc att agc agc tat        96
Asp Arg Val Thr Ile Thr Cys Arg Ala Ser Gln Gly Ile Ser Ser Tyr
            20                  25                  30 ctg gcg tgg tac cag cag aaa cca ggt aaa gca ccg aaa cta tta att       144
Leu Ala Trp Tyr Gln Gln Lys Pro Gly Lys Ala Pro Lys Leu Leu Ile
        35                  40                  45 tat gca gcc agc agc ttg caa agc ggg gtc ccg tcc cgt ttt agc ggc       192
Tyr Ala Ala Ser Ser Leu Gln Ser Gly Val Pro Ser Arg Phe Ser Gly
    50                  55                  60 tct gga tcc ggc act gat ttt acc ctg acc att agc agc ctg caa cct       240
Ser Gly Ser Gly Thr Asp Phe Thr Leu Thr Ile Ser Ser Leu Gln Pro
65                  70                  75                  80 gaa gac ttt gcg acc tat tat tgc cag cag cat tat acc acc ccg ccg       288
Glu Asp Phe Ala Thr Tyr Tyr Cys Gln Gln His Tyr Thr Thr Pro Pro
            85                  90                  95 acc ttt ggc cag ggt acg aaa gtt gaa att aaa cgt acg                   327
Thr Phe Gly Gln Gly Thr Lys Val Glu Ile Lys Arg Thr
            100                 105
```

<210> SEQ ID NO 43
<211> LENGTH: 109
<212> TYPE: PRT
<213> ORGANISM: Artificial Sequence
<220> FEATURE:
<223> OTHER INFORMATION: Description of Artificial Sequence: Synthetic V
      kappa consensus gene

<400> SEQUENCE: 43

```
Asp Ile Gln Met Thr Gln Ser Pro Ser Ser Leu Ser Ala Ser Val Gly
 1               5                  10                  15
```

```
Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
                100                 105
```

<210> SEQ ID NO 44
<211> LENGTH: 342
<212> TYPE: DNA
<213> ORGANISM: Artificial Sequence
<220> FEATURE:
<223> OTHER INFORMATION: Description of Artificial Sequence: Synthetic V
      kappa consensus gene
<220> FEATURE:
<221> NAME/KEY: CDS
<222> LOCATION: (1)..(342)

<400> SEQUENCE: 44

```
gat atc gtg atg acc cag agc cca ctg agc ctg cca gtg act ccg ggc      48
Asp Ile Val Met Thr Gln Ser Pro Leu Ser Leu Pro Val Thr Pro Gly
  1               5                  10                  15 gag cct gcg agc att agc tgc aga agc agc caa agc ctg ctg cat agc      96
Glu Pro Ala Ser Ile Ser Cys Arg Ser Ser Gln Ser Leu Leu His Ser
                20                  25                  30 aac ggc tat aac tat ctg gat tgg tac ctt caa aaa cca ggt caa agc     144
Asn Gly Tyr Asn Tyr Leu Asp Trp Tyr Leu Gln Lys Pro Gly Gln Ser
            35                  40                  45 ccg cag cta tta att tat ctg ggc agc aac cgt gcc agt ggg gtc ccg     192
Pro Gln Leu Leu Ile Tyr Leu Gly Ser Asn Arg Ala Ser Gly Val Pro
        50                  55                  60 gat cgt ttt agc ggc tct gga tcc ggc acc gat ttt acc ctg aaa att     240
Asp Arg Phe Ser Gly Ser Gly Ser Gly Thr Asp Phe Thr Leu Lys Ile
65                  70                  75                  80 agc cgt gtg gaa gct gaa gac gtg ggc gtg tat tat tgc cag cag cat     288
Ser Arg Val Glu Ala Glu Asp Val Gly Val Tyr Tyr Cys Gln Gln His
                85                  90                  95 tat acc acc ccg ccg acc ttt ggc cag ggt acg aaa gtt gaa att aaa     336
Tyr Thr Thr Pro Pro Thr Phe Gly Gln Gly Thr Lys Val Glu Ile Lys
                100                 105                 110 cgt acg                                                              342
Arg Thr
```

<210> SEQ ID NO 45
<211> LENGTH: 114
<212> TYPE: PRT
<213> ORGANISM: Artificial Sequence
<220> FEATURE:
<223> OTHER INFORMATION: Description of Artificial Sequence: Synthetic V
      kappa consensus gene

<400> SEQUENCE: 45

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
```

```
                    20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln His
                85                  90                  95

Tyr Thr Thr Pro Pro Thr Phe Gly Gln Gly Thr Lys Val Glu Ile Lys
            100                 105                 110

Arg Thr

<210> SEQ ID NO 46
<211> LENGTH: 330
<212> TYPE: DNA
<213> ORGANISM: Artificial Sequence
<220> FEATURE:
<223> OTHER INFORMATION: Description of Artificial Sequence: Synthetic V
      kappa consensus gene
<220> FEATURE:
<221> NAME/KEY: CDS
<222> LOCATION: (1)..(330)

<400> SEQUENCE: 46 gat atc gtg ctg acc cag agc ccg gcg acc ctg agc ctg tct ccg ggc    48
Asp Ile Val Leu Thr Gln Ser Pro Ala Thr Leu Ser Leu Ser Pro Gly
1               5                   10                  15 gaa cgt gcg acc ctg agc tgc aga gcg agc cag agc gtg agc agc agc    96
Glu Arg Ala Thr Leu Ser Cys Arg Ala Ser Gln Ser Val Ser Ser Ser
            20                  25                  30 tat ctg gcg tgg tac cag cag aaa cca ggt caa gca ccg cgt cta tta   144
Tyr Leu Ala Trp Tyr Gln Gln Lys Pro Gly Gln Ala Pro Arg Leu Leu
        35                  40                  45 att tat ggc gcg agc agc cgt gca act ggg gtc ccg gcg cgt ttt agc   192
Ile Tyr Gly Ala Ser Ser Arg Ala Thr Gly Val Pro Ala Arg Phe Ser
    50                  55                  60 ggc tct gga tcc ggc acg gat ttt acc ctg acc att agc agc ctg gaa   240
Gly Ser Gly Ser Gly Thr Asp Phe Thr Leu Thr Ile Ser Ser Leu Glu
65                  70                  75                  80 cct gaa gac ttt gcg gtg tat tat tgc cag cag cat tat acc acc ccg   288
Pro Glu Asp Phe Ala Val Tyr Tyr Cys Gln Gln His Tyr Thr Thr Pro
                85                  90                  95 ccg acc ttt ggc cag ggt acg aaa gtt gaa att aaa cgt acg             330
Pro Thr Phe Gly Gln Gly Thr Lys Val Glu Ile Lys Arg Thr
            100                 105                 110

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic V
      kappa consensus gene

<400> SEQUENCE: 47

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
              35                  40                  45
Ile Tyr Gly Ala Ser Ser Arg Ala Thr Gly Val Pro Ala Arg Phe Ser
         50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln His Tyr Thr Thr Pro
                 85                  90                  95

Pro Thr Phe Gly Gln Gly Thr Lys Val Glu Ile Lys Arg Thr
            100                 105                 110

<210> SEQ ID NO 48
<211> LENGTH: 345
<212> TYPE: DNA
<213> ORGANISM: Artificial Sequence
<220> FEATURE:
<223> OTHER INFORMATION: Description of Artificial Sequence: Synthetic V
      kappa consensus gene
<220> FEATURE:
<221> NAME/KEY: CDS
<222> LOCATION: (1)..(345)

<400> SEQUENCE: 48 gat atc gtg atg acc cag agc ccg gat agc ctg gcg gtg agc ctg ggc      48
Asp Ile Val Met Thr Gln Ser Pro Asp Ser Leu Ala Val Ser Leu Gly
 1               5                  10                  15 gaa cgt gcg acc att aac tgc aga agc agc cag agc gtg ctg tat agc      96
Glu Arg Ala Thr Ile Asn Cys Arg Ser Ser Gln Ser Val Leu Tyr Ser
                20                  25                  30 agc aac aac aaa aac tat ctg gcg tgg tac cag cag aaa cca ggt cag     144
Ser Asn Asn Lys Asn Tyr Leu Ala Trp Tyr Gln Gln Lys Pro Gly Gln
            35                  40                  45 ccg ccg aaa cta tta att tat tgg gca tcc acc cgt gaa agc ggg gtc     192
Pro Pro Lys Leu Leu Ile Tyr Trp Ala Ser Thr Arg Glu Ser Gly Val
         50                  55                  60 ccg gat cgt ttt agc ggc tct gga tcc ggc act gat ttt acc ctg acc     240
Pro Asp Arg Phe Ser Gly Ser Gly Ser Gly Thr Asp Phe Thr Leu Thr
 65                  70                  75                  80 att tcg tcc ctg caa gct gaa gac gtg gcg gtg tat tat tgc cag cag     288
Ile Ser Ser Leu Gln Ala Glu Asp Val Ala Val Tyr Tyr Cys Gln Gln
                 85                  90                  95 cat tat acc acc ccg ccg acc ttt ggc cag ggt acg aaa gtt gaa att     336
His Tyr Thr Thr Pro Pro Thr Phe Gly Gln Gly Thr Lys Val Glu Ile
            100                 105                 110 aaa cgt acg                                                         345
Lys Arg Thr
        115

<210> SEQ ID NO 49
<211> LENGTH: 115
<212> TYPE: PRT
<213> ORGANISM: Artificial Sequence
<220> FEATURE:
<223> OTHER INFORMATION: Description of Artificial Sequence: Synthetic V
      kappa consensus gene

<400> SEQUENCE: 49

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45
```

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Thr Thr Pro Pro Thr Phe Gly Gln Gly Thr Lys Val Glu Ile
            100                 105                 110

Lys Arg Thr
        115

<210> SEQ ID NO 50
<211> LENGTH: 327
<212> TYPE: DNA
<213> ORGANISM: Artificial Sequence
<220> FEATURE:
<223> OTHER INFORMATION: Description of Artificial Sequence: Synthetic V
      lambda consensus gene
<220> FEATURE:
<221> NAME/KEY: CDS
<222> LOCATION: (1)..(327)

<400> SEQUENCE: 50 cag agc gtg ctg acc cag ccg cct tca gtg agt ggc gca cca ggt cag       48
Gln Ser Val Leu Thr Gln Pro Pro Ser Val Ser Gly Ala Pro Gly Gln
 1               5                  10                  15 cgt gtg acc atc tcg tgt agc ggc agc agc agc aac att ggc agc aac       96
Arg Val Thr Ile Ser Cys Ser Gly Ser Ser Ser Asn Ile Gly Ser Asn
             20                  25                  30 tat gtg agc tgg tac cag cag ttg ccc ggg acg gcg ccg aaa ctg ctg      144
Tyr Val Ser Trp Tyr Gln Gln Leu Pro Gly Thr Ala Pro Lys Leu Leu
         35                  40                  45 att tat gat aac aac cag cgt ccc tca ggc gtg ccg gat cgt ttt agc      192
Ile Tyr Asp Asn Asn Gln Arg Pro Ser Gly Val Pro Asp Arg Phe Ser
     50                  55                  60 gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80 agc gaa gac gaa gcg gat tat tat tgc cag cag cat tat acc acc ccg      288
Ser Glu Asp Glu Ala Asp Tyr Tyr Cys Gln Gln His Tyr Thr Thr Pro
                 85                  90                  95 cct gtg ttt ggc ggc ggc acg aag tta acc gtt ctt ggc                  327
Pro Val Phe Gly Gly Gly Thr Lys Leu Thr Val Leu Gly
            100                 105

<210> SEQ ID NO 51
<211> LENGTH: 109
<212> TYPE: PRT
<213> ORGANISM: Artificial Sequence
<220> FEATURE:
<223> OTHER INFORMATION: Description of Artificial Sequence: Synthetic V
      lambda consensus gene

<400> SEQUENCE: 51

Gln Ser Val Leu Thr Gln Pro Pro Ser Val Ser Gly Ala Pro Gly Gln
 1               5                  10                  15

Arg Val Thr Ile Ser Cys Ser Gly Ser Ser Ser Asn Ile Gly Ser Asn
             20                  25                  30

Tyr Val Ser Trp Tyr Gln Gln Leu Pro Gly Thr Ala Pro Lys Leu Leu
         35                  40                  45

Ile Tyr Asp Asn Asn Gln Arg Pro Ser Gly Val Pro Asp Arg Phe Ser
```

```
                    50                  55                  60
Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Gln His Tyr Thr Thr Pro
                 85                  90                  95

Pro Val Phe Gly Gly Gly Thr Lys Leu Thr Val Leu Gly
            100                 105

<210> SEQ ID NO 52
<211> LENGTH: 330
<212> TYPE: DNA
<213> ORGANISM: Artificial Sequence
<220> FEATURE:
<223> OTHER INFORMATION: Description of Artificial Sequence: Synthetic V
      lambda consensus gene
<220> FEATURE:
<221> NAME/KEY: CDS
<222> LOCATION: (1)..(330)

<400> SEQUENCE: 52 cag agc gca ctg acc cag cca gct tca gtg agc ggc tca cca ggt cag      48
Gln Ser Ala Leu Thr Gln Pro Ala Ser Val Ser Gly Ser Pro Gly Gln
 1               5                  10                  15 agc att acc atc tcg tgt acg ggt act agc agc gat gtg ggc ggc tat      96
Ser Ile Thr Ile Ser Cys Thr Gly Thr Ser Ser Asp Val Gly Gly Tyr
             20                  25                  30 aac tat gtg agc tgg tac cag cag cat ccc ggg aag gcg ccg aaa ctg     144
Asn Tyr Val Ser Trp Tyr Gln Gln His Pro Gly Lys Ala Pro Lys Leu
         35                  40                  45 atg att tat gat gtg agc aac cgt ccc tca ggc gtg agc aac cgt ttt     192
Met Ile Tyr Asp Val Ser Asn Arg Pro Ser Gly Val Ser Asn Arg Phe
     50                  55                  60 agc gga tcc aaa agc ggc aac acc gcg agc ctg acc att agc ggc ctg     240
Ser Gly Ser Lys Ser Gly Asn Thr Ala Ser Leu Thr Ile Ser Gly Leu
 65                  70                  75                  80 caa gcg gaa gac gaa gcg gat tat tat tgc cag cag cat tat acc acc     288
Gln Ala Glu Asp Glu Ala Asp Tyr Tyr Cys Gln Gln His Tyr Thr Thr
                 85                  90                  95 ccg cct gtg ttt ggc ggc ggc acg aag tta acc gtt ctt ggc             330
Pro Pro Val Phe Gly Gly Gly Thr Lys Leu Thr Val Leu Gly
            100                 105                 110

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic V
      lambda consensus gene

<400> SEQUENCE: 53

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80
```

```
Gln Ala Glu Asp Glu Ala Asp Tyr Tyr Cys Gln Gln His Tyr Thr Thr
                85                  90                  95

Pro Pro Val Phe Gly Gly Gly Thr Lys Leu Thr Val Leu Gly
            100                 105                 110

<210> SEQ ID NO 54
<211> LENGTH: 321
<212> TYPE: DNA
<213> ORGANISM: Artificial Sequence
<220> FEATURE:
<223> OTHER INFORMATION: Description of Artificial Sequence: Synthetic V
      lambda consensus gene
<220> FEATURE:
<221> NAME/KEY: CDS
<222> LOCATION: (1)..(321)

<400> SEQUENCE: 54 agc tat gaa ctg acc cag ccg cct tca gtg agc gtt gca cca ggt cag      48
Ser Tyr Glu Leu Thr Gln Pro Pro Ser Val Ser Val Ala Pro Gly Gln
  1               5                  10                  15 acc gcg cgt atc tcg tgt agc ggc gat gcg ctg ggc gat aaa tac gcg      96
Thr Ala Arg Ile Ser Cys Ser Gly Asp Ala Leu Gly Asp Lys Tyr Ala
                 20                  25                  30 agc tgg tac cag cag aaa ccc ggg cag gcg cca gtt ctg gtg att tat     144
Ser Trp Tyr Gln Gln Lys Pro Gly Gln Ala Pro Val Leu Val Ile Tyr
             35                  40                  45 gat gat tct gac cgt ccc tca ggc atc ccg gaa cgc ttt agc gga tcc     192
Asp Asp Ser Asp Arg Pro Ser Gly Ile Pro Glu Arg Phe Ser Gly Ser
         50                  55                  60 aac agc ggc aac acc gcg acc ctg acc att agc ggc act cag gcg gaa     240
Asn Ser Gly Asn Thr Ala Thr Leu Thr Ile Ser Gly Thr Gln Ala Glu
 65                  70                  75                  80 gac gaa gcg gat tat tat tgc cag cag cat tat acc acc ccg cct gtg     288
Asp Glu Ala Asp Tyr Tyr Cys Gln Gln His Tyr Thr Thr Pro Pro Val
                 85                  90                  95 ttt ggc ggc ggc acg aag tta acc gtt ctt ggc                         321
Phe Gly Gly Gly Thr Lys Leu Thr Val Leu Gly
            100                 105

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic V
      lambda consensus gene

<400> SEQUENCE: 55

Ser Tyr Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
                 20                  25                  30

Ser Trp Tyr Gln Gln Lys Pro Gly Gln Ala Pro Val Leu Val Ile Tyr
             35                  40                  45

Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Gln His Tyr Thr Thr Pro Pro Val
                 85                  90                  95

Phe Gly Gly Gly Thr Lys Leu Thr Val Leu Gly
            100                 105
```

<210> SEQ ID NO 56
<211> LENGTH: 361
<212> TYPE: DNA
<213> ORGANISM: Artificial Sequence
<220> FEATURE:
<223> OTHER INFORMATION: Description of Artificial Sequence: Synthetic V heavy chain gene sequence
<220> FEATURE:
<221> NAME/KEY: CDS
<222> LOCATION: (1)..(360)

<400> SEQUENCE: 56

| cag | gtg | caa | ttg | gtt | cag | tct | ggc | gcg | gaa | gtg | aaa | aaa | ccg | ggc | agc | 48 |
| Gln | Val | Gln | Leu | Val | Gln | Ser | Gly | Ala | Glu | Val | Lys | Lys | Pro | Gly | Ser | |
| 1 | | | | 5 | | | | | 10 | | | | | 15 | | |

| agc | gtg | aaa | gtg | agc | tgc | aaa | gcc | tcc | gga | ggc | act | ttt | agc | agc | tat | 96 |
| Ser | Val | Lys | Val | Ser | Cys | Lys | Ala | Ser | Gly | Gly | Thr | Phe | Ser | Ser | Tyr | |
| | | | 20 | | | | | 25 | | | | | 30 | | | |

| gcg | att | agc | tgg | gtg | cgc | caa | gcc | cct | ggg | cag | ggt | ctc | gag | tgg | atg | 144 |
| Ala | Ile | Ser | Trp | Val | Arg | Gln | Ala | Pro | Gly | Gln | Gly | Leu | Glu | Trp | Met | |
| | | 35 | | | | | 40 | | | | | 45 | | | | |

| ggc | ggc | att | att | ccg | att | ttt | ggc | acg | gcg | aac | tac | gcg | cag | aag | ttt | 192 |
| Gly | Gly | Ile | Ile | Pro | Ile | Phe | Gly | Thr | Ala | Asn | Tyr | Ala | Gln | Lys | Phe | |
| 50 | | | | | 55 | | | | | 60 | | | | | | |

| cag | ggc | cgg | gtg | acc | att | acc | gcg | gat | gaa | agc | acc | agc | acc | gcg | tat | 240 |
| Gln | Gly | Arg | Val | Thr | Ile | Thr | Ala | Asp | Glu | Ser | Thr | Ser | Thr | Ala | Tyr | |
| 65 | | | | 70 | | | | | 75 | | | | | 80 | | |

| atg | gaa | ctg | agc | agc | ctg | cgt | agc | gaa | gat | acg | gcc | gtg | tat | tat | tgc | 288 |
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |

| gcg | cgt | tgg | ggc | ggc | gat | ggc | ttt | tat | gcg | atg | gat | tat | tgg | ggc | caa | 336 |
| Ala | Arg | Trp | Gly | Gly | Asp | Gly | Phe | Tyr | Ala | Met | Asp | Tyr | Trp | Gly | Gln | |
| | | | 100 | | | | | 105 | | | | | 110 | | | |

| ggc | acc | ctg | gtg | acg | gtt | agc | tca | g | | | | | | | | 361 |
| Gly | Thr | Leu | Val | Thr | Val | Ser | Ser | | | | | | | | | |
| | | 115 | | | | | 120 | | | | | | | | | |

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic V heavy chain gene sequence

<400> SEQUENCE: 57

| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |

| Ser | Val | Lys | Val | Ser | Cys | Lys | Ala | Ser | Gly | Gly | Thr | Phe | Ser | Ser | Tyr |
| | | | 20 | | | | | 25 | | | | | 30 | | |

| Ala | Ile | Ser | Trp | Val | Arg | Gln | Ala | Pro | Gly | Gln | Gly | Leu | Glu | Trp | Met |
| | | 35 | | | | | 40 | | | | | 45 | | | |

| Gly | Gly | Ile | Ile | Pro | Ile | Phe | Gly | Thr | Ala | Asn | Tyr | Ala | Gln | Lys | Phe |
| 50 | | | | | 55 | | | | | 60 | | | | | |

| Gln | Gly | Arg | Val | Thr | Ile | Thr | Ala | Asp | Glu | Ser | Thr | Ser | Thr | Ala | Tyr |
| 65 | | | | 70 | | | | | 75 | | | | | 80 | |

| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |

| Ala | Arg | Trp | Gly | Gly | Asp | Gly | Phe | Tyr | Ala | Met | Asp | Tyr | Trp | Gly | Gln |
| | | | 100 | | | | | 105 | | | | | 110 | | |

```
Gly Thr Leu Val Thr Val Ser Ser
        115                 120

<210> SEQ ID NO 58
<211> LENGTH: 361
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(360)

<400> SEQUENCE: 58 cag gtg caa ttg gtt cag agc ggc gcg gaa gtg aaa aaa ccg ggc gcg        48
Gln Val Gln Leu Val Gln Ser Gly Ala Glu Val Lys Lys Pro Gly Ala
  1               5                  10                  15 agc gtg aaa gtg agc tgc aaa gcc tcc gga tat acc ttt acc agc tat        96
Ser Val Lys Val Ser Cys Lys Ala Ser Gly Tyr Thr Phe Thr Ser Tyr
             20                  25                  30 tat atg cac tgg gtc cgc caa gcc cct ggg cag ggt ctc gag tgg atg       144
Tyr Met His Trp Val Arg Gln Ala Pro Gly Gln Gly Leu Glu Trp Met
         35                  40                  45 ggc tgg att aac ccg aat agc ggc ggc acg aac tac gcg cag aag ttt       192
Gly Trp Ile Asn Pro Asn Ser Gly Gly Thr Asn Tyr Ala Gln Lys Phe
     50                  55                  60 cag ggc cgg gtg acc atg acc cgt gat acc agc att agc acc gcg tat       240
Gln Gly Arg Val Thr Met Thr Arg Asp Thr Ser Ile Ser Thr Ala Tyr
 65                  70                  75                  80 atg gaa ctg agc agc ctg cgt agc gaa gat acg gcc gtg tat tat tgc       288
Met Glu Leu Ser Ser Leu Arg Ser Glu Asp Thr Ala Val Tyr Tyr Cys
                 85                  90                  95 gcg cgt tgg ggc ggc gat ggc ttt tat gcg atg gat tat tgg ggc caa       336
Ala Arg Trp Gly Gly Asp Gly Phe Tyr Ala Met Asp Tyr Trp Gly Gln
            100                 105                 110 ggc acc ctg gtg acg gtt agc tca g                                      361
Gly Thr Leu Val Thr Val Ser Ser
        115                 120

<210> SEQ ID NO 59
<211> LENGTH: 120
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 59

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Gly Asp Gly Phe Tyr Ala Met Asp Tyr Trp Gly Gln
```

-continued

```
                  100                 105                 110
Gly Thr Leu Val Thr Val Ser Ser
        115                 120

<210> SEQ ID NO 60
<211> LENGTH: 364
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(363)

<400> SEQUENCE: 60 cag gtg caa ttg aaa gaa agc ggc ccg gcc ctg gtg aaa ccg acc caa      48
Gln Val Gln Leu Lys Glu Ser Gly Pro Ala Leu Val Lys Pro Thr Gln
  1               5                  10                  15 acc ctg acc ctg acc tgt acc ttt tcc gga ttt agc ctg tcc acg tct      96
Thr Leu Thr Leu Thr Cys Thr Phe Ser Gly Phe Ser Leu Ser Thr Ser
             20                  25                  30 ggc gtt ggc gtg ggc tgg att cgc cag ccg cct ggg aaa gcc ctc gag     144
Gly Val Gly Val Gly Trp Ile Arg Gln Pro Pro Gly Lys Ala Leu Glu
         35                  40                  45 tgg ctg gct ctg att gat tgg gat gat gat aag tat tat agc acc agc     192
Trp Leu Ala Leu Ile Asp Trp Asp Asp Asp Lys Tyr Tyr Ser Thr Ser
     50                  55                  60 ctg aaa acg cgt ctg acc att agc aaa gat act tcg aaa aat cag gtg     240
Leu Lys Thr Arg Leu Thr Ile Ser Lys Asp Thr Ser Lys Asn Gln Val
 65                  70                  75                  80 gtg ctg act atg acc aac atg gac ccg gtg gat acg gcc acc tat tat     288
Val Leu Thr Met Thr Asn Met Asp Pro Val Asp Thr Ala Thr Tyr Tyr
                 85                  90                  95 tgc gcg cgt tgg ggc ggc gat ggc ttt tat gcg atg gat tat tgg ggc     336
Cys Ala Arg Trp Gly Gly Asp Gly Phe Tyr Ala Met Asp Tyr Trp Gly
            100                 105                 110 caa ggc acc ctg gtg acg gtt agc tca g                               364
Gln Gly Thr Leu Val Thr Val Ser Ser
        115                 120

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 61

Gln Val Gln Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45

Trp Leu Ala Leu Ile Asp Trp Asp Asp Asp Lys Tyr Tyr Ser Thr Ser
     50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95
```

```
Cys Ala Arg Trp Gly Gly Asp Gly Phe Tyr Ala Met Asp Tyr Trp Gly
            100                 105                 110

Gln Gly Thr Leu Val Thr Val Ser Ser
        115                 120

<210> SEQ ID NO 62
<211> LENGTH: 361
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(360)

<400> SEQUENCE: 62 gaa gtg caa ttg gtg gaa agc ggc ggc ggc ctg gtg caa ccg ggc ggc        48
Glu Val Gln Leu Val Glu Ser Gly Gly Gly Leu Val Gln Pro Gly Gly
  1               5                  10                  15 agc ctg cgt ctg agc tgc gcg gcc tcc gga ttt acc ttt agc agc tat        96
Ser Leu Arg Leu Ser Cys Ala Ala Ser Gly Phe Thr Phe Ser Ser Tyr
             20                  25                  30 gcg atg agc tgg gtg cgc caa gcc cct ggg aag ggt ctc gag tgg gtg       144
Ala Met Ser Trp Val Arg Gln Ala Pro Gly Lys Gly Leu Glu Trp Val
         35                  40                  45 agc gcg att agc ggt agc ggc ggc agc acc tat tat gcg gat agc gtg       192
Ser Ala Ile Ser Gly Ser Gly Gly Ser Thr Tyr Tyr Ala Asp Ser Val
     50                  55                  60 aaa ggc cgt ttt acc att tca cgt gat aat tcg aaa aac acc ctg tat       240
Lys Gly Arg Phe Thr Ile Ser Arg Asp Asn Ser Lys Asn Thr Leu Tyr
 65                  70                  75                  80 ctg caa atg aac agc ctg cgt gcg gaa gat acg gcc gtg tat tat tgc       288
Leu Gln Met Asn Ser Leu Arg Ala Glu Asp Thr Ala Val Tyr Tyr Cys
                 85                  90                  95 gcg cgt tgg ggc ggc gat ggc ttt tat gcg atg gat tat tgg ggc caa       336
Ala Arg Trp Gly Gly Asp Gly Phe Tyr Ala Met Asp Tyr Trp Gly Gln
            100                 105                 110 ggc acc ctg gtg acg gtt agc tca g                                     361
Gly Thr Leu Val Thr Val Ser Ser
        115                 120

<210> SEQ ID NO 63
<211> LENGTH: 120
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 63

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 64
<211> LENGTH: 358
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(357)

<400> SEQUENCE: 64 cag gtg caa ttg caa gaa agt ggt ccg ggc ctg gtg aaa ccg agc gaa      48
Gln Val Gln Leu Gln Glu Ser Gly Pro Gly Leu Val Lys Pro Ser Glu
  1               5                  10                  15 acc ctg agc ctg acc tgc acc gtt tcc gga ggc agc att agc agc tat      96
Thr Leu Ser Leu Thr Cys Thr Val Ser Gly Gly Ser Ile Ser Ser Tyr
             20                  25                  30 tat tgg agc tgg att cgc cag ccg cct ggg aag ggt ctc gag tgg att     144
Tyr Trp Ser Trp Ile Arg Gln Pro Pro Gly Lys Gly Leu Glu Trp Ile
         35                  40                  45 ggc tat att tat tat agc ggc agc acc aac tat aat ccg agc ctg aaa     192
Gly Tyr Ile Tyr Tyr Ser Gly Ser Thr Asn Tyr Asn Pro Ser Leu Lys
     50                  55                  60 agc cgg gtg acc att agc gtt gat act tcg aaa aac cag ttt agc ctg     240
Ser Arg Val Thr Ile Ser Val Asp Thr Ser Lys Asn Gln Phe Ser Leu
 65                  70                  75                  80 aaa ctg agc agc gtg acg gcg gcg gat acg gcc gtg tat tat tgc gcg     288
Lys Leu Ser Ser Val Thr Ala Ala Asp Thr Ala Val Tyr Tyr Cys Ala
                 85                  90                  95 cgt tgg ggc ggc gat ggc ttt tat gcg atg gat tat tgg ggc caa ggc     336
Arg Trp Gly Gly Asp Gly Phe Tyr Ala Met Asp Tyr Trp Gly Gln Gly
            100                 105                 110 acc ctg gtg acg gtt agc tca g                                       358
Thr Leu Val Thr Val Ser Ser
        115

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 65

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
```

65                  70                  75                  80
Lys Leu Ser Ser Val Thr Ala Ala Asp Thr Ala Val Tyr Tyr Cys Ala
                        85                  90                  95

Arg Trp Gly Gly Asp Gly Phe Tyr Ala Met Asp Tyr Trp Gln Gly
            100                 105                 110

Thr Leu Val Thr Val Ser Ser
        115

<210> SEQ ID NO 66
<211> LENGTH: 361
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(360)

<400> SEQUENCE: 66 gaa gtg caa ttg gtt cag agc ggc gcg gaa gtg aaa aaa ccg ggc gaa         48
Glu Val Gln Leu Val Gln Ser Gly Ala Glu Val Lys Lys Pro Gly Glu
1               5                   10                  15 agc ctg aaa att agc tgc aaa ggt tcc gga tat tcc ttt acg agc tat         96
Ser Leu Lys Ile Ser Cys Lys Gly Ser Gly Tyr Ser Phe Thr Ser Tyr
            20                  25                  30 tgg att ggc tgg gtg cgc cag atg cct ggg aag ggt ctc gag tgg atg        144
Trp Ile Gly Trp Val Arg Gln Met Pro Gly Lys Gly Leu Glu Trp Met
        35                  40                  45 ggc att att tat ccg ggc gat agc gat acc cgt tat tct ccg agc ttt        192
Gly Ile Ile Tyr Pro Gly Asp Ser Asp Thr Arg Tyr Ser Pro Ser Phe
    50                  55                  60 cag ggc cag gtg acc att agc gcg gat aaa agc att agc acc gcg tat        240
Gln Gly Gln Val Thr Ile Ser Ala Asp Lys Ser Ile Ser Thr Ala Tyr
65                  70                  75                  80 ctt caa tgg agc agc ctg aaa gcg agc gat acg gcc atg tat tat tgc        288
Leu Gln Trp Ser Ser Leu Lys Ala Ser Asp Thr Ala Met Tyr Tyr Cys
                85                  90                  95 gcg cgt tgg ggc ggc gat ggc ttt tat gcg atg gat tat tgg ggc caa        336
Ala Arg Trp Gly Gly Asp Gly Phe Tyr Ala Met Asp Tyr Trp Gly Gln
            100                 105                 110 ggc acc ctg gtg acg gtt agc tca g                                      361
Gly Thr Leu Val Thr Val Ser Ser
        115                 120

<210> SEQ ID NO 67
<211> LENGTH: 120
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 67

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 68
<211> LENGTH: 370
<212> TYPE: DNA
<213> ORGANISM: Artificial Sequence
<220> FEATURE:
<223> OTHER INFORMATION: Description of Artificial Sequence: Synthetic V heavy chain gene sequence
<220> FEATURE:
<221> NAME/KEY: CDS
<222> LOCATION: (1)..(369)

<400> SEQUENCE: 68

```
cag gtg caa ttg caa cag tct ggt ccg ggc ctg gtg aaa ccg agc caa        48
Gln Val Gln Leu Gln Gln Ser Gly Pro Gly Leu Val Lys Pro Ser Gln
  1               5                  10                  15 acc ctg agc ctg acc tgt gcg att tcc gga gat agc gtg agc agc aac        96
Thr Leu Ser Leu Thr Cys Ala Ile Ser Gly Asp Ser Val Ser Ser Asn
             20                  25                  30 agc gcg gcg tgg aac tgg att cgc cag tct cct ggg cgt ggc ctc gag      144
Ser Ala Ala Trp Asn Trp Ile Arg Gln Ser Pro Gly Arg Gly Leu Glu
         35                  40                  45 tgg ctg ggc cgt acc tat tat cgt agc aaa tgg tat aac gat tat gcg      192
Trp Leu Gly Arg Thr Tyr Tyr Arg Ser Lys Trp Tyr Asn Asp Tyr Ala
     50                  55                  60 gtg agc gtg aaa agc cgg att acc atc aac ccg gat act tcg aaa aac      240
Val Ser Val Lys Ser Arg Ile Thr Ile Asn Pro Asp Thr Ser Lys Asn
 65                  70                  75                  80 cag ttt agc ctg caa ctg aac agc gtg acc ccg gaa gat acg gcc gtg      288
Gln Phe Ser Leu Gln Leu Asn Ser Val Thr Pro Glu Asp Thr Ala Val
                 85                  90                  95 tat tat tgc gcg cgt tgg ggc ggc gat ggc ttt tat gcg atg gat tat      336
Tyr Tyr Cys Ala Arg Trp Gly Gly Asp Gly Phe Tyr Ala Met Asp Tyr
            100                 105                 110 tgg ggc caa ggc acc ctg gtg acg gtt agc tca g                         370
Trp Gly Gln Gly Thr Leu Val Thr Val Ser Ser
        115                 120
```

<210> SEQ ID NO 69
<211> LENGTH: 123
<212> TYPE: PRT
<213> ORGANISM: Artificial Sequence
<220> FEATURE:
<223> OTHER INFORMATION: Description of Artificial Sequence: Synthetic V heavy chain gene sequence

<400> SEQUENCE: 69

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Gly Arg Gly Leu Glu
         35                  40                  45
```

```
Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
        115                 120

<210> SEQ ID NO 70
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gaatgcatac gctgatatcc agatgaccca gagcccgtct agcctgagc                49

<210> SEQ ID NO 71
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cgctctgcag gtaatggtca cacgatcacc cacgctcgcg ctcaggctag acgggc        56

<210> SEQ ID NO 72
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gaccattacc tgcagagcga gccagggcat tagcagctat ctggcgtggt accagcag     58

<210> SEQ ID NO 73
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctttgcaagc tgctggctgc ataaattaat agtttcggtg ctttacctgg tttctgctgg    60
taccacgcca g                                                         71

<210> SEQ ID NO 74
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
```

```
cagccagcag cttgcaaagc ggggtcccgt cccgttttag cggctctgga tccggcactg    60
attttac                                                              67

<210> SEQ ID NO 75
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gataataggt cgcaaagtct tcaggttgca ggctgctaat ggtcagggta aaatcagtgc    60
cggatcc                                                              67

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cgatatcgtg atgacccaga gcccactgag cctgccagtg actccgggcg agcc          54

<210> SEQ ID NO 77
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gccgttgcta tgcagcaggc tttggctgct tctgcagcta atgctcgcag gctcgcccgg    60
agtcac                                                               66

<210> SEQ ID NO 78
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctgctgcata gcaacggcta taactatctg gattggtacc ttcaaaaacc aggtcaaagc    60
cc                                                                   62

<210> SEQ ID NO 79
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cgatccggga ccccactggc acggttgctg cccagataaa ttaatagctg cgggctttga    60
cctggttttt g                                                         71
```

<210> SEQ ID NO 80
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
agtggggtcc cggatcgttt tagcggctct ggatccggca ccgattttac cctgaaaatt    60
agccgtgtg    69

<210> SEQ ID NO 81
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
ccatgcaata atacacgccc acgtcttcag cttccacacg gctaattttc aggg    54

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
gaatgcatac gctgatatcg tgctgaccca gagcccgg    38

<210> SEQ ID NO 83
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
cgctctgcag ctcagggtcg cacgttcgcc cggagacagg ctcagggtcg ccgggctctg    60
ggtcagc    67

<210> SEQ ID NO 84
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
ccctgagctg cagagcgagc cagagcgtga gcagcagcta tctggcgtgg taccag    56

<210> SEQ ID NO 85
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85

```
gcacggctgc tcgcgccata aattaataga cgcggtgctt gacctggttt ctgctggtac    60
cacgccagat ag                                                        72

<210> SEQ ID NO 86
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gcgcgagcag ccgtgcaact ggggtcccgg cgcgttttag cggctctgga tccggcacgg    60
attttac                                                              67

<210> SEQ ID NO 87
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gataatacac cgcaaagtct tcaggttcca ggctgctaat ggtcagggta aaatccgtgc    60
cggatc                                                               66

<210> SEQ ID NO 88
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gaatgcatac gctgatatcg tgatgaccca gagcccggat agcctggcg              49

<210> SEQ ID NO 89
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcttctgcag ttaatggtcg cacgttcgcc caggctcacc gccaggctat ccgggc        56

<210> SEQ ID NO 90
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cgaccattaa ctgcagaagc agccagagcg tgctgtatag cagcaacaac aaaaactatc    60
tggcgtggta ccag                                                      74

<210> SEQ ID NO 91
<211> LENGTH: 63
<212> TYPE: DNA
```

<210> SEQ ID NO 92
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
gatgcccaat aaattaatag tttcggcggc tgacctggtt tctgctggta ccacgccaga    60
tag    63

<210> SEQ ID NO 92
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
aaactattaa tttattgggc atccacccgt gaaagcgggg tcccggatcg ttttagcggc    60
tctggatccg gcac    74

<210> SEQ ID NO 93
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
gataatacac cgccacgtct tcagcttgca gggacgaaat ggtcagggta aaatcagtgc    60
cggatccaga gcc    73

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
gaatgcatac gctcagagcg tgctgaccca gccgccttca gtgagtgg    48

<210> SEQ ID NO 95
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
caatgttgct gctgctgccg ctacacgaga tggtcacacg ctgacctggt gcgccactca    60
ctgaaggcgg c    71

<210> SEQ ID NO 96
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
ggcagcagca gcaacattgg cagcaactat gtgagctggt accagcagtt gcccgggac       59

<210> SEQ ID NO 97
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ccggcacgcc tgagggacgc tggttgttat cataaatcag cagtttcggc gccgtcccgg       60
gcaactgc                                                                68

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ccctcaggcg tgccggatcg ttttagcgga tccaaaagcg gcaccagcgc gagccttgcg       60

<210> SEQ ID NO 99
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccgcttcgtc ttcgctttgc aggcccgtaa tcgcaaggct cgcgctgg                    48

<210> SEQ ID NO 100
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gaatgcatac gctcagagcg cactgaccca gccagcttca gtgagcggc                   49

<210> SEQ ID NO 101
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cgctgctagt acccgtacac gagatggtaa tgctctgacc tggtgagccg ctcactgaag       60
ctgg                                                                    64

<210> SEQ ID NO 102
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
gtacgggtac tagcagcgat gtgggcggct ataactatgt gagctggtac cagcagcatc    60
ccgg    64

<210> SEQ ID NO 103
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cgcctgaggg acggttgctc acatcataaa tcatcagttt cggcgccttc ccgggatgct    60
gctggtac    68

<210> SEQ ID NO 104
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
caaccgtccc tcaggcgtga gcaaccgttt tagcggatcc aaaagcggca acaccgcgag    60
cc    62

<210> SEQ ID NO 105
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ccgcttcgtc ttccgcttgc aggccgctaa tggtcaggct cgcggtgttg ccg    53

<210> SEQ ID NO 106
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gaatgcatac gctagctatg aactgaccca gccgccttca gtgagcg    47

<210> SEQ ID NO 107
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cgcccagcgc atcgccgcta cacgagatac gcgcggtctg acctggtgca acgctcactg    60
aaggcggc    68

<210> SEQ ID NO 108
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ggcgatgcgc tgggcgataa atacgcgagc tggtaccagc agaaacccgg gcaggcgc          58

<210> SEQ ID NO 109
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gcgttccggg atgcctgagg gacggtcaga atcatcataa atcaccagaa ctggcgcctg          60
cccgggtttc                                                                70

<210> SEQ ID NO 110
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
caggcatccc ggaacgcttt agcggatcca acagcggcaa caccgcgacc ctgaccatta          60
gcgg                                                                      64

<210> SEQ ID NO 111
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ccgcttcgtc ttccgcctga gtgccgctaa tggtcagggt c                             41

<210> SEQ ID NO 112
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gctcttcacc cctgttacca aagcccaggt gcaattg                                  37

<210> SEQ ID NO 113
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggctttgcag ctcactttca cgctgctgcc cggttttttc acttccgcgc cagactgaac    60
caattgcacc tgggctttg    79

<210> SEQ ID NO 114
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gaaagtgagc tgcaaagcct ccggaggcac ttttagcagc tatgcgatta gctgggtgcg    60
ccaagcccct gggcagggtc    80

<210> SEQ ID NO 115
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gccctgaaac ttctgcgcgt agttcgccgt gccaaaaatc ggaataatgc cgcccatcca    60
ctcgagaccc tgcccagggg c    81

<210> SEQ ID NO 116
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gcgcagaagt ttcagggccg ggtgaccatt accgcggatg aaagcaccag caccgcgtat    60
atggaactga gcagcctgcg    80

<210> SEQ ID NO 117
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gcgcgcaata atacacggcc gtatcttcgc tacgcaggct gctcagttcc    50

<210> SEQ ID NO 118
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ggctttgcag ctcactttca cgctcgcgcc cggttttttc acttccgcgc cgctctgaac    60
caattgcacc tgggctttg    79

<210> SEQ ID NO 119
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gaaagtgagc tgcaaagcct ccggatatac ctttaccagc tattatatgc actgggtccg    60
ccaagcccct gggcagggtc                                                80

<210> SEQ ID NO 120
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gccctgaaac ttctgcgcgt agttcgtgcc gccgctattc gggttaatcc agcccatcca    60
ctcgagaccc tgcccagggg c                                              81

<210> SEQ ID NO 121
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gcgcagaagt tcagggccg ggtgaccatg acccgtgata ccagcattag caccgcgtat    60
atggaactga gcagcctgcg                                                80

<210> SEQ ID NO 122
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ggtacaggtc agggtcaggg tttgggtcgg tttcaccagg gccgggccgc tttctttcaa    60
ttgcacctgg gctttg                                                    76

<210> SEQ ID NO 123
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctgaccctga cctgtacctt ttccggattt agcctgtcca cgtctggcgt tggcgtgggc    60
tggattcgcc agccgcctgg gaaag                                          85

<210> SEQ ID NO 124
<211> LENGTH: 83
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 124
gcgttttcag gctggtgcta taatacttat catcatccca atcaatcaga gccagccact     60
cgagggcttt cccaggcggc tgg                                             83

<210> SEQ ID NO 125
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gcaccagcct gaaaacgcgt ctgaccatta gcaaagatac ttcgaaaaat caggtggtgc     60
tgactatgac caacatgg                                                   78

<210> SEQ ID NO 126
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gcgcgcaata ataggtggcc gtatccaccg ggtccatgtt ggtcatagtc agc            53

<210> SEQ ID NO 127
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cgaagtgcaa ttggtggaaa gcggcggcgg cctggtgcaa ccgggcggca g              51

<210> SEQ ID NO 128
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
catagctgct aaaggtaaat ccggaggccg cgcagctcag acgcaggctg ccgcccggtt     60
gcac                                                                  64

<210> SEQ ID NO 129
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gatttacctt tagcagctat gcgatgagct gggtgcgcca agcccctggg aagggtctcg     60
```
agtgggtgag                                                              70

<210> SEQ ID NO 130
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggcctttcac gctatccgca taataggtgc tgccgccgct accgctaatc gcgctcaccc        60
actcgagacc c                                                            71

<210> SEQ ID NO 131
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
cggatagcgt gaaaggccgt tttaccattt cacgtgataa ttcgaaaaac accctgtatc        60
tgcaaatgaa cag                                                          73

<210> SEQ ID NO 132
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
cacgcgcgca ataatacacg gccgtatctt ccgcacgcag gctgttcatt tgcagataca        60
gg                                                                      62

<210> SEQ ID NO 133
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggtcaggctc agggtttcgc tcggtttcac caggcccgga ccactttctt gcaattgcac        60
ctgggctttg                                                              70

<210> SEQ ID NO 134
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gaaaccctga gcctgacctg caccgtttcc ggaggcagca ttagcagcta ttattggagc        60
tggattcgcc agccgc                                                       76

<210> SEQ ID NO 135

```
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gattatagtt ggtgctgccg ctataataaa tatagccaat ccactcgaga cccttcccag    60
gcggctggcg aatccag                                                  77

<210> SEQ ID NO 136
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cggcagcacc aactataatc cgagcctgaa aagccgggtg accattagcg ttgatacttc    60
gaaaaaccag tttagcctg                                                79

<210> SEQ ID NO 137
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gcgcgcaata atacacggcc gtatccgccg ccgtcacgct gctcagtttc aggctaaact    60
ggtttttcg                                                           69

<210> SEQ ID NO 138
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gctcttcacc cctgttacca aagccgaagt gcaattg                            37

<210> SEQ ID NO 139
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cctttgcagc taattttcag gctttcgccc ggttttttca cttccgcgcc gctctgaacc    60
aattgcactt cggctttgg                                                79

<210> SEQ ID NO 140
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 140
cctgaaaatt agctgcaaag gttccggata ttcctttacg agctattgga ttggctgggt    60
gcgccagatg cctgg                                                    75

<210> SEQ ID NO 141
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cggagaataa cgggtatcgc tatcgcccgg ataaataatg cccatccact cgagaccctt    60
cccaggcatc tggcgcac                                                 78

<210> SEQ ID NO 142
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cgatacccgt tattctccga gctttcaggg ccaggtgacc attagcgcgg ataaaagcat    60
tagcaccgcg tatcttc                                                  77

<210> SEQ ID NO 143
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gcgcgcaata atacatggcc gtatcgctcg ctttcaggct gctccattga agatacgcgg    60
tgctaatg                                                            68

<210> SEQ ID NO 144
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gaaatcgcac aggtcaggct cagggtttgg ctcggtttca ccaggcccgg accagactgt    60
tgcaattgca cctgggcttt g                                             81

<210> SEQ ID NO 145
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gcctgacctg tgcgatttcc ggagatagcg tgagcagcaa cagcgcggcg tggaactgga    60
```

```
ttcgccagtc tcctgggcg                                              79

<210> SEQ ID NO 146
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
caccgcataa tcgttatacc atttgctacg ataataggta cggcccagcc actcgaggcc    60
acgcccagga gactggcg                                                 78

<210> SEQ ID NO 147
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ggtataacga ttatgcggtg agcgtgaaaa gccggattac catcaacccg gatacttcga    60
aaaaccagtt tagcctgc                                                 78

<210> SEQ ID NO 148
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gcgcgcaata atacacggcc gtatcttccg gggtcacgct gttcagttgc aggctaaact    60
ggtttttc                                                           68

<210> SEQ ID NO 149
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggctgaagac gtgggcgtgt attattgcca gcagcattat accaccccgc cgacctttgg    60
ccagggtac                                                          69

<210> SEQ ID NO 150
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gcggaaaaat aaacacgctc ggagcagcca ccgtacgttt aatttcaact ttcgtaccct    60
ggccaaaggt c                                                       71
```

<210> SEQ ID NO 151
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gagcgtgttt atttttccgc cgagcgatga acaactgaaa agcggcacgg cgagcgtggt    60
gtgcctgctg    70

<210> SEQ ID NO 152
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cagcgcgttg tctactttcc actgaacttt cgcttcacgc ggataaaagt tgttcagcag    60
gcacaccacg c    71

<210> SEQ ID NO 153
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gaaagtagac aacgcgctgc aaagcggcaa cagccaggaa agcgtgaccg aacaggatag    60
caaagatag    69

<210> SEQ ID NO 154
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gtttttcata atccgctttg ctcagggtca gggtgctgct cagagaatag gtgctatctt    60
tgctatcctg ttcg    74

<210> SEQ ID NO 155
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gcaaagcgga ttatgaaaaa cataaagtgt atgcgtgcga agtgacccat caaggtctga    60
gcagcccggt g    71

<210> SEQ ID NO 156
<211> LENGTH: 57
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 156
ggcatgctta tcaggcctcg ccacgattaa aagatttagt caccgggctg ctcagac        57

<210> SEQ ID NO 157
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggcgtctaga ggccaaggca ccctggtgac ggttagctca gcgtcgac                  48

<210> SEQ ID NO 158
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gtgcttttgc tgctcggagc cagcggaaac acgcttggac ctttggtcga cgctgagcta    60
acc                                                                   63

<210> SEQ ID NO 159
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ctccgagcag caaaagcacc agcggcggca cggctgccct gggctgcctg gttaaagatt    60
atttcc                                                                66

<210> SEQ ID NO 160
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ctggtcagcg ccccgctgtt ccagctcacg gtgactggtt ccgggaaata atctttaacc    60
aggca                                                                 65

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
agcggggcgc tgaccagcgg cgtgcatacc tttccggcgg tgctgcaaag cagcggcctg    60
```

<210> SEQ ID NO 162
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gtgcctaagc tgctgctcgg cacggtcaca acgctgctca ggctatacag gccgctgctt    60
tgcag                                                                65

<210> SEQ ID NO 163
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gagcagcagc ttaggcactc agacctatat ttgcaacgtg aaccataaac cgagcaacac    60
c                                                                    61

<210> SEQ ID NO 164
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gcgcgaattc gcttttcggt tccactttt tatccacttt ggtgttgctc ggtttatgg     59

<210> SEQ ID NO 165
<211> LENGTH: 333
<212> TYPE: DNA
<213> ORGANISM: Artificial Sequence
<220> FEATURE:
<223> OTHER INFORMATION: Description of Artificial Sequence: Synthetic C
      kappa gene sequence
<220> FEATURE:
<221> NAME/KEY: CDS
<222> LOCATION: (7)..(321)

<400> SEQUENCE: 165 cgtacg gtg gct gct ccg agc gtg ttt att ttt ccg ccg agc gat gaa        48
       Val Ala Ala Pro Ser Val Phe Ile Phe Pro Pro Ser Asp Glu
         1               5                  10 caa ctg aaa agc ggc acg gcg agc gtg gtg tgc ctg ctg aac aac ttt       96
Gln Leu Lys Ser Gly Thr Ala Ser Val Val Cys Leu Leu Asn Asn Phe
 15                  20                  25                  30 tat ccg cgt gaa gcg aaa gtt cag tgg aaa gta gac aac gcg ctg caa      144
Tyr Pro Arg Glu Ala Lys Val Gln Trp Lys Val Asp Asn Ala Leu Gln
                 35                  40                  45 agc ggc aac agc cag gaa agc gtg acc gaa cag gat agc aaa gat agc      192
Ser Gly Asn Ser Gln Glu Ser Val Thr Glu Gln Asp Ser Lys Asp Ser
             50                  55                  60 acc tat tct ctg agc agc acc ctg acc ctg agc aaa gcg gat tat gaa      240
Thr Tyr Ser Leu Ser Ser Thr Leu Thr Leu Ser Lys Ala Asp Tyr Glu
         65                  70                  75 aaa cat aaa gtg tat gcg tgc gaa gtg acc cat caa ggt ctg agc agc      288
Lys His Lys Val Tyr Ala Cys Glu Val Thr His Gln Gly Leu Ser Ser

```
                80                  85                  90
ccg gtg act aaa tct ttt aat cgt ggc gag gcc tgataagcat gc        333
Pro Val Thr Lys Ser Phe Asn Arg Gly Glu Ala
 95                 100                 105
```

<210> SEQ ID NO 166
<211> LENGTH: 105
<212> TYPE: PRT
<213> ORGANISM: Artificial Sequence
<220> FEATURE:
<223> OTHER INFORMATION: Description of Artificial Sequence: Synthetic C
      kappa gene sequence

<400> SEQUENCE: 166

```
Val Ala Ala Pro Ser Val Phe Ile Phe Pro Ser Asp Glu Gln Leu
 1               5                  10                  15

Lys Ser Gly Thr Ala Ser Val Val Cys Leu Leu Asn Asn Phe Tyr Pro
                20                  25                  30

Arg Glu Ala Lys Val Gln Trp Lys Val Asp Asn Ala Leu Gln Ser Gly
            35                  40                  45

Asn Ser Gln Glu Ser Val Thr Glu Gln Asp Ser Lys Asp Ser Thr Tyr
         50                 55                  60

Ser Leu Ser Ser Thr Leu Thr Leu Ser Lys Ala Asp Tyr Glu Lys His
 65                 70                  75                  80

Lys Val Tyr Ala Cys Glu Val Thr His Gln Gly Leu Ser Ser Pro Val
                85                  90                  95

Thr Lys Ser Phe Asn Arg Gly Glu Ala
                100                 105
```

<210> SEQ ID NO 167
<211> LENGTH: 327
<212> TYPE: DNA
<213> ORGANISM: Artificial Sequence
<220> FEATURE:
<223> OTHER INFORMATION: Description of Artificial Sequence: Synthetic
      CH1 gene sequence
<220> FEATURE:
<221> NAME/KEY: CDS
<222> LOCATION: (6)..(317)

<400> SEQUENCE: 167

```
gctca gcg tcg acc aaa ggt cca agc gtg ttt ccg ctg gct ccg agc agc        50
      Ala Ser Thr Lys Gly Pro Ser Val Phe Pro Leu Ala Pro Ser Ser
       1               5                  10                  15 aaa agc acc agc ggc ggc acg gct gcc ctg ggc tgc ctg gtt aaa gat         98
Lys Ser Thr Ser Gly Gly Thr Ala Ala Leu Gly Cys Leu Val Lys Asp
                20                  25                  30 tat ttc ccg gaa cca gtc acc gtg agc tgg aac agc ggg gcg ctg acc        146
Tyr Phe Pro Glu Pro Val Thr Val Ser Trp Asn Ser Gly Ala Leu Thr
            35                  40                  45 agc ggc gtg cat acc ttt ccg gcg gtg ctg caa agc agc ggc ctg tat        194
Ser Gly Val His Thr Phe Pro Ala Val Leu Gln Ser Ser Gly Leu Tyr
         50                 55                  60 agc ctg agc agc gtt gtg acc gtg ccg agc agc agc tta ggc act cag        242
Ser Leu Ser Ser Val Val Thr Val Pro Ser Ser Ser Leu Gly Thr Gln
 65                 70                  75 acc tat att tgc aac gtg aac cat aaa ccg agc aac acc aaa gtg gat        290
Thr Tyr Ile Cys Asn Val Asn His Lys Pro Ser Asn Thr Lys Val Asp
                80                  85                  90                  95 aaa aaa gtg gaa ccg aaa agc gaa ttc tgataagctt                         327
Lys Lys Val Glu Pro Lys Ser Glu Phe
                100
```

<210> SEQ ID NO 168
<211> LENGTH: 104
<212> TYPE: PRT
<213> ORGANISM: Artificial Sequence
<220> FEATURE:
<223> OTHER INFORMATION: Description of Artificial Sequence: Synthetic
      CH1 gene sequence

<400> SEQUENCE: 168

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Glu Phe
            100
```

<210> SEQ ID NO 169
<211> LENGTH: 408
<212> TYPE: DNA
<213> ORGANISM: Artificial Sequence
<220> FEATURE:
<223> OTHER INFORMATION: Description of Artificial Sequence: Synthetic
      C lambda gene segment
<220> FEATURE:
<221> NAME/KEY: CDS
<222> LOCATION: (85)..(396)

<400> SEQUENCE: 169

```
gaagacgaag cggattatta ttgccagcag cattatacca ccccgcctgt gtttggcggc      60
ggcacgaagt taaccgttct tggc cag ccg aaa gcc gca ccg agt gtg acg       111
                          Gln Pro Lys Ala Ala Pro Ser Val Thr
                            1               5 ctg ttt ccg ccg agc agc gaa gaa ttg cag gcg aac aaa gcg acc ctg      159
Leu Phe Pro Pro Ser Ser Glu Glu Leu Gln Ala Asn Lys Ala Thr Leu
 10                  15                  20                  25 gtg tgc ctg att agc gac ttt tat ccg gga gcc gtg aca gtg gcc tgg      207
Val Cys Leu Ile Ser Asp Phe Tyr Pro Gly Ala Val Thr Val Ala Trp
                30                  35                  40 aag gca gat agc agc ccc gtc aag gcg gga gtg gag acc acc aca ccc      255
Lys Ala Asp Ser Ser Pro Val Lys Ala Gly Val Glu Thr Thr Thr Pro
            45                  50                  55 tcc aaa caa agc aac aac aag tac gcg gcc agc agc tat ctg agc ctg      303
Ser Lys Gln Ser Asn Asn Lys Tyr Ala Ala Ser Ser Tyr Leu Ser Leu
        60                  65                  70 acg cct gag cag tgg aag tcc cac aga agc tac agc tgc cag gtc acg      351
Thr Pro Glu Gln Trp Lys Ser His Arg Ser Tyr Ser Cys Gln Val Thr
    75                  80                  85 cat gag ggg agc acc gtg gaa aaa acc gtt gcg ccg act gag gcc           396
His Glu Gly Ser Thr Val Glu Lys Thr Val Ala Pro Thr Glu Ala
 90                  95                  100 tgataagcat gc                                                          408
```

<210> SEQ ID NO 170
<211> LENGTH: 104
<212> TYPE: PRT
<213> ORGANISM: Artificial Sequence
<220> FEATURE:
<223> OTHER INFORMATION: Description of Artificial Sequence: Synthetic
      C lambda gene segment

<400> SEQUENCE: 170

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Ser Ser Pro Val
         35                  40                  45

Lys Ala Gly Val Glu Thr Thr Thr Pro Ser Lys Gln Ser Asn Asn Lys
     50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Ala
            100

<210> SEQ ID NO 171
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gaagacaagc ggattattat tgccagcagc attataccac cccgcctgtg tttggcggcg     60
gcacgaagtt aaccgttc                                                   78

<210> SEQ ID NO 172
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
caattcttcg ctgctcggcg gaaacagcgt cacactcggt gcggctttcg gctggccaag     60
aacggttaac ttcgtgccgc                                                 80

<210> SEQ ID NO 173
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cgccgagcag cgaagaattg caggcgaaca aagcgaccct ggtgtgcctg attagcgact     60
tttatccggg agccgtgaca                                                 80

<210> SEQ ID NO 174

```
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tgtttggagg gtgtggtggt ctccactccc gccttgacgg ggctgctatc tgccttccag     60
gccactgtca cggctcccgg                                                  80

<210> SEQ ID NO 175
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ccacaccctc caaacaaagc aacaacaagt acgcggccag cagctatctg agcctgacgc     60
ctgagcagtg gaagtcccac agaagctaca gctg                                  94

<210> SEQ ID NO 176
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gcatgcttat caggcctcag tcggcgcaac ggttttttcc acggtgctcc cctcatgcgt     60
gacctggcag ctgtagcttc                                                  80

<210> SEQ ID NO 177
<211> LENGTH: 843
<212> TYPE: DNA
<213> ORGANISM: Artificial Sequence
<220> FEATURE:
<223> OTHER INFORMATION: Description of Artificial Sequence: Synthetic
      single chain  fragment VH3-V kappa 2
<220> FEATURE:
<221> NAME/KEY: CDS
<222> LOCATION: (1)..(843)

<400> SEQUENCE: 177 atg aaa caa agc act att gca ctg gca ctc tta ccg ttg ctc ttc acc        48
Met Lys Gln Ser Thr Ile Ala Leu Ala Leu Leu Pro Leu Leu Phe Thr
 1               5                  10                  15 cct gtt acc aaa gcc gac tac aaa gat gaa gtg caa ttg gtg gaa agc        96
Pro Val Thr Lys Ala Asp Tyr Lys Asp Glu Val Gln Leu Val Glu Ser
             20                  25                  30 ggc ggc ggc ctg gtg caa ccg ggc ggc agc ctg cgt ctg agc tgc gcg       144
Gly Gly Gly Leu Val Gln Pro Gly Gly Ser Leu Arg Leu Ser Cys Ala
         35                  40                  45 gcc tcc gga ttt acc ttt agc agc tat gcg atg agc tgg gtg cgc caa       192
Ala Ser Gly Phe Thr Phe Ser Ser Tyr Ala Met Ser Trp Val Arg Gln
     50                  55                  60 gcc cct ggg aag ggt ctc gag tgg gtg agc gcg att agc ggt agc ggc       240
Ala Pro Gly Lys Gly Leu Glu Trp Val Ser Ala Ile Ser Gly Ser Gly
 65                  70                  75                  80 ggc agc acc tat tat gcg gat agc gtg aaa ggc cgt ttt acc att tca       288
Gly Ser Thr Tyr Tyr Ala Asp Ser Val Lys Gly Arg Phe Thr Ile Ser
```

```
                                85                     90                     95
cgt gat aat tcg aaa aac acc ctg tat ctg caa atg aac agc ctg cgt      336
Arg Asp Asn Ser Lys Asn Thr Leu Tyr Leu Gln Met Asn Ser Leu Arg
            100                 105                 110 gcg gaa gat acg gcc gtg tat tat tgc gcg cgt tgg ggc ggc gat ggc      384
Ala Glu Asp Thr Ala Val Tyr Tyr Cys Ala Arg Trp Gly Gly Asp Gly
            115                 120                 125 ttt tat gcg atg gat tat tgg ggc caa ggc acc ctg gtg acg gtt agc      432
Phe Tyr Ala Met Asp Tyr Trp Gly Gln Gly Thr Leu Val Thr Val Ser
    130                 135                 140 tca gcg ggt ggc ggt tct ggc ggc ggt ggg agc ggt ggc ggt ggt tct      480
Ser Ala Gly Gly Gly Ser Gly Gly Gly Gly Ser Gly Gly Gly Gly Ser
145                 150                 155                 160 ggc ggt ggt ggt tcc gat atc gtg atg acc cag agc cca ctg agc ctg      528
Gly Gly Gly Gly Ser Asp Ile Val Met Thr Gln Ser Pro Leu Ser Leu
                165                 170                 175 cca gtg act ccg ggc gag cct gcg agc att agc tgc aga agc agc caa      576
Pro Val Thr Pro Gly Glu Pro Ala Ser Ile Ser Cys Arg Ser Ser Gln
            180                 185                 190 agc ctg ctg cat agc aac ggc tat aac tat ctg gat tgg tac ctt caa      624
Ser Leu Leu His Ser Asn Gly Tyr Asn Tyr Leu Asp Trp Tyr Leu Gln
        195                 200                 205 aaa cca ggt caa agc ccg cag cta tta att tat ctg ggc agc aac cgt      672
Lys Pro Gly Gln Ser Pro Gln Leu Leu Ile Tyr Leu Gly Ser Asn Arg
    210                 215                 220 gcc agt ggg gtc ccg gat cgt ttt agc ggc tct gga tcc ggc acc gat      720
Ala Ser Gly Val Pro Asp Arg Phe Ser Gly Ser Gly Ser Gly Thr Asp
225                 230                 235                 240 ttt acc ctg aaa att agc cgt gtg gaa gct gaa gac gtg ggc gtg tat      768
Phe Thr Leu Lys Ile Ser Arg Val Glu Ala Glu Asp Val Gly Val Tyr
                245                 250                 255 tat tgc cag cag cat tat acc acc ccg ccg acc ttt ggc cag ggt acg      816
Tyr Cys Gln Gln His Tyr Thr Thr Pro Pro Thr Phe Gly Gln Gly Thr
            260                 265                 270 aaa gtt gaa att aaa cgt acg gaa ttc                                  843
Lys Val Glu Ile Lys Arg Thr Glu Phe
        275                 280
```

<210> SEQ ID NO 178
<211> LENGTH: 281
<212> TYPE: PRT
<213> ORGANISM: Artificial Sequence
<220> FEATURE:
<223> OTHER INFORMATION: Description of Artificial Sequence: Synthetic
      single chain fragment VH3-V kappa 2

<400> SEQUENCE: 178

```
Met Lys Gln Ser Thr Ile Ala Leu Ala Leu Leu Pro Leu Leu Phe Thr
1               5                   10                  15

Pro Val Thr Lys Ala Asp Tyr Lys Asp Glu Val Gln Leu Val Glu Ser
            20                  25                  30

Gly Gly Gly Leu Val Gln Pro Gly Gly Ser Leu Arg Leu Ser Cys Ala
        35                  40                  45

Ala Ser Gly Phe Thr Phe Ser Ser Tyr Ala Met Ser Trp Val Arg Gln
    50                  55                  60

Ala Pro Gly Lys Gly Leu Glu Trp Val Ser Ala Ile Ser Gly Ser Gly
65                  70                  75                  80

Gly Ser Thr Tyr Tyr Ala Asp Ser Val Lys Gly Arg Phe Thr Ile Ser
                85                  90                  95
```

```
Arg Asp Asn Ser Lys Asn Thr Leu Tyr Leu Gln Met Asn Ser Leu Arg
            100                 105                 110

Ala Glu Asp Thr Ala Val Tyr Tyr Cys Ala Arg Trp Gly Gly Asp Gly
        115                 120                 125

Phe Tyr Ala Met Asp Tyr Trp Gly Gln Gly Thr Leu Val Thr Val Ser
    130                 135                 140

Ser Ala Gly Gly Ser Gly Gly Gly Ser Gly Gly Gly Gly Ser
145                 150                 155                 160

Gly Gly Gly Ser Asp Ile Val Met Thr Gln Ser Pro Leu Ser Leu
            165                 170                 175

Pro Val Thr Pro Gly Glu Pro Ala Ser Ile Ser Cys Arg Ser Ser Gln
            180                 185                 190

Ser Leu Leu His Ser Asn Gly Tyr Asn Tyr Leu Asp Trp Tyr Leu Gln
        195                 200                 205

Lys Pro Gly Gln Ser Pro Gln Leu Leu Ile Tyr Leu Gly Ser Asn Arg
    210                 215                 220

Ala Ser Gly Val Pro Asp Arg Phe Ser Gly Ser Gly Ser Gly Thr Asp
225                 230                 235                 240

Phe Thr Leu Lys Ile Ser Arg Val Glu Ala Glu Asp Val Gly Val Tyr
            245                 250                 255

Tyr Cys Gln Gln His Tyr Thr Thr Pro Pro Thr Phe Gly Gln Gly Thr
        260                 265                 270

Lys Val Glu Ile Lys Arg Thr Glu Phe
    275                 280

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Cys Ala Arg Trp Gly Gly Asp Gly Phe Tyr Ala Met Asp Tyr Trp
1               5                   10                  15

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Cys Ala Arg Phe Gly Lys Met Asn Tyr Asp Tyr Trp
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Cys Ala Arg His Arg Thr Glu Trp His Asp Tyr Trp
1               5                   10
```

```
<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Ala Arg Val Arg Glu Leu Tyr His Asp Tyr Trp
 1               5                  10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Ala Arg Lys Phe Leu Lys Ala Arg Asp Tyr Trp
 1               5                  10

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Ala Arg Trp Asn Thr Thr Gly Tyr Asp Tyr Trp
 1               5                  10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Cys Ala Arg Ile Asn Glu Ala Gln Pro Asp Tyr Trp
 1               5                  10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Ala Arg Thr Ala Ile Thr Arg Asp Tyr Trp
 1               5                  10

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187
```

-continued

Cys Ala Arg Trp Tyr Asn Arg Asn Ser Asp Tyr Trp
 1               5                  10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Ala Arg Ser Val Gly Asp Ser Lys Asp Tyr Trp
 1               5                  10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Cys Ala Arg Ser Lys Thr Phe Ala Ala Asp Tyr Trp
 1               5                  10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Cys Ala Arg Val Ala Pro Gln Tyr Asp Tyr Trp
 1               5                  10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Cys Ala Arg Met Gln Ser Glu Trp Met Asp Tyr Trp
 1               5                  10

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Cys Ala Arg Tyr Phe Val His Phe Leu Tyr Thr Met Val Met Asp Val
 1               5                  10                  15

Trp

<210> SEQ ID NO 193
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Ala Arg Met Ala Leu Arg Ala Ser Gly Lys Tyr Ile Met Asp Val
 1               5                  10                  15

Trp

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Ala Arg Lys Asn Gln Met Val Phe His Ala Arg Lys Phe Asp Val
 1               5                  10                  15

Trp

<210> SEQ ID NO 195
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Cys Ala Arg Thr Gln Ser Phe Trp Glu Gln Gln Lys Val Met Asp Tyr
 1               5                  10                  15

Trp

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Ala Arg Tyr Pro Tyr Arg Ser Asn Phe Phe Met Pro Met Asp Val
 1               5                  10                  15

Trp

<210> SEQ ID NO 197
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Cys Ala Arg Gly Ser Gly Ser Glu His Trp Ser Ile Phe Asp Val Trp
 1               5                  10                  15

<210> SEQ ID NO 198
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 198

Cys Ala Arg Arg Asn Pro Trp Asn Val Asn Tyr Leu His Phe Asp Val
1               5                   10                  15

Trp

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Cys Ala Arg Met Lys Pro Met Leu Asn Arg Asp Gly Thr Met Asp Val
1               5                   10                  15

Trp

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Cys Ala Arg Lys Gly Ser Glu Phe Leu Glu Thr Asp Val Met Asp Tyr
1               5                   10                  15

Trp

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Cys Ala Arg Ser Trp Thr Asn Asp Lys Pro Asn Phe Ile Met Asp Val
1               5                   10                  15

Trp

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Cys Ala Arg Tyr Ala Gly Thr Thr Phe Lys Gln Gly Pro Met Asp Tyr
1               5                   10                  15

Trp

<210> SEQ ID NO 203
<211> LENGTH: 17
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Cys Ala Arg Lys Arg Met Met Gln Asn Pro Arg Phe Arg Phe Asp Val
 1               5                  10                  15

Trp

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Cys Ala Arg Arg Ser Lys Gln Lys Arg Lys Met Arg Phe Asp Val
 1               5                  10                  15

Trp

<210> SEQ ID NO 205
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Ala Arg Arg Asn Gly Lys Arg His Leu Arg His Arg Phe Asp Val
 1               5                  10                  15

Trp

<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Cys Ala Arg Arg Lys Met Arg Lys Arg Ile Lys Arg Arg Phe Asp Val
 1               5                  10                  15

Trp

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Cys Ala Arg Tyr Arg Lys Ile Met Lys Trp Lys Asn Ser Phe Asp Val
 1               5                  10                  15

Trp

<210> SEQ ID NO 208

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Cys Ala Arg Leu Ile Glu Val His Pro Ser Phe Asp Gln Met Asp Val
 1               5                  10                  15

Trp

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Cys Ala Arg Arg Lys Pro Met Phe Leu Lys Lys Ala Val Phe Asp Val
 1               5                  10                  15

Trp

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Cys Ala Arg Arg Lys Phe His Arg Tyr Ser Thr Val Lys Phe Asp Tyr
 1               5                  10                  15

Trp

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Cys Ala Arg Arg Lys Thr Met Arg Ser Arg Val Lys Tyr Phe Asp Tyr
 1               5                  10                  15

Trp

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Cys Ala Arg Lys Lys Arg Ser Trp Arg Arg Met Asp Arg Phe Asp Val
 1               5                  10                  15

Trp
```

```
<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Ala Arg Arg Asn Pro Arg Arg Gly Arg Met Asn Arg Phe Asp Val
 1               5                  10                  15

Trp

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Cys Ala Arg Lys Gly Lys Lys Lys Phe Ala Arg Pro Arg Phe Asp Val
 1               5                  10                  15

Trp

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Cys Ala Arg Arg Met Val His Lys Gly Lys Arg Lys Ile Phe Asp Val
 1               5                  10                  15

Trp

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Cys Ala Arg Arg Lys His Ile Thr Tyr Pro Arg Lys Gln Phe Asp Val
 1               5                  10                  15

Trp

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Cys Ala Arg Arg Trp Thr Lys Arg Arg Ser Phe Ala Arg Phe Asp Val
 1               5                  10                  15

Trp
```

```
<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Cys Ala Arg Lys Lys Leu Lys Gln Tyr Thr Phe Ser Arg Phe Asp Tyr
 1               5                  10                  15

Trp

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Cys Ala Arg Thr Arg Pro Trp Gln Ala Thr Arg Lys Gly Phe Asp Val
 1               5                  10                  15

Trp

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Cys Ala Arg Asn Gln Trp Glu Phe Lys Asn Arg Arg Lys Met Asp Tyr
 1               5                  10                  15

Trp

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Cys Ala Arg Lys Arg Trp Met Trp Pro Ile Gly Lys Arg Phe Asp Tyr
 1               5                  10                  15

Trp

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Cys Ala Arg Tyr Ser Leu Trp Arg Leu Asp Glu Tyr Phe Phe Asp Tyr
 1               5                  10                  15

Trp
```

```
<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Cys Ala Arg Val Pro Trp Gly Asp Phe Trp Ser Trp His Met Asp Val
  1               5                  10                  15

Trp

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Cys Ala Arg Asn Gly Leu Glu Pro Arg His Arg Lys Met Met Asp Tyr
  1               5                  10                  15

Trp

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Cys Ala Arg Ile Met Lys Ala Pro Pro Asp Tyr Trp
  1               5                  10

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Cys Ala Arg Arg Lys Thr Trp His Trp Phe Tyr Lys Arg Met Asp Tyr
  1               5                  10                  15

Trp

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Cys Ala Arg Trp Lys Asp Met Trp Ser Gln Val Tyr Val Met Asp Tyr
  1               5                  10                  15

Trp
```

-continued

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Cys Ala Arg Asn Lys Gln Gln Met Arg Phe Arg Arg Phe Met Asp Tyr
 1               5                  10                  15

Trp

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Cys Ala Arg Asn Met Leu Ala Leu Ser Arg Gly Lys Glu Met Asp Val
 1               5                  10                  15

Trp

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Cys Ala Arg Asn Met Arg Leu Met Arg Met Arg Lys Asn Phe Asp Val
 1               5                  10                  15

Trp

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Cys Ala Arg Tyr Ile Lys Gln Ala Lys Arg Lys Leu Ala Phe Asp Tyr
 1               5                  10                  15

Trp

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Cys Ala Arg Tyr Asn Arg His Ala Trp Gln Lys Met Gln Phe Asp Tyr
 1               5                  10                  15

Trp

-continued

```
<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Ala Arg Tyr Val Lys Tyr Ala Arg Asn Lys Met Gln Phe Asp Tyr
 1               5                  10                  15

Trp

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Ala Arg Tyr Lys Arg Gly Ala Trp Met Lys Thr Met Phe Asp Val
 1               5                  10                  15

Trp

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Cys Ala Arg Arg Lys Pro Leu Arg Arg Ile Met Lys Trp Phe Asp Tyr
 1               5                  10                  15

Trp

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Cys Ala Arg Tyr Arg Lys Arg Ala Ser Arg Gln Met Gln Phe Asp Tyr
 1               5                  10                  15

Trp

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Cys Ala Arg Gln Arg Tyr Arg Ser Lys Ile Lys Gly His Phe Asp Val
 1               5                  10                  15
```

-continued

Trp

<210> SEQ ID NO 238
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Cys Ala Arg Trp Arg Asp Phe Asn Ser Tyr Asp Pro Met Asp Tyr Trp
1               5                   10                  15

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Cys Ala Arg Met Ala Asp Leu Asp Asn Tyr Trp Val Gln Phe Asp Tyr
1               5                   10                  15

Trp

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Cys Ala Arg Leu Gln Ala Tyr Leu Lys Pro His His Trp Met Asp Tyr
1               5                   10                  15

Trp

<210> SEQ ID NO 241
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Ala Arg Arg Leu Ile Glu Gln Ala Arg Asp His Val Met Asp Tyr
1               5                   10                  15

Trp

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Cys Ala Arg Ser Trp His Asn Ser Gln Phe Thr Gln Ser Phe Asp Val
1               5                   10                  15

Trp

```
<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Cys Ala Arg Val Asp His Phe Gln Thr Glu Asn Glu Trp Met Asp Tyr
 1               5                  10                  15

Trp

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Cys Ala Arg Asp Trp Pro Thr Leu Ile Phe Trp Tyr Trp Phe Asp Tyr
 1               5                  10                  15

Trp

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Cys Ala Arg Gly Phe Gly Phe Thr Glu Asp Tyr Trp
 1               5                  10

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Cys Ala Arg Gln Phe Asp Glu Asp Ser Phe Val Arg Arg Phe Asp Val
 1               5                  10                  15

Trp

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Cys Ala Arg Ile Leu Lys Glu Ser Ser Lys Ser Arg Gln Met Asp Val
 1               5                  10                  15

Trp
```

```
<210> SEQ ID NO 248
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Ala Arg Glu Gln Asp Glu Tyr Gly Ala Ile Arg Ile Met Asp Tyr
 1               5                  10                  15

Trp

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Cys Ala Arg Asn His Phe Glu Ala Ser Trp Pro Arg Arg Gln Met Asp
 1               5                  10                  15

Val Trp

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Ala Arg Glu Asn Glu Trp Val Asp Met Ile Leu Asp Met Asp Tyr
 1               5                  10                  15

Trp

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Ala Arg Gln Tyr Ser Glu Thr Arg Trp Val Arg Lys Phe Asp Tyr
 1               5                  10                  15

Trp

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Cys Ala Arg Gln Phe Lys Glu Ser Lys Thr Arg Arg Lys Phe Asp Val
 1               5                  10                  15

Trp
```

<210> SEQ ID NO 253
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Cys Ala Arg Lys Lys Thr Gln Tyr Val His Asp Trp Arg Met Asp Val
 1               5                  10                  15

Trp

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Cys Ala Arg Arg Trp Arg Glu Thr Lys Ser Lys Arg Phe Phe Asp Val
 1               5                  10                  15

Trp

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Cys Ala Arg Asp Tyr Ile Met Glu Phe Asp Tyr Trp
 1               5                  10

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Cys Ala Arg Gln Phe Glu Glu Thr Lys Gln Arg Arg Leu Met Asp Tyr
 1               5                  10                  15

Trp

<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Cys Ala Arg Asp Gln Gly Phe Tyr Ala Ile Asp Tyr Val Met Asp Tyr
 1               5                  10                  15

Trp

```
<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Ala Arg Val Phe Thr Tyr Met Tyr Asn Tyr Phe Arg Phe Asp Val
1               5                   10                  15

Trp

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Cys Ala Arg Val Phe Phe Glu Gln Met Glu Val Val Arg Met Asp Val
1               5                   10                  15

Trp

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Cys Ala Arg Glu Lys Glu Tyr Arg Leu Ser Trp Ser Gln Met Asp Tyr
1               5                   10                  15

Trp

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Ala Arg Tyr Pro Ser Arg Trp Ala Pro Asn Trp Tyr Met Asp Tyr
1               5                   10                  15

Trp

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Ala Arg Asp Gly Gly Phe Lys Pro Leu Thr His Phe Phe Asp Val
1               5                   10                  15

Trp
```

<210> SEQ ID NO 263
<211> LENGTH: 143
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 263

```
acatgtaagc ttcccccccc ccttaattaa cccccccccc tgtacaccccc ccccccgcta      60 gccccccccc ccagatctcc cccccccccga cgtccccccct ctagaccccc ccccccgcatg    120 cccccccccc cgaattcgac gtc                                               143
```

<210> SEQ ID NO 264
<211> LENGTH: 1947
<212> TYPE: DNA
<213> ORGANISM: Artificial Sequence
<220> FEATURE:
<223> OTHER INFORMATION: Description of Artificial Sequence: Synthetic
      vector
<220> FEATURE:
<221> NAME/KEY: CDS
<222> LOCATION: (132)..(989)

<400> SEQUENCE: 264

```
caggtggcac ttttcgggga aatgtgcgcg gaacccctat ttgtttattt ttctaaatac       60
attcaaatat gtatccgctc atgagacaat aaccctgata aatgcttcaa taatattgaa      120
aaaggaagag t atg agt att caa cat ttc cgt gtc gcc ctt att ccc ttt       170
             Met Ser Ile Gln His Phe Arg Val Ala Leu Ile Pro Phe
               1               5                  10 ttt gcg gca ttt tgc ctt cct gtt ttt gct cac cca gaa acg ctg gtg        218
Phe Ala Ala Phe Cys Leu Pro Val Phe Ala His Pro Glu Thr Leu Val
         15                  20                  25 aaa gta aaa gat gct gaa gat cag ttg ggt gca cga gtg ggt tac atc        266
Lys Val Lys Asp Ala Glu Asp Gln Leu Gly Ala Arg Val Gly Tyr Ile
 30                  35                  40                  45 gaa ctg gat ctc aac agc ggt aag atc ctt gag agt ttt cgc ccc gaa        314
Glu Leu Asp Leu Asn Ser Gly Lys Ile Leu Glu Ser Phe Arg Pro Glu
                 50                  55                  60 gaa cgt ttt cca atg atg agc act ttt aaa gtt ctg cta tgt ggc gcg        362
Glu Arg Phe Pro Met Met Ser Thr Phe Lys Val Leu Leu Cys Gly Ala
             65                  70                  75 gta tta tcc cgt att gac gcc ggg caa gag caa ctc ggt cgc cgc ata        410
Val Leu Ser Arg Ile Asp Ala Gly Gln Glu Gln Leu Gly Arg Arg Ile
         80                  85                  90 cac tat tct cag aat gac ttg gtt gag tac tca cca gtc aca gaa aag        458
His Tyr Ser Gln Asn Asp Leu Val Glu Tyr Ser Pro Val Thr Glu Lys
     95                 100                 105 cat ctt acg gat ggc atg aca gta aga gaa tta tgc agt gct gcc ata        506
His Leu Thr Asp Gly Met Thr Val Arg Glu Leu Cys Ser Ala Ala Ile
110                 115                 120                 125 acc atg agt gat aac act gcg gcc aac tta ctt ctg aca acg atc gga        554
Thr Met Ser Asp Asn Thr Ala Ala Asn Leu Leu Leu Thr Thr Ile Gly
                130                 135                 140 gga ccg aag gag cta acc gct ttt ttg cac aac atg ggg gat cat gta        602
Gly Pro Lys Glu Leu Thr Ala Phe Leu His Asn Met Gly Asp His Val
            145                 150                 155 act cgc ctt gat cgt tgg gaa ccg gag ctg aat gaa gcc ata cca aac        650
Thr Arg Leu Asp Arg Trp Glu Pro Glu Leu Asn Glu Ala Ile Pro Asn
        160                 165                 170
```

-continued

```
gac gag cgt gac acc acg atg cct gta gca atg gca aca acg ttg cgc      698
Asp Glu Arg Asp Thr Thr Met Pro Val Ala Met Ala Thr Thr Leu Arg
    175                 180                 185 aaa cta tta act ggc gaa cta ctt act cta gct tcc cgg caa caa tta      746
Lys Leu Leu Thr Gly Glu Leu Leu Thr Leu Ala Ser Arg Gln Gln Leu
190                 195                 200                 205 ata gac tgg atg gag gcg gat aaa gtt gca gga cca ctt ctg cgc tcg      794
Ile Asp Trp Met Glu Ala Asp Lys Val Ala Gly Pro Leu Leu Arg Ser
                210                 215                 220 gcc ctt ccg gct ggc tgg ttt att gct gat aaa tct gga gcc ggt gag      842
Ala Leu Pro Ala Gly Trp Phe Ile Ala Asp Lys Ser Gly Ala Gly Glu
            225                 230                 235 cgt ggg tct cgc ggt atc att gca gca ctg ggg cca gat ggt aag ccc      890
Arg Gly Ser Arg Gly Ile Ile Ala Ala Leu Gly Pro Asp Gly Lys Pro
        240                 245                 250 tcc cgt atc gta gtt atc tac acg acg ggg agt cag gca act atg gat      938
Ser Arg Ile Val Val Ile Tyr Thr Thr Gly Ser Gln Ala Thr Met Asp
    255                 260                 265 gaa cga aat aga cag atc gct gag ata ggt gcc tca ctg att aag cat      986
Glu Arg Asn Arg Gln Ile Ala Glu Ile Gly Ala Ser Leu Ile Lys His
270                 275                 280                 285 tgg       taactgtcag accaagttta ctcatatata ctttagattg atttaaaact   1039
Trp tcattttttaa tttaaaagga tctaggtgaa gatccttttt gataatctca tgaccaaaat  1099
cccttaacgt gagttttcgt tccactgagc gtcagacccc gtagaaaaga tcaaaggatc  1159
ttcttgagat cctttttttc tgcgcgtaat ctgctgcttg caaacaaaaa aaccaccgct  1219
accagcggtg gtttgtttgc cggatcaaga gctaccaact cttttttccga aggtaactgg  1279 cttcagcaga gcgcagatac caaatactgt ccttctagtg tagccgtagt taggccacca  1339
cttcaagaac tctgtagcac cgcctacata cctcgctctg ctaatcctgt taccagtggc  1399
tgctgccagt ggcgataagt cgtgtcttac cgggttggac tcaagacgat agttaccgga  1459
taaggcgcag cggtcgggct gaacggggggg ttcgtgcaca cagcccagct tggagcgaac  1519
gacctacacc gaactgagat acctacagcg tgagctatga gaaagcgcca cgcttcccga  1579
agggagaaag gcggacaggt atccggtaag cggcagggtc ggaacaggag agcgcacgag  1639
ggagcttcca gggggaaacg cctggtatct ttatagtcct gtcgggtttc gccacctctg  1699
acttgagcgt cgatttttgt gatgctcgtc agggggggcgg agcctatgga aaaacgccag  1759
caacgcggcc ttttttacggt tcctggcctt ttgctggcct tttgctcaca tgtaagcttc  1819
ccccccccct taattaaccc ccccccctgt acaccccccc ccgctagcc cccccccca   1879 gatctccccc cccccgacgt cccccctcta gaccccccccc ccgcatgccc cccccccga   1939 attcacgt                                                          1947
```

<210> SEQ ID NO 265
<211> LENGTH: 286
<212> TYPE: PRT
<213> ORGANISM: Artificial Sequence
<220> FEATURE:
<223> OTHER INFORMATION: Description of Artificial Sequence: Synthetic vector

<400> SEQUENCE: 265

Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys

```
                        20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Ile His Tyr Ser
                85                  90                  95

Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
        275                 280                 285

<210> SEQ ID NO 266
<211> LENGTH: 142
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 266
gacgtcttaa tgtgagttag ctcactcatt aggcacccca ggctttacac tttatgcttc      60
cggctcgtat gttgtgtgga attgtgagcg gataacaatt tcacacagga aacagctatg     120
accatgatta cgaatttcta ga                                              142

<210> SEQ ID NO 267
<211> LENGTH: 520
<212> TYPE: DNA
<213> ORGANISM: Artificial Sequence
<220> FEATURE:
<223> OTHER INFORMATION: Description of Artificial Sequence: Synthetic
      vector
<220> FEATURE:
<221> NAME/KEY: CDS
<222> LOCATION: (1)..(510)
```

-continued

```
<400> SEQUENCE: 267 gaa ttc gag cag aag ctg atc tct gag gag gat ctg tag ggt ggt ggc      48
Glu Phe Glu Gln Lys Leu Ile Ser Glu Glu Asp Leu     Gly Gly Gly
 1               5                  10                      15 tct ggt tcc ggt gat ttt gat tat gaa aag atg gca aac gct aat aag      96
Ser Gly Ser Gly Asp Phe Asp Tyr Glu Lys Met Ala Asn Ala Asn Lys
             20                  25                  30 ggg gct atg acc gaa aat gcc gat gaa aac gcg cta cag tct gac gct     144
Gly Ala Met Thr Glu Asn Ala Asp Glu Asn Ala Leu Gln Ser Asp Ala
         35                  40                  45 aaa ggc aaa ctt gat tct gtc gct act gat tac ggt gct gct atc gat     192
Lys Gly Lys Leu Asp Ser Val Ala Thr Asp Tyr Gly Ala Ala Ile Asp
     50                  55                  60 ggt ttc att ggt gac gtt tcc ggc ctt gct aat ggt aat ggt gct act     240
Gly Phe Ile Gly Asp Val Ser Gly Leu Ala Asn Gly Asn Gly Ala Thr
 65                  70                  75 ggt gat ttt gct ggc tct aat tcc caa atg gct caa gtc ggt gac ggt     288
Gly Asp Phe Ala Gly Ser Asn Ser Gln Met Ala Gln Val Gly Asp Gly
 80                  85                  90                  95 gat aat tca cct tta atg aat aat ttc cgt caa tat tta cct tcc ctc     336
Asp Asn Ser Pro Leu Met Asn Asn Phe Arg Gln Tyr Leu Pro Ser Leu
                100                 105                 110 cct caa tcg gtt gaa tgt cgc cct ttt gtc ttt ggc gct ggt aaa cca     384
Pro Gln Ser Val Glu Cys Arg Pro Phe Val Phe Gly Ala Gly Lys Pro
            115                 120                 125 tat gaa ttt tct att gat tgt gac aaa ata aac tta ttc cgt ggt gtc     432
Tyr Glu Phe Ser Ile Asp Cys Asp Lys Ile Asn Leu Phe Arg Gly Val
        130                 135                 140 ttt gcg ttt ctt tta tat gtt gcc acc ttt atg tat gta ttt tct acg     480
Phe Ala Phe Leu Leu Tyr Val Ala Thr Phe Met Tyr Val Phe Ser Thr
    145                 150                 155 ttt gct aac ata ctg cgt aat aag gag tct tgataagctt                  520
Phe Ala Asn Ile Leu Arg Asn Lys Glu Ser
160                 165

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      vector

<400> SEQUENCE: 268

Glu Phe Glu Gln Lys Leu Ile Ser Glu Glu Asp Leu
 1               5                  10

<210> SEQ ID NO 269
<211> LENGTH: 123
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 269
gggggggggg aagcttgacc tgtgaagtga aaatggcgc agattgtgcg acatttttt      60 tgtctgccgt ttaattaaag ggggggggg gccggcctgg ggggggtgt acaggggggg     120 ggg                                                                 123

<210> SEQ ID NO 270
```

```
<211> LENGTH: 470
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 270
gctagcacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg gggcatccct ttagggttcc     180
gatttagtgc tttacggcac ctcgacccca aaaaacttga ttagggtgat ggttctcgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgtttacaat ttcatgtaca                470

<210> SEQ ID NO 271
<211> LENGTH: 733
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 271
agatctgacc aaaatccctt aacgtgagtt ttcgttccac tgagcgtcag accccgtaga      60
aaagatcaaa ggatcttctt gagatccttt ttttctgcgc gtaatctgct gcttgcaaac     120
aaaaaaacca ccgctaccag cggtggtttg tttgccggat caagagctac caactctttt     180
tccgaaggta actggctaca gcagagcgca gataccaaat actgttcttc tagtgtagcc     240
gtagttaggc caccacttca agaactctgt agcaccgcct acatacctcg ctctgctaat     300
cctgttacca gtggctgctg ccagtggcga taagtcgtgt cttaccgggt tggactcaag     360
acgatagtta ccggataagg cgcagcggtc gggctgaacg gggggttcgt gcacacagcc     420
cagcttggag cgaacgacct acaccgaact gagataccta cagcgtgagc tatgagaaag     480
cgccacgctt cccgaaggga gaaaggcgga caggtatccg gtaagcggca gggtcggaac     540
aggagagcgc acgagggagc ttccaggggg aaacgcctgg tatctttata gtcctgtcgg     600
gtttcgccac ctctgacttg agcgtcgatt tttgtgatgc tcgtcagggg ggcggagcct     660
atggaaaaac gccagcaacg cggccttttt acggttcctg gccttttgct ggccttttgc     720
tcacatggct agc                                                        733

<210> SEQ ID NO 272
<211> LENGTH: 813
<212> TYPE: DNA
<213> ORGANISM: Artificial Sequence
<220> FEATURE:
<223> OTHER INFORMATION: Description of Artificial Sequence: Synthetic
      vector
<220> FEATURE:
<221> NAME/KEY: CDS
<222> LOCATION: (102)..(758)

<400> SEQUENCE: 272
gggacgtcgg gtgaggttcc aactttcacc ataatgaaat aagatcacta ccggcgtat       60 tttttgagtt atcgagattt tcaggagcta aggaagctaa a atg gag aaa aaa atc    116
```

```
                        Met Glu Lys Lys Ile
                         1               5 act gga tat acc acc gtt gat ata tcc caa tgg cat cgt aaa gaa cat    164
Thr Gly Tyr Thr Thr Val Asp Ile Ser Gln Trp His Arg Lys Glu His
             10                  15                  20 ttt gag gca ttt cag tca gtt gct caa tgt acc tat aac cag acc gtt    212
Phe Glu Ala Phe Gln Ser Val Ala Gln Cys Thr Tyr Asn Gln Thr Val
         25                  30                  35 cag ctg gat att acg gcc ttt tta aag acc gta aag aaa aat aag cac    260
Gln Leu Asp Ile Thr Ala Phe Leu Lys Thr Val Lys Lys Asn Lys His
     40                  45                  50 aag ttt tat ccg gcc ttt att cac att ctt gcc cgc ctg atg aat gct    308
Lys Phe Tyr Pro Ala Phe Ile His Ile Leu Ala Arg Leu Met Asn Ala
 55                  60                  65 cac ccg gag ttc cgt atg gca atg aaa gac ggt gag ctg gtg ata tgg    356
His Pro Glu Phe Arg Met Ala Met Lys Asp Gly Glu Leu Val Ile Trp
 70                  75                  80                  85 gat agt gtt cac cct tgt tac acc gtt ttc cat gag caa act gaa acg    404
Asp Ser Val His Pro Cys Tyr Thr Val Phe His Glu Gln Thr Glu Thr
             90                  95                 100 ttt tca tcg ctc tgg agt gaa tac cac gac gat ttc cgg cag ttt cta    452
Phe Ser Ser Leu Trp Ser Glu Tyr His Asp Asp Phe Arg Gln Phe Leu
         105                 110                 115 cac ata tat tcg caa gat gtg gcg tgt tac ggt gaa aac ctg gcc tat    500
His Ile Tyr Ser Gln Asp Val Ala Cys Tyr Gly Glu Asn Leu Ala Tyr
     120                 125                 130 ttc cct aaa ggg ttt att gag aat atg ttt ttc gtc tca gcc aat ccc    548
Phe Pro Lys Gly Phe Ile Glu Asn Met Phe Phe Val Ser Ala Asn Pro
135                 140                 145 tgg gtg agt ttc acc agt ttt gat tta aac gta gcc aat atg gac aac    596
Trp Val Ser Phe Thr Ser Phe Asp Leu Asn Val Ala Asn Met Asp Asn
150                 155                 160                 165 ttc ttc gcc ccc gtt ttc act atg ggc aaa tat tat acg caa ggc gac    644
Phe Phe Ala Pro Val Phe Thr Met Gly Lys Tyr Tyr Thr Gln Gly Asp
             170                 175                 180 aag gtg ctg atg ccg ctg gcg att cag gtt cat cat gcc gtt tgt gat    692
Lys Val Leu Met Pro Leu Ala Ile Gln Val His His Ala Val Cys Asp
         185                 190                 195 ggc ttc cat gtc ggc aga atg ctt aat gaa tta caa cag tac tgc gat    740
Gly Phe His Val Gly Arg Met Leu Asn Glu Leu Gln Gln Tyr Cys Asp
     200                 205                 210 gag tgg cag ggc ggg gcg taatttttt aaggcagtta ttgggtgccc            788
Glu Trp Gln Gly Gly Ala
    215 ttaaacgcct ggtgctagat cttcc                                        813

<210> SEQ ID NO 273
<211> LENGTH: 219
<212> TYPE: PRT
<213> ORGANISM: Artificial Sequence
<220> FEATURE:
<223> OTHER INFORMATION: Description of Artificial Sequence: Synthetic
      vector

<400> SEQUENCE: 273

Met Glu Lys Lys Ile Thr Gly Tyr Thr Thr Val Asp Ile Ser Gln Trp
 1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
```

```
              35                  40                  45
Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

```
<210> SEQ ID NO 274
<211> LENGTH: 2755
<212> TYPE: DNA
<213> ORGANISM: Artificial Sequence
<220> FEATURE:
<223> OTHER INFORMATION: Description of Artificial Sequence: Synthetic
      vector
<220> FEATURE:
<221> NAME/KEY: CDS
<222> LOCATION: (3)..(509)

<400> SEQUENCE: 274 aa ttc gag cag aag ctg atc tct gag gag gat ctg tag ggt ggt ggc      47
   Phe Glu Gln Lys Leu Ile Ser Glu Glu Asp Leu     Gly Gly Gly
    1               5                  10 tct ggt tcc ggt gat ttt gat tat gaa aag atg gca aac gct aat aag     95
Ser Gly Ser Gly Asp Phe Asp Tyr Glu Lys Met Ala Asn Ala Asn Lys
 15                  20                  25                  30 ggg gct atg acc gaa aat gcc gat gaa aac gcg cta cag tct gac gct    143
Gly Ala Met Thr Glu Asn Ala Asp Glu Asn Ala Leu Gln Ser Asp Ala
                35                  40                  45 aaa ggc aaa ctt gat tct gtc gct act gat tac ggt gct gct atc gat    191
Lys Gly Lys Leu Asp Ser Val Ala Thr Asp Tyr Gly Ala Ala Ile Asp
         50                  55                  60 ggt ttc att ggt gac gtt tcc ggc ctt gct aat ggt aat ggt gct act    239
Gly Phe Ile Gly Asp Val Ser Gly Leu Ala Asn Gly Asn Gly Ala Thr
 65                  70                  75 ggt gat ttt gct ggc tct aat tcc caa atg gct caa gtc ggt gac ggt    287
Gly Asp Phe Ala Gly Ser Asn Ser Gln Met Ala Gln Val Gly Asp Gly
                 80                  85                  90 gat aat tca cct tta atg aat aat ttc cgt caa tat tta cct tcc ctc    335
Asp Asn Ser Pro Leu Met Asn Asn Phe Arg Gln Tyr Leu Pro Ser Leu
 95                 100                 105                 110 cct caa tcg gtt gaa tgt cgc cct ttt gtc ttt ggc gct ggt aaa cca    383
Pro Gln Ser Val Glu Cys Arg Pro Phe Val Phe Gly Ala Gly Lys Pro
```

-continued

```
                115                 120                 125
tat gaa ttt tct att gat tgt gac aaa ata aac tta ttc cgt ggt gtc    431
Tyr Glu Phe Ser Ile Asp Cys Asp Lys Ile Asn Leu Phe Arg Gly Val
            130                 135                 140 ttt gcg ttt ctt tta tat gtt gcc acc ttt atg tat gta ttt tct acg    479
Phe Ala Phe Leu Leu Tyr Val Ala Thr Phe Met Tyr Val Phe Ser Thr
        145                 150                 155 ttt gct aac ata ctg cgt aat aag gag tct tgataagctt gacctgtgaa      529
Phe Ala Asn Ile Leu Arg Asn Lys Glu Ser
    160                 165 gtgaaaaatg cgcagattg tgcgacattt tttttgtctg ccgtttaatt aaagggggggg   589
gggggccggc ctgggggggg gtgtacatga aattgtaaac gttaatatttt tgttaaaatt   649
cgcgttaaat ttttgttaaa tcagctcatt ttttaaccaa taggccgaaa tcggcaaaat   709
cccttataaa tcaaaagaat agaccgagat agggttgagt gttgttccag tttggaacaa   769
gagtccacta ttaagaacg tggactccaa cgtcaaaggg cgaaaaaccg tctatcaggg    829
cgatggccca ctacgagaac catcaccccta atcaagtttt tggggtcga ggtgccgtaa    889
agcactaaat cggaaccccta aagggagccc ccgatttaga gcttgacggg gaaagccggc   949
gaacgtggcg agaaaggaag ggaagaaagc gaaaggagcg ggcgctaggg cgctggcaag  1009
tgtagcggtc acgctgcgcg taaccaccac acccgccgcg cttaatgcgc cgctacaggg  1069
cgcgtgctag ccatgtgagc aaaaggccag caaaaggcca ggaaccgtaa aaaggccgcg  1129
ttgctggcgt ttttccatag gctccgcccc cctgacgagc atcacaaaaa tcgacgctca  1189
agtcagaggt ggcgaaaccc gacaggacta taaagatacc aggcgtttcc ccctggaagc  1249
tccctcgtgc gctctcctgt tccgaccctg ccgcttaccg gatacctgtc cgcctttctc  1309
ccttcgggaa gcgtggcgct ttctcatagc tcacgctgta ggtatctcag ttcggtgtag  1369
gtcgttcgct ccaagctggg ctgtgtgcac gaaccccccg ttcagcccga ccgctgcgcc  1429
ttatccggta actatcgtct tgagtccaac ccggtaagac acgacttatc gccactggca  1489
gcagccactg gtaacaggat tagcagagcg aggtatgtag gcggtgctac agagttcttg  1549
aagtggtggc ctaactacgg ctacactaga agaacagtat ttggtatctg cgctctgctg  1609
tagccagtta ccttcggaaa aagagttggt agctcttgat ccggcaaaca aaccaccgct  1669
ggtagcggtg gtttttttgt ttgcaagcag cagattacgc gcagaaaaaa aggatctcaa  1729
gaagatcctt tgatctttc tacggggtct gacgctcagt ggaacgaaaa ctcacgttaa  1789
gggattttgg tcagatctag caccaggcgt ttaagggcac caataactgc cttaaaaaaa  1849
ttacgccccg ccctgccact catcgcagta ctgttgtaat tcattaagca ttctgccgac  1909
atggaagcca tcacaaacgg catgatgaac ctgaatcgcc agcggcatca gcaccttgtc  1969
gccttgcgta taatatttgc ccatagtgaa acgggggcg aagaagttgt ccatattggc  2029
tacgtttaaa tcaaaactgg tgaaactcac ccagggattg gctgagacga aaacatatt   2089
ctcaataaac cctttaggga ataggccag gttttcaccg taacacgcca catcttgcga  2149
atatatgtgt agaaactgcc ggaaatcgtc gtggtattca ctccagagcg atgaaaacgt  2209
ttcagtttgc tcatggaaaa cggtgtaaca agggtgaaca ctatcccata tcaccagctc  2269
accgtctttc attgccatac ggaactccgg gtgagcattc atcaggcggg caagaatgtg  2329
aataaaggcc ggataaaact tgtgcttatt tttctttacg gtctttaaaa aggccgtaat  2389
atccagctga acggtctggt tataggtaca ttgagcaact gactgaaatg cctcaaaatg  2449
ttctttacga tgccattggg atatatcaac ggtggtatat ccagtgattt ttttctccat  2509
```

-continued

```
tttagcttcc ttagctcctg aaaatctcga taactcaaaa aatacgcccg gtagtgatct    2569
tatttcatta tggtgaaagt tggaacctca cccgacgtct aatgtgagtt agctcactca    2629
ttaggcaccc caggctttac actttatgct tccggctcgt atgttgtgtg gaattgtgag    2689
cggataacaa tttcacacag gaaacagcta tgaccatgat tacgaatttc tagagcatgc    2749
gggggg                                                                2755
```

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic vector

<400> SEQUENCE: 275

Phe Glu Gln Lys Leu Ile Ser Glu Glu Asp Leu
1               5                   10

<210> SEQ ID NO 276
<211> LENGTH: 219
<212> TYPE: PRT
<213> ORGANISM: Artificial Sequence
<220> FEATURE:
<223> OTHER INFORMATION: Description of Artificial Sequence: Synthetic vector sequence

<400> SEQUENCE: 276

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
        50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 277
<211> LENGTH: 173
<212> TYPE: DNA
<213> ORGANISM: Artificial Sequence
<220> FEATURE:
<223> OTHER INFORMATION: Description of Artificial Sequence: Synthetic
    DNA cassette

<400> SEQUENCE: 277

```
gacgtcttaa tgtgagttag ctcactcatt aggcacccca ggctttacac tttatgcttc      60
cggctcgtat gttgtgtgga attgtgagcg ataacaatt tcacacagga aacagctatg     120
accatgtcta gaataacttc gtataatgta cgctatacga agttatcgca tgc           173
```

<210> SEQ ID NO 278
<211> LENGTH: 47
<212> TYPE: DNA
<213> ORGANISM: Artificial Sequence
<220> FEATURE:
<223> OTHER INFORMATION: Description of Artificial Sequence: Synthetic
    DNA cassette

<400> SEQUENCE: 278

```
agatctcata acttcgtata atgtatgcta tacgaagtta tgacgtc                   47
```

<210> SEQ ID NO 279
<211> LENGTH: 1255
<212> TYPE: DNA
<213> ORGANISM: Artificial Sequence
<220> FEATURE:
<223> OTHER INFORMATION: Description of Artificial Sequence: Synthetic
    vector sequence
<220> FEATURE:
<221> NAME/KEY: CDS
<222> LOCATION: (1)..(1245)

<400> SEQUENCE: 279

```
gaa ttc ggt ggt ggt gga tct gcg tgc gct gaa acg gtt gaa agt tgt       48
Glu Phe Gly Gly Gly Gly Ser Ala Cys Ala Glu Thr Val Glu Ser Cys
 1               5                  10                  15 tta gca aaa tcc cat aca gaa aat tca ttt act aac gtc tgg aaa gac       96
Leu Ala Lys Ser His Thr Glu Asn Ser Phe Thr Asn Val Trp Lys Asp
             20                  25                  30 gac aaa act tta gat cgt tac gct aac tat gag ggc tgt ctg tgg aat      144
Asp Lys Thr Leu Asp Arg Tyr Ala Asn Tyr Glu Gly Cys Leu Trp Asn
         35                  40                  45 gct aca ggc gtt gta gtt tgt act ggt gac gaa act cag tgt tac ggt      192
Ala Thr Gly Val Val Val Cys Thr Gly Asp Glu Thr Gln Cys Tyr Gly
     50                  55                  60 aca tgg gtt cct att ggg ctt gct atc cct gaa aat gag ggt ggt ggc      240
Thr Trp Val Pro Ile Gly Leu Ala Ile Pro Glu Asn Glu Gly Gly Gly
 65                  70                  75                  80 tct gag ggt ggc ggt tct gag ggt ggc ggt tct gag ggt ggc ggt act      288
Ser Glu Gly Gly Gly Ser Glu Gly Gly Gly Ser Glu Gly Gly Gly Thr
                 85                  90                  95 aaa cct cct gag tac ggt gat aca cct att ccg ggc tat act tat atc      336
Lys Pro Pro Glu Tyr Gly Asp Thr Pro Ile Pro Gly Tyr Thr Tyr Ile
            100                 105                 110 aac cct ctc gac ggc act tat ccg cct ggt act gag caa aac ccc gct      384
Asn Pro Leu Asp Gly Thr Tyr Pro Pro Gly Thr Glu Gln Asn Pro Ala
        115                 120                 125 aat cct aat cct tct ctt gag gag tct cag cct ctt aat act ttc atg      432
Asn Pro Asn Pro Ser Leu Glu Glu Ser Gln Pro Leu Asn Thr Phe Met
    130                 135                 140
```

```
ttt cag aat aat agg ttc cga aat agg cag ggg gca tta act gtt tat      480
Phe Gln Asn Asn Arg Phe Arg Asn Arg Gln Gly Ala Leu Thr Val Tyr
145                 150                 155                 160 acg ggc act gtt act caa ggc act gac ccc gtt aaa act tat tac cag      528
Thr Gly Thr Val Thr Gln Gly Thr Asp Pro Val Lys Thr Tyr Tyr Gln
                165                 170                 175 tac act cct gta tca tca aaa gcc atg tat gac gct tac tgg aac ggt      576
Tyr Thr Pro Val Ser Ser Lys Ala Met Tyr Asp Ala Tyr Trp Asn Gly
            180                 185                 190 aaa ttc aga gac tgc gct ttc cat tct ggc ttt aat gag gat tta ttt      624
Lys Phe Arg Asp Cys Ala Phe His Ser Gly Phe Asn Glu Asp Leu Phe
        195                 200                 205 gtt tgt gaa tat caa ggc caa tcg tct gac ctg cct caa cct cct gtc      672
Val Cys Glu Tyr Gln Gly Gln Ser Ser Asp Leu Pro Gln Pro Pro Val
    210                 215                 220 aat gct ggc ggc ggc tct ggt ggt ggt tct ggt ggc ggc tct gag ggt      720
Asn Ala Gly Gly Gly Ser Gly Gly Gly Ser Gly Gly Gly Ser Glu Gly
225                 230                 235                 240 ggt ggc tct gag ggt ggc ggt tct gag ggt ggc ggc tct gag gga ggc      768
Gly Gly Ser Glu Gly Gly Gly Ser Glu Gly Gly Gly Ser Glu Gly Gly
                245                 250                 255 ggt tcc ggt ggt ggc tct ggt tcc ggt gat ttt gat tat gaa aag atg      816
Gly Ser Gly Gly Gly Ser Gly Ser Gly Asp Phe Asp Tyr Glu Lys Met
            260                 265                 270 gca aac gct aat aag ggg gct atg acc gaa aat gcc gat gaa aac gcg      864
Ala Asn Ala Asn Lys Gly Ala Met Thr Glu Asn Ala Asp Glu Asn Ala
        275                 280                 285 cta cag tct gac gct aaa ggc aaa ctt gat tct gtc gct act gat tac      912
Leu Gln Ser Asp Ala Lys Gly Lys Leu Asp Ser Val Ala Thr Asp Tyr
    290                 295                 300 ggt gct gct atc gat ggt ttc att ggt gac gtt tcc ggc ctt gct aat      960
Gly Ala Ala Ile Asp Gly Phe Ile Gly Asp Val Ser Gly Leu Ala Asn
305                 310                 315                 320 ggt aat ggt gct act ggt gat ttt gct ggc tct aat tcc caa atg gct     1008
Gly Asn Gly Ala Thr Gly Asp Phe Ala Gly Ser Asn Ser Gln Met Ala
                325                 330                 335 caa gtc ggt gaa ggt gat aat tca cct tta atg aat aat ttc cgt caa     1056
Gln Val Gly Glu Gly Asp Asn Ser Pro Leu Met Asn Asn Phe Arg Gln
            340                 345                 350 tat tta cct tcc atc cct caa tcg gtt gaa tgt cgc cct ttt gtc ttt     1104
Tyr Leu Pro Ser Ile Pro Gln Ser Val Glu Cys Arg Pro Phe Val Phe
        355                 360                 365 ggc gct ggt aaa ccc tat gaa ttt tct att gat tgt gac aaa ata aac     1152
Gly Ala Gly Lys Pro Tyr Glu Phe Ser Ile Asp Cys Asp Lys Ile Asn
    370                 375                 380 tta ttc cgt ggt gtc ttt gcg ttt ctt tta tat gtt gcc acc ttt atg     1200
Leu Phe Arg Gly Val Phe Ala Phe Leu Leu Tyr Val Ala Thr Phe Met
385                 390                 395                 400 tat gta ttt tct acg ttt gct aac ata ctg cgt aat aag gag tct         1245
Tyr Val Phe Ser Thr Phe Ala Asn Ile Leu Arg Asn Lys Glu Ser
                405                 410                 415 tgataagctt                                                          1255

<210> SEQ ID NO 280
<211> LENGTH: 415
<212> TYPE: PRT
<213> ORGANISM: Artificial Sequence
<220> FEATURE:
<223> OTHER INFORMATION: Description of Artificial Sequence: Synthetic
      vector sequence
```

-continued

```
<400> SEQUENCE: 280

Glu Phe Gly Gly Gly Gly Ser Ala Cys Ala Glu Thr Val Glu Ser Cys
 1               5                  10                  15

Leu Ala Lys Ser His Thr Glu Asn Ser Phe Thr Asn Val Trp Lys Asp
             20                  25                  30

Asp Lys Thr Leu Asp Arg Tyr Ala Asn Tyr Glu Gly Cys Leu Trp Asn
         35                  40                  45

Ala Thr Gly Val Val Val Cys Thr Gly Asp Glu Thr Gln Cys Tyr Gly
     50                  55                  60

Thr Trp Val Pro Ile Gly Leu Ala Ile Pro Glu Asn Glu Gly Gly Gly
 65                  70                  75                  80

Ser Glu Gly Gly Gly Ser Glu Gly Gly Ser Glu Gly Gly Gly Thr
             85                  90                  95

Lys Pro Pro Glu Tyr Gly Asp Thr Pro Ile Pro Gly Tyr Thr Tyr Ile
            100                 105                 110

Asn Pro Leu Asp Gly Thr Tyr Pro Pro Gly Thr Glu Gln Asn Pro Ala
        115                 120                 125

Asn Pro Asn Pro Ser Leu Glu Glu Ser Gln Pro Leu Asn Thr Phe Met
    130                 135                 140

Phe Gln Asn Asn Arg Phe Arg Asn Arg Gln Gly Ala Leu Thr Val Tyr
145                 150                 155                 160

Thr Gly Thr Val Thr Gln Gly Thr Asp Pro Val Lys Thr Tyr Tyr Gln
                165                 170                 175

Tyr Thr Pro Val Ser Ser Lys Ala Met Tyr Asp Ala Tyr Trp Asn Gly
            180                 185                 190

Lys Phe Arg Asp Cys Ala Phe His Ser Gly Phe Asn Glu Asp Leu Phe
        195                 200                 205

Val Cys Glu Tyr Gln Gly Gln Ser Ser Asp Leu Pro Gln Pro Pro Val
    210                 215                 220

Asn Ala Gly Gly Gly Ser Gly Gly Gly Ser Gly Gly Ser Glu Gly
225                 230                 235                 240

Gly Gly Ser Glu Gly Gly Ser Glu Gly Gly Ser Glu Gly Gly
                245                 250                 255

Gly Ser Gly Gly Gly Ser Gly Ser Gly Asp Phe Asp Tyr Glu Lys Met
            260                 265                 270

Ala Asn Ala Asn Lys Gly Ala Met Thr Glu Asn Ala Asp Glu Asn Ala
        275                 280                 285

Leu Gln Ser Asp Ala Lys Gly Lys Leu Asp Ser Val Ala Thr Asp Tyr
    290                 295                 300

Gly Ala Ala Ile Asp Gly Phe Ile Gly Asp Val Ser Gly Leu Ala Asn
305                 310                 315                 320

Gly Asn Gly Ala Thr Gly Asp Phe Ala Gly Ser Asn Ser Gln Met Ala
                325                 330                 335

Gln Val Gly Glu Gly Asp Asn Ser Pro Leu Met Asn Asn Phe Arg Gln
            340                 345                 350

Tyr Leu Pro Ser Ile Pro Gln Ser Val Glu Cys Arg Pro Phe Val Phe
        355                 360                 365

Gly Ala Gly Lys Pro Tyr Glu Phe Ser Ile Asp Cys Asp Lys Ile Asn
    370                 375                 380

Leu Phe Arg Gly Val Phe Ala Phe Leu Leu Tyr Val Ala Thr Phe Met
385                 390                 395                 400

Tyr Val Phe Ser Thr Phe Ala Asn Ile Leu Arg Asn Lys Glu Ser
                405                 410                 415
```

<210> SEQ ID NO 281
<211> LENGTH: 502
<212> TYPE: DNA
<213> ORGANISM: Artificial Sequence
<220> FEATURE:
<223> OTHER INFORMATION: Description of Artificial Sequence: Synthetic vector sequence
<220> FEATURE:
<221> NAME/KEY: CDS
<222> LOCATION: (4)..(492)

<400> SEQUENCE: 281

```
cgg gaa ttc gga ggc ggt tcc ggt ggt ggc tct ggt tcc ggt gat ttt      48
    Glu Phe Gly Gly Gly Ser Gly Gly Gly Ser Gly Ser Gly Asp Phe
    1               5                   10                  15 gat tat gaa aag atg gca aac gct aat aag ggg gct atg acc gaa aat      96
Asp Tyr Glu Lys Met Ala Asn Ala Asn Lys Gly Ala Met Thr Glu Asn
                20                  25                  30 gcc gat gaa aac gcg cta cag tct gac gct aaa ggc aaa ctt gat tct     144
Ala Asp Glu Asn Ala Leu Gln Ser Asp Ala Lys Gly Lys Leu Asp Ser
            35                  40                  45 gtc gct act gat tac ggt gct gct atc gat ggt ttc att ggt gac gtt     192
Val Ala Thr Asp Tyr Gly Ala Ala Ile Asp Gly Phe Ile Gly Asp Val
        50                  55                  60 tcc ggc ctt gct aat ggt aat ggt gct act ggt gat ttt gct ggc tct     240
Ser Gly Leu Ala Asn Gly Asn Gly Ala Thr Gly Asp Phe Ala Gly Ser
    65                  70                  75 aat tcc caa atg gct caa gtc ggt gac ggt gat aat tca cct tta atg     288
Asn Ser Gln Met Ala Gln Val Gly Asp Gly Asp Asn Ser Pro Leu Met
80                  85                  90                  95 aat aat ttc cgt caa tat tta cct tcc ctc cct caa tcg gtt gaa tgt     336
Asn Asn Phe Arg Gln Tyr Leu Pro Ser Leu Pro Gln Ser Val Glu Cys
                100                 105                 110 cgc cct ttt gtc ttt ggc gct ggt aaa cca tat gaa ttt tct att gat     384
Arg Pro Phe Val Phe Gly Ala Gly Lys Pro Tyr Glu Phe Ser Ile Asp
            115                 120                 125 tgt gac aaa ata aac tta ttc cgt ggt gtc ttt gcg ttt ctt tta tat     432
Cys Asp Lys Ile Asn Leu Phe Arg Gly Val Phe Ala Phe Leu Leu Tyr
        130                 135                 140 gtt gcc acc ttt atg tat gta ttt tct acg ttt gct aac ata ctg cgt     480
Val Ala Thr Phe Met Tyr Val Phe Ser Thr Phe Ala Asn Ile Leu Arg
    145                 150                 155 aat aag gag tct tgataagctt                                           502
Asn Lys Glu Ser
160
```

<210> SEQ ID NO 282
<211> LENGTH: 163
<212> TYPE: PRT
<213> ORGANISM: Artificial Sequence
<220> FEATURE:
<223> OTHER INFORMATION: Description of Artificial Sequence: Synthetic vector sequence

<400> SEQUENCE: 282

```
Glu Phe Gly Gly Gly Ser Gly Gly Gly Ser Gly Ser Gly Asp Phe Asp
1               5                   10                  15

Tyr Glu Lys Met Ala Asn Ala Asn Lys Gly Ala Met Thr Glu Asn Ala
            20                  25                  30

Asp Glu Asn Ala Leu Gln Ser Asp Ala Lys Gly Lys Leu Asp Ser Val
        35                  40                  45
```

```
Ala Thr Asp Tyr Gly Ala Ala Ile Asp Gly Phe Ile Gly Asp Val Ser
 50                  55                  60

Gly Leu Ala Asn Gly Asn Gly Ala Thr Gly Asp Phe Ala Gly Ser Asn
 65                  70                  75                  80

Ser Gln Met Ala Gln Val Gly Asp Gly Asp Asn Ser Pro Leu Met Asn
                 85                  90                  95

Asn Phe Arg Gln Tyr Leu Pro Ser Leu Pro Gln Ser Val Glu Cys Arg
            100                 105                 110

Pro Phe Val Phe Gly Ala Gly Lys Pro Tyr Glu Phe Ser Ile Asp Cys
        115                 120                 125

Asp Lys Ile Asn Leu Phe Arg Gly Val Phe Ala Phe Leu Leu Tyr Val
    130                 135                 140

Ala Thr Phe Met Tyr Val Phe Ser Thr Phe Ala Asn Ile Leu Arg Asn
145                 150                 155                 160

Lys Glu Ser

<210> SEQ ID NO 283
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 283
gcatgccata acttcgtata atgtacgcta tacgaagtta taagctt                    47

<210> SEQ ID NO 284
<211> LENGTH: 1163
<212> TYPE: DNA
<213> ORGANISM: Artificial Sequence
<220> FEATURE:
<223> OTHER INFORMATION: Description of Artificial Sequence: Synthetic
      gene cassette
<220> FEATURE:
<221> NAME/KEY: CDS
<222> LOCATION: (82)..(978)

<400> SEQUENCE: 284
gggggtgtac attcaaatat gtatccgctc atgagacaat aaccctgata aatgcttcaa      60
taatattgaa aaggaagag t atg agt att caa cat ttc cgt gtc gcc ctt       111
                       Met Ser Ile Gln His Phe Arg Val Ala Leu
                         1               5                  10 att ccc ttt ttt gcg gca ttt tgc ctt cct gtt ttt gct cac cca gaa      159
Ile Pro Phe Phe Ala Ala Phe Cys Leu Pro Val Phe Ala His Pro Glu
                 15                  20                  25 acg ctg gtg aaa gta aaa gat gct gag gat cag ttg ggt gcg cga gtg      207
Thr Leu Val Lys Val Lys Asp Ala Glu Asp Gln Leu Gly Ala Arg Val
             30                  35                  40 ggt tac atc gaa ctg gat ctc aac agc ggt aag atc ctt gag agt ttt      255
Gly Tyr Ile Glu Leu Asp Leu Asn Ser Gly Lys Ile Leu Glu Ser Phe
         45                  50                  55 cgc ccc gaa gaa cgt ttt cca atg atg agc act ttt aaa gtt ctg cta      303
Arg Pro Glu Glu Arg Phe Pro Met Met Ser Thr Phe Lys Val Leu Leu
     60                  65                  70 tgt ggc gcg gta tta tcc cgt att gac gcc ggg caa gag caa ctc ggt      351
Cys Gly Ala Val Leu Ser Arg Ile Asp Ala Gly Gln Glu Gln Leu Gly
 75                  80                  85                  90 cgc cgc ata cac tat tct cag aat gac ttg gtt gag tac tca cca gtc      399
Arg Arg Ile His Tyr Ser Gln Asn Asp Leu Val Glu Tyr Ser Pro Val
                 95                 100                 105
```

-continued

```
aca gaa aag cat ctt acg gat ggc atg aca gta aga gaa tta tgc agt     447
Thr Glu Lys His Leu Thr Asp Gly Met Thr Val Arg Glu Leu Cys Ser
        110                 115                 120 gct gcc ata acc atg agt gat aac act gcg gcc aac tta ctt ctg aca     495
Ala Ala Ile Thr Met Ser Asp Asn Thr Ala Ala Asn Leu Leu Leu Thr
            125                 130                 135 acg atc gga gga ccg aag gag cta acc gct ttt ttg cac aac atg ggg     543
Thr Ile Gly Gly Pro Lys Glu Leu Thr Ala Phe Leu His Asn Met Gly
        140                 145                 150 gat cat gta act cgc ctt gat cgt tgg gaa ccg gag ctg aat gaa gcc     591
Asp His Val Thr Arg Leu Asp Arg Trp Glu Pro Glu Leu Asn Glu Ala
155                 160                 165                 170 ata cca aac gac gag cgt gac acc acg atg cct gta gca atg gca aca     639
Ile Pro Asn Asp Glu Arg Asp Thr Thr Met Pro Val Ala Met Ala Thr
                175                 180                 185 acg ttg cgc aaa cta tta act ggc gaa cta ctt act cta gct tcc cgg     687
Thr Leu Arg Lys Leu Leu Thr Gly Glu Leu Leu Thr Leu Ala Ser Arg
            190                 195                 200 caa cag tta ata gac tgg atg gag gcg gat aaa gtt gca gga cca ctt     735
Gln Gln Leu Ile Asp Trp Met Glu Ala Asp Lys Val Ala Gly Pro Leu
        205                 210                 215 ctg cgc tcg gcc ctt ccg gct ggc tgg ttt att gct gat aaa tct gga     783
Leu Arg Ser Ala Leu Pro Ala Gly Trp Phe Ile Ala Asp Lys Ser Gly
    220                 225                 230 gcc ggt gag cgt ggg tct cgc ggt atc att gca gca ctg ggg cca gat     831
Ala Gly Glu Arg Gly Ser Arg Gly Ile Ile Ala Ala Leu Gly Pro Asp
235                 240                 245                 250 ggt aag ccc tcc cgt atc gta gtt atc tac acg acg ggg agt cag gca     879
Gly Lys Pro Ser Arg Ile Val Val Ile Tyr Thr Thr Gly Ser Gln Ala
                255                 260                 265 act atg gat gaa cga aat aga cag atc gct gag ata ggt gcc tca ctg     927
Thr Met Asp Glu Arg Asn Arg Gln Ile Ala Glu Ile Gly Ala Ser Leu
            270                 275                 280 att aag cat tgg gta act gtc aga cca agt tta ctc ata tat act tta     975
Ile Lys His Trp Val Thr Val Arg Pro Ser Leu Leu Ile Tyr Thr Leu
        285                 290                 295 gat tgatttaaaa cttcattttt aatttaaaag gatctaggtg aagatccttt         1028
Asp ttgataatct catgaccaaa atcccttaac gtgagttttc gttccactga gcgtcagacc  1088
ccgtagaaaa gatcaaagga tcttcttgag atccttttttg ataatggccg gccccccccc 1148 ttaattaagg ggggg                                                   1163
```

<210> SEQ ID NO 285
<211> LENGTH: 299
<212> TYPE: PRT
<213> ORGANISM: Artificial Sequence
<220> FEATURE:
<223> OTHER INFORMATION: Description of Artificial Sequence: Synthetic gene cassette

<400> SEQUENCE: 285

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
              20                  25                  30

Asp Ala Glu Asp Gln Leu Gly Ala Arg Val Gly Tyr Ile Glu Leu Asp
          35                  40                  45

Leu Asn Ser Gly Lys Ile Leu Glu Ser Phe Arg Pro Glu Glu Arg Phe
```

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
290                 295

<210> SEQ ID NO 286
<211> LENGTH: 470
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 286

| gctagcacgc gccctgtagc ggcgcattaa gcgcggcggg tgtggtggtt acgcgcagcg | 60  |
| tgaccgctac acttgccagc gccctagcgc ccgctccttt cgctttcttc ccttcctttc | 120 |
| tcgccacgtt cgccggcttt ccccgtcaag ctctaaatcg gggctccct  ttagggttcc | 180 |
| gatttagtgc tttacggcac ctcgacccca aaaaacttga ttagggtgat ggttctcgta | 240 |
| gtgggccatc gccctgatag acggtttttc gccctttgac gttggagtcc acgttcttta | 300 |
| atagtggact cttgttccaa actggaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgtttacaat ttcatgtaca             | 470 |

<210> SEQ ID NO 287
<211> LENGTH: 832
<212> TYPE: DNA
<213> ORGANISM: Artificial Sequence

```
<220> FEATURE:
<223> OTHER INFORMATION: Description of Artificial Sequence: Synthetic
      DNA cassette

<400> SEQUENCE: 287
agatctaata agatgatctt cttgagatcg ttttggtctg cgcgtaatct cttgctctga      60
aaacgaaaaa accgccttgc agggcggttt ttcgtaggtt ctctgagcta ccaactcttt    120
gaaccgaggt aactggcttg gaggagcgca gtcactaaaa cttgtcctttt cagtttagcc    180 ttaaccggcg catgacttca agactaactc ctctaaatca attaccagtg ctgctgcca    240 gtggtgcttt tgcatgtctt tccgggttgg actcaagacg atagttaccg gataaggcgc   300
agcggtcgga ctgaacgggg ggttcgtgca tacagtccag cttggagcga actgcctacc   360
cggaactgag tgtcaggcgt ggaatgagac aaacgcggcc ataacagcgg aatgacaccg   420
gtaaaccgaa aggcaggaac aggagagcgc aggagggagc cgccaggggg aaacgcctgg   480
tatctttata gtcctgtcgg gtttcgccac cactgatttg agcgtcagat ttcgtgatgc   540
ttgtcagggg ggcggagcct atggaaaaac ggctttgccg cggccctctc acttccctgt   600
taagtatctt cctggcatct tccaggaaat ctccgccccg ttcgtaagcc atttccgctc   660
gccgcagtcg aacgaccgag cgtagcgagt cagtgagcga ggaagcggaa tatatcctgt   720
atcacatatt ctgctgacgc accggtgcag ccttttttct cctgccacat gaagcacttc   780
actgacaccc tcatcagtgc caacatagta agccagtata cactccgcta gc            832

<210> SEQ ID NO 288
<211> LENGTH: 49
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 288
agatctcata acttcgtata atgtatgcta tacgaagtta ttcagatct               49

<210> SEQ ID NO 289
<211> LENGTH: 96
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 289
tctagagcat gcgtaggaga aaataaaatg aaacaaagca ctattgcact ggcactctta    60
ccgttgctct tcaccctgt taccaaagcc gaattc                              96

<210> SEQ ID NO 290
<211> LENGTH: 120
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 290
tctagagcat gcgtaggaga aaataaaatg aaacaaagca ctattgcact ggcactctta    60
ccgttgctct tcaccctgt taccaaagcc gactacaaag atgaagtgca attggaattc   120

<210> SEQ ID NO 291
```

```
<211> LENGTH: 96
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 291
tctagaggtt gaggtgattt tatgaaaaag aatatcgcat ttcttcttgc atctatgttc    60
gttttttcta ttgctacaaa tgcatacgct gaattc                              96

<210> SEQ ID NO 292
<211> LENGTH: 1221
<212> TYPE: DNA
<213> ORGANISM: Artificial Sequence
<220> FEATURE:
<223> OTHER INFORMATION: Description of Artificial Sequence: Synthetic
      gene cassette
<220> FEATURE:
<221> NAME/KEY: CDS
<222> LOCATION: (79)..(1158)

<400> SEQUENCE: 292
gctagcatcg aatggcgcaa aacctttcgc ggtatggcat gatagcgccc ggaagagagt    60
caattcaggg tggtgaat gtg aaa cca gta acg tta tac gat gtc gca gag     111
                    Val Lys Pro Val Thr Leu Tyr Asp Val Ala Glu
                     1               5                  10 tat gcc ggt gtc tct tat cag acc gtt tcc cgc gtg gtg aac cag gcc    159
Tyr Ala Gly Val Ser Tyr Gln Thr Val Ser Arg Val Val Asn Gln Ala
         15                  20                  25 agc cac gtt tct gcg aaa acg cgg gaa aaa gtg gaa gcg gcg atg gcg    207
Ser His Val Ser Ala Lys Thr Arg Glu Lys Val Glu Ala Ala Met Ala
     30                  35                  40 gag ctg aat tac att cct aac cgc gtg gca caa caa ctg gcg ggc aaa    255
Glu Leu Asn Tyr Ile Pro Asn Arg Val Ala Gln Gln Leu Ala Gly Lys
 45                  50                  55 cag tcg ttg ctg att ggc gtt gcc acc tcc agt ctg gcc ctg cac gcg    303
Gln Ser Leu Leu Ile Gly Val Ala Thr Ser Ser Leu Ala Leu His Ala
 60                  65                  70                  75 ccg tcg caa att gtc gcg gcg att aaa tct cgc gcc gat caa ctg ggt    351
Pro Ser Gln Ile Val Ala Ala Ile Lys Ser Arg Ala Asp Gln Leu Gly
                 80                  85                  90 gcc agc gtg gtc gtg tcg atg gta gaa cga agc ggc gtc gaa gcc tgt    399
Ala Ser Val Val Val Ser Met Val Glu Arg Ser Gly Val Glu Ala Cys
             95                 100                 105 aaa gcg gcg gtg cac aat ctt ctc gcg caa cgt gtc agt ggg ctg att    447
Lys Ala Ala Val His Asn Leu Leu Ala Gln Arg Val Ser Gly Leu Ile
         110                 115                 120 att aac tat ccg ctg gat gac cag gat gct att gct gtg gaa gct gcc    495
Ile Asn Tyr Pro Leu Asp Asp Gln Asp Ala Ile Ala Val Glu Ala Ala
     125                 130                 135 tgc act aat gtt ccg gcg tta ttt ctt gat gtc tct gac cag aca ccc    543
Cys Thr Asn Val Pro Ala Leu Phe Leu Asp Val Ser Asp Gln Thr Pro
140                 145                 150                 155 atc aac agt att att ttc tcc cat gag gac ggt acg cga ctg ggc gtg    591
Ile Asn Ser Ile Ile Phe Ser His Glu Asp Gly Thr Arg Leu Gly Val
                 160                 165                 170 gag cat ctg gtc gca ttg ggc cac cag caa atc gcg ctg tta gct ggc    639
Glu His Leu Val Ala Leu Gly His Gln Gln Ile Ala Leu Leu Ala Gly
             175                 180                 185 cca tta agt tct gtc tcg gcg cgt ctg cgt ctg gct ggc tgg cat aaa    687
Pro Leu Ser Ser Val Ser Ala Arg Leu Arg Leu Ala Gly Trp His Lys
```

```
tat ctc act cgc aat caa att cag ccg ata gcg gaa cgg gaa ggc gac      735
Tyr Leu Thr Arg Asn Gln Ile Gln Pro Ile Ala Glu Arg Glu Gly Asp
        205                 210                 215 tgg agt gcc atg tcc ggt ttt caa caa acc atg caa atg ctg aat gag      783
Trp Ser Ala Met Ser Gly Phe Gln Gln Thr Met Gln Met Leu Asn Glu
220                 225                 230                 235 ggc atc gtt ccc act gcg atg ctg gtt gcc aac gat cag atg gcg ctg      831
Gly Ile Val Pro Thr Ala Met Leu Val Ala Asn Asp Gln Met Ala Leu
                240                 245                 250 ggc gca atg cgt gcc att acc gag tcc ggg ctg cgc gtt ggt gcg gac      879
Gly Ala Met Arg Ala Ile Thr Glu Ser Gly Leu Arg Val Gly Ala Asp
            255                 260                 265 atc tcg gta gtg gga tac gac gat acc gag gac agc tca tgt tat atc      927
Ile Ser Val Val Gly Tyr Asp Asp Thr Glu Asp Ser Ser Cys Tyr Ile
        270                 275                 280 ccg ccg ctg acc acc atc aaa cag gat ttt cgc ctg ctg ggg caa acc      975
Pro Pro Leu Thr Thr Ile Lys Gln Asp Phe Arg Leu Leu Gly Gln Thr
285                 290                 295 agc gtg gac cgc ttg ctg caa ctc tct cag ggc cag gcg gtg aag ggc     1023
Ser Val Asp Arg Leu Leu Gln Leu Ser Gln Gly Gln Ala Val Lys Gly
300                 305                 310                 315 aat cag ctg ttg ccc gtc tca ctg gtg aaa aga aaa acc acc ctg gct     1071
Asn Gln Leu Leu Pro Val Ser Leu Val Lys Arg Lys Thr Thr Leu Ala
                320                 325                 330 ccc aat acg caa acc gcc tct ccc cgc gcg ttg gcc gat tca ctg atg     1119
Pro Asn Thr Gln Thr Ala Ser Pro Arg Ala Leu Ala Asp Ser Leu Met
            335                 340                 345 cag ctg gca cga cag gtt tcc cga ctg gaa agc ggg cag tgaggctacc     1168
Gln Leu Ala Arg Gln Val Ser Arg Leu Glu Ser Gly Gln
        350                 355                 360 cgataaaagc ggcttcctga caggaggccg ttttgttttg cagcccactt aag         1221

<210> SEQ ID NO 293
<211> LENGTH: 360
<212> TYPE: PRT
<213> ORGANISM: Artificial Sequence
<220> FEATURE:
<223> OTHER INFORMATION: Description of Artificial Sequence: Synthetic
      gene cassette

<400> SEQUENCE: 293

Val Lys Pro Val Thr Leu Tyr Asp Val Ala Glu Tyr Ala Gly Val Ser
 1               5                  10                  15

Tyr Gln Thr Val Ser Arg Val Val Asn Gln Ala Ser His Val Ser Ala
                20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
        50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
                100                 105                 110

Asn Leu Leu Ala Gln Arg Val Ser Gly Leu Ile Ile Asn Tyr Pro Leu
            115                 120                 125
```

```
Asp Asp Gln Asp Ala Ile Ala Val Glu Ala Ala Cys Thr Asn Val Pro
130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
                180                 185                 190

Ser Ala Arg Leu Arg Leu Ala Gly Trp His Lys Tyr Leu Thr Arg Asn
                195                 200                 205

Gln Ile Gln Pro Ile Ala Glu Arg Glu Gly Asp Trp Ser Ala Met Ser
210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
                260                 265                 270

Tyr Asp Asp Thr Glu Asp Ser Ser Cys Tyr Ile Pro Pro Leu Thr Thr
                275                 280                 285

Ile Lys Gln Asp Phe Arg Leu Leu Gly Gln Thr Ser Val Asp Arg Leu
290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
                340                 345                 350

Val Ser Arg Leu Glu Ser Gly Gln
                355                 360

<210> SEQ ID NO 294
<211> LENGTH: 2380
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 294
gatctagcac caggcgttta agggcaccaa taactgcctt aaaaaaatta cgccccgccc      60
tgccactcat cgcagtactg ttgtaattca ttaagcattc tgccgacatg gaagccatca    120
caaacggcat gatgaacctg aatcgccagc ggcatcagca ccttgtcgcc ttgcgtataa    180
tatttgccca tagtgaaaac gggggcgaag aagttgtcca tattggctac gtttaaatca    240
aaactggtga aactcaccca gggattggct gagacgaaaa acatattctc aataaaccct    300
ttagggaaat aggccaggtt ttcaccgtaa cacgccacat cttgcgaata tatgtgtaga    360
aactgccgga atcgtcgtg gtattcactc cagagcgatg aaaacgtttc agtttgctca    420
tggaaaacgg tgtaacaagg gtgaacacta tcccatatca ccagctcacc gtctttcatt    480
gccatacgga actccgggtg agcattcatc aggcgggcaa gaatgtgaat aaaggccgga    540
taaaacttgt gcttattttt ctttacggtc tttaaaaagg ccgtaatatc cagctgaacg    600
gtctggttat aggtacattg agcaactgac tgaaatgcct caaaatgttc tttacgatgc    660
cattgggata tatcaacggt ggtatatcca gtgatttttt tctccatttt agcttcctta    720
```

```
gctcctgaaa atctcgataa ctcaaaaaat acgcccggta gtgatcttat ttcattatgg    780
tgaaagttgg aacctcaccc gacgtctaat gtgagttagc tcactcatta ggcaccccag    840
gctttacact ttatgcttcc ggctcgtatg ttgtgtggaa ttgtgagcgg ataacaattt    900
cacacaggaa acagctatga ccatgattac gaatttctag accccccccc cgcatgccat    960
aacttcgtat aatgtacgct atacgaagtt ataagcttga cctgtgaagt gaaaatggc    1020 gcagattgtg cgacattttt tttgtctgcc gtttaattaa agggggggg gggccggcct    1080 ggggggggt gtacatgaaa ttgtaaacgt taatattttg ttaaaattcg cgttaaattt    1140
ttgttaaatc agctcatttt ttaaccaata ggccgaaatc ggcaaaatcc cttataaatc    1200
aaaagaatag accgagatag ggttgagtgt tgttccagtt tggaacaaga gtccactatt    1260
aaagaacgtg gactccaacg tcaaagggcg aaaaccgtc tatcagggcg atggcccact    1320
acgagaacca tcaccctaat caagtttttt ggggtcgagg tgccgtaaag cactaaatcg    1380
gaaccctaaa gggagccccc gatttagagc ttgacgggga agccggcga acgtggcgag    1440 aaaggaaggg aagaaagcga aaggagcggg cgctagggcg ctggcaagtg tagcggtcac    1500
gctgcgcgta accaccacac ccgccgcgct taatgcgccg ctacagggcg cgtgctagcg    1560
gagtgtatac tggcttacta tgttggcact gatgagggtg tcagtgaagt gcttcatgtg    1620
gcaggagaaa aaggctgca ccggtgcgtc agcagaatat gtgatacagg atatattccg    1680
cttcctcgct cactgactcg ctacgctcgg tcgttcgact gcggcgagcg gaaatggctt    1740
acgaacgggg cggagatttc ctggaagatg ccaggaagat acttaacagg gaagtgagag    1800
ggccgcggca aagccgtttt tccataggct ccgcccccct gacaagcatc acgaaatctg    1860
acgctcaaat cagtggtggc gaaacccgac aggactataa agataccagg cgtttccccc    1920
tggcggctcc ctcctgcgct ctcctgttcc tgcctttcgg tttaccggtg tcattccgct    1980 gttatgccg cgtttgtctc attccacgcc tgacactcag ttccgggtag gcagttcgct    2040
ccaagctgga ctgtatgcac gaaccccccg ttcagtccga ccgctgcgcc ttatccggta    2100
actatcgtct tgagtccaac ccggaaagac atgcaaaagc accactggca gcagccactg    2160
gtaattgatt tagaggagtt agtcttgaag tcatgcgccg gttaaggcta aactgaaagg    2220 acaagttta gtgactgcgc tcctccaagc cagttacctc ggttcaaaga gttggtagct    2280
cagagaacct acgaaaaacc gccctgcaag gcggttttt cgttttcaga gcaagagatt    2340
acgcgcagac caaaacgatc tcaagaagat catcttatta                          2380
```

<210> SEQ ID NO 295
<211> LENGTH: 219
<212> TYPE: PRT
<213> ORGANISM: Artificial Sequence
<220> FEATURE:
<223> OTHER INFORMATION: Description of Artificial Sequence: Synthetic
    vector sequence

<400> SEQUENCE: 295

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

```
Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 296
<211> LENGTH: 3488
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 296
gtacatgaaa ttgtaaacgt taatattttg ttaaaattcg cgttaaattt ttgttaaatc      60
agctcatttt ttaaccaata ggccgaaatc ggcaaaatcc cttataaatc aaaagaatag     120
accgagatag ggttgagtgt tgttccagtt tggaacaaga gtccactatt aaagaacgtg     180
gactccaacg tcaaagggcg aaaaaccgtc tatcagggcg atggcccact acgagaacca     240
tcaccctaat caagtttttt ggggtcgagg tgccgtaaag cactaaatcg aaccctaaa     300 gggagccccc gatttagagc ttgacgggga agccggcga acgtggcgag aaaggaaggg      360
aagaaagcga aaggagcggg cgctagggcg ctggcaagtg tagcggtcac gctgcgcgta     420
accaccacac ccgccgcgct taatgcgccc ctacagggcg cgtgctagcg gagtgtatac     480
tggcttacta tgttggcact gatgagggtg tcagtgaagt gcttcatgtg gcaggagaaa     540
aaaggctgca ccggtgcgtc agcagaatat gtgatacaga atatattccg cttcctcgct     600
cactgactcg ctacgctcgg tcgttcgact gcggcgagcg gaaatggctt acgaacgggg     660
cggagatttc ctggaagatg ccaggaagat acttaacagg gaagtgagag ggccgcggca     720
aagccgtttt tccataggct ccgcccccct gacaagcatc acgaaatctg acgctcaaat     780
cagtggtggc gaaacccgac aggactataa agataccagg cgtttccccc tggcggctcc     840
ctcctgcgct ctcctgttcc tgcctttcgg tttaccggtg tcattccgct gttatggccg     900
cgtttgtctc attccacgcc tgacactcag ttccgggtag gcagttcgct ccaagctgga     960
ctgtatgcac gaaccccccg ttcagtccga ccgctgcgcc ttatccggta actatcgtct    1020
tgagtccaac ccggaaagac atgcaaaagc accactggca gcagccactg gtaattgatt    1080
tagaggagtt agtcttgaag tcatgcgccg gttaaggcta aactgaaagg acaagtttta    1140
```

-continued

| | |
|---|---|
| gtgactgcgc tcctccaagc cagttacctc ggttcaaaga gttggtagct cagagaacct | 1200 |
| acgaaaaacc gccctgcaag gcggttttt cgttttcaga gcaagagatt acgcgcagac | 1260 |
| caaaacgatc tcaagaagat catcttatta gatctagcac caggcgttta agggcaccaa | 1320 |
| taactgcctt aaaaaaatta cgccccgccc tgccactcat cgcagtactg ttgtaattca | 1380 |
| ttaagcattc tgccgacatg gaagccatca caaacggcat gatgaacctg aatcgccagc | 1440 |
| ggcatcagca ccttgtcgcc ttgcgtataa tatttgccca tagtgaaaac gggggcgaag | 1500 |
| aagttgtcca tattggctac gtttaaatca aaactggtga aactcaccca gggattggct | 1560 |
| gagacgaaaa acatattctc aataaaccct ttagggaaat aggccaggtt ttcaccgtaa | 1620 |
| cacgccacat cttgcgaata tatgtgtaga actgccgga atcgtcgtg gtattcactc | 1680 |
| cagagcgatg aaaacgtttc agtttgctca tggaaaacg tgtaacaagg gtgaacacta | 1740 |
| tcccatatca ccagctcacc gtctttcatt gccatacgga actccgggtg agcattcatc | 1800 |
| aggcgggcaa gaatgtgaat aaaggccgga taaaacttgt gcttattttt ctttacggtc | 1860 |
| tttaaaaagg ccgtaatatc cagctgaacg gtctggttat aggtacattg agcaactgac | 1920 |
| tgaaatgcct caaaatgttc tttacgatgc cattgggata tatcaacggt ggtatatcca | 1980 |
| gtgatttttt tctccatttt agcttcctta gctcctgaaa atctcgataa ctcaaaaaat | 2040 |
| acgcccggta gtgatcttat ttcattatgg tgaaagttgg aacctcaccc gacgtctaat | 2100 |
| gtgagttagc tcactcatta ggcaccccag gctttacact ttatgcttcc ggctcgtatg | 2160 |
| ttgtgtggaa ttgtgagcgg ataacaattt cacacaggaa acagctatga ccatgattac | 2220 |
| gaatttctag accccccccc cgcatgccat aacttcgtat aatgtacgct atacgaagtt | 2280 |
| ataagcttga cctgtgaagt gaaaaatggc gcagattgtg cgacattttt tttgtctgcc | 2340 |
| gtttaattaa gggggggggc cggccattat caaaaaggat ctcaagaaga tcctttgatc | 2400 |
| ttttctacgg ggtctgacgc tcagtggaac gaaaactcac gttaagggat tttggtcatg | 2460 |
| agattatcaa aaaggatctt cacctagatc cttttaaatt aaaaatgaag ttttaaatca | 2520 |
| atctaaagta tatatgagta aacttggtct gacagttacc caatgcttaa tcagtgaggc | 2580 |
| acctatctca gcgatctgtc tatttcgttc atccatagtt gcctgactcc ccgtcgtgta | 2640 |
| gataactacg atacgggagg gcttaccatc tggccccagt gctgcaatga taccgcgaga | 2700 |
| cccacgctca ccggctccag atttatcagc aataaaccag ccagccggaa gggccgagcg | 2760 |
| cagaagtggt cctgcaactt tatccgcctc catccagtct attaactgtt gccgggaagc | 2820 |
| tagagtaagt agttcgccag ttaatagttt gcgcaacgtt gttgccattg ctacaggcat | 2880 |
| cgtggtgtca cgctcgtcgt ttggtatggc ttcattcagc tccggttccc aacgatcaag | 2940 |
| gcgagttaca tgatccccca tgttgtgcaa aaaagcggtt agctccttcg gtcctccgat | 3000 |
| cgttgtcaga agtaagttgg ccgcagtgtt atcactcatg gttatggcag cactgcataa | 3060 |
| ttctcttact gtcatgccat ccgtaagatg cttttctgtg actggtgagt actcaaccaa | 3120 |
| gtcattctga aatagtgta tgcggcgacc gagttgctct tgcccggcgt caatacggga | 3180 |
| taataccgcg ccacatagca gaactttaaa agtgctcatc attggaaaac gttcttcggg | 3240 |
| gcgaaaactc tcaaggatct taccgctgtt gagatccagt tcgatgtaac ccactcgcgc | 3300 |
| acccaactga tcctcagcat cttttacttt caccagcgtt tctgggtgag caaaaacagg | 3360 |
| aaggcaaaat gccgcaaaaa agggaataag ggcgacacgg aaatgttgaa tactcatact | 3420 |
| cttcctttt caatattatt gaagcattta tcagggttat tgtctcatga gcggatacat | 3480 |

-continued atttgaat                                                              3488

<210> SEQ ID NO 297
<211> LENGTH: 219
<212> TYPE: PRT
<213> ORGANISM: Artificial Sequence
<220> FEATURE:
<223> OTHER INFORMATION: Description of Artificial Sequence: Synthetic
      vector sequence

<400> SEQUENCE: 297

Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
                 20                  25                  30

Tyr Asn Gln Thr Val Gln Leu Asp Ile Thr Ala Phe Leu Lys Thr Val
             35                  40                  45

Lys Lys Asn Lys His Lys Phe Tyr Pro Ala Phe Ile His Ile Leu Ala
 50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
                100                 105                 110

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
        130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 298
<211> LENGTH: 299
<212> TYPE: PRT
<213> ORGANISM: Artificial Sequence
<220> FEATURE:
<223> OTHER INFORMATION: Description of Artificial Sequence: Synthetic
      vector sequence

<400> SEQUENCE: 298

Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
                 20                  25                  30

Asp Ala Glu Asp Gln Leu Gly Ala Arg Val Gly Tyr Ile Glu Leu Asp
             35                  40                  45

Leu Asn Ser Gly Lys Ile Leu Glu Ser Phe Arg Pro Glu Glu Arg Phe
 50                  55                  60

Pro Met Met Ser Thr Phe Lys Val Leu Leu Cys Gly Ala Val Leu Ser

```
                65                  70                  75                  80
Arg Ile Asp Ala Gly Gln Glu Gln Leu Gly Arg Arg Ile His Tyr Ser
                    85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
    290                 295

<210> SEQ ID NO 299
<211> LENGTH: 2728
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 299
gatctcataa cttcgtataa tgtatgctat acgaagttat gacgtctaat gtgagttagc      60
tcactcatta ggcacccag gctttacact ttatgcttcc ggctcgtatg ttgtgtggaa     120
ttgtgagcgg ataacaattt cacacaggaa acagctatga ccatgattac gaatttctag    180
accccccccc cgcatgccat aacttcgtat aatgtacgct atacgaagtt ataagcttga    240
cctgtgaagt gaaaaatggc gcagattgtg cgacatttt tttgtctgcc gtttaattaa     300
gggggggggc cggccattat caaaaaggat ctcaagaaga tcctttgatc ttttctacgg    360
ggtctgacgc tcagtggaac gaaaactcac gttaagggat tttggtcatg agattatcaa    420
aaaggatctt cacctagatc cttttaaatt aaaaatgaag ttttaaatca atctaaagta    480
tatatgagta aacttggtct gacagttacc aatgcttaa tcagtgaggc acctatctca     540
gcgatctgtc tatttcgttc atccatagtt gcctgactcc ccgtcgtgta gataactacg    600
atacgggagg gcttaccatc tggccccagt gctgcaatga taccgcgaga cccacgctca    660
ccggctccag atttatcagc aataaaccag ccagccggaa gggccgagcg cagaagtggt    720
```

```
cctgcaactt tatccgcctc catccagtct attaactgtt gccgggaagc tagagtaagt    780
agttcgccag ttaatagttt gcgcaacgtt gttgccattg ctacaggcat cgtggtgtca    840
cgctcgtcgt ttggtatggc ttcattcagc tccggttccc aacgatcaag gcgagttaca    900
tgatccccca tgttgtgcaa aaagcggtt agctccttcg gtcctccgat cgttgtcaga     960
agtaagttgg ccgcagtgtt atcactcatg gttatggcag cactgcataa ttctcttact   1020
gtcatgccat ccgtaagatg cttttctgtg actggtgagt actcaaccaa gtcattctga   1080
gaatagtgta tgcggcgacc gagttgctct tgcccggcgt caatacggga taataccgcg   1140
ccacatagca gaactttaaa agtgctcatc attggaaaac gttcttcggg gcgaaaactc   1200
tcaaggatct taccgctgtt gagatccagt tcgatgtaac ccactcgcgc acccaactga   1260
tcctcagcat cttttacttt caccagcgtt tctgggtgag caaaaacagg aaggcaaaat   1320
gccgcaaaaa agggaataag ggcgacacgg aaatgttgaa tactcatact cttccttttt   1380
caatattatt gaagcattta tcagggttat tgtctcatga gcggatacat atttgaatgt   1440
acatgaaatt gtaaacgtta atattttgtt aaaattcgcg ttaaattttt gttaaatcag   1500
ctcatttttt aaccaatagg ccgaaatcgg caaaatccct tataaatcaa agaatagac    1560 cgagataggg ttgagtgttg ttccagtttg gaacaagagt ccactattaa agaacgtgga   1620
ctccaacgtc aaagggcgaa aaaccgtcta tcagggcgat ggcccactac gagaaccatc   1680
accctaatca gttttttgg ggtcgaggtg ccgtaaagca ctaaatcgga accctaaagg    1740
gagcccccga tttagagctt gacggggaaa gccggcgaac gtggcgagaa aggaagggaa   1800
gaaagcgaaa ggagcgggcg ctagggcgct ggcaagtgta gcggtcacgc tgcgcgtaac   1860
caccacaccc gccgcgctta atgcgccgct acagggcgcg tgctagcgga gtgtatactg   1920
gcttactatg ttggcactga tgagggtgtc agtgaagtgc ttcatgtggc aggagaaaaa   1980
aggctgcacc ggtgcgtcag cagaatatgt gatacaggat atattccgct tcctcgctca   2040
ctgactcgct acgctcggtc gttcgactgc ggcgagcgga atggcttac gaacggggcg    2100 gagatttcct ggaagatgcc aggaagatac ttaacaggga agtgagaggg ccgcggcaaa   2160
gccgtttttc cataggctcc gcccccctga caagcatcac gaaatctgac gctcaaatca   2220
gtggtggcga aacccgacag gactataaag ataccaggcg tttccccctg gcggctccct   2280
cctgcgctct cctgttcctg cctttcggtt taccggtgtc attccgctgt tatggccgcg   2340
tttgtctcat tccacgcctg acactcagtt ccgggtaggc agttcgctcc aagctggact   2400
gtatgcacga accccccgtt cagtccgacc gctgcgcctt atccggtaac tatcgtcttg   2460
agtccaaccc ggaaagacat gcaaaagcac cactggcagc agccactggt aattgattta   2520
gaggagttag tcttgaagtc atgcgccggt taaggctaaa ctgaaaggac aagttttagt   2580
gactgcgctc ctccaagcca gttacctcgg ttcaaagagt tggtagctca gagaacctac   2640
gaaaaaccgc cctgcaaggc ggttttttcg ttttcagagc aagagattac gcgcagacca   2700
aaacgatctc aagaagatca tcttatta                                       2728
```

<210> SEQ ID NO 300
<211> LENGTH: 299
<212> TYPE: PRT
<213> ORGANISM: Artificial Sequence
<220> FEATURE:
<223> OTHER INFORMATION: Description of Artificial Sequence: Synthetic vector sequence

<400> SEQUENCE: 300

```
Met Ser Ile Gln His Phe Arg Val Ala Leu Ile Pro Phe Phe Ala Ala
 1               5                  10                  15
Phe Cys Leu Pro Val Phe Ala His Pro Glu Thr Leu Val Lys Val Lys
                20                  25                  30
Asp Ala Glu Asp Gln Leu Gly Ala Arg Val Gly Tyr Ile Glu Leu Asp
            35                  40                  45
Leu Asn Ser Gly Lys Ile Leu Glu Ser Phe Arg Pro Glu Arg Phe
    50                  55                  60
Pro Met Met Ser Thr Phe Lys Val Leu Leu Cys Gly Ala Val Leu Ser
 65                  70                  75                  80
Arg Ile Asp Ala Gly Gln Glu Gln Leu Gly Arg Arg Ile His Tyr Ser
                85                  90                  95
Gln Asn Asp Leu Val Glu Tyr Ser Pro Val Thr Glu Lys His Leu Thr
            100                 105                 110
Asp Gly Met Thr Val Arg Glu Leu Cys Ser Ala Ala Ile Thr Met Ser
            115                 120                 125
Asp Asn Thr Ala Ala Asn Leu Leu Leu Thr Thr Ile Gly Gly Pro Lys
    130                 135                 140
Glu Leu Thr Ala Phe Leu His Asn Met Gly Asp His Val Thr Arg Leu
145                 150                 155                 160
Asp Arg Trp Glu Pro Glu Leu Asn Glu Ala Ile Pro Asn Asp Glu Arg
                165                 170                 175
Asp Thr Thr Met Pro Val Ala Met Ala Thr Thr Leu Arg Lys Leu Leu
            180                 185                 190
Thr Gly Glu Leu Leu Thr Leu Ala Ser Arg Gln Gln Leu Ile Asp Trp
            195                 200                 205
Met Glu Ala Asp Lys Val Ala Gly Pro Leu Leu Arg Ser Ala Leu Pro
210                 215                 220
Ala Gly Trp Phe Ile Ala Asp Lys Ser Gly Ala Gly Glu Arg Gly Ser
225                 230                 235                 240
Arg Gly Ile Ile Ala Ala Leu Gly Pro Asp Gly Lys Pro Ser Arg Ile
                245                 250                 255
Val Val Ile Tyr Thr Thr Gly Ser Gln Ala Thr Met Asp Glu Arg Asn
            260                 265                 270
Arg Gln Ile Ala Glu Ile Gly Ala Ser Leu Ile Lys His Trp Val Thr
            275                 280                 285
Val Arg Pro Ser Leu Leu Ile Tyr Thr Leu Asp
    290                 295

<210> SEQ ID NO 301
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tatgagatct cataacttcg tataatgtac gctatacgaa gttat            45

<210> SEQ ID NO 302
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 302
taataacttc gtatagcata cattatacga agttatgaga tctca              45

<210> SEQ ID NO 303
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
cattttttgc cctcgttatc tacgcatgcg ataacttcgt atagcgtaca ttatacgaag  60
ttattctaga catggtcata gctgtttcct g                               91

<210> SEQ ID NO 304
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
gggggaattc cggtggtggt ggatctgcgt gcgctgaaac ggttgaaagt tg        52

<210> SEQ ID NO 305
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305 ccccccccaag cttatcaaga ctccttatta cg                            32

<210> SEQ ID NO 306
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306 gggggggaa ttcggaggcg gttccggtgg tggc                            34

<210> SEQ ID NO 307
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggggggggaa ttcgagcaga agctgatctc tgaggaggat ctgtagggtg gtggctctgg  60
ttccggtgat tttg                                                  74

<210> SEQ ID NO 308
<211> LENGTH: 37
<212> TYPE: DNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 308
ccataacttc gtataatgta cgctatacga agttata                              37

<210> SEQ ID NO 309
<211> LENGTH: 45
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 309
agcttataac ttcgtatagc gtacattata cgaagttatg gcatg                     45

<210> SEQ ID NO 310
<211> LENGTH: 76
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 310
agcttgacct gtgaagtgaa aaatggcgca gattgtgcga cattttttt gtctgccgtt      60 taattaaagg gggggt                                                     76

<210> SEQ ID NO 311
<211> LENGTH: 75
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 311
gtacaccccc ccccaggccg gccccccccc ccctttaatt aaacggcaga caaaaaaat      60 gtcgcacaat ctgcg                                                      75

<210> SEQ ID NO 312
<211> LENGTH: 35
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 312
gggggggtgt acattcaaat atgtatccgc tcatg                                35

<210> SEQ ID NO 313
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 313
gggttacatc gaactggatc tc                                              22

<210> SEQ ID NO 314
<211> LENGTH: 59

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ccagttcgat gtaacccact cgcgcaccca actgatcctc agcatctttt actttcacc        59

<210> SEQ ID NO 315
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
actctagctt cccggcaaca gttaatagac tggatggagg cgg                        43

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ctgttgccgg gaagctagag taag                                             24

<210> SEQ ID NO 317
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ccccccctta attaggggg ggggccggcc attatcaaaa aggatctcaa gaagatcc          58

<210> SEQ ID NO 318
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318 gggggggggct agcacgcgcc ctgtagcggc gcattaa                              37

<210> SEQ ID NO 319
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ccccccctgt acatgaaatt gtaaacgtta atattttg                              38

<210> SEQ ID NO 320
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 320
gggcgatggc ccactacgag aaccatcacc ctaatc                                36

<210> SEQ ID NO 321
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321 gggggggagat ctaataagat gatcttcttg ag                                   32

<210> SEQ ID NO 322
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gagttggtag ctcagagaac ctacgaaaaa ccgccctgca aggcg                      45

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gtaggttctc tgagctacca actc                                             24

<210> SEQ ID NO 324
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gtttccccct ggcggctccc tcctgcgctc tcctgttcct gcc                        43

<210> SEQ ID NO 325
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
aggagggagc cgccaggggg aaac                                             24

<210> SEQ ID NO 326
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 326
gacatcagcg ctagcggagt gtatac                                          26

<210> SEQ ID NO 327
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gatctcataa cttcgtataa tgtatgctat acgaagttat tca                       43

<210> SEQ ID NO 328
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gatctgaata acttcgtata gcatacatta tacgaagtta tgaga                     45

<210> SEQ ID NO 329
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gggggggaga tctgaccaaa atcccttaac gtgag                                35

<210> SEQ ID NO 330
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
ggtatctgcg ctctgctgta gccagttacc ttcgg                                35

<210> SEQ ID NO 331
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331 ccccccccgct agccatgtga gcaaaaggcc agcaa                               35

<210> SEQ ID NO 332
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 332
gggacgtcgg gtgaggttcc aac                                              23

<210> SEQ ID NO 333
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
ccatacggaa ctccgggtga gcattcatc                                        29

<210> SEQ ID NO 334
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ccggagttcc gtatgg                                                      16

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
acgtttaaat caaaactgg                                                   19

<210> SEQ ID NO 336
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ccagttttga tttaaacgta gccaatatgg acaacttctt cgcccccgtt ttcactatgg      60
gcaaatatt                                                              69

<210> SEQ ID NO 337
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ggaagatcta gcaccaggcg tttaag                                           26

<210> SEQ ID NO 338
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 338
gaggccggcc atcgaatggc gcaaaac                                          27

<210> SEQ ID NO 339
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
cgcgtaccgt cctcatggga gaaaataata c                                     31

<210> SEQ ID NO 340
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ccatgaggac ggtacgcgac tgggcgtgga gcatctggtc gcattgggtc accagcaaat      60
ccgctgttag ctggcccatt aag                                              83

<210> SEQ ID NO 341
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gtcagcggcg ggatataaca tgagctgtcc tcggtatcgt cg                         42

<210> SEQ ID NO 342
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gttatatccc gccgctgacc accatcaaac                                       30

<210> SEQ ID NO 343
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
catcagtgaa tcggccaacg cgcggggaga ggcggtttgc gtattgggag ccagggtggt      60
ttttc                                                                  65

<210> SEQ ID NO 344
```

```
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
ggttaattaa cctcactgcc cgctttccag tcgggaaacc tgtcgtgcca gctgcatcag      60
tgaatcggcc aac                                                        73

<210> SEQ ID NO 345
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ctagactagt gtttaaaccg gaccgggggg gggcttaagg ggggggggg                  50

<210> SEQ ID NO 346
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ctagcccccc ccccccttaa gccccccccc ggtccggttt aaacactagt                 50

<210> SEQ ID NO 347
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ctagactagt gtttaaaccg gaccgggggg gggcttaagg ggggggggg                  50

<210> SEQ ID NO 348
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
ccccccctta agtgggctgc aaaacaaaac ggcctcctgt caggaagccg cttttatcgg      60
gtagcctcac tgcccgcttt cc                                              82

<210> SEQ ID NO 349
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gttgttgtgc cacgcggtta ggaatgtaat tcagctccgc                           40
```

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
aaccgcgtgg cacaacaac                                                  19

<210> SEQ ID NO 351
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
cttcgttcta ccatcgacac gaccacgctg gcacccagtt g                         41

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
gtgtcgatgg tagaacgaag                                                 20

<210> SEQ ID NO 353
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ccacagcaat agcatcctgg tcatccagcg gatagttaat aatcagccca ctgacacgtt     60
gcgcgag                                                               67

<210> SEQ ID NO 354
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
gaccaggatg ctattgctgt gg                                              22

<210> SEQ ID NO 355
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
cagcgcgatt tgctggtggc ccaatgcgac cagatgc    37

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
caccagcaaa tcgcgctg    18

<210> SEQ ID NO 357
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
cccggactcg gtaatggcac gcattgcgcc cagcgcc    37

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gccattaccg agtccggg    18

<210> SEQ ID NO 359
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
aattccacca tcatcaccat tgacgtcta    29

<210> SEQ ID NO 360
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
agcttagacg tcaatggtga tgatggtgg    29

<210> SEQ ID NO 361
<211> LENGTH: 1289
<212> TYPE: DNA
<213> ORGANISM: Artificial Sequence
<220> FEATURE:
<223> OTHER INFORMATION: Description of Artificial Sequence: Synthetic
      gene cassette

<400> SEQUENCE: 361
cgcgttaacc tcaggtgacc aagcccctgg ccaaggtccc gtacgttcga agattaccat    60

-continued

```
cacgtggatc cggtaccagg ccggccatta tcaaaaagga tctcaagaag atcctttgat    120
cttttctacg gggtctgacg ctcagtggaa cgaaaactca cgttaaggga ttttggtcat    180
gagattatca aaaggatctt tcacctagat ccttttaaat aaaaatgaa gttttaaatc     240 aatctaaagt atatatgagt aaacttggtc tgacagttac caatgcttaa tcagtgaggc    300
acctatctca gcgatctgtc tatttcgttc atccatagtt gcctgactcc cgtcgtgta    360 gataactacg atacgggagg gcttaccatc tggccccagt gctgcaatga taccgcgaga    420
cccacgctca ccggctccag atttatcagc aataaaccag ccagccggaa gggccgagcg    480
cagaagtggt cctgcaactt tatccgcctc catccagtct attaactgtt gccgggaagc    540
tagagtaagt agttcgccag ttaatagttt gcgcaacgtt gttgccattg ctacaggcat    600
cgtggtgtca cgctcgtcgt ttggtatggc ttcattcagc tccggttccc aacgatcaag    660
gcgagttaca tgatccccca tgttgtgcaa aaaagcggtt agctccttcg gtcctccgat    720
cgttgtcaga agtaagttgg ccgcagtgtt atcactcatg gttatggcag cactgcataa    780
ttctcttact gtcatgccat ccgtaagatg cttttctgtg actggtgagt actcaaccaa    840
gtcattctga aatagtgta tgcggcgacc gagttgctct gcccggcgt caatacggga     900 taataccgcg ccacatagca gaactttaaa agtgctcatc attggaaaac gttcttcggg    960
gcgaaaactc tcaaggatct taccgctgtt gagatccagt tcgatgtaac ccactcgtgc   1020
acccaactga tcttcagcat cttttacttt caccagcgtt tctgggtgag caaaaacagg   1080
aaggcaaaat gccgcaaaaa agggaataag ggcgacacgg aaatgttgaa tactcatact   1140 cttcctttt caatattatt gaagcattta tcagggttat tgtctcatga gcggatacat    1200
atttgaatgt actcggccgc acgagctgca ggcgccatta atggctcgag cgcgcttcag   1260
cgctttgtct tccggatgta catgaaatt                                    1289
```

<210> SEQ ID NO 362
<211> LENGTH: 286
<212> TYPE: PRT
<213> ORGANISM: Artificial Sequence
<220> FEATURE:
<223> OTHER INFORMATION: Description of Artificial Sequence: Synthetic gene cassette

<400> SEQUENCE: 362

```
Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
    65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
```

-continued

```
                130                 135                 140
Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
                180                 185                 190

Thr Gly Glu Leu Leu Thr Leu Ala Ser Arg Gln Gln Leu Ile Asp Trp
                195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
                275                 280                 285
```

<210> SEQ ID NO 363
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 363
gccctgcaag cggaagac                                                    18

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 364
ggctttcgaa tggccaaagg                                                  20

<210> SEQ ID NO 365
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (43)..(45)
<223> OTHER INFORMATION: region represents a variable trinucleotide combination capable of coding any natural occurring amino acid other than Cys or Pro
<220> FEATURE:
<221> NAME/KEY: modified_base
<222> LOCATION: (52)..(54)
<223> OTHER INFORMATION: region represents a variable trinucleotide combination capable of coding any natural occurring amino acid other than Cys
<220> FEATURE:
<221> NAME/KEY: modified_base
<222> LOCATION: (58)..(60)
<223> OTHER INFORMATION: region represents a variable trinucleotide

```
    combination capable of coding any natural occurring amino acid
    other than Cys

<400> SEQUENCE: 365
gccctgcaag cggaagactt tgcgryttat tattgchwkc agnnndvtdv tnnnyctnnn       60
acctttggcc attcgaaagc c                                                81

<210> SEQ ID NO 366
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(45)
<223> OTHER INFORMATION: region represents a variable trinucleotide
      combination capable of coding any natural occurring amino acid
      other than Cys or Pro
<220> FEATURE:
<221> NAME/KEY: modified_base
<222> LOCATION: (52)..(54)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (58)..(60)
<223> OTHER INFORMATION: region represents a variable trinucleotide
      combination capable of coding any natural occurring amino acid
      other than Cys

<400> SEQUENCE: 366
gccctgcaag cggaagacgt gggcgtgtat tattgchwkc agnnndvtdv tnnnyctnnn       60
acctttggcc attcgaaagc c                                                81

<210> SEQ ID NO 367
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(45)
<223> OTHER INFORMATION: region represents a variable trinucleotide
      combination capable of coding any natural occurring amino acid
      other than Cys or Pro
<220> FEATURE:
<221> NAME/KEY: modified_base
<222> LOCATION: (52)..(54)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (58)..(60)
<223> OTHER INFORMATION: region represents a variable trinucleotide
      combination capable of coding any natural occurring amino acid
      other than Cys

<400> SEQUENCE: 367
gccctgcaag cggaagacgt ggcggtgtat tattgchwkc agnnndvtdv tnnnyctnnn       60
acctttggcc attcgaaagc c                                                81

<210> SEQ ID NO 368
<211> LENGTH: 108
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(49)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (50)..(52)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (53)..(55)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (56)..(58)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (59)..(61)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (62)..(64)
<223> OTHER INFORMATION: region represents a variable trinucleotide
      combination capable of coding any natural occurring amino acid
      other than Cys

<400> SEQUENCE: 368
cctgcaagcg gaagacgaag cggattatta ttgccagagc yrkgacnnnn nnnnnnnnnn      60
nnnnggcggc ggcacgaagt taaccgttct tggccaggaa ttcgagcc                  108

<210> SEQ ID NO 369
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(49)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (50)..(52)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (53)..(55)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (56)..(58)
<223> OTHER INFORMATION: region represents a variable trinucleotide
      combination capable of coding any natural occurring amino acid
      other than Cys or Trp
```

```
<220> FEATURE:
<221> NAME/KEY: modified_base
<222> LOCATION: (59)..(61)
<223> OTHER INFORMATION: region represents a variable trinucleotide
      combination capable of coding any natural occurring amino acid
      other than Cys

<400> SEQUENCE: 369
cctgcaagcg gaagacgaag cggattatta ttgccagagc yrkgacnnnn nnnnnnnnnn    60
nggcggcggc acgaagttaa ccgttcttgg ccaggaattc gagcc                  105

<210> SEQ ID NO 370
<211> LENGTH: 102
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(49)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (50)..(52)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (53)..(55)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (56)..(58)
<223> OTHER INFORMATION: region represents a variable trinucleotide
      combination capable of coding any natural occurring amino acid
      other than Cys

<400> SEQUENCE: 370
cctgcaagcg gaagacgaag cggattatta ttgccagagc yrkgacnnnn nnnnnnnngg    60
cggcggcacg aagttaaccg ttcttggcca ggaattcgag cc                     102

<210> SEQ ID NO 371
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
ggctcgaatt cctggcc                                                  17

<210> SEQ ID NO 372
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (21)..(23)
<223> OTHER INFORMATION: region represents a variable trinucleotide
      combination capable of coding any natural occurring amino acid
      other than Cys
```

```
-continued

<220> FEATURE:
<221> NAME/KEY: modified_base
<222> LOCATION: (27)..(29)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (30)..(32)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (33)..(35)
<223> OTHER INFORMATION: region represents a variable trinucleotide
      combination capable of coding any natural occurring amino acid
      other than Cys or not present
<220> FEATURE:
<221> NAME/KEY: modified_base
<222> LOCATION: (42)..(44)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (48)..(50)
<223> OTHER INFORMATION: region represents a variable trinucleotide
      combination capable of coding any natural occurring amino acid
      other than Cys

<400> SEQUENCE: 372
agggtctcga gtgggtgagc nnnattnnnn nnnnnrvtrv tnnnaccnnn tatgcggata     60
gcgtgaaagg ccgttttacc atttcacgtg ataattcgaa aaacacca                 108
```

The invention claimed is:

1. A modular replicable vector, comprising a plurality of vector modules, wherein each vector module is (a) flanked by DNA cleavage sites unique within said vector, and (b) essentially devoid of DNA cleavage sites comprised in a nucleotide sequence selected from the group consisting of V-kappa-1 (SEQ ID NO: 42), V-kappa-2 (SEQ ID NO: 44), V-kappa-3 (SEQ ID NO: 46), V-kappa-4 (SEQ ID NO: 48), V-lambda-1 (SEQ ID NO: 50), V-lambda-2 (SEQ ID NO: 52), V-lambda-3 (SEQ ID NO: 54), VH1A (SEQ ID NO: 56), VH1B (SEQ ID NO: 58), VH2 (SEQ ID NO: 60), VH3 (SEQ ID NO: 62), VH4 (SEQ ID NO: 64), VH5 (SEQ ID NO: 66), and VH6 (SEQ ID NO: 68) at the boundaries between each consensus framework region and each complementarity determining region.

2. The vector according to claim 1, wherein said vector is selected from the group consisting of pCAL 4 (SEQ ID NO: 274), pCALO-1 (SEQ ID NO: 294), pCALO-2 (SEQ ID NO: 296), pCALO-3 (SEQ ID NO: 299) and pMCS (SEQ ID NO: 264).

3. The vector according to claim 1, wherein said vector is a phagemid vector.

4. The vector according to claim 1, comprising (a) an origin of replication selected from the group consisting of an origin of single-stranded replication, an origin of double-stranded replication for a low copy number plasmid and an origin of double-stranded replication for a high copy number plasmid; and (b) a plurality of vector modules selected from the group consisting of a promoter element, an operator element, a repressor element, a terminator element, a resistance gene, a recombination site, a filamentous phage gene III, a truncated filamentous phage gene III, a signal sequence, a purification tag, a detection tag, and a sequence encoding an additional (poly)peptide moiety.

5. A modular replicable vector, comprising (i) a nucleotide sequence encoding an immunoglobulin variable region, comprising a modular sequence of four consensus framework regions interspaced by three complementarity determining regions CDR1, CDR2, and CDR3, wherein said nucleotide sequence comprises DNA cleavage sites at the boundary of each consensus framework region and each complementarity determining region, and (ii) a plurality of vector modules, wherein each vector module is flanked by DNA cleavage sites, wherein each of said DNA cleavage sites of (i) and (ii) is unique within said vector, and wherein said immunoglobulin variable region is a heavy chain or a light chain.

6. The vector according to claim 5, wherein said framework regions correspond to the framework regions contained in a sequence selected from the group consisting of V-kappa-1 (SEQ ID NO: 42), V-kappa-2 (SEQ ID NO: 44), V-kappa-3 (SEQ ID NO: 46), and V-kappa-4 (SEQ ID NO: 48), V-lambda-1 (SEQ ID NO: 50), V-lambda-2 (SEQ ID NO: 52), and V-lambda-3 (SEQ ID NO: 54).

7. The vector according to claim 5, wherein said framework regions correspond to the framework regions contained in a sequence selected from the group consisting of VH1A (SEQ ID NO: 56), VH1B (SEQ ID NO: 58), VH2 (SEQ ID NO: 60), VH3 (SEQ ID NO: 62), VH4 (SEQ ID NO: 64), VH5 (SEQ ID NO: 66), and VH6 (SEQ ID NO: 68).

8. The vector according to claim 5, comprising (a) an origin of replication selected from the group consisting of an origin of double-stranded replication for a low copy number plasmid and an origin of double-stranded replication for a high copy number plasmid; and (b) a plurality of vector modules selected from the group consisting of a promoter element, an operator element, a repressor element, a terminator element, a resistance gene, a recombination site, a filamentous phage gene III, a truncated filamentous phage gene III, a signal sequence, a purification tag, a detection tag, and a sequence encoding an additional (poly)peptide moiety.

9. The vector according to claim 5, wherein said additional moiety is selected from the group consisting of a toxin, a cytokine, a reporter enzyme, a metal-binding moiety, a peptide, a tag suitable for detection and/or purification, a homo-association domain and a hetero-association domain.

10. The vector according to claim 5, wherein said vector is a phagemid vector.

11. The vector according to claim 5, wherein said nucleotide sequence is selected from the group consisting of V-kappa-1 (SEQ ID NO: 42), V-kappa-2 (SEQ ID NO: 44), V-kappa-3 (SEQ ID NO: 46), and V-kappa-4 (SEQ ID NO: 48).

12. The vector according to claim 5, wherein said nucleotide sequence is selected from the group consisting of V-lambda-1 (SEQ ID NO: 50), V-lambda-2 (SEQ ID NO: 52), and V-lambda-3 (SEQ ID NO: 54).

13. The vector according to claim 5, wherein said nucleotide sequence is selected from the group consisting of VH1A (SEQ ID NO: 56), VH1B (SEQ ID NO: 58), VH2 (SEQ ID NO: 60), VH3 (SEQ ID NO: 62), VH4 (SEQ ID NO: 64), VH5 (SEQ ID NO: 66), and VH6 (SEQ ID NO: 68).

* * * * *